US012502080B2

(12) United States Patent
Islam

(10) Patent No.: US 12,502,080 B2
(45) **Date of Patent: *Dec. 23, 2025**

(54) CAMERA BASED WEARABLE DEVICES WITH ARTIFICIAL INTELLIGENCE ASSISTANTS

(71) Applicant: Omni Medsci, Inc., Ann Arbor, MI (US)

(72) Inventor: Mohammed N. Islam, Ann Arbor, MI (US)

(73) Assignee: OMNI MEDSCI, INC., Ann Arbor, MI (US)

( * ) Notice: Subject to any disclaimer, the term of this patent is extended or adjusted under 35 U.S.C. 154(b) by 211 days.

This patent is subject to a terminal disclaimer.

(21) Appl. No.: 18/386,877

(22) Filed: Nov. 3, 2023

(65) Prior Publication Data

US 2024/0130621 A1 Apr. 25, 2024
US 2024/0225454 A9 Jul. 11, 2024

Related U.S. Application Data

(63) Continuation-in-part of application No. 18/118,013, filed on Mar. 6, 2023, now Pat. No. 12,226,188,
(Continued)

(51) Int. Cl.
*A61B 5/00* (2006.01)
*A61B 5/145* (2006.01)
(Continued)

(52) U.S. Cl.
CPC .......... *A61B 5/0088* (2013.01); *A61B 5/0013* (2013.01); *A61B 5/0022* (2013.01);
(Continued)

(58) Field of Classification Search
CPC ... A61B 5/0088; A61B 5/0013; A61B 5/0022; A61B 5/0075; A61B 5/0086;
(Continued)

(56) References Cited

U.S. PATENT DOCUMENTS 4,063,106 A 12/1977 Ashkin et al.
4,158,750 A 6/1979 Sakoe et al.
(Continued)

FOREIGN PATENT DOCUMENTS

CA 2458123 9/2004
CN 101849821 A 10/2010
(Continued)

OTHER PUBLICATIONS

Inter Partes Review No. IPR2021-00453; Judgment Final Written Decision on Remand of U.S. Pat. No. 10,517,484; *Apple Inc. v. Omni Medsci, Inc.*; pp. 1-14; dated Feb. 14, 2025.
(Continued)

*Primary Examiner* — Md M Rahman
(74) *Attorney, Agent, or Firm* — Brooks Kushman P.C.

(57) ABSTRACT

An optical sensing system comprises a human interface structure to be applied to a user. The system comprises a time-of-flight sensor with an array of laser diodes with Bragg reflectors operating in the near-infrared, a detection system, and a processor generating a time-of-flight measurement and a first image. The system also includes a first camera system capturing a second image, and a second camera system illuminated by light emitting diodes to monitor one or more eyes of the user. In communication with or operating on the processor is an artificial intelligence assistant, which comprises a multi-modal generative artificial intelligence model. The system may be part of wearable eyewear such as smart glasses or extended reality goggles. The system may perform gesture analysis, eye tracking and speed recognition, and video and verbal outputs can be provided to the user. An artificial intelligence agent may have awareness of the environment.

20 Claims, 114 Drawing Sheets

Related U.S. Application Data which is a continuation-in-part of application No. 17/666,518, filed on Feb. 7, 2022, now Pat. No. 11,596,311, which is a continuation of application No. 17/135,233, filed on Dec. 28, 2020, now Pat. No. 11,241,156, which is a continuation of application No. 16/669,794, filed on Oct. 31, 2019, now Pat. No. 10,874,304, which is a continuation of application No. 16/284,514, filed on Feb. 25, 2019, now abandoned, which is a continuation of application No. 16/016,649, filed on Jun. 24, 2018, now Pat. No. 10,213,113, which is a continuation of application No. 15/860,065, filed on Jan. 2, 2018, now Pat. No. 10,098,546, which is a continuation of application No. 15/686,198, filed on Aug. 25, 2017, now Pat. No. 9,861,286, which is a continuation of application No. 15/357,136, filed on Nov. 21, 2016, now Pat. No. 9,757,040, which is a continuation of application No. 14/651,367, filed as application No. PCT/US2013/075736 on Dec. 17, 2013, now Pat. No. 9,500,635, said application No. 16/669,794 is a continuation of application No. 16/506,885, filed on Jul. 9, 2019, now Pat. No. 10,517,484, which is a continuation of application No. 16/272,069, filed on Feb. 11, 2019, now abandoned, which is a continuation of application No. 16/029,611, filed on Jul. 8, 2018, now Pat. No. 10,201,283, which is a continuation of application No. 15/888,052, filed on Feb. 4, 2018, now Pat. No. 10,136,819, which is a continuation of application No. 15/212,549, filed on Jul. 18, 2016, now Pat. No. 9,885,698, which is a continuation of application No. 14/650,897, filed as application No. PCT/US2013/075700 on Dec. 17, 2013, now Pat. No. 9,494,567, said application No. 16/506,885 is a continuation of application No. 16/004,359, filed on Jun. 9, 2018, now Pat. No. 11,109,761, which is a continuation of application No. 14/109,007, filed on Dec. 17, 2013, now Pat. No. 9,993,159, said application No. 16/506,885 is a continuation of application No. 16/188,194, filed on Nov. 12, 2018, now Pat. No. 10,386,230, which is a continuation of application No. 16/004,154, filed on Jun. 8, 2018, now Pat. No. 10,126,283, which is a continuation of application No. 15/855,201, filed on Dec. 27, 2017, now Pat. No. 9,995,722, which is a continuation of application No. 15/711,907, filed on Sep. 21, 2017, now Pat. No. 9,897,584, which is a continuation of application No. 15/357,225, filed on Nov. 21, 2016, now Pat. No. 9,797,876, which is a continuation of application No. 14/650,981, filed as application No. PCT/US2013/075767 on Dec. 17, 2013, now Pat. No. 9,500,634, said application No. 16/506,885 is a continuation of application No. 16/241,628, filed on Jan. 7, 2019, now Pat. No. 10,441,176, which is a continuation of application No. 16/015,737, filed on Jun. 22, 2018, now Pat. No. 10,172,523, which is a continuation of application No. 15/594,053, filed on May 12, 2017, now Pat. No. 10,188,299, which is a continuation of application No. 14/875,709, filed on Oct. 6, 2015, now Pat. No. 9,651,533, which is a continuation of application No. 14/108,986, filed on Dec. 17, 2013, now Pat. No. 9,164,032, said application No. 16/506,885 is a continuation of application No. 16/284,514, filed on Feb. 25, 2019, now abandoned.

(60) Provisional application No. 61/754,698, filed on Jan. 21, 2013, provisional application No. 61/747,477, filed on Dec. 31, 2012, provisional application No. 61/747,472, filed on Dec. 31, 2012, provisional application No. 61/747,487, filed on Dec. 31, 2012, provisional application No. 61/747,485, filed on Dec. 31, 2012, provisional application No. 61/747,553, filed on Dec. 31, 2012.

(51) Int. Cl.

| | |
|---|---|
| ***A61B 5/1455*** | (2006.01) |
| ***A61C 19/04*** | (2006.01) |
| ***G01J 3/02*** | (2006.01) |
| ***G01J 3/10*** | (2006.01) |
| ***G01J 3/14*** | (2006.01) |
| ***G01J 3/28*** | (2006.01) |
| ***G01J 3/42*** | (2006.01) |
| ***G01J 3/453*** | (2006.01) |
| ***G01N 21/35*** | (2014.01) |
| ***G01N 21/3504*** | (2014.01) |
| ***G01N 21/3563*** | (2014.01) |
| ***G01N 21/359*** | (2014.01) |
| ***G01N 21/39*** | (2006.01) |
| ***G01N 21/88*** | (2006.01) |
| ***G01N 33/02*** | (2006.01) |
| ***G01N 33/15*** | (2006.01) |
| ***G01N 33/44*** | (2006.01) |
| ***G01N 33/49*** | (2006.01) |
| ***G16H 40/67*** | (2018.01) |
| ***G16Z 99/00*** | (2019.01) |
| *H01S 3/30* | (2006.01) |

(52) U.S. Cl.

CPC .......... *A61B 5/0075* (2013.01); *A61B 5/0086* (2013.01); *A61B 5/14532* (2013.01); *A61B 5/14546* (2013.01); *A61B 5/1455* (2013.01); *A61B 5/4547* (2013.01); *A61B 5/6801* (2013.01); *A61B 5/7203* (2013.01); *A61B 5/7257* (2013.01); *A61B 5/7405* (2013.01); *A61B 5/742* (2013.01); *A61C 19/04* (2013.01); *G01J 3/02* (2013.01); *G01J 3/0218* (2013.01); *G01J 3/108* (2013.01); *G01J 3/14* (2013.01); *G01J 3/28* (2013.01); *G01J 3/2823* (2013.01); *G01J 3/42* (2013.01); *G01J 3/453* (2013.01); *G01N 21/35* (2013.01); *G01N 21/3504* (2013.01); *G01N 21/3563* (2013.01); *G01N 21/359* (2013.01); *G01N 21/39* (2013.01); *G01N 21/88* (2013.01); *G01N 33/02* (2013.01); *G01N 33/025* (2013.01); *G01N 33/15* (2013.01); *G01N 33/442* (2013.01); *G01N 33/49* (2013.01); *G16H 40/67* (2018.01); *G16Z 99/00* (2019.02); *G01N 2201/129* (2013.01); *H01S 3/302* (2013.01)

(58) Field of Classification Search

CPC ........... A61B 5/14532; A61B 5/14546; A61B 5/1455; A61B 5/4547; A61B 5/6801; A61B 5/7203; A61B 5/7257; A61B 5/7405; A61B 5/742; A61B 5/0024; A61B 2562/0233; A61B 2562/0238; A61B 2562/146; A61B 2576/02; A61C 19/04; A61C 1/0046; G01J 3/02; G01J 3/0218; G01J 3/108; G01J 3/14; G01J 3/28; G01J 3/2823; G01J 3/42; G01J 3/453; G01J 3/1838; G01J 2003/104; G01J 2003/1208; G01J 2003/2826; G01J 2003/064; G01J 2003/1213; G01J 3/0208; G01J 3/0224; G01J 3/0245; G01J 3/0264; G01J 3/06; G01J 3/1895; G01J 3/32; G01N 21/35;

G01N 21/3504; G01N 21/3563; G01N 21/359; G01N 21/39; G01N 21/88; G01N 33/02; G01N 33/025; G01N 33/15; G01N 33/442; G01N 33/49; G01N 21/85; G01N 21/9508; G01N 2021/3513; G01N 2021/3595; G01N 2021/399; G01N 2201/061; G01N 2201/06113; G01N 2201/062; G01N 2201/08; G01N 2201/12; G01N 2201/129; G01N 2021/1793; G01N 2201/0214; G01N 2201/0216; G01N 2201/0221; G01N 2201/0612; G01N 2201/0691; G01N 2333/00; G16H 40/67; G16H 40/20; G16H 70/40; G16Z 99/00; G01M 3/38; H01S 3/0092; H01S 3/06758; H01S 3/302; H01S 3/06754; H01S 3/10023; Y02A 90/10

USPC .......................................................... 356/300

See application file for complete search history.

(56) References Cited

U.S. PATENT DOCUMENTS 4,221,997 A 9/1980 Flemming
4,275,266 A 6/1981 Lasar
4,374,618 A 2/1983 Howard
4,403,605 A 9/1983 Tanikawa
4,462,080 A 7/1984 Johnstone et al.
4,516,207 A 5/1985 Moriyama et al.
4,523,884 A 6/1985 Clement et al.
4,605,080 A 8/1986 Lemelson
4,641,292 A 2/1987 Tunnell et al.
4,704,696 A 11/1987 Reimer et al.
4,728,974 A 3/1988 Nio et al.
4,762,455 A 8/1988 Coughlan et al.
4,776,016 A 10/1988 Hansen
4,958,910 A 9/1990 Taylor et al.
4,989,253 A 1/1991 Liang et al.
5,078,140 A 1/1992 Kwoh
5,084,880 A 1/1992 Esterowitz et al.
5,086,401 A 2/1992 Glassman et al.
5,134,620 A 7/1992 Huber
5,142,930 A 9/1992 Allen et al.
5,180,378 A 1/1993 Kung et al.
5,191,628 A 3/1993 Byron
5,218,655 A 6/1993 Mizrahi
5,230,023 A 7/1993 Nakano
5,246,004 A 9/1993 Clarke et al.
5,267,152 A 11/1993 Yang et al.
5,267,256 A 11/1993 Saruwatari et al.
5,267,323 A 11/1993 Kimura
5,300,097 A 4/1994 Lerner et al.
5,303,148 A 4/1994 Mattson et al.
5,305,427 A 4/1994 Nagata
5,313,306 A 5/1994 Kuban et al.
5,323,404 A 6/1994 Grubb
5,345,538 A 9/1994 Narayannan et al.
5,368,224 A 11/1994 Richardson et al.
5,400,165 A 3/1995 Gnauck et al.
5,408,409 A 4/1995 Glassman et al.
5,458,122 A 10/1995 Hethuin
5,497,769 A 3/1996 Gratton et al.
5,544,654 A 8/1996 Murphy et al.
5,563,710 A 10/1996 Webb et al.
5,572,999 A 11/1996 Funda et al.
5,617,871 A 4/1997 Burrows
5,631,758 A 5/1997 Knox et al.
5,687,734 A 11/1997 Dempsey et al.
5,695,493 A 12/1997 Nakajima et al.
5,696,778 A 12/1997 MacPherson
5,704,351 A 1/1998 Mortara et al.
5,718,234 A 2/1998 Warden et al.
5,746,206 A 5/1998 Mannheimer
5,747,806 A 5/1998 Khalil et al.
5,748,103 A 5/1998 Flach et al.
5,774,213 A 6/1998 Trebino et al.
5,792,204 A 8/1998 Snell
5,795,300 A 8/1998 Bryars
5,812,978 A 9/1998 Nolan
5,855,550 A 1/1999 Lai et al.
5,862,803 A 1/1999 Besson et al.
5,867,305 A 2/1999 Waarts et al.
5,891,022 A 4/1999 Pologe
5,912,749 A 6/1999 Harstead et al.
5,919,134 A 7/1999 Diab
5,944,659 A 8/1999 Flach et al.
5,950,629 A 9/1999 Taylor et al.
5,957,854 A 9/1999 Besson et al.
5,970,457 A 10/1999 Brant et al.
6,014,249 A 1/2000 Fermann et al.
6,031,603 A 2/2000 Fine et al.
6,043,927 A 3/2000 Islam
6,044,283 A 3/2000 Fein et al.
6,078,833 A 6/2000 Hueber
6,115,673 A 9/2000 Malin et al.
6,181,414 B1 1/2001 Raz et al.
6,185,535 B1 2/2001 Hedin et al.
6,200,309 B1 3/2001 Rice et al.
6,212,310 B1 4/2001 Waarts et al.
6,224,542 B1 5/2001 Chang et al.
6,246,707 B1 6/2001 Yin et al.
6,246,896 B1 6/2001 Dumoulin et al.
6,273,858 B1 8/2001 Fox et al.
6,278,975 B1 8/2001 Brant et al.
6,281,471 B1 8/2001 Smart
6,285,897 B1 9/2001 Kilcoyne et al.
6,289,238 B1 9/2001 Besson et al.
6,301,271 B1 10/2001 Sanders et al.
6,301,273 B1 10/2001 Sanders et al.
6,325,978 B1 12/2001 Labuda et al.
6,333,803 B1 12/2001 Kurotori et al.
6,337,462 B1 1/2002 Smart
6,340,806 B1 1/2002 Smart et al.
6,350,261 B1 2/2002 Domankevitz et al.
6,364,834 B1 4/2002 Reuss et al.
6,374,006 B1 4/2002 Islam et al.
6,381,391 B1 4/2002 Islam et al.
6,402,691 B1 6/2002 Peddicord et al.
6,407,853 B1 6/2002 Samson et al.
6,436,107 B1 8/2002 Wang et al.
6,441,747 B1 8/2002 Khair et al.
6,442,430 B1 8/2002 Ferek-Petric
6,443,890 B1 9/2002 Schulze et al.
6,450,172 B1 9/2002 Hartlaub et al.
6,453,201 B1 9/2002 Daum et al.
6,454,705 B1 9/2002 Cosentino et al.
6,458,120 B1 10/2002 Shen et al.
6,462,500 B1 10/2002 L'Hegarat et al.
6,463,361 B1 10/2002 Wang et al.
6,480,656 B1 11/2002 Islam et al.
6,505,133 B1 1/2003 Hanna et al.
6,509,566 B1 1/2003 Wamsley et al.
6,512,936 B1 1/2003 Monfre et al.
6,526,300 B1 2/2003 Kiani et al.
6,534,012 B1 3/2003 Hazen et al.
6,549,702 B2 4/2003 Islam et al.
6,567,431 B2 5/2003 Tabirian et al.
6,587,702 B1 7/2003 Ruchti et al.
6,603,910 B2 8/2003 Islam et al.
6,605,080 B1 8/2003 Altshuler et al.
6,611,643 B2 8/2003 Birk et al.
6,619,835 B2 9/2003 Kita
6,625,180 B2 9/2003 Bufetov et al.
6,631,025 B2 10/2003 Islam et al.
6,640,117 B2 10/2003 Makarewicz et al.
6,659,947 B1 12/2003 Carter et al.
6,659,999 B1 12/2003 Anderson et al.
6,701,170 B2 3/2004 Stetson
6,708,048 B1 3/2004 Chance
6,731,967 B1 5/2004 Turcott
6,738,652 B2 5/2004 Mattu et al.
6,760,148 B2 7/2004 Islam
6,773,922 B2 8/2004 Jeng et al.

(56) References Cited

U.S. PATENT DOCUMENTS

| | | | |
|---|---|---|---|
| 6,788,965 | B2 | 9/2004 | Ruchti et al. |
| 6,802,811 | B1 | 10/2004 | Slepian |
| 6,816,241 | B2 | 11/2004 | Grubisic |
| 6,847,336 | B1 | 1/2005 | Lemelson et al. |
| 6,864,978 | B1 | 3/2005 | Hazen et al. |
| 6,885,498 | B2 | 4/2005 | Islam |
| 6,885,683 | B1 | 4/2005 | Fermann et al. |
| 6,898,451 | B2 | 5/2005 | Wuori |
| 6,916,096 | B2 | 7/2005 | Eberl et al. |
| 6,943,936 | B2 | 9/2005 | Islam et al. |
| 6,990,364 | B2 | 1/2006 | Ruchti et al. |
| 7,010,336 | B2 | 3/2006 | Lorenz et al. |
| 7,027,467 | B2 | 4/2006 | Baev et al. |
| 7,029,628 | B2 | 4/2006 | Tam et al. |
| 7,060,061 | B2 | 6/2006 | Altshuler et al. |
| 7,105,823 | B2 | 9/2006 | Abrahamsson et al. |
| 7,133,710 | B2 | 11/2006 | Acosta et al. |
| 7,139,076 | B1 | 11/2006 | Marbach |
| 7,167,300 | B2 | 1/2007 | Fermann et al. |
| 7,184,148 | B2 | 2/2007 | Alphonse |
| 7,209,657 | B1 | 4/2007 | Islam |
| 7,233,816 | B2 | 6/2007 | Blank et al. |
| 7,259,906 | B1 | 8/2007 | Islam |
| 7,263,288 | B1 | 8/2007 | Islam |
| 7,278,966 | B2 | 10/2007 | Hjelt et al. |
| 7,294,105 | B1 | 11/2007 | Islam |
| 7,299,080 | B2 | 11/2007 | Acosta et al. |
| 7,317,938 | B2 | 1/2008 | Lorenz et al. |
| 7,318,909 | B2 | 1/2008 | Lehmann et al. |
| 7,332,784 | B2 | 2/2008 | Mills et al. |
| 7,356,364 | B1 | 4/2008 | Bullock et al. |
| 7,395,158 | B2 | 7/2008 | Monfre et al. |
| 7,433,116 | B1 | 10/2008 | Islam |
| 7,468,036 | B1 | 12/2008 | Rulkov et al. |
| 7,519,253 | B2 | 4/2009 | Islam |
| 7,519,406 | B2 | 4/2009 | Blank et al. |
| 7,620,674 | B2 | 11/2009 | Ruchti et al. |
| 7,648,463 | B1 | 1/2010 | Elhag et al. |
| 7,697,966 | B2 | 4/2010 | Monfre et al. |
| 7,771,320 | B2 | 8/2010 | Riley et al. |
| 7,787,503 | B2 | 8/2010 | Wadsworth |
| 7,787,924 | B2 | 8/2010 | Acosta et al. |
| 7,800,818 | B2 | 9/2010 | Mattsson |
| 7,807,718 | B2 | 10/2010 | Hashim et al. |
| 7,847,234 | B2 | 12/2010 | Meyers et al. |
| 7,848,605 | B2 | 12/2010 | Ridder et al. |
| 7,890,158 | B2 | 2/2011 | Rowe et al. |
| 8,000,574 | B2 | 8/2011 | Buchter et al. |
| 8,108,036 | B2 | 1/2012 | Tran |
| 8,145,286 | B2 | 3/2012 | Arai et al. |
| 8,157,730 | B2 | 4/2012 | LeBoeuf et al. |
| 8,158,175 | B2 | 4/2012 | Bourg, Jr. |
| 8,158,493 | B2 | 4/2012 | Shah et al. |
| 8,172,761 | B1 | 5/2012 | Rulkov et al. |
| 8,180,422 | B2 | 5/2012 | Rebec |
| 8,180,591 | B2 | 5/2012 | Yuen et al. |
| 8,198,589 | B2 | 6/2012 | Tolton et al. |
| 8,213,007 | B2 | 7/2012 | Wang et al. |
| 8,310,336 | B2 | 11/2012 | Muhsin et al. |
| 8,315,682 | B2 | 11/2012 | Such et al. |
| 8,320,621 | B2 | 11/2012 | McEldowney |
| 8,430,310 | B1 | 4/2013 | Ho et al. |
| 8,463,576 | B2 | 6/2013 | Yuen et al. |
| 8,472,108 | B2 | 6/2013 | Islam |
| 8,475,367 | B1 | 7/2013 | Yuen et al. |
| 8,509,882 | B2 | 8/2013 | Albert et al. |
| 8,587,771 | B2 | 11/2013 | Xu et al. |
| 8,649,838 | B2 | 2/2014 | Chen et al. |
| RE44,875 | E | 4/2014 | Kiani et al. |
| 8,725,226 | B2 | 5/2014 | Isaacson |
| 8,749,796 | B2 | 6/2014 | Pesach et al. |
| 8,755,871 | B2 | 6/2014 | Weng et al. |
| 8,767,190 | B2 | 7/2014 | Hall |
| 8,788,002 | B2 | 7/2014 | LeBoeuf et al. |
| 8,928,893 | B2 | 1/2015 | Findlay et al. |
| 8,945,017 | B2 | 2/2015 | Venkatraman et al. |
| 8,948,832 | B2 | 2/2015 | Hong et al. |
| 8,954,135 | B2 | 2/2015 | Yuen et al. |
| 8,963,069 | B2 | 2/2015 | Drader et al. |
| 9,006,641 | B2 | 4/2015 | Drader |
| 9,110,163 | B2 | 8/2015 | Rogan |
| 9,142,117 | B2 | 9/2015 | Muhsin et al. |
| 9,151,829 | B2 | 10/2015 | Campbell |
| 9,164,032 | B2 | 10/2015 | Islam |
| 9,171,985 | B2 | 10/2015 | Dutton et al. |
| 9,179,876 | B2 | 11/2015 | Ochs et al. |
| 9,192,329 | B2 | 11/2015 | Al-Ali |
| 9,207,121 | B2 | 12/2015 | Adler |
| 9,236,519 | B2 | 1/2016 | Mazzillo et al. |
| 9,241,676 | B2 | 1/2016 | Lisogurski et al. |
| 9,265,456 | B2 | 2/2016 | Kirenko et al. |
| 9,273,846 | B1 | 3/2016 | Rossi et al. |
| 9,316,735 | B2 | 4/2016 | Baxter |
| 9,326,712 | B1 | 5/2016 | Kiani |
| 9,417,734 | B2 | 8/2016 | Raynor et al. |
| 9,430,093 | B2 | 8/2016 | Harrison et al. |
| 9,596,990 | B2 | 3/2017 | Park et al. |
| 9,651,533 | B2 | 5/2017 | Islam |
| 9,675,250 | B2 | 6/2017 | Tverskoy |
| 9,723,993 | B2 | 8/2017 | Vermeulen |
| 9,757,040 | B2 | 9/2017 | Islam |
| 9,770,213 | B2 | 9/2017 | Kirenko et al. |
| 9,820,658 | B2 | 11/2017 | Tran |
| 9,860,522 | B2 | 1/2018 | Lapstun |
| 9,861,286 | B1 | 1/2018 | Islam |
| 9,885,698 | B2 | 2/2018 | Islam |
| 9,891,309 | B2 | 2/2018 | Hudman et al. |
| 9,915,726 | B2 | 3/2018 | Bailey et al. |
| 10,043,485 | B2 | 8/2018 | Kestelli et al. |
| 10,117,588 | B2 | 11/2018 | Lee et al. |
| 10,188,299 | B2 | 1/2019 | Islam |
| 10,213,113 | B2 | 2/2019 | Islam |
| 10,359,505 | B2 | 7/2019 | Buettgen et al. |
| 10,376,192 | B2 | 8/2019 | Lee et al. |
| 10,441,173 | B2 | 10/2019 | Shan et al. |
| 10,517,484 | B2 | 12/2019 | Islam |
| 10,646,167 | B2 | 5/2020 | De Haan |
| 10,694,988 | B2 | 6/2020 | Lee et al. |
| 10,695,004 | B2 | 6/2020 | Gaudet et al. |
| 10,705,191 | B2 | 7/2020 | Ryu et al. |
| 10,806,354 | B2 | 10/2020 | Hutchinson et al. |
| 10,824,837 | B2 | 11/2020 | Yeke Yazdandoost et al. |
| 10,838,206 | B2 | 11/2020 | Fortin-Deschenes et al. |
| 10,922,395 | B2 | 2/2021 | Morestin et al. |
| 10,952,683 | B2 | 3/2021 | Jones et al. |
| 11,403,754 | B2 | 8/2022 | Hutchinson et al. |
| 11,625,098 | B2 | 4/2023 | Beyhs |
| 2002/0013518 | A1 | 1/2002 | West et al. |
| 2002/0019584 | A1 | 2/2002 | Schulze et al. |
| 2002/0032468 | A1 | 3/2002 | Hill et al. |
| 2002/0082612 | A1 | 6/2002 | Moll et al. |
| 2002/0109621 | A1 | 8/2002 | Khair et al. |
| 2002/0115914 | A1 | 8/2002 | Russ |
| 2002/0128846 | A1 | 9/2002 | Miller |
| 2002/0178003 | A1 | 11/2002 | Gehrke et al. |
| 2003/0022126 | A1 | 1/2003 | Buchalla et al. |
| 2003/0107739 | A1 | 6/2003 | Lehmann et al. |
| 2003/0109055 | A1 | 6/2003 | Lehmann et al. |
| 2003/0152307 | A1 | 8/2003 | Drasek et al. |
| 2003/0208113 | A1 | 11/2003 | Mault et al. |
| 2004/0174914 | A1 | 9/2004 | Fukatsu |
| 2004/0240037 | A1 | 12/2004 | Harter |
| 2005/0049468 | A1 | 3/2005 | Carlson et al. |
| 2005/0111500 | A1 | 5/2005 | Harter et al. |
| 2005/0133691 | A1 | 6/2005 | Doppke et al. |
| 2005/0209516 | A1 | 9/2005 | Fraden |
| 2006/0058683 | A1 | 3/2006 | Chance |
| 2006/0198397 | A1 | 9/2006 | Korolev et al. |
| 2006/0223032 | A1 | 10/2006 | Fried et al. |
| 2006/0245461 | A1 | 11/2006 | Islam |
| 2006/0268393 | A1 | 11/2006 | Islam |
| 2006/0281982 | A1 | 12/2006 | Grata et al. |
| 2006/0283931 | A1 | 12/2006 | Polli et al. |
| 2007/0021670 | A1 | 1/2007 | Mandelis et al. |

(56) References Cited

U.S. PATENT DOCUMENTS

| | | | |
|---|---|---|---|
| 2007/0078348 | A1 | 4/2007 | Holman |
| 2008/0086318 | A1 | 4/2008 | Gilley et al. |
| 2008/0105665 | A1 | 5/2008 | Kondo |
| 2008/0240502 | A1 | 10/2008 | Freedman et al. |
| 2009/0024041 | A1 | 1/2009 | Cho et al. |
| 2009/0028193 | A1 | 1/2009 | Islam |
| 2009/0105605 | A1 | 4/2009 | Abreu |
| 2009/0156932 | A1 | 6/2009 | Zharov |
| 2009/0185274 | A1 | 7/2009 | Shpunt |
| 2009/0204110 | A1 | 8/2009 | Islam |
| 2009/0244288 | A1 | 10/2009 | Fujimoto et al. |
| 2009/0287067 | A1 | 11/2009 | Dorogusker et al. |
| 2010/0007717 | A1 | 1/2010 | Spektor et al. |
| 2010/0046067 | A1 | 2/2010 | Fermann et al. |
| 2010/0118123 | A1 | 5/2010 | Freedman et al. |
| 2010/0160794 | A1 | 6/2010 | Banet et al. |
| 2010/0160798 | A1 | 6/2010 | Banet et al. |
| 2010/0217099 | A1 | 8/2010 | LeBoeuf et al. |
| 2010/0217102 | A1 | 8/2010 | LeBoeuf et al. |
| 2010/0284082 | A1 | 11/2010 | Shpunt et al. |
| 2010/0322490 | A1 | 12/2010 | Pan et al. |
| 2010/0331637 | A1 | 12/2010 | Ting et al. |
| 2011/0040197 | A1 | 2/2011 | Welch et al. |
| 2011/0143364 | A1 | 6/2011 | Kim et al. |
| 2011/0188054 | A1 | 8/2011 | Petronius et al. |
| 2011/0208015 | A1 | 8/2011 | Welch et al. |
| 2011/0237911 | A1 | 9/2011 | Lamego et al. |
| 2011/0267688 | A1 | 11/2011 | Kleppe et al. |
| 2011/0282167 | A1 | 11/2011 | Ridder et al. |
| 2011/0292376 | A1 | 12/2011 | Kukushkin et al. |
| 2012/0013722 | A1 | 1/2012 | Wong et al. |
| 2012/0041767 | A1 | 2/2012 | Hoffman et al. |
| 2012/0075432 | A1 | 3/2012 | Bilbrey et al. |
| 2012/0197093 | A1 | 8/2012 | LeBoeuf et al. |
| 2012/0203077 | A1 | 8/2012 | He et al. |
| 2012/0239013 | A1 | 9/2012 | Islam |
| 2012/0245439 | A1 | 9/2012 | Andre et al. |
| 2012/0310062 | A1 | 12/2012 | Li et al. |
| 2012/0316455 | A1 | 12/2012 | Rahman et al. |
| 2013/0274569 | A1 | 10/2013 | Islam |
| 2013/0281795 | A1 | 10/2013 | Varadan |
| 2013/0303921 | A1 | 11/2013 | Chu et al. |
| 2013/0327966 | A1 | 12/2013 | Fidler et al. |
| 2014/0078510 | A1 | 3/2014 | Rubio Guivernau et al. |
| 2014/0081100 | A1 | 3/2014 | Muhsin et al. |
| 2014/0152632 | A1 | 6/2014 | Shedletsky et al. |
| 2014/0236021 | A1 | 8/2014 | Islam |
| 2014/0249427 | A1 | 9/2014 | Liu |
| 2014/0275852 | A1 | 9/2014 | Hong et al. |
| 2014/0275854 | A1 | 9/2014 | Venkatraman et al. |
| 2015/0011851 | A1 | 1/2015 | Mehta et al. |
| 2015/0338509 | A1 | 11/2015 | Lange |
| 2016/0045118 | A1 | 2/2016 | Kiani |
| 2016/0181325 | A1 | 6/2016 | Johnson et al. |
| 2016/0232828 | A1 | 8/2016 | Jia et al. |
| 2016/0242657 | A1 | 8/2016 | Wang et al. |
| 2016/0327476 | A1 | 11/2016 | Islam |
| 2018/0156660 | A1 | 6/2018 | Turgeon et al. |
| 2018/0231373 | A1 | 8/2018 | Pesach et al. |
| 2019/0294868 | A1 | 9/2019 | Martinez |
| 2021/0096726 | A1 | 4/2021 | Faulkner et al. |
| 2022/0225006 | A1 | 7/2022 | Allec et al. |
| 2023/0000376 | A1 | 1/2023 | Maman et al. |

FOREIGN PATENT DOCUMENTS

| | | | |
|---|---|---|---|
| DE | 102010012987 | A1 | 10/2010 |
| EP | 1148666 | A2 | 10/2001 |
| JP | 2000074829 | | 3/2000 |
| JP | 2005270544 | A | 10/2005 |
| WO | 1997015240 | A1 | 5/1997 |
| WO | 1997049340 | A1 | 12/1997 |
| WO | 2001050959 | A1 | 7/2001 |
| WO | 2001089362 | A2 | 11/2001 |
| WO | 2002027640 | A2 | 4/2002 |
| WO | 2002028123 | A2 | 4/2002 |
| WO | 2005013843 | A2 | 2/2005 |
| WO | 2007061772 | A1 | 5/2007 |
| WO | 2009130464 | A1 | 10/2009 |
| WO | 2012135952 | A1 | 10/2012 |
| WO | 2013012938 | A1 | 1/2013 |
| WO | 2015084376 | A1 | 6/2015 |
| WO | WO2021149048 | A1 | 7/2021 |
| WO | WO2022074652 | A1 | 4/2022 |
| WO | WO2022084991 | A1 | 4/2022 |

OTHER PUBLICATIONS

United States Court of Appeals for the Federal Circuit, Appeal from the United States Patent and Trademark Office, Patent Trial and Appeal Board in No. IPR2021-00453, *Apple Inc.* v. *Omni Medsci, Inc.*, Case No. 2023-1034, Dated Jun. 21, 2024, 14 pgs.

Inter Partes Review No. IPR2020-00175; Petition for Inter Partes Review of U.S. Pat. No. 10,188,299; *Apple Inc.* v. *Omni Medsci, Inc.*; pp. 1-91; dated Dec. 11, 2019.

Inter Partes Review No. IPR2020-00209; Petition for Inter Partes Review of U.S. Pat. No. 10,213,113; *Apple Inc.* v. *Omni Medsci, Inc.*; pp. 1-91; dated Dec. 11, 2019.

File History for U.S. Pat. No. 10,213,113 issued Feb. 26, 2019, 686 pps.

Declaration of Brian W. Anthony , PhD, regarding U.S. Pat. No. 10,213,113 in IPR2020-00209, Dec. 11, 2019, 101 pps.

United States District Court Eastern District of Texas Marshall Division; *Omni Medsci, Inc.* vs. *Apple Inc.*; Civil Action No. 2:18-cv-00429; Second Amended Complaint; Feb. 26, 2019; 274 pps.

United States District Court Northern District of California Oakland Division; *Omni Medsci, Inc.* vs. *Apple Inc.*; Civil Action No. 19-cv-05673-YGR; Order staying the case; Nov. 20, 2019, 5 pps.

File History for U.S. Pat. No. 10,188,299 issued Jan. 29, 2019, 787 pps.

Declaration of Brian W. Anthony , PhD, regarding U.S. Pat. No. 10,188,299 in IPR2020-00175, Dec. 11, 2019, 119 pps.

United States District Court Eastern District of Texas Marshall Division; *Omni Medsci, Inc.* vs. *Apple Inc.*; Civil Action No. 2:18-cv-429; Amended Complaint; Jan. 28, 2019; 169 pps.

Inter Partes Review No. IPR2019-00916; Final Written Decision of U.S. Pat. No. 9,651,533 *Apple Inc.* v. *Omni Medsci, Inc.*; pp. 1-67; dated Oct. 14, 2020.

Miles et al., “Time of Flight Cameras: Principles, Methods, and Applications”, Springer, pp. 1-95, Nov. 2012, SpringerBriefs in Computer Science.

Dal Mutto C et al., “Time-of-Flight Cameras and Microsoft Kinect Tm, A user perspective on technology and applications”, pp. 1-116, Jan. 24, 2013, published by Springer.

Blum, Robert et al., “GaAs lasers eye multiple targets”, www.compoundsemiconductor.net, Jan. / Feb. 2013, pp. 61-64, Angel Business Communications.

Inter Partes Review No. IPR2021-00453; Petition for Inter Partes Review of U.S. Pat. No. 10,517,484; *Apple Inc.* v. *Omni Medsci, Inc.*; pp. 1-103; dated Jan. 22, 2021.

File History for U.S. Pat. No. 10,517,484 issued Dec. 24, 2019, 1223 pages.

Declaration of Brian Anthony regarding U.S. Pat. No. 10,517,484 in IPR2021-00453, Jan. 22, 2021, 138 pages.

Affidavit of Process Server, *Omni MedSci, Inc.* v. *Apple Inc.*, No. 3:20-cv-00563-KAW (N.D. Cal.), Jan. 29, 2020, 1 page.

Deposition Transcript of Duncan Leo MacFarlane, Ph.D., P.E., *Apple Inc.* v. *Omni MedSci, Inc.*, IPR2019-00916 (PTAB Apr. 16, 2020), 102 pages.

Omni Preliminary Proposed Claim Constructions, Nov. 1, 2018. Case No. 2:18-cv-134-RWS, 1 page.

Order Granting Motion to Stay Pending Interlocutory Appeal Related to Standing Question, *Omni MedSci, Inc.* v. *Apple Inc.*, No. 20-cv-00563-YGR (N.D. Cal. Apr. 28, 2020), 2 pages.

Carlos F. Benitez-Quiroz, Ramprakah Srinivasan, and Aleix M. Martinez, “Facial color is an efficient mechanism to visually trans-

(56) References Cited

OTHER PUBLICATIONS mit emotion," Proceedings of the National Academy of Science PNAS, Apr. 3, 2018, vol. 115, No. 14, pp. 3581-3586.
Kaiwen Guo, Tianqu Zhai, Elton Pashollari, Christopher J. Varlamos, Aymaan Ahmed, and Mohammed N. Islam, "Contactless Vital Sign Monitoring System for Heart and Respiratory Rate Measurements with Motion Compensation Using a Near-Infrared Time-of-Flight Camera," Applied Sciences, 2021, 11, 10913. https://doi.org/10.3390/app112210913.
Kaiwen Guo, Tianqu Zhai, Manoj H. Purushothama, Alexander Dobre, Shawn Meah, Elton Pashollari, Aabhaas Vaish, Carl DeWILDE and Mohammed N. Islam, "Contactless Vital Sign Monitoring System for In-Vehicle Driver Monitoring Using a Near-Infrared Time-of-Flight Camera," Applied Sciences, 2022, 12, 4416. https://doi.org/10.3390/app12094416.
"The 6 best LiDAR Apps and Games for iphone 12," http://www.mickeysworkshop.com/product-design/2021/1/23 (printed from web on Aug. 8, 2022).
Samuel Kim, Irfan Wisanggeni, Ryan Ros, Rania Hussein, "Detecting Fatigue Driving through PERCLOS: A Review," International Journal of Image Processing (IJIP), vol. 14, Issue 1, 2020, pp. 1-7.
Tereza Soukupova and Jan Cech, "Real-Time Eye Blink Detection using Facial Landmarks," 21st Computer Vision Winter Workshop, Luka Cehovin, Rok Mandeljc, Vitormir Struc (eds), Rimske Toplice, Slovenia, Feb. 3-5, 2016.
C. Fabian Benitez-Quiroz, Ramprakash Srinivasan and Aleix M. Martinez, "Discriminant Functional Learning of Color Features for the Recognition of Facial Action Units and Their Intensities," IEEE Transactions on Pattern Analysis and Machine Intelligence, vol. 41, No. 12, Dec. 2019, pp. 2835-2845.
Ramprakash Srinivasan, Julie D. Golomb and Aleix M. Martinez, "A Neural Basis of Facial Action Recognition in Humans," The Journal of Neuroscience, Apr. 20, 2016, vol. 36, No. 16, pp. 4434-4442.
Suhandi Junaedi and Habibullah Akbar, "Driver Drowsiness Detection Based on Face Feature and PERCLOS," Journal of Physics: Conference Series, 1090, 012037 (2018).
"Camera Phone," on Wikipedia, https://en.wikipedia.org/wiki/Camera_Phone, printed Aug. 19, 2022.
Preethi Padmanabhan, Chao Zhang, and Edoardo Charbon, "Modeling and Analysis of a Direct Time-of-Flight Sensor Architecture for LiDAR Applications," Sensors, 2019, 19, 5464; doi:10.3390/s19245464, www.mdpi.com/journal/sensors.
Application Note: Time-of-flight Basics, Melexis, AUH-2022, pp. 1-14.
Dingkang Wang, Connor Watkins and Huikai Xie, "Mems Mirrors for LiDAR: A Review," Micromachines 2020, 11, 456; doi:10.3390/mi11050456, www.mdpi.com/journal/micromachines.
Karl Joachim Ebeling, Rainer Michalzik and Holger Moench, "Vertical-cavity surface-emitting laser technology applications with focus on sensor and three-dimensional imaging," Japanese Journal of Applied Physics, 57, 08PA02 (2018), pp. 1-11.
Stella C. Gerdemann, Katherine McAuliffe, Peter R. Blake, Daniel B.M. Haun and Robert Hepach, "the ontogeny of children's social emotions in response to (un)fairness," 2022. Royal Society Open Science 9:191456. https://doi.org/10.1098/rsos.191456.
Robert Hepach, Amrisha Vaish and Michael Tomasello, "Novel paradigms to measure variability of behavior in early childhood: posture, gaze and pupil dilation," (2015), Frontiers in Psychology 6:858. doi: 10.3389/fpsyg.2015.00858, www.frontiersin.org.
Andrew Barszczyk and Kang Lee, "Measuring Blood Pressure: from Cuff to Smartphone," Current Hypertension Reports. (2019) 21:84 https://doi.org/10.1007/s11906-019-0990-3.
Deye Yang, Guomin Xiao, Jing Wei and Hong Luo, "Preliminary assessment of video-based blood pressure measurement according to ANSI/AAMI/ISO81060-2:2013 guideline accuracy criteria: Anura smartphone app with transdermal optimal imaging technology," Brief Report in Blood Pressure Monitoring. (2020) 25: 295-298.
Andrew Barszczyk, Weihong Zhou and Kang Lee, "Aim and Transdermal Optical Imaging," Springer Nature Switzerland AG 2021, N. Lidstromer, H. Ashrafian (eds.), Artificial Intelligence in Medicine, https://doi.org/10.1007/978-3-030-58080-3_250-1.
Hudda Salih, Si Jia Wu, Evgueni Kabakov, Kang Lee and Weihong Zhou, "Smartphone-based identification of critical levels of glycated hemoglobin A1c using transdermal optical imaging," Primary Research Article published in Journal of Natural Sciences, published Mar. 30, 2021, vol. 2, No. 1; doi: https://doi.org/10.33137/jns.v2i1.34645.
"Effects of diabetes on the body and organs," https://www.medicalnewstoday.com/articles/317483#faq (printed from the web Oct. 13, 2022).
Jiehui Sun, Keqin Han, Miao Xu, Lujuan Li, Jin Qian, Li Li and Xuejin Li, "Blood viscosity in subjects with type 2 diabetes Mellitus: Roles of hyperglycemia and elevated plasma fibrinogen," 2022, Frontiers in Physiology. 13:827428. doi: 10.3389/fphys.2022.827428. www.frontiersin.org.
Ying Li, Xiu-Xia Tian, Tiemin Liu, Rui-Tao Wang, "Association between whole blood viscosity and arterial stiffness in patients with type 2 diabetes mellitus," Springer published on-line Oct. 14, 2014, Endocrine, DOI: 10.1007/s12020-014-0451-3.
G.E. McVeigh, "Arterial Compliance in Hypertension and Diabetes mellitus," American Journal of Nephrology. 1996; 16:217-222.
"Compliance (physiology)," from Wikipedia, https://en.wikipedia.org/wiki/Compliance_(physiology), printed from web Jan. 10, 2023.
Chenguang Zhao, Dongwei Li, Yuanjun Kong, Hongyu Liu, Yiqing Hu, Haijing Niu, Ole Jensen, Xiaoli Li, Hanli Liu, Yan Song, "Transcranial photobiomodulation enhances visual working memory capacity in humans," Scientific Advances. 8, eqbq3211, pp. 1-12 (2022).
Fabrizio Dos Santos Cardoso, Farzad Salehpour, Norberto Cysne Coimbra, Francisco Gonzalez-Lima and Sergio Gomes Da Silva, "Photobiomodulation for the treatment of neuroinflammation: A systematic review of controlled laboratory animal studies," Frontiers in Neuroscience. (2022) 16:1006031. doi: 10.3389/fnins.2022.1006031.
Fabrizio Dos Santos Cardoso, Douglas W. Barrett, Zachary Wade, Sergio Gomes Da Silva and F. Gonzalez-Lima, "Photobiomodulation for the aging brain," Ageing Research Reviews. 70 (2021) 101415.
Fabrizio Dos Santos Cardoso, Farzad Salehpour, Norberto Cysne Coimbra, Francisco Gonzalez-Lima and Sergio Gomes Da Silva, "Photobiomodulation of cytochrome c oxidase by chronic transcranial laser in young and aged brains," Frontiers in Neuroscience. (2022) 16:818005. doi: 10.3389/fnins.2022.818005.
Agnes S. Chan, Tsz-Lok Lee, Michael R. Hamblin, Mei-Chun Cheung, "Photoneuromodulation makes a difficult cognitive task less arduous," www.nature.com/scientificreports. Science Reports (2021) 11:13688; https://doi.org/10.1038/s41598-021-93228-2.
Celeste L. Saucedo, Emily C. Courtois, Zachary S. Wade, Meghan N. Kelley, Nusha Kheradbin, Douglas W. Barrett, F. Gonzalez-Lima, "Transcranial laser simulation: Mitochondrial and cerebrovascular effects in younger and older healthy adults." Brain Stimulation, 14 (2021) 440-449; http://www.journals.elsevier.com/brain-stimulation.
"The science behind how laser therapy works." https://lightforcemedical.com/photobiomodulation-therapy-pbm/, printed from the web Jan. 18, 2023.
Meeri Kim, "Can low-power light improve working memory?" https://www.optica-opn.org/home/newsroom/2022/december/can_low-power_light_improve_working_memory/, printed from web Jan. 18, 2023.
Christoph F. Geissler, Jorn Schneider, Christian Frings, "Shedding light on the prefrontal correlates of mental workload in simulated driving: a functional near-infrared spectroscopy study," www.nature.com/scientificreports. Scientific Reports (2021) 11:705; https://doi.org/10.1038/s41598-020-80477-w.
Marie Cheour, "Parts of the brain used while driving," written Dec. 5, 2018, https://healthfully.com/parts-of-the-brain-involved-with-hearing-4113334.html, printed from web Jan. 22, 2023.
Hannah J. Foy, Patrick Runham, Peter Chapman, "Prefrontal cortex activation and young driver behavior: a fNIRS study," (2016) PLoS ONE 11 (5): e0156512. doi: 10.1371/journal.pone.0156512.
Kayoko Yoshino, Noriyuki Oka, Kouji Yamamoto, Hideki Takahashi, and Toshinori Kato, "Correlation of prefrontal cortical activation

(56) References Cited

OTHER PUBLICATIONS with changing vehicle speeds in actual driving: a vector-based functional near-infrared spectroscopy study," Frontiers in Human Neuroscience, www.frontiersin.org, Dec. 2013, vol. 7, Article 895; doi: 10.3389/fnhum.2013.00895.
Fangqing Zhengren, George Chernyshov, Dingding Zheng, "Cognitive load assessment from facial temperature using smart eyewear," MDR, Keio University (2020).
Naomi P. Friedman and Trevor W. Robbins, "The role of prefrontal cortex in cognitive control and execution function," Neuropsychopharmacology (2022) 47:72-89; https://doi.org/10.1038/s441386-021-01132-0.
Kanji Matsukawa, Ryota Asahara, Miho Yoshikawa and Kana Endo, "Deactivation of the prefrontal cortex during exposure to pleasantly-charged emotional challenge," www.nature.com/scientificreports. (2018) 8:14540; doi: 10.1038/s41598-018-32752-0.
Hugo Mitre-Hernandez, Jorge Sanchez-Rodriguez, Sergio Nava-Munoz and Carlos Lara- Alvarez, "Classifying the difficulty levels of working memory tasks by using pupillary response," PeerJ 10:e12864; http://doi.org/10.7717/peerj.12864.
Krzysztof Krejtz, Andrew T. Duchowski, Anna Niedzielska, Cezary Biele, Izabela Krejtz, "Eye tracking cognitive load using pupil diameter and microsaccades with fixed gaze," (2018) PLoS ONE 13 (9): e0203629. https://doi.org/10.1371/journal.pone.0203629.
Hamidur Rahmah, Mobyen Uddin Ahmed, Shaibal Barua, Peter Funk and Shahina Begum, "Vision-based driver's cognitive load classification considering eye movement using machine learning and deep learning," Sensors, 2021, 21, 8019. https://doi.org/10.3390/s21238019.
Product Document by AMS OSRAM on "Belago 1.1 Dot-Pattern Infrared Illuminator" Datasheet DS000676, Apr. 21, 2021.
Inter Partes Review No. 2021-00453; Decision Granting Institution of Inter Partes Review of U.S. Pat. No. 10,517,484, *Apple, Inc.* v. *Omni Medsci, Inc.*; pp. 1-50, dated Aug. 6, 2021.
Inter Partes Review No. IPR2020-00175; Judgement Final Written Decision of U.S. Pat. No. 10,188,299; *Apple, Inc.* v. *Omni Medsci, Inc.*; pp. 1-71; dated Jun. 14, 2021.
Claim Construction Memorandum Opinion and Order. Case No. 2:18-CV-000134-RWS (Jun. 24, 2019).
Claim Construction Memorandum Opinion and Order. Case No. 2:18-CV-000429-RWS (Aug. 14, 2019).
Declaration of Brian W. Anthony, PhD regarding U.S. Pat. No. 10,098,546 filed in IPR2020-00029 (Oct. 17, 2019).
Declaration of Brian W. Anthony, PhD regarding U.S. Pat. No. 9,651,533 filed in IPR2019-00913 (Apr. 10, 2019).
Declaration of Brian W. Anthony, PhD regarding U.S. Pat. No. 9,651,533 filed in IPR2019-00916 (Apr. 10, 2019).
Declaration of Brian W. Anthony, PhD regarding U.S. Pat. No. 9,757,040 filed in IPR2019-00910 (Apr. 10, 2019).
Declaration of Brian W. Anthony, PhD regarding U.S. Pat. No. 9,757,040 filed in IPR2019-00917 (Apr. 10, 2019).
Declaration of Brian W. Anthony, PhD regarding U.S. Pat. No. 9,861,286 filed in IPR2019-00911 (Apr. 10, 2019).
Declaration of Brian W. Anthony, PhD regarding U.S. Pat. No. 9,861,286 filed in IPR2019-00914 (Apr. 10, 2019).
Declaration of Brian W. Anthony, PhD regarding U.S. Pat. No. 9,885,698 filed in IPR2019-00912 (Apr. 10, 2019).
Declaration of Brian W. Anthony, PhD regarding U.S. Pat. No. 9,885,698 filed in IPR2019-00915 (Apr. 10, 2019).
File History for U.S. Pat. No. 10,098,546, issued Oct. 16, 2018.
Inter Partes Review No. IPR2020-00029; Petition for Inter Partes Review of U.S. Pat. No. 10,098,546; *Apple Inc.* v. *Omni Medsci, Inc.*; dated Oct. 17, 2019.
Lister et al., Optical properties of human skin (Journal of Biomedical Optics 2012).
Mark Nelson & Jean-Loup Gailly, The Data Compression Book (Cary Sullivan et al. eds.) (2nd ed. 1996).
Newton, H., Newton's Telecom Dictionary (18th ed. 2002).
Order, *Omni MedSci, Inc.* v. *Apple Inc.*, No. 2:18-cv-134-RWS in the United States District Court for the Eastern District of Texas Marshall Division (Aug. 16, 2019), ECF No. 283.
Proof of Service of Summons in *Omni MedSci, Inc.* v. *Apple Inc.*, No. 2:18-cv-429 (E.D. Tex.).
Aaviksoo, J., et al., "Observation of optical precursors at pulse propagation in GaAs", Physical Review A, vol. 44, No. 9, Nov. 1, 1991, pp. R5353-R5356.
Abeeluck, Akheelesh K., et al., "Continuous-wave pumping in the anomalous- and normal dispersion regimes of nonlinear fibers for supercontinuum generaffon", Optics Letters, vol. 30, No. 1, Jan. 1, 2005, pp. 61-63.
Absorption Coefficient and Penetration Depth, The Science of Solar, available at https://photon.libretexts.org/The_Science_of_ Solar/Solar Basics/C._Semico-nductors_and_Solar_Interactions/III._Absorption_of_Light_and_Generation/1.-Absorption_Coefficient_and_Penetration_Depth (Last Updated Nov. 3, 2018).
Akbari, H. K. Uto, Y. Kosugi, K. Kojima, N. Tanaka, "Cancer detection using infrared hyperspectral imaging," Cancer Science, vol. 102, No. 4, pp. 852-857 (Apr. 2011).
Amended Joint Claim Construction and Prehearing Statement filed in Case No. 2:18-cv-134-RWS (Dkt. #102) (Jan. 11, 2019).
Analysis of Edible Oils Using FT-NIR Spectroscopy. Bruker Optics, www.azom.com/article.aspx?ArticleID=5981, Mar. 10, 2012.
Andreoli, G. B. Bulgarelli, B. Hosgood, D. Tarchi, "Hyperspectral analysis of oil and oil-impacted soils for remote sensing purposes," Institute for the Protection and Security of the Citizen, European Commission Joint Research Centre, EUR 22739 EN (Mar. 2007).
Apple Inc.'s Preliminary Claim Constructions and Extrinsic Evidence Pursuant to Patent Local Rule 4-2 served in Case No. 2:18-cv-134-RWS (Nov. 1, 2018).
Application Brief the role of infrared microprobe analysis in forensic drug analysis, www.smithsdetection.com, Jun. 27, 2005.
Aris, Ishak Bin, "An Internet-Based Blood Pressure Monitoring System for Patients"; Journal of Telemedicine and Telecare 2001; pp. 51-53.
Arnold, T., M. De Biasio, R. Leitner, "Near-Infrared Imaging Spectroscopy for Counterfeit Drug Detection," Next Generation Spectroscopic Technologies IV, edited by M. A. Druy, R.A. Crocombe, Proceedings of SPIE, vol. 8032, 80320Y-1 to 7, (2011).
Asada et al., Mobile Monitoring with Wearable Photoplethysmographic Biosensors, Technical and Clinical Aspects of a Ring Sensor for Ambulatory, Telemetric, Continuous Health Monitoring in the Field, in the Hospital, and in the Home, IEEE Engineering in Medicine and Biology Magazine, (May/Jun. 2003) 13 pages.
Asada et al., The MIT Ring: History, Technology, and Challenges of Wearable Health Monitoring, MIT Industrial Liaison Program (2010) R&D Conference, MA, 72 pages.
Asada; Charts 1-3: Asada-533; U.S. Pat. No. 9,651,533 vs. Asada; *Omni MedSci, Inc.* v. *Apple Inc.*, pp. 1-188; May 22, 2019.
Asare et al., Analysis of Multi-Spectral Photoplethysmograph Biosensors, Proc. SPIE 8801, Novel Biophotonic Techniques and Applications II, 880106 (Jun. 2013), European Conferences on Biomedical Optics, Munich, Germany, 7 pages.
Asobe, Masaki, "Nonlinear Optical Properties of Chalcogenide Glass Fibers and Their Application to All-Optical Switching", Optical Fiber Technology, vol. 3, Article No. OF970214, 1997, pp. 142-148.
Asobe, Masaki, et al., "Third-order nonlinear spectroscopy in As2S3 chalcogenide glass fibers", J. Appl. Phys. 77 (11), Jun. 1, 1995, pp. 5518-5523.
Avdokhin, A. V., et al., "Continuous-wave, high-power, Raman continuum generation in holey fibers", Optics Letters, vol. 28, No. 15, Aug. 1, 2003, pp. 1353-1355.
Ayvaz, Huseyin, et al. "Application of infrared microspectroscopy and chemometric analysis for screening the acrylamide content in potato chips." Analytical Methods 5.8 (2013): 2020-2027.
B. Rigas, P.T.T. Wong, "Human Colon Adenocarcinoma Cell Lines Display Infrared Spectroscopic Features," Cancer Research, Jan. 1, 1992, pp. 84-88.
Barolet, Daniel, Light-Emitting Diodes (LEDs) in Dermatology, Seminars in Cutaneous Medicine and Surgery 27:227-238 (2008).

(56) References Cited

OTHER PUBLICATIONS

Bashkatov, A., et al., Optical properties of human skin, subcutaneous and mucous tissues in the wavelength range from 400 to 2000 nm, Journal of Physics D: Applied Physics 38 (2005) 2543-2555.
Baum P., et al., Strategic Intelligence Monitor on Personal Health Systems, Phase 2: Market Developments—Remote Patient Monitoring and Treatment, Telecare, Fitness/Wellness and mHealth, JRC Scientific and Policy Reports of European Commission (2013).
Beck, Mattias, et al., "Continuous Wave Operation of a Mid-Infrared Semiconductor Laser at Room Temperature," Science vol. 295, www.sciencemag.org, Jan. 11, 2002, pp. 301-305.
Belikov, A. V., A. V. Skripnik, K.V. Shatilova, "Study of the dynamics of the absorption spectra of human tooth enamel and dentine under heating and ablation by submillisecond pulse radiation of an erbium laser with a generation wavelength of 2.79 um," Optics and Spectroscopy, vol. 109, No. 2, pp. 211-216 (2010).
Bellisola, G. C. Sorio, "Infrared spectroscopy and microscopy in cancer research and diagnosis," American Journal of Cancer Research, vol. 2, No. 1, pp. 1-21 (2012).
Bizheva, K, et al., "Compact, broad-bandwidth fiberlaserforsub-2-pm axial resolution optical coherence tomography in the 1300-nm wavelength region," Optics Letters, vol. 28, No. 9, May 1, 2003, pp. 707-709.
Blank, T.B., T.L. Ruchti, A.D. Lorenz, S.L. Monfre, M.R. Makarewicz, M. Mattu, K.H. Hazen, "Clinical results from a non-invasive blood glucose monitor," Optical Diagnostics and Sensing of Biological Fluids and Glucose and Cholesterol Monitoring II, A. V. Priezzhev and G.L. Cote, Editors, Proceedings of SPIE, vol. 4624, pp. 1019 (2002).
Boppart, Stephen A., et al., "Imaging developing neural morphology using optical coherence tomography", Journal of Neuroscience Methods 70, 1996, pp. 65-72.
Boppart, Stephen A., et al., "Noninvasive assessment of the developing Xenopus cardiovascular system using optical coherence tomography", Prec. Natl. Acad. Sci. USA, vol. 94, Apr. 1997, pp. 4256-4261.
Borlinghaus, R., "Colours Count: how the challenge of fluorescence was solved in confocal microscopy," in Modern Research and Educational Topics in Microscopy, A. Mendez-Vilas and J. Diaz, eds, pp. 890-899, Formatex (2007).
Borlinghaus, R., "The White Confocal: Continuous Spectral Tuning in Excitation and Emission," in Optical Fluorescence Microscopy, A. Diaspro (Ed), Chapter 2, pp. 37-54, ISBN 978-3-642-15174-3, Springer-Verlag, Berlin (2011).
Borlinghaus, R.T., L. Kuschel, "White Light Laser: The Ultimate Source for Confocal Microscopy," http://www.leica-microsystems.com/science-lab/white-light-laser (Jun. 27, 2012).
Borrelli, N. F., et al., "Resonant and non-resonant effects in photonic glasses", Journal of Non-Crystalline Solids 185, 1995, pp. 109-122.
Boult, Maggi, et al., "Percutaneous Endoscopic Laser Discectomy", Systematic Review, Aust. N.Z.J. Surg., vol. 70, Apr. 7, 2000, pp. 475-479.
Boult, Maggi, et al., "Systematic Review of Percutaneous Endoscopic Laser Discectomy: Update and Re-appraisal", Australian Safety and Efficacy Register of New Interventional Procedures—Surgical Report No. 5, Feb. 2000, 49 pages.
Branche et al., Signal Quality and Power Consumption of a New Prototype Reflectance Pulse Oximeter Sensor, Proceedings of the IEEE 31st Annual Northeast Bioengineering Conference (2005), Hoboken, NJ, 2 pages.
Bronzino, Joseph D.; "The Biomedical Engineering Handbook", (1995).
Büning-Pfaue, Hans. "Analysis of water in food by near infrared spectroscopy." Food Chemistry 82.1 (2003): 107-115.
Burmen, M. P. Usenik, A. Fidler, F. Pernus, B. Likar, "A construction of standardized near infrared hyper-spectral teeth database—a first step in the development of reliable diagnostic tool for quantification and early detection of caries," Lasers in Dentistry XVII, edited by P. Rechmann, D. Fried, Proceedings of SPIE, vol. 7884, Paper 78840E (2011).
Busse, Lynda E., et al., "Design Parameters for Fluoride Multimode Fibers", Journal of Lightwave Technology, vol. 9, No. 7, Jul. 1991, pp. 828-831.
Buttussi, F., et al., MOPET: A context-aware and user-adaptive wearable system for fitness training, Artificial Intelligence in Medicine (2008) 42, 153-163.
Cai et al., Implementation of a Wireless Pulse Oximeter Based on Wrist Band Sensor, College of Biological Science and Medical Engineering Southeast University, (2010) 3rd International Conference on Biomedical Engineering and Informatics, Nanjing, China, 4 pages.
Camacho, Nancy P., et al., "FTIR Microscopic Imaging of Collagen and Proteoglycan in Bovine Cartilage," Biopolymers (Biospectroscopy), vol. 62, 2001, pp. 1-8.
Cardinal, T., et al., "Non-linear optical properties of chalcogenide glasses in the system As—S—Se", Journal of Non-Crystalline Solids 256 & 257, 1999, pp. 353-360.
Champert, Pierre-Alain, et al., "White-light supercontinuum generation in normally dispersive optical fiber using original multi-wavelength pumping system", Optics Express, vol. 12, No. 19, Sep. 20, 2004, pp. 4366-4371.
Choi, Joon Y., et al., "Thermal, Mechanical, Optical, and Morphologic Changes in Bovine Nucleus Pulposus Induced by Nd: YAG (λ=1.32 um) Laser Irradiation", Lasers in Surgery and Medicine, vol. 28, 2001, pp. 248-254.
Choi, Seung-Ho, et al., "Observation of Optical Precursors in Water", Physical Review Letters, vol. 92, No. 19, May 14, 2004, pp. 193903-1-193903-.3.
Chung, S., D. Fried, M. Staninec, C.L. Darling, "Multispectral near-IR reflectance and transillumination imaging of teeth," Biomedical Optics Express, vol. 2, No. 10, pp. 2804-2814 (2011).
Chung, S., D. Fried, M. Staninec, C.L. Darling, "Near infrared imaging of teeth at wavelengths between 1200 and 1600nm," Proceedings of the Society of Photo Optical Instrument Engineering, paper 7884 (2011).
Clark, R.N., J.M. Curchin, T. M. Hoefen, G.A. Swayze, "Reflectance Spectroscopy of organic compounds: 1. Alkanes," Journal of Geophysical Research, vol. 114, pp. E03001 1 to E03001 19, (2009).
Coen, Stephane, et al., "Supercontinuum generation by stimulated Raman scattering and parametric four-wave mixing in photonic crystal fibers", J. Opt. Soc. Am. B, vol. 19, No. 4, Apr. 2002, pp. 753-764.
Compendium of Chemical Terminology Gold Book, International Union of Pure and Applied Chemistry, Version 2.3.3 (Feb. 24, 2014).
Computer Motion, Inc. "HERMES™ O.R. Control Center—510(k) Summary of Safety and Effectiveness," Oct. 11, 2002, 5 pages.
Computer Motion, Inc., "501(k) Summary-ZEUS® MicroWrist™M Surgical System and Accessories," Sep. 24, 2002, 6 pages.
Curriculum Vitae of Brian W. Anthony, PhD (Nov. 18, 2018).
D'Amico, Anthony V., et al., "Optical Coherence Tomography as a Method for Identifying Benign and Malignant Microscopic Structures in the Prostate Gland", Basic Science, Urology 55 (5), 2000, pp. 783-787.
De Boer, Johannes F., et al., "Determination of the depth-resolved Stokes parameters of light backscattered from turbid media by use of polarization-sensitive optical coherence omography", Optics Letters, vol. 24, No. 5; Mar. 1, 1999, pp. 300-302.
De Boer, Johannes F., et al., "Imaging thermally damaged tissue by polarization sensitive optical coherence tomography", Optics Express 212, vol. 3, No. 6, Sep. 14, 1998, pp. 212-218.
Demircan, Ayhan, et al., "Supercontinuum generation by the modulation instability", Optics Communications 244, 2005, pp. 181-185.
Desthieux, B., et al., "111 ?W (0. 5 mJ) pulse amplification at 1.5 um using a gated cascade of three erbium-doped fiber amplifiers," Appl. Phys. Lett. vol. 63, Aug. 2, 1993, pp. 586-588.
District Court Preliminary Claim Constructions in Case No. 2:18-cv-134-RWS from Court at Markman hearing.
Dr. Mohammed Islam, Faculty Profile, University of Michigan, College of Engineering (available at https://islam.engin.umich.edu) (2019 The Regents of the University of Michigan).

(56) References Cited

OTHER PUBLICATIONS

Drexler, C., Hirmer, M., Danilov, S., Giglberger, S., Putzger, J., Niklas, A., Jager, A., Hiller, K., Loffler, S., Schmalz, G., Redlich, B., Schulz, I., Monkman, G., Ganichev, S. "Infrared spectroscopy for clinical diagnosis of dental pulp vitality." Infrared, Millimeter, and Terahertz Waves (IRMMW-THz), 2012 37th International Conference on. IEEE (2012).
Drexler, Wolfgang, "Ultrahigh-resolution optical coherence tomography", Journal of Biomedical Optics, vol. 9, No. 1, Jan./Feb. 2004, pp. 47-74.
Dubois, A., et al., "Three-dimensional cellular-level imaging using full-field optical coherence tomography", Physics in Medicine and Biology, Phys. Med. Biol. 49, 2004, pp. 1227-1234.
Dudley, John M., et al., "Supercontinuum generation in air-silica microstructured fibers with nanosecond and femtosecond pulse pumping", J. Opt. Soc. Am. B, vol. 19, No. 4, Apr. 2002, pp. 765-771.
Edwards, Glenn S., et al., "Advantage of the Mark-III FEL for biophysical research and biomedical applications", J. Synchrotron Rad. vol. 10, 2003, pp. 354-357.
Edwards, Glenn, et al., Tissue ablation by a free-electron laser tuned to the amide II band, Nature, vol. 371, Sep. 29, 1994, pp. 416-419.
Embedded-Lab, Introducing Easy Pulse: A DIY Photoplethysmographic Sensor for Measuring Hearth Rate, posted on www.Embedded-Lab.com Sep. 12, 2012, by R-B, 10 pages.
Enejder, A.M.K., T.G. Scecina, J. Oh, M. Hunter, W.C. Shih, S. Sasic, G.L. Horowitz, M.S. Feld, "Raman spectroscopy for noninvasive glucose measurements," Journal of Biomedical Optics, vol. 10, No. 3, 031114 (2005).
Evers, D.J., B.H.W. Hendriks, G.W. Lucassen, T.J.M. Ruers, "Optical spectroscopy: current advances and future applications in cancer diagnosis and therapy," Future Oncology, vol. 8, No. 3, pp. 307-320 (2012).
Evers, D.J., R. Nachabe, H.M. Klomp, J.W. van Sandick, M.W. Wouters, G. W. Lucassen, B.H.W. Hendriks, J. Wesseling, T.J.M. Ruers, "Diffuse reflectance spectroscopy: a new guidance tool for improvement of biopsy procedures in lung malignancies," Clinical Lung Cancer, article identifier 10.1016/j.clc.2012.02.001, 8 pages, (2012).
Excerpt from Claim Construction Markman Hearing Transcript filed in Case No. 2:18-cv-134-RWS (Feb. 6, 2019) vol. 1, pp. 1, 2, 21, 22.
Excerpts from Merriam-Webster's Collegiate Dictionary Eleventh Edition (2011).
Excerpts from the American Heritage Dictionary, 5th Edition (Jul. 2012).
Extended European Search Report for European Application No. 13867874.3 dated Jul. 15, 2016.
Extended European Search Report for European Application No. 13867892.5 dated Jul. 22, 2016.
Extended European Search Report for European Application No. 17155541.0 dated May 24, 2017.
Extended European Search Report for European Application No. 17156625.0 dated Mar. 20, 2017.
F. Kuhn, K. Oppermann, B. Horig, "Hydrocarbon Index-and algorithm for hyperspectral detection of hydrocarbons," International Journal of Remote Sensing, vol. 25, No. 12, pp. 2467-2473 (Jun. 20, 2004).
Falk, Peter, et al., "Supercontinuum generation in a photonic crystal fiber with two zero-dispersion wavelengths tapered to normal dispersion at all wavelengths", Optics Express, vol. 13, No. 19, Sep. 19, 2005, pp. 7535-7540.
Fantini, S. A. Sassaroli, "Near-infrared optical mammography for breast cancer detection with intrinsic contrast," Annals of Biomedical Engineering, vol. 40, No. 2, pp. 398-407 (Feb. 2012).
Faralli, S., et al., "Impact of Double Rayleigh Scattering Noise in Distributed Higher Order Raman Pumping Schemes", IEEE Photonics Technology Letters, vol. 15, No. 6, Jun. 2003, pp. 804-806.
Fedotova, O., et al., "Supercontinuum generation in planar rib waveguides enabled by anomalous dispersion", Optics Express, vol. 14, No. 4, Feb. 20, 2006, pp. 1512-1517.
File History for U.S. Pat. No. 9,651,533 issued May 16, 2017.
File History for U.S. Pat. No. 9,757,040 issued Sep. 12, 2017.
File History for U.S. Pat. No. 9,861,286 issued Jan. 9, 2018.
File History for U.S. Pat. No. 9,885,698 issued Feb. 6, 2018.
Final Office Action dated Oct. 21, 2016 for U.S. Appl. No. 14/875,709.
Fried, D. M. Staninec, C.L. Darling, "Near-infrared imaging of dental decay at 1310nm," Journal of Laser Dentistry, vol. 18, No. 1, pp. 8-16 (2010).
G. Edwards, et al., "Comparison of OPA and Mark-III FEL for Tissue Ablation at 6.45 Microns," Department of Physics and Free Electron Laser Laboratory, Duke University, 2002, 7 pages.
G.S. Edwards et al., "Free-electron-laser-based biophysical and biomedical instrumentation," American Institute of Physics, vol. 74, No. 7, Jul. 2003, pp. 3207-3245.
Galvis-Sánchez, Andrea C., et al. "Fourier transform near-infrared spectroscopy application for sea salt quality evaluation." Journal of agricultural and food chemistry 59.20 (2011): 11109-11116.
GE Healthcare, GE Ohmeda TufSat Oximeter for Clinicians on the go, (2012), A General Electric Co., www.gehealthcare.com, GE, Finland, 4 pages.
GE Healthcare, TuffSat User's Guide and Service Manual Electromagnetic Compatibility (EMC), (Mar. 2005) Helsinki, Finland, 43 pages.
Genty, G., et al., "Enhanced bandwidth of supercontinuum generated m microstructured fibers", Optics Express, vol. 12, No. 15, Jul. 26, 2004, pp. 3471-3480.
Genty, G., et al., "Supercontinuum generation in large mode-area microstructured fibers", Optics Express, vol. 13, No. 21, Oct. 17, 2005, pp. 8625-8633.
Glenn Edwards, "Biomedical and potential clinical applications for pulsed lasers operating near 6.45 um," Society of Photo-Optical Instrumentation Engineers, 1995, 2 pages.
H. Harry Asada et al.; Mobile Monitoring With Wearable Photoplethysmographic Biosensors; IEEE Engineering in Medicine and Biology Magazine, Jun. 2003; 13 pps.
Haase, Norbert U. "Prediction of potato processing quality by near infrared reflectance spectroscopy of ground raw tubers" Journal of Near Infrared Spectroscopy 19.1 (2011): 37-45.
Hafez, M. I., et al., "The Effect of Irrigation on Peak Temperatures in Nerve Root, Dura, and Intervertebral Disc During Laser-Assisted Foraminoplasty", Lasers in Surgery and Medicine, vol. 29, 2001, pp. 33-37.
Hagen, C. L., et al., "Generation of a Continuum Extending to the Midinfrared by Pumping ZBLAN Fiber With an Ultrafast 1550-nm Source", IEEE Photonics Technology Letters, vol. 18, No. 1, Jan. 1, 2006, pp. 91-93.
Hamilton, James D., et al., "High Frequency Optoacoustic Arrays Using Etalon Detection", IEEE Transactions on Ultrasonics, Ferroelectrics, and Frequency Control, vol. 47, No. 1, Jan. 2000, pp. 160-169.
Hamilton, James D., et al., "High Frequency Ultrasound Imaging Using an Active Optical Detector", IEEE Transactions on Ultrasonics, Ferroelectrics, and Frequency Control, vol. 45, No. 3, May 1998, pp. 719-727.
Hamilton, James D., et al., "High Frequency Ultrasound Imaging with Optical Arrays", IEEE Transactions on Ultrasonics, Ferroelectrics, and Frequency Control, vol. 45, No. 1, Jan. 1998, pp. 216-235.
Harbold, J. M., et al., "Highly nonlinear As-S-Se glasses for all-optical switching", Optics Letters, vol. 27, No. 2, Jan. 15, 2002, pp. 119-121.
Harbold, Jeffrey M., et al., "Highly Nonlinear Ge-As-Se and Ge-As-S-Se Glasses for All-Optical Switching", IEEE Photonics Technology Letters, vol. 14, No. 6, Jun. 2002, pp. 822-824.
Harman-Boehm, I. A. Gal, A.M. Raykhman, J.D. Zahn, E. Naidis, Y. Mayzel, "Noninvasive glucose monitoring: a novel approach," Journal of Diabetes Science and Technology, vol. 3, No. 2 pp. 253-260 (2009).

(56) References Cited

OTHER PUBLICATIONS

Harrington, James A., "Infrared Fiber Optics", OSA Handbook, vol. III, white paper, to be published by McGraw Hill, Undated, 13 pages.
Hartmann, R., and H. Büning-Pfaue. "NIR determination of potato constituents." Potato research 41.4 (1998): 327-334.
Hazen, K.H., M.A. Arnold, G.W. Small, "Measurement of glucose and other analytes in undiluted human serum with near-infrared transmission spectroscopy," Analytica Chimica Acta, vol. 371, pp. 255-267 (1998).
Herranz, M., A. Ruibal, "Optical imaging in breast cancer diagnosis: the next evolution," Journal of Oncology, vol. 2012, article ID 863747, 10 pages, (2012).
Hilligsoe, Karen Marie, et al., "Supercontinuum generation in a photonic crystal fiber with two zero dispersion wavelengths", Optics Express, vol. 12, No. 6, Mar. 22, 2004, pp. 1045-1054.
Hirmer, Marion, Danilov, Sergey, Giglberger, Stephan, Putzger, Jurgen, Niklas, Andreas, Jager, Andreas, Hiller, Karl-Anton, Loffler, Susanne, Schmalz, Gottfried, Redlich, Britta, Schulz, Irene, Monkman, Gareth, Ganichev, Sergey. "Spectroscopic Study of Human Teeth and Blood from Visible to Terahertz Frequencies for Clinical Diagnosis of Dental Pulp Vitality." Journal of Infrared, Millimeter, and Terahertz Waves 33.3 (2012): 366-375.
Hirosawa, N. Y. Sakamoto, H. Katayama, S. Tonooka, K. Yano, "In vivo investigation of progressive alternations in rat mammary gland tumors by near-infrared spectroscopy," Analytical Biochemistry, vol. 305, pp. 156-165 (2002).
Hori, Takashi, et al., "Experimental and numerical analysis of widely broadened supercontinuum generation in highly nonlinear dispersion-shifted fiber with a femtosecond pulse", J. Opt. Soc. Am. B, vol. 21, No. 11, Nov. 2004, pp. 1969-1980.
Hori, Takashi, et al., "Flatly broadened, wideband and low noise supercontinuum generation in highly nonlinear hybrid fiber", Optics Express, vol. 12, No. 2, Jan. 26, 2004, pp. 317-324.
Humphreys et al., Noncontact Simultaneous Dual Wavelength Photoplethysmography: A Further Step Toward Noncontact Pulse Oximetry, (2007) Review of Scientific Instruments 78, 044304, American Institute of Physics, 6 pages.
Husakou, Anton V., et al., "Supercontinuum generation, four-wave mixing, and fission of higher- order solitons in photonic-crystal fibers", J. Opt. Soc. Am. B, vol. 19, No. 9, Sep. 2002, pp. 2171-2182.
I.B. Ads, A.A.E. Wagie, N.B. Mariun, A.B.E. Jammal, "An Internet-based blood pressure monitoring system for patients," Journal of Telemedicine and Telecare, 2001, pp. 51-53.
Iatridis, James C., et al., "Is the Nucleus Pulposus a Solid or a Fluid? Mechanical Behaviors of the Nucleus Pulposus of the Human Intervertebral Disc", Spine, vol. 21(10), May 15, 1996, pp. 1174-1184.
Inoue, H., et al., "Computer simulation of the vibrational spectra and properties of fluoride glasses based on ZrF4", Journal of Non-Crystalline Solids, vol. 161, 1993, pp. 118-122.
Inter Partes Review No. IPR2019-00910; Petition for Inter Partes Review of U.S. Pat. No. 9,757,040; *Apple Inc.* v. *Omni Medsci, Inc.*; pp. 1-96; dated Apr. 10, 2019.
Inter Partes Review No. IPR2019-00911; Petition for Inter Partes Review of U.S. Pat. No. 9,861,286; *Apple Inc.* v. *Omni Medsci, Inc.*; pp. 1-83; dated Apr. 10, 2019.
Inter Partes Review No. IPR2019-00912; Petition for Inter Partes Review of U.S. Pat. No. 9,885,698; *Apple Inc.* v. *Omni Medsci, Inc.*; pp. 1-94; dated Apr. 10, 2019.
Inter Partes Review No. IPR2019-00913; Petition for Inter Partes Review of U.S. Pat. No. 9,651,533; *Apple Inc.* v. *Omni Medsci, Inc.*; pp. 1-96; dated Apr. 10, 2019.
Inter Partes Review No. IPR2019-00914; Petition for Inter Partes Review of U.S. Pat. No. 9,861,286; *Apple Inc.* v. *Omni Medsci, Inc.*; pp. 1-90; dated Apr. 10, 2019.
Inter Partes Review No. IPR2019-00915; Petition for Inter Partes Review of U.S. Pat. No. 9,885,698; *Apple Inc.* v. *Omni Medsci, Inc.*; pp. 1-91; dated Apr. 10, 2019.
Inter Partes Review No. IPR2019-00916; Petition for Inter Partes Review of U.S. Pat. No. 9,651,533; *Apple Inc.* v. *Omni Medsci, Inc.*; pp. 1-90; dated Apr. 10, 2019.
Inter Partes Review No. IPR2019-00917; Petition for Inter Partes Review of U.S. Pat. No. 9,757,040; *Apple Inc.* v. *Omni Medsci, Inc.*; pp. 1-93; dated Apr. 10, 2019.
International Preliminary Report on Patentability for International Application No. PCT/US2013/07567 dated Jul. 9, 2015.
International Preliminary Report on Patentability for International Application No. PCT/US2013/075700 dated Jul. 9, 2015.
International Preliminary Report on Patentability for International Application No. PCT/US2013/075736 dated Jul. 9, 2015.
International Search Report and Written Opinion for International Application No. PCT/US2013/075700 dated Apr. 24, 2014.
International Search Report and Written Opinion for International Application No. PCT/US2013/075736 dated Apr. 7, 2014.
International Search Report and Written Opinion for International Application No. PCT/US2013/075767 dated Oct. 14, 2014.
Islam, M. N., et al., "Broad bandwidths from frequency-shifting solitons in fibers", Optics Letters, vol. 14, No. 7, Apr. 1, 1989, pp. 370-372.
Islam, M. N., et al., "Femtosecond distributed soliton spectrum in fibers", J. Opt. Soc. Am. B, vol. 6, No. 6, Jun. 1989, pp. 1149-1158.
Istepanian, Robert H., "The Comparative Performance of Mobile Telemedical Systems based on the IS-54 and GSM Cellular Telephone Standards"; Journal of Telemedicine and Telecare 1999; pp. 97-104.
J. Sanghera, I. Aggarwal, "IR Fiber Optics at NRL," undated, 10 pages.
J. Sanghera, L.B. Shaw, I.D. Aggarwal, "Applications of chalcogenide glass optical fibers," Academic of Science, 2003, pp. 1-11.
J.G. Webster; Design of Pulse Oximeters; Medical Science Series; Taylor & Francis Group; CRC Press; Oct. 23, 1997; 260 pps.
Jackson, Stuart D., et al., "Theory and numerical simulation of nth-order cascaded Raman fiber lasers", J. Opt. Soc. Am. B, vol. 18, No. 9, Sep. 2001, pp. 1297-1306.
Jarman, Richard H., "Novel optical fiber lasers", Current Opinion in Solid State and Materials Science, 1996, pp. 199-203.
Jasco Application Note No. 200DR0188-E, "Rapid Identification of illegal drug using NIR (identification of MDMA tablet)", Sep. 4, 2008.
Jung et al., Design of a Low-Power Consumption Wearable Reflectance Pulse Oximetry for Ubiquitous Healthcare System, International Conference on Control, Automation and Systems (Oct. 2008), in COEX, Seoul, Korea, 4 pages.
K.M. Joos, et al. "Optic Nerve Sheath Fenestration with a Novel Wavelength Produced by the Free Electron Laser (FEL)," Lasers in Surgery and Medicine, 27: 2000,191-205.
Karlsson, L. "Caries detection methods based on changes in optical properties between healthy and carious tissue," International Journal of Dentistry, vol. 2010, Article ID 270729, 9 pages (2010).
Kays, Sandra E., William R. Windham, and Franklin E. Barton. "Prediction of total dietary fiber in cereal products using near-infrared reflectance spectroscopy." Journal of Agricultural and food chemistry 44.8 (1996): 2266-2271.
Kim-K.D., G.S. Son, S.S. Lim, S.S. Lee, "Measurement of glucose level exploiting a relative optical absorption at discrete probe wavelengths," Japanese Journal of Applied Physics, vol. 48, 077001 (2009).
Kobtsev, Serguei M., et al., "Modelling of high-power supercontinuum generation in highly nonlinear, dispersion shifted fibers at CW pump", Optics Express, vol. 13, No. 18, Sep. 5, 2005, pp. 6912-6918.
Konderpati, V.R., H.M. Heise, J. Backhaus, "Recent applications of near-infrared spectroscopy in cancer diagnosis and therapy," Annals of Bioanalytic Chemistry, vol. 390, pp. 125-139 (2008).
Kowalevicz, Andrew M., et al., "Ultrahigh resolution optical coherence tomography using a superluminescent light source" Optics Express 349, vol. 10, No. 7, Apr. 8, 2002, pp. 349-353.
Krantz, M., et al., The mobile fitness coach: Towards individualized skill assessment using personalized mobile devices, Pervasive and Mobile Computing (Jun. 2012).

(56) References Cited

OTHER PUBLICATIONS

Kumar, V.V. Ravi Kanth, et al., "Extruded soft glass photonic crystal fiber for ultrabroad supercontinuum generation", Optics Express, vol. 10, No. 25, Dec. 16, 2002, pp. 1520-1525.
Kurylyak et al., Smartphone-Based Photoplethysmogram Measurement, Department of Electronics, Computer and System Sciences, (2012) River Publishers, University of Calabria, Italy, 30 pages.
Kutz, J. Nathan, et al., Enhanced Supercontinuum Generation through Dispersion-Management, Optics Express, vol. 13, No. 11, May 30, 2005, pp. 3989-3998.
Lee, Ju Han, et al., "Continuous-wave supercontinuum laser based on an erbium-doped fiber ring cavity incorporating a highly non-linear optical fiber", Optics Letters, vol. 30, No. 19, Oct. 1, 2005, pp. 2599-2601.
Lee, Ju Han, et al., "Experimental performance comparison for various continuous-wave supercontinuum schemes: ring cavity and single pass structures", Optics Express, vol. 13, No. 13, Jun. 27, 2005, pp. 4848-4853.
Leff, D.R., O.J. Warren, L.C. Enfield, A. Gibson, T. Athanasion, D.K. Patten, J. Hebden, G.Z. Yang, A. Darzi, "Diffuse optical imaging of the healthy and diseased breast: a systematic review," Breast Cancer Research Treatment, vol. 108, pp. 9-22 (2008).
Leon-Saval, S. G., et al., "Supercontinuum generation in submicron fibre waveguides", Optics Express, vol. 12, No. 13, Jun. 28, 2004, pp. 2864-2869.
Li et al., A Wireless Reflective Pulse Oximeter with Digital Baseline Control for Unfiltered Photoplethysmograms, (Jun. 2012) IEEE Transactions on Biomedical Circuits and Systems, vol. 6, No. 3, 10 pages.
Li Xingde, et al., "Imaging needle for optical coherence tomography", Optics Letters, vol. 25, No. 20, Oct. 15, 2000, pp. 1520-1522.
Lisogurski; Charts 1-3: Lisogurski-533; U.S. Pat. No. 9,651,533 vs. Lisogurski; Omni MedSci, Inc. v. Apple Inc., pp. 1-84; May 22, 2019.
Lucas, Jacques, "Infrared glasses", Current Opinion in Solid State & Materials Science 4, 1999. pp. 181-187.
Luo et al., A Non-Invasive Dual-Channel Oximeter Based on Near-Infrared Spectroscopy (NIRS), Biophotonics Lab, Center of Advanced Research in Photonics (2007), The Chinese University of Hong Kong, China, 2 pages.
Lussi, A., R. Hibst, R. Paulus, "Diagnodent: An optical method for caries detection," Journal of Dental Research, vol. 83, special issue C, pp. C80-C83 (2004).
M. Kumar, M.N. Islam, F.L. Terry, M.J. Freeman, A. Chan, M. Neelakandan, T. Manzur, "Stand-off detection of solid targets with diffuse reflection spectroscopy using a high-power mid-infrared supercontinuum source," Applied Optics, vol. 51, No. 15, pp. 2794-2807 (May 20, 2012).
Maia, A., L. Karlsson, W. Margulis, A. Gomes, "Evaluation of two imaging techniques: near- infrared transillumination and dental radiographs for the detection of early approximal enamel canes," Dentomaxillofacial Radiology, vol. 40, pp. 429-433 (2011).
Malin, S.F., T.L. Ruchti, T.B. Blank, S.N. Thennadil, S.L. Monfre, "Noninvasive prediction of glucose by near-infrared diffuse reflectance spectroscopy," Clinical Chemistry, vol. 45, No. 9, pp. 1651-1658 (1999).
Marbach, R., T. Koschinsky, F.A. Gries, H.M. Heise, "Noninvasive blood glucose assay by near- infrared diffuse reflectance spectroscopy of the human inner lip," Applied Spectroscopy, vol. 47, No. 7, pp. 875-881 (1993).
Mccoy, R.M., J.G. Blake, K.L. Andrews, "Detecting hydrocarbon microseepage," Oil and Gas Journal, pp. 40-45 (May 28, 2001).
Mehrotra, R. A. Gupta, A. Kaushik, N. Prakash, H. Kandpal, "Infrared spectroscopic analysis of tumor pathology," Indian Journal of Experimental Biology, vol. 45, pp. 71-76 (Jan. 2007).
Mendelson et al., A Wearable Reflectance Pulse Oximeter for Remote Physiological Monitoring, (Aug./Sep. 2006) Proceedings of the 28th IEEE Embs Annual International Conference New York City, Ny, 4 pages.
Michaels, C.A., T. Masiello, p. M. Chu, "Fourier transform spectrometry with a near-infrared supercontinuum source," Applied Spectroscopy, vol. 63, No. 5, pp. 538-543 (2009).
Mizunami, Toru, et al., "Gain saturation characteristics of Raman amplification in silica and fluoride glass optical fibers", Optics Communications 97, 1993, pp. 74-78.
Moon, Sucbei, et al., "Generation of octave-spanning supercontinuum with 1550-nm amplified diode-laser pulses and a dispersion-shifted fiber", Optics Express, vol. 14, No. 1, Jan. 9, 2006, pp. 270-278.
Morón et al., A Wireless Monitoring System for Pulse-Oximetry Sensors, (2005) Electronic Technology Department, University of Malaga, Spain, 6 pages.
Moros, J. N. Gallpienso, R. Vilches, S. Garrigues, M. DeLa Guardia, "Nondestructive direct determination of heroin in seized illicit street drugs by diffuse reflectance near-infrared spectroscopy," Analytical Chemistry, vol. 80, No. 19, pp. 7257-7265 (Oct. 1, 2008).
Moros,J., J. Kuligowski, G. Quintas, S. Garrigues, M. DeLa Guardia, "New cut-off criterion for uninformative variable elimination in multivariate calibration of near-infrared spectra for the determination of heroin in illicit street drugs," Analytica Chimica Acta, vol. 630, pp. 150-160 (2008).
Mussot, Arnaud, et al., "Generation of a broadband single-mode supercontinuum in a conventional dispersion-shifted fiber by use of a subnanosecond microchip laser", Optics Letters, vol. 28, No. 19, Oct. 1, 2003, pp. 1820-1822.
Na, J, J.H. Baek, S.Y. Ryu, C. Lee, B.H. Lee, "Tomographic imaging of incipient dental-caries using optical coherence tomography and comparison with various modalities," Optical Review, vol. 16, No. 4, pp. 426-431 (2009).
Nachabe, R., D.J. Evers, B.H.W. Hendriks, G.W. Lucassen, M.van der Voort, E.J. Rutgers, M.J.V. Peeters, J.A. Van der Hage, H.S. Oldenburg, J. Wesseling, T.J.M. Ruers, "Diagnosis of breast cancer using diffuse optical spectroscopy from 500 to 1600nm: comparison of classification methods," Journal of Biomedical Optics, vol. 16, No. 8, article 087010, 12 pages (Aug. 2011).
Nang, Yimin, et al., "Ultrahigh-resolution optical coherence tomography by broadband continuum generation from a photonic crystal fiber", Optics Letters, vol. 28, No. 3, Feb. 1, 2003, pp. 182-184.
Nassif, N. A., et al., "In vivo high-resolution video-rate spectral-domain optical coherence tomography of the human retina and optic nerve", Optics Express, vol. 12, No. 3, Feb. 9, 2004, pp. 367-375.
Nellcor; Charts 1-3: Nellcor-533; U.S. Pat. No. 9,651,533 vs. Nellcor; Omni MedSci, Inc. v. Apple Inc., pp. 1-155; May 22, 2019.
New and Emerging Techniques-Surgical, Rapid Review, Laser Discectomy, Australian Safety and Efficacy Register of New Interventional Procedures-Surgical, Jun. 2003, 12 pages.
Ng, Choo Lum, Randy L. Wehling, and Susan L Cuppett. "Method for determining frying oil degradation by near-infrared spectroscopy." Journal of agricultural and food chemistry 55.3 (2007): 593-597.
Ni, Yongnian, Minghua Mei, and Serge Kokot. "Analysis of complex, processed substances with the use of NIR spectroscopy and chemometrics: Classification and prediction of properties-The potato crisps example." Chemometrics and Intelligent Laboratory Systems 105.2 (2011): 147-156.
Nicholson, J. W., "Supercontinuum generation in ultraviolet-irradiated fibers", Optics Letters, vol. 29, No. 20, Oct. 15, 2004, pp. 2363-2365.
Nicholson, J. W., et al., "All-fiber, octave-spanning supercontinuum", Optics Letters, vol. 28, No. 8, Apr. 15, 2003, pp. 643-645.
Nicholson, J. W., et al., "High power, single mode, all-fiber source of femtosecond pulses at 1550 nm and its use in supercontinuum generation", Optics Express, vol. 12, No. 13, Jun. 28, 2004, pp. 3025-3034.
Nicholson, J. W., et al., "Pulsed and continuous-wave supercontinuum generation in highly nonlinear, dispersion-shifted fibers", Applied Physics B 77, 2003, pp. 211-218.
Nishida, Yoshiki, et al., "Reliability of Fluoride Fiber Module for Optical Amplifier Use", IEEE Photonics Technology Letters, vol. 11, No. 12, Dec. 1999, pp. 1596-1598.
Nishizawa, N., "Generation and application of high-quality supercontinuum sources," Optical Fiber Technology, vol. 18, pp. 394-402 (2012).

(56) References Cited

OTHER PUBLICATIONS

Non-Final Office Action for U.S. Appl. No. 14/875,709 dated May 26, 2016.
Noreen, R., C.C. Chien, M. Delugin, S. Yao, R. Pineau, Y. Hwu, M. Moenner, C. Petibois, "Detection of collagens in brain tumors based on FTIR imaging and chemometrics," Annals of Bioanalytic Chemistry, vol. 401, pp. 845-852 (2011).
Notice of Allowance for U.S. Appl. No. 14/875,709 dated Jan. 10, 2017.
Nowak, G. A., et al., "Low-power high-efficiency wavelength conversion based on modulational instability in high-nonlinearity fiber," Optics Letters, vol. 23, No. 12, Jun. 15, 1998, pp. 936-938.
Nowak, George A., et al., "Stable supercontinuum generation in short lengths of conventional dispersion-shifted fiber", Applied Optics, vol. 38, No. 36, Dec. 20, 1999, pp. 7364-7369.
Nunnally, W.C., S.K. Holland, G. Laufer, "Wide field of view solar occultation gas filter correlation radiometer for stratospheric methane measurements from a sounding rocket," Thermosense Xxv, K.E. Elliot, X.P. Maldague, Editors, Proceedings of SPIE, vol. 5073, pp. 122-130 (2003).
Olesberg, J.T., L. Liu, V.V. Zee, M.A. Arnold, "In vivo near-infrared spectroscopy of rat skin tissue with varying blood glucose levels," Analytic Chemistry, vol. 78, No. 1, pp. 215-223 (2006).
Olesberg, J.T., M.A. Arnold, C. Mermelstein, J. Schmitz, J. Wagner, "Tunable laser diode system for noninvasive blood glucose measurements," Applied Spectroscopy, vol. 59, No. 12, pp. 1480-1484 (2005).
Olsen, B.A., M.W. Borer, F.M. Perry, R.A. Forbes, "Screening for counterfeit drugs using near- infrared spectroscopy," Pharmaceutical Technology, pp. 62-71 (Jun. 2002).
Omni MedSci Inc.'s Opening Claim Construction Brief filed in Case No. 2:18-cv-134-RWS (Dkt. #85) (Dec. 20, 2018).
*Omni Medsci, Inc.* V. *Apple Inc.*; Case No. 2:18-cv-134-RWS (E.D. Tex.); Defendant's Invalidity Contentions, Aug. 28, 2018 (Exhibit A), 66 pps.
*Omni Medsci, Inc.* V. *Apple Inc.*; Case No. 2:18-cv-134-RWS (E.D. Tex.); Defendants Invalidity Contentions, Aug. 28, 2018 (Exhibit AA), 75 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit B), 73 pps.
*Omni Medsci, Inc.* V. *Apple Inc.*; Case No. 2:18-cv-134-RWS (E.D. Tex.); Defendants Invalidity Contentions, Aug. 28, 2018 (Exhibit BB), 65 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit C), 85 pps.
*Omni Medsci, Inc.* V. *Apple Inc.*; Case No. 2:18-cv-134-RWS (E.D. Tex.); Defendants Invalidity Contentions, Aug. 28, 2018 (Exhibit CC), 320 pps.
*Omni Medsci, Inc.* V. *Apple Inc.*; Case No. 2:18-cv-134-RWS (E.D. Tex.); Defendant's Invalidity Contentions, Aug. 28, 2018 (Exhibit D), 38 pps.
*Omni Medsci, Inc.* V. *Apple Inc.*; Case No. 2:18-cv-134-RWS (E.D. Tex.); Defendants Invalidity Contentions, Aug. 28, 2018 (Exhibit DD), 240 pps.
*Omni Medsci, Inc.* V. *Apple Inc.*; Case No. 2:18-cv-134-RWS (E.D. Tex.); Defendants Invalidity Contentions, Aug. 28, 2018 (Exhibit E), 120 pps.
*Omni Medsci, Inc.* V. *Apple Inc.*; Case No. 2:18-cv-134-RWS (E.D. Tex.); Defendants Invalidity Contentions, Aug. 28, 2018 (Exhibit F), 40 pps.
*Omni Medsci, Inc.* V. *Apple Inc.*; Case No. 2:18-cv-134-RWS (E.D. Tex.); Defendants Invalidity Contentions, Aug. 28, 2018 (Exhibit G), 66 pps.
*Omni Medsci, Inc.* V. *Apple Inc.*; Case No. 2:18-cv-134-RWS (E.D. Tex.); Defendants Invalidity Contentions, Aug. 28, 2018 (Exhibit H), 74 pps.
*Omni Medsci, Inc.* V. *Apple Inc.*; Case No. 2:18-cv-134-RWS (E.D. Tex.); Defendants Invalidity Contentions, Aug. 28, 2018 (Exhibit I), 102 pps.
*Omni Medsci, Inc.* V. *Apple Inc.*; Case No. 2:18-cv-134-RWS (E.D. Tex.); Defendants Invalidity Contentions, Aug. 28, 2018 (Exhibit J), 64 pps.
*Omni Medsci, Inc.* V. *Apple Inc.*; Case No. 2:18-cv-134-RWS (E.D. Tex.); Defendants Invalidity Contentions, Aug. 28, 2018 (Exhibit K), 77 pps.
*Omni Medsci, Inc.* V. *Apple Inc.*; Case No. 2:18-cv-134-RWS (E.D. Tex.); Defendants Invalidity Contentions, Aug. 28, 2018 (Exhibit L), 64 pps.
*Omni Medsci, Inc.* V. *Apple Inc.*; Case No. 2:18-cv-134-RWS (E.D. Tex.); Defendants Invalidity Contentions, Aug. 28, 2018 (Exhibit M), 119 pps.
*Omni Medsci, Inc.* V. *Apple Inc.*; Case No. 2:18-cv-134-RWS (E.D. Tex.); Defendants Invalidity Contentions, Aug. 28, 2018 (Exhibit N), 50 pps.
*Omni Medsci, Inc.* V. *Apple Inc.*; Case No. 2:18-cv-134-RWS (E.D. Tex.); Defendants Invalidity Contentions, Aug. 28, 2018 (Exhibit O), 63 pps.
*Omni Medsci, Inc.* V. *Apple Inc.*; Case No. 2:18-cv-134-RWS (E.D. Tex.); Defendants Invalidity Contentions, Aug. 28, 2018 (Exhibit P), 78 pps.
*Omni Medsci, Inc.* V. *Apple Inc.*; Case No. 2:18-cv-134-RWS (E.D. Tex.); Defendants Invalidity Contentions, Aug. 28, 2018 (Exhibit Q), 69 pps.
*Omni Medsci, Inc.* V. *Apple Inc.*; Case No. 2:18-cv-134-RWS (E.D. Tex.); Defendants Invalidity Contentions, Aug. 28, 2018 (Exhibit R), 61 pps.
*Omni Medsci, Inc.* V. *Apple Inc.*; Case No. 2:18-cv-134-RWS (E.D. Tex.); Defendants Invalidity Contentions, Aug. 28, 2018 (Exhibit S), 50 pps.
*Omni Medsci, Inc.* V. *Apple Inc.*; Case No. 2:18-cv-134-RWS (E.D. Tex.); Defendants Invalidity Contentions, Aug. 28, 2018 (Exhibit T), 174 pps.
*Omni Medsci, Inc.* V. *Apple Inc.*; Case No. 2:18-cv-134-RWS (E.D. Tex.); Defendants Invalidity Contentions, Aug. 28, 2018 (Exhibit U), 334 pps.
*Omni Medsci, Inc.* V. *Apple Inc.*; Case No. 2:18-cv-134-RWS (E.D. Tex.); Defendants Invalidity Contentions, Aug. 28, 2018 (Exhibit V), 137 pps.
*Omni Medsci, Inc.* V. *Apple Inc.*; Case No. 2:18-cv-134-RWS (E.D. Tex.); Defendants Invalidity Contentions, Aug. 28, 2018 (Exhibit W), 384 pps.
*Omni Medsci, Inc.* V. *Apple Inc.*; Case No. 2:18-cv-134-RWS (E.D. Tex.); Defendants Invalidity Contentions, Aug. 28, 2018 (Exhibit X), 291 pps.
*Omni Medsci, Inc.* V. *Apple Inc.*; Case No. 2:18-cv-134-RWS (E.D. Tex.); Defendants Invalidity Contentions, Aug. 28, 2018 (Exhibit Y), 120 pps.
*Omni Medsci, Inc.* V. *Apple Inc.*; Case No. 2:18-cv-134-RWS (E.D. Tex.); Defendants Invalidity Contentions, Aug. 28, 2018 (Exhibit Z), 53 pps.
Omre, A., Bluetooth Low Energy: Wireless Connectivity for Medical Monitoring, Journal of Diabetes Science & Technology , vol. 4, Issue 2 (Mar. 2010).
Ooen, Stephane, et al., "Supercontinuum generation by stimulated Raman scattering and Darametric four-wave mixing in photonic crystal fibers", J. Opt. Soc. Am. B, vol. 19, No. 4, Apr. 2002, pp. 753-764.
Ooi ET, Zhang XQ, Chen JH, Soh PH, Ng K, Yeo JH, "Non-invasive glucose measurement using multiple laser diodes," Optical Diagnostic and Sensing VII, edited by Gerard L. Cote, Alexander V. Priezzhev, Proc. of SPIE vol. 6445, 64450K , (2007).
Oughstun, Kurt E., "Influence of precursor fields on ultrashort pulse autocorrelation measurements and pulse width evolution", Optics Express, vol. 8, No. 8, Apr. 9, 2001, pp. 481-491.
P.A. Thielen and L.B. Shaw, et al., "Small-core As-Se fiber for Raman amplification," Optics Leti- ers, vol. 28, No. 16, Aug. 15, 2003, 3 pages.
Palou, A. J. Cruz, M. Blanco, J. Tomas, J. De Los Rios, M. Alcala, "Determination of drug, excipients and coating distribution in

(56) References Cited

OTHER PUBLICATIONS pharmaceutical tablets using NIR-CI," Journal of Pharmaceutical Analysis, vol. 2, No. 2, pp. 90-97 (2012).
Pan, Yingtian, et al., "Hand-held arthroscopic optical coherence tomography for in vivo high- resolution imaging of articular cartilage", Journal of Biomedical Optics 8(4), Oct. 2003, pp. 648-654.
Papemyi, S. B., et al., "Sixth-Order Cascaded Raman Amplification", OFC/NFOEC, 2005, 3 pages.
Parawira, S. "Classification of hyperspectral breast images for cancer detection," Dec. 4, 2009, downloaded from WWW, 5 pages.
Park, Jesung, et al., "Analysis of birefringent image in the retinal nerve fiber layer by polarization sensitive optical coherence tomography", Ophthalmic Technologies XIV, Proceedings of SPIE, vol. 5314, 2004, pp. 188-194.
Park; Charts 1-3: Park-533; U.S. Pat. No. 9,651,533 vs. Park; *Omni MedSci, Inc.* v. *Apple Inc.*, pp. 1-171; May 22, 2019.
Passat, "Solid-State Lasers and Optical Components," Jul. 14, 2003, 5 pages.
Patel, S., et al., A review of wearable sensors and systems with application rehabilitation, Journal of Neuroengineering & Rehabilitation 2012 9:21.
Patterson et al., Ratiometric Artifact Reduction in Low Power Reflective Photoplethysmography, (Aug. 2011) IEEE Transactions on Biomedical Circuits and Systems, vol. 5, No. 4, 9 pages.
PCT/US06/44451, Notification of Transmittal of the International Search Report and the Written Opinion of the International Searching Authority, or the Declaration, dated Nov. 29, 2007, 12 pages.
Pedreschi, F., V. H. Segtnan, and S. H. Knutsen. "On-line monitoring of fat, dry matter and acrylamide contents in potato chips using near infrared interactance and visual reflectance imaging." Food Chemistry 121.2 (2010): 616-620.
Peláez, LED Power Reduction Trade-Offs for Ambulatory Pulse Oximetry, Conference Proceedings of the 29th Annual International Conference of the IEEE Embs (Aug. 2007) Lyon, France, 4 pages.
U.S. Appl. No. 12/206,432, "System and Method for Voice Control of Medical Devices," by Mohammed N. Islam, filed Sep. 8, 2008.
Pezzaniti, J.L., T.W. Jeng, L. McDowell, G.M. Oosta, "Preliminary investigation of near-infrared spectroscopic measurements of urea, creatinine, glucose, protein and ketone in urine," Clinical Biochemistry, vol. 34, pp. 239-246 (2001).
Pierce, Mark C., et al., "Advances in Optical Coherence Tomography imaging for Dermatology", Optical Coherence Tomography Advances, The Journal of Investigative Dermatology, Sep. 3, 2004, pp. 458-463.
Pojic, M. J. Mastilovic, N. Majcen, "The application of near infrared spectroscopy in wheat quality control," Infrared Spectroscopy-Life and Biomedical Sciences, pp. 167-184 (2012).
Povazay, B., et al., "Submicrometer axial resolution optical coherence tomography", Optical Letters, vol. 27, No. 20, Oct. 15, 2002, pp. 1800-1802.
Proof of Service of Summons in Omni MedSci, Inc. v. Apple Inc., No. 2:18-cv-134 (E.D. Tex.) (Dkt. #12) (Apr. 13, 2018).
R.H. Istepanian, B. Woodward, p. A. Bales, S. Chen, B. Luk, "The comparative performance of mobile telemediCal systems based on the IS-54 and GSM cellular telephone standards," Journal of Telemedicine and Telecare, 1999, pp. 97-104.
R.Rox Anderson, et al., "Selective Photothermolysis: Precise Microsurgery by Selective Absorption of Pulsed Radiation," Department of Dermatology, Harvard Medical School, Science, vol. 220, Apr. 29, 1983, 4 pages.
Rambla, F.J., S. Garrigues, M. DeLa Guardia, "PLS-NIR determination of total sugar, glucose, fructose and sucrose in aqueous solutions of fruit juices," Analytica Chimica Acta, vol. 344, pp. 41-53 (1997).
Ranka, Jinendra K., et al., "Visible continuum generation in air-silica microstructure optical fibers with anomalous dispersion at 800 nm", Optics Letters, vol. 25, No. 1, Jan. 1, 2000, pp. 25-27.
Rauf Adil, "The Usage of Tablets in the HealthCare Industry," available at https://www.healthcareitnews.com/blog/usage-tablets-healthcare-industry (Aug. 2, 2012).
Reese, E.L, E.E. Fisher, D.A. Horowitz, "Photoelectric densitometry of the circulation of the human dental pulp," The Journal of the Baltimore College of Dental Surgery, vol. 26, No. 1, pp. 6-18 (1971).
Reich, G. "Near-infrared spectroscopy and imaging: basic principles and pharmaceutical applications," Advanced Drug Delivery Reviews, vol. 57, pp. 1109-1143 (2005).
Rein, Alan, and Luis Rodriguez-Saona. "Measurement of Acrylamide in Potato Chips by Portable FTIR Analyzers." (2013).
Rhee et al., Artifact-Resistant Power-Efficient Design of Finger-Ring Plethysmographic Sensors, IEEE Transactions on Biomedical Engineering (Jul. 2001), vol. 48, No. 7, Cambridge, MA, 11 pages.
Robert S. Jones et al.; Near-Infrared Transillumination at 1310-nm for the Imaging of Early Dental Decay; vol. 11; No. 18; Optics Express 2259; Sep. 8, 2003.
Rodionova, O.Y., L.P. Houmoller, A.L. Pomerantsev, p. Geladi, J. Burger, V.L. Dorofeyev, A.P. Arzamastsev, "NIR spectrometry for counterfeit drug detection: a feasibility study," Analytica Chimica Acta, vol. 549, pp. 151-158 (2005).
Roggan, Andre, et al., "Optical Properties of Circulating Human Blood in the Wavelength Range 400-2500 NM", Journal of Biomedical Optics, vol. 4, No. 1, Jan. 1999, pp. 36-46.
Roggo, Y. P. Chalus, L. Maurer, C. Lema-Martinez, A. Edmond, N. Jent, "A review of near infrared spectroscopy and chemometrics in pharmaceutical technologies," Journal of Pharmaceutical and Biomedical Analysis, vol. 44, pp. 683-700 (2007).
Rollins, Andrew M., et al., "Real-time in vivo imaging of human gastrointestinal ultrastructure by use of endoscopic optical coherence tomography with a novel efficient interferometer design", Optics Letters, vol. 24, No. 19, Oct. 1, 1999, pp. 1358-1360.
S.D. Khan, S. Jacobson, "Remote sensing and geochemistry for detecting hydrocarbon microseepages," GSA Bulletin, vol. 120, No. 1/2, pp. 96-105 (Jan./Feb. 2008).
Saliminia, A., et al., "Ultra-broad and coherent white light generation in silica glass by focused femtosecond pulses at 1.5pm", Optics Express, vol. 13, No. 15, Jul. 25, 2005, pp. 5731-5738.
Sanghera, J. S., et al., Active and passive chalcogenide glass optical fibers for IR applications: a review, Journal of Non-Crystalline Solids 256 & 257, 1999, pp. 6-16.
Scafi, S.H.F., C. Pasquini, "Identification of counterfeit drugs using near-infrared spectroscopy," Analyst, vol. 126, pp. 2218-2224 (2001).
Schmitt, Joseph, et al., "Intravascular Optical Coherence Tomography Opens a Window Onto Coronary Artery Disease", Optics & Photonics News, Feb. 2004, pp. 20-25.
Schneider, R.C., K.A. Kovar, "Analysis of ecstasy tablets: comparison of reflectance and transmittance near infrared spectroscopy," Forensic Science International, vol. 134, pp. 187-195 (2003).
Schreiber, T., et al., "Supercontinuum generation by femtosecond single and dual wavelength pumping in photonic crystal fibers with two zero dispersion wavelengths", Optics Express, vol. 13, No. 23, Nov. 14, 2005, pp. 9556-9569.
Schreiner et al., Blood Oxygen Level Measurement with a Chest-Based Pulse Oximetry Prototype System, Computing in Cardiology (2010) NIBEC, University of Ulster, Newtownabbey, Northern Ireland, 4 pages.
Schubert, E.F., Light-Emitting Diodes (Cambridge Univ. Press, 2nd ed. Reprinted 2014).
Schulz, I., J. Putzger, A. Niklas, M. Brandt, A. Jager, A. Hardt, S. Knorzer, K.A. Hiller, S. Loffler, G. Schmalz, S.N. Danilov, S. Giglberger, M. Hirmer, S.D. Ganichev, G. Monkman, "PPG signal acquisition and analysis on in vitro tooth model for dental pulp vitality assessment," ARC Submission 16, (2012).
Seefeldt, Michael, et al., "Compact white-light source with an average output power of 2.4 Wand 900 nm spectral bandwidth", Optics Communications 216, pp. 199-202.
Segtnan, Vegard H., et al. "Screening of acrylamide contents in potato crisps using process variable settings and near-infrared spectroscopy." Molecular nutrition & food research 50.9 (2006): 811-817.
September, Danwille Jacqwin Franco. Detection and quantification of spice adulteration by near infrared hyperspectral imaging. Diss. Stellenbosch: University of Stellenbosch, 2011.

(56) References Cited

OTHER PUBLICATIONS

Shaw, et al., IR Supercontinuum Generation in As-Se Photonic Crystal Fiber, Optical Society of America, Copyright 2005, 3 pages.
Shiroma, Cecilia, and Luis Rodriguez-Saona. "Application of NIR and MIR spectroscopy in quality control of potato chips." Journal of Food Composition and Analysis 22.6 (2009): 596-605.
Shiroma, Cecilia. "Rapid quality control of potato chips using near and mid-infrared spectroscopy." (2007).
Shu-Fang, T. C. Jian-Ping, Z. Mi, "The information of oil and gas micro-seepage in Dongsheng Region of Inner Mongolia extraction based on the airborne hyperspectral remote sensing image," Remote Sensing of the Environment, 16th National Symposium on Remote Sensing of China, edited by Q. Tong, Proceedings of SPIE, vol. 7123, 71230K-1 to 8, (2008).
Slusher, Richard, et al., "Highly nonlinear composite chalcogenide/polymer fibers", OSA 2004, 1 page.
Slusher, Richart E., et al., "Large Raman gain and nonlinear phase shills in high-purity As2So3 chalcogenide fibers", J. Opt. Soc. Am. B, vol. 21, No. 6, Jun. 2004, pp. 1146-1155.
Smektala, F., et al., "Chalcogenide glasses with large non-linear refractive indices", Journal of Non-Crystalline Solids 239, 1998, pp. 139-142.
Smith, J.L., "The Pursuit of Noninvasive Glucose: Hunting the Deceitful Turkey," 2nd Edition, pp. 1-141 (2011).
Sobol, Emil, et al., "Time-resolved, light scattering measurements of cartilage and cornea denaturation due to free electron laser radiation", Journal of Biomedical Optics, vol. 8, No. 2, Apr. 2003, pp. 216-222.
Sondermann, N., K.A. Kovar, "Identification of ecstasy in complex matrices using near-infrared spectroscopy," Forensic Science International, vol. 102, pp. 133-147 (1999).
Staninec, M., S.M. Douglas, C.L. Darling, K. Chan, H. Kang, R. C. Lee, D. Fried, "Nondestructive clinical assessment of occlusal caries lesions using near-IR imaging methods," Lasers in Surgery and Medicine, vol. 43, No. 10, pp. 951-959 (2011).
State-Specific Trends in Chronic Kidney Failure-United States, 1990-2001, Morbidity and Mortality Weekly Report, Department of Health and Human Services Centers for Disease Control and Prevention, vol. 53, No. 39, copied from internet: file://C:\Documents and Settings\eturlo\Desktop\State-Specific Trends in Chronic Kidney . . . Feb. 12, 2010, Oct. 8, 2004, pp. 918-920.
Sun, Y., C.F. Booker, S. Kumari, R.N. Day, M. Davidson, A. Periasamy, "Characterization of an orange acceptor fluorescent protein for sensitized spectral fluorescence resonant energy transfer microscopy using a white-light laser," Journal of Biomedical Optics, vol. 14, No. 5, paper 054009 (2009).
Swan, M., Sensor Mania! The Internet of Things, Wearable Computing, Objective Metrics, and the Quantified Self 2.0, Journal of Sensor and Actuator Networks (2012).
Takushima, Yuichi, High average power, depolarized super-continuum generation using a 1.55-um ASE noise source, Optics Express, vol. 13, No. 15, Jul. 25, 2005, pp. 5871.-5877.
Tanaka, Keiji, "Optical nonlinearity in photonic glasses", Journal of Materials Science: Materials in Electronics 16, 2005, pp. 633-643.
Taos, Inc., Infrared Light-to-Voltage Optical Sensors, (2006) Texas Advanced Optoelectronic Solutions Inc., The Lumenology Company, TX, 14 pages.
Taroni, P. D. Cornelli, A. Giusto, A. Pifferi, N. Shah, L. Spinelli, A. Torricelli, R. Cubeddu, "Assessment of collagen absorption and related potential diagnostic applications," Diffuse Optical Imaging of Tissue, edited by B.W. Pogue, R. Cubeddu, Proceedings of SPIE-OSA Biomedical Optics, SPIE vol. 6629, paper 66290D, 5 pages, (2007).
Taroni, P., "Diffuse optical imaging and spectroscopy of the breast: a brief outline of history and perspectives," Photochemical Photobiological Science, vol. 11, pp. 241-250 (2012).
Tearney, Guillermo J., et al., "In vivo Endoscopic Optical Biopsy with Optical Coherence Tomography", Science, New Series, vol. 276, Jun. 27, 1997, pp. 2037-2039.
Technology Transfer Policy, Office of Technology Transfer -- University of Michigan (available at https://techtransfer.umich.edu/for-inventors/policies/technology-transfer- - policy/) (revision effective Jun. 1, 2009).
The Bylaws of the University of Michigan Board of Regents, (available at http://www.regents.umich.edu/bylaws/bylawsrevised_09-18.pdf) (last updated Sep. 20, 2018).
Thennadil, S.N., J.L. Rennert, B.J. Wenzel, K.H. Hazen, T.L. Ruchti, M.B. Block, "Comparison of glucose concentration in interstitial fluid, and capillary and venous blood during rapid changes in blood glucose levels," Diabetes Technology & Therapeutics, vol. 3, No. 3, pp. 357-365 (2001).
Thongtrangan, Issada, et al., "Minimally invasive spinal surgery: a historical perspective", Neurosurg. Focus, vol. 16, Article 13, Jan. 2004, pp. 1-10.
Thybo, Anette Kistrup, et al. "Prediction of sensory texture of cooked potatoes using uniaxial compression, near infrared spectroscopy and low field1H NMR spectroscopy." LWT-Food Science and Technology 33.2 (2000): 103-111.
Tolton, B.T., "A concept for a gas-filter correlation radiometer to remotely sense the atmospheric carbon dioxide col. from space," Notes and Correspondence, Journal of Atmospheric and Oceanic Technology, vol. 21, pp. 837-852, (May 2004).
Tombelaine, Vincent, et al., "Ultra wide band supercontinuum generation in air-silica holey fibers by SHG-induced modulation instabilities", Optics Express, vol. 13, No. 19, Sep. 19, 2005, pp. 7399-7404.
Travers, J. C., et al., "Extended blue supercontinuum generation in cascaded holey fibers", Optics Letters, vol. 30, No. 23, Dec. 1, 2005, pp. 3132-3134.
Travers, J. C., et al., "Extended continuous-wave supercontinuum generation in a low-water-loss holey fiber", Optics Letters, vol. 30, No. 15, Aug. 1, 2005, pp. 1938-1940.
Troy, T.L., S.N. Thennadil, "Optical properties of human skin in the near infrared wavelength range of 1000 to 2200nm," Journal of Biomedical Optics, vol. 6, No. 2, pp. 167-176, (2001).
U.S. Appl. No. 10/652,276, "System and Method for Voice Control of Medical devices," by Mohammed N. Islam, abandoned filed Aug. 29, 2003.
U.S. Appl. No. 10/757,341, "System and Method for Voice Control of Medical devices," by Mohammed N. Islam, filed Jan. 13, 2004.
U.S. Appl. No. 12/206,432, "System and Method for Voice Control of Medical Devices," by Mohammed N. Islam, pending filed Sep. 8, 2008.
U.S. Appl. No. 61/350,673; titled: Opticoustic Sensor; Inventor: Massi Joe E. Kiani; filed Jun. 2, 2010.
U.S. Appl. No. 61/747,472, filed Dec. 31, 2012.
U.S. Appl. No. 61/747,477, filed Dec. 31, 2012.
U.S. Appl. No. 61/747,487, filed Dec. 31, 2012.
U.S. Appl. No. 61/754,698, filed Jan. 21, 2013.
U.S. Patent and Trademark Office, Notice of Allowance and Fee(s) Due for U.S. Appl. No. 12/206,432, filed Sep. 8, 2008, Mohammed N. Islam, Date filed: Aug. 28, 2009.
U.S. Patent and Trademark Office, Office Action for U.S. Appl. No. 12/206,432, filed Sep. 8, 2008, Mohammed N, Islam, Date Filed: Mar. 12, 2009.
United States District Court Eastern District of Texas Marshall Division; Defendant and Counter Claimant Apple Inc.'s Amended Answer, Affirmative Defenses, and Counterclaims to Complaint of Plaintiff and Counter Defendant Omni Medsci, Inc.; Document 38; Jul. 19, 2018; 32 pps.
United States District Court Eastern District of Texas Marshall Division; *Omni Medsci, Inc.* vs. *Apple Inc.*; Civil Action No. 2:18-cv-00134 Jury Trial Demanded; Defendant's Invalidity Contentions; Aug. 28, 2018; 33 pps.
Unterhuber, A., et al., "Advances in broad bandwidth light sources for ultrahigh resolution optical coherence tomography", Physics in Medicine and Biology, Phys. Med. Biol. 49, 2004, pp. 1235-1246.
Urban, J. P. G., et al., "The Nucleus of the Intervertebral Disc from Development to Degeneration" Amer. Zool., vol. 40, 2000, pp. 53-61.

(56) References Cited

OTHER PUBLICATIONS

Urbas, A., M.W. Manning, A. Daugherty, L.A. Cassis, R.A. Lodder, "Near-infrared spectrometry of abdominal aortic aneurysm in the ApoE Mouse," Analytical Chemistry, vol. 75, No. 15, pp. 3650-3655 (Jul. 15, 2003).
Valencell; Charts 1-3: Valencell-533; U.S. Pat. No. 9,651,533 vs. Valencell; *Omni MedSci, Inc.* v. *Apple Inc.*, pp. 1-122; May 22, 2019.
Van Der Meer, F. P. Van Dijk, H. Van Der Werff, H. Yang, "Remote sensing and petroleum seepage: a review and case study," Terra Nova, vol. 14, No. 1, pp. 1-17 (2002).
Van Der Meer, F., P. Van Dijk, S. Kroonenberg, Y. Hong, H. Lang, "Hyperspectral hydrocarbon microseepage detection and monitoring: potentials and limitations," Second EARSEI workshop on imaging spectroscopy, pp. 1-9 (2000).
Venugopalan, V., "Optical Society of America BIOMED Topical Meeting Tutorial on Tissue Optics", Apr. 27, 2004, pp. 1-32.
Vinay V. Alexander et al.; Modulation Instability High Power All-Fiber Supercontinuum Lasers and Their Applications; Optical Fiber Technology 18; 2012; pp. 349-374.
Wadsworth, W. J., et al., "Supercontinuum and four-wave mixing with Q-switched pulses in endlessly single-mode photonic crystal fibres", Optics Express, vol. 12, No. 2, Jan. 26, 2004, pp. 299-309.
Wadsworth, William J., et al., "Supercontinuum generation in photonic crystal fibers and Optical fiber tapers: a novel light source", J. Opt. Soc. Am. B, vol. 19, No. 9, Sep. 2002, pp. 2148-2155.
Walsh, M.J., R.K. Reddy, R. Bhargava, "Label-free biomedical imaging with mid-IR spectroscopy," IEEE Journal of Selected Topics in Quantum Electronics, article identifier 10.1109/JSTQE.2011.2182635, 12 pages, (2011).
Wang et al., Multichannel Reflective PPG Earpiece Sensor with Passive Motion Cancellation, (Dec. 2007) IEEE Transactions on Biomedical Circuits and Systems, vol. 1, No. 4, 7 pages.
Wang, Lihong V., Multiscale photoacoustic microscopy and computed tomography, Sep. 2009, Nature Photonics, vol. 3, pp. 503-509.
Wang, Yimin, et al., "Ultrahigh-resolution optical coherence tomography by broadband continuum generation from a photonic crystal fiber", Optics Letters, vol. 28, No. 3, Feb. 1, 2003, pp. 182-184.
Watari, M., H. Migashiyama, N. Mitsui, M. Tomo, Y. Ozaki, "On-line monitoring of the density of linear low-density polyethylene in a real plant by near-infrared spectroscopy and chemometrics," Applied Spectroscopy, vol. 58, No. 2, pp. 248-255 (2004).
Webster, Design of Pulse Oximeters, Medical Science Series (1997), Department of Electrical and Computer Engineering, University of Wisconsin-Madison, Institute of Physics Publishing, Bristol and Philadelphia, 267 pages.
Wedding, B.B., C. Wright, S. Grauf, R.D. White, "The application of near infrared spectroscopy for the assessment of avocado quality attributes," Infrared Spectroscopy-Life and Biomedical Sciences, pp. 211-230 (2011).
Werle, Peter, et al., "Near- and mid-infrared laser-optical sensors for gas analysis", Optics and Lasers in Engineering 37, 2002, pp. 101-114.
Westbrook, Paul S., "Improved Supercontinuum Generation Through UV Processing of Highly Nonlinear Fibers", Journal of Lightwave Technology, vol. 23, No. 1, Jan. 2005, pp. 13-18.
Williams, Phil. "Near-Infrared Spectroscopy of Cereals." Handbook of vibrational spectroscopy (2006).
Wuthrich, Stefan, et al., "Optical damage thresholds at 2.94 um in fluoride glass fibers", Applied Optics, vol. 31, No. 27, Sep. 20, 1992, pp. 5833-5837.
Xiao, J. Q. Tian, Y. Lu, L. Wang, X. Qi, B. Wen, "Extraction of hydrocarbon content information by using hyperspectral image at Liaodong Bay, China," downloaded from world wide web on Apr. 6, 2012.
Xie, T .- Q., et al., "Detection of tumorigenesis in urinary bladder with optical coherence tomography: optical characterization of morphological changes", Optics Express, vol. 10, No. 24, Dec. 2, 2002, 2003, pp. 1431-1443.
Xie, Tuqiang, et al., "Endoscopic optical coherence tomography with a modified microelectromechanical systems mirror for detection of bladder cancers", Applied Optics, vol. 42, No. 31, Nov. 1, 2003, pp. 6422-6426.
Xu, D., G. Ni, T. Jiang, L. Jiang, M. Chi, "Integration of field work and hyperspectral data for oil and gas exploration," IEEE 1-4244-1212-9/07, pp. 3194-3197 (2007).
Xu, D-Q, G-Q Ni, L-L Jiang, Y-T Shen, T. Li, S-L Ge, X-B Shu, "Exploring for natural gas using reflectance spectra of surface soils," Advances in Space Research, vol. 41, pp. 1800-1817 (2008).
Yamaha, BODiBEAT, Body, Music, in Sync., BF-1 Quick Guide, Player/Heart Rate Monitor: Quick Manual, 120 pages.
Yeh, S-J, C.F. Hanna, O.S. Khalil, "Monitoring blood glucose changes in cutaneous tissue by temperature-modulated localized reflectance measurements," Clinical Chemistry, vol. 49, No. 6, pp. 924-934 (2003).
Zakian, C. I. Pretty, R. Ellwood, "Near-infrared hyperspectral imaging of teeth for dental canes detection," Journal of Biomedical Optics, vol. 16, No. 6, 064047 (2009).
Ziegler, U., A.G. Bittermann, M. Hoechli, "Introduction to Confocal Laser Scanning Microscopy (LEICA)," www.zmb.unizh.ch, May 29, 2013.
Inter Partes Review No. IPR2025-01249; Petition for Inter Partes Review of U.S. Pat. No. 9,055,868; *Samsung Electronics Co., Ltd. et al.* v. *Omni Medsci, Inc.*; pp. 1-82; dated Aug. 5, 2025.
Inter Partes Review No. IPR2025-01250; Petition for Inter Partes Review of U.S. Pat. No. 9,651,533; *Samsung Electronics Co., Ltd. et al.* v. *Omni Medsci, Inc.*; pp. 1-80; dated Aug. 5, 2025.
Inter Partes Review No. IPR2025-01251; Petition for Inter Partes Review of U.S. Pat. No. 10,874,304; *Samsung Electronics Co., Ltd. et al.* v. *Omni Medsci, Inc.*; pp. 1-98; dated Aug. 5, 2025.
Inter Partes Review No IPR2025-01252; Petition for Inter Partes Review of U.S. Pat. No. 11,160,455; *Samsung Electronics Co., Ltd. et al.* v. *Omni Medsci, Inc.*; pp. 1-102; dated Aug. 5, 2025.
Inter Partes Review No IPR2025-01253; Petition for Inter Partes Review of U.S. Pat. No. 12,193,790; *Samsung Electronics Co., Ltd. et al.* v. *Omni Medsci, Inc.*; pp. 1-57; dated Aug. 5, 2025.
Inter Partes Review No. IPR2025-01254; Petition for Inter Partes Review of U.S. Pat. No. 12,268,475; *Samsung Electronics Co., Ltd. et al.* v. *Omni Medsci, Inc.*; pp. 1-92; dated Aug. 5, 2025.
Post Grant Review No. PGR2025-00063; Petition for Post Grant Review of U.S. Pat. No. 12,268,475; *Samsung Electronics Co., Ltd. et al.* v. *Omni Medsci, Inc.*; pp. 1-94; dated Aug. 5, 2025.
Post Grant Review No PGR2025-00064; Petition for Post Grant Review of U.S. Pat. No. 12,193,790; *Samsung Electronics Co., Ltd. et al.* v. *Omni Medsci, Inc.*; pp. 1-58; dated Aug. 5, 2025.

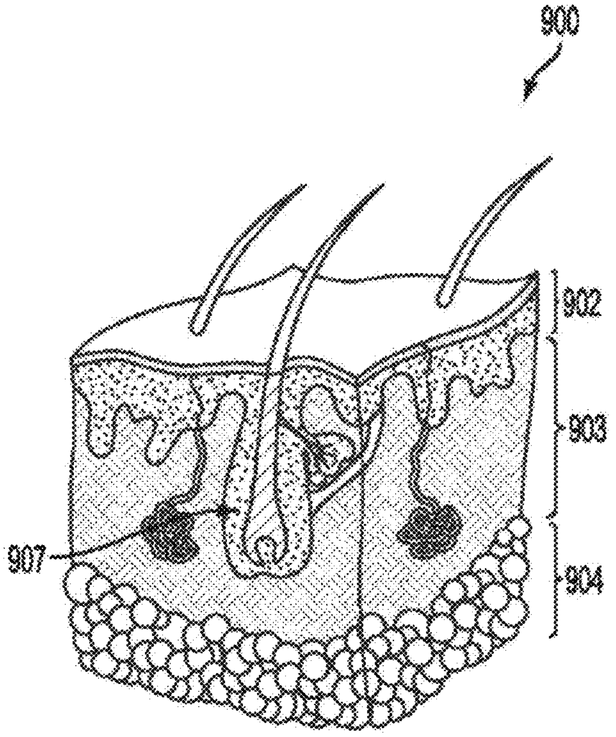
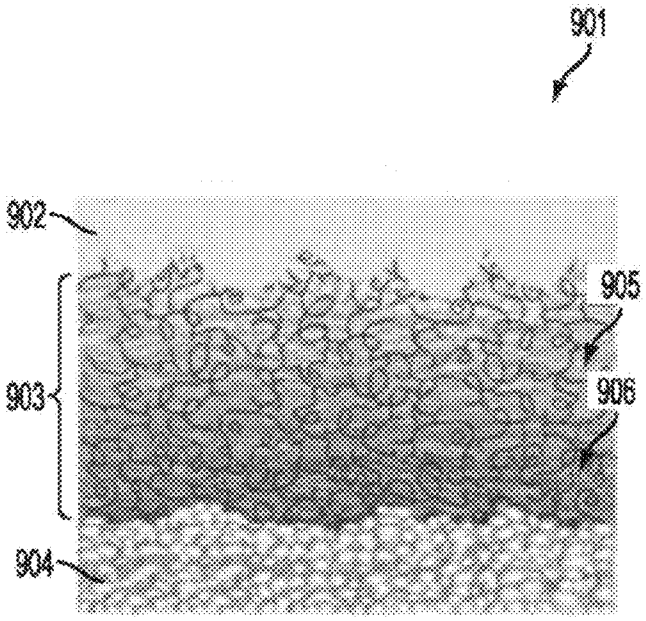
FIG. 9

3500

3501

3502

3800

3900

5700

5800

| TENTATIVE FREQUENCIES OF HEROIN BANDS (nm) | ACTUALLY MEASURED PEAK FREQUENCIES (nm) | FORMS OF MODES OF VIBRATION ASSIGNMENT |
|---|---|---|
| 1160 | 1157 | C—O STRETCH FOURTH OVERTONE |
| 1195 | 1190 | C—H SECOND OVERTONE |
| | 1200 | C—H SECOND OVERTONE |
| 1360 | 1357 | C—H COMBINATION |
| 1395 | 1391 | C—H COMBINATION |
| 1420 | 1425 | O—H FIRST OVERTONE |
| 1570 | 1570 | N—H STRETCH FIRST OVERTONE |
| 1685 | 1684 | C—H STRETCH FIRST OVERTONE |
| 1705 | 1709 | C—H STRETCH FIRST OVERTONE |
| 1725 | 1727 | C—H STRETCH FIRST OVERTONE |
| 1765 | 1767 | C—H STRETCH FIRST OVERTONE |
| 1780 | 1780 | C—H STRETCH FIRST OVERTONE |
| 1920 | 1914 | C—O STRETCH SECOND OVERTONE |
| 1950 | 1936 | C—O STRETCH SECOND OVERTONE |
| 1990 | 2000 | N—H STRETCH/N—H BEND COMBINATION |
| 2070 | 2074 | N—H DEFORMATION OVERTONE |
| 2090 | 2100 | C—H COMBINATION |
| 2140 | 2135 | C—H STRETCH/C—O STRETCH COMBINATION OR SYM C—H DEFORMATION |
| | 2144 | C—H STRETCH/C—O STRETCH COMBINATION OR SYM C—H DEFORMATION |

TO FIG. 58B

FIG. 58A

FROM FIG. 58A

| | | |
|---|---|---|
| 2170 | 2172 | ASYMMETRIC C—H STRETCH/C—H DEFORMATION COMBINATION |
| 2180 | 2178 | N—H BEND SECOND OVERTONE OR C—H STRETCH/C—O STRETCH COMBINATION, OR C—O STRETCH C—N STRETCH; N—H IN-PLANE BEND. |
| 2200 | 2194 | CH STRETCH/C—O STRETCH COMBINATION |
| 2280 | 2284 | C—H STRETCH/$CH_2$ DEFORMATION |
| 2300 | 2300 | C—H BEND SECOND OVERTONE |
| 2325 | 2320 | CH STRETCH/$CH_2$ DEFORMATION COMBINATION |
| 2352 | 2352 | $CH_2$ BEND SECOND OVERTONE |
| 2380 | 2384 | C—H STRETCH/C—C STRETCH COMBINATION |
| 2470 | 2454 | C—H COMBINATION OR SYM C—N—C STRETCH OVERTONE |
| 2488 | 2485 | C—H STRETCH/C—C STRETCH COMBINATION |
| 2530 | 2524 | ASYMMETRIC C—N—C STRETCH FIRST OVERTONE |
| 2530 | 2537 | ASYMMETRIC C—N—C STRETCH FIRST OVERTONE |

FIG. 58B

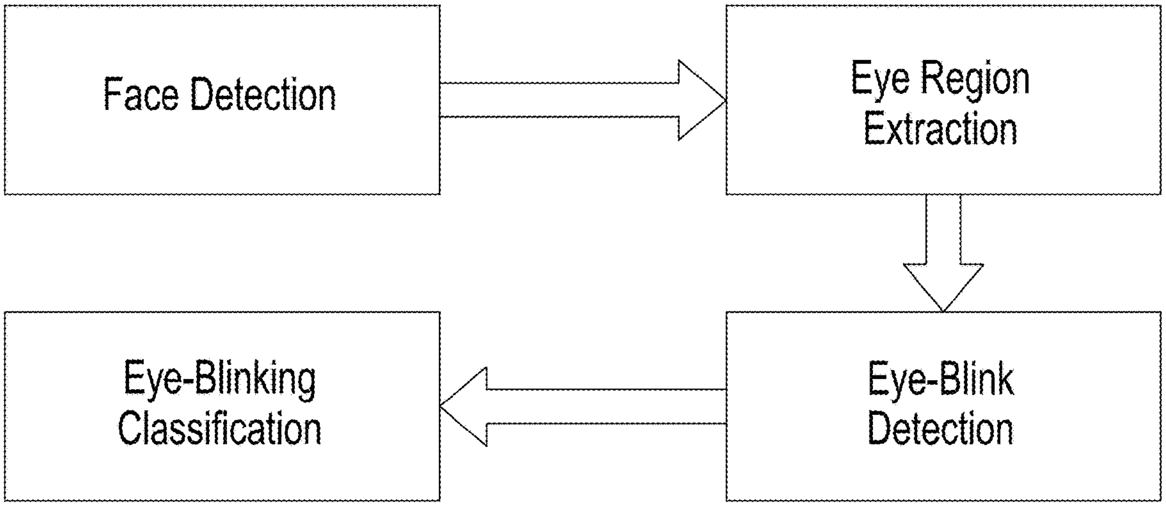
$$EAR = \frac{\|p_2 - p_6\| + \|p_3 - p_5\|}{2\|p_1 - p_4\|}$$
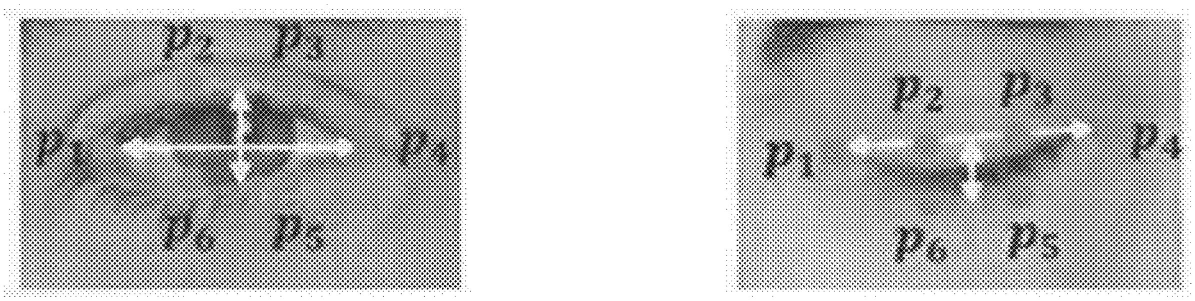
Fig. 90

CAMERA BASED WEARABLE DEVICES WITH ARTIFICIAL INTELLIGENCE ASSISTANTS

CROSS-REFERENCE TO RELATED APPLICATIONS

This application is a Continuation-In-Part of U.S. application Ser. No. 18/118,013 filed Mar. 6, 2023 (now U.S. Pat. No. 12,226,188 issued Feb. 18, 2025), which is a Continuation-In-Part of U.S. application Ser. No. 17/666,518 filed Feb. 7, 2022 (now U.S. Pat. No. 11,596,311 issued Mar. 7, 2023), which is a Continuation of U.S. application Ser. No. 17/135,233 filed Dec. 28, 2020 (now U.S. Pat. No. 11,241,156 issued Feb. 8, 2022), which is a Continuation of U.S. application Ser. No. 16/669,794 filed Oct. 31, 2019 (now U.S. Pat. No. 10,874,304), which is a Continuation of U.S. application Ser. No. 16/284,514 filed Feb. 25, 2019 (now abandoned), which is a Continuation of U.S. application Ser. No. 16/016,649 filed Jun. 24, 2018 (now U.S. Pat. No. 10,213,113), which is a Continuation of U.S. application Ser. No. 15/860,065 filed Jan. 2, 2018 (now U.S. Pat. No. 10,098,546), which is a Continuation of U.S. application Ser. No. 15/686,198 filed Aug. 25, 2017 (now U.S. Pat. No. 9,861,286), which is a Continuation of U.S. application Ser. No. 15/357,136 filed Nov. 21, 2016 (now U.S. Pat. No. 9,757,040), which is a Continuation of U.S. application Ser. No. 14/651,367 filed Jun. 11, 2015 (now U.S. Pat. No. 9,500,635), which is the U.S. national phase of PCT Application No. PCT/US2013/075736 filed Dec. 17, 2013, which claims the benefit of U.S. provisional application Ser. No. 61/747,477 filed Dec. 31, 2012 and U.S. provisional application Ser. No. 61/754,698 filed Jan. 21, 2013, the disclosures of which are hereby incorporated by reference in their entirety.

U.S. application Ser. No. 16/669,794 (now U.S. Pat. No. 10,874,304) is also a continuation of U.S. application Ser. No. 16/506,885 filed Jul. 9, 2019 (now U.S. Pat. No. 10,517,484), which is a continuation of U.S. application Ser. No. 16/272,069 filed Feb. 11, 2019 (now abandoned), which is a continuation of U.S. application Ser. No. 16/029,611 filed Jul. 8, 2018 (now U.S. Pat. No. 10,201,283), which is a continuation of U.S. application Ser. No. 15/888,052 filed Feb. 4, 2018 (now U.S. Pat. No. 10,136,819), which is a continuation of U.S. application Ser. No. 15/212,549 filed Jul. 18, 2016 (now U.S. Pat. No. 9,885,698), which is a continuation of U.S. application Ser. No. 14/650,897 filed Jun. 10, 2015 (now U.S. Pat. No. 9,494,567), which is a U.S. National Phase of PCT/US2013/075700 filed Dec. 17, 2013, which claims the benefit of U.S. provisional application Ser. No. 61/747,472 filed Dec. 31, 2012, the disclosures of all of which are hereby incorporated in their entirety by reference herein.

U.S. application Ser. No. 16/506,885 (now U.S. Pat. No. 10,517,484) is also a continuation of U.S. application Ser. No. 16/004,359 filed Jun. 9, 2018 (now U.S. Pat. No. 11,109,761), which is a continuation of U.S. application Ser. No. 14/109,007 filed Dec. 17, 2013 (now U.S. Pat. No. 9,993,159), which claims the benefit of U.S. provisional application Ser. No. 61/747,553 filed Dec. 31, 2012, the disclosures of all of which are hereby incorporated in their entirety by reference herein.

U.S. application Ser. No. 16/506,885 (now U.S. Pat. No. 10,517,484) is also a continuation of U.S. application Ser. No. 16/188,194 filed Nov. 12, 2018 (now U.S. Pat. No. 10,386,230), which is a continuation of U.S. application Ser. No. 16/004,154 filed Jun. 8, 2018 (now U.S. Pat. No. 10,126,283), which is a continuation of U.S. application Ser. No. 15/855,201 filed Dec. 27, 2017 (now U.S. Pat. No. 9,995,722), which is a continuation of U.S. application Ser. No. 15/711,907 filed Sep. 21, 2017 (now U.S. Pat. No. 9,897,584), which is a divisional of U.S. application Ser. No. 15/357,225 filed Nov. 21, 2016 (now U.S. Pat. No. 9,797,876), which is a continuation of U.S. application Ser. No. 14/650,981 filed Jun. 10, 2015 (now U.S. Pat. No. 9,500,634), which is the U.S. national phase of PCT Application No. PCT/US2013/075767 filed Dec. 17, 2013, which claims the benefit of U.S. provisional application Ser. No. 61/747,485 filed Dec. 31, 2012, the disclosures of all of which are hereby incorporated by reference in their entirety.

U.S. application Ser. No. 16/506,885 (now U.S. Pat. No. 10,517,484) is also a continuation of U.S. application Ser. No. 16/241,628 filed Jan. 7, 2019 (now U.S. Pat. No. 10,441,176), which is a continuation of U.S. Ser. No. 16/015,737 filed Jun. 22, 2018 (now U.S. Pat. No. 10,172,523), which is a continuation of U.S. Ser. No. 15/594,053 filed May 12, 2017 (now U.S. Pat. No. 10,188,299), which is a continuation of U.S. application Ser. No. 14/875,709 filed Oct. 6, 2015 (now U.S. Pat. No. 9,651,533), which is a continuation of U.S. application Ser. No. 14/108,986 filed Dec. 17, 2013 (now U.S. Pat. No. 9,164,032), which claims the benefit of U.S. provisional application Ser. No. 61/747,487 filed Dec. 31, 2012, the disclosures of all of which are hereby incorporated in their entirety by reference herein.

U.S. application Ser. No. 16/506,885 (now U.S. Pat. No. 10,517,484) is also a continuation of U.S. application Ser. No. 16/284,514 filed Feb. 25, 2019, which is a continuation of U.S. application Ser. No. 16/016,649 filed Jun. 24, 2018 (now U.S. Pat. No. 10,213,113), which is a continuation of U.S. application Ser. No. 15/860,065 filed Jan. 2, 2018 (now U.S. Pat. No. 10,098,546), which is a Continuation of U.S. application Ser. No. 15/686,198 filed Aug. 25, 2017 (now U.S. Pat. No. 9,861,286), which is a continuation of U.S. application Ser. No. 15/357,136 filed Nov. 21, 2016 (now U.S. Pat. No. 9,757,040), which is a continuation of U.S. application Ser. No. 14/651,367 filed Jun. 11, 2015 (now U.S. Pat. No. 9,500,635), which is the U.S. national phase of PCT Application No. PCT/US2013/075736 filed Dec. 17, 2013, which claims the benefit of U.S. provisional application Ser. No. 61/747,477 filed Dec. 31, 2012 and U.S. provisional application Ser. No. 61/754,698 filed Jan. 21, 2013, the disclosures of all of which are hereby incorporated by reference in their entirety.

This application is related to U.S. provisional application Ser. No. 61/747,472 filed Dec. 31, 2012; Ser. No. 61/747,481 filed Dec. 31, 2012; Ser. No. 61/747,485 filed Dec. 31, 2012; Ser. No. 61/747,487 filed Dec. 31, 2012; Ser. No. 61/747,492 filed Dec. 31, 2012; and Ser. No. 61/747,553 filed Dec. 31, 2012, the disclosures of which are hereby incorporated by reference in their entirety herein.

This application has a common priority date with commonly owned U.S. application Ser. No. 14/650,897 filed Jun. 10, 2015 (now U.S. Pat. No. 9,494,567), which is the U.S. national phase of International Application PCT/US2013/075700 entitled Near-Infrared Lasers For Non-Invasive Monitoring Of Glucose, Ketones, HBA1C, And Other Blood Constituents; U.S. application Ser. No. 14/108,995 filed Dec. 17, 2013 (published as US 2014/0188092) entitled Focused Near-Infrared Lasers For Non-Invasive Vasectomy And Other Thermal Coagulation Or Occlusion Procedures; U.S. application Ser. No. 14/650,981 filed Jun. 10, 2015 (now U.S. Pat. No. 9,500,634), which is the U.S. national phase of International Application PCT/US2013/075767 entitled Short-Wave Infrared Super-Continuum Lasers For Natural Gas Leak Detection, Exploration, And Other Active Remote Sensing Applications; U.S. application Ser. No. 14/108,986 filed Dec. 17, 2013 (now U.S. Pat. No. 9,164,032) entitled Short-Wave Infrared Super-Continuum Lasers For Detecting Counterfeit Or Illicit Drugs And Pharmaceutical Process Control; U.S. application Ser. No. 14/108,974 filed Dec. 17, 2013 (Published as US2014/0188094) entitled Non-Invasive Treatment Of Varicose Veins; and U.S. application Ser. No. 14/109,007 filed Dec. 17, 2013 (Published as US2014/0236021) entitled Near-Infrared Super-Continuum Lasers For Early Detection Of Breast And Other Cancers, the disclosures of all of which are hereby incorporated in their entirety by reference herein.

BACKGROUND

With the growing obesity epidemic, the number of individuals with diabetes is also increasing dramatically. For example, there are over 200 million people who have diabetes. Diabetes control requires monitoring of the glucose level, and most glucose measuring systems available commercially require drawing of blood. Depending on the severity of the diabetes, a patient may have to draw blood and measure glucose four to six times a day. This may be extremely painful and inconvenient for many people. In addition, for some groups, such as soldiers in the battlefield, it may be dangerous to have to measure periodically their glucose level with finger pricks.

Thus, there is an unmet need for non-invasive glucose monitoring (e.g., monitoring glucose without drawing blood). The challenge has been that a non-invasive system requires adequate sensitivity and selectivity, along with repeatability of the results. Yet, this is a very large market, with an estimated annual market of over $10B in 2011 for self-monitoring of glucose levels.

One approach to non-invasive monitoring of blood constituents or blood analytes is to use near-infrared spectroscopy, such as absorption spectroscopy or near-infrared diffuse reflection or transmission spectroscopy. Some attempts have been made to use broadband light sources, such as tungsten lamps, to perform the spectroscopy. However, several challenges have arisen in these efforts. First, many other constituents in the blood also have signatures in the near-infrared, so spectroscopy and pattern matching, often called spectral fingerprinting, is required to distinguish the glucose with sufficient confidence. Second, the non-invasive procedures have often transmitted or reflected light through the skin, but skin has many spectral artifacts in the near-infrared that may mask the glucose signatures. Moreover, the skin may have significant water and blood content. These difficulties become particularly complicated when a weak light source is used, such as a lamp. More light intensity can help to increase the signal levels, and, hence, the signal-to-noise ratio.

As described in this disclosure, by using brighter light sources, such as fiber-based supercontinuum lasers, super-luminescent laser diodes, light-emitting diodes or a number of laser diodes, the near-infrared signal level from blood constituents may be increased. By shining light through the teeth, which have fewer spectral artifacts than skin in the near-infrared, the blood constituents may be measured with less interfering artifacts. Also, by using pattern matching in spectral fingerprinting and various software techniques, the signatures from different constituents in the blood may be identified. Moreover, value-add services may be provided by wirelessly communicating the monitored data to a handheld device such as a smart phone, and then wirelessly communicating the processed data to the cloud for storing, processing, and transmitting to several locations.

Dental care and the prevention of dental decay or dental caries has changed in the United States over the past several decades, due to the introduction of fluoride to drinking water, the use of fluoride dentifrices and rinses, application of topical fluoride in the dental office, and improved dental hygiene. Despite these advances, dental decay continues to be the leading cause of tooth loss. With the improvements over the past several decades, the majority of newly discovered carious lesions tend to be localized to the occlusal pits and fissures of the posterior dentition and the proximal contact sites. These early carious lesions may be often obscured in the complex and convoluted topography of the pits and fissures or may be concealed by debris that frequently accumulates in those regions of the posterior teeth. Moreover, such lesions are difficult to detect in the early stages of development.

Dental caries may be a dynamic disease that is characterized by tooth demineralization leading to an increase in the porosity of the enamel surface. Leaving these lesions untreated may potentially lead to cavities reaching the dentine and pulp and perhaps eventually causing tooth loss. Occlusal surfaces (bite surfaces) and approximal surfaces (between the teeth) are among the most susceptible sites of demineralization due to acid attack from bacterial by-products in the biofilm. Therefore, there is a need for detection of lesions at an early stage, so that preventive agents may be used to inhibit or reverse the demineralization.

Traditional methods for caries detection include visual examination and tactile probing with a sharp dental exploration tool, often assisted by radiographic (x-ray) imaging. However, detection using these methods may be somewhat subjective; and, by the time that caries are evident under visual and tactile examination, the disease may have already progressed to an advanced stage. Also, because of the ionizing nature of x-rays, they are dangerous to use (limited use with adults, and even less used with children). Although x-ray methods are suitable for approximal surface lesion detection, they offer reduced utility for screening early caries in occlusal surfaces due to their lack of sensitivity at very early stages of the disease.

Some of the current imaging methods are based on the observation of the changes of the light transport within the tooth, namely absorption, scattering, transmission, reflection and/or fluorescence of light. Porous media may scatter light more than uniform media. Taking advantage of this effect, the Fiber-optic trans-illumination is a qualitative method used to highlight the lesions within teeth by observing the patterns formed when white light, pumped from one side of the tooth, is scattered away and/or absorbed by the lesion. This technique may be difficult to quantify due to an uneven light distribution inside the tooth.

Another method called quantitative light-induced fluorescence—QLF—relies on different fluorescence from solid teeth and caries regions when excited with bright light in the visible. For example, when excited by relatively high intensity blue light, healthy tooth enamel yields a higher intensity of fluorescence than does demineralized enamel that has been damaged by caries infection or any other cause. On the other hand, for excitation by relatively high intensity of red light, the opposite magnitude change occurs, since this is the region of the spectrum for which bacteria and bacterial by-products in carious regions absorb and fluoresce more pronouncedly than do healthy areas. However, the image provided by QLF may be difficult to assess due to relatively poor contrast between healthy and infected areas. Moreover, QLF may have difficulty discriminating between white spots and stains because both produce similar effects. Stains on teeth are commonly observed in the occlusal sites of teeth, and this obscures the detection of caries using visible light.

As described in this disclosure, the near-infrared region of the spectrum offers a novel approach to imaging carious regions because scattering is reduced and absorption by stains is low. For example, it has been demonstrated that the scattering by enamel tissues reduces in the form of 1/(wavelength)$^3$, e.g., inversely as the cube of wavelength. By using a broadband light source in the short-wave infrared (SWIR) part of the spectrum, which corresponds approximately to 1400 nm to 2500 nm, lesions in the enamel and dentine may be observed. In one embodiment, intact teeth have low reflection over the SWIR wavelength range. In the presence of caries, the scattering increases, and the scattering is a function of wavelength; hence, the reflected signal decreases with increasing wavelength. Moreover, particularly when caries exist in the dentine region, water build up may occur, and dips in the SWIR spectrum corresponding to the water absorption lines may be observed. The scattering and water absorption as a function of wavelength may thus be used for early detection of caries and for quantifying the degree of demineralization.

SWIR light may be generated by light sources such as lamps, light emitting diodes, one or more laser diodes, super-luminescent laser diodes, and fiber-based super-continuum sources. The SWIR super-continuum light sources advantageously may produce high intensity and power, as well as being a nearly transform-limited beam that may also be modulated. Also, apparatuses for caries detection may include C-clamps over teeth, a handheld device with light input and light detection, which may also be attached to other dental equipment such as drills. Alternatively, a mouth-guard type apparatus may be used to simultaneously illuminate one or more teeth. Fiber optics may be conveniently used to guide the light to the patient as well as to transport the signal back to one or more detectors and receivers.

Remote sensing or hyper-spectral imaging often uses the sun for illumination, and the short-wave infrared (SWIR) windows of about 1.5-1.8 microns and about 2-2.5 microns may be attractive because the atmosphere transmits in these wavelength ranges. Although the sun can be a bright and stable light source, its illumination may be affected by the time-of-day variations in the sun angle as well as weather conditions. For example, the sun may be advantageously used for applications such as hyper-spectral imaging only between about 9 am to 3 pm, and it may be difficult to use the sun during cloudy days or during inclement weather. In one embodiment, the hyper-spectral sensors measure the reflected solar signal at hundreds (e.g., 100 to 200+) contiguous and narrow wavelength bands (e.g., bandwidth between 5 nm and 10 nm). Hyper-spectral images may provide spectral information to identify and distinguish between spectrally similar materials, providing the ability to make proper distinctions among materials with only subtle signature differences. In the SWIR wavelength range, numerous gases, liquids and solids have unique chemical signatures, particularly materials comprising hydro-carbon bonds, O—H bonds, N—H bonds, etc. Therefore, spectroscopy in the SWIR may be attractive for stand-off or remote sensing of materials based on their chemical signature, which may complement other imaging information.

A SWIR super-continuum (SC) source may be able to replace at least in part the sun as an illumination source for active remote sensing, spectroscopy, or hyper-spectral imaging. In one embodiment, reflected light spectroscopy may be implemented using the SWIR light source, where the spectral reflectance can be the ratio of reflected energy to incident energy as a function of wavelength. Reflectance varies with wavelength for most materials because energy at certain wavelengths may be scattered or absorbed to different degrees. Using a SWIR light source may permit 24/7 detection of solids, liquids, or gases based on their chemical signatures. As an example, natural gas leak detection and exploration may require the detection of methane and ethane, whose primary constituents include hydro-carbons. In the SWIR, for instance, methane and ethane exhibit various overtone and combination bands for vibrational and rotational resonances of hydro-carbons. In one embodiment, diffuse reflection spectroscopy or absorption spectroscopy may be used to detect the presence of natural gas. The detection system may include a gas filter correlation radiometer, in a particular embodiment. Also, one embodiment of the SWIR light source may be an all-fiber integrated SWIR SC source, which leverages the mature technologies from the telecommunications and fiber optics industry. Beyond natural gas, active remote sensing in the SWIR may also be used to identify other materials such as vegetation, greenhouse gases or environmental pollutants, soils and rocks, plastics, illicit drugs, counterfeit drugs, firearms and explosives, paints, and various building materials.

Counterfeiting of pharmaceuticals is a significant issue in the healthcare community as well as for the pharmaceutical industry worldwide. For example, according to the World Health Organization, in 2006 the market for counterfeit drugs worldwide was estimated at around $43 Billion. Moreover, the use of counterfeit medicines may result in treatment failure or even death. For instance, in 1995 dozens of children in Haiti and Nigeria died after taking counterfeit medicinal syrups that contained diethylene glycol, an industrial solvent. As another example, in Asia one report estimated that 90% of Viagra sold in Shanghai, China, was counterfeit. With more pharmaceuticals being purchased through the internet, the problem of counterfeit drugs coming from across the borders into the United States has been growing rapidly.

A rapid, non-destructive, non-contact optical method for screening or identification of counterfeit pharmaceuticals is needed. Spectroscopy using near-infrared or short-wave infrared (SWIR) light may provide such a method, because most pharmaceuticals comprise organic compounds that have overtone or combination absorption bands in this wavelength range (e.g., between approximately 1-2.5 microns). Moreover, most drug packaging materials are at least partially transparent in the near-infrared or SWIR, so that drug compositions may be detected and identified through the packaging non-destructively. Also, using a near-infrared or SWIR light source with a spatially coherent beam permits screening at stand-off or remote distances. Beyond identifying counterfeit drugs, the near-infrared or SWIR spectroscopy may have many other beneficial applications. For example, spectroscopy may be used for rapid screening of illicit drugs or to implement process analytical technology in pharmaceutical manufacturing. There are also a wide array of applications in assessment of quality in the food industry, including screening of fruit, vegetables, grains and meats.

In one embodiment, a near-infrared or SWIR super-continuum (SC) source may be used as the light source for spectroscopy, active remote sensing, or hyper-spectral imaging. One embodiment of the SWIR light source may be an all-fiber integrated SWIR SC source, which leverages the mature technologies from the telecommunications and fiber optics industry. Exemplary fiber-based super-continuum sources may emit light in the near-infrared or SWIR between approximately 1.4-1.8 microns, 2-2.5 microns, 1.4-2.4 microns, 1-1.8 microns, or any number of other bands. In particular embodiments, the detection system may be a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

Breast cancer is considered to be the most common cancer among women in industrialized countries. It is believed that early diagnosis and consequent therapy could significantly reduce mortality. Mammography is considered the gold standard among imaging techniques in diagnosing breast pathologies. However, the use of ionizing radiation in mammography may have adverse effects and lead to other complications. Moreover, screening x-ray mammography may be limited by false positives and negatives, leading to unnecessary physical and psychological morbidity. Although breast cancer is one of the focuses of this disclosure, the same techniques may also be applied to other cancer types, including, for example, skin, prostate, brain, pancreatic, and colorectal cancer.

Diagnostic methods for assessment and therapy follow-up of breast cancer include mammography, ultrasound, and magnetic resonance imaging. The most effective screening technique at this time is x-ray mammography, with an overall sensitivity for breast cancer detection around 75%, which is even further reduced in women with dense breasts to around 62%. Moreover, x-ray mammography has a 22% false positive rate in women under 50, and the method cannot accurately distinguish between benign and malignant tumors. Magnetic resonance imaging and ultrasound are sometimes used to augment x-ray mammography, but they have limitations such as high cost, low throughput, limited specificity and low sensitivity. Thus, there is a continued need to detect cancers earlier for treatment, missed by mammography, and to add specificity to the procedures.

Optical breast imaging may be an attractive technique for breast cancer to screen early, augment with mammography, or use in follow-on treatments. Also, optical breast imaging may be performed by intrinsic tissue contrast alone (e.g., hemoglobin, water, collagen, and lipid content), or with the use of exogenous fluorescent probes that target specific molecules. For example, near-infrared (NIR) light may be used to assess optical properties, where the absorption and scattering by the tissue components may change with carcinoma. For most of the studies conducted to date, NIR light in the wavelength range of 600-1000 nm has been used for sufficient tissue penetration; these wavelengths have permitted imaging up to several centimeters deep in soft tissue. Optical breast imaging using fluorescent contrast agents may improve lesion contrast and may potentially permit detection of changes in breast tissue earlier. In one embodiment, the fluorescent probes may either bind specifically to certain targets associated with cancer or may non-specifically accumulate at the tumor site.

Optical methods of imaging and spectroscopy can be non-invasive using non-ionizing electromagnetic radiation, and these techniques could be exploited for screening of wide populations and for therapy monitoring. "Optical mammography" may be a diffuse optical imaging technique that aims at detecting breast cancer, characterizing its physiological and pathological state, and possibly monitoring the efficacy of the therapeutic treatment. The main constituents of breast tissue may be lipid, collagen, water, blood, and other structural proteins. These constituents may exhibit marked and characteristic absorption features in the NIR wavelength range. Thus, diffuse optical imaging and spectroscopy in the NIR may be helpful for diagnosing and monitoring breast cancer. Another advantage of such imaging is that optical instruments tend to be portable and more cost effective as compared to other instrumentation that is conventionally used for medical diagnosis. This can be particularly true, if the mature technologies for telecommunications and fiber optics are exploited.

Spectroscopy using NIR or short-wave infrared (SWIR) light may be beneficial, because most tissue has organic compounds that have overtone or combination absorption bands in this wavelength range (e.g., between approximately 0.8-2.5 microns). In one embodiment, a NIR or SWIR super-continuum (SC) laser that is an all-fiber integrated source may be used as the light source for diagnosing cancerous tissue. Exemplary fiber-based super-continuum sources may emit light in the NIR or SWIR between approximately 1.4-1.8 microns, 2-2.5 microns, 1.4-2.4 microns, 1-1.8 microns, or any number of other bands. In particular embodiments, the detection system may be one or more photo-detectors, a dispersive spectrometer, a Fourier transform infrared spectrometer, or a hyper-spectral imaging detector or camera. In addition, reflection or diffuse reflection light spectroscopy may be implemented using the SWIR light source, where the spectral reflectance can be the ratio of reflected energy to incident energy as a function of wavelength.

For breast cancer, experiments have shown that with growing cancer the collagen content increases while the lipid content decreases. Therefore, early breast cancer detection may involve the monitoring of absorption or scattering features from collagen and lipids. In addition, NIR spectroscopy may be used to determine the concentrations of hemoglobin, water, as well as oxygen saturation of hemoglobin and optical scattering properties in normal and cancerous breast tissue. For optical imaging to be effective, it may also be desirable to select the wavelength range that leads to relatively high penetration depths into the tissue. In one embodiment, it may be advantageous to use optical wavelengths in the range of about 1000-1400 nm. In another embodiment, it may be advantageous to use optical wavelengths in the range of about 1600-1800 nm. Higher optical power densities may be used to increase the signal-to-noise ratio of the detected light through the diffuse scattering tissue, and surface cooling or focused light may be beneficial for preventing pain or damage to the skin and outer layer surrounding the breast tissue. Since optical energy may be non-ionizing, different exposure times may be used without danger or harmful radiation.

SUMMARY

In one embodiment, a remote sensing system is disclosed. The remote sensing system comprises a human interface structure configured to be physically applied to a user that has an inward side facing the user and an outward side. A time-of-flight sensor is directly or indirectly attached to the outward side. The time-of-flight sensor comprises an array of laser diodes configured to generate laser light having one or more optical wavelengths between 600 nanometers and 1000 nanometers. At least one laser diode of the array comprises one or more Bragg reflectors. At least one of the laser diodes pulses at a modulation frequency between 10

Megahertz and 1 Gigahertz and has a phase associated with the modulation frequency. At least a portion of the laser light generated by the array of laser diodes is configured to be directed to an object. A detection system comprising at least one photo-detector, a lens and a spectral filter at an input to the at least one photo-detector. A processor processes digitized signals received from the at least one photo-detector. The detection system is configured to (i) measure a phase shift of at least a reflected portion of the laser light from the array of laser diodes reflected from the object relative to the at least a portion of the laser light generated by the array of laser diodes, (ii) measure a time-of-flight measurement of the at least a reflected portion of the laser light from the array of laser diodes reflected from the object relative to the at least a portion of the laser light generated by the array of laser diodes, and (iii) generate a first image of the object based at least in part on an amplitude of the at least a reflected portion of the laser light from the array of laser diodes reflected from the object. The detection system is configured to synchronize to the pulse of the at least one of the laser diodes. The processor is configured to generate the time-of-flight measurement. The remote sensing system including the processor further comprises a first camera system directly or indirectly attached to the outward side. The first camera system is coupled to a lens system and the processor. The first camera system is configured to capture a second image including at least a part of the object. The remote sensing system including the processor further being coupled to a second camera system directly or indirectly attached to the inward side. The second camera system is configured to be illuminated by one or more light emitting diodes generating incoherent light configured to operate in a near-infrared wavelength range, wherein the second camera system is configured to at least in part monitor one or more eyes of the user.

In another embodiment, a wearable system is disclosed. The wearable system comprises smart glasses configured to be worn by a user that comprise an outward side configured to be opposite an inward side facing the user. One or more cameras that are CMOS back-illuminated sensors attached to the outward side of the smart glasses and configured to capture a camera image or a camera video including an object. The one or more cameras are also configured to perform hand tracking for gesture analysis.

The smart glasses comprising touch sensors configured to accept user inputs and motion tracking sensors configured to track user movements. The smart glasses further comprise a processor, one or more displays attached to the inward side, speakers, and one or more microphones configured to receive sound inputs including voice control or interactions. The smart glasses including the processor are configured to be coupled to a smart phone for further processing capabilities. The wearable system including the processor is configured to be coupled to a non-transitory computer readable medium. Smart glasses data comprises the camera image, the camera video, the sound inputs, the gesture analysis or the user inputs. The smart glasses data is configured to serve as at least a part of an input to an artificial intelligence assistant configured to communicate with or operate on the processor. The artificial intelligence assistant comprises a multi-modal generative artificial intelligence model comprising a transformer including self-attention and positional encoding layers and is configured to perform computer vision processing and natural language processing. The multi-modal generative artificial intelligence model is configured to recognize at least some of the object captured in the camera image or the camera video.

In yet another embodiment, a measurement system is disclosed. The measurement system comprises an array of laser diodes configured to generate a light having an initial light intensity and one or more optical wavelengths. At least a portion of the one or more optical wavelengths is a near-infrared wavelength between 700 nanometers and 2500 nanometers. At least a portion of the array of laser diodes comprises one or more Bragg reflectors. The array of laser diodes is further coupled to driver electronics and one or more safety shut-offs. A beam splitter is configured to receive at least a portion of the light from the array of laser diodes and to direct at least some of the portion of the light from the array of laser diodes to an object. The beam splitter is further configured to separate a received portion of the light into a plurality of spatially separated lights. A detection system comprises a first camera system. The detection system further comprises one or more lenses and one or more spectral filters in front of at least a part of the first camera system. The detection system is further coupled to a processor configured to be coupled to a non-transitory computer readable medium. The detection system is configured to receive at least a portion of the plurality of spatially separated lights reflected from the object and configured to capture a first image. The detection system is further configured to be synchronized to the at least a portion of the array of laser diodes comprising Bragg reflectors. The measurement system including the processor is further configured to be coupled to an active illuminator comprising one or more semiconductor diodes that are pulsed. Light from the active illuminator is configured to be directed to at least a part of the object. The detection system further configured to receive at least a portion of the light from the active illuminator reflected from the object and configured to capture a second image. The detection system is also configured to be synchronized to the pulsing of the one or more semiconductor diodes. The measurement system including the processor is configured to combine at least a portion of the first image and at least a portion of the second image to create a combined image. The measurement system including the processor further being coupled to a second camera system configured to be illuminated by one or more light emitting diodes generating incoherent light configured to operate in a near-infrared wavelength range. The second camera system is configured to at least in part monitor one or more eyes of a user.

BRIEF DESCRIPTION OF THE DRAWINGS

For a more complete understanding of the present disclosure, and for further features and advantages thereof, reference is now made to the following description taken in conjunction with the accompanying drawings, in which:

FIG. 9 shows a schematic of the human skin. In particular, the dermis may comprise significant amounts of collagen, elastin, lipids, and water.

FIG. 58A lists possible band assignments for the various spectral features in pure heroin.

FIG. 58B also lists possible band assignments for the various spectral features in pure heroin.

Figure 81:
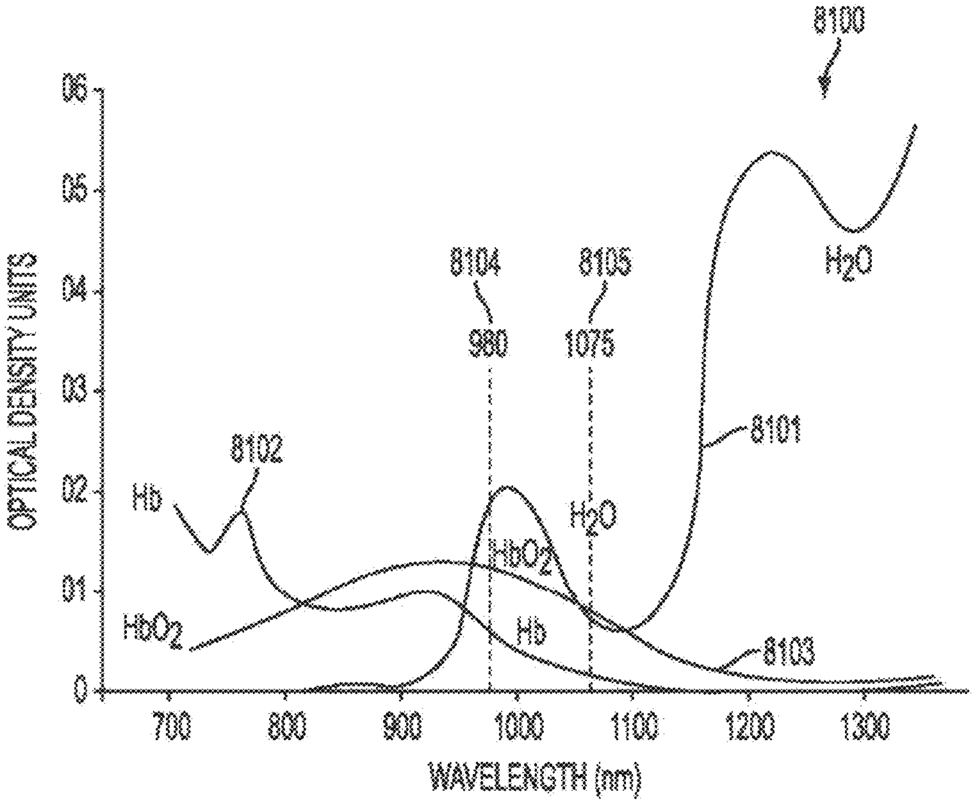

FIG. 81 illustrates the optical absorption or density as a function of wavelength between approximately 700 nm and 1300 nm for water, hemoglobin and oxygenated hemoglobin.

Figure 82:
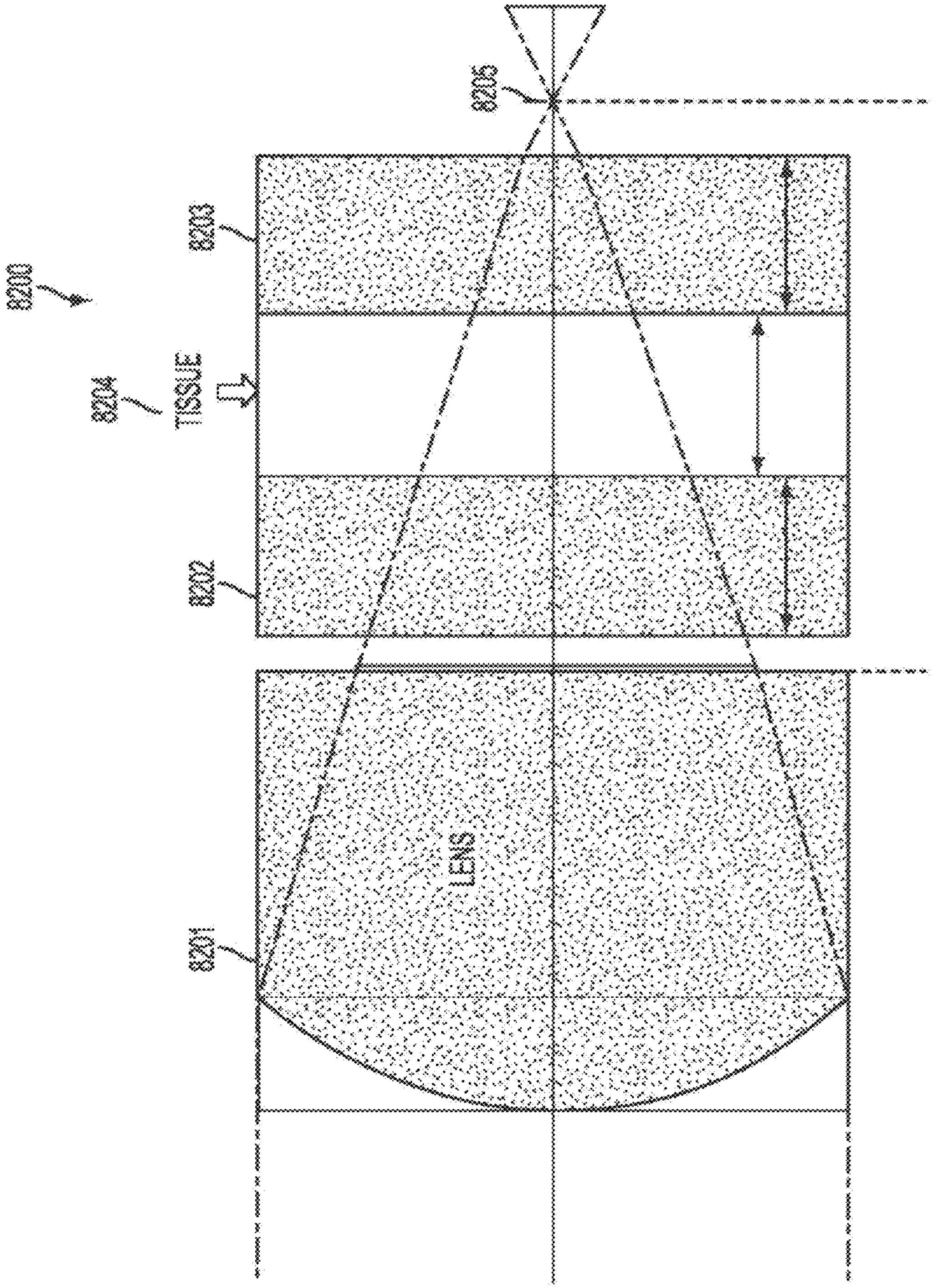

FIG. 82 shows a set-up used for in vitro damage experiments using focused infrared light. After a lens system, the tissue is placed between two microscope slides.

Figure 83A:
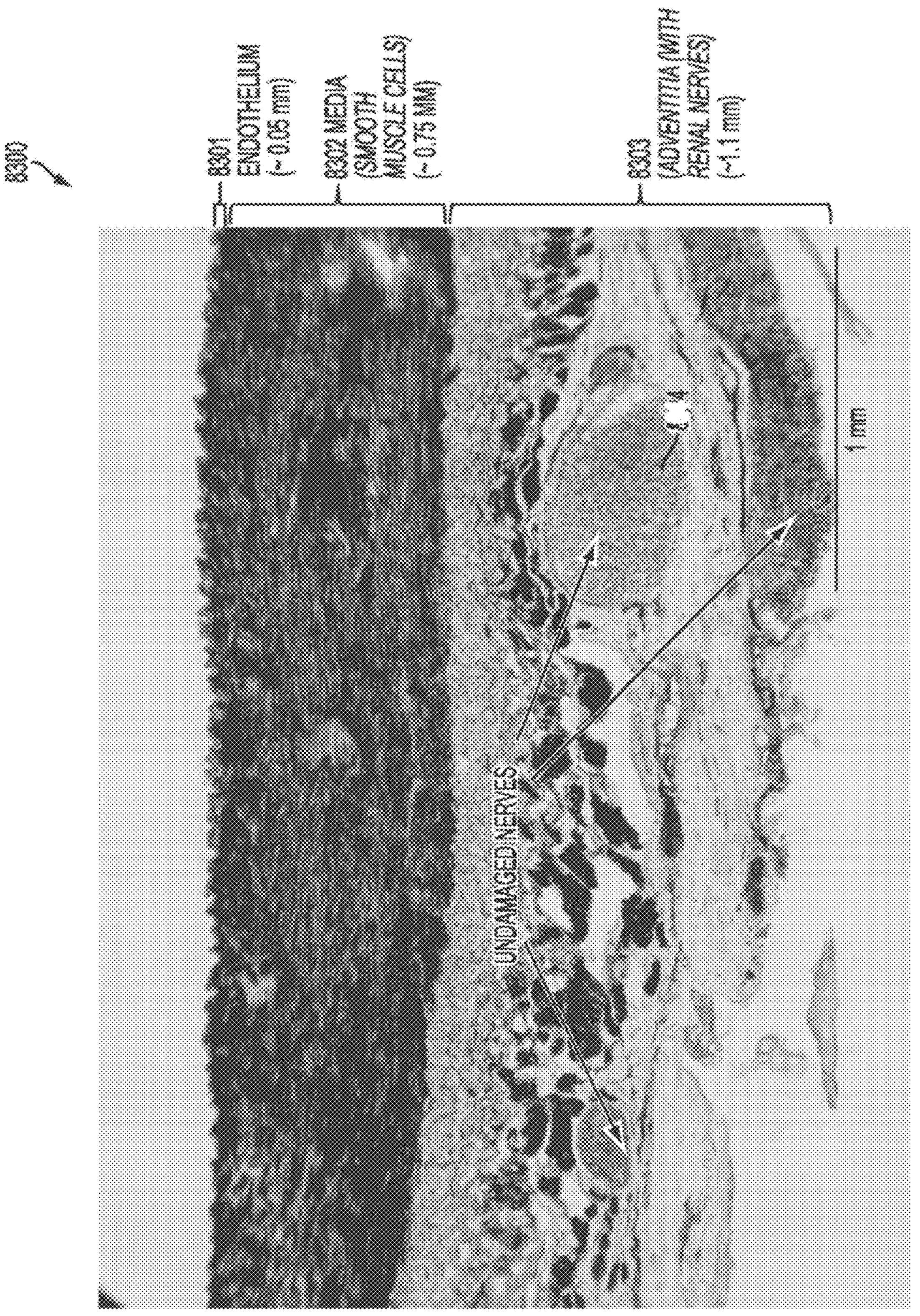

FIG. 83A presents histology of renal arteries comprising endothelium, media and adventitia layers and some renal nerves in or below the adventitia and illustrates renal arteries with no laser exposure.

Figure 83B:
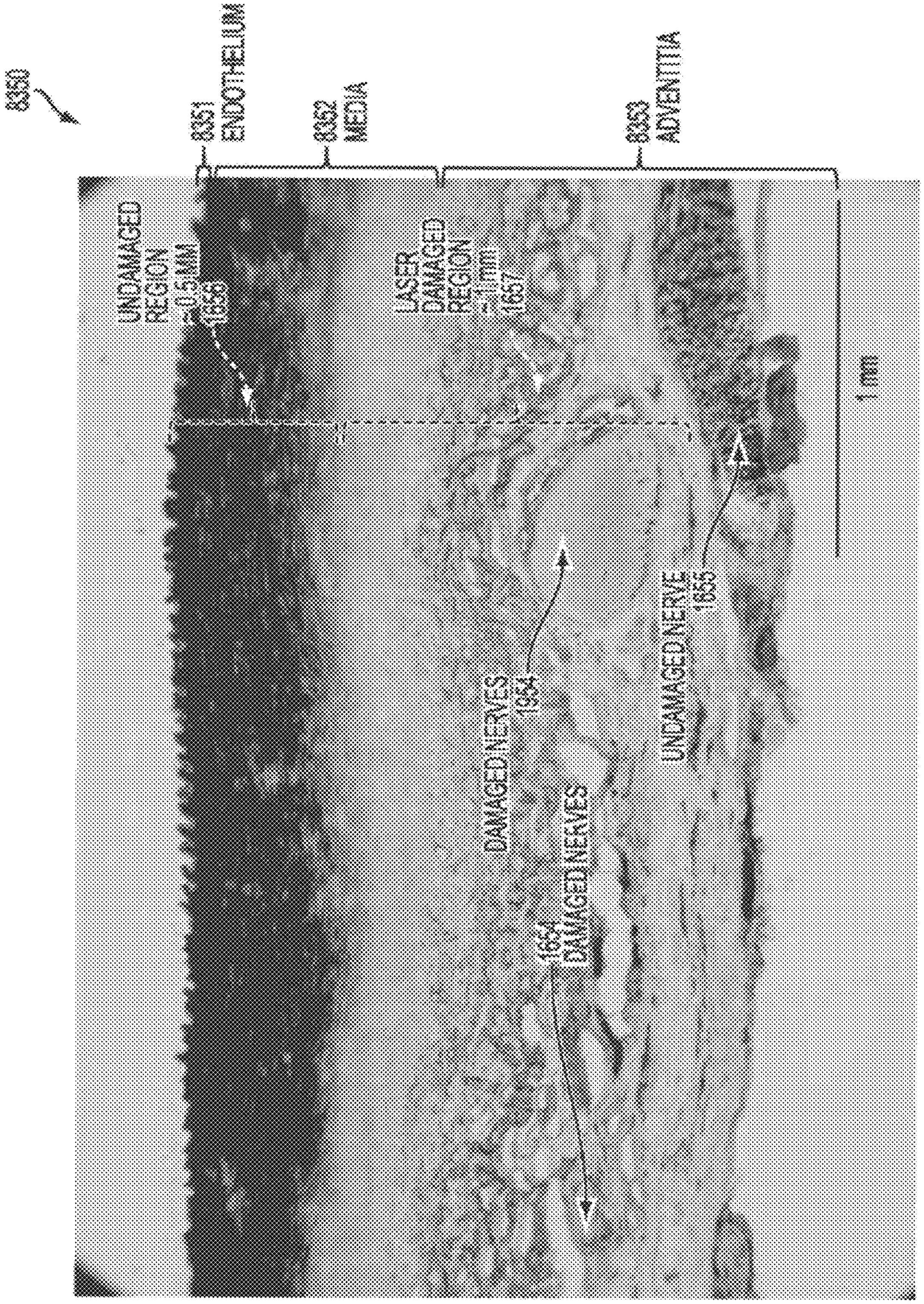

FIG. 83B presents histology of renal arteries comprising endothelium, media and adventitia layers and some renal nerves in or below the adventitia and illustrates renal arteries after focused laser exposure, with the laser light near 1708 nm.

Figure 84:
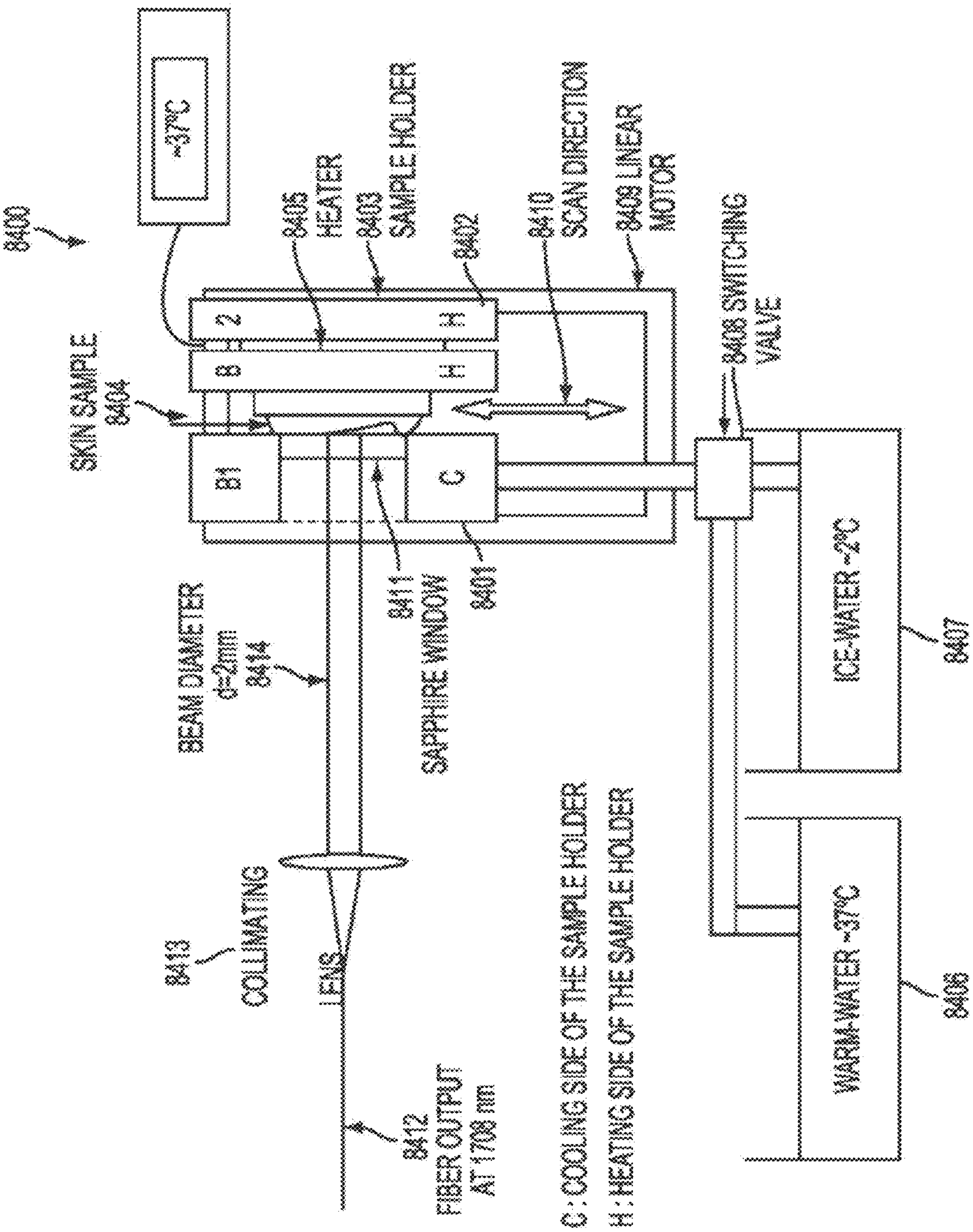

FIG. 84 illustrates the experimental set-up for ex vivo skin laser treatment with surface cooling to protect the epidermis and top layer of the dermis.

Figures 85A, 85B, 85C, 85D:
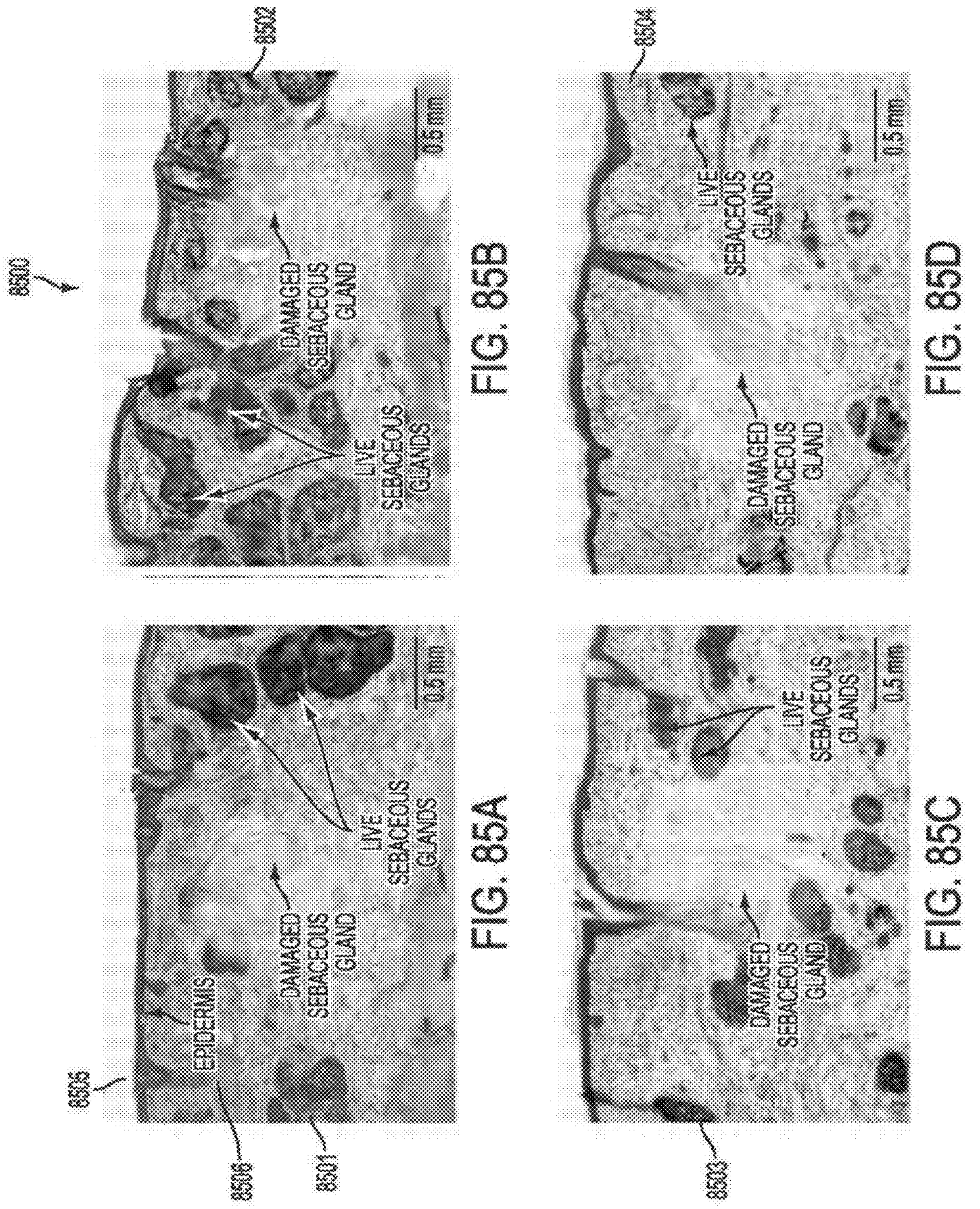

FIG. 85A shows MTT histo-chemistry of ex vivo human skin treated with ~1708 nm laser and cold window (5 seconds precool; 2 mm diameter spot exposure for 3 seconds) at 725 mW corresponding to ~70 J/cm2 average fluence.

FIG. 85B also shows MTT histo-chemistry of ex vivo human skin treated with ~1708 nm laser and cold window (5 seconds precool; 2 mm diameter spot exposure for 3 seconds) at 725 mW corresponding to ~70 J/cm2 average fluence.

FIG. 85C shows MTT histo-chemistry of ex vivo human skin treated with ~1708 nm laser and cold window (5 seconds precool; 2 mm diameter spot exposure for 3 seconds) at 830 mW corresponding to ~80 J/cm2 average fluence.

FIG. 85D also shows MTT histo-chemistry of ex vivo human skin treated with ~1708 nm laser and cold window (5 seconds precool; 2 mm diameter spot exposure for 3 seconds) at 830 mW corresponding to ~80 J/cm2 average fluence.

Figure 86A:
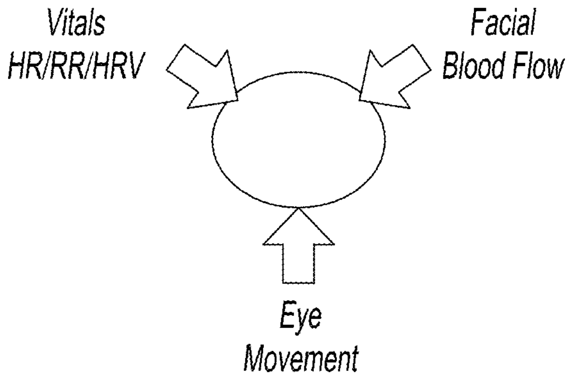

FIG. 86A illustrates that the Camera-based System combined with Processing (CSP) may evaluate multiple pieces of information on a person's face, such as facial blood flow, eye movements (such as eye blinks, gaze direction, pupil dilation, and percent of eye closure), and vital signs/physiological parameters (such as heart rate, respiratory rate, and heart rate variability).

Figure 86B:
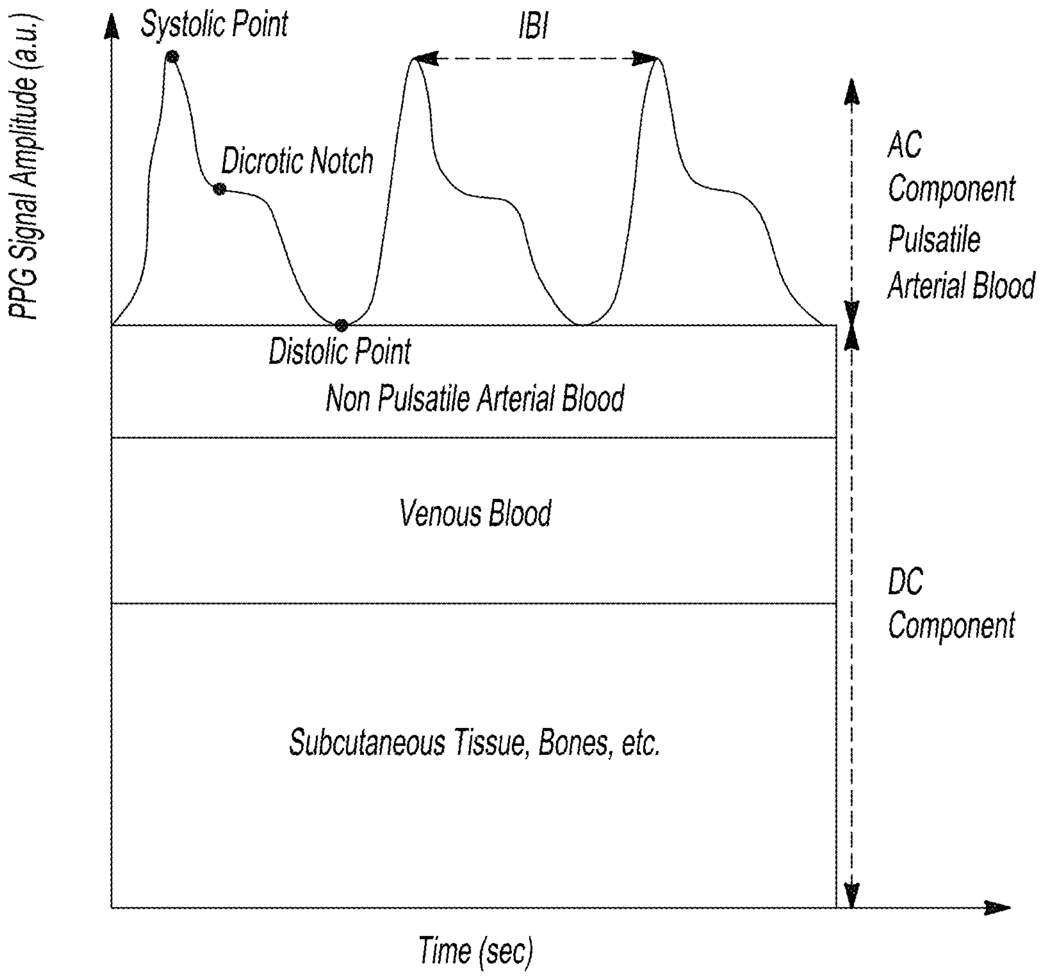

FIG. 86B shows the photo-plethysmography (PPG) signal with a pulsating AC component and more-or-less steady DC component.

Figure 86C:
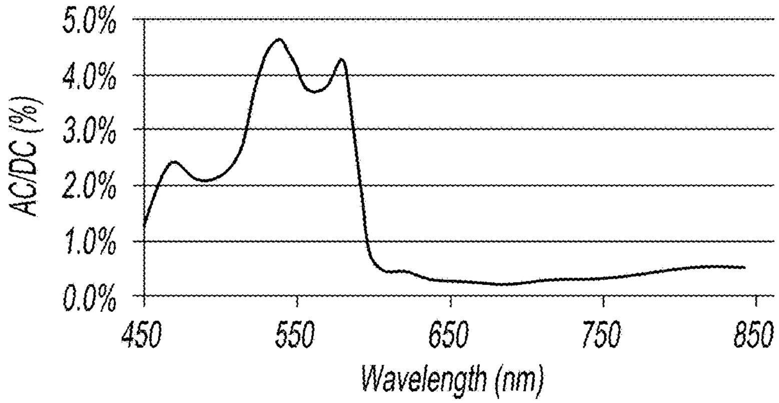

FIG. 86C shows the wavelength dependence of the AC/DC ratio of a reflection based PPG signal.

Figure 86D:
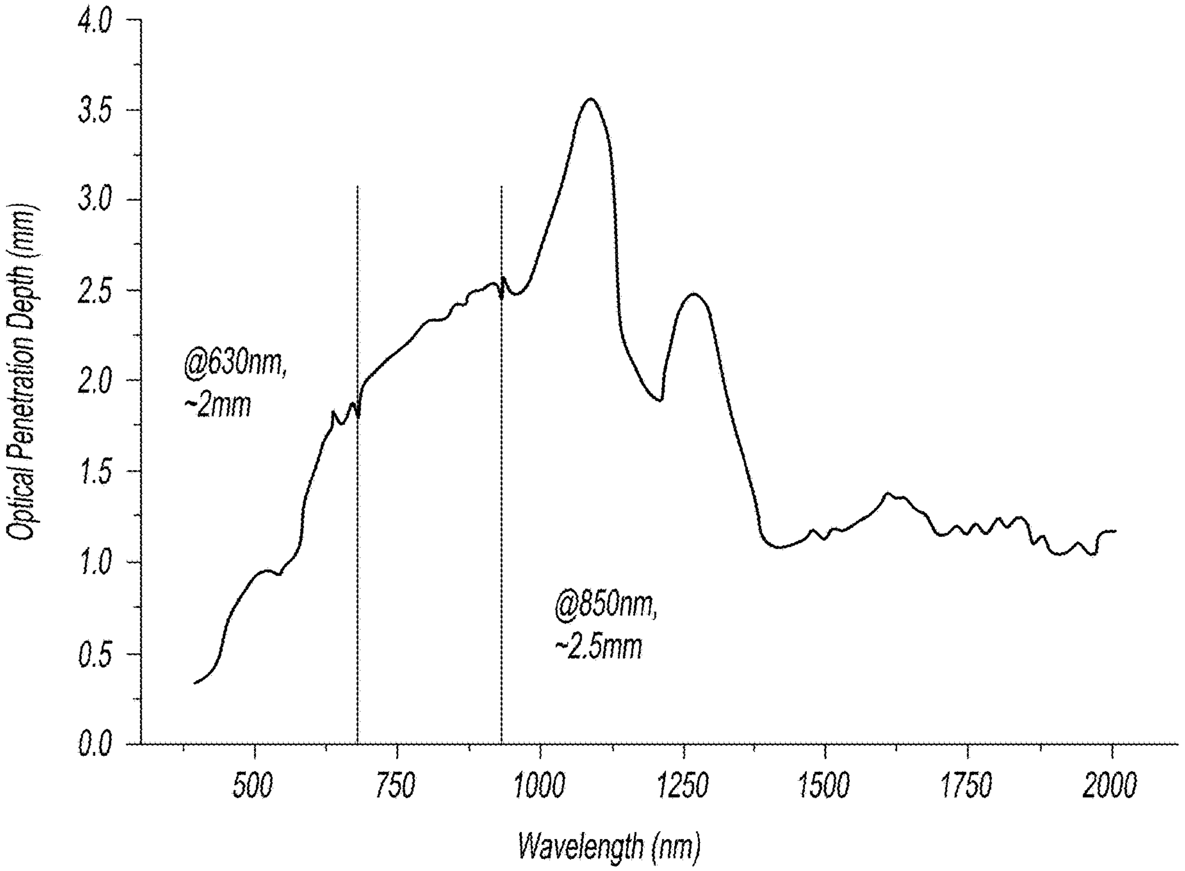

FIG. 86D illustrates the optical penetration depth of human skin as a function of wavelength. Green light is approximately 530 nm, red light is approximately 630 nm, and exemplary near-infrared wavelengths include 850 nm, 905 nm, 940 nm or 1064 nm.

Figure 87A:
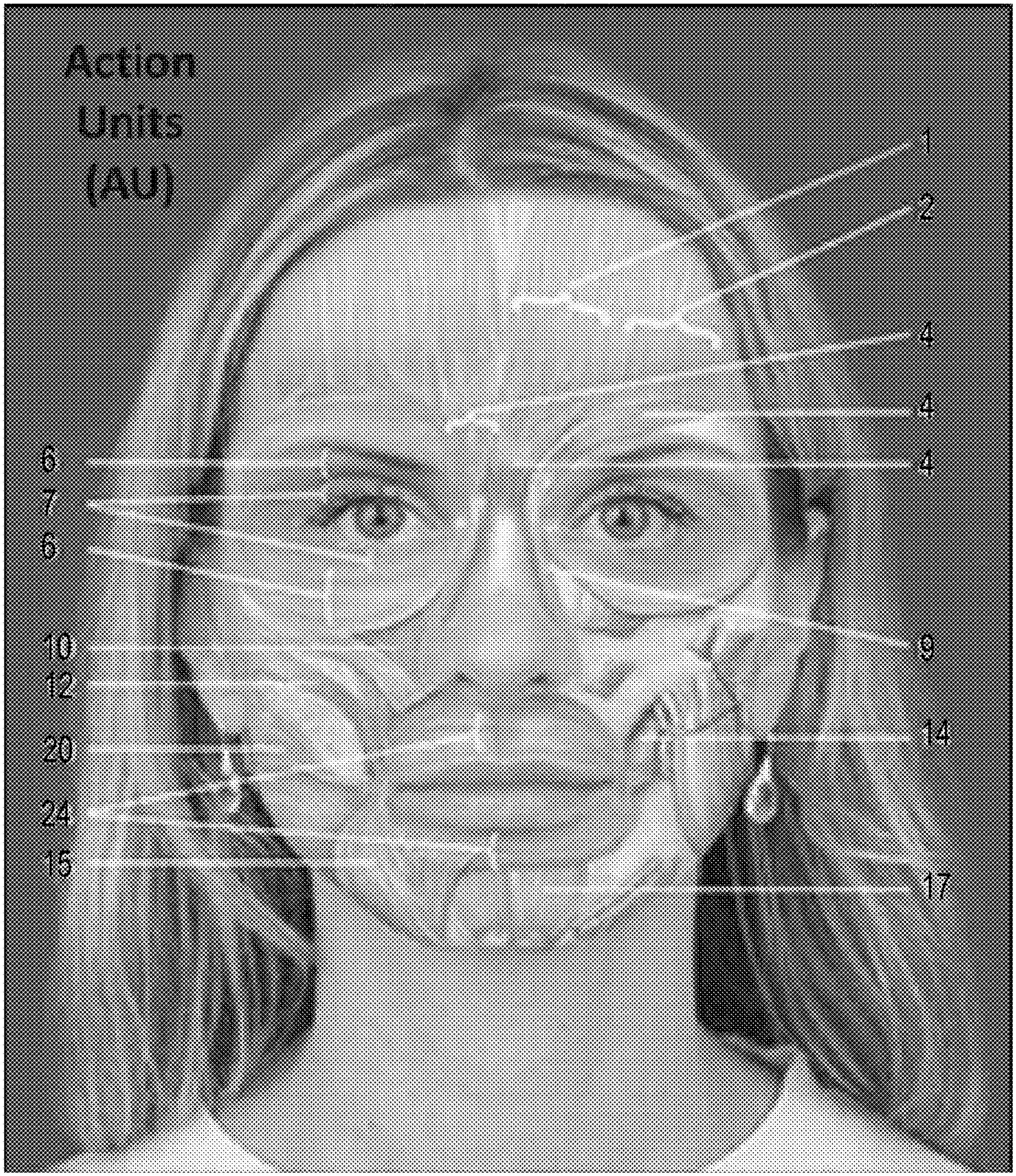

FIG. 87A shows some of the muscles on the face that lie below the skin, and the numbers point to different activation of muscles that are represented by different Action Units (AU).

Figure 87B:
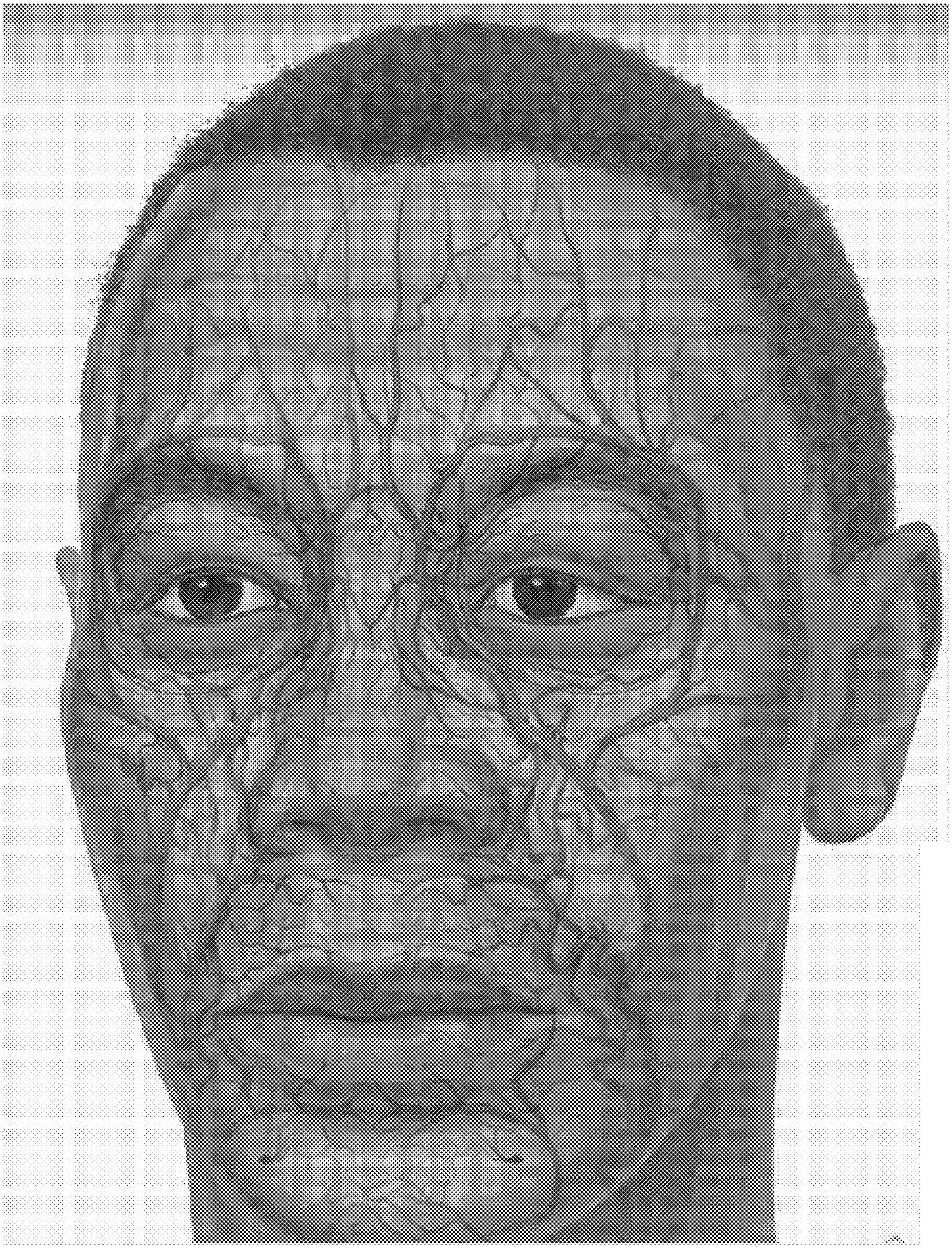

FIG. 87B illustrates some of the blood vessels near the surface of the skin in the face, including arteries and veins.

Figure 88:
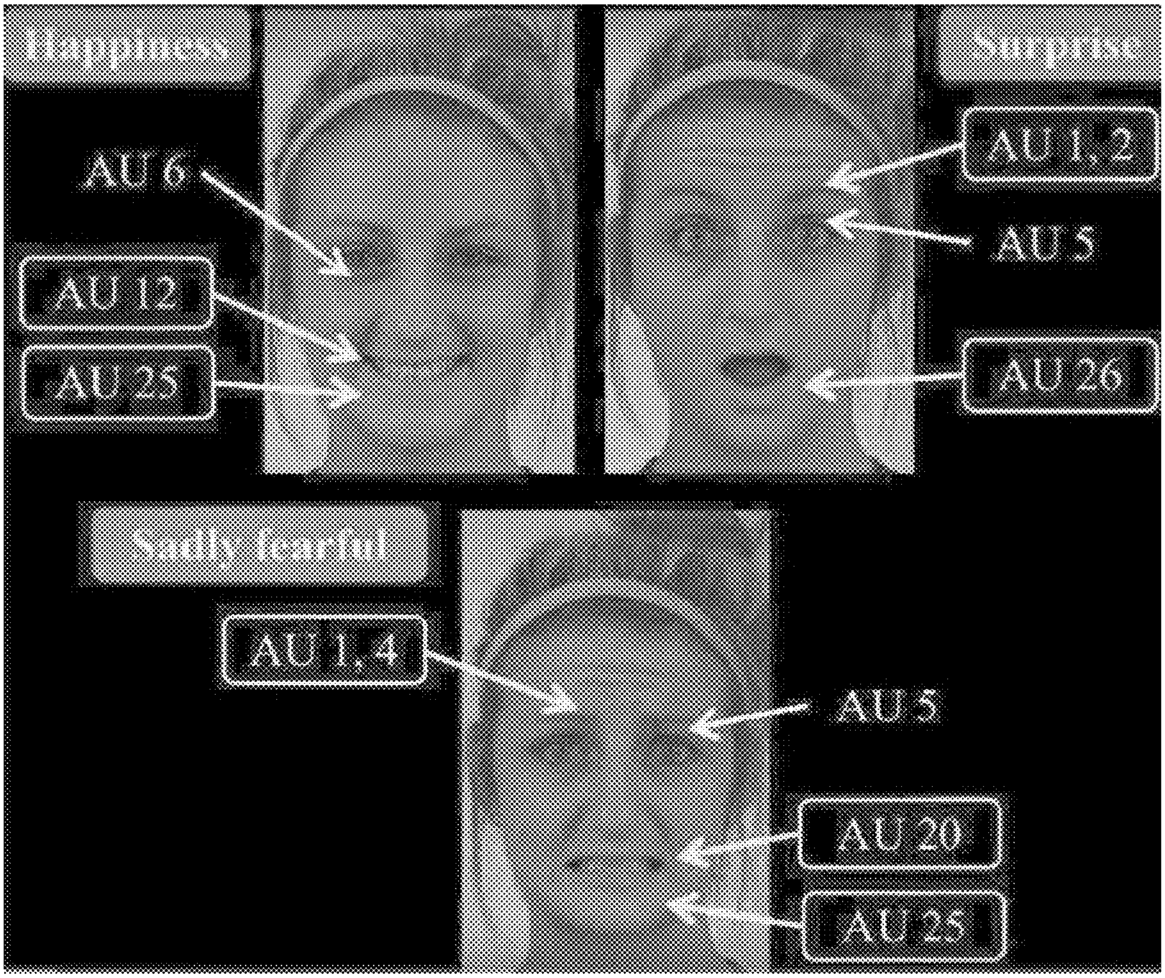

FIG. 88 shows some of the facial expressions and the corresponding action units that are activated to achieve the facial expression corresponding to happiness, surprise, or sadly fearful.

Figure 89A:
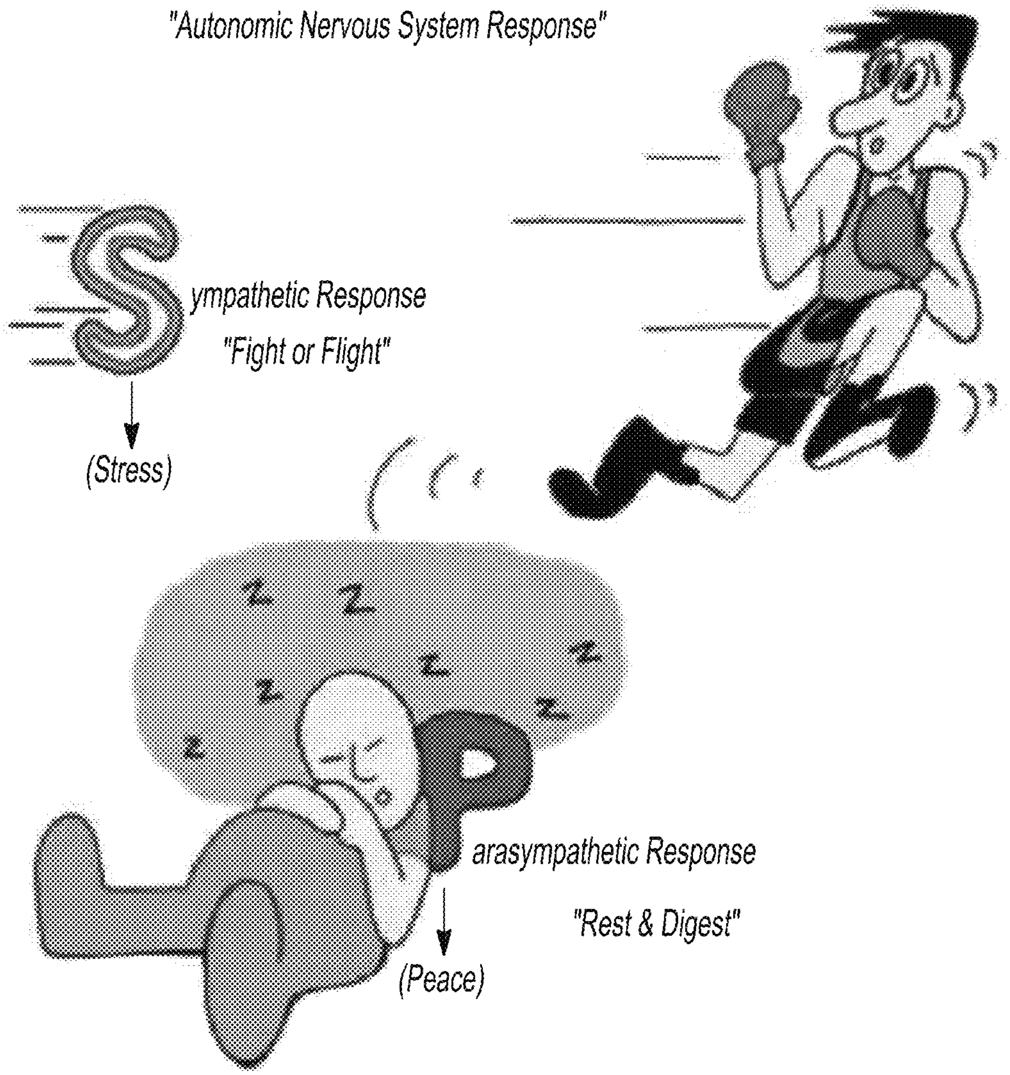
Figure 89B:
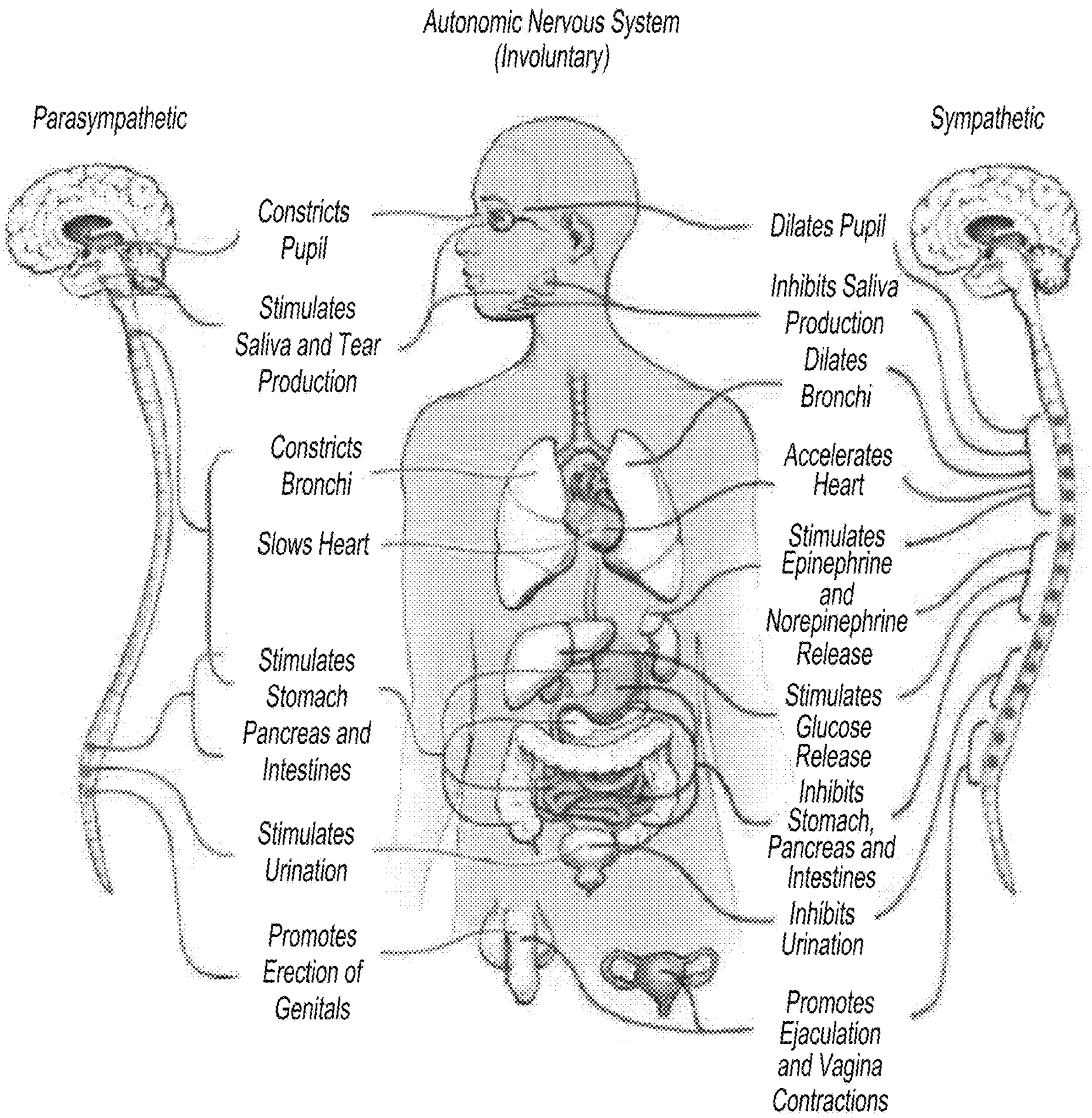

FIG. 89 shows on the left that the autonomic nervous system has two branches, the sympathetic "fight or flight" and the parasympathetic "rest and digest." The right side shows some of the bodily functions controlled by different branches of the autonomic nervous system.

FIG. 90 illustrates on the top an exemplary flow chart of the steps for a method for eye blink and closure detection. The bottom show that the eye aspect ratio (EAR) may be determined using the coordinates on the eye pictures, P1 through P6.

Figure 91:
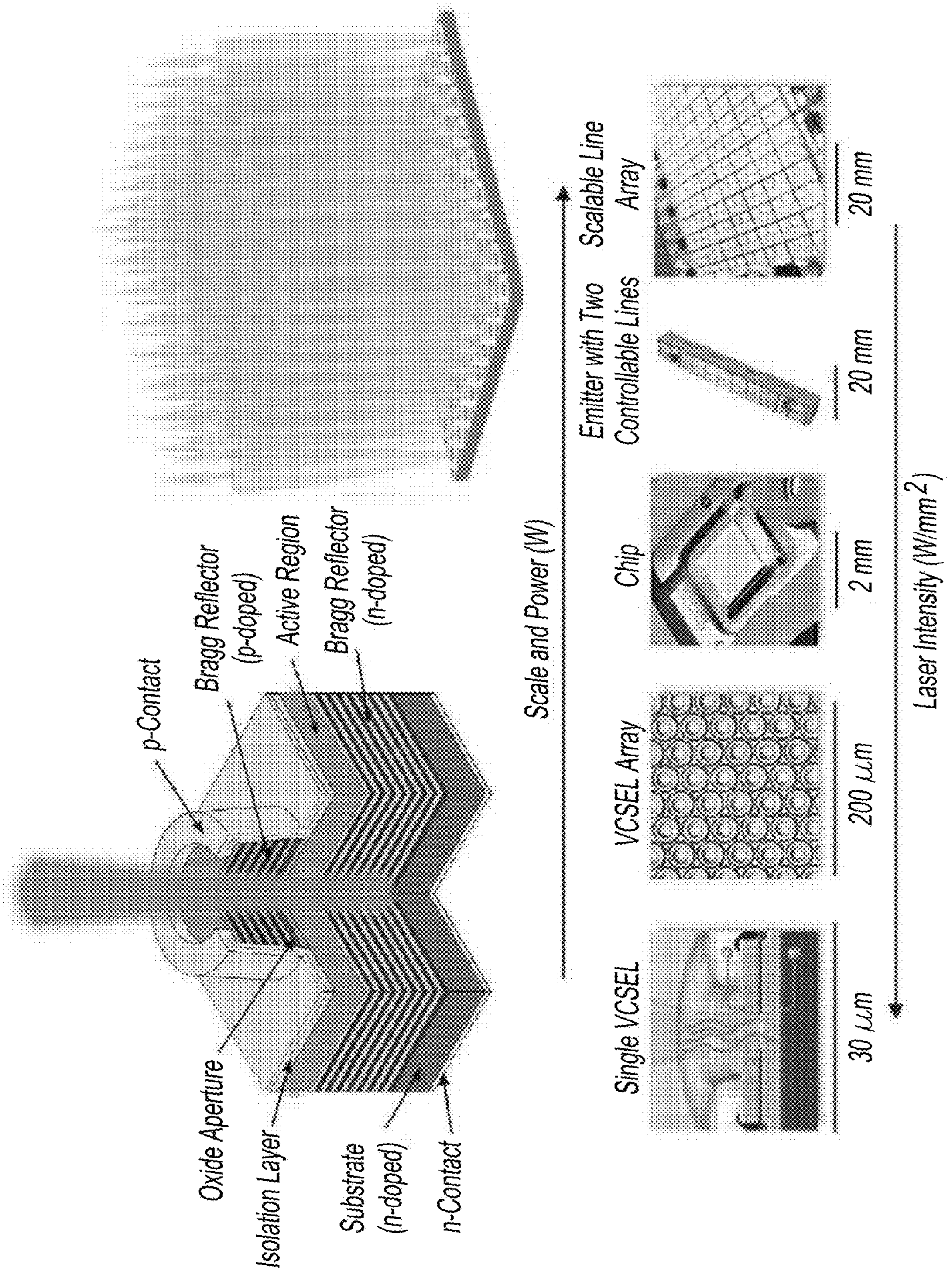

FIG. 91 top left shows a cut-away cross-section of an exemplary vertical cavity surface emitting laser (VCSEL) device. The top right shows that the beam from an array of VCSELs can be spatially combined to increase the output power level. The bottom shows from left to right a single VCSEL, a VCSEL array, a VCSEL chip, and emitter array with two controllable lines, and a scalable 2D VCSEL array.

Figure 92:
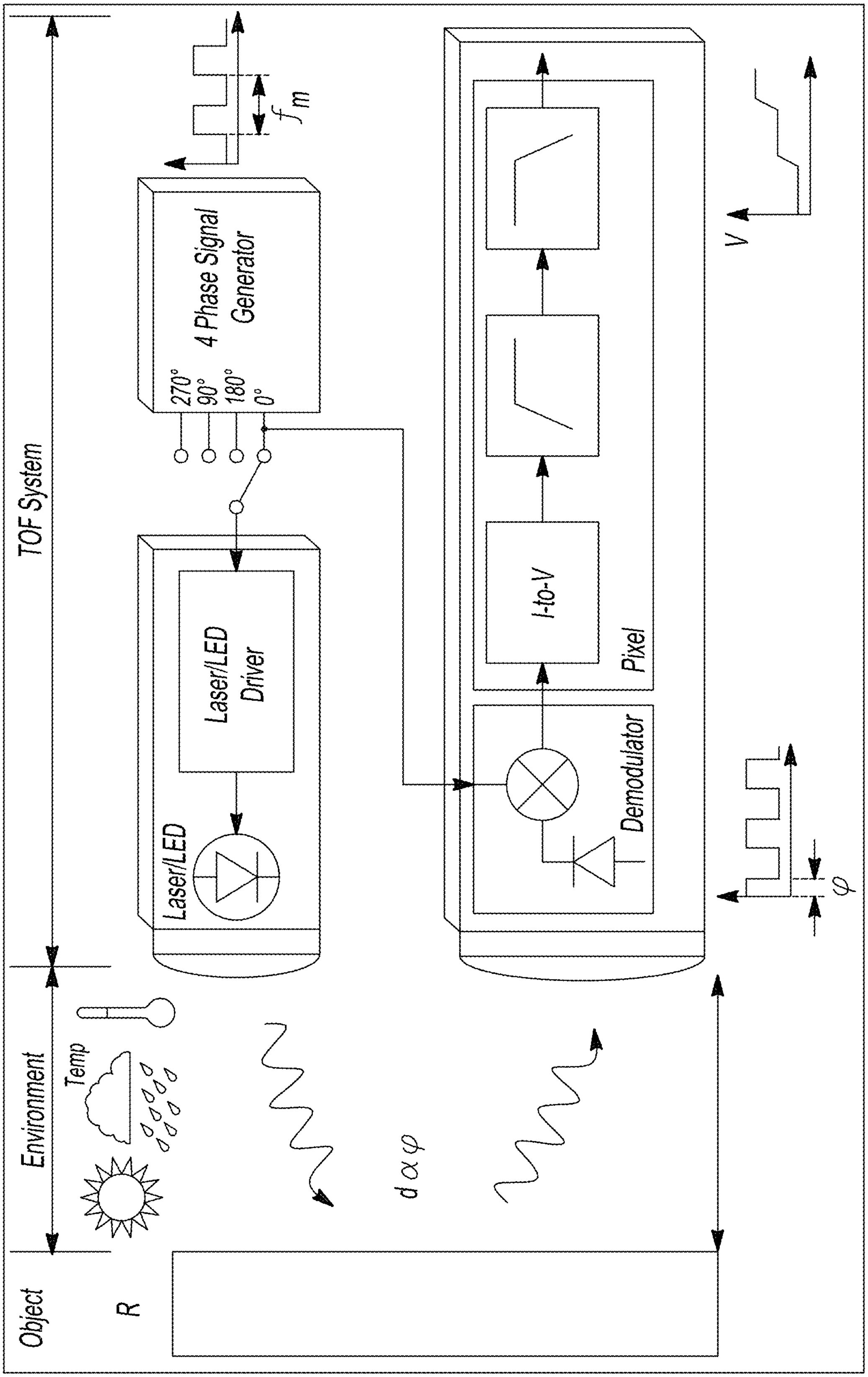

FIG. 92 illustrates an exemplary block diagram of a model of a pixel for an indirect time-of-flight (iToF) sensor.

Figure 93:
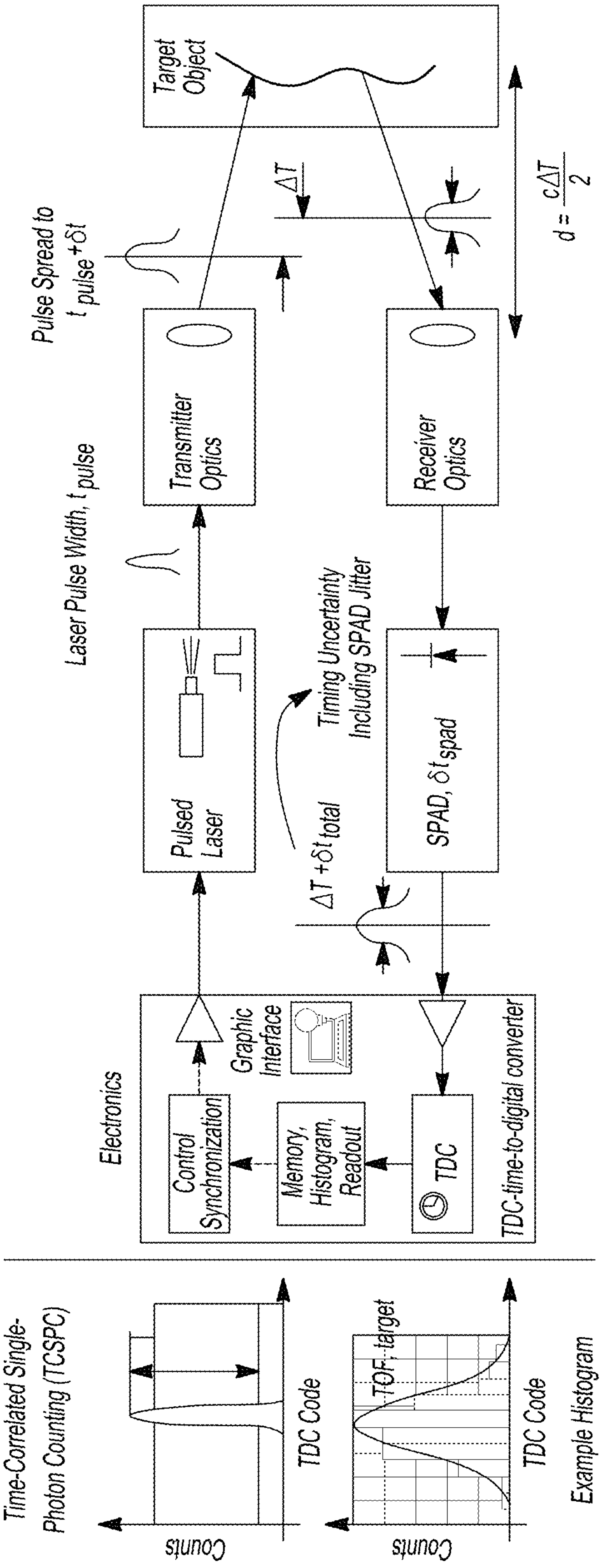

FIG. 93 shows an exemplary block diagram of a direct time-of-flight (dToF) sensor.

Figure 94:
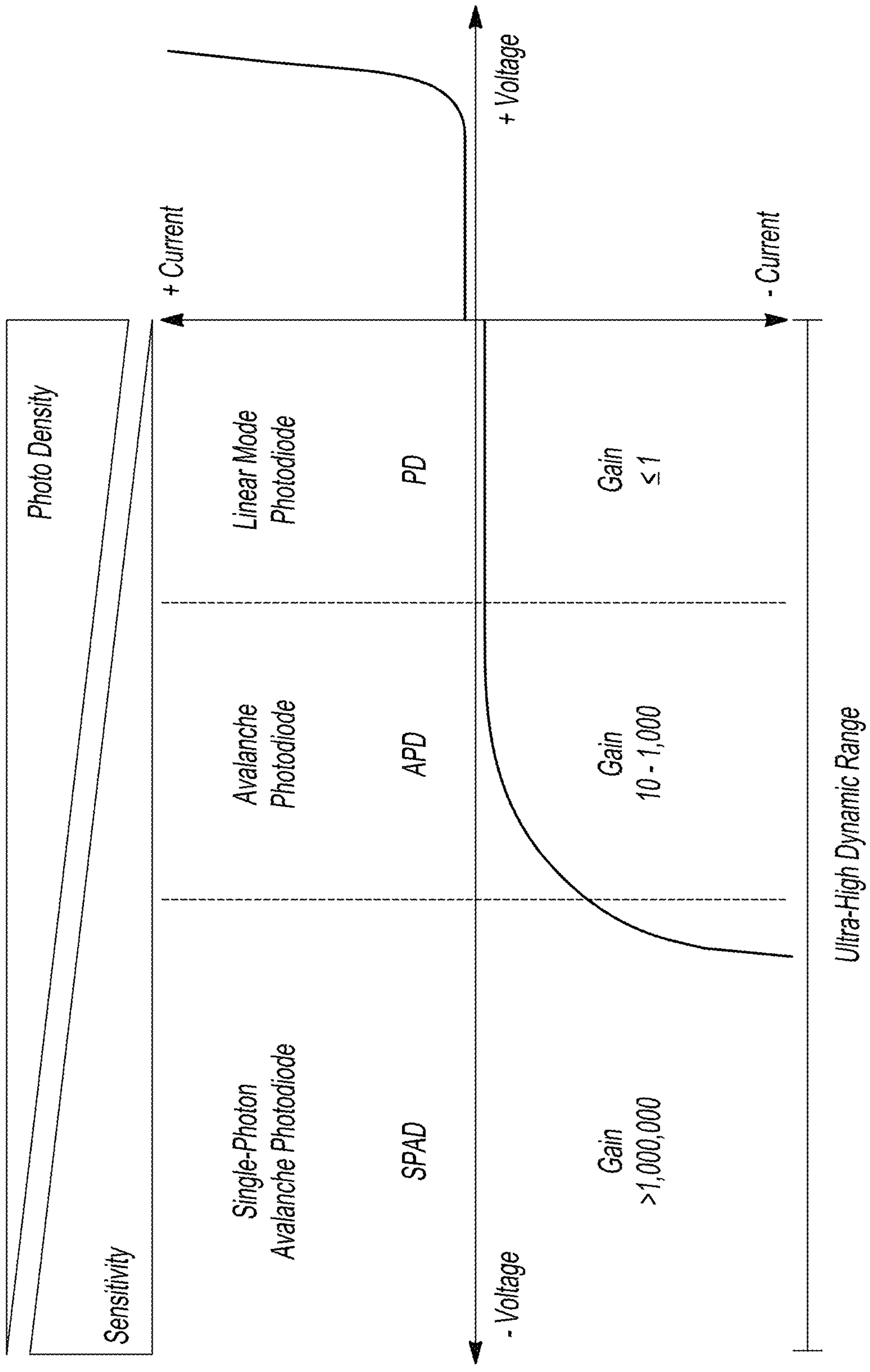

FIG. 94 illustrates that single-photon avalanche photodiodes (SPADs) are p-n junction photo-diodes where the junction is biased well above (in this case toward the left) its reverse bias breakdown voltage.

Figure 95:
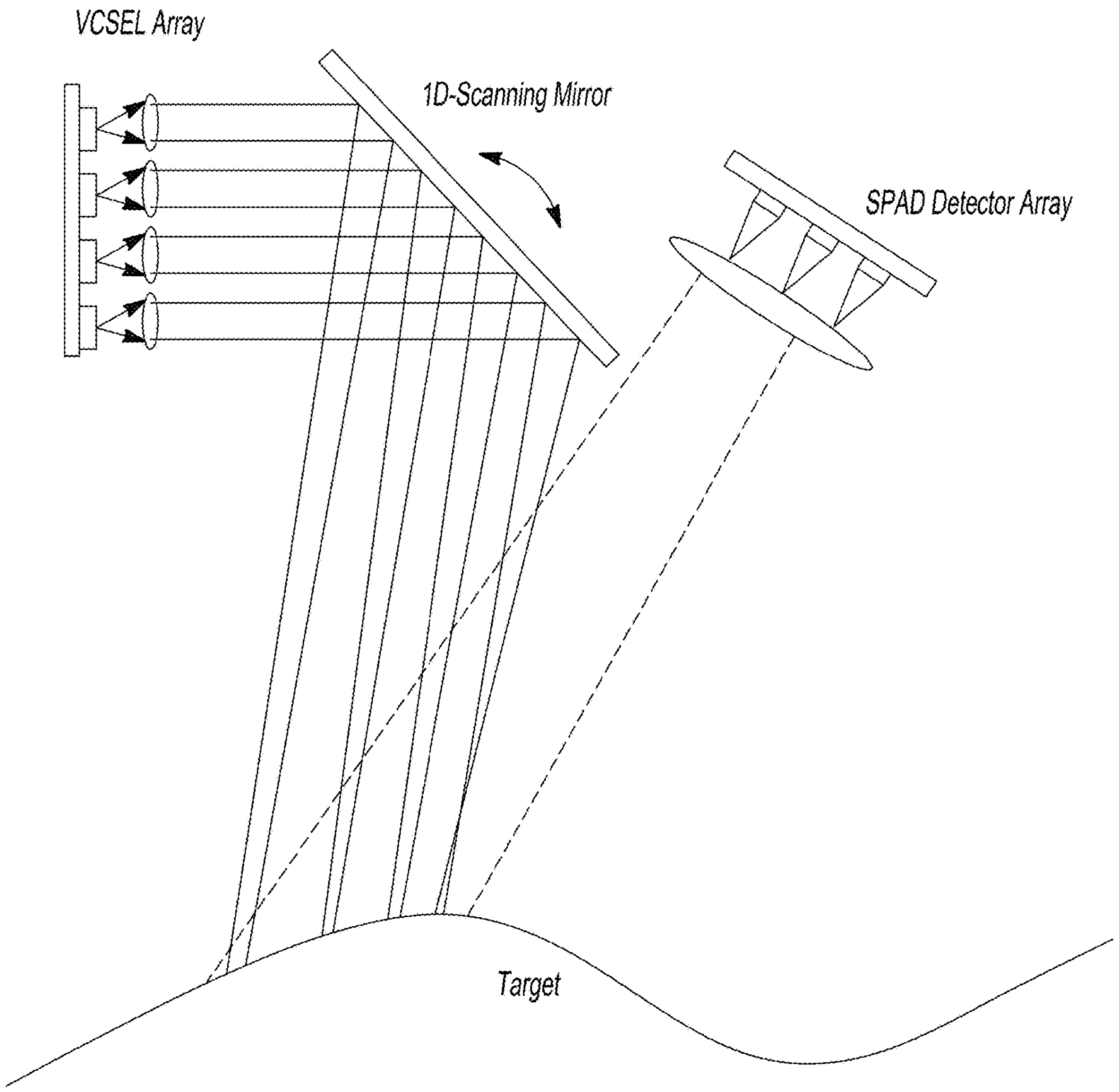

FIG. 95 illustrates an exemplary configuration for a one-dimensional line scan where a scanning mirror is placed after the light source and scans a line across the target that in turn reaches the detector array.

Figure 96:
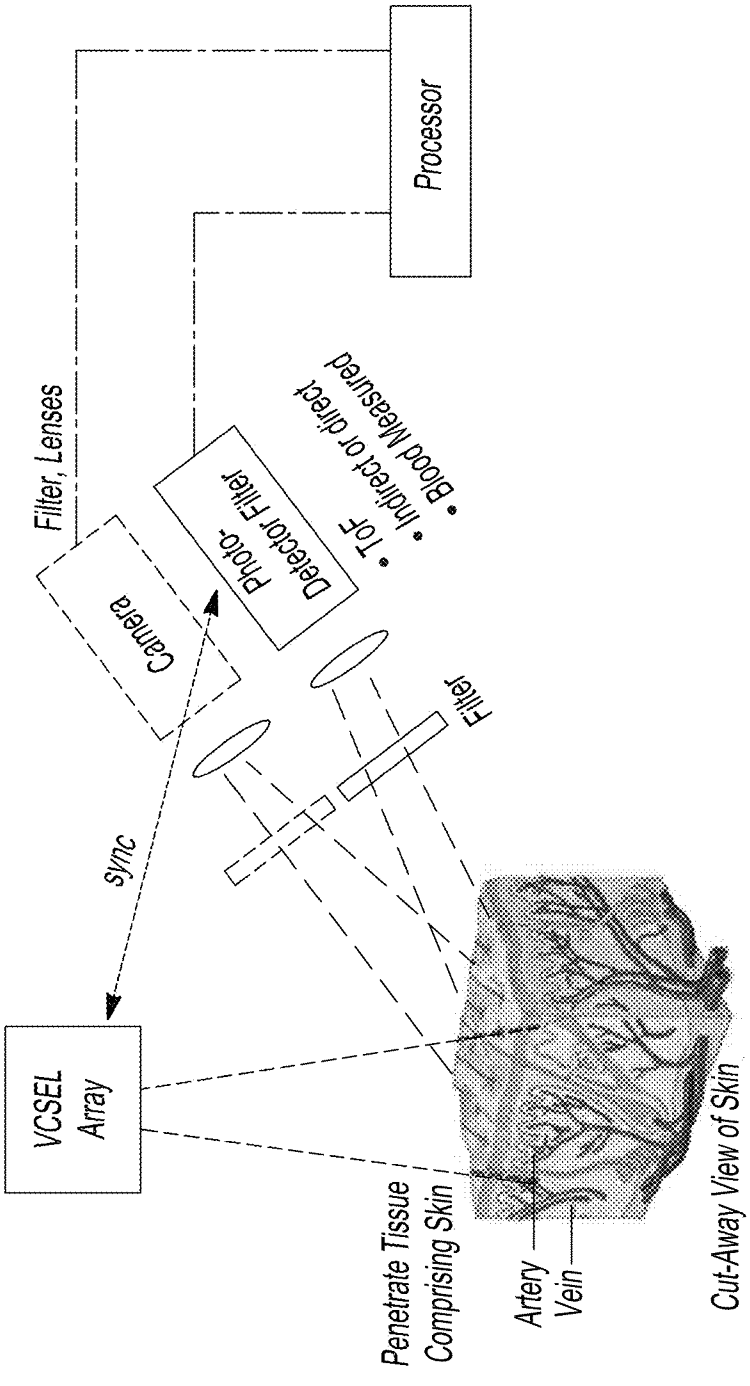

FIG. 96 shows a preferred embodiment of the CSP system. The light source may be a one or more VCSELs or VCSEL arrays, whose light may be incident on and penetrate tissue comprising skin. Some of the reflected light may be captured by one or more photo-detectors or a photo-detector array and/or a RGB or NIR camera. There may be spectral filters and/or lenses placed in front of the photo-detectors and/or camera. The photo-detector and camera signals may be co-registered, and the outputs from the photo-detector and camera may be sent to a processor.

DETAILED DESCRIPTION

Section 1: Near-Infrared Lasers for Non-Invasive Monitoring of Glucose, Ketones, HbA1c, and Other Blood Constituents As required, detailed embodiments of the present disclosure are described herein; however, it is to be understood that the disclosed embodiments are merely exemplary of the disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Various ailments or diseases may require measurement of the concentration of one or more blood constituents. For example, diabetes may require measurement of the blood glucose and HbA1c levels. On the other hand, diseases or disorders characterized by impaired glucose metabolism may require the measurement of ketone bodies in the blood. Examples of impaired glucose metabolism diseases include Alzheimer's, Parkinson's, Huntington's, and Lou Gehrig's or amyotrophic lateral sclerosis (ALS). Techniques related to near-infrared spectroscopy or hyper-spectral imaging may be particularly advantageous for non-invasive monitoring of some of these blood constituents.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

Spectrum for Glucose

Figure 1:
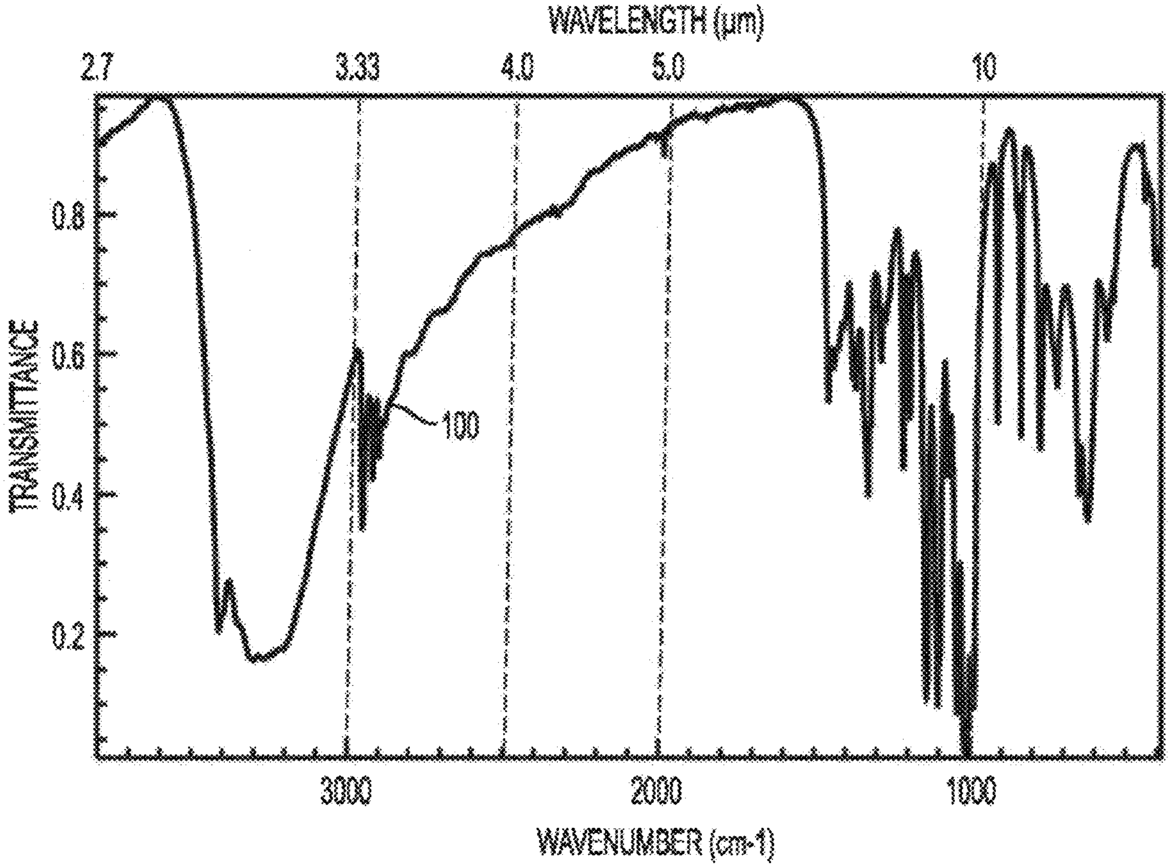
FIG. 1 plots the transmittance versus wavenumber for glucose in the mid-wave and long-wave infrared wavelengths between approximately 2.7 to 12 microns.

One molecule of interest is glucose. The glucose molecule has the chemical formula C6H12O6, so it has a number of hydro-carbon bonds. An example of the infrared transmittance of glucose 100 is illustrated in FIG. 1. The vibrational spectroscopy shows that the strongest lines for bending and stretching modes of C—H and O—H bonds lie in the wavelength range of approximately 6-12 microns. However, light sources and detectors are more difficult in the mid-wave infrared and long-wave infrared, and there is also strongly increasing water absorption in the human body beyond about 2.5 microns. Although weaker, there are also non-linear combinations of stretching and bending modes between about 2 to 2.5 microns, and first overtone of C—H stretching modes between approximately 1.5-1.8 microns. These signatures may fall in valleys of water absorption, permitting non-invasive detection through the body. In addition, there are yet weaker features from the second overtones and higher-order combinations between about 0.8-1.2 microns; in addition to being weaker, these features may also be masked by absorption in the hemoglobin. Hence, the short-wave infrared (SWIR) wavelength range of approximately 1.4 to 2.5 microns may be an attractive window for near-infrared spectroscopy of blood constituents.

Figure 2:
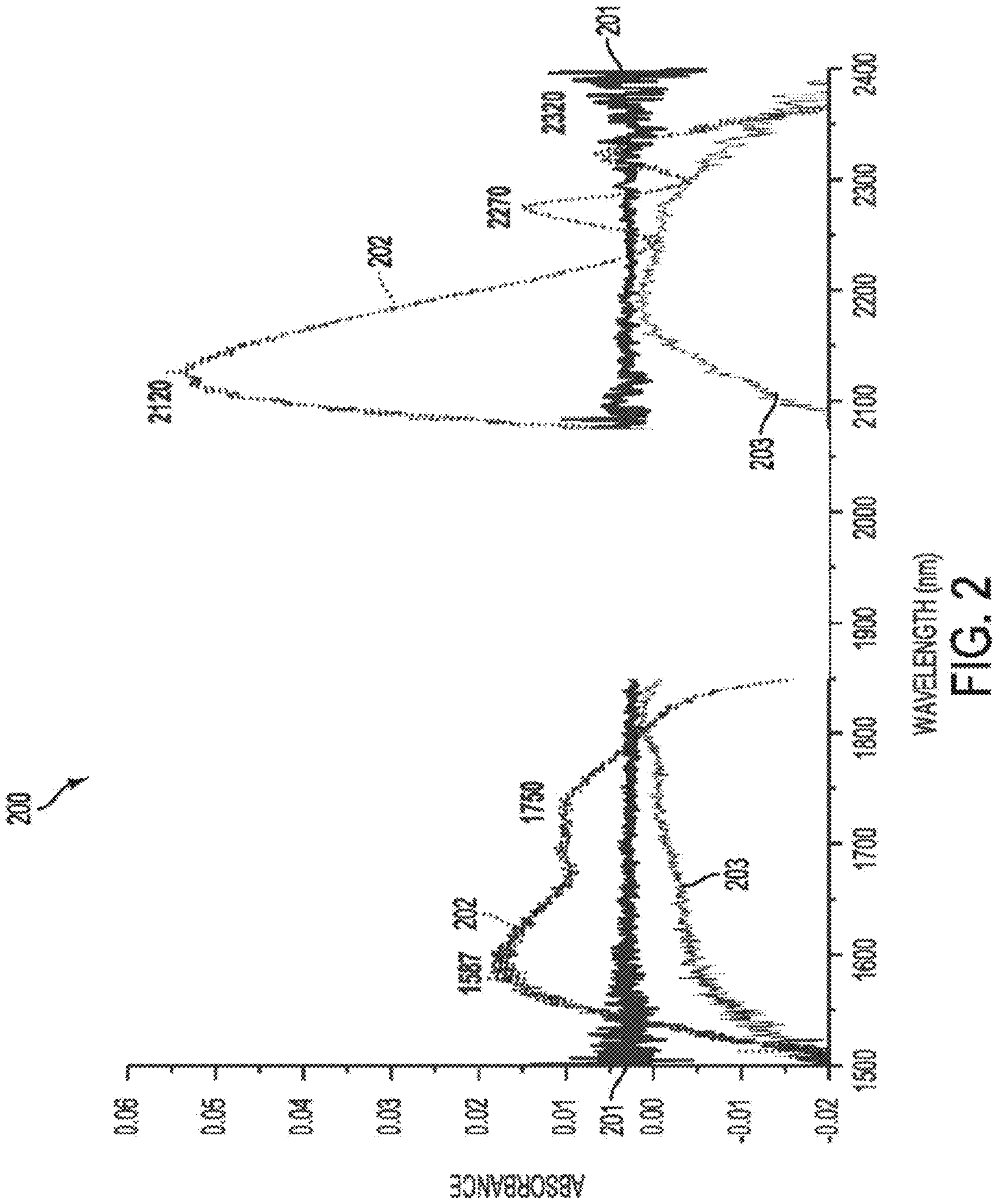
FIG. 2 illustrates measurements of the absorbance of different blood constituents, such as glucose, hemoglobin, and hemoglobin A1c. The measurements are done using an FTIR spectrometer in samples with a 1 mm path length.

As an example, measurements of the optical absorbance 200 of hemoglobin, glucose and HbA1c have been performed using a Fourier-Transform Infrared Spectrometer—FTIR. As FIG. 2 shows, in the SWIR wavelength range hemoglobin is nearly flat in spectrum 201 (the noise at the edges is due to the weaker light signal in the measurements). On the other hand, the glucose absorbance 202 has at least five distinct peaks near 1587 nm, 1750 nm, 2120 nm, 2270 nm and 2320 nm.

Figure 3A:
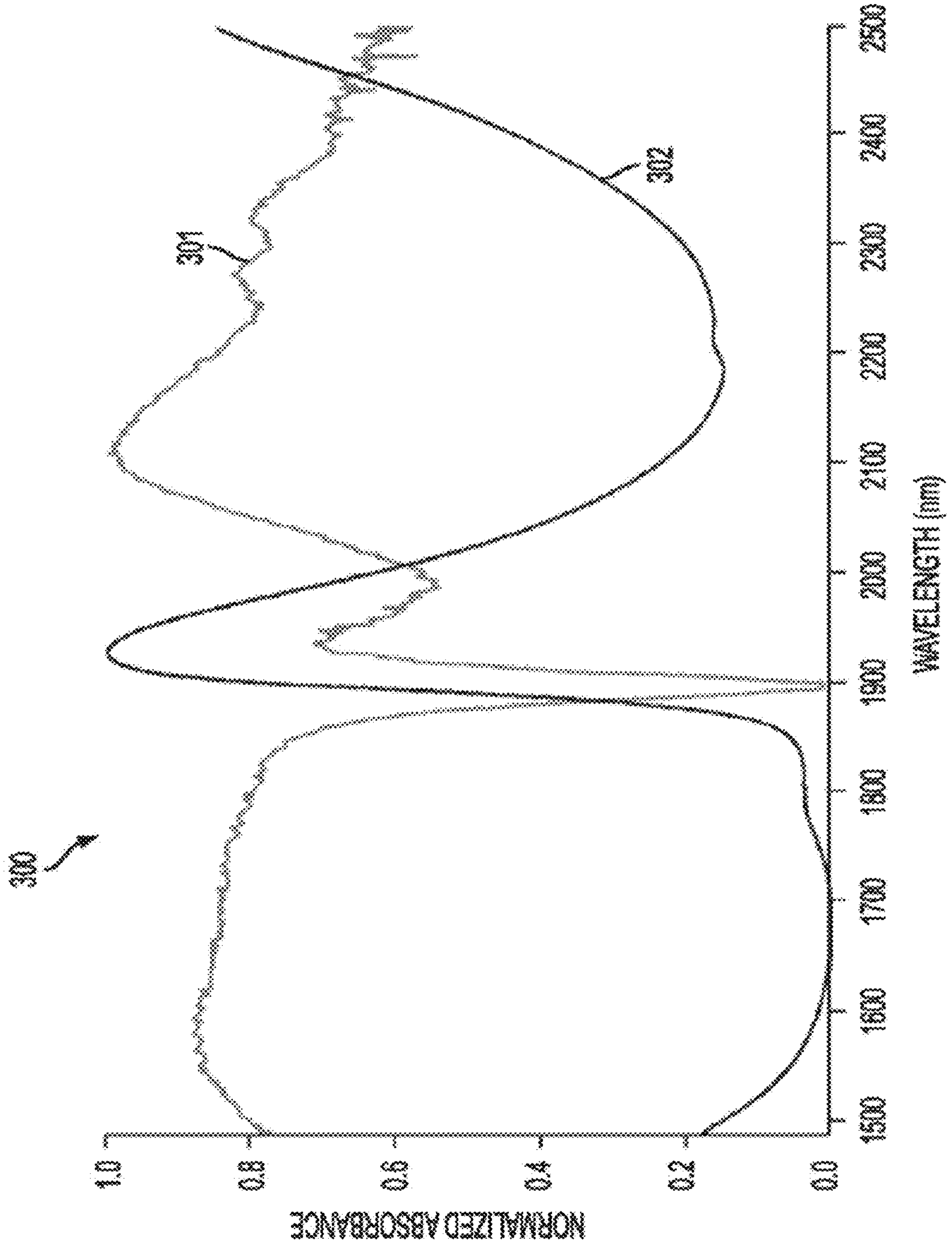
FIG. 3A shows the normalized absorbance of water and glucose (not drawn to scale). Water shows transmission windows between about 1500-1850 nm and 2050-2500 nm.
Figure 3B:
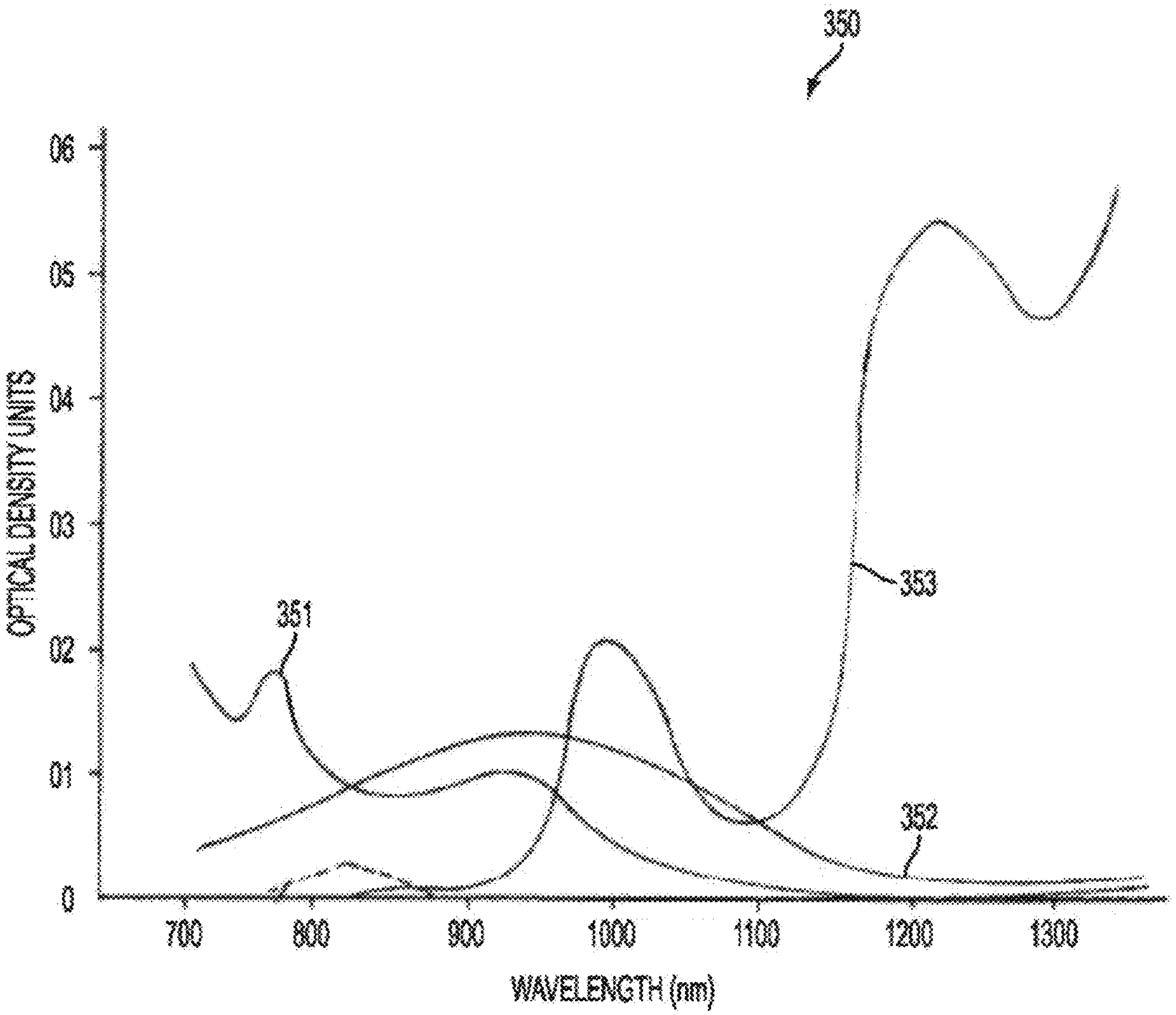
FIG. 3B illustrates the absorbance of hemoglobin and oxygenated hemoglobin overlapped with water.

FIG. 3A overlaps 300 the normalized absorbance of glucose 301 with the absorbance of water 302 (not drawn to scale). It may be seen that water has an absorbance feature between approximately 1850 nm and 2050 nm, but water 302 also has a nice transmission window between approximately 1500-1850 nm and 2050 to 2500 nm. For wavelengths less than about 1100 nm, the absorption of hemoglobin 351 and oxygenated hemoglobin 352 in FIG. 3B has a number of features 350, which may make it more difficult to measure blood constituents. Also, beyond 2500 nm the water absorption becomes considerably stronger over a wide wavelength range. Therefore, an advantageous window for measuring glucose and other blood constituents may be in the SWIR between 1500 and 1850 nm and 2050 to 2500 nm. These are exemplary wavelength ranges, and other ranges can be used that would still fall within the scope of this disclosure.

One further consideration in choosing the laser wavelength is known as the "eye safe" window for wavelengths longer than about 1400 nm. In particular, wavelengths in the eye safe window may not transmit down to the retina of the eye, and therefore, these wavelengths may be less likely to create permanent eye damage. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 4A:
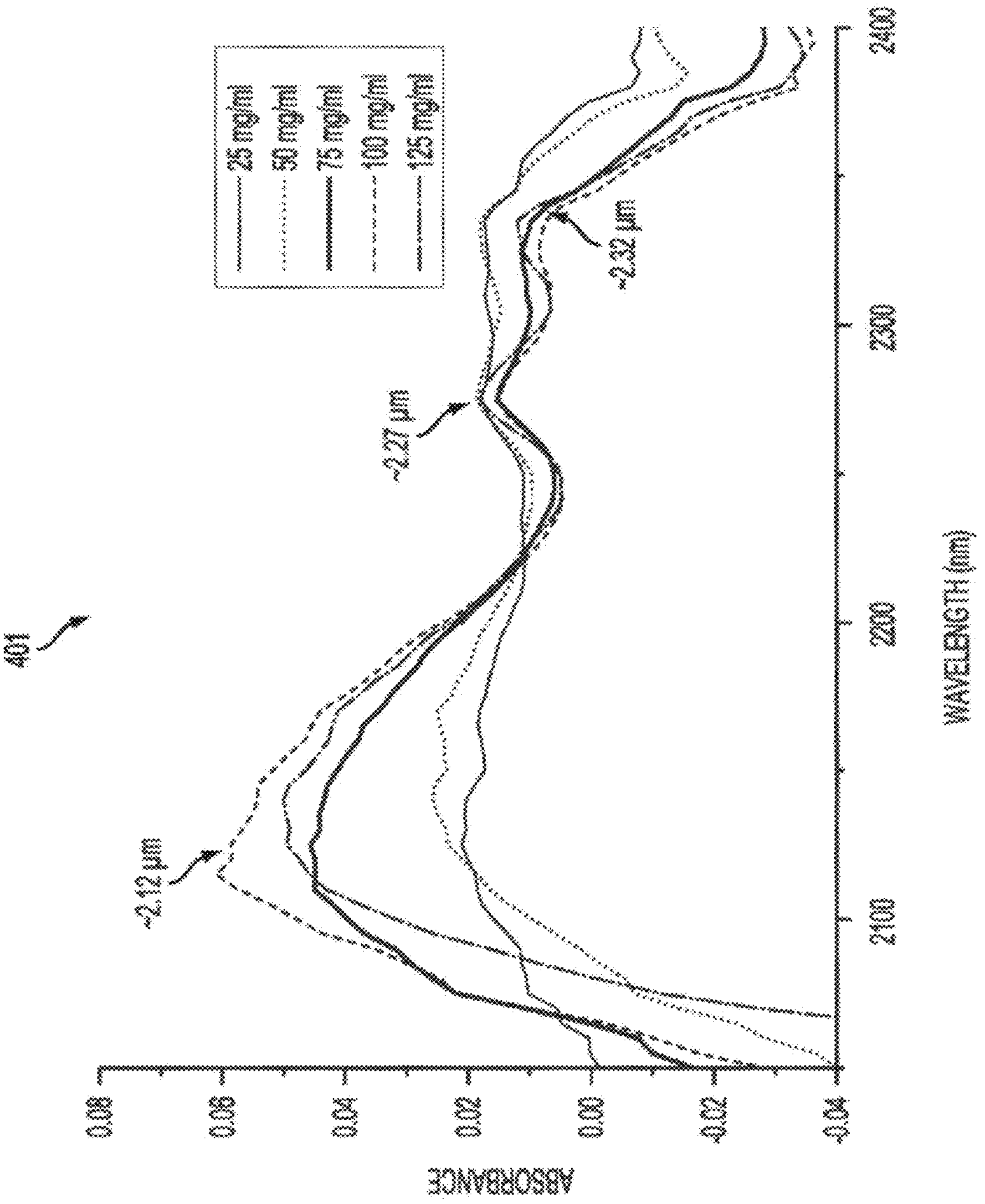
FIG. 4A shows measured absorbance in different concentrations of glucose solution over the wavelength range of about 2000 to 2400 nm. This data is collected using a SWIR super-continuum laser with the sample path length of about 1.1 mm.
Figure 4B:
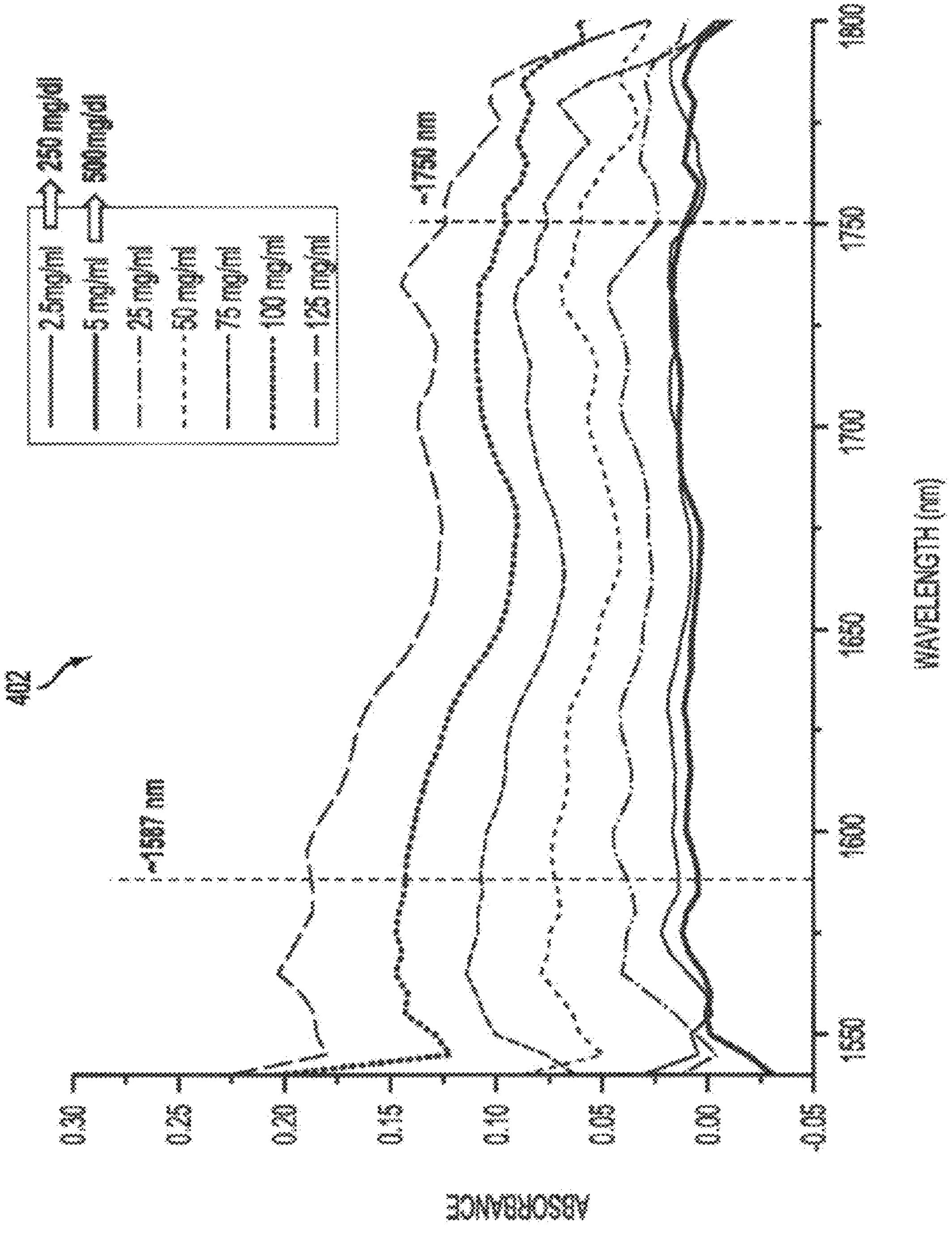
FIG. 4B illustrates measured absorbance in different concentrations of glucose solution over the wavelength range of about 1550 to 1800 nm. The data is collected using a SWIR super-continuum laser with a sample path length of about 10 mm.

Beyond measuring blood constituents such as glucose using FTIR spectrometers, measurements have also been conducted in another embodiment using super-continuum lasers, which will be described later in this disclosure. In this particular embodiment, some of the exemplary preliminary data for glucose absorbance are illustrated in FIGS. 4A and 4B. The optical spectra 401 in FIG. 4A for different levels of glucose concentration in the wavelength range between 2000 and 2400 nm show the three absorption peaks near 2120 nm (2.12 μm), 2270 nm (2.27 μm) and 2320 nm (2.32 μm). Moreover, the optical spectra 402 in FIG. 4B for different levels of glucose concentration in the wavelength range between 1500 and 1800 nm show the two broader absorption peaks near 1587 nm and 1750 nm. It should be appreciated that although data measured with FTIR spectrometers or super-continuum lasers have been illustrated, other light sources can also be used to obtain the data, such as super-luminescent laser diodes, light emitting diodes, a plurality of laser diodes, or even bright lamp sources that generate adequate light in the SWIR.

Figure 5:
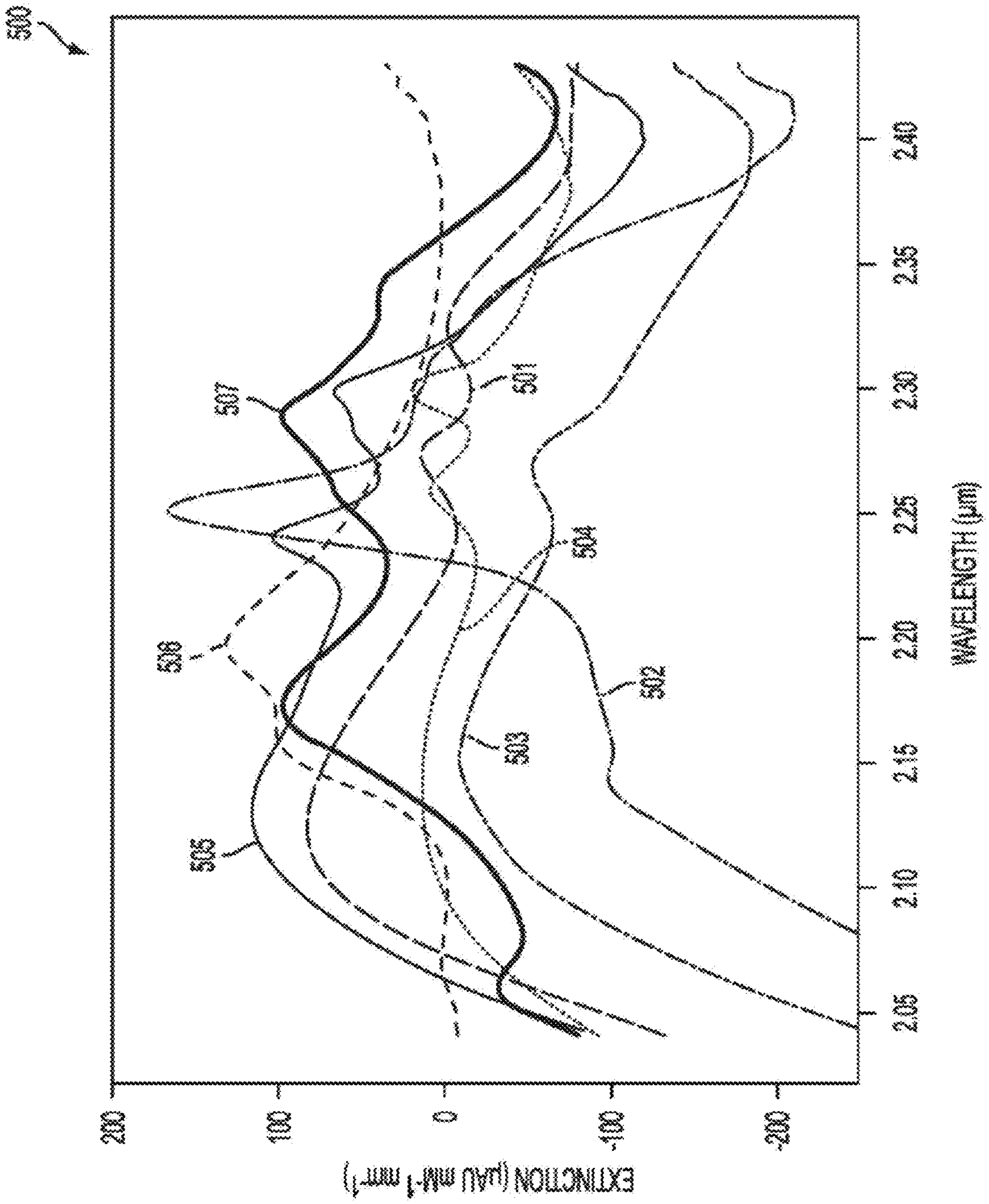
FIG. 5 illustrates the spectrum for different blood constituents in the wavelength range of about 2 to 2.45 microns (2000 to 2450 nm).

Although glucose has a distinctive signature in the SWIR wavelength range, one problem of non-invasive glucose monitoring is that many other blood constituents also have hydro-carbon bonds. Consequently, there can be interfering signals from other constituents in the blood. As an example, FIG. 5 illustrates the spectrum 500 for different blood constituents in the wavelength range of 2 to 2.45 microns. The glucose absorption spectrum 501 can be unique with its three peaks in this wavelength range. However, other blood constituents such as triacetin 502, ascorbate 503, lactate 504, alanine 505, urea 506, and BSA 507 also have spectral features in this wavelength range. To distinguish the glucose 501 from these overlapping spectra, it may be advantageous to have information at multiple wavelengths. In addition, it may be advantageous to use pattern matching algorithms and other software and mathematical methods to identify the blood constituents of interest. In one embodiment, the spectrum may be correlated with a library of known spectra to determine the overlap integrals, and a threshold function may be used to quantify the concentration of different constituents. This is just one way to perform the signal processing, and many other techniques, algorithms, and software may be used and would fall within the scope of this disclosure.

Ketone Bodies Monitoring

Beyond glucose, there are many other blood constituents that may also be of interest for health or disease monitoring. In another embodiment, it may be desirous to monitor the level of ketone bodies in the blood stream. Ketone bodies are three water-soluble compounds that are produced as by-products when fatty acids are broken down for energy in the liver. Two of the three are used as a source of energy in the heart and brain, while the third is a waste product excreted from the body. In particular, the three endogenous ketone bodies are acetone, acetoacetic acid, and beta-hydroxybutyrate or 3-hydroxybutyrate, and the waste product ketone body is acetone.

Ketone bodies may be used for energy, where they are transported from the liver to other tissues. The brain may utilize ketone bodies when sufficient glucose is not available for energy. For instance, this may occur during fasting, strenuous exercise, low carbohydrate, ketogenic diet and in neonates. Unlike most other tissues that have additional energy sources such as fatty acids during periods of low blood glucose, the brain cannot break down fatty acids and relies instead on ketones. In one embodiment, these ketone bodies are detected.

Ketone bodies may also be used for reducing or eliminating symptoms of diseases or disorders characterized by impaired glucose metabolism. For example, diseases associated with reduced neuronal metabolism of glucose include Parkinson's disease, Alzheimer's disease, amyotrophic lateral sclerosis (ALS, also called Lou Gehrig's disease), Huntington's disease and epilepsy. In one embodiment, monitoring of alternate sources of ketone bodies that may be administered orally as a dietary supplement or in a nutritional composition to counteract some of the glucose metabolism impairments is performed. However, if ketone bodies supplements are provided, there is also a need to monitor the ketone level in the blood stream. For instance, if elevated levels of ketone bodies are present in the body, this may lead to ketosis; hyperketonemia is also an elevated level of ketone bodies in the blood. In addition, both acetoacetic acid and beta-hydroxybutyric acid are acidic, and, if levels of these ketone bodies are too high, the pH of the blood may drop, resulting in ketoacidosis.

The general formula for ketones is CnH2n0. In organic chemistry, a ketone is an organic compound with the structure RC(=O)R', where R and R' can be a variety of carbon-containing substituents. It features a carbonyl group (C=O) bonded to two other carbon atoms. Because the ketones contain the hydrocarbon bonds, there might be expected to be features in the SWIR, similar in structure to those found for glucose.

Figure 6:
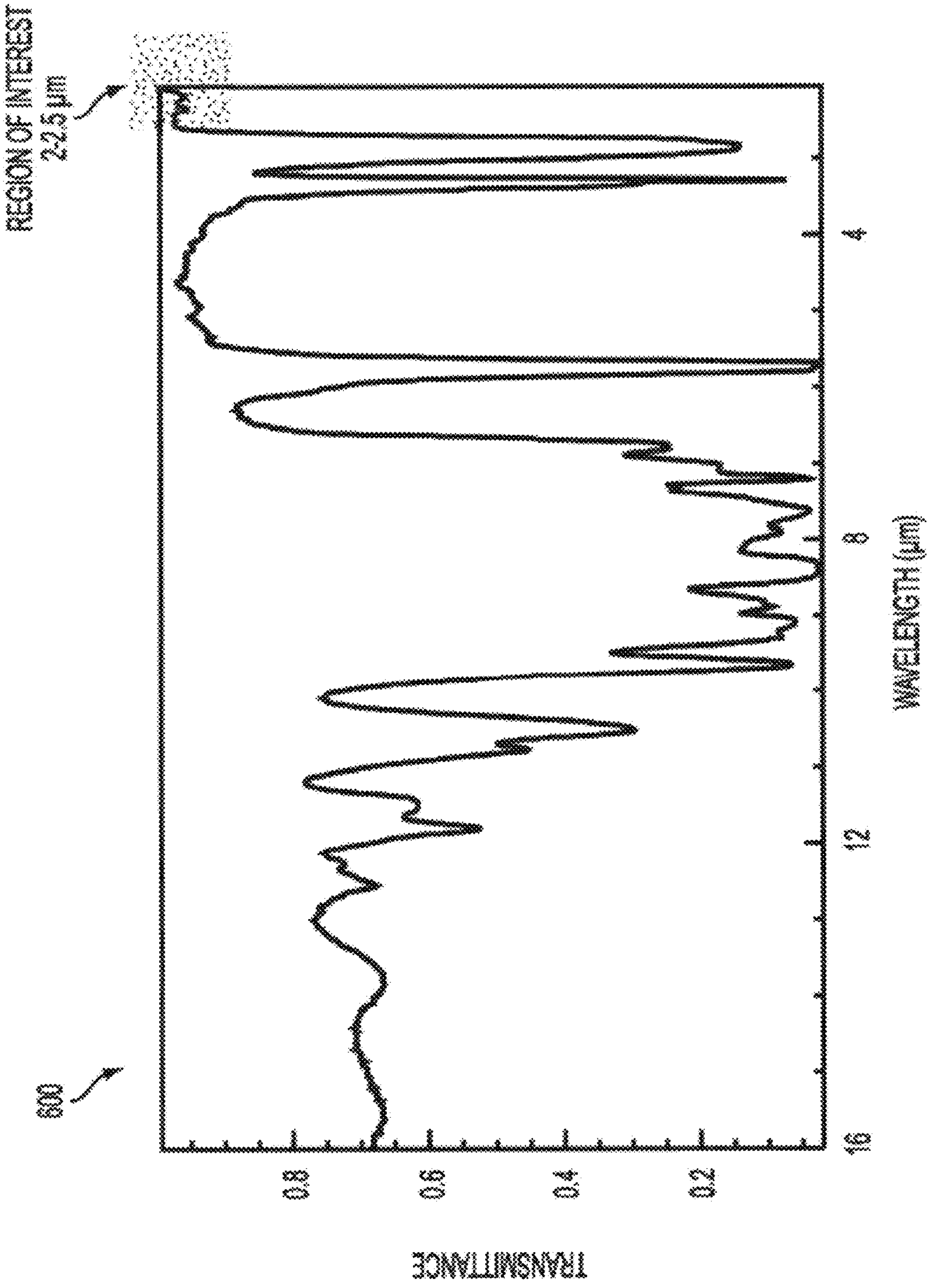
FIG. 6 shows the transmittance versus wavelength in microns for the ketone 3-hydroxybutyrate. The wavelength range is approximately 2 to 16 microns.

The infrared spectrum 600 for the ketone 3-hydroxybutyrate is illustrated in FIG. 6. Just as in glucose, there are significant features in the mid- and long-wave infrared between 6 to 12 microns, but these may be difficult to observe non-invasively. On the other hand, there are some features in the SWIR that may be weaker, but they could potentially be observed non-invasively, perhaps through blood and water.

Figure 7:
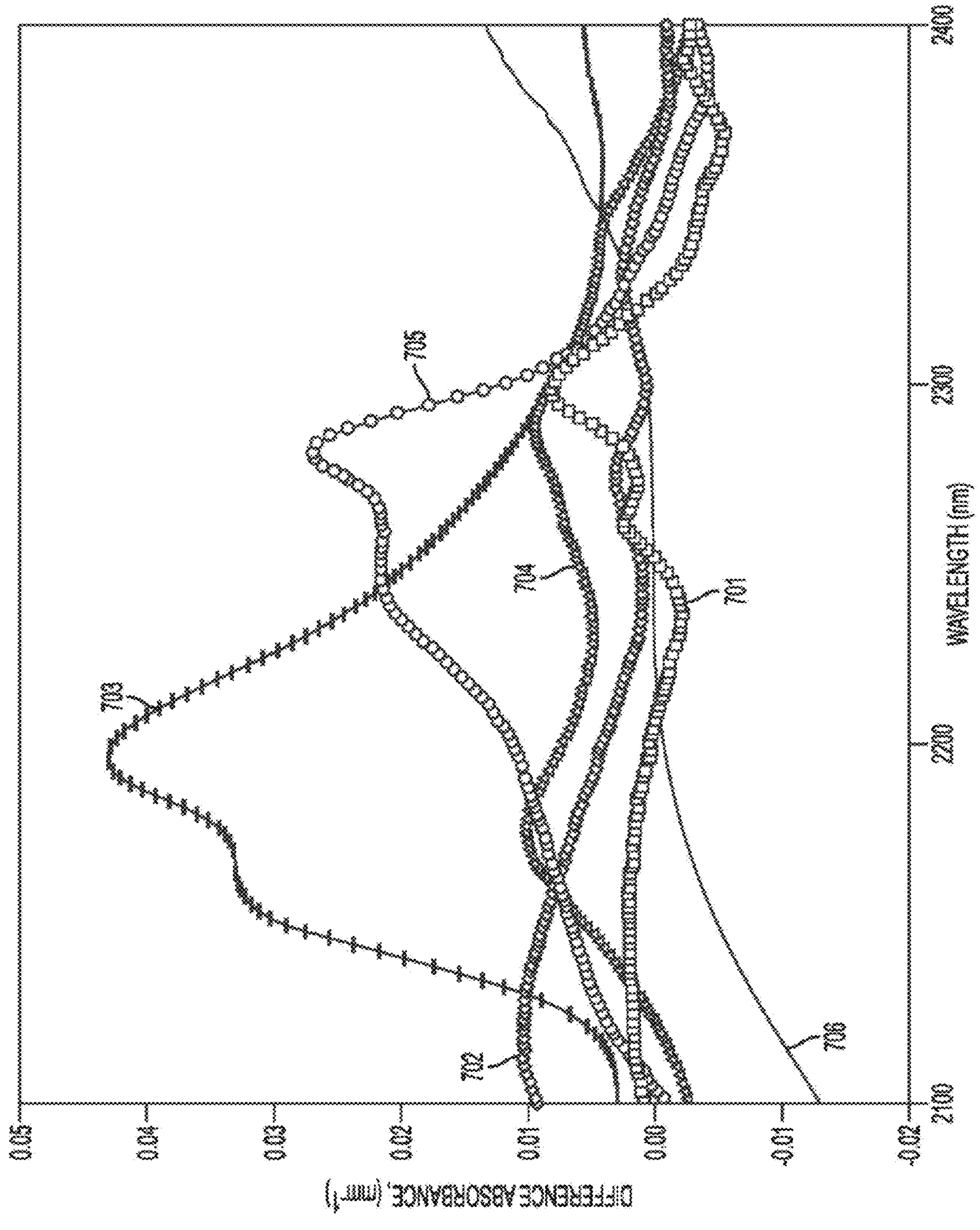
FIG. 7 illustrates the optical absorbance for ketones as well as some other blood constituents in the wavelength range of about 2100 to 2400 nm.

The optical spectra 700 for ketones as well as some other blood constituents are exemplified in FIG. 7 in the wavelength range of 2100 nm to 2400 nm. In this embodiment, the absorbance for ketones is 701, while the absorbance for glucose is 702. However, there are also features in this wavelength range for other blood constituents, such as urea 703, albumin or blood protein 704, creatinine 705, and nitrite 706. In this wavelength range of 2100 to 2400 nm, the features for ketone 701 seem more spectrally pronounced than even glucose.

Figure 8A:
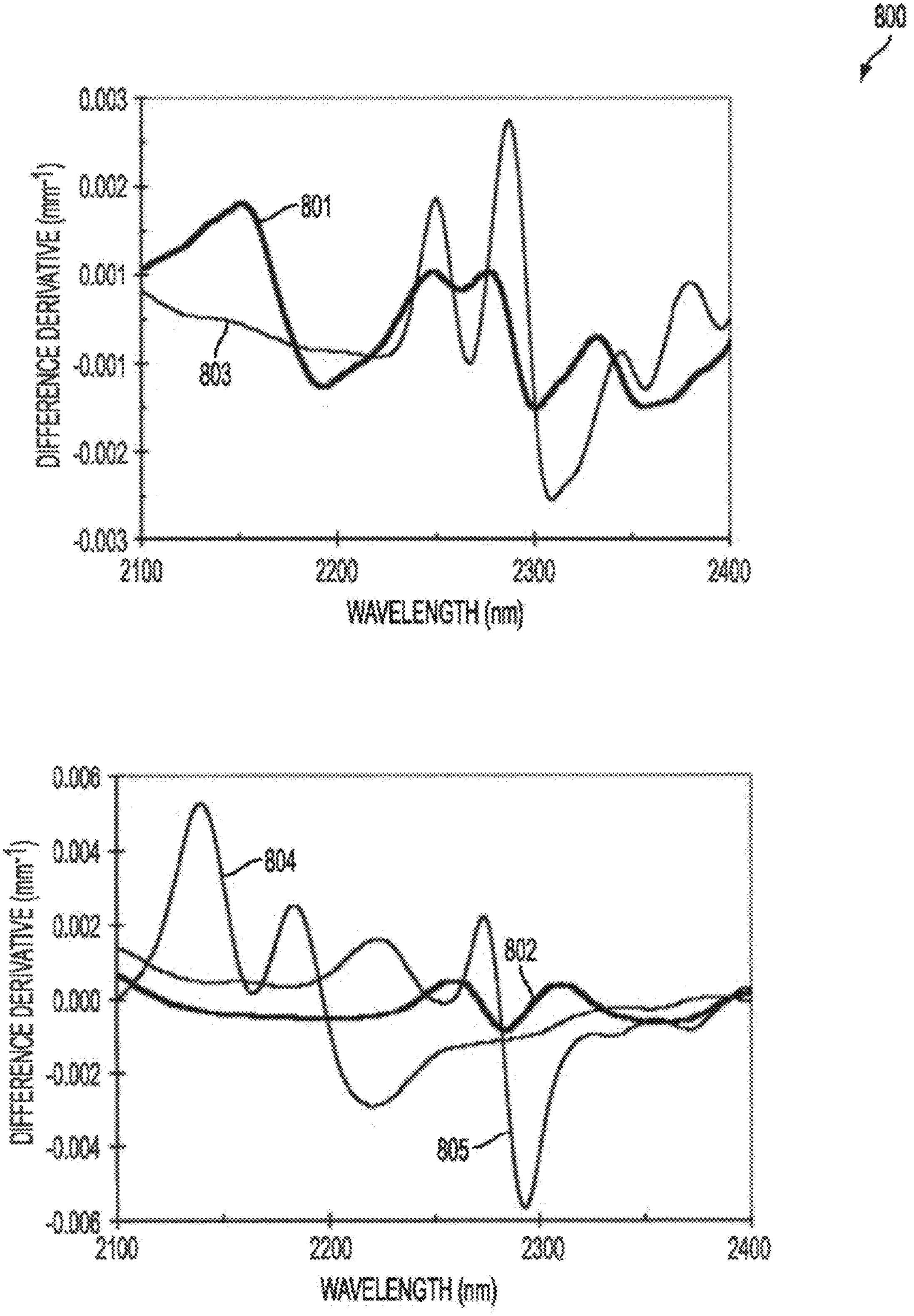
FIG. 8A shows the first derivative spectra of ketone and protein at concentrations of 10 g/L (left). In addition, the first derivative spectra of urea, creatinine, and glucose are shown on the right at concentrations of 10 g/L.

Different signal processing techniques can be used to enhance the spectral differences between different constituents. In one embodiment, the first or second derivatives of the spectra may enable better discrimination between substances. The first derivative may help remove any flat offset or background, while the second derivative may help to remove any sloped offset or background. In some instances, the first or second derivative may be applied after curve fitting or smoothing the reflectance, transmittance, or absorbance. For example, FIG. 8A illustrates the derivative spectra for ketone 801 and glucose 802, which can be distinguished from the derivative spectra for protein 803, urea 804 and creatinine 805. Based on FIG. 8A, it appears that ketones 801 may have a more pronounced difference than even glucose 802 in the wavelength range between 2100 and 2400 nm. Therefore, ketone bodies should also be capable of being monitored using a non-invasive optical technique in the SWIR, and a different pattern matching library could be used for glucose and ketones.

Hemoglobin A1C Monitoring

Another blood constituent that may be of interest for monitoring of health or diseases is hemoglobin A1c, also known as HbA1c or glycated hemoglobin (glycol-hemoglobin or glycosylated hemoglobin). HbA1c is a form of hemoglobin that is measured primarily to identify the average plasma glucose concentration over prolonged periods of time. Thus, HbA1c may serve as a marker for average blood glucose levels over the previous months prior to the measurements.

In one embodiment, when a physician suspects that a patient may be diabetic, the measurement of HbA1c may be one of the first tests that are conducted. An HbA1c level less than approximately 6% may be considered normal. On the other hand, an HbA1c level greater than approximately 6.5% may be considered to be diabetic. In diabetes mellitus, higher amounts of HbA1c indicate poorer control of blood glucose levels. Thus, monitoring the HbA1c in diabetic patients may improve treatment. Current techniques for measuring HbA1c require drawing blood, which may be inconvenient and painful. The point-of-care devices use immunoassay or boronate affinity chromatography, as an example. Thus, there is also an unmet need for non-invasive monitoring of HbA1c.

FIG. 2 illustrates the FTIR measurements of HbA1c absorbance 203 over the wavelength range between 1500 and 2400 nm for a concentration of approximately 1 mg/ml. Whereas the absorbance of hemoglobin 201 over this wavelength range is approximately flat, the HbA1c absorbance 203 shows broad features and distinct curvature. Although the HbA1c absorbance 203 does not appear to exhibit as pronounced features as glucose 202, the non-invasive SWIR measurement should be able to detect HbA1c with appropriate pattern matching algorithms. Moreover, the spectrum for HbA1c may be further enhanced by using first or second derivative data, as seen for ketones in FIG. 8A. Beyond absorption, reflectance, or transmission spectroscopy, it may also be possible to detect blood constituents such as HbA1c using Raman spectroscopy or surface-enhanced Raman spectroscopy. In general, Raman spectroscopy may require higher optical power levels.

As an illustration, non-invasive measurement of blood constituents such as glucose, ketone bodies, and HbA1c has been discussed thus far. However, other blood constituents can also be measured using similar techniques, and these are also intended to be covered by this disclosure. In other embodiments, blood constituents such as proteins, albumin, urea, creatinine or nitrites could also be measured. For instance, the same type of SWIR optical techniques might be used, but the pattern matching algorithms and software could use different library features or functions for the different constituents.

Figure 8B:
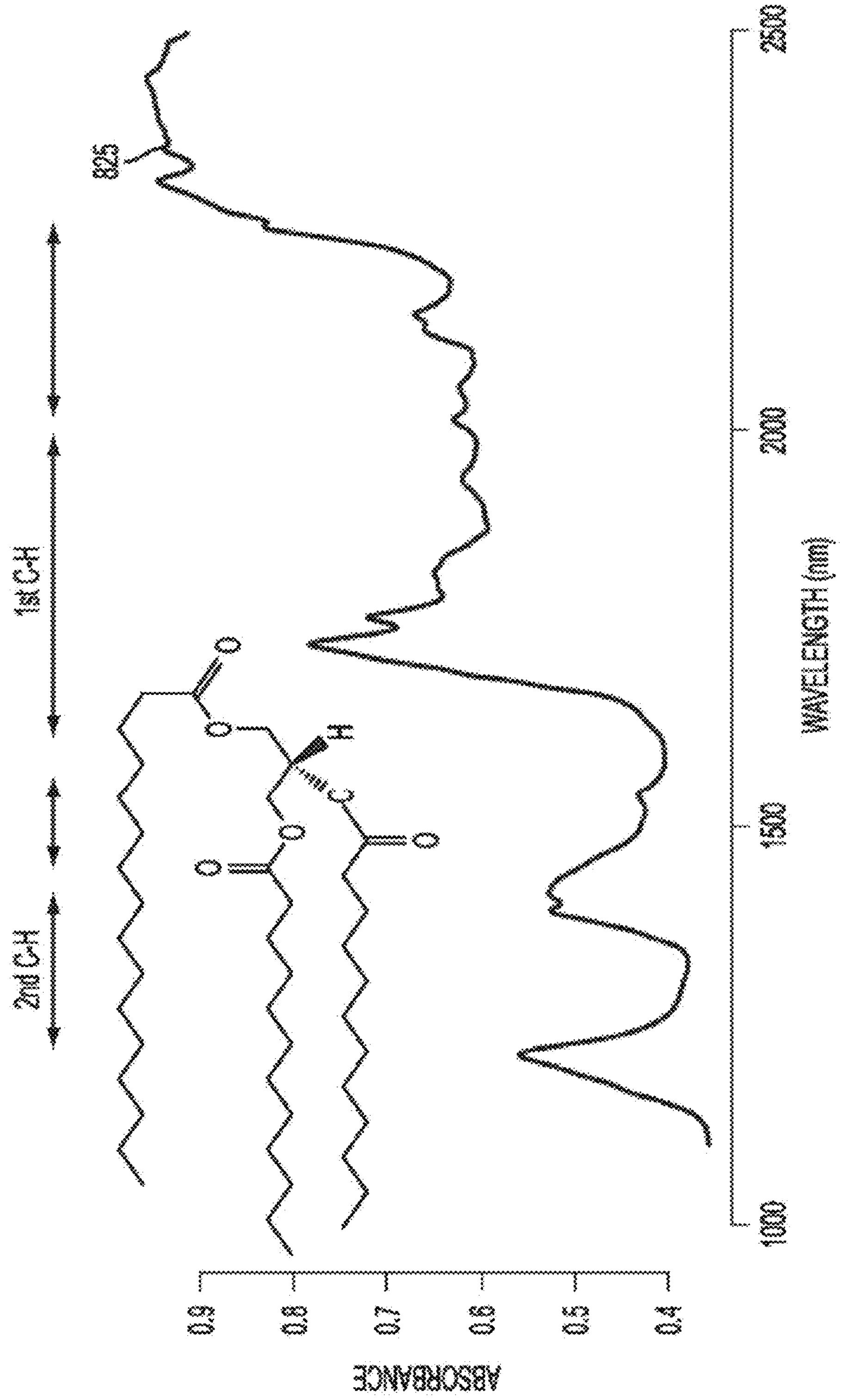
FIG. 8B illustrates the near infrared absorbance for triglyceride.

In yet another embodiment, the optical techniques described in this disclosure could also be used to measure levels of triglycerides. Triglycerides are bundles of fats that may be found in the blood stream, particularly after ingesting meals. The body manufactures triglycerides from carbohydrates and fatty foods that are eaten. In other words, triglycerides are the body's storage form of fat. Triglycerides are comprised of three fatty acids attached to a glycerol molecule, and measuring the level of triglycerides may be important for diabetics. The triglyceride levels or concentrations in blood may be rated as follows: desirable or normal may be less than 150 mg/dl; borderline high may be 150-199 mg/dl; high may be 200-499 mg/dl; and very high may be 500 mg/dl or greater. FIG. 8B illustrates one example of the near-infrared absorbance 825 for triglycerides. There are distinct absorbance peaks in the spectrum that should be measurable. The characteristic absorption bands may be assigned as follows: (a) the first overtones of C—H stretching vibrations (1600-1900 nm); (b) the region of second overtones of C—H stretching vibrations (1100-1250 nm); and, (c) two regions (2000-2200 nm and 1350-1500 nm) that comprise bands due to combinations of C—H stretching vibrations and other vibrational modes.

Figure 8C:
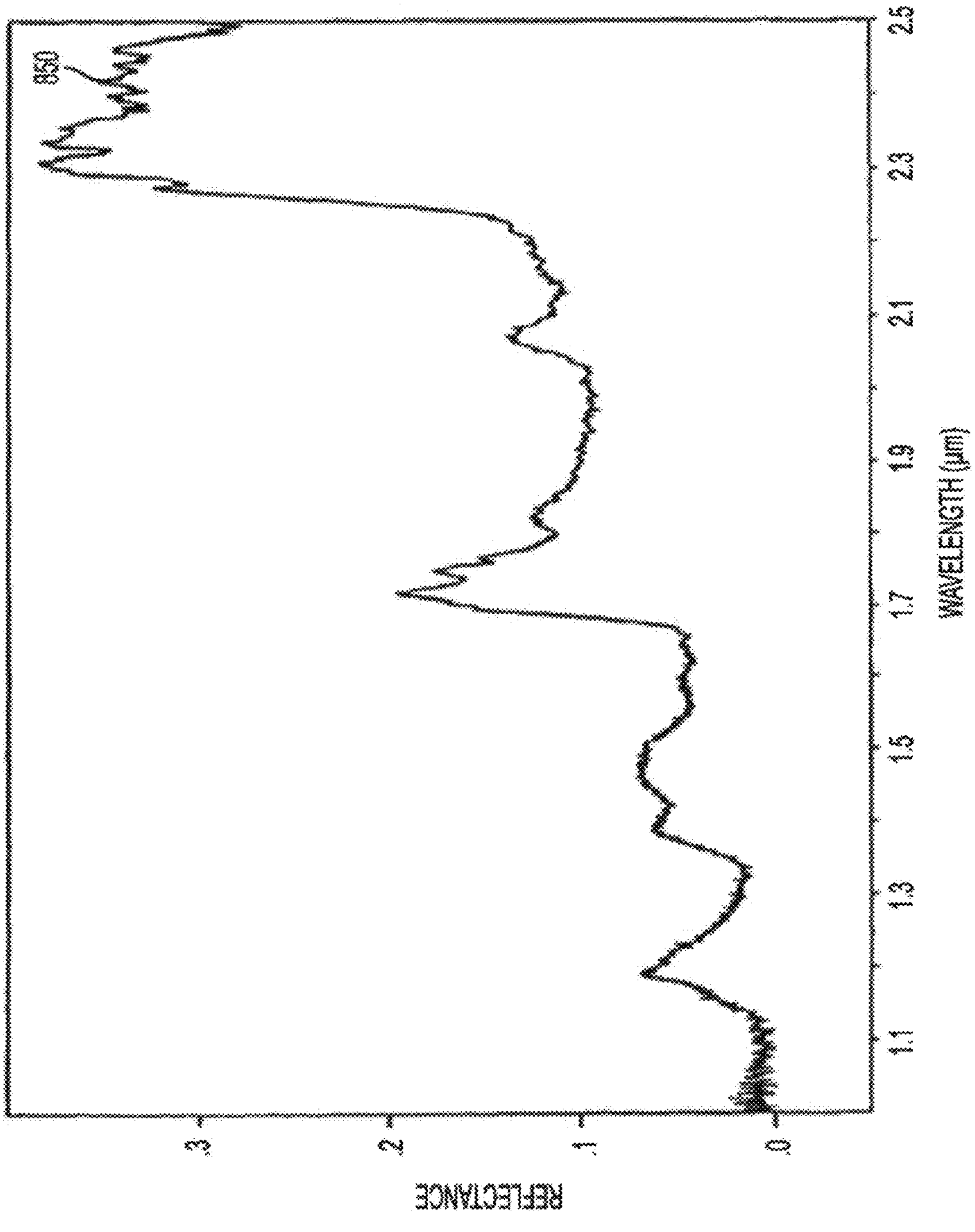
FIG. 8C shows the near-infrared reflectance spectrum for cholesterol.
Figure 8D:
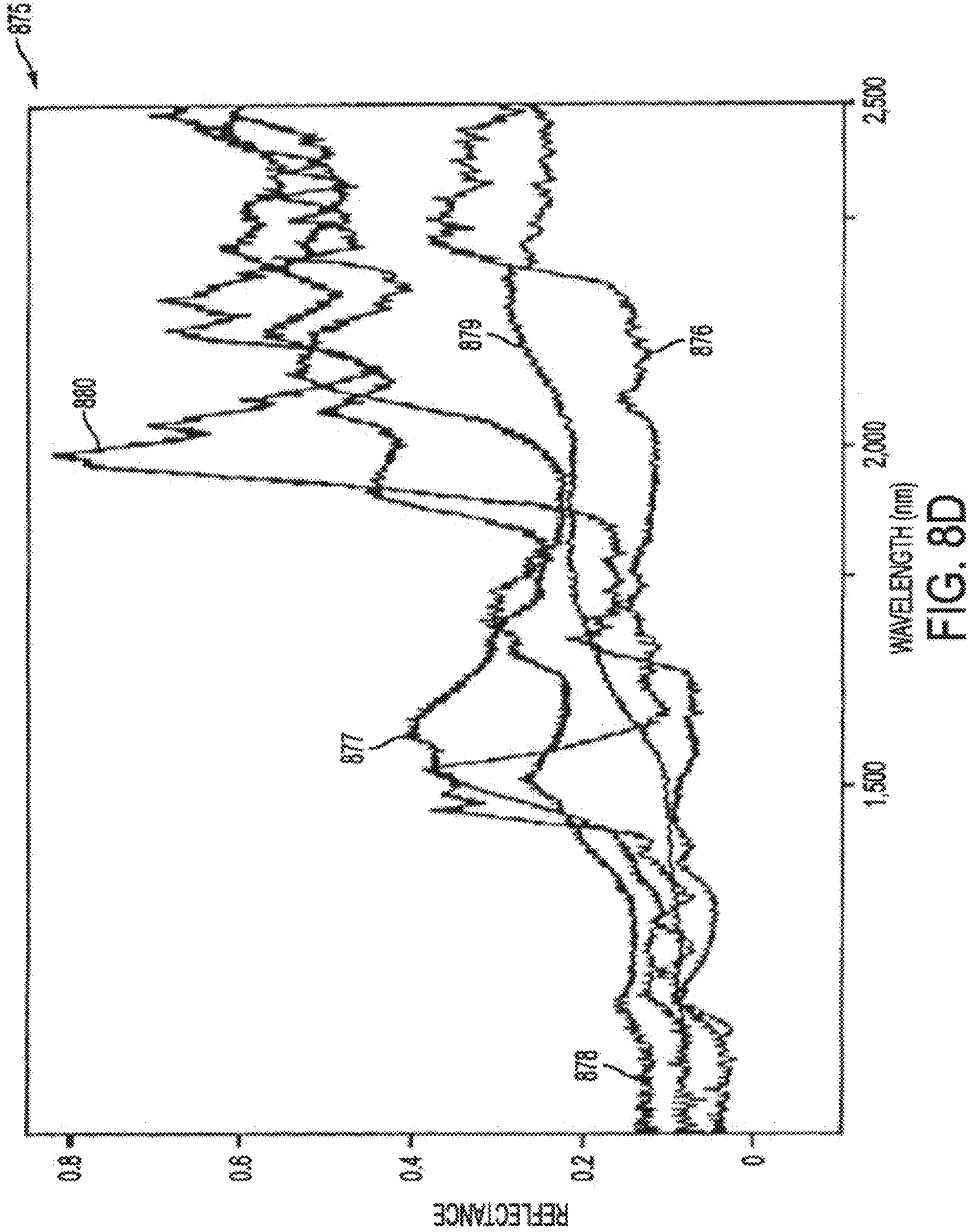
FIG. 8D illustrates the near-infrared reflectance versus wavelength for various blood constituents, including cholesterol, glucose, albumin, uric acid, and urea.

A further example of blood compositions that can be detected or measured using near-infrared light includes cholesterol monitoring. For example, FIG. 8C shows the near-infrared reflectance spectrum for cholesterol 850 with wavelength in microns (μm). Distinct absorption peaks are observable near 1210 nm (1.21 μm), 1720 nm (1.72 μm), and between 2300-2500 nm (2.3-2.5 μm). Also, there are other features near 1450 nm (1.45 μm) and 2050 nm (2.05 μm). In FIG. 8D the near-infrared reflectances 875 are displayed versus wavelength (nm) for various blood constituents. The spectrum for cholesterol 876 is overlaid with glucose 877, albumin 878, uric acid 879, and urea 880. As may be noted from FIG. 8D, at about 1720 nm and 2300 nm, cholesterol 876 reaches approximate reflectance peaks, while some of the other analytes are in a more gradual mode. Various signal processing methods may be used to identify and quantify the concentration of cholesterol 876 and/or glucose 877, or some of the other blood constituents.

As illustrated by FIGS. 5 and 7, one of the issues in measuring a particular blood constituent is the interfering and overlapping signal from other blood constituents. The selection of the constituent of interest may be improved using a number of techniques. For example, a higher light level or intensity may improve the signal-to-noise ratio for the measurement. Second, mathematical modeling and signal processing methodologies may help to reduce the interference, such as multivariate techniques, multiple linear regression, and factor-based algorithms, for example. For instance, a number of mathematical approaches include multiple linear regression, partial least squares, and principal component regression (PCR). Also, as illustrated in FIG. 8A, various mathematical derivatives, including the first and second derivatives, may help to accentuate differences between spectra. In addition, by using a wider wavelength range and using more sampling wavelengths may improve the ability to discriminate one signal from another. These are just examples of some of the methods of improving the ability to discriminate between different constituents, but other techniques may also be used and are intended to be covered by this disclosure.

Interference from Skin

Several proposed non-invasive glucose monitoring techniques rely on transmission, absorption, and/or diffuse reflection through the skin to measure blood constituents or blood analytes in veins, arteries, capillaries or in the tissue itself. However, on top of the interference from other blood constituents or analytes, the skin also introduces significant interference. For example, chemical, structural, and physiological variations occur that may produce relatively large and nonlinear changes in the optical properties of the tissue sample. In one embodiment, the near-infrared reflectance or absorbance spectrum may be a complex combination of the tissue scattering properties that result from the concentration and characteristics of a multiplicity of tissue components including water, fat, protein, collagen, elastin, and/or glucose. Moreover, the optical properties of the skin may also change with environmental factors such as humidity, temperature and pressure. Physiological variation may also cause changes in the tissue measurement over time and may vary based on lifestyle, health, aging, etc. The structure and composition of skin may also vary widely among individuals, between different sites within an individual, and over time on the same individual. Thus, the skin introduces a dynamic interference signal that may have a wide variation due to a number of parameters.

FIG. 9 shows a schematic cross-section of human skin 900, 901. The top layer of the skin is epidermis 902, followed by a layer of dermis 903 and then subcutaneous fat 904 below the dermis. The epidermis 902, with a thickness of approximately 10-150 microns, may provide a barrier to infection and loss of moisture and other body constituents. The dermis 903 ranges in thickness from approximately 0.5 mm to 4 mm (averages approximately 1.2 mm over most of the body) and may provide the mechanical strength and elasticity of skin.

In the dermis 903, water may account for approximately 70% of the volume. The next most abundant constituent in the dermis 903 may be collagen 905, a fibrous protein comprising 70-75% of the dry weight of the dermis 903. Elastin fibers 906, also a protein, may also be plentiful in the dermis 903, although they constitute a smaller portion of the bulk. In addition, the dermis 903 may contain a variety of structures (e.g., sweat glands, hair follicles with adipose rich sebaceous glands 907 near their roots, and blood vessels) and other cellular constituents.

Below the dermis 903 lies the subcutaneous layer 904 comprising mostly adipose tissue. The subcutaneous layer 904 may be by volume approximately 10% water and may be comprised primarily of cells rich in triglycerides or fat. With this complicated structure of the skin 900,901, the concentration of glucose may vary in each layer according to a variety of factors including the water content, the relative sizes of the fluid compartments, the distribution of capillaries, the perfusion of blood, the glucose uptake of cells, the concentration of glucose in blood, and the driving forces (e.g., osmotic pressure) behind diffusion.

Figure 10:
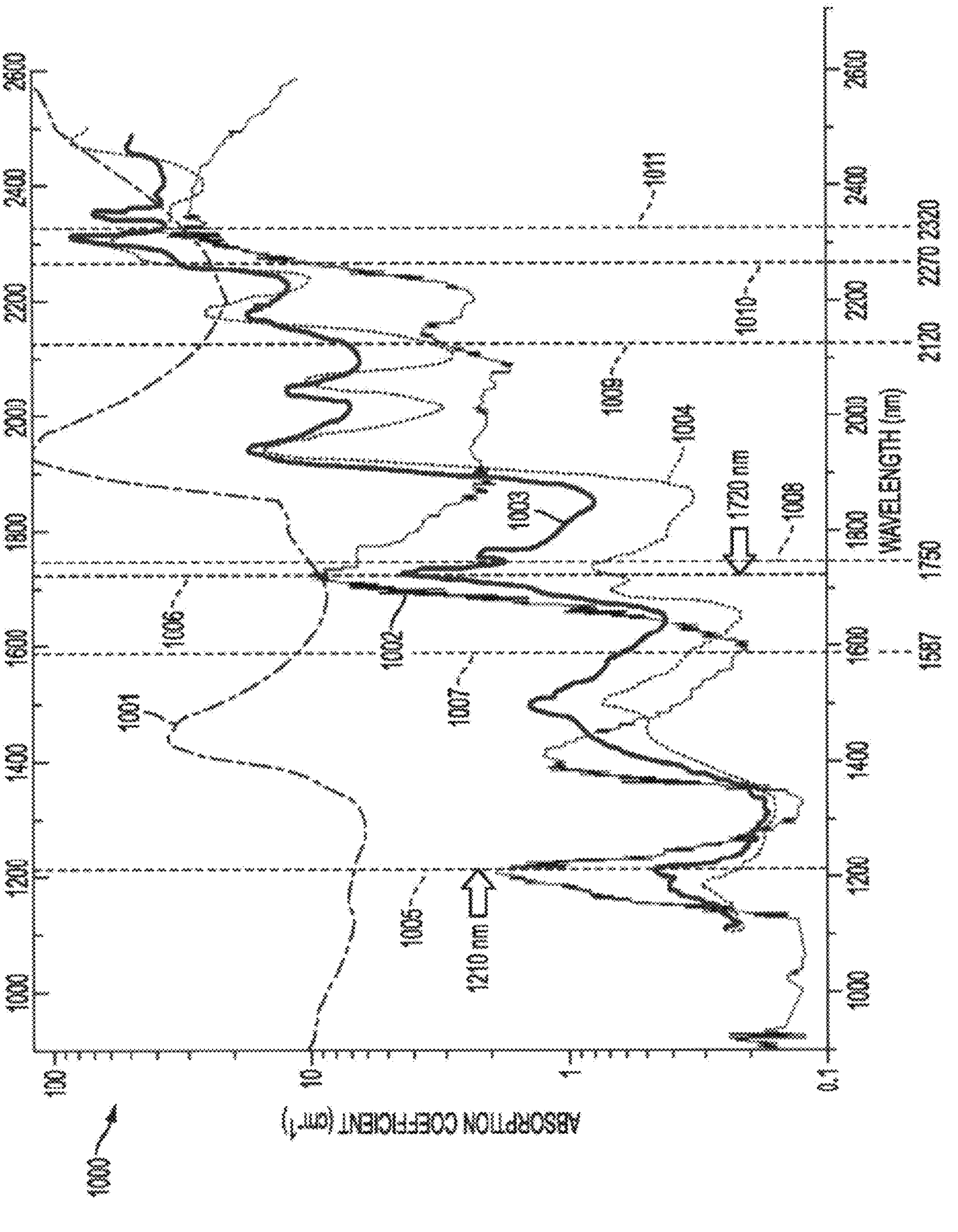
FIG. 10 illustrates the absorption coefficients for water (including scattering), adipose, collagen, and elastin.

To better understand the interference that the skin introduces when attempting to measure glucose, the absorption coefficient for the various skin constituents should be examined. For example, FIG. 10 illustrates 1000 the absorption coefficients for water (including scattering) 1001, adipose 1002, collagen 1003 and elastin 1004. Note that the absorption curves for water 1001 and adipose 1002 are calibrated, whereas the absorption curves for collagen 1003 and elastin 1004 are in arbitrary units. Also shown are vertical lines demarcating the wavelengths near 1210 nm 1005 and 1720 nm 1006. In general, the water absorption increases with increasing wavelength. With the increasing absorption beyond about 2000 nm, it may be difficult to achieve deeper penetration into biological tissue in the infrared wavelengths beyond approximately 2500 nm.

Although the absorption coefficient may be useful for determining the material in which light of a certain infrared wavelength will be absorbed, to determine the penetration depth of the light of a certain wavelength may also require the addition of scattering loss to the curves. For example, the water curve 1001 includes the scattering loss curve in addition to the water absorption. In particular, the scattering loss can be significantly higher at shorter wavelengths. In one embodiment, near the wavelength of 1720 nm (vertical line 1006 shown in FIG. 10), the adipose absorption 1002 can still be higher than the water plus scattering loss 1001. For tissue that contains adipose, collagen and elastin, such as the dermis of the skin, the total absorption can exceed the light energy lost to water absorption and light scattering at 1720 nm. On the other hand, at 1210 nm the adipose absorption 1002 can be considerably lower than the water plus scattering loss 1001, particularly since the scattering loss can be dominant at these shorter wavelengths.

The interference for glucose lines observed through skin may be illustrated by overlaying the glucose lines over the absorption curves 1000 for the skin constituents. For example, FIG. 2 illustrated that the glucose absorption 202 included features centered around 1587 nm, 1750 nm, 2120 nm, 2270 nm and 2320 nm. On FIG. 10 vertical lines have been drawn at the glucose line wavelengths of 1587 nm 1007, 1750 nm 1008, 2120 nm 1009, 2270 nm 1010 and 2320 nm 1011. In one embodiment, it may be difficult to detect the glucose lines near 1750 nm 1008, 2270 nm 1010 and 2320 nm 1011 due to significant spectral interference from other skin constituents. On the other hand, the glucose line near 1587 m 1007 may be more easily detected because it peaks while most of the other skin constituents are sloped downward toward an absorption valley. Moreover, the glucose line near 2120 nm 1009 may also be detectable for similar reasons, although adipose may have conflicting behavior due to local absorption minimum and maximum nearby in wavelength.

Thus, beyond the problem of other blood constituents or analytes having overlapping spectral features (e.g., FIG. 5), it may be difficult to observe glucose spectral signatures through the skin and its constituents of water, adipose, collagen and elastin. One approach to overcoming this difficulty may be to try to measure the blood constituents in veins that are located at relatively shallow distances below the skin. Veins may be more beneficial for the measurement than arteries, since arteries tend to be located at deeper levels below the skin. Also, in one embodiment it may be advantageous to use a differential measurement to subtract out some of the interfering absorption lines from the skin. For example, an instrument head may be designed to place one probe above a region of skin over a blood vein, while a second probe may be placed at a region of the skin without a noticeable blood vein below it. Then, by differencing the signals from the two probes, at least part of the skin interference may be cancelled out.

Figure 11:
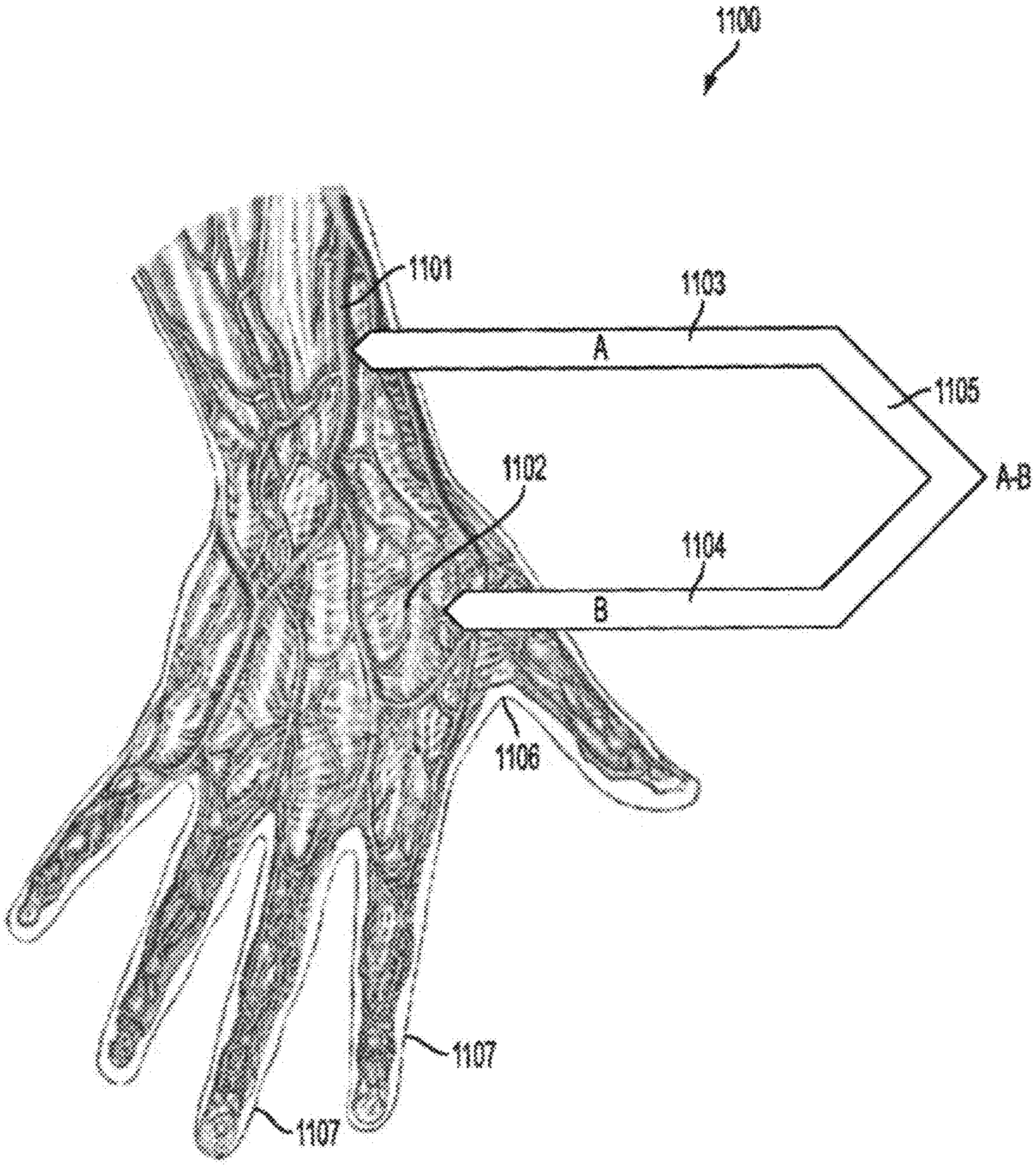
FIG. 11 shows the dorsal of the hand, where a differential measurement may be made to at least partially compensate for or subtract out the skin interference.
Figure 12:
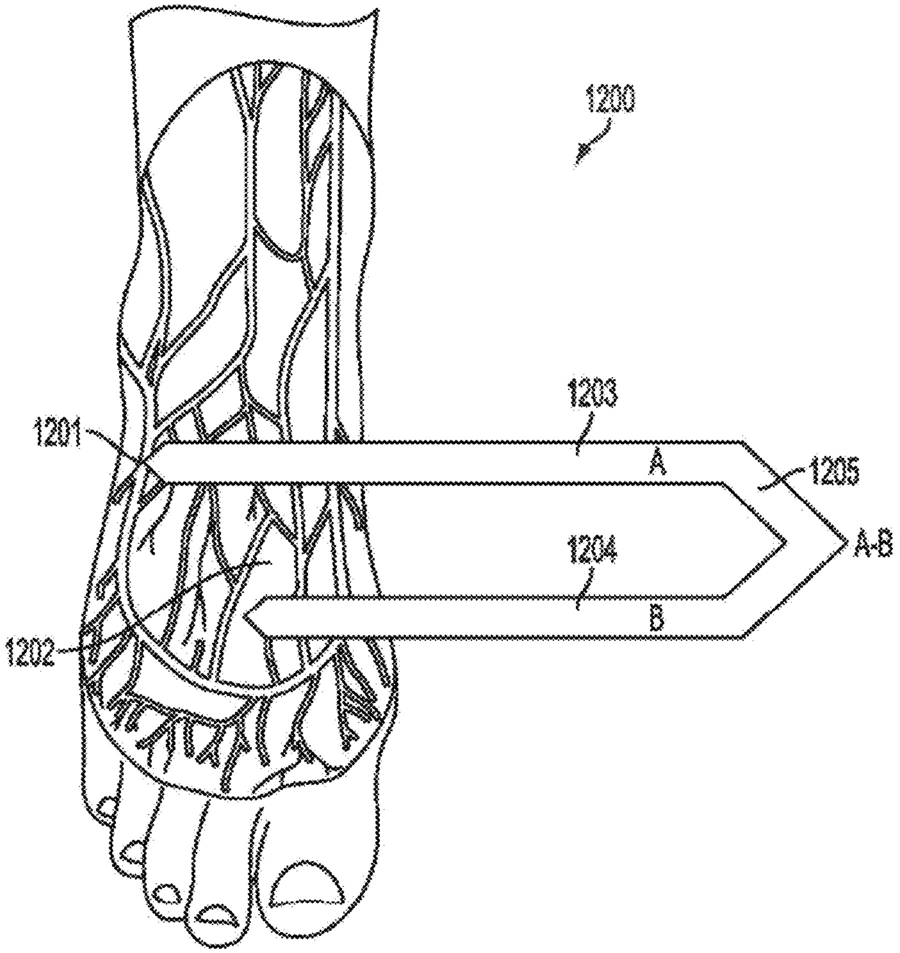
FIG. 12 shows the dorsal of the foot, where a differential measurement may be made to at least partially compensate for or subtract out the skin interference.

Two representative embodiments for performing such a differential measurement are illustrated in FIG. 11 and FIG. 12. In one embodiment shown in FIG. 11, the dorsal of the hand 1100 may be used for measuring blood constituents or analytes. The dorsal of the hand 1100 may have regions that have distinct veins 1101 as well as regions where the veins are not as shallow or pronounced 1102. By stretching the hand and leaning it backwards, the veins 1101 may be accentuated in some cases. A near-infrared diffuse reflectance measurement may be performed by placing one probe 1103 above the vein-rich region 1101. To turn this into a differential measurement, a second probe 1104 may be placed above a region without distinct veins 1102. Then, the outputs from the two probes may be subtracted 1105 to at least partially cancel out the features from the skin. The subtraction may be done preferably in the electrical domain, although it can also be performed in the optical domain or digitally/mathematically using sampled data based on the electrical and/or optical signals. Although one example of using the dorsal of the hand 1100 is shown, many other parts of the hand can be used within the scope of this disclosure. For example, alternate methods may use transmission through the webbing between the thumb and the fingers 1106, or transmission or diffuse reflection through the tips of the fingers 1107.

In another embodiment, the dorsal of the foot 1200 may be used instead of the hand. One advantage of such a configuration may be that for self-testing by a user, the foot may be easier to position the instrument using both hands. One probe 1203 may be placed over regions where there are more distinct veins 1201, and a near-infrared diffuse reflectance measurement may be made. For a differential measurement, a second probe 1204 may be placed over a region with less prominent veins 1202, and then the two probe signals may be subtracted, either electronically or optically, or may be digitized/sampled and processed mathematically depending on the particular application and implementation. As with the hand, the differential measurements may be intended to compensate for or subtract out (at least in part) the interference from the skin. Since two regions are used in close proximity on the same body part, this may also aid in removing some variability in the skin from environmental effects such as temperature, humidity, or pressure. In addition, it may be advantageous to first treat the skin before the measurement, by perhaps wiping with a cloth or treated cotton ball, applying some sort of cream, or placing an ice cube or chilled bag over the region of interest.

Although two embodiments have been described, many other locations on the body may be used using a single or differential probe within the scope of this disclosure. In yet another embodiment, the wrist may be advantageously used, particularly where a pulse rate is typically monitored. Since the pulse may be easily felt on the wrist, there is underlying the region a distinct blood flow. Other embodiments may use other parts of the body, such as the ear lobes, the tongue, the inner lip, the nails, the eye, or the teeth. Some of these embodiments will be further described below. The ear lobes or the tip of the tongue may be advantageous because they are thinner skin regions, thus permitting transmission rather than diffuse reflection. However, the interference from the skin is still a problem in these embodiments. Other regions such as the inner lip or the bottom of the tongue may be contemplated because distinct veins are observable, but still the interference from the skin may be problematic in these embodiments. The eye may seem as a viable alternative because it is more transparent than skin. However, there are still issues with scattering in the eye. For example, the anterior chamber of the eye (the space between the cornea and the iris) comprises a fluid known as aqueous humor. However, the glucose level in the eye chamber may have a significant temporal lag on changes in the glucose level compared to the blood glucose level.

Figure 13:
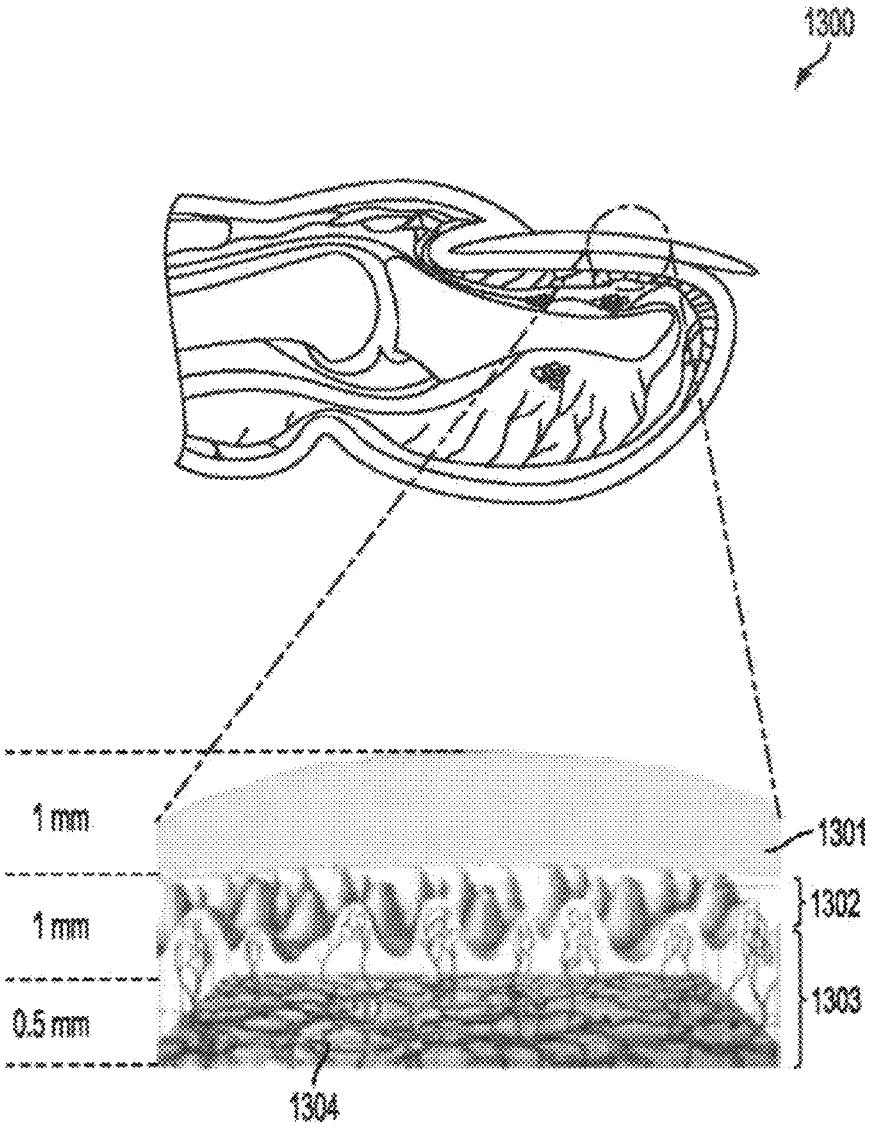
FIG. 13 illustrates a typical human nail tissue structure and the capillary vessels below it.

Because of the complexity of the interference from skin in non-invasive glucose monitoring (e.g., FIG. 10), other parts of the body without skin above blood vessels or capillaries may be alternative candidates for measuring blood constituents. One embodiment may involve transmission or reflection through human nails. As an example, FIG. 13 illustrates a typical human nail tissue structure 1300 and the capillary vessels below it. The fingernail 1301 is approximately 1 mm thick, and below this resides a layer of epidermis 1302 with a thickness of approximately 1 mm. The dermis 1304 is also shown, and within particularly the top about 0.5 mm of dermis are a significant number of capillary vessels. To measure the blood constituents, the light exposed on the top of the fingernail must penetrate about 2-2.5 mm or more, and the reflected light (round trip passage) should be sufficiently strong to measure. In one embodiment, the distance required to penetrate could be reduced by drilling a hole in the fingernail 1301.

Figure 14:
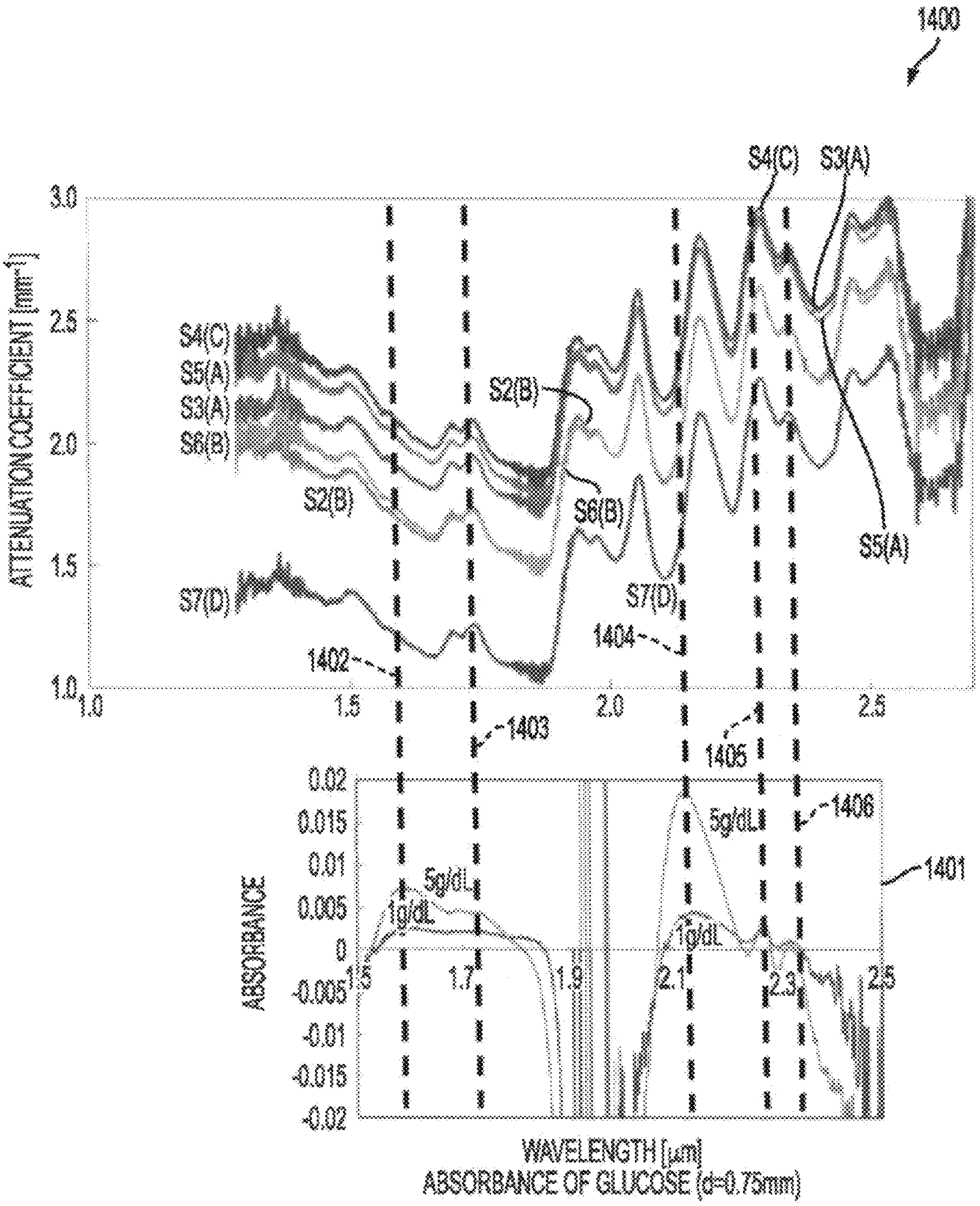
FIG. 14 shows the attenuation coefficient for seven nail samples that are allowed to stand in an environment with a humidity level of 14%. These coefficients are measured using an FTIR spectrometer over the near-infrared wavelength range of approximately 1 to 2.5 microns. Below is also included the spectrum of glucose.

In this alternative embodiment using the fingernail, there may still be interference from the nail's spectral features. For example, FIG. 14 illustrates the attenuation coefficient 1400 for seven nail samples that are allowed to stand in an environment with a humidity level of 14%. These coefficients are measured using an FTIR spectrometer over the near-infrared wavelength range of approximately 1 to 2.5 microns. These spectra are believed to correspond to the spectra of keratin contained in the nail plate. The base lines for the different samples are believed to differ because of the influence of scattering. Several of the absorption peaks observed correspond to peaks of keratin absorption, while other features may appear from the underlying epidermis and dermis. It should also be noted that the attenuation coefficients 1400 also vary considerably depending on humidity level or water content as well as temperature and other environmental factors. Moreover, the attenuation coefficient may also change in the presence of nail polish of various sorts.

Similar to skin, the large variations in attenuation coefficient for fingernails also may interfere with the absorption peaks of glucose. As an example, in FIG. 14 below the fingernail spectrum is also shown the glucose spectrum 1401 for two different glucose concentrations. The vertical lines 1402, 1403, 1404, 1405 and 1406 are drawn to illustrate the glucose absorption peaks and where they lie on the fingernail spectra 1400. As is apparent, the nail has interfering features that may be similar to skin, particularly since both have spectra that vary not only in wavelength but also with environmental factors. In one embodiment, it may be possible to see the glucose peaks 1402 and 1404 through the fingernail, but it may be much more difficult to observe the glucose peaks near 1403, 1405 and 1406.

Transmission or Reflection Through Teeth

Figure 15:
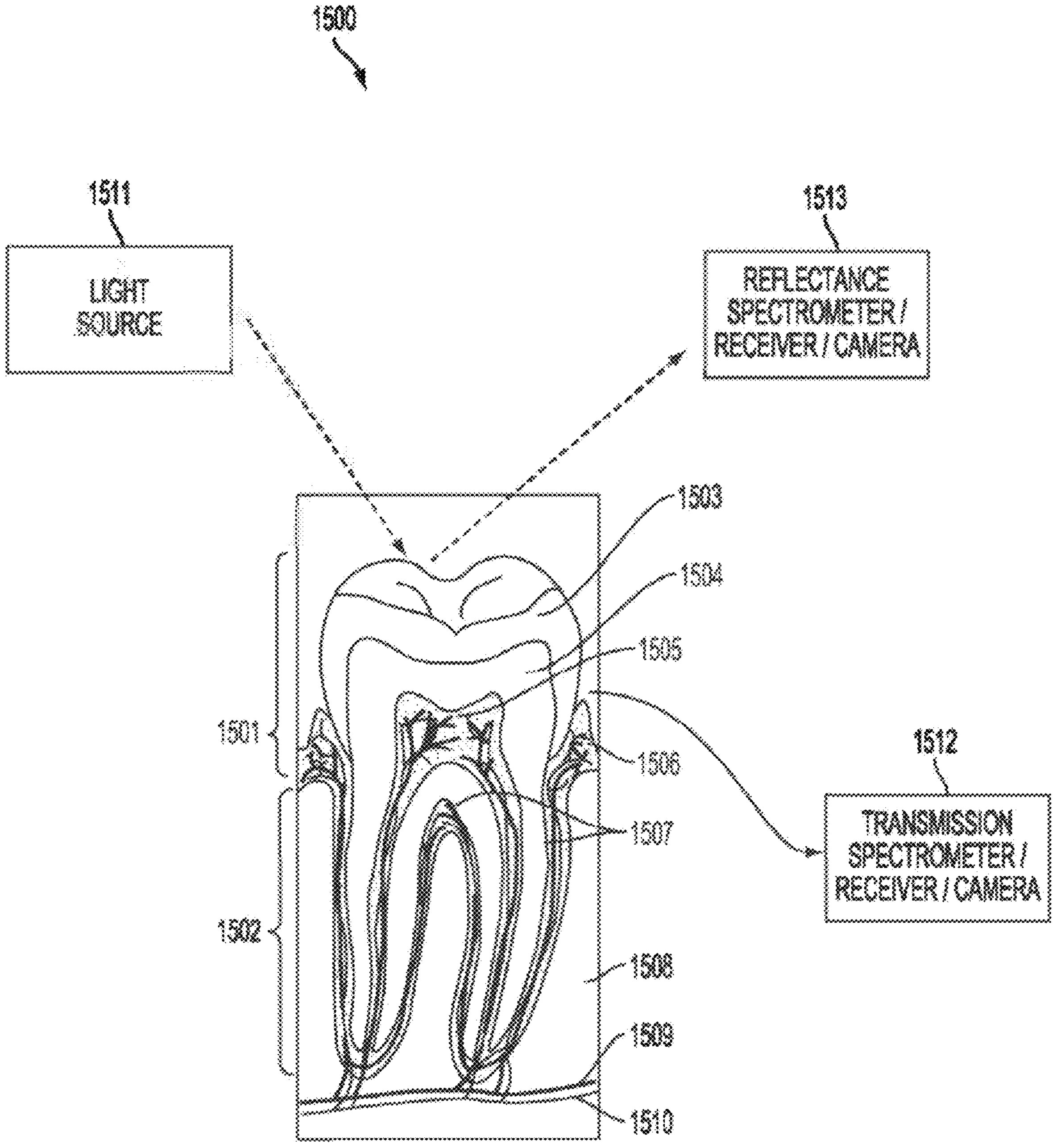
FIG. 15 illustrates the structure of a tooth.

Yet another embodiment may observe the transmittance or reflectance through teeth to measure blood constituents or analytes. FIG. 15 illustrates an exemplary structure of a tooth 1500. The tooth 1500 has a top layer called the crown 1501 and below that a root 1502 that reaches well into the gum 1506 and bone 1508 of the mouth. The exterior of the crown 1501 is an enamel layer 1503, and below the enamel is a layer of dentine 1504 that sits atop a layer of cementum 1507. Below the dentine 1504 is a pulp region 1505, which comprises within it blood vessels 1509 and nerves 1510. If the light can penetrate the enamel 1503 and dentine 1504, then the blood flow and blood constituents can be measured through the blood vessels in the dental pulp 1505. While it may be true that the amount of blood flow in the dental pulp 1505 may be less since it comprises capillaries, the smaller blood flow could still be advantageous if there is less interfering spectral features from the tooth.

Figure 16A:
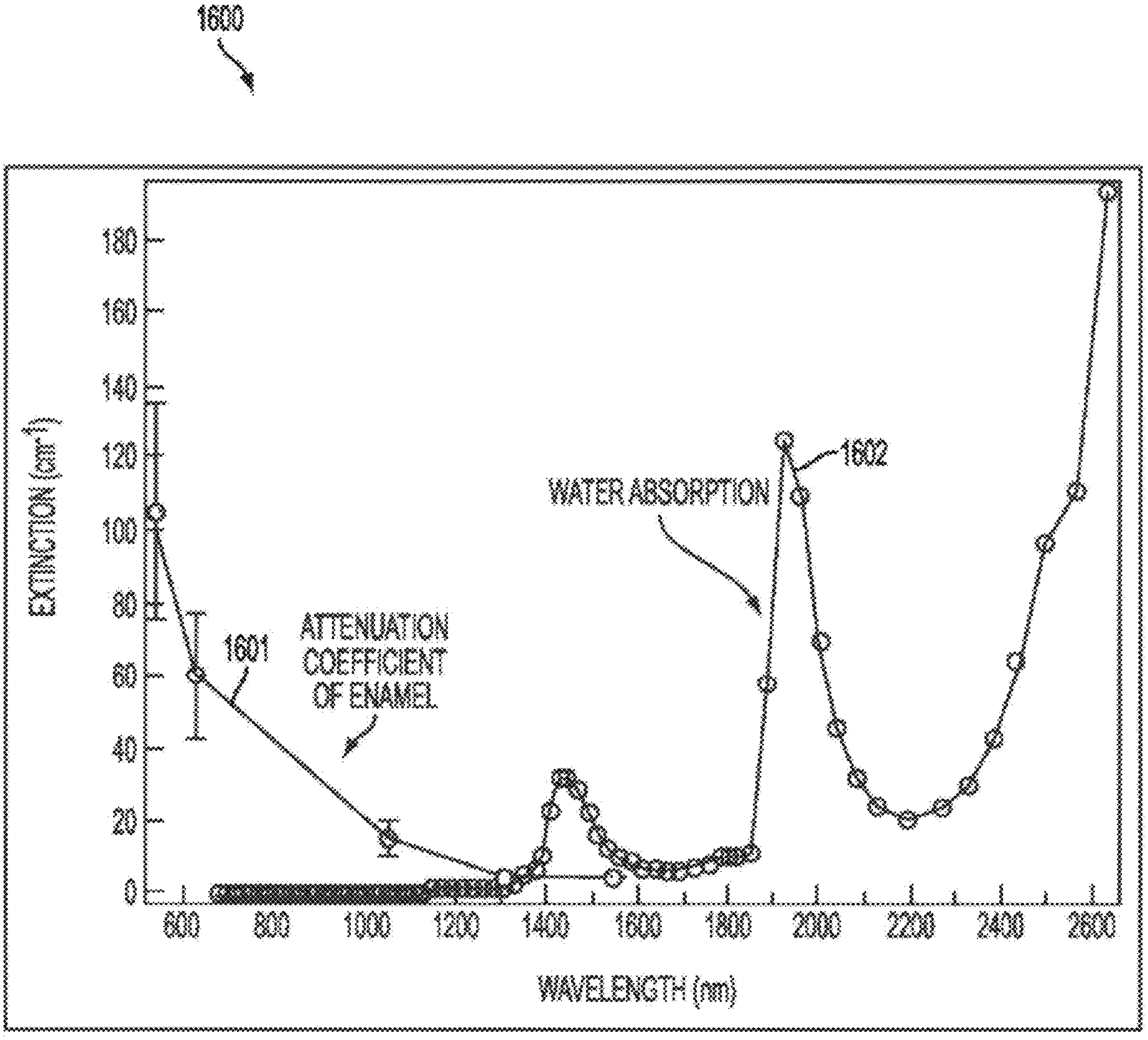
FIG. 16A shows the attenuation coefficient for dental enamel and water versus wavelength from approximately 600 nm to 2600 nm.

The transmission, absorption and reflection from teeth has been studied in the near infrared, and, although there are some features, the enamel and dentine appear to be fairly transparent in the near infrared (particularly wavelengths between 1500 and 2500 nm). For example, the absorption or extinction ratio for light transmission has been studied. FIG. 16A illustrates the attenuation coefficient 1600 for dental enamel 1601 (filled circles) and the absorption coefficient of water 1602 (open circles) versus wavelength. Near-infrared light may penetrate much further without scattering through all the tooth enamel, due to the reduced scattering coefficient in normal enamel. Scattering in enamel may be fairly strong in the visible, but decreases as approximately 1/(wavelength)3 [i.e., inverse of the cube of the wavelength] with increasing wavelength to a value of only 2-3 cm−1 at 1310 nm and 1550 nm in the near infrared. Therefore, enamel may be virtually transparent in the near infrared with optical attenuation 1-2 orders of magnitude less than in the visible range.

Figure 16B:
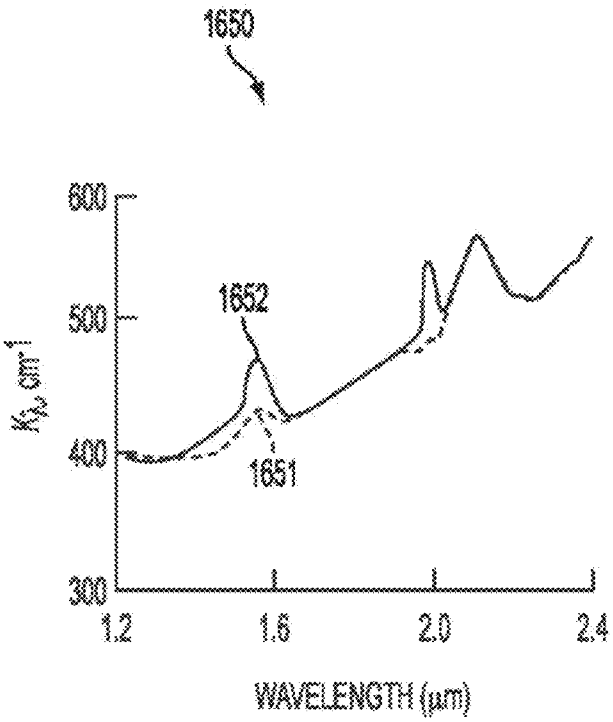
FIG. 16B illustrates the absorption spectrum of intact enamel and dentine in the wavelength range of approximately 1.2 to 2.4 microns.

As another example, FIG. 16B illustrates the absorption spectrum 1650 of intact enamel 1651 (dashed line) and dentine 1652 (solid line) in the wavelength range of approximately 1.2 to 2.4 microns. In the near infrared there are two absorption bands around 1.5 and 2 microns. The band with a peak around 1.57 microns may be attributed to the overtone of valent vibration of water present in both enamel and dentine. In this band, the absorption is greater for dentine than for enamel, which may be related to the large water content in this tissue. In the region of 2 microns, dentine may have two absorption bands, and enamel one. The band with a maximum near 2.1 microns may belong to the overtone of vibration of PO hydroxyapatite groups, which is the main substance of both enamel and dentine. Moreover, the band with a peak near 1.96 microns in dentine may correspond to water absorption (dentine may contain substantially higher water than enamel).

Figure 17:
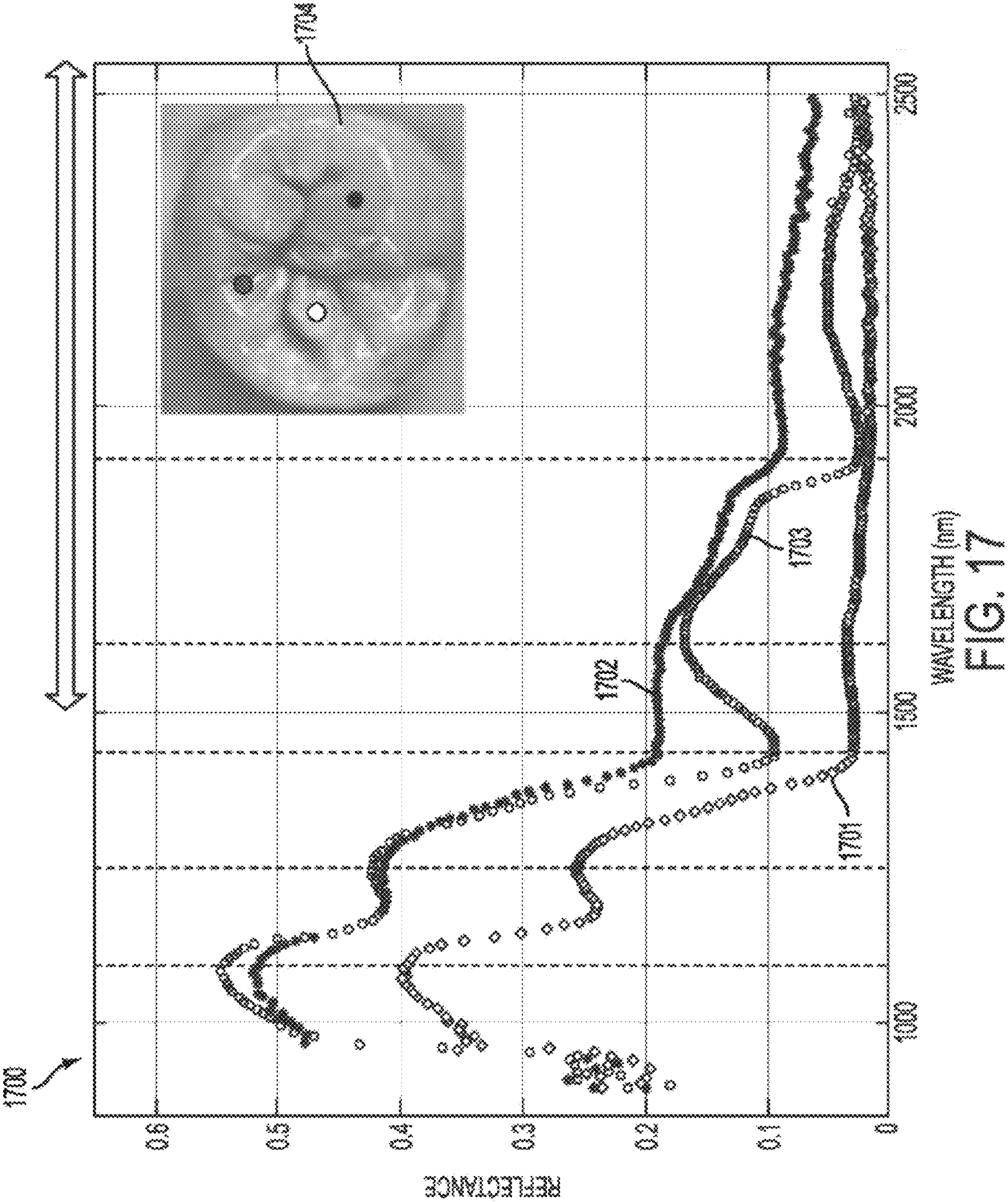
FIG. 17 shows the near infrared spectral reflectance over the wavelength range of approximately 800 nm to 2500 nm from an occlusal tooth surface. The black diamonds correspond to the reflectance from a sound, intact tooth section. The asterisks correspond to a tooth section with an enamel lesion. The circles correspond to a tooth section with a dentine lesion.

In addition to the absorption coefficient, the reflectance from intact teeth and teeth with dental caries (e.g., cavities) has been studied. In one embodiment, FIG. 17 shows the near infrared spectral reflectance 1700 over the wavelength range of approximately 800 nm to 2500 nm from an occlusal (e.g., top/bottom) tooth surface 1704. The curve with black diamonds 1701 corresponds to the reflectance from a sound, intact tooth section. The curve with asterisks * 1702 corresponds to a tooth section with an enamel lesion. The curve with circles 1703 corresponds to a tooth section with a dentine lesion. Thus, when there is a lesion, more scattering occurs and there may be an increase in the reflected light.

For wavelengths shorter than approximately 1400 nm, the shapes of the spectra remain similar, but the amplitude of the reflection changes with lesions. Between approximately 1400 nm and 2500 nm, an intact tooth 1701 has low reflectance (e.g., high transmission), and the reflectance appears to be more or less independent of wavelength. On the other hand, in the presence of lesions 1702 and 1703, there is increased scattering, and the scattering loss may be wavelength dependent. For example, the scattering loss may decrease as $1/(\text{wavelength})^3$—so, the scattering loss decreases with longer wavelengths. When there is a lesion in the dentine 1703, more water can accumulate in the area, so there is also increased water absorption. For example, the dips near 1450 nm and 1900 nm correspond to water absorption, and the reflectance dips are particularly pronounced in the dentine lesion 1703. One other benefit of the absorption, transmission or reflectance in the near infrared may be that stains and non-calcified plaque are not visible in this wavelength range, enabling better discrimination of defects, cracks, and demineralized areas.

Compared with the interference from skin 1000 in FIG. 10 or fingernails 1400 in FIG. 14, the teeth appear to introduce much less interference for non-invasive monitoring of blood constituents. The few features in FIG. 16B or 17 may be calibrated out of the measurement. Also, using an intact tooth 1701 may further minimize any interfering signals. Furthermore, since the tooth comprises relatively hard tissue, higher power from the light sources in the near infrared may be used without damaging the tissue, such as with skin.

Human Interface for Measurement System

A number of different types of measurements may be used to sample the blood in the dental pulp. The basic feature of the measurements should be that the optical properties are measured as a function of wavelength at a plurality of wavelengths. As further described below, the light source may output a plurality of wavelengths, or a continuous spectrum over a range of wavelengths. In a preferred embodiment, the light source may cover some or all of the wavelength range between approximately 1400 nm and 2500 nm. The signal may be received at a receiver, which may also comprise a spectrometer or filters to discriminate between different wavelengths. The signal may also be received at a camera, which may also comprise filters or a spectrometer. In an alternate embodiment, the spectral discrimination using filters or a spectrometer may be placed after the light source rather than at the receiver. The receiver usually comprises one or more detectors (optical-to-electrical conversion element) and electrical circuitry. The receiver may also be coupled to analog to digital converters, particularly if the signal is to be fed to a digital device.

Referring to FIG. 15, one or more light sources 1511 may be used for illumination. In one embodiment, a transmission measurement may be performed by directing the light source output 1511 to the region near the interface between the gum 1506 and dentine 1504. In one embodiment, the light may be directed using a light guide or a fiber optic. The light may then propagate through the dental pulp 1505 to the other side, where the light may be incident on one or more detectors or another light guide to transport the signal to a spectrometer, receiver or camera 1512. In another embodiment, the light source may be directed to one or more locations near the interface between the gum 1506 and dentine 1504 (in one example, could be from the two sides of the tooth). The transmitted light may then be detected in the occlusal surface above the tooth using a spectrometer, receiver, or camera 1512. In yet another embodiment, a reflectance measurement may be conducted by directing the light source output 1511 to, for example, the occlusal surface of the tooth, and then detecting the reflectance at a spectrometer, receiver or camera 1513. Although a few embodiments for measuring the blood constituents through a tooth are described, other embodiments and techniques may also be used and are intended to be covered by this disclosure.

Figure 18A:
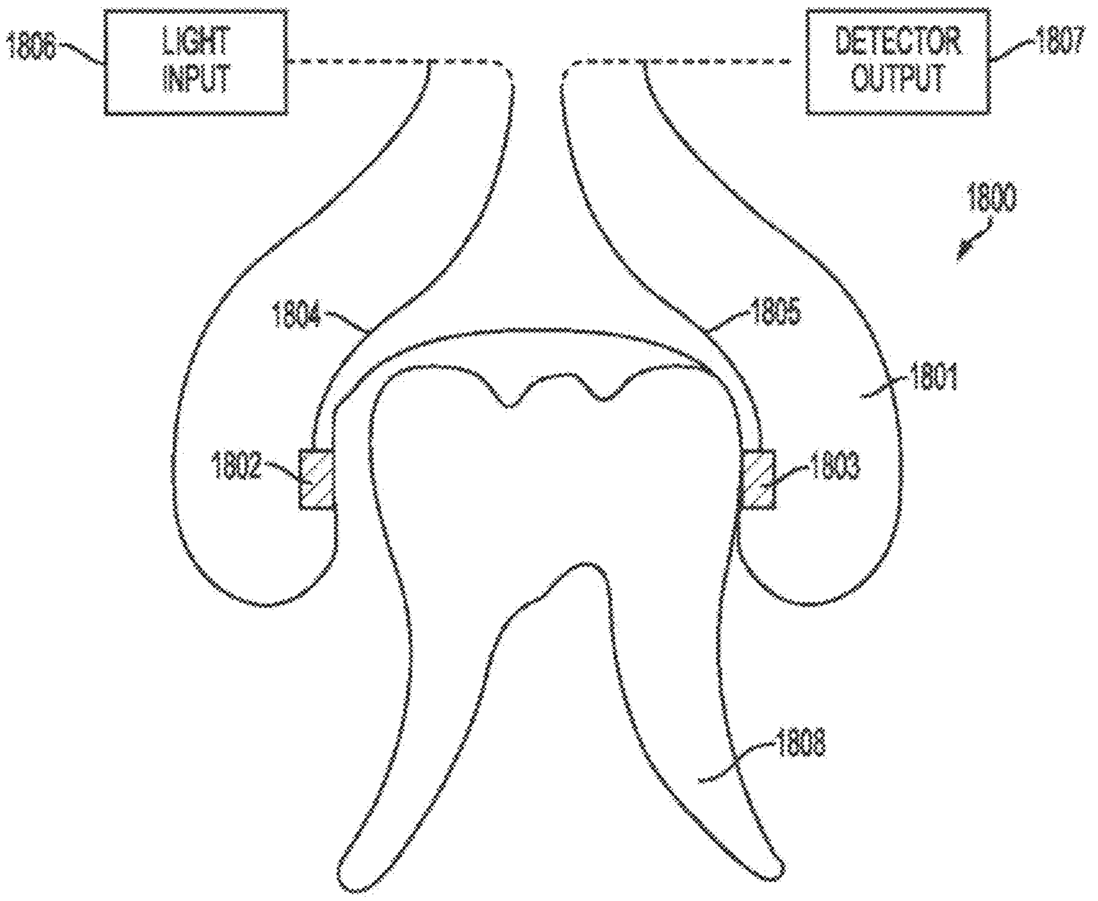
FIG. 18A illustrates a clamp design of a human interface to cap over one or more teeth and perform a non-invasive measurement of blood constituents.

The human interface for the non-invasive measurement of blood constituents may be of various forms. In one embodiment, a "clamp" design 1800 may be used to cap over one or more teeth, as illustrated in FIG. 18A. The clamp design may be different for different types of teeth, or it may be flexible enough to fit over different types of teeth. For example, different types of teeth include the molars (toward the back of the mouth), the premolars, the canine, and the incisors (toward the front of the mouth). One embodiment of the clamp-type design is illustrated in FIG. 18A for a molar tooth 1808. The C-clamp 1801 may be made of a plastic or rubber material, and it may comprise a light source input 1802 and a detector output 1803 on the front or back of the tooth.

The light source input 1802 may comprise a light source directly, or it may have light guided to it from an external light source. Also, the light source input 1802 may comprise a lens system to collimate or focus the light across the tooth.

The detector output 1803 may comprise a detector directly, or it may have a light guide to transport the signal to an external detector element. The light source input 1802 may be coupled electrically or optically through 1804 to a light input 1806. For example, if the light source is external in 1806, then the coupling element 1804 may be a light guide, such as a fiber optic. Alternately, if the light source is contained in 1802, then the coupling element 1804 may be electrical wires connecting to a power supply in 1806. Similarly, the detector output 1803 may be coupled to a detector output unit 1807 with a coupling element 1805, which may be one or more electrical wires or a light guide, such as a fiber optic. This is just one example of a clamp over one or more teeth, but other embodiments may also be used and are intended to be covered by this disclosure.

Figure 18B:
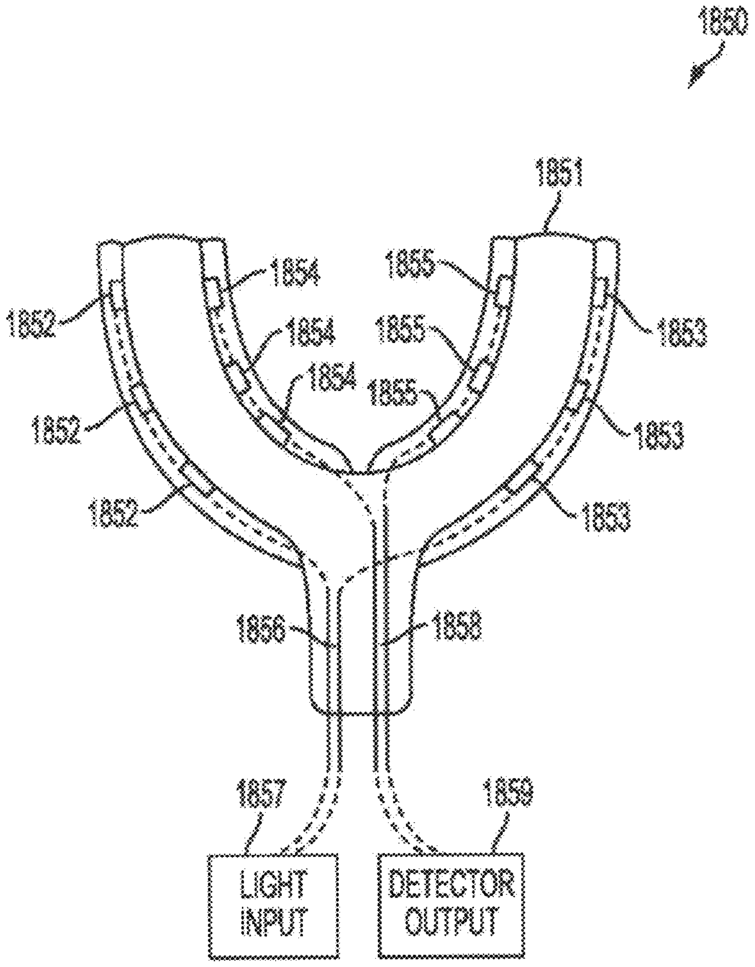
FIG. 18B shows a mouth guard design of a human interface to perform a non-invasive measurement of blood constituents.

In yet another embodiment, one or more light source ports and sensor ports may be used in a mouth-guard type design. For example, one embodiment of a dental mouth guard 1850 is illustrated in FIG. 18B. The structure of the mouth guard 1851 may be similar to mouth guards used in sports (e.g., when playing football or boxing) or in dental trays used for applying fluoride treatment, and the mouth guard may be made from plastic or rubber materials, for example. As an example, the mouth guard may have one or more light source input ports 1852, 1853 and one or more detector output ports 1854, 1855. Although six input and output ports are illustrated, any number of ports may be used.

Similar to the clamp design describe above, the light source inputs 1852, 1853 may comprise one or more light sources directly, or they may have light guided to them from an external light source. Also, the light source inputs 1852, 1853 may comprise lens systems to collimate or focus the light across the teeth. The detector outputs 1854, 1855 may comprise one or more detectors directly, or they may have one or more light guides to transport the signals to an external detector element. The light source inputs 1852, 1853 may be coupled electrically or optically through 1856 to a light input 1857. For example, if the light source is external in 1857, then the one or more coupling elements 1856 may be one or more light guides, such as a fiber optic. Alternately, if the light sources are contained in 1852, 1853, then the coupling element 1856 may be one or more electrical wires connecting to a power supply in 1857. Similarly, the detector outputs 1854, 1855 may be coupled to a detector output unit 1859 with one or more coupling elements 1858, which may be one or more electrical wires or one or more light guides, such as a fiber optic. This is just one example of a mouth guard design covering a plurality of teeth, but other embodiments may also be used and are intended to be covered by this disclosure. For instance, the position of the light source inputs and detector output ports could be exchanged, or some mixture of locations of light source inputs and detector output ports could be used.

Other elements may be added to the human interface designs of FIG. 18 and are also intended to be covered by this disclosure. For instance, in one embodiment it may be desirable to have replaceable inserts that may be disposable. Particularly in a doctor's office or hospital setting, the same instrument may be used with a plurality of patients. Rather than disinfecting the human interface after each use, it may be preferable to have disposable inserts that can be thrown away after each use. In one embodiment, a thin plastic coating material may enclose the clamp design of FIG. 18A or mouth guard design of FIG. 18B. The coating material may be inserted before each use, and then after the measurement is exercised the coating material may be peeled off and replaced. Such a design may save the physician or user considerable time, while at the same time provide the business venture with a recurring cost revenue source. Any coating material or other disposable device may be constructed of a material having suitable optical properties that may be considered during processing of the signals used to detect any anomalies in the teeth.

Light Sources for Near Infrared

There are a number of light sources that may be used in the near infrared. To be more specific, the discussion below will consider light sources operating in the so-called short wave infrared (SWIR), which may cover the wavelength range of approximately 1400 nm to 2500 nm. Other wavelength ranges may also be used for the applications described in this disclosure, so the discussion below is merely provided for exemplary types of light sources. The SWIR wavelength range may be valuable for a number of reasons. First, the SWIR corresponds to a transmission window through water and the atmosphere. For example, 302 in FIG. 3A and 1602 in FIG. 16A illustrate the water transmission windows. Also, through the atmosphere, wavelengths in the SWIR have similar transmission windows due to water vapor in the atmosphere. Second, the so-called "eye-safe" wavelengths are wavelengths longer than approximately 1400 nm. Third, the SWIR covers the wavelength range for nonlinear combinations of stretching and bending modes as well as the first overtone of C—H stretching modes. Thus, for example, glucose and ketones among other substances may have unique signatures in the SWIR. Moreover, many solids have distinct spectral signatures in the SWIR, so particular solids may be identified using stand-off detection or remote sensing. For instance, many explosives have unique signatures in the SWIR.

Different light sources may be selected for the SWIR based on the needs of the application. Some of the features for selecting a particular light source include power or intensity, wavelength range or bandwidth, spatial or temporal coherence, spatial beam quality for focusing or transmission over long distance, and pulse width or pulse repetition rate. Depending on the application, lamps, light emitting diodes (LEDs), laser diodes (LD's), tunable LD's, super-luminescent laser diodes (SLDs), fiber lasers or super-continuum sources (SC) may be advantageously used. Also, different fibers may be used for transporting the light, such as fused silica fibers, plastic fibers, mid-infrared fibers (e.g., tellurite, chalcogenides, fluorides, ZBLAN, etc), or a hybrid of these fibers.

Lamps may be used if low power or intensity of light is required in the SWIR, and if an incoherent beam is suitable. In one embodiment, in the SWIR an incandescent lamp that can be used is based on tungsten and halogen, which have an emission wavelength between approximately 500 nm to 2500 nm. For low intensity applications, it may also be possible to use thermal sources, where the SWIR radiation is based on the black body radiation from the hot object. Although the thermal and lamp based sources are broadband and have low intensity fluctuations, it may be difficult to achieve a high signal-to-noise ratio in a non-invasive blood constituent measurement due to the low power levels. Also, the lamp based sources tend to be energy inefficient.

In another embodiment, LED's can be used that have a higher power level in the SWIR wavelength range. LED's also produce an incoherent beam, but the power level can be higher than a lamp and with higher energy efficiency. Also, the LED output may more easily be modulated, and the LED provides the option of continuous wave or pulsed mode of operation. LED's are solid state components that emit a wavelength band that is of moderate width, typically between about 20 nm to 40 nm. There are also so-called super-luminescent LEDs that may even emit over a much wider wavelength range. In another embodiment, a wide band light source may be constructed by combining different LEDs that emit in different wavelength bands, some of which could preferably overlap in spectrum. One advantage of LEDs as well as other solid state components is the compact size that they may be packaged into.

In yet another embodiment, various types of laser diodes may be used in the SWIR wavelength range. Just as LEDs may be higher in power but narrower in wavelength emission than lamps and thermal sources, the LDs may be yet higher in power but yet narrower in wavelength emission than LEDs. Different kinds of LDs may be used, including Fabry-Perot LDs, distributed feedback (DFB) LDs, distributed Bragg reflector (DBR) LDs. Since the LDs have relatively narrow wavelength range (typically under 10 nm), in one embodiment a plurality of LDs may be used that are at different wavelengths in the SWIR. For example, in a preferred embodiment for non-invasive glucose monitoring, it may be advantageous to use LDs having emission spectra near some or all of the glucose spectral peaks (e.g., near 1587 nm, 1750 nm, 2120 nm, 2270 nm, and 2320 nm). The various LDs may be spatially multiplexed, polarization multiplexed, wavelength multiplexed, or a combination of these multiplexing methods. Also, the LDs may be fiber pig-tailed or have one or more lenses on the output to collimate or focus the light. Another advantage of LDs is that they may be packaged compactly and may have a spatially coherent beam output. Moreover, tunable LDs that can tune over a range of wavelengths are also available. The tuning may be done by varying the temperature, or electrical current may be used in particular structures, such as distributed Bragg reflector LDs. In another embodiment, external cavity LDs may be used that have a tuning element, such as a fiber grating or a bulk grating, in the external cavity.

In another embodiment, super-luminescent laser diodes may provide higher power as well as broad bandwidth. An SLD is typically an edge emitting semiconductor light source based on super-luminescence (e.g., this could be amplified spontaneous emission). SLDs combine the higher power and brightness of LDs with the low coherence of conventional LEDs, and the emission band for SLD's may be 5 to 100 nm wide, preferably in the 60 to 100 nm range. Although currently SLDs are commercially available in the wavelength range of approximately 400 nm to 1700 nm, SLDs could and may in the future be made to cover a broader region of the SWIR.

Figure 19:
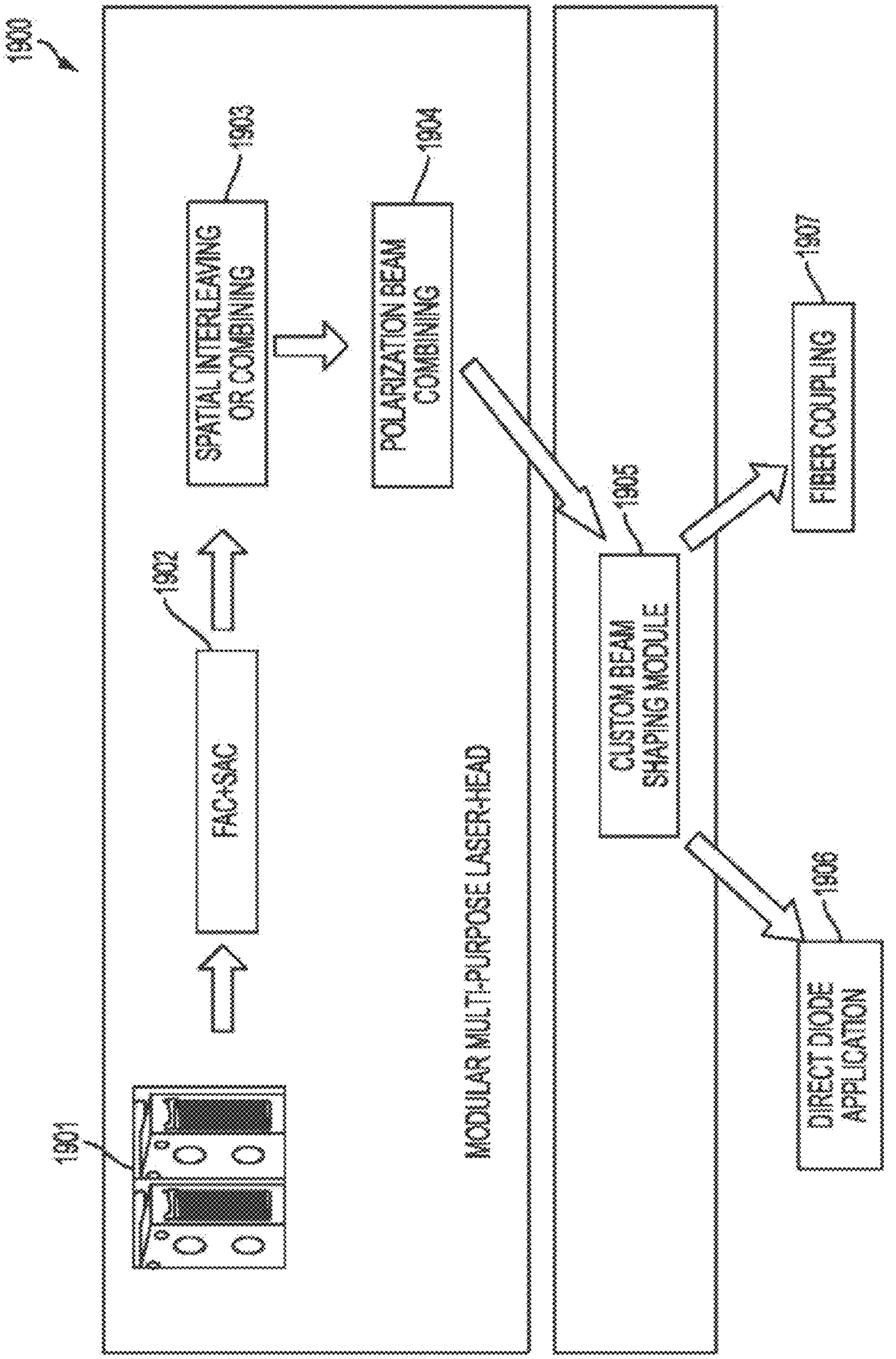
FIG. 19 illustrates a block diagram or building blocks for constructing high power laser diode assemblies.

In yet another embodiment, high power LDs for either direct excitation or to pump fiber lasers and SC light sources may be constructed using one or more laser diode bar stacks. As an example, FIG. 19 shows an example of the block diagram 1900 or building blocks for constructing the high power LDs. In this embodiment, one or more diode bar stacks 1901 may be used, where the diode bar stack may be an array of several single emitter LDs. Since the fast axis (e.g., vertical direction) may be nearly diffraction limited while the slow-axis (e.g., horizontal axis) may be far from diffraction limited, different collimators 1902 may be used for the two axes.

Then, the brightness may be increased by spatially combining the beams from multiple stacks 1903. The combiner may include spatial interleaving, it may include wavelength multiplexing, or it may involve a combination of the two. Different spatial interleaving schemes may be used, such as using an array of prisms or mirrors with spacers to bend one array of beams into the beam path of the other. In another embodiment, segmented mirrors with alternate high-reflection and anti-reflection coatings may be used. Moreover, the brightness may be increased by polarization beam combining 1904 the two orthogonal polarizations, such as by using a polarization beam splitter. In one embodiment, the output may then be focused or coupled into a large diameter core fiber. As an example, typical dimensions for the large diameter core fiber range from approximately 100 microns in diameter to 400 microns or more. Alternatively or in addition, a custom beam shaping module 1905 may be used, depending on the particular application. For example, the output of the high power LD may be used directly 1906, or it may be fiber coupled 1907 to combine, integrate, or transport the high power LD energy. These high power LDs may grow in importance because the LD powers can rapidly scale up. For example, instead of the power being limited by the power available from a single emitter, the power may increase in multiples depending on the number of diodes multiplexed and the size of the large diameter fiber. Although FIG. 19 is shown as one embodiment, some or all of the elements may be used in a high power LD, or additional elements may also be used.

SWIR Super-Continuum Lasers

Each of the light sources described above have particular strengths, but they also may have limitations. For example, there is typically a trade-off between wavelength range and power output. Also, sources such as lamps, thermal sources, and LEDs produce incoherent beams that may be difficult to focus to a small area and may have difficulty propagating for long distances. An alternative source that may overcome some of these limitations is an SC light source. Some of the advantages of the SC source may include high power and intensity, wide bandwidth, spatially coherent beam that can propagate nearly transform limited over long distances, and easy compatibility with fiber delivery.

Supercontinuum lasers may combine the broadband attributes of lamps with the spatial coherence and high brightness of lasers. By exploiting a modulational instability initiated supercontinuum (SC) mechanism, an all-fiber-integrated SC laser with no moving parts may be built using commercial-off-the-shelf (COTS) components. Moreover, the fiber laser architecture may be a platform where SC in the visible, near-infrared/SWIR, or mid-IR can be generated by appropriate selection of the amplifier technology and the SC generation fiber. But until now, SC lasers were used primarily in laboratory settings since typically large, table-top, mode-locked lasers were used to pump nonlinear media such as optical fibers to generate SC light. However, those large pump lasers may now be replaced with diode lasers and fiber amplifiers that gained maturity in the telecommunications industry.

Figure 20:
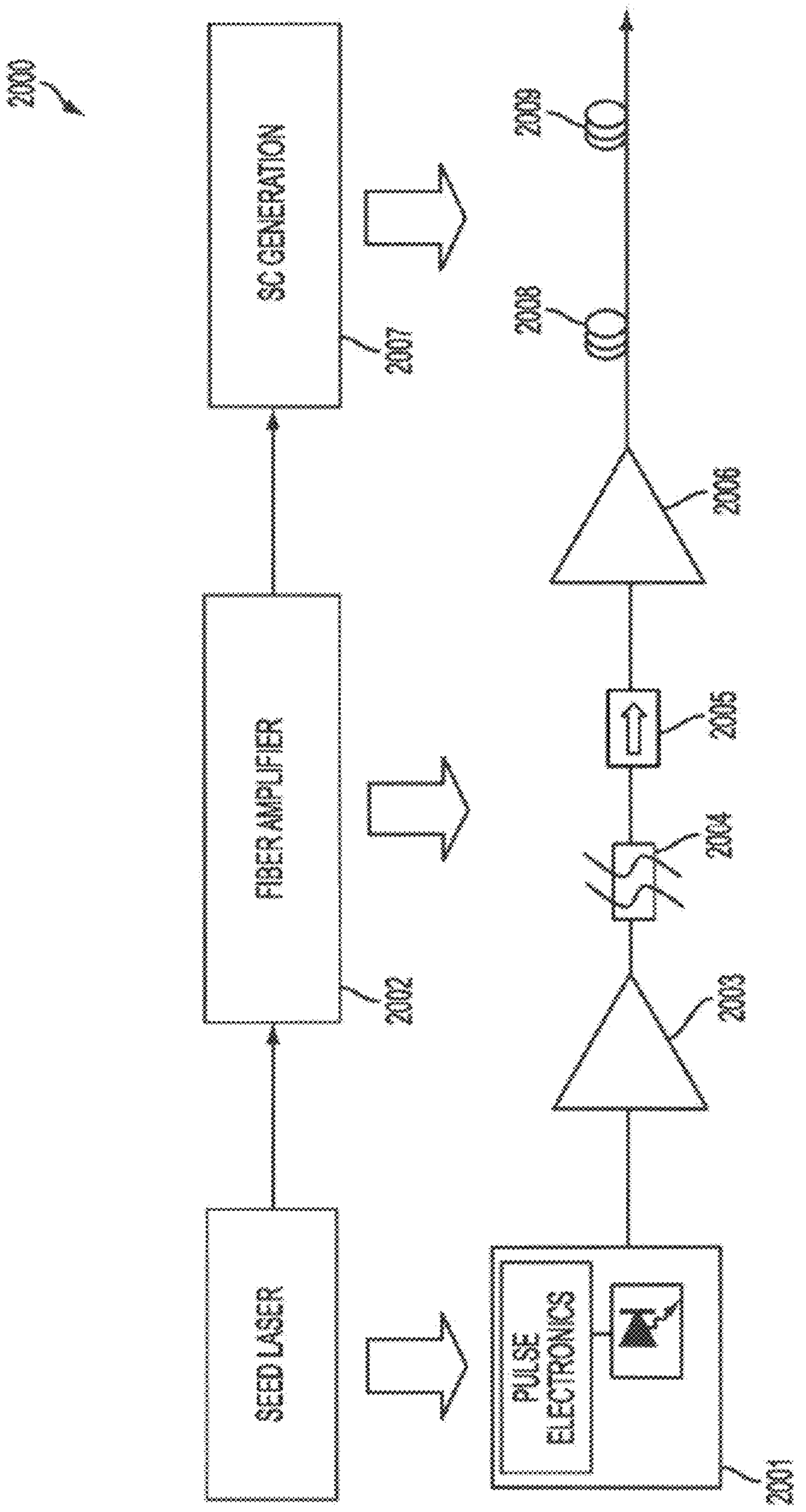
FIG. 20 shows a platform architecture for different wavelength ranges for an all-fiber-integrated, high powered, super-continuum light source.

In one embodiment, an all-fiber-integrated, high-powered SC light source 2000 may be elegant for its simplicity (FIG. 20). The light may be first generated from a seed laser diode 2001. For example, the seed LD 2001 may be a distributed feedback laser diode with a wavelength near 1542 or 1550 nm, with approximately 0.5-2.0 ns pulsed output, and with a pulse repetition rate between a kilohertz to about 100 MHz or more. The output from the seed laser diode may then be amplified in a multiple-stage fiber amplifier 2002 comprising one or more gain fiber segments. In one embodiment, the first stage pre-amplifier 2003 may be designed for optimal noise performance. For example, the pre-amplifier 2003 may be a standard erbium-doped fiber amplifier or an erbium/ytterbium doped cladding pumped fiber amplifier. Between amplifier stages 2003 and 2006, it may be advantageous to use band-pass filters 2004 to block amplified spontaneous emission and isolators 2005 to prevent spurious reflections. Then, the power amplifier stage 2006 may use a cladding-pumped fiber amplifier that may be optimized to minimize nonlinear distortion. The power amplifier fiber 2006 may also be an erbium-doped fiber amplifier, if only low or moderate power levels are to be generated.

The SC generation 2007 may occur in the relatively short lengths of fiber that follow the pump laser. In one exemplary embodiment, the SC fiber length may range from a few millimeters to 100 m or more. In one embodiment, the SC generation may occur in a first fiber 2008 where the modulational-instability initiated pulse break-up primarily occurs, followed by a second fiber 2009 where the SC generation and spectral broadening primarily occurs.

In one embodiment, one or two meters of standard single-mode fiber (SMF) after the power amplifier stage may be followed by several meters of SC generation fiber. For this example, in the SMF the peak power may be several kilowatts and the pump light may fall in the anomalous group-velocity dispersion regime-often called the soliton regime. For high peak powers in the dispersion regime, the nanosecond pulses may be unstable due to a phenomenon known as modulational instability, which is basically parametric amplification in which the fiber nonlinearity helps to phase match the pulses. As a consequence, the nanosecond pump pulses may be broken into many shorter pulses as the modulational instability tries to form soliton pulses from the quasi-continuous-wave background. Although the laser diode and amplification process starts with approximately nanosecond-long pulses, modulational instability in the short length of SMF fiber may form approximately 0.5 ps to several-picosecond-long pulses with high intensity. Thus, the few meters of SMF fiber may result in an output similar to that produced by mode-locked lasers, except in a much simpler and cost-effective manner.

The short pulses created through modulational instability may then be coupled into a nonlinear fiber for SC generation. The nonlinear mechanisms leading to broadband SC may include four-wave mixing or self-phase modulation along with the optical Raman effect. Since the Raman effect is self-phase-matched and shifts light to longer wavelengths by emission of optical photons, the SC may spread to longer wavelengths very efficiently. The short-wavelength edge may arise from four-wave mixing, and often times the short wavelength edge may be limited by increasing group-velocity dispersion in the fiber. In many instances, if the particular fiber used has sufficient peak power and SC fiber length, the SC generation process may fill the long-wavelength edge up to the transmission window.

Mature fiber amplifiers for the power amplifier stage 2006 include ytterbium-doped fibers (near 1060 nm), erbium-doped fibers (near 1550 nm), erbium/ytterbium-doped fibers (near 1550 nm), or thulium-doped fibers (near 2000 nm). In various embodiments, candidates for SC fiber 2009 include fused silica fibers (for generating SC between 0.8-2.7 μm), mid-IR fibers such as fluorides, chalcogenides, or tellurites (for generating SC out to 4.5 μm or longer), photonic crystal fibers (for generating SC between 0.4 and 1.7 μm), or combinations of these fibers. Therefore, by selecting the appropriate fiber-amplifier doping for 2006 and nonlinear fiber 2009, SC may be generated in the visible, near-IR/SWIR, or mid-IR wavelength region.

The configuration 2000 of FIG. 20 is just one particular example, and other configurations can be used and are intended to be covered by this disclosure. For example, further gain stages may be used, and different types of lossy elements or fiber taps may be used between the amplifier stages. In another embodiment, the SC generation may occur partially in the amplifier fiber and in the pig-tails from the pump combiner or other elements. In yet another embodiment, polarization maintaining fibers may be used, and a polarizer may also be used to enhance the polarization contrast between amplifier stages. Also, not discussed in detail are many accessories that may accompany this set-up, such as driver electronics, pump laser diodes, safety shut-offs, and thermal management and packaging.

Figure 21:
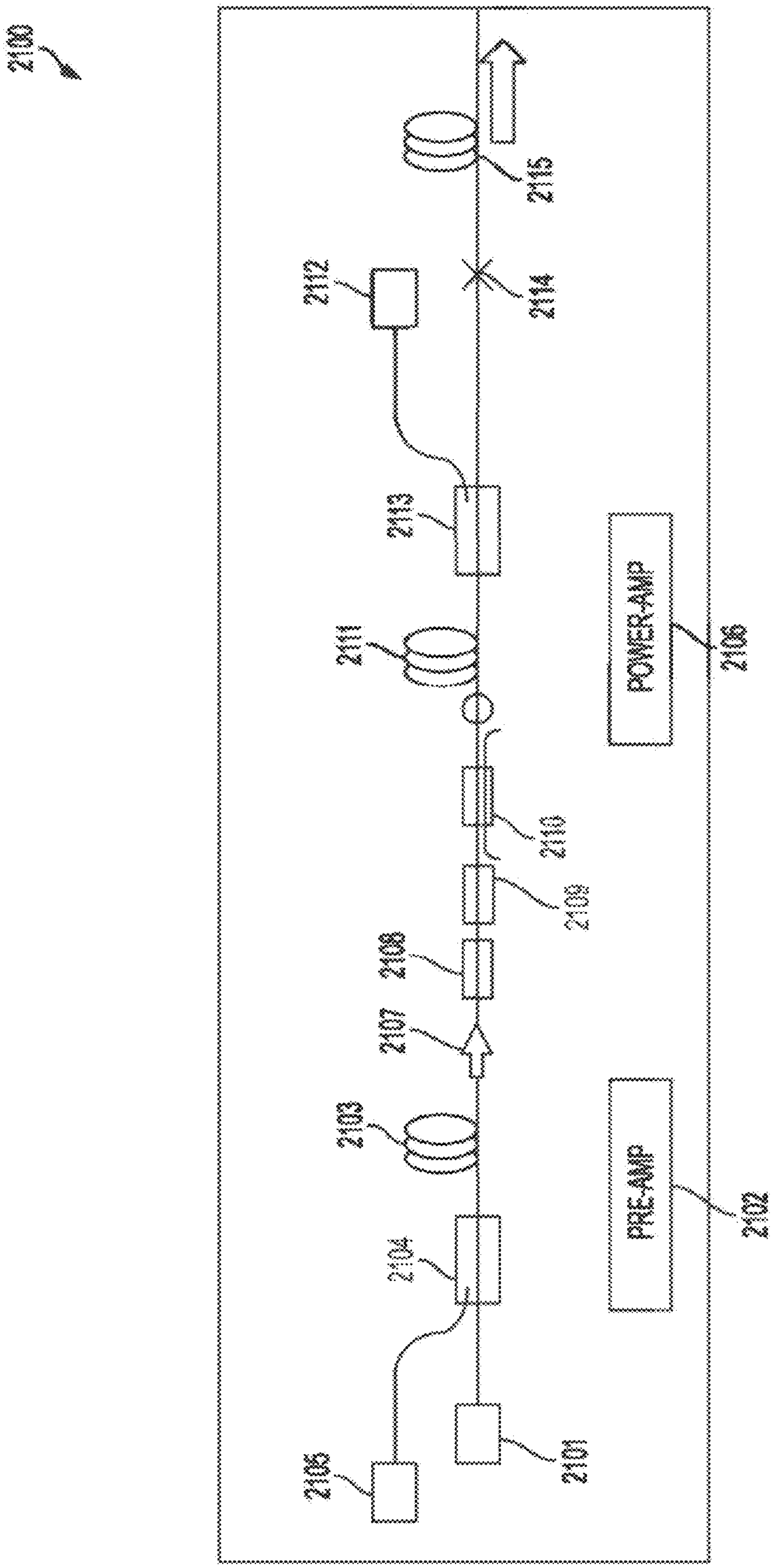
FIG. 21 illustrates one embodiment of a short-wave infrared (SWIR) super-continuum (SC) light source.

One example of an SC laser that operates in the SWIR used in one embodiment is illustrated in FIG. 21. This SWIR SC source 2100 produces an output of up to approximately 5 W over a spectral range of about 1.5 to 2.4 microns, and this particular laser is made out of polarization maintaining components. The seed laser 2101 is a distributed feedback (DFB) laser operating near 1542 nm producing approximately 0.5 nanosecond (ns) pulses at an about 8 MHz repetition rate. The pre-amplifier 2102 is forward pumped and uses about 2 m length of erbium/ytterbium cladding pumped fiber 2103 (often also called dual-core fiber) with an inner core diameter of 12 microns and outer core diameter of 130 microns. The pre-amplifier gain fiber 2103 is pumped using a 10 W 940 nm laser diode 2105 that is coupled in using a fiber combiner 2104.

In this particular 5 W unit, the mid-stage between amplifier stages 2102 and 2106 comprises an isolator 2107, a band-pass filter 2108, a polarizer 2109 and a fiber tap 2110. The power amplifier 2106 uses a 4 m length of the 12/130 micron erbium/ytterbium doped fiber 2111 that is counter-propagating pumped using one or more 30 W 940 nm laser diodes 2112 coupled in through a combiner 2113. An approximately 1-2 meter length of the combiner pig-tail helps to initiate the SC process, and then a length of PM-1550 fiber 2115 (polarization maintaining, single-mode, fused silica fiber optimized for 1550 nm) is spliced 2114 to the combiner output.

Figure 22:
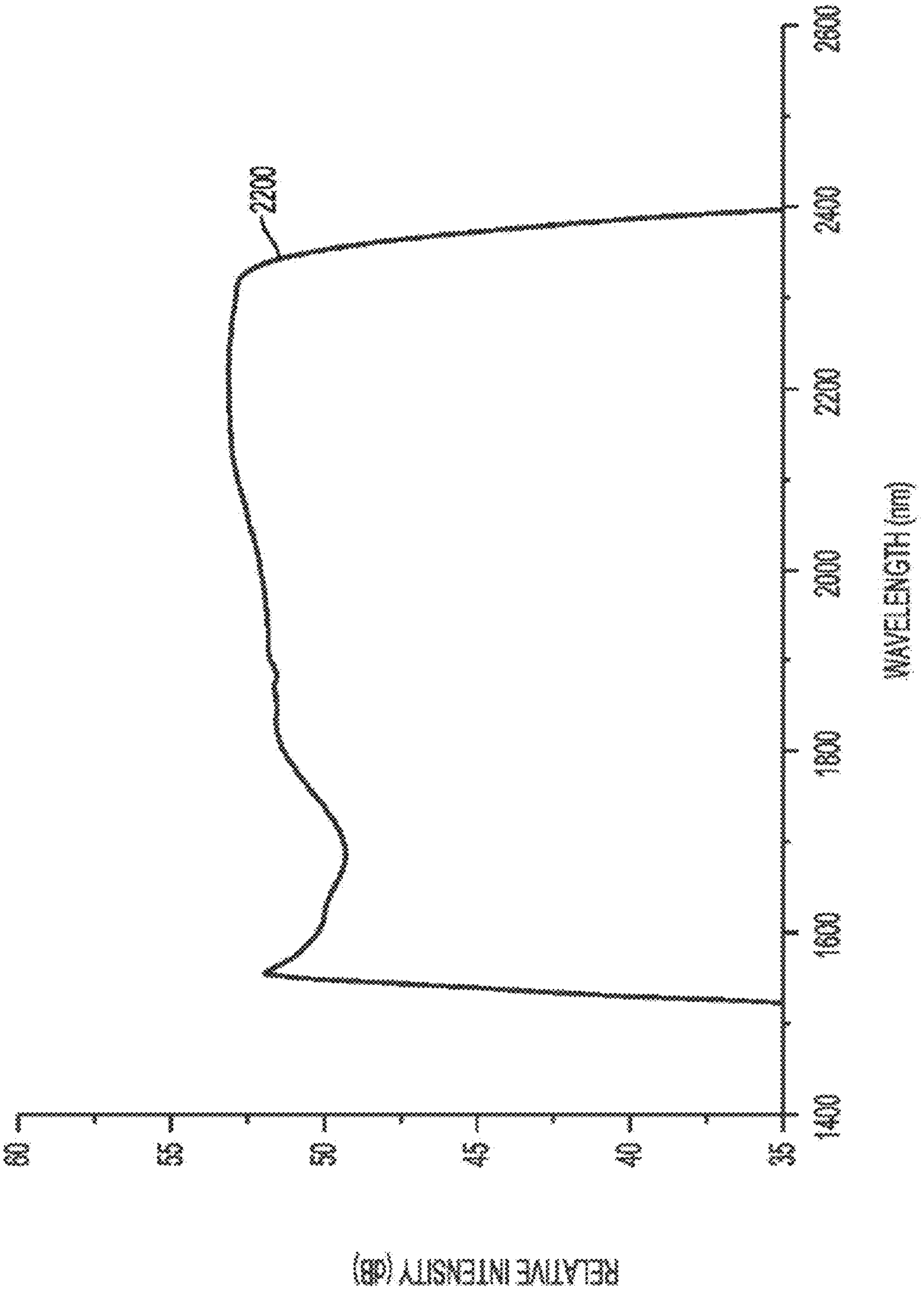
FIG. 22 shows the output spectrum from the SWIR SC laser of FIG. 21 when ~10 m length of fiber for SC generation is used. This fiber is a single-mode, non-dispersion shifted fiber that is optimized for operation near 1550 nm.

If an output fiber of about 10 m in length is used, then the resulting output spectrum 2200 is shown in FIG. 22. The details of the output spectrum 2200 depend on the peak power into the fiber, the fiber length, and properties of the fiber such as length and core size, as well as the zero dispersion wavelength and the dispersion properties. For example, if a shorter length of fiber is used, then the spectrum actually reaches to longer wavelengths (e.g., a 2 m length of SC fiber broadens the spectrum to ~2500 nm). Also, if extra-dry fibers are used with less O—H content, then the wavelength edge may also reach to a longer wavelength. To generate more spectrum toward the shorter wavelengths, the pump wavelength (in this case ~1542 nm) should be close to the zero dispersion wavelength in the fiber. For example, by using a dispersion shifted fiber or so-called non-zero dispersion shifted fiber, the short wavelength edge may shift to shorter wavelengths.

Although one particular example of a 5 W SWIR-SC has been described, different components, different fibers, and different configurations may also be used consistent with this disclosure. For instance, another embodiment of the similar configuration 2100 in FIG. 21 may be used to generate high powered SC between approximately 1060 and 1800 nm. For this embodiment, the seed laser 2101 may be a 1064 nm distributed feedback (DFB) laser diode, the pre-amplifier gain fiber 2103 may be a ytterbium-doped fiber amplifier with 10/125 microns dimensions, and the pump laser 2105 may be a 10 W 915 nm laser diode. In the mid-stage, a mode field adapter may be included in addition to the isolator 2107, band pass filter 2108, polarizer 2109 and tap 2110. The gain fiber 2111 in the power amplifier may be a 20 m length of ytterbium-doped fiber with 25/400 microns dimension for example. The pump 2112 for the power amplifier may be up to six pump diodes providing 30 W each near 915 nm, for example. For this much pump power, the output power in the SC may be as high as 50 W or more.

In another embodiment, it may be desirous to generate high power SWIR SC over 1.4-1.8 microns and separately 2-2.5 microns (the window between 1.8 and 2 microns may be less important due to the strong water and atmospheric absorption). For example, the top SC source of FIG. 23 can lead to bandwidths ranging from about 1400 nm to 1800 nm or broader, while the lower SC source of FIG. 23 can lead to bandwidths ranging from about 1900 nm to 2500 nm or broader. Since these wavelength ranges are shorter than about 2500 nm, the SC fiber can be based on fused silica fiber. Exemplary SC fibers include standard single-mode fiber SMF, high-nonlinearity fiber, high-NA fiber, dispersion shifted fiber, dispersion compensating fiber, and photonic crystal fibers. Non-fused-silica fibers can also be used for SC generation, including chalcogenides, fluorides, ZBLAN, tellurites, and germanium oxide fibers.

Figure 23:
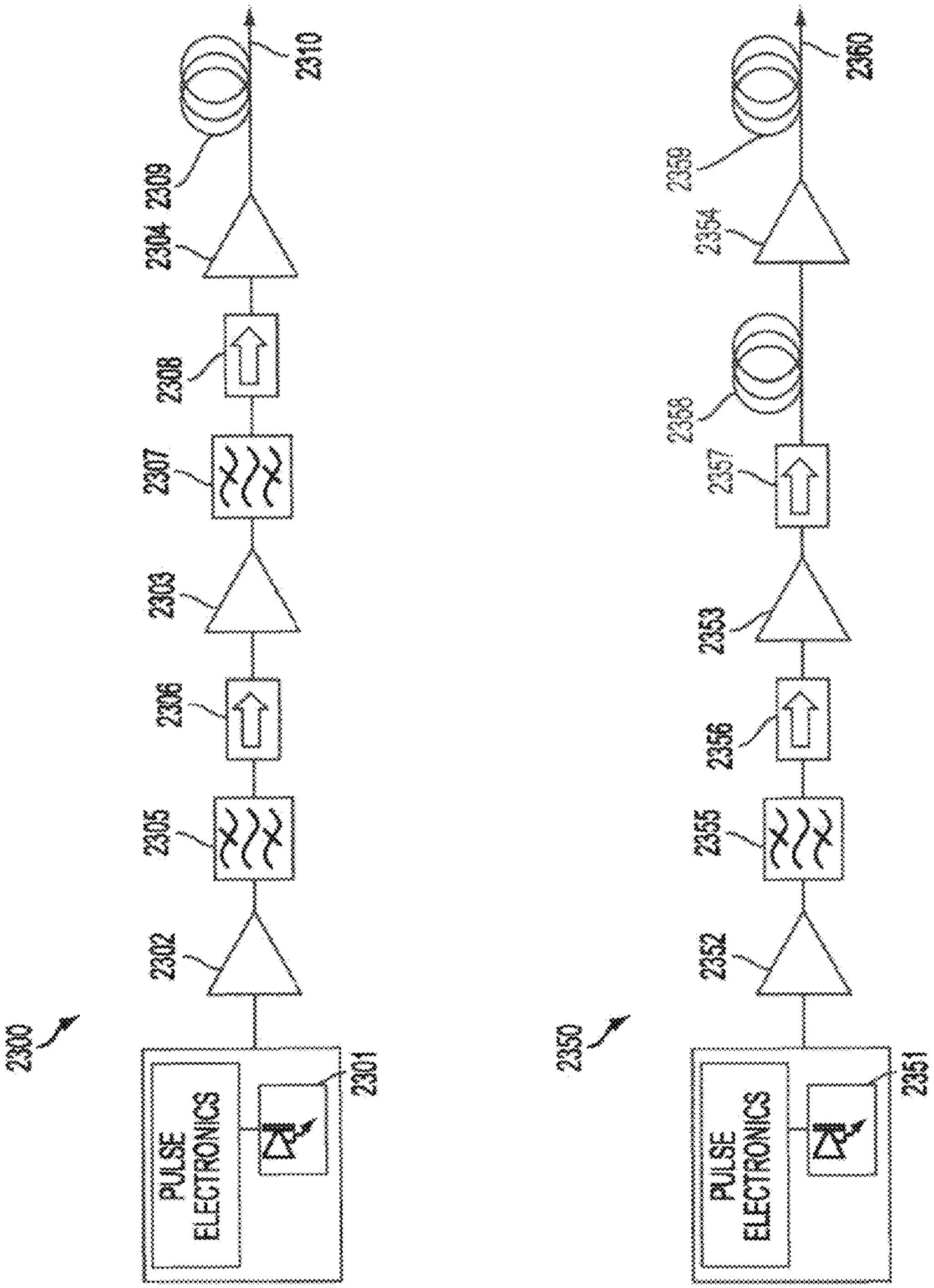
FIG. 23 illustrates high power SWIR-SC lasers that may generate light between approximately 1.4-1.8 microns (top) or approximately 2-2.5 microns (bottom).

In one embodiment, the top of FIG. 23 illustrates a block diagram for an SC source 2300 capable of generating light between approximately 1400 and 1800 nm or broader. As an example, a pump fiber laser similar to FIG. 21 can be used as the input to a SC fiber 2309. The seed laser diode 2301 can comprise a DFB laser that generates, for example, several milliwatts of power around 1542 or 1553 nm. The fiber pre-amplifier 2302 can comprise an erbium-doped fiber amplifier or an erbium/ytterbium doped double clad fiber. In this example a mid-stage amplifier 2303 can be used, which can comprise an erbium/ytterbium doped double-clad fiber. A bandpass filter 2305 and isolator 2306 may be used between the pre-amplifier 2302 and mid-stage amplifier 2303. The power amplifier stage 2304 can comprise a larger core size erbium/ytterbium doped double-clad fiber, and another bandpass filter 2307 and isolator 2308 can be used before the power amplifier 2304. The output of the power amplifier can be coupled to the SC fiber 2309 to generate the SC output 2310. This is just one exemplary configuration for an SC source, and other configurations or elements may be used consistent with this disclosure.

In yet another embodiment, the bottom of FIG. 23 illustrates a block diagram for an SC source 2350 capable of generating light between approximately 1900 and 2500 nm or broader. As an example, the seed laser diode 2351 can comprise a DFB or DBR laser that generates, for example, several milliwatts of power around 1542 or 1553 nm. The fiber pre-amplifier 2352 can comprise an erbium-doped fiber amplifier or an erbium/ytterbium doped double-clad fiber. In this example a mid-stage amplifier 2353 can be used, which can comprise an erbium/ytterbium doped double-clad fiber. A bandpass filter 2355 and isolator 2356 may be used between the pre-amplifier 2352 and mid-stage amplifier 2353. The power amplifier stage 2354 can comprise a thulium doped double-clad fiber, and another isolator 2357 can be used before the power amplifier 2354. Note that the output of the mid-stage amplifier 2353 can be approximately near 1550 nm, while the thulium-doped fiber amplifier 2354 can amplify wavelengths longer than approximately 1900 nm and out to about 2100 nm. Therefore, for this configuration wavelength shifting may be required between 2353 and 2354. In one embodiment, the wavelength shifting can be accomplished using a length of standard single-mode fiber 2358, which can have a length between approximately 5 and 50 meters, for example. The output of the power amplifier 2354 can be coupled to the SC fiber 2359 to generate the SC output 2360. This is just one exemplary configuration for an SC source, and other configurations or elements can be used consistent with this disclosure. For example, the various amplifier stages can comprise different amplifier types, such as erbium doped fibers, ytterbium doped fibers, erbium/ytterbium co-doped fibers and thulium doped fibers. One advantage of the SC lasers illustrated in FIGS. 20-23 are that they may use all-fiber components, so that the SC laser can be all-fiber, monolithically integrated with no moving parts. The all-integrated configuration can consequently be robust and reliable.

FIGS. 20-23 are examples of SC light sources that may be advantageously used for SWIR light generation in various medical diagnostic and therapeutic applications. However, many other versions of the SC light sources may also be made that are intended to also be covered by this disclosure. For example, the SC generation fiber could be pumped by a mode-locked laser, a gain-switched semiconductor laser, an optically pumped semiconductor laser, a solid state laser, other fiber lasers, or a combination of these types of lasers. Also, rather than using a fiber for SC generation, either a liquid or a gas cell might be used as the nonlinear medium in which the spectrum is to be broadened.

Even within the all-fiber versions illustrated such as in FIG. 21, different configurations could be used consistent with the disclosure. In an alternate embodiment, it may be desirous to have a lower cost version of the SWIR SC laser of FIG. 21. One way to lower the cost could be to use a single stage of optical amplification, rather than two stages, which may be feasible if lower output power is required or the gain fiber is optimized. For example, the pre-amplifier stage 2102 might be removed, along with at least some of the mid-stage elements. In yet another embodiment, the gain fiber could be double passed to emulate a two stage amplifier. In this example, the pre-amplifier stage 2102 might be removed, and perhaps also some of the mid-stage elements. A mirror or fiber grating reflector could be placed after the power amplifier stage 2106 that may preferentially reflect light near the wavelength of the seed laser 2101. If the mirror or fiber grating reflector can transmit the pump light near 940 nm, then this could also be used instead of the pump combiner 2113 to bring in the pump light 2112. The SC fiber 2115 could be placed between the seed laser 2101 and the power amplifier stage 2106 (SC is only generated after the second pass through the amplifier, since the power level may be sufficiently high at that time). In addition, an output coupler may be placed between the seed laser diode 2101 and the SC fiber, which now may be in front of the power amplifier 2106. In a particular embodiment, the output coupler could be a power coupler or divider, a dichroic coupler (e.g., passing seed laser wavelength but outputting the SC wavelengths), or a wavelength division multiplexer coupler. This is just one further example, but a myriad of other combinations of components and architectures could also be used for SC light sources to generate SWIR light that are intended to be covered by this disclosure.

Wireless Link to the Cloud

The non-invasive blood constituent or analytes measurement device may also benefit from communicating the data output to the "cloud" (e.g., data servers and processors in the web remotely connected) via wired and/or wireless communication strategies. The non-invasive devices may be part of a series of biosensors applied to the patient, and collectively these devices form what might be called a body area network or a personal area network. The biosensors and non-invasive devices may communicate to a smart phone, tablet, personal data assistant, computer, and/or other microprocessor-based device, which may in turn wirelessly or over wire and/or fiber optically transmit some or all of the signal or processed data to the internet or cloud. The cloud or internet may in turn send the data to doctors or health care providers as well as the patients themselves. Thus, it may be possible to have a panoramic, high-definition, relatively comprehensive view of a patient that doctors can use to assess and manage disease, and that patients can use to help maintain their health and direct their own care.

In a particular embodiment 2400, the physiological measurement device or non-invasive blood constituent measurement device 2401 may comprise a transmitter 2403 to communicate over a first communication link 2404 in the body area network or personal area network to a receiver in a smart phone, tablet cell phone, PDA, or computer 2405. For the measurement device 2401, it may also be advantageous to have a processor 2402 to process some of the physiological data, since with processing the amount of data to transmit may be less (hence, more energy efficient). The first communication link 2404 may operate through the use of one of many wireless technologies such as Bluetooth, Zigbee, WiFi, IrDA (infrared data association), wireless USB, or Z-wave, to name a few. Alternatively, the communication link 2404 may occur in the wireless medical band between 2360 and 2390 MHz, which the FCC allocated for medical body area network devices, or in other designated medical device or WMTS bands. These are examples of devices that can be used in the body area network and surroundings, but other devices could also be used and are included in the scope of this disclosure.

The personal device 2405 may store, process, display, and transmit some of the data from the measurement device 2401. The device 2405 may comprise a receiver, transmitter, display, voice control and speakers, and one or more control buttons or knobs and a touch screen. Examples of the device 2405 include smart phones such as the Apple iPhones® or phones operating on the Android or Microsoft systems. In one embodiment, the device 2405 may have an application, software program, or firmware to receive and process the data from the measurement device 2401. The device 2405 may then transmit some or all of the data or the processed data over a second communication link 2406 to the internet or "cloud" 2407. The second communication link 2406 may advantageously comprise at least one segment of a wireless transmission link, which may operate using WiFi or the cellular network. The second communication link 2406 may additionally comprise lengths of fiber optic and/or communication over copper wires or cables.

The internet or cloud 2407 may add value to the measurement device 2401 by providing services that augment the physiological data collected. In a particular embodiment, some of the functions performed by the cloud include: (a) receive at least a fraction of the data from the device 2405; (b) buffer or store the data received; (c) process the data using software stored on the cloud; (d) store the resulting processed data; and (e) transmit some or all of the data either upon request or based on an alarm. As an example, the data or processed data may be transmitted 2408 back to the originator (e.g., patient or user), it may be transmitted 2409 to a health care provider or doctor, or it may be transmitted 2410 to other designated recipients.

The cloud 2407 may provide a number of value-add services. For example, the cloud application may store and process the physiological data for future reference or during a visit with the healthcare provider. If a patient has some sort of medical mishap or emergency, the physician can obtain the history of the physiological parameters over a specified period of time. In another embodiment, if the physiological parameters fall out of acceptable range, alarms may be delivered to the user 2408, the healthcare provider 2409, or other designated recipients 2410. These are just some of the features that may be offered, but many others may be possible and are intended to be covered by this disclosure. As an example, the device 2405 may also have a GPS sensor, so the cloud 2407 may be able to provide time, data and position along with the physiological parameters. Thus, if there is a medical emergency, the cloud 2407 could provide the location of the patient to the healthcare provider 2409 or other designated recipients 2410. Moreover, the digitized data in the cloud 2407 may help to move toward what is often called "personalized medicine." Based on the physiological parameter data history, medication or medical therapies may be prescribed that are customized to the particular patient.

Beyond the above benefits, the cloud application 2407 and application on the device 2405 may also have financial value for companies developing measurement devices 2401 such as a non-invasive blood constituent monitor. In the case of glucose monitors, the companies make the majority of their revenue on the measurement strips. However, with a non-invasive monitor, there is no need for strips, so there is less of an opportunity for recurring costs (e.g., the razor/razor blade model does not work for non-invasive devices). On the other hand, people may be willing to pay a periodic fee for the value-add services provided on the cloud 2407. Diabetic patients, for example, would probably be willing to pay a periodic fee for monitoring their glucose levels, storing the history of the glucose levels, and having alarm warnings when the glucose level falls out of range. Similarly, patients taking ketone bodies supplement for treatment of disorders characterized by impaired glucose metabolism (e.g., Alzheimer's, Parkinson's, Huntington's or ALS) may need to monitor their ketone bodies level. These patients would also probably be willing to pay a periodic fee for the value-add services provided on the cloud 2407. Thus, by leveraging the advances in wireless connectivity and the widespread use of handheld devices such as smart phones that can wirelessly connect to the cloud, businesses can build a recurring cost business model even using non-invasive measurement devices.

Described herein are just some examples of the beneficial use of near-infrared or SWIR lasers for non-invasive monitoring of glucose, ketones, HbA1c and other blood constituents. However, many other medical procedures can use the near-infrared or SWIR light consistent with this disclosure and are intended to be covered by the disclosure.

Section 2: Short-Wave Infrared Super-Continuum Lasers for Early Detection of Dental Caries Near-infrared (NIR) and SWIR light may be preferred for caries detection compared to visible light imaging because the NIR/SWIR wavelengths generally have lower absorption by stains and deeper penetration into teeth. Hence, NIR/SWIR light may provide a caries detection method that can be non-invasive, non-contact and relatively stain insensitive. Broadband light may provide further advantages because carious regions may demonstrate spectral signatures from water absorption and the wavelength dependence of porosity in the scattering of light.

In general, the near-infrared region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 25:
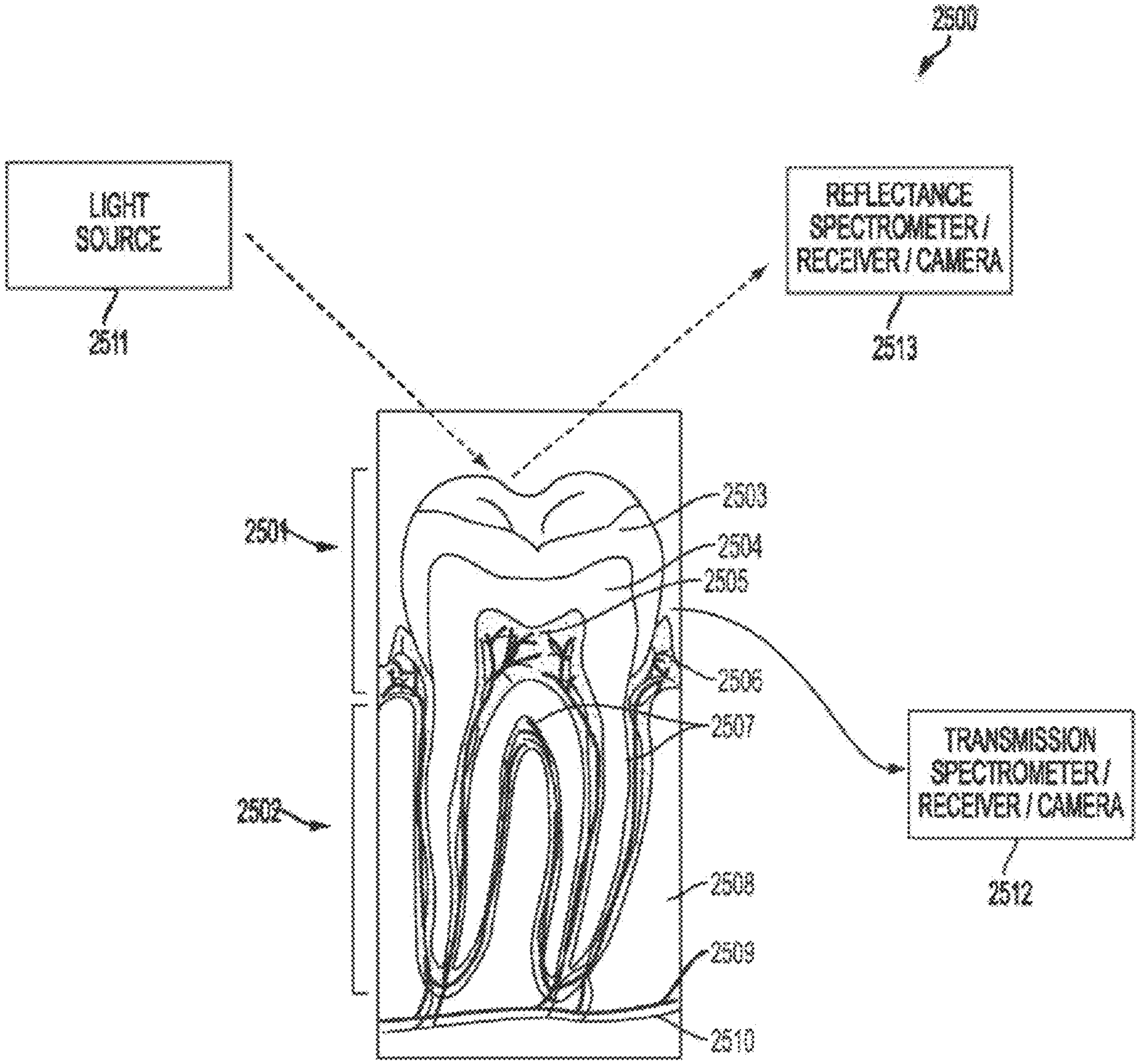
FIG. 25 illustrates the structure of a tooth.

FIG. 25 illustrates the structure of an exemplary cross-section of a tooth 2500. The tooth 2500 has a top layer called the crown 2501 and below that a root 2502 that reaches well into the gum 2506 and bone 2508 of the mouth. The exterior of the crown 2501 is an enamel layer 2503, and below the enamel is a layer of dentine 2504 that sits atop a layer of cementum 2507. Below the dentine 2504 is a pulp region 2505, which comprises within it blood vessels 2509 and nerves 2510. If the light can penetrate the enamel 2503 and dentine 2504, then the blood flow and blood constituents may be measured through the blood vessels in the dental pulp 2505. While the amount of blood flow in the capillaries of the dental pulp 2505 may be less than an artery or vein, the smaller blood flow could still be advantageous for detecting or measuring blood constituents as compared to detection through the skin if there is less interfering spectral features from the tooth.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption, or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this disclosure, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium, for example. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium, and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth or at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

Transmission or Reflection Through Teeth

Figure 26A:
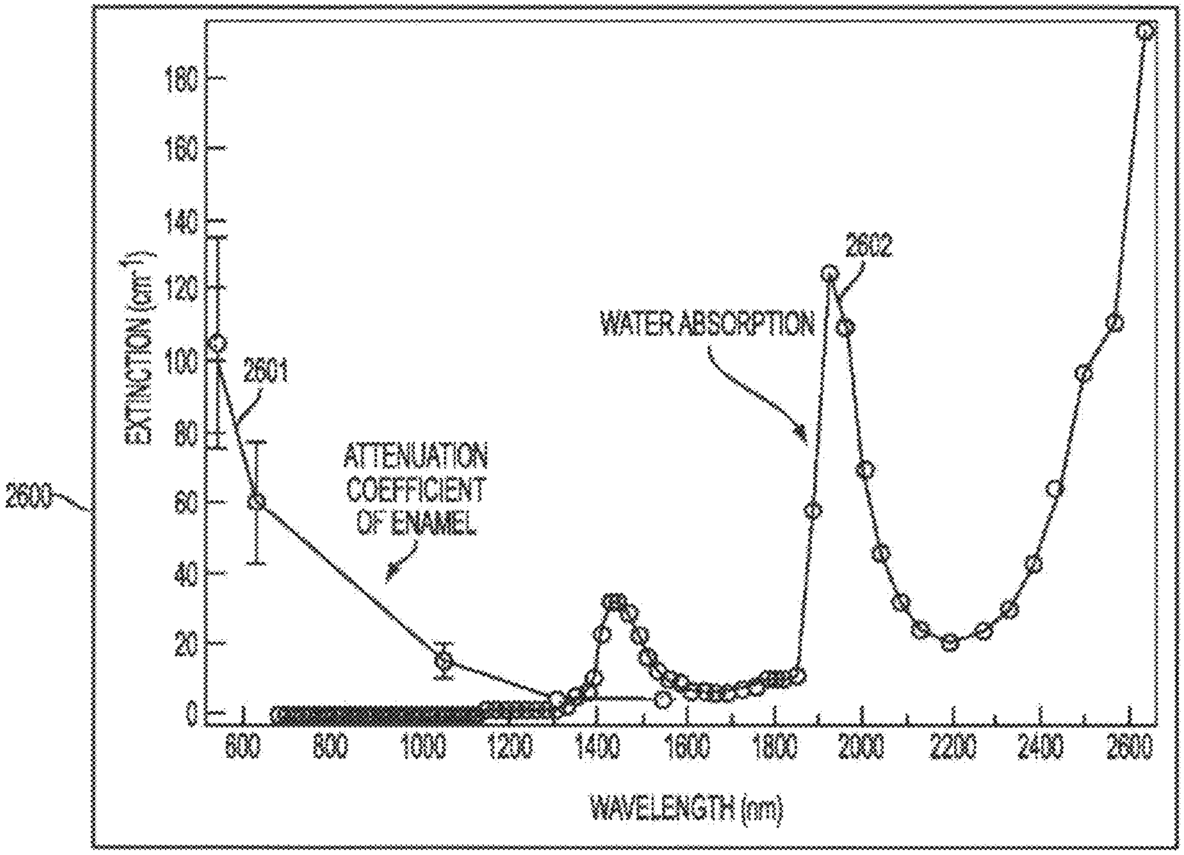
FIG. 26A shows the attenuation coefficient for dental enamel and water versus wavelength from approximately 600 nm to 2600 nm.

The transmission, absorption and reflection from teeth has been studied in the near infrared, and, although there are some features, the enamel and dentine appear to be fairly transparent in the near infrared (particularly SWIR wavelengths between about 1400 and 2500 nm). For example, the absorption or extinction ratio for light transmission has been studied. FIG. 26A illustrates the attenuation coefficient 2600 for dental enamel 2601 (filled circles) and the absorption coefficient of water 2602 (open circles) versus wavelength. Near-infrared light may penetrate much further without scattering through all the tooth enamel, due to the reduced scattering coefficient in normal enamel. Scattering in enamel may be fairly strong in the visible, but decreases as approximately 1/(wavelength)3 [i.e., inverse of the cube of the wavelength] with increasing wavelength to a value of only 2-3 cm−1 at 1310 nm and 1550 nm in the near infrared. Therefore, enamel may be virtually transparent in the near infrared with optical attenuation 1-2 orders of magnitude less than in the visible range.

Figure 26B:
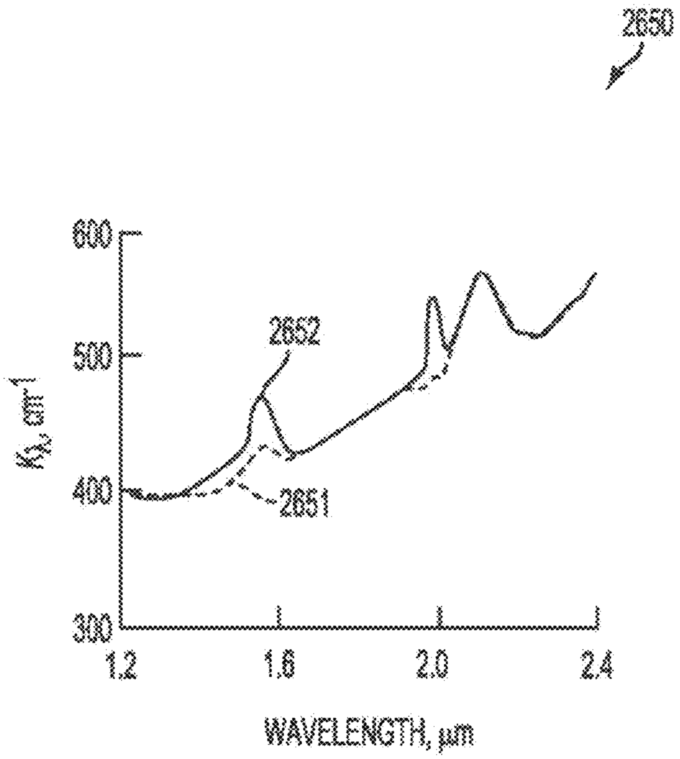
FIG. 26B illustrates the absorption spectrum of intact enamel and dentine in the wavelength range of approximately 1.2 to 2.4 microns.

As another example, FIG. 26B illustrates the absorption spectrum 2650 of intact enamel 2651 (dashed line) and dentine 2652 (solid line) in the wavelength range of approximately 1.2 to 2.4 microns. In the near infrared there are two absorption bands in the areas of about 1.5 and 2 microns. The band with a peak around 1.57 microns may be attributed to the overtone of valent vibration of water present in both enamel and dentine. In this band, the absorption is greater for dentine than for enamel, which may be related to the large water content in this tissue. In the region of 2 microns, dentine may have two absorption bands, and enamel one. The band with a maximum near 2.1 microns may belong to the overtone of vibration of PO hydroxyapatite groups, which is the main substance of both enamel and dentine. Moreover, the band with a peak near 1.96 microns in dentine may correspond to water absorption (dentine may contain substantially higher water than enamel).

Figure 27:
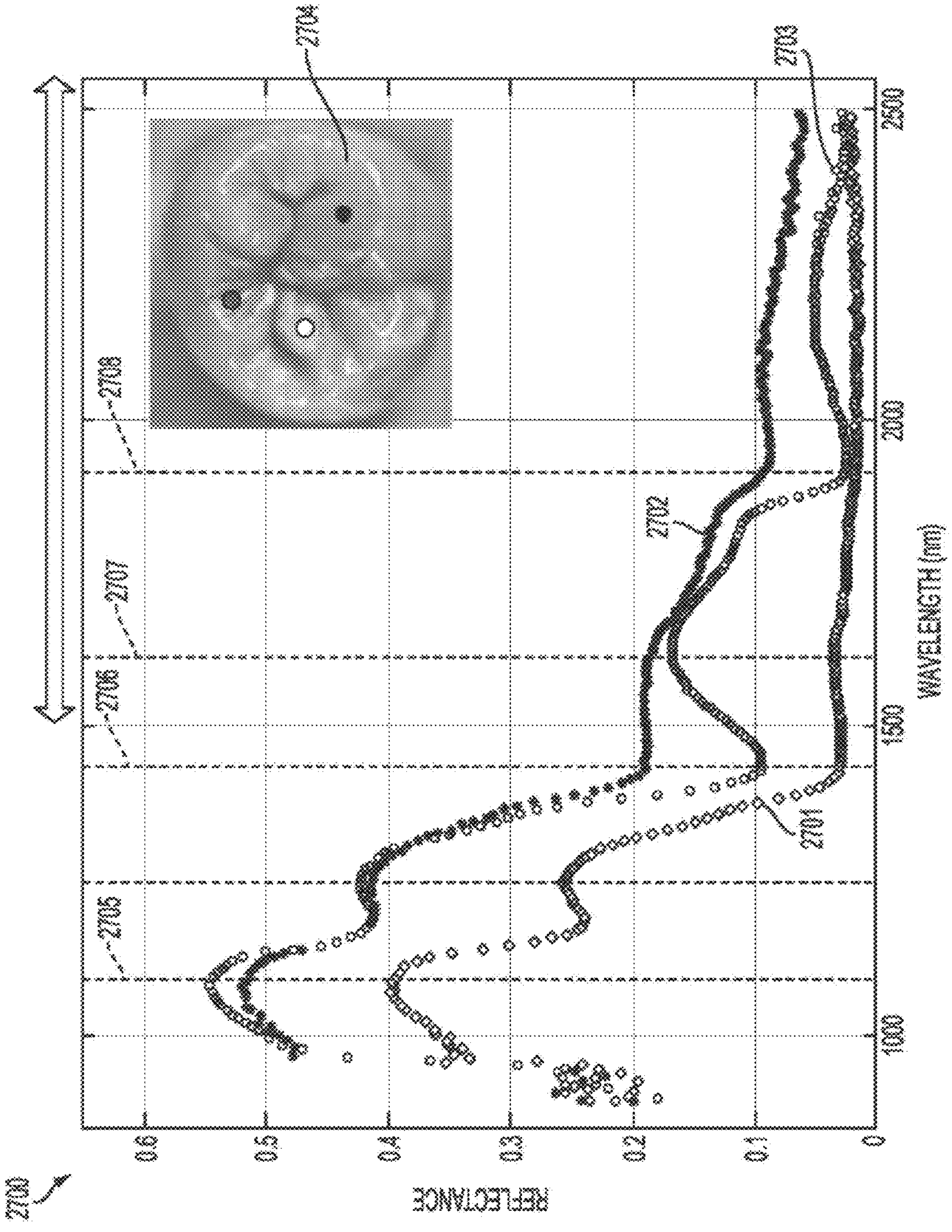
FIG. 27 shows the near infrared spectral reflectance over the wavelength range of approximately 800 nm to 2500 nm from an occlusal tooth surface. The black diamonds correspond to the reflectance from a sound, intact tooth section. The asterisks correspond to a tooth section with an enamel lesion. The circles correspond to a tooth section with a dentine lesion.

In addition to the absorption coefficient, the reflectance from intact teeth and teeth with dental caries (e.g., cavities) has been studied. In one embodiment, FIG. 27 shows the near infrared spectral reflectance 2700 over the wavelength range of approximately 800 nm to 2500 nm from an occlusal (e.g., top) tooth surface 2704. The curve with black diamonds 2701 corresponds to the reflectance from a sound, intact tooth section. The curve with asterisks (*) 2702 corresponds to a tooth section with an enamel lesion. The curve with circles 2703 corresponds to a tooth section with a dentine lesion. Thus, when there is a lesion, more scattering occurs and there may be an increase in the reflected light.

For wavelengths shorter than approximately 1400 nm, the shapes of the spectra remain similar, but the amplitude of the reflection changes with lesions. Between approximately 1400 nm and 2500 nm, an intact tooth 2701 has low reflectance (e.g., high transmission), and the reflectance appears to be more or less independent of wavelength. On the other hand, in the presence of lesions 2702 and 2703, there is increased scattering, and the scattering loss may be wavelength dependent. For example, the scattering loss may decrease as the inverse of some power of wavelength, such as 1/(wavelength)3—so, the scattering loss decreases with longer wavelengths. When there is a lesion in the dentine 2703, more water can accumulate in the area, so there is also increased water absorption. For example, the dips near 1450 nm and 1900 nm may correspond to water absorption, and the reflectance dips are particularly pronounced in the dentine lesion 2703.

FIG. 27 may point to several novel techniques for early detection and quantification of carious regions. One method may be to use a relatively narrow wavelength range (for example, from a laser diode or super-luminescent laser diode) in the wavelength window below 1400 nm. In one embodiment, wavelengths in the vicinity of 1310 nm may be used, which is a standard telecommunications wavelength where appropriate light sources are available. Also, it may be advantageous to use a super-luminescent laser diode rather than a laser diode, because the broader bandwidth may avoid the production of laser speckle that can produce interference patterns due to light's scattering after striking irregular surfaces. As FIG. 27 shows, the amplitude of the reflected light (which may also be proportional to the inverse of the transmission) may increase with dental caries. Hence, comparing the reflected light from a known intact region with a suspect region may help identify carious regions. However, one difficulty with using a relatively narrow wavelength range and relying on amplitude changes may be the calibration of the measurement. For example, the amplitude of the reflected light may depend on many factors, such as irregularities in the dental surface, placement of the light source and detector, distance of the measurement instrument from the tooth, etc.

In one embodiment, use of a plurality of wavelengths can help to better calibrate the dental caries measurement. For example, a plurality of laser diodes or super-luminescent laser diodes may be used at different center wavelengths. Alternately, a lamp or alternate broadband light source may be used followed by appropriate filters, which may be placed after the light source or before the detectors. In one example, wavelengths near 1090 nm, 1440 nm and 1610 nm may be employed. The reflection from the tooth 2705 appears to reach a local maximum near 1090 nm in the representative embodiment illustrated. Also, the reflectance near 1440 nm 2706 is higher for dental caries, with a distinct dip particularly for dentine caries 2703. Near 1610 nm 2707, the reflection is also higher for carious regions. By using a plurality of wavelengths, the values at different wavelengths may help quantify a caries score. In one embodiment, the degree of enamel lesions may be proportional to the ratio of the reflectance near 1610 nm divided by the reflectance near 1090 nm. Also, the degree of dentine lesion may be proportional to the difference between the reflectance near 1610 nm and 1440 nm, with the difference then divided by the reflectance near 1090 nm. Although one set of wavelengths has been described, other wavelengths may also be used and are intended to be covered by this disclosure.

In yet another embodiment, it may be further advantageous to use all of some fraction of the SWIR between approximately 1400 and 2500 nm. For example, a SWIR super-continuum light source could be used, or a lamp source could be used. On the receiver side, a spectrometer and/or dispersive element could be used to discriminate the various wavelengths. As FIG. 27 shows, an intact tooth 2701 has a relatively low and featureless reflectance over the SWIR. On the other hand, with a carious region there is more scattering, so the reflectance 2702, 2703 increases in amplitude. Since the scattering is inversely proportional to wavelength or some power of wavelength, the carious region reflectance 2702, 2703 also decreases with increasing wavelength. Moreover, the carious region may contain more water, so there are dips in the reflectance near the water absorption lines 2706 and 2708. The degree of caries or caries score may be quantified by the shape of the spectrum over the SWIR, taking ratios of different parts of the spectrum, or some combination of this and other spectral processing methods.

Although several methods of early caries detection using spectral reflectance have been described, other techniques could also be used and are intended to be covered by this disclosure. For example, transmittance may be used rather than reflectance, or a combination of the two could be used. Moreover, the transmittance, reflectance and/or absorbance could also be combined with other techniques, such as quantitative light-induced fluorescence or fiber-optic trans-illumination. Also, the SWIR could be advantageous, but other parts of the infrared, near-infrared or visible wavelengths may also be used consistent with this disclosure.

One other benefit of the absorption, transmission or reflectance in the near infrared and SWIR may be that stains and non-calcified plaque are not visible in this wavelength range, enabling better discrimination of defects, cracks, and demineralized areas. For example, dental calculus, accumulated plaque, and organic stains and debris may interfere significantly with visual diagnosis and fluorescence-based caries detection schemes in occlusal surfaces. In the case of using quantitative light-induced fluorescence, such confounding factors typically may need to be removed by prophylaxis (abrasive cleaning) before reliable measurements can be taken. Surface staining at visible wavelengths may further complicate the problem, and it may be difficult to determine whether pits and fissures are simply stained or demineralized. On the other hand, staining and pigmentation generally interfere less with NIR or SWIR imaging. For example, NIR and SWIR light may not be absorbed by melanin and porphyrins produced by bacteria and those found in food dyes that accumulate in dental plaque and are responsible for the pigmentation.

Human Interface for Measurement System

A number of different types of measurements may be used to image for dental caries, particularly early detection of dental caries. A basic feature of the measurements may be that the optical properties are measured as a function of wavelength at a plurality of wavelengths. As further described below, the light source may output a plurality of wavelengths, or a continuous spectrum over a range of wavelengths. In one embodiment, the light source may cover some or all of the wavelength range between approximately 1400 nm and 2500 nm. The signal may be received at a receiver, which may also comprise a spectrometer or filters to discriminate between different wavelengths. The signal may also be received at a camera, which may also comprise filters or a spectrometer. In one embodiment, the spectral discrimination using filters or a spectrometer may be placed after the light source rather than at the receiver. The receiver usually comprises one or more detectors (optical-to-electrical conversion element) and electrical circuitry. The receiver may also be coupled to analog to digital converters, particularly if the signal is to be fed to a digital device.

Referring to FIG. 25, one or more light sources 2511 may be used for illumination. In one embodiment, a transmission measurement may be performed by directing the light source output 2511 to the region near the interface between the gum 2506 and dentine 2504. In one embodiment, the light may be directed using a light guide or a fiber optic. The light may then propagate through the dental pulp 2505 to the other side, where the light may be incident on one or more detectors or another light guide to transport the signal to 2512 a spectrometer, receiver, and/or camera, for example. In one embodiment, the light source may be directed to one or more locations near the interface between the gum 2506 and dentine 2504 (in one example, could be from the two sides of the tooth). The transmitted light may then be detected in the occlusal surface above the tooth using a 2512 spectrometer, receiver, or camera, for example. In another embodiment, a reflectance measurement may be conducted by directing the light source output 2511 to, for example, the occlusal surface of the tooth, and then detecting the reflectance at a 2513 spectrometer, receiver or camera. Although a few embodiments for imaging the tooth are described, other embodiments and techniques may also be used and are intended to be covered by this disclosure. These optical techniques may measure optical properties such as reflectance, transmittance, absorption, or luminescence.

Figure 28:
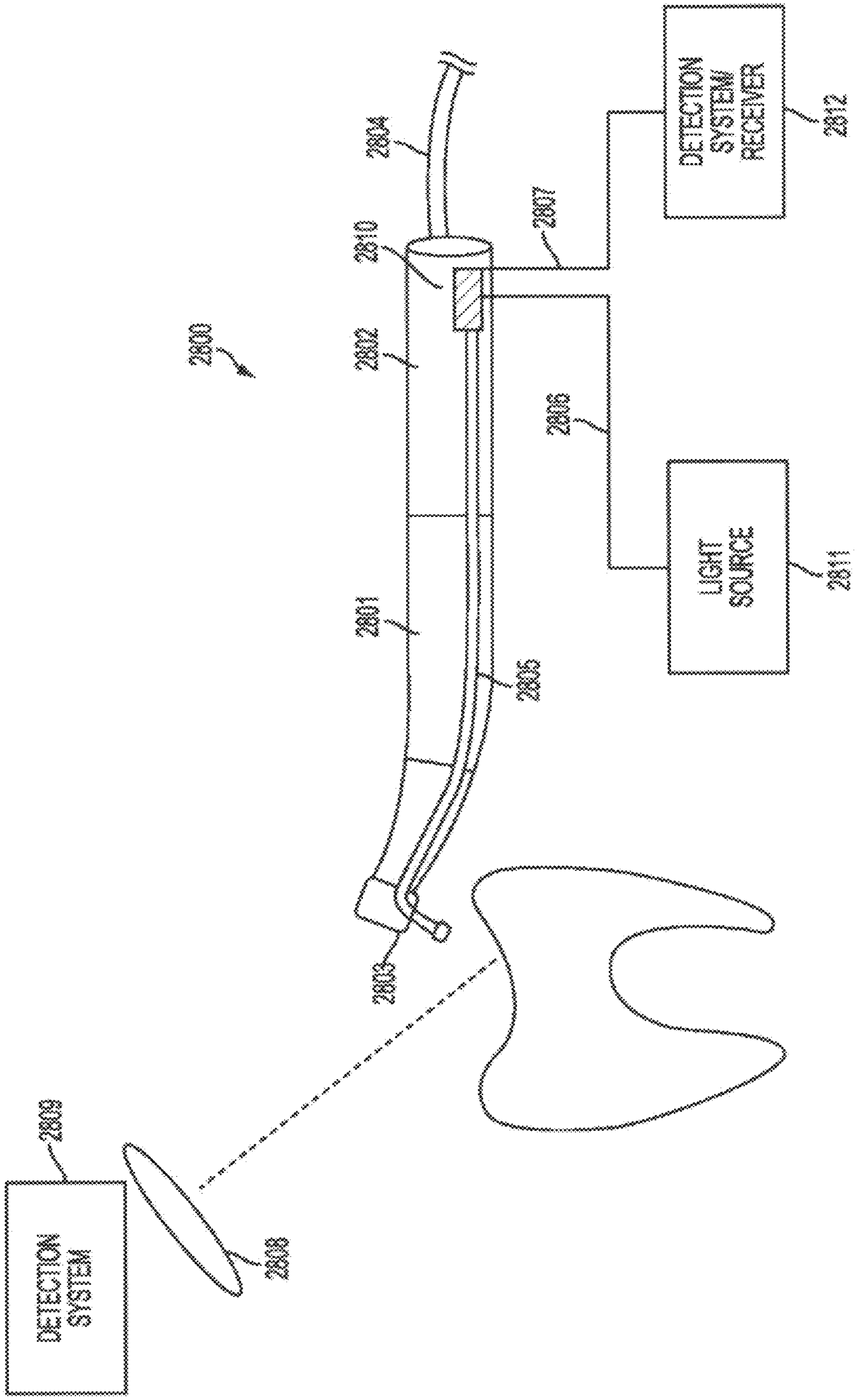
FIG. 28 illustrates a hand-held dental tool design of a human interface that may also be coupled with other dental tools.

In one embodiment, FIG. 28 shows that the light source and/or detection system may be integrated with a dental hand-piece 2800. The hand-piece 2800 may also include other dental equipment, such as a drill, pick, air spray or water cooling stream. The dental hand-piece 2800 may include a housing 2801 and a motor housing 2802 (in some embodiments such as with a drill, a motor may be placed in this section). The end of hand-piece 2803 that interfaces with the tooth may be detachable, and it may also have the light input and output end. The dental hand-piece 2800 may also have an umbilical cord 2804 for connecting to power supplies, diagnostics, or other equipment, for example.

A light guide 2805 may be integrated with the hand-piece 2800, either inside the housing 2801, 2802 or adjacent to the housing. In one embodiment, a light source 2810 may be contained within the housing 2801, 2802. In an alternative embodiment, the hand-piece 2800 may have a coupler 2810 to couple to an external light source 2811 and/or detection system or receiver 2812. The light source 2811 may be coupled to the hand-piece 2800 using a light guide or fiber optic cable 2806. In addition, the detection system or receiver 2812 may be coupled to the hand-piece 2800 using one or more light guides, fiber optic cable or a bundle of fibers 2807.

The light incident on the tooth may exit the hand-piece 2800 through the end 2803. The end 2803 may also have a lens system or curved mirror system to collimate or focus the light. In one embodiment, if the light source is integrated with a tool such as a drill, then the light may reach the tooth at the same point as the tip of the drill. The reflected or transmitted light from the tooth may then be observed externally and/or guided back through the light guide 405 in the hand-piece 2800. If observed externally, there may be a lens system 408 for collecting the light and a detection system 2809 that may have one or more detectors and electronics. If the light is to be guided back through the hand-piece 2800, then the reflected light may transmit through the light guide 2805 back to the detection system or receiver 2812. In one embodiment, the incident light may be guided by a fiber optic through the light guide 2805, and the reflected light may be captured by a series of fibers forming a bundle adjacent to or surrounding the incident light fiber.

Figure 29:
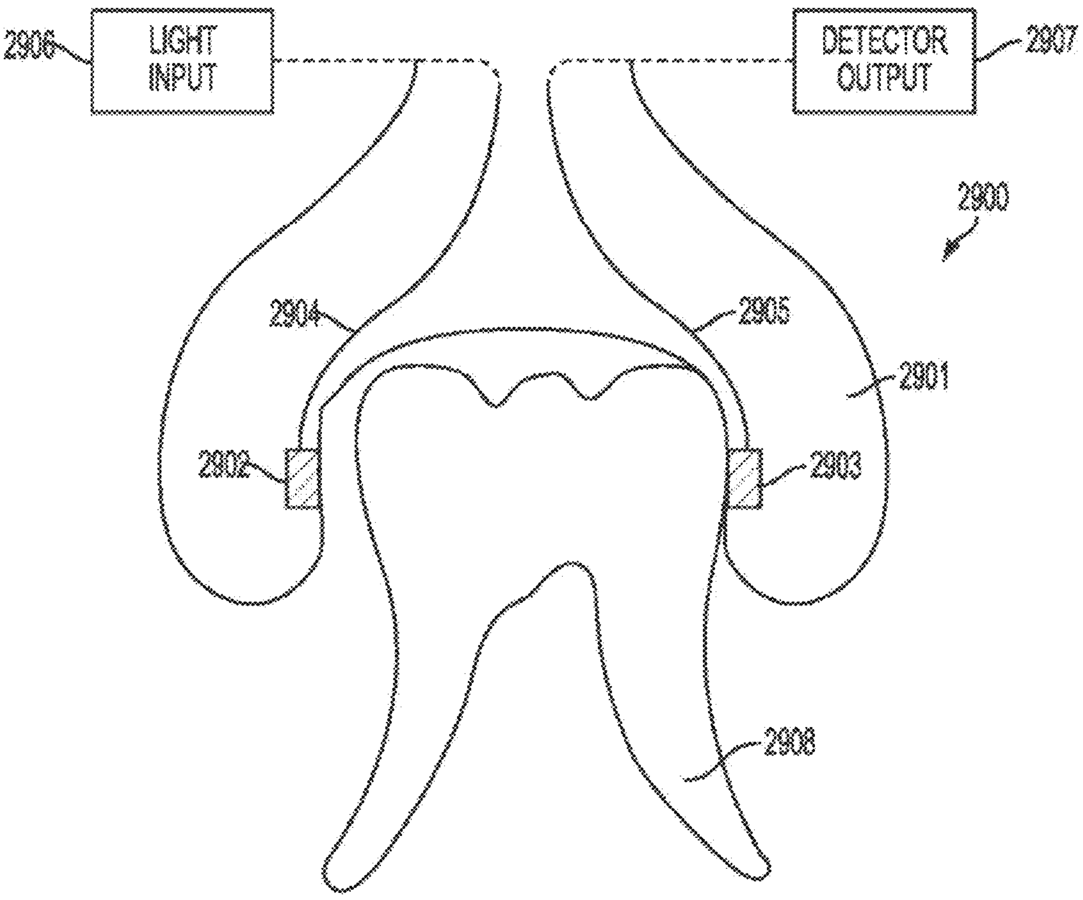
FIG. 29 illustrates a clamp design of a human interface to cap over one or more teeth and perform a non-invasive measurement for dental caries.

In another embodiment, a "clamp" design 2900 may be used as a cap over one or more teeth, as illustrated in FIG. 29. The clamp design may be different for different types of teeth, or it may be flexible enough to fit over different types of teeth. For example, different types of teeth include the molars (toward the back of the mouth), the premolars, the canine, and the incisors (toward the front of the mouth). One embodiment of the clamp-type design is illustrated in FIG. 29 for a molar tooth 2908. The C-clamp 2901 may be made of a plastic or rubber material, and it may comprise a light source input 2902 and a detector output 2903 on the front or back of the tooth, for example.

The light source input 2902 may comprise a light source directly, or it may have light guided to it from an external light source. Also, the light source input 2902 may comprise a lens system to collimate or focus the light across the tooth. The detector output 2903 may comprise a detector directly, or it may have a light guide to transport the signal to an external detector element. The light source input 2902 may be coupled electrically or optically through 2904 to a light input 2906. For example, if the light source is external in 2906, then the coupling element 2904 may be a light guide, such as a fiber optic. Alternately, if the light source is contained in 2902, then the coupling element 2904 may be electrical wires connecting to a power supply in 2906. Similarly, the detector output 2903 may be coupled to a detector output unit 2907 with a coupling element 2905, which may be one or more electrical wires or a light guide, such as a fiber optic. This is just one example of a clamp over one or more teeth, but other embodiments may also be used and are intended to be covered by this disclosure. For example, if reflectance from the teeth is to be used in the measurement, then the light input 2902 and detected light input 2903 may be on the same side of the tooth.

Figure 30:
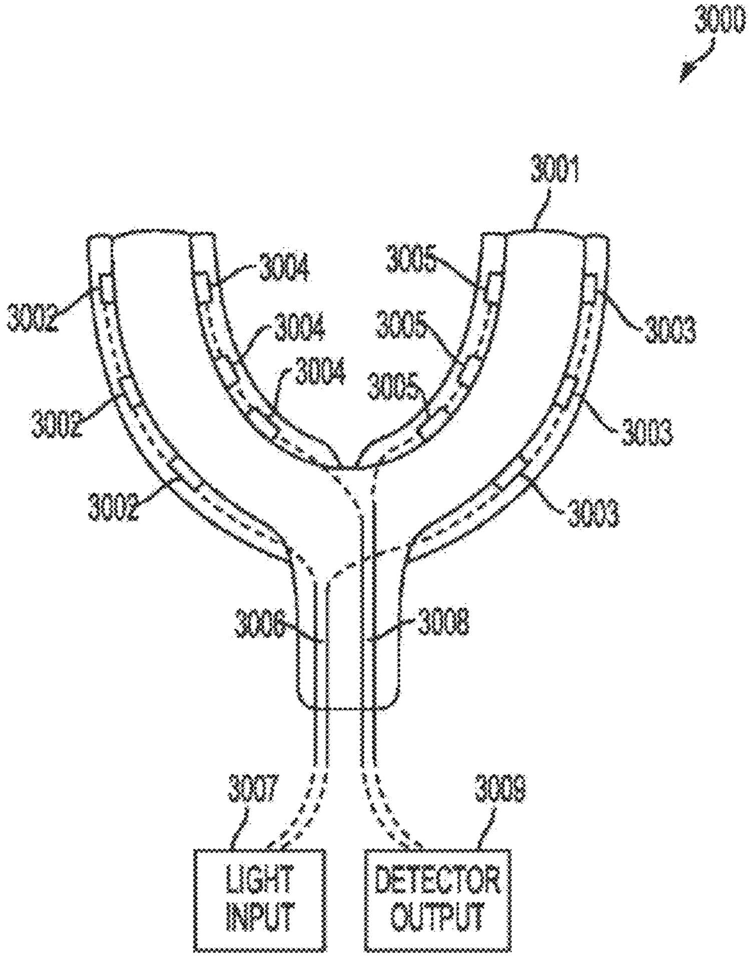
FIG. 30 shows a mouth guard design of a human interface to perform a non-invasive measurement for dental caries.

In yet another embodiment, one or more light source ports and sensor ports may be used in a mouth-guard type design. For example, one embodiment of a dental mouth guard 3000 is illustrated in FIG. 30. The structure of the mouth guard 3001 may be similar to mouth guards used in sports (e.g., when playing football or boxing) or in dental trays used for applying fluoride treatment, and the mouth guard may be made from plastic, rubber, or any other suitable materials. As an example, the mouth guard may have one or more light source input ports 3002, 3003 and one or more detector output ports 3004, 3005. Although six input and output ports are illustrated, any number of ports may be used.

Similar to the clamp design described above, the light source inputs 3002, 3003 may comprise one or more light sources directly, or they may have light guided to them from an external light source. Also, the light source inputs 3002, 3003 may comprise lens systems to collimate or focus the light across the teeth. The detector outputs 3004, 3005 may comprise one or more detectors directly, or they may have one or more light guides to transport the signals to an external detector element. The light source inputs 3002, 3003 may be coupled electrically or optically through 3006 to a light input 3007. For example, if the light source is external in 3007, then the one or more coupling elements 3006 may be one or more light guides, such as a fiber optic. Alternately, if the light sources are contained in 3002, 3003, then the coupling element 3006 may be one or more electrical wires connecting to a power supply in 3007. Similarly, the detector outputs 3004, 3005 may be coupled to a detector output unit 3009 with one or more coupling elements 3008, which may be one or more electrical wires or one or more light guides, such as a fiber optic. This is just one example of a mouth guard design covering a plurality of teeth, but other embodiments may also be used and are intended to be covered by this disclosure. For instance, the position of the light source inputs and detector output ports could be exchanged, or some mixture of locations of light source inputs and detector output ports could be used. Also, if reflectance from the teeth is to be measured, then the light sources and detectors may be on the same side of the tooth. Moreover, it may be advantageous to pulse the light source with a particular pulse width and pulse repetition rate, and then the detection system can measure the pulsed light returned from or transmitted through the tooth. Using a lock-in type technique (e.g., detecting at the same frequency as the pulsed light source and also possibly phase locked to the same signal), the detection system may be able to reject background or spurious signals and increase the signal-to-noise ratio of the measurement.

Other elements may be added to the human interface designs of FIGS. 28-30 and are also intended to be covered by this disclosure. For instance, in one embodiment it may be desirable to have replaceable inserts that may be disposable. Particularly in a dentist's or doctor's office or hospital setting, the same instrument may be used with a plurality of patients. Rather than disinfecting the human interface after each use, it may be preferable to have disposable inserts that can be thrown away after each use. In one embodiment, a thin plastic coating material may enclose the clamp design of FIG. 29 or mouth guard design of FIG. 30. The coating material may be inserted before each use, and then after the measurement is exercised the coating material may be peeled off and replaced. The coating or covering material may be selected based on suitable optical properties that do not affect the measurement, or known optical properties that can be calibrated or compensated for during measurement. Such a design may save the dentist or physician or user considerable time, while at the same time provide the business venture with a recurring cost revenue source.

Wireless Link to the Cloud

The non-invasive dental caries measurement device may also benefit from communicating the data output to the "cloud" (e.g., data servers and processors in the web remotely connected) via wireless means. The non-invasive devices may be part of a series of biosensors applied to the patient, and collectively these devices form what might be called a body area network or a personal area network. The biosensors and non-invasive devices may communicate to a smart phone, tablet, personal data assistant, computer and/or other microprocessor-based device, which may in turn wirelessly or over wire and/or fiber optic transmit some or all of the signal or processed data to the internet or cloud. The cloud or internet may in turn send the data to dentists, doctors or health care providers as well as the patients themselves. Thus, it may be possible to have a panoramic, high-definition, relatively comprehensive view of a patient that doctors and dentists can use to assess and manage disease, and that patients can use to help maintain their health and direct their own care.

In a particular embodiment 3100, the non-invasive measurement device 3101 may comprise a transmitter 3103 to communicate over a first communication link 3104 in the body area network or personal area network to a receiver in a smart phone, tablet, cell phone, PDA, and/or computer 3105, for example. For the measurement device 3101, it may also be advantageous to have a processor 3102 to process some of the measured data, since with processing the amount of data to transmit may be less (hence, more energy efficient). The first communication link 3104 may operate through the use of one of many wireless technologies such as Bluetooth, Zigbee, WiFi, IrDA (infrared data association), wireless USB, or Z-wave, to name a few. Alternatively, the communication link 3104 may occur in the wireless medical band between 2360 MHz and 2390 MHz, which the FCC allocated for medical body area network devices, or in other designated medical device or WMTS bands. These are examples of devices that can be used in the body area network and surroundings, but other devices could also be used and are included in the scope of this disclosure.

The personal device 3105 may store, process, display, and transmit some of the data from the measurement device 3101. The device 3105 may comprise a receiver, transmitter, display, voice control and speakers, and one or more control buttons or knobs and a touch screen. Examples of the device 3105 include smart phones such as the Apple iPhones® or phones operating on the Android or Microsoft systems. In one embodiment, the device 3105 may have an application, software program, or firmware to receive and process the data from the measurement device 3101. The device 3105 may then transmit some or all of the data or the processed data over a second communication link 3106 to the internet or "cloud" 3107. The second communication link 3106 may advantageously comprise at least one segment of a wireless transmission link, which may operate using WiFi or the cellular network. The second communication link 3106 may additionally comprise lengths of fiber optic and/or communication over copper wires or cables.

The internet or cloud 3107 may add value to the measurement device 3101 by providing services that augment the measured data collected. In a particular embodiment, some of the functions performed by the cloud include: (a) receive at least a fraction of the data from the device 3105; (b) buffer or store the data received; (c) process the data using software stored on the cloud; (d) store the resulting processed data; and (e) transmit some or all of the data either upon request or based on an alarm. As an example, the data or processed data may be transmitted 3108 back to the originator (e.g., patient or user), it may be transmitted 3109 to a health care provider or doctor or dentist, or it may be transmitted 3110 to other designated recipients.

Service providers coupled to the cloud 3107 may provide a number of value-add services. For example, the cloud application may store and process the dental data for future reference or during a visit with the dentist or healthcare provider. If a patient has some sort of medical mishap or emergency, the physician can obtain the history of the dental or physiological parameters over a specified period of time. In another embodiment, alarms, warnings or reminders may be delivered to the user 3108, the healthcare provider 3109, or other designated recipients 3110. These are just some of the features that may be offered, but many others may be possible and are intended to be covered by this disclosure. As an example, the device 3105 may also have a GPS sensor, so the cloud 3107 may be able to provide time, date, and position along with the dental or physiological parameters. Thus, if there is a medical or dental emergency, the cloud 3107 could provide the location of the patient to the dental or healthcare provider 3109 or other designated recipients 3110. Moreover, the digitized data in the cloud 3107 may help to move toward what is often called "personalized medicine." Based on the dental or physiological parameter data history, medication or medical/dental therapies may be prescribed that are customized to the particular patient. Another advantage for commercial entities may be that by leveraging the advances in wireless connectivity and the widespread use of handheld devices such as smart phones that can wirelessly connect to the cloud, businesses can build a recurring cost business model even using non-invasive measurement devices.

Described herein are just some examples of the beneficial use of near-infrared or SWIR lasers for non-invasive measurements of dental caries and early detection of carious regions. However, many other dental or medical procedures can use the near-infrared or SWIR light consistent with this disclosure and are intended to be covered by the disclosure.

Section 3: Short-Wave Infrared Super-Continuum Lasers for Natural Gas Leak Detection, Exploration, and Other Active Remote Sensing Applications One advantage of optical systems is that they can perform non-contact, stand-off or remote sensing distance spectroscopy of various materials. For remote sensing particularly, it may also be necessary to operate in atmospheric transmission windows. For example, two windows in the SWIR that transmit through the atmosphere are approximately 1.4-1.8 microns and 2-2.5 microns. In general, the near-infrared region of the electromagnetic spectrum covers between approximately 0.7 microns (700 nm) to about 2.5 microns (2500 nm). However, it may also be advantageous to use just the short-wave infrared between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the NIR wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering from some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

Figure 32:
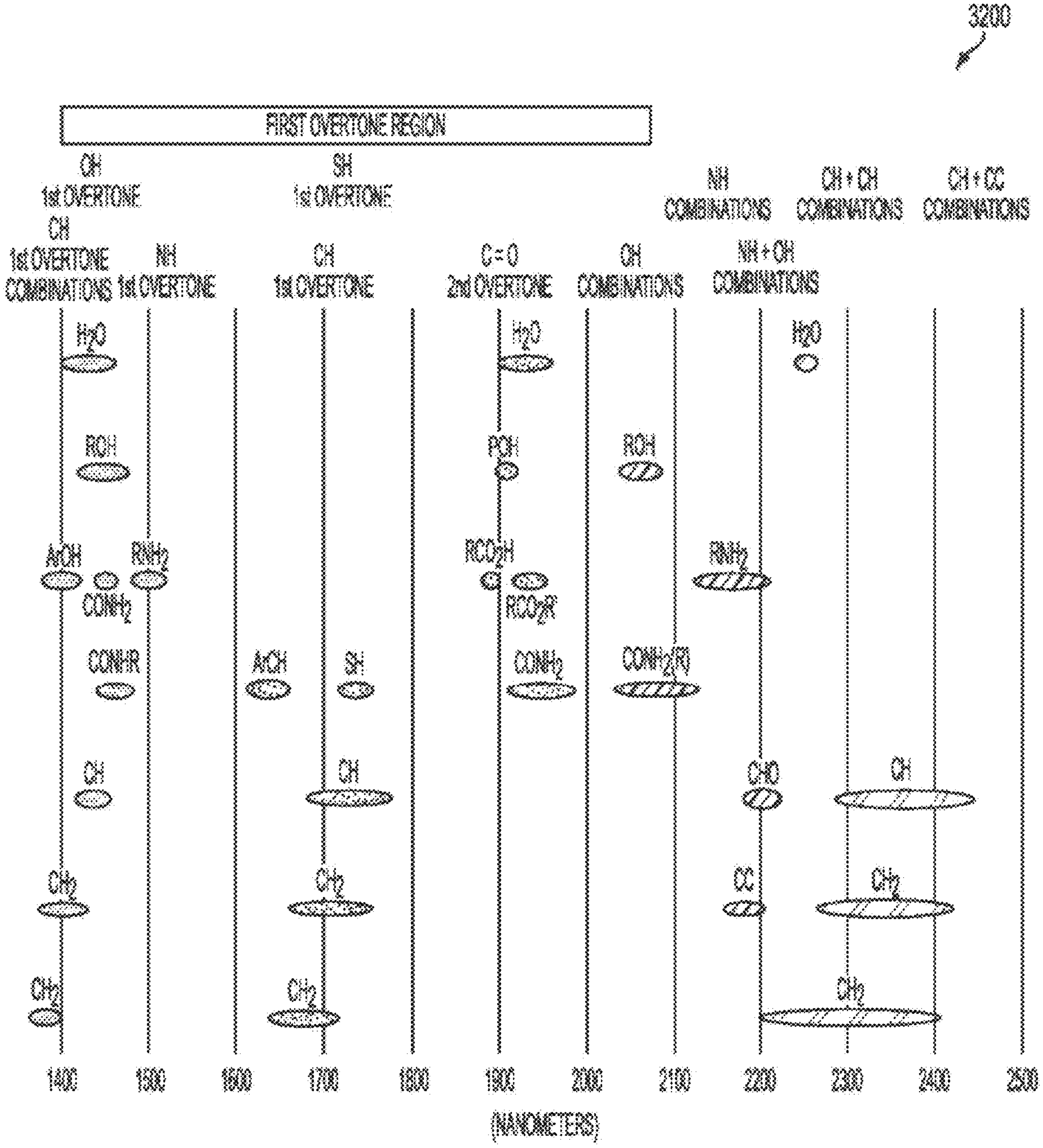
FIG. 32 illustrates wavelength bands for different chemical compounds over the SWIR wavelength range of approximately 1400 nm to 2500 nm. Also indicated are whether the bands are overtone or combination bands.

The SWIR wavelength range may be particularly valuable for identifying materials based on their chemical composition because the wavelength range comprises overtones and combination bands for numerous chemical bonds. As an example, FIG. 32 illustrates some of the wavelength bands for different chemical compositions. In 100 is plotted wavelength ranges in the SWIR (between 1400 and 2500 nm) for different chemical compounds that have vibrational or rotational resonances, along with whether the bands are overtone or combination bands. Numerous hydro-carbons are represented, along with oxygen-hydrogen and carbon-oxygen bonds. Thus, gases, liquids and solids that comprise these chemical compounds may exhibit spectral features in the SWIR wavelength range. In a particular embodiment, the spectra of organic compounds may be dominated by the C—H stretch. The C—H stretch fundamental occurs near 3.4 microns, the first overtone is near 1.7 microns, and a combination band occurs near 2.3 microns.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging the sun may be used as the illumination source, and the daytime illumination may comprise direct solar illumination as well as scattered solar (skylight), which is caused by the presence of the atmosphere. However, the sun illumination changes with time of day, clouds or inclement weather may block the sun light, and the sun light is not accessible in the night time. Therefore, it would be advantageous to have a broadband light source covering the SWIR that may be used in place of the sun to identify or classify materials in remote sensing or stand-off detection applications.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, parametric amplification, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this disclosure, the term "remote sensing" may include the measuring of properties of an object from a distance, without physically sampling the object, for example by detection of the interactions of the object with an electromagnetic field. In one embodiment, the electromagnetic field may be in the optical wavelength range, including the infrared or SWIR. One particular form of remote sensing may be stand-off detection, which may range from non-contact up to hundreds of meters away, for example.

Remote Sensing of Natural Gas Leaks

Natural gas may be a hydro-carbon gas mixture comprising primarily methane, with other hydro-carbons, carbon dioxide, nitrogen and hydrogen sulfide. Natural gas is important because it is an important energy source to provide heating and electricity. Moreover, it may also be used as fuel for vehicles and as a chemical feedstock in the manufacture of plastics and other commercially important organic chemicals. Although methane is the primary component of natural gas, to uniquely identify natural gas through spectroscopy requires monitoring of both methane and ethane. If only methane is used, then areas like cow pastures could be mistaken for natural gas fields or leaks. More specifically, the typical composition of natural gas is as follows:

| Component | Range (mole %) |
|---|---|
| Methane | 87.0-96.0 |
| Ethane | 1.5-5.1 |
| Propane | 0.1-1.5 |
| Iso-butane | 0.01-0.3 |
| Normal-butane | 0.01-0.3 |
| Iso-pentane | Trace-0.14 |
| Normal-pentane | Trace-0.04 |
| Hexanes plus | Trace-0.06 |
| Nitrogen | 0.7-5.6 |
| Carbon dioxide | 0.1-1.0 |
| Oxygen | 0.01-0.1 |
| Hydrogen | Trace-0.02 |

As one example of remote sensing of natural gas, a helicopter or aircraft may be flown at some elevation. The light source for remote sensing may direct the light beam toward the ground, and the diffuse reflected light may then be measured using a detection system on the aircraft. Thus, the helicopter or aircraft may be sampling a column area below it for natural gas, or whatever the material of interest is. In yet another embodiment, the column may sense aerosols of various sorts, as an example. Various kinds of SWIR light sources will be discussed later in this disclosure. The detection system may comprise, in one embodiment, a spectrometer followed by one or more detectors. In another embodiment, the detection system may be a dispersive element (examples include prisms, gratings, or other wavelength separators) followed by one or more detectors or detector arrays. In yet another embodiment, the detection system may comprise a gas-filter correlation radiometer. These are merely specific examples of the detection system, but combinations of these or other detection systems may also be used and are contemplated within the scope of this disclosure. Also, the use of aircraft is one particular example of a remote sensing system, but other system configurations may also be used and are included in the scope of this disclosure. For example, the light source and detection system may be placed in a fixed location, and for reflection the light source and detectors may be close to one another, while for transmission the light source and detectors may be at different locations. In yet another embodiment, the system could be placed on a vehicle such as an automobile or a truck, or the light source could be placed on one vehicle, while the detection system is on another vehicle. If the light source and detection system are compact and lightweight, they might even be carried by a person in the field, either in their hands or in a backpack.

Both methane and ethane are hydro-carbons with unique spectral signatures. For example, ethane is C2H6, while methane is CH4. Also, methane and ethane have infrared absorption bands near 1.6 microns, 2.4 microns, 3.3 microns and 7 microns. It should be noted that the approximately 7 micron lines cannot be observed generally due to atmospheric absorption. Although the fundamental lines near 3.3 microns are stronger absorption features, the light sources and detectors in the mid-infrared may be more difficult to implement. Hence, the focus here is on observing the SWIR lines that fall in atmospheric transparency windows.

Figure 33A:
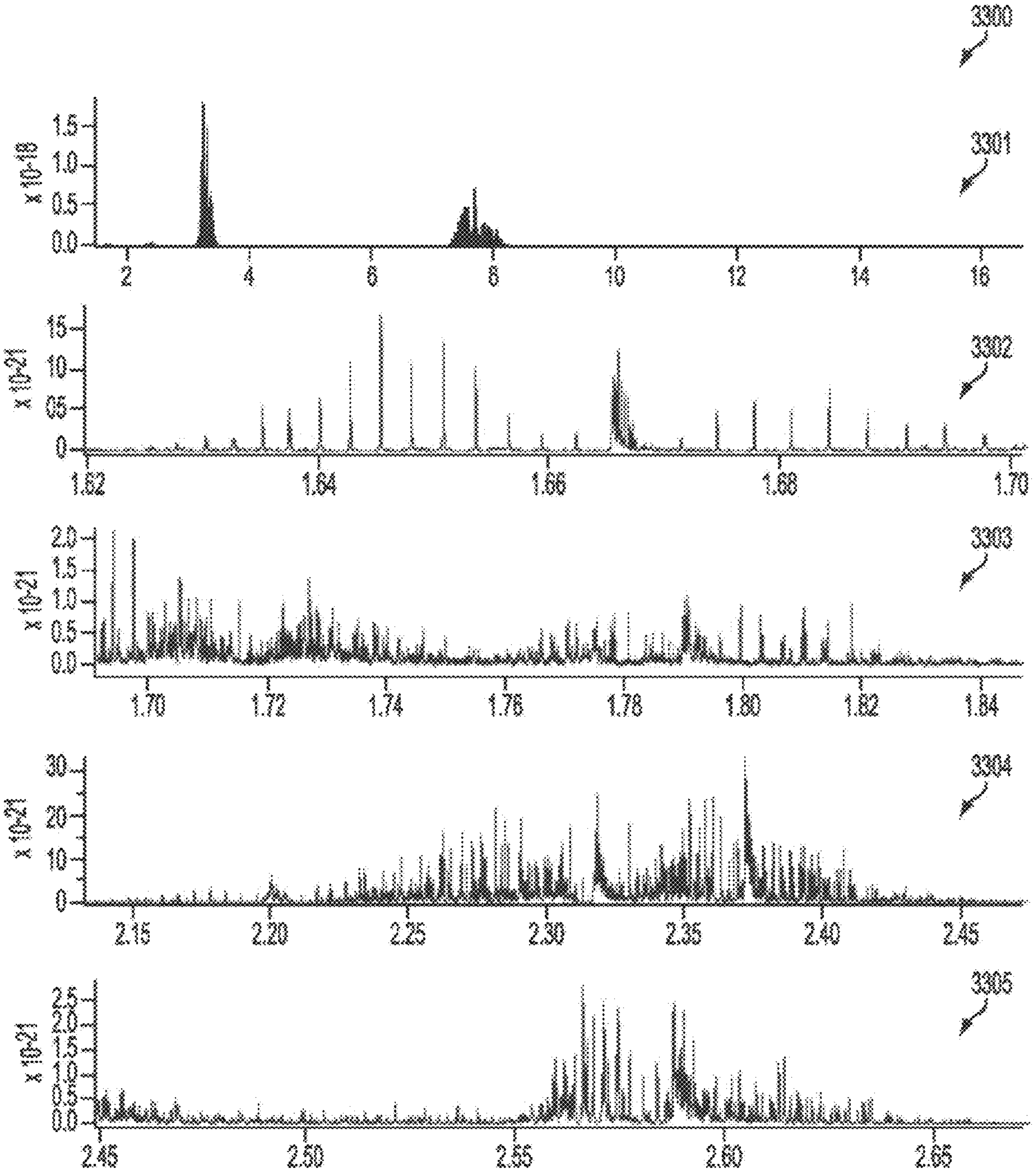
FIG. 33A shows the absorption spectra for methane.
Figure 33B:
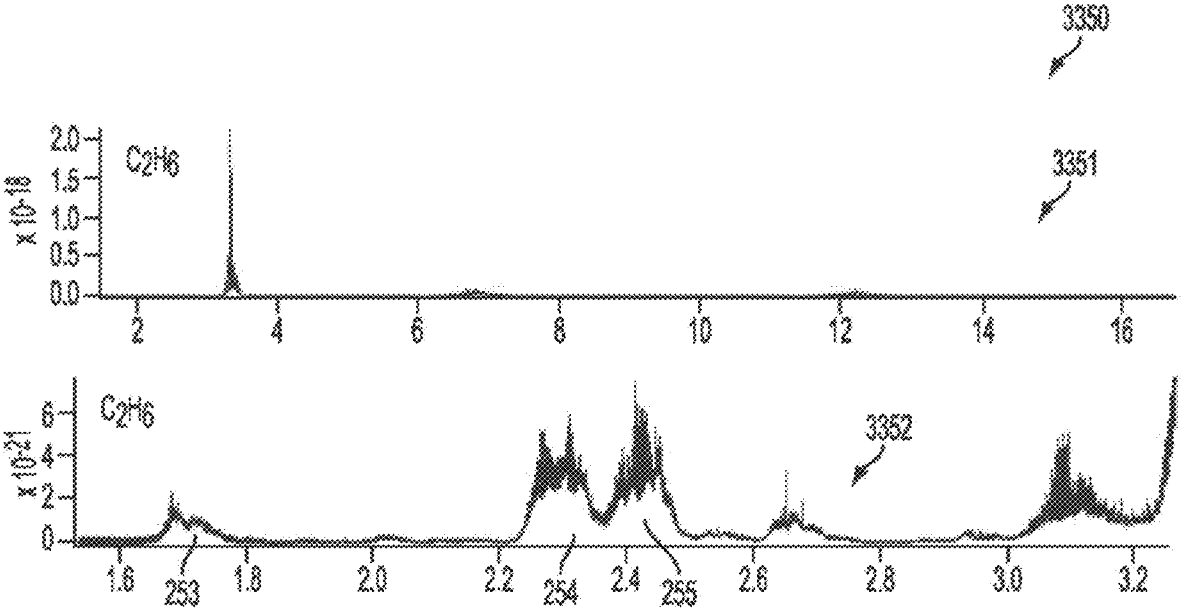
FIG. 33B shows the absorption spectra for ethane.

FIG. 33 illustrates the absorption spectra for methane (FIG. 33A) and ethane (FIG. 33B) (from http://vpl.astro-.washington.edu/spectra). The curves 3300 plot on a linear scale the absorption cross-section versus wavelength (in microns) for various methane lines. The curve 3301 covers the wavelength range between approximately 1.5-16 microns, while the curves below provide blown-up views of different wavelength ranges (3302 for approximately 1.62-1.7 microns, 3303 for approximately 1.7-1.84 microns, 3304 for approximately 2.15-2.45 microns, and 3305 for approximately 2.45-2.65 microns). The curves 3302 and 3303 fall within about the first SWIR atmospheric transmission window between approximately 1.4-1.8 microns, while the curves 3304 and 3305 fall within the second SWIR atmospheric transmission window between approximately 2-2.5 microns. As can be seen, there are numerous spectral features for identifying methane in the SWIR. In addition, there are even stronger features near 3.4-3.6 microns and around 7-8 microns, although these require different light sources and detection systems.

FIG. 33B illustrates the absorption spectra for ethane. The curves 3350 plot on a linear scale the absorption cross-section versus wavelength (in microns) for various ethane lines. The curve 3351 covers the wavelength range between approximately 1.5-16 microns, while the curve 3352 expands the scale between about 1.6-3.2 microns. The features 3353 fall within about the first SWIR atmospheric transmission window between approximately 1.4-1.8 microns, while the features 3354 and 3355 fall within the second SWIR atmospheric transmission window between approximately 2-2.5 microns. There are distinct spectral features for identifying ethane as well in the SWIR. In addition, there are even stronger features near 3.4-3.6 microns and around 7 microns.

For detecting natural gas leaks, a SWIR light source and a detection system could be used in transmission or reflection. The area surrounding the source or natural gas pipeline may be surveyed, and the detection system may monitor the methane and ethane concentration, or even the presence of these two gases. The region may be scanned to cover an area larger than the laser beam. Also, if a certain quantity of natural gas is detected, an alarm may be set-off to alert the operator or people nearby. This is just one example of the natural gas leak detection, but other configurations and techniques may be used and are intended to be covered by this disclosure.

Natural gas leak detection is one example where active remote sensing or hyper-spectral imaging can be used to detect hydro-carbons or organic compounds. However, there are many other examples where the technique may be used to perform reflectance spectroscopy of organic compounds, and these are also intended to be covered by this disclosure. In one particular embodiment, alkanes may be detected, where alkanes are hydro-carbon molecules comprising single carbon-carbon bonds. Alkanes have the general formula CnH2n+2 and are open chain, aliphatic or non-cyclic molecules. Below are examples of some of the alkanes, which include methane and ethane, as well as more complicated compounds.

| | Formula |
|---|---|
| Methane | $CH_4$ |
| Ethane | $C_2H_6$ |
| Propane | $C_3H_8$ |
| Butme | $C_4H_{10}$ |
| Pentane | $C_5H_{12}$ |
| Hexane | $C_6H_{14}$ |
| Heptane | $C_7H_{16}$ |
| Octane | $C_8H_{18}$ |
| Nonane | $C_9H_{20}$ |
| Decane | $C_{10}H_{22}$ |
| Paraffin | $C_{20}H_{42+}$ |
| Polyethylene (LDPE, HDPE) | $(C_2H_4)_n$ or $(CH_2CH_2)_n$ |
| Polyvinylchloride (PVC) | $(C_2H_3Cl)_n$ or $(CHClCH_2)_n$ |
| Polypropylene | $(C_3H_5)_n$ or $\{CH(CH_3)CH_2\}_n$ |
| Polyethylene terephthalate (PETE) | $C_{10}H_8O_4$ or $\{(CO_2)_2C_6H_4(CH_2)_2\}_n$ |
| Nylon (polyamide) | $C_{12}H_{24}O_4N_2$ or $\{C_{10}H_{22}(CO_2)_2(NH)_2\}_n$ |

Figure 34:
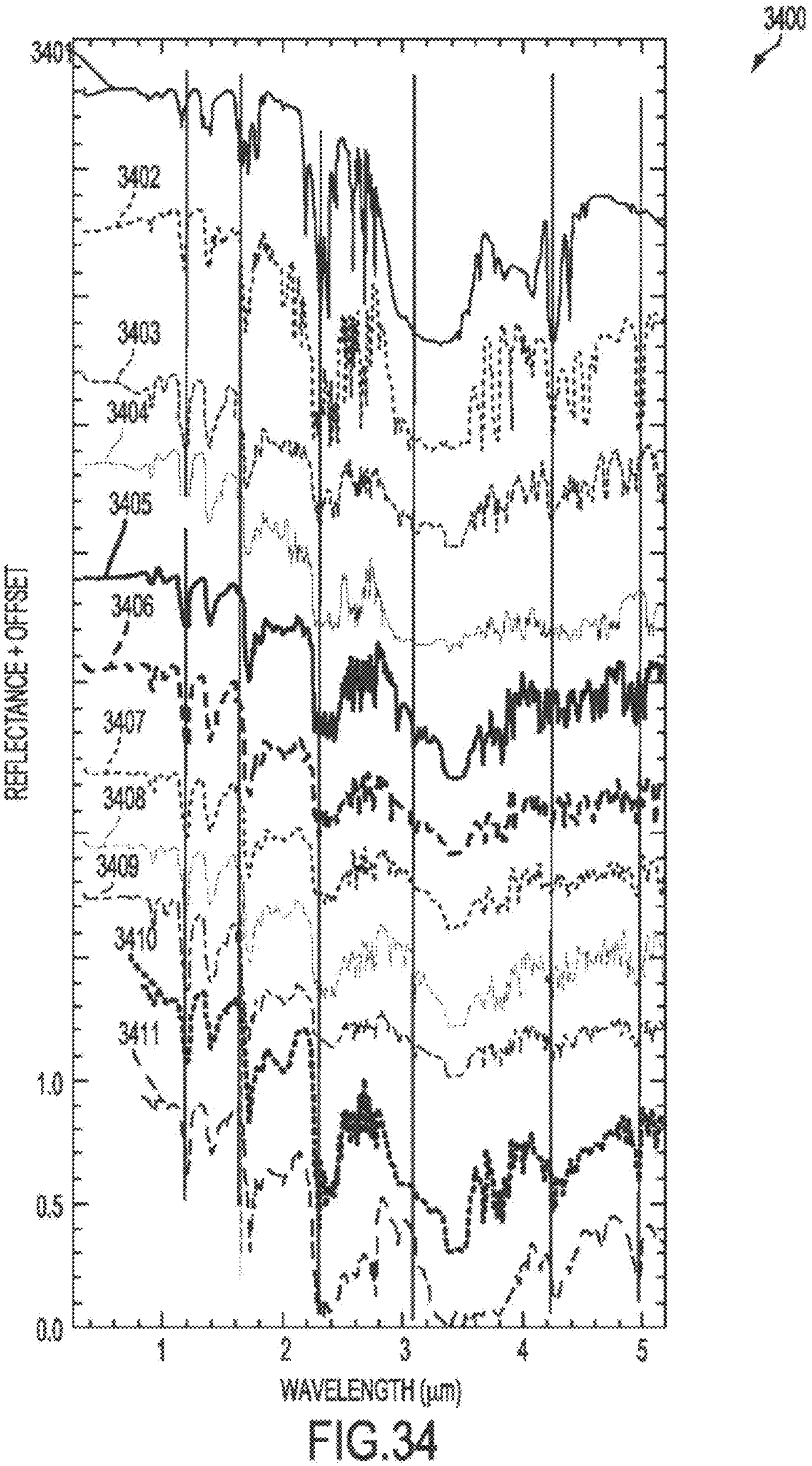
FIG. 34 illustrates the reflectance spectra for some members of the alkane family plus paraffin.

FIG. 34 illustrates the reflectance spectra 3400 for some members of the alkane family plus paraffin. The vertical lines indicate positions of constant wavelength and are aligned with apparent absorptions in the methane spectrum at 1.19, 1.67, 2.32, 3.1, 4.23 and 4.99 microns. The spectra ore offset to enable easier viewing, and the offsets are of the following amounts: 3401 methane 4.1; 3402 ethane 3.6; 3403 propane 3.3; 3404 butane 2.8; 3405 pentane 2.3; 3406 hexane 2.0; 3407 heptane 1.5; 3408 octane 1.2; 3409 nonane 0.85; 3410 decane 0.4; and 3411 paraffin 0.05. The reflectance of alkanes in the near-infrared may be dominated by absorptions due to combinations and overtones of bands at longer wavelengths. Although this wavelength range is mostly unexplored by organic spectroscopists, the near-infrared may be valuable for terrestrial and planetary remote sensing studies. Alkanes may have the fundamental absorptions due to a variety of C—H stretches between approximately 3.3-3.5 microns. The first overtone may be a relatively deep triplet near 1.7 microns. This triplet appears in most of the series, but the exact wavelength position may move. Another absorption band may be present near 1.2 microns, and this is likely the second overtone of the C—H stretch. The third C—H stretch overtone is near 0.9 microns. There is yet another near-infrared feature near 1.396 microns, which may correspond to the combinations of the first overtone of the C—H stretch with each of the two C—H band positions at approximately 1.35 microns and 1.37 microns. Moreover, there may be complex absorptions between 2.2-2.5 microns. For example, there may be a number of narrow individual absorption bands atop an overall absorption suite about 0.3 microns wide. A few absorption lines retain their location for most of the series 300, notably the 2.311 micron and 2.355 micron absorptions. This wavelength window may have multiple combinations and overtones, including contributions from the C—H stretch, CH3 asymmetric bend combination, and C—H stretch/CH3 symmetric bend combination.

Remote Sensing for Natural Gas Exploration

In addition to remote sensing to detect natural gas leaks, the same or similar system could also be used to explore for natural gas fields, whether under land or under water. Whereas a natural gas leak from a pipeline or building may be above the ground or only a few meters below the ground, natural gas exploration may occur for gas and oil that are much further below the ground, or under the water in a bay, lake, sea or ocean. For example, the exploration for natural gas and oil may be performed by determining the reflectance spectra of surface anomalies. The surface manifestations of oil and gas reservoirs may be used to map the petroleum potential of an area, particularly related to the seepage of oil and gas to the surface along faults or imperfect reservoir seals. The visible products of such seepage (e.g., oil and tar deposits) are generally referred to as macro-seeps, whereas the invisible gaseous products may be referred to as micro-seeps.

Figure 35A:
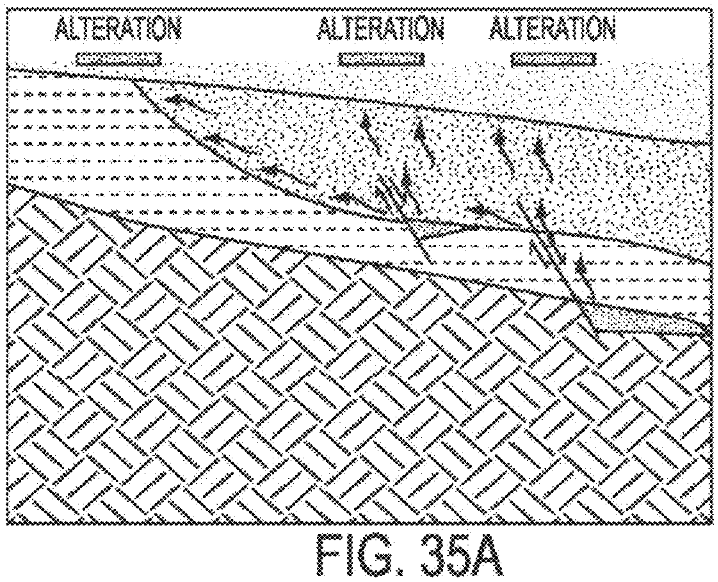
FIG. 35A depicts that micro-seepages may result from the vertical movement of hydro-carbons from their respective reservoirs to the surface. It is assumed that the rock column, including the seal rock, comprises interconnected fractures or micro-fracture systems.
Figure 35B:
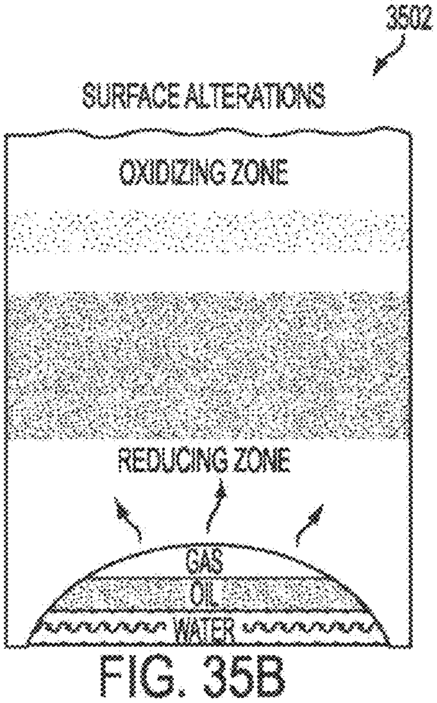
FIG. 35B illustrates that surface alterations may occur because leaking hydro-carbons set up near-surface oxidation and/or reduction zones that favor the development of a diverse array of chemical and mineralogical changes.

As illustrated by 3500 in FIG. 35, micro-seepages may result from the vertical movement of hydrocarbons 3501 from their respective reservoirs to the surface. These hydrocarbon micro-seepages involve buoyant, relatively rapid, vertical ascent of ultra-small bubbles of light hydrocarbons (primarily methane through the butanes) through a network of interconnected, groundwater-filled joints and bedding planes (3501). One of the assumptions required for micro-seepage to occur is that a rock column, including the seal rock, comprises extensive interconnected fractures or micro-fracture systems.

Direct detection methods may involve measurements of hydrocarbons, either in the form of oil accumulations or concentrations of escaping vapors, such as methane through butane. In addition, there are also indirect methods that may involve the measurement of secondary alternations that arise from the seepage of the hydrocarbons. For instance, hydrocarbon-induced alterations may include microbial anomalies, mineralogical changes, bleaching of red beds, clay mineral alterations, and electrochemical changes. These alterations occur because leaking hydrocarbons set up near-surface oxidation and/or reduction zones that favor the development of a diverse array of chemical and mineralogical changes, c.f. 3502 in FIG. 35. Such alterations 3502 may be distinct from adjacent rocks and, thus, may in some instance be detectable by various remote sensing techniques.

The diagnostic spectral features of methane and crude oil may comprise four distinct hydrocarbon absorption bands. For example, two bands near 1.18 microns and 1.38 microns may be narrow and sharply defined, although they may also be fairly weak. The other two spectral features may be near 1.68-1.72 microns and 2.3-2.45 microns; these bands may be broader, but they are also stronger than the previous two bands. The bands near 1.7 microns and 2.3 microns are spectral overtones or combinations of C—H vibrational modes. Moreover, hydrocarbon induced alterations associated with indirect detection may express themselves in a variety of spectral changes, such as mineralogical changes (calcium carbonate mineralization, near 2.35 microns), bleaching of red beds (near 1 micron), and clay minerals alterations (near 2.2 microns), among other changes.

Figure 36A:
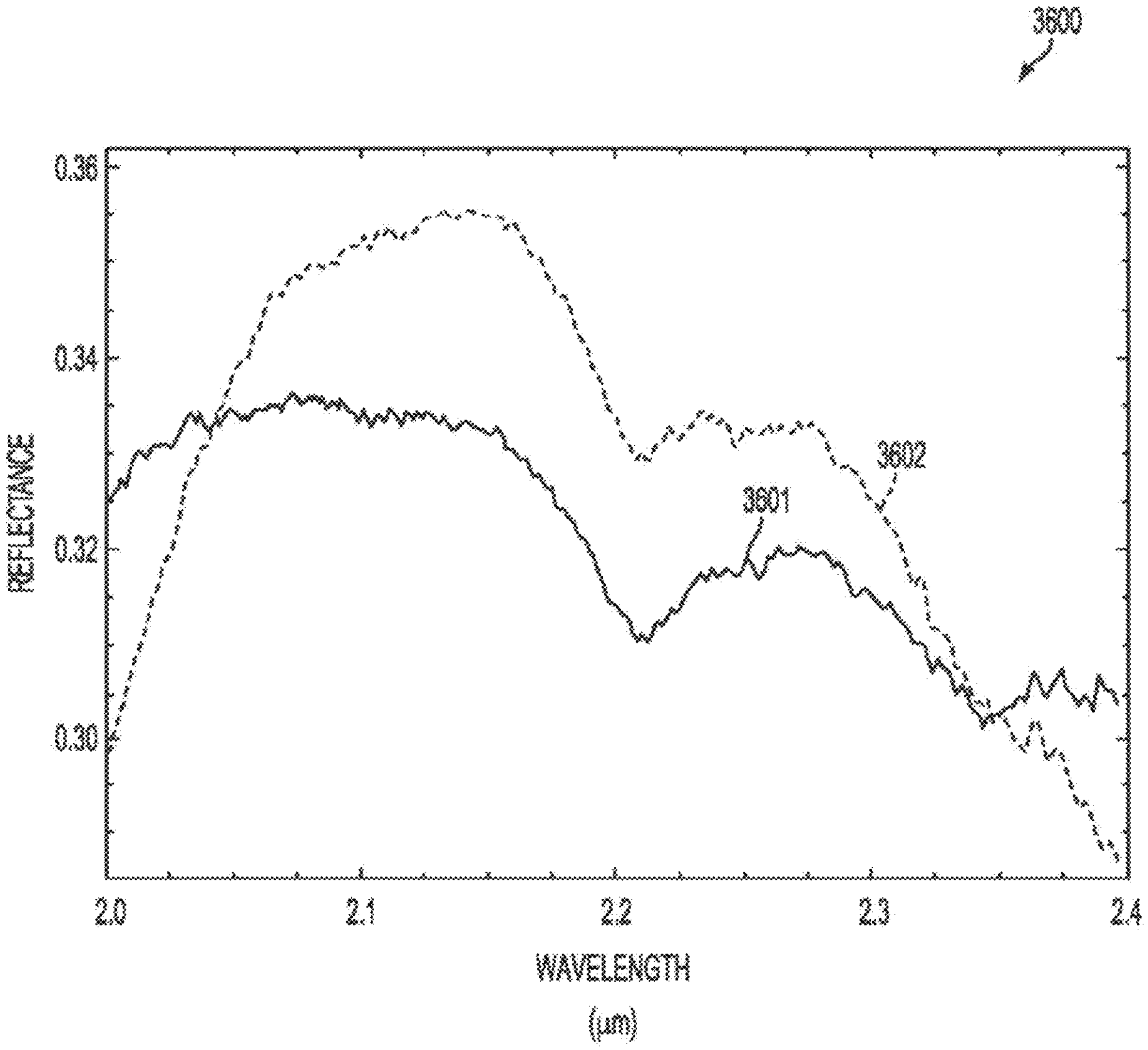
FIG. 36A shows the reflectance spectra for locations with natural gas fields (3601) and locations without natural gas fields (3602).

Various field tests have been conducted that verify the spectral signatures associated with natural gas fields, either land-based or water-based (e.g., in bays). In one example shown in FIG. 36A, the reflectance spectra 3600 was collected for different locations between approximately 2 microns and 2.4 microns. In 3601 the reflectance is plotted versus wavelength for locations with gas fields, while in 3602 the reflectance is plotted for locations without gas fields. The macroscopic features of the reflectance spectra of surface soils show two broad absorption bands near 2.2 microns and 2.33 microns with complex shapes. The slightly positive slope in the region of 2.3-2.4 microns with natural gas suggests that hydrocarbons are overriding the spectral signature of clays in this region.

Figure 36B:
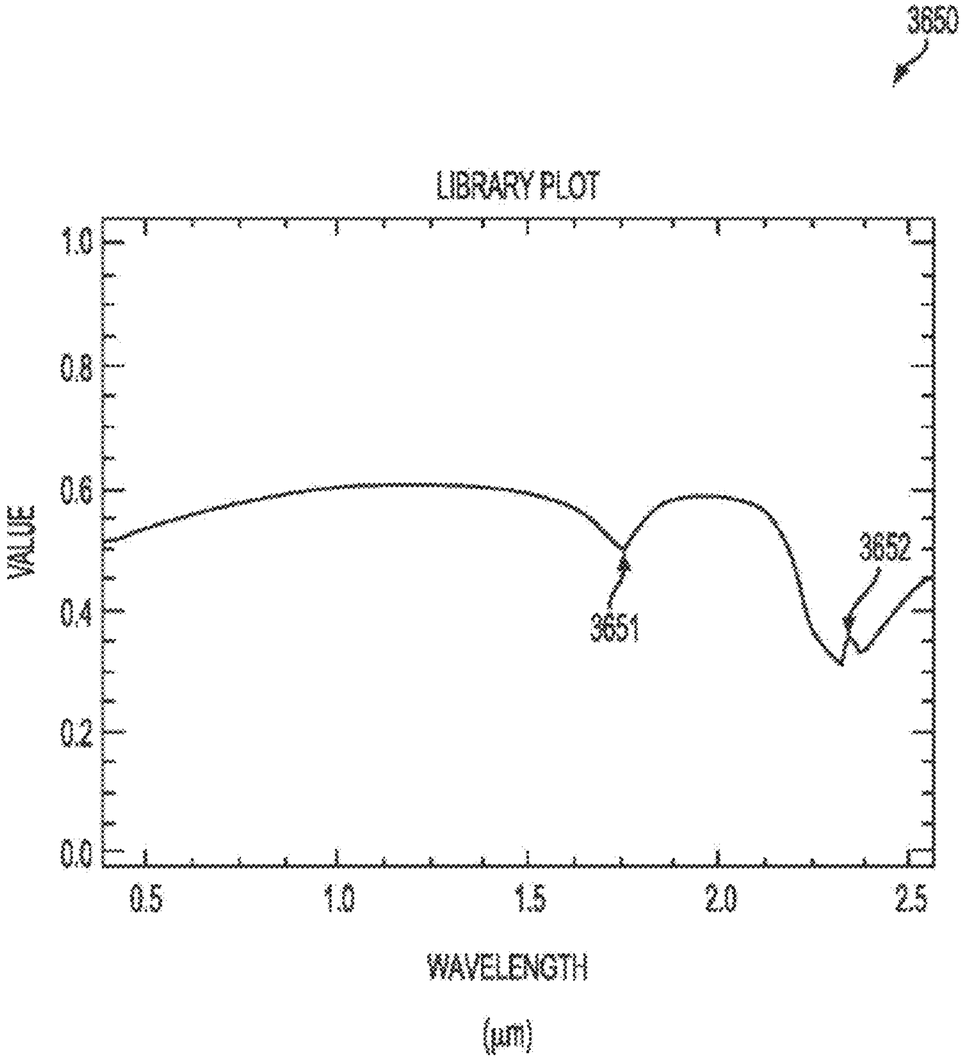
FIG. 36B illustrates spectra from field tests over regions with natural gas, which show two spectral features: one near 1.725 microns and another doublet between about 2.311 microns and 2.36 microns.

In yet another embodiment, field tests were conducted over a wider spectra range from approximately 0.5 microns to 2.5 microns (FIG. 36B). As the curve 3650 illustrates, two absorption features are found for the hydrocarbon spectral reflectance curve: one near 1.725 microns 3651 and a double absorption at approximately 2.311-2.36 microns 3652. Thus, in these two field trial examples, oil-gas reservoir areas were identifiable using feature bands of 1650-1750 nm and 2000-2400 nm. In addition, the remote sensing method may be used for off-shore oil and gas exploration and marine pollution investigation, to name just a few examples.

Other Uses of Active Remote Sensing or Hyperspectral Imaging

Active and/or hyper-spectral remote sensing may be used in a wide array of applications. Although originally developed for mining and geology (the ability of spectral imaging to identify various minerals may be ideal for the mining and oil industries, where it can be used to look for ore and oil), hyper-spectral remote sensing has spread to fields as diverse as ecology and surveillance. The table below illustrates some of the applications that can benefit from hyper-spectral remote sensing.

| | |
|---|---|
| Atmosphere | Water vapor, cloud properties, aerosols |
| Ecology | Chlorophyll, leaf water, cellulose, pigments, lignin |
| Geology | Mineral and soil types |
| Coastal Waters | Chlorophyll, phytoplankton, dissolved organic materials, suspended sediments |
| Snow/Ice | Snow cover fraction, grainsize, melting |
| Biomass Burning | Subpixel temperatures, smoke |
| Commercial | Mineral (oil) exploration, agriculture and forest production |

Figure 37:
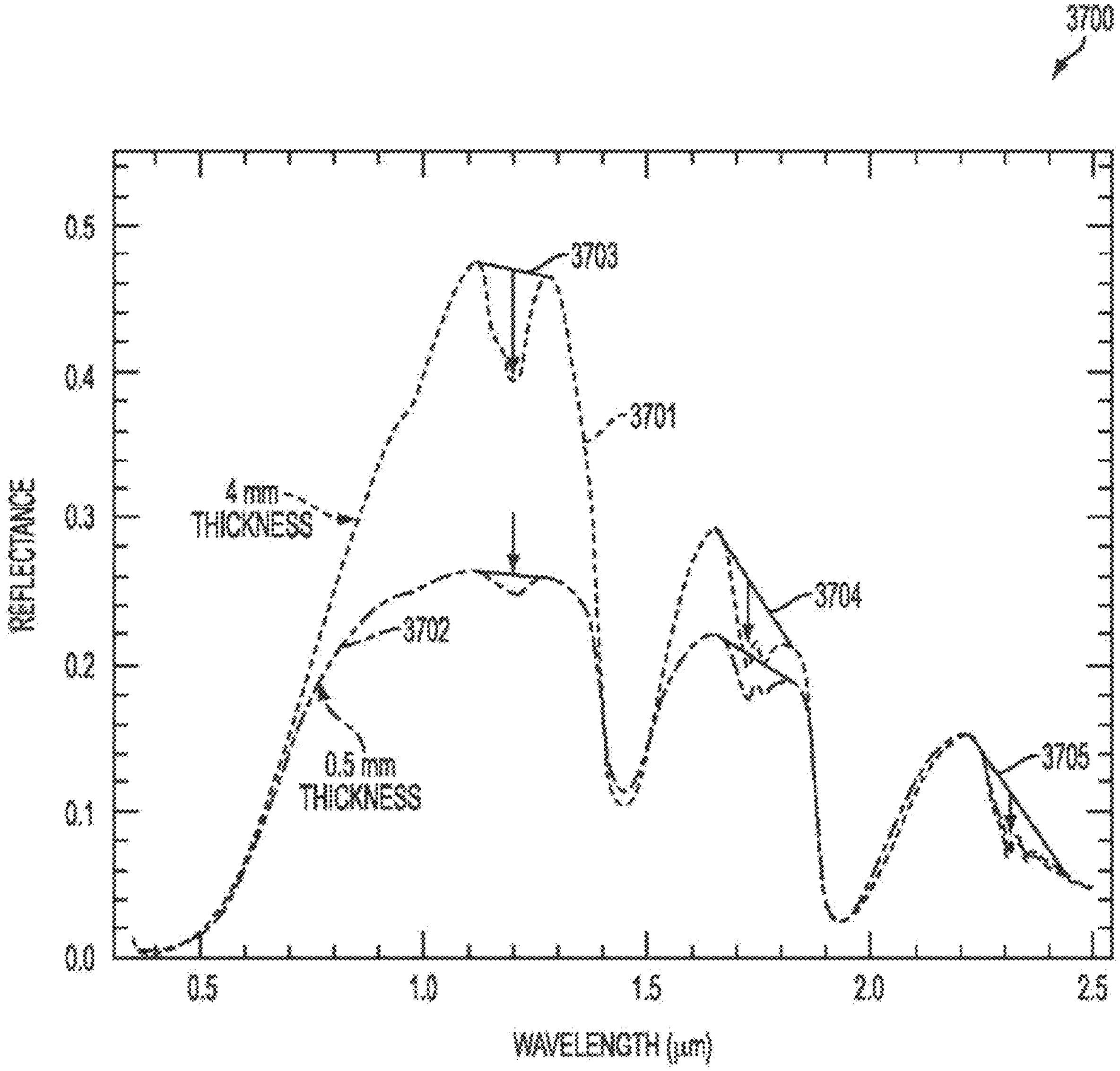
FIG. 37 shows the reflectance spectra of a sample of oil emulsion from the Gulf of Mexico 2010 oil spill (different thicknesses of oil).

In one embodiment, near-infrared imaging spectroscopy data may be used to create qualitative images of thick oil or oil spills on water. This may provide a rapid remote sensing method to map the locations of thick parts of an oil spill. While color imagery may show locations of thick oil, it is difficult to assess relative thickness or volume with just color imagery. As an example, FIG. 37 illustrates the reflectance spectra 3700 of a sample of oil emulsion from the Gulf of Mexico 2010 oil spill. Curve 3701 is a 4 mm thickness of oil, while curve 3702 is a 0.5 mm thickness. Whereas the data in the visible hardly changes with oil thickness, in the near-infrared the change in reflectance spectra is much more dependent on the oil thickness. The data shows, for example, the C—H features near 1.2 microns 3703, 1.73 microns 3704, and 2.3 microns 3705. Thus, in the infrared wavelengths, both the reflectance levels and absorption features due to organic compounds may vary in strength with oil thickness.

Figure 38:
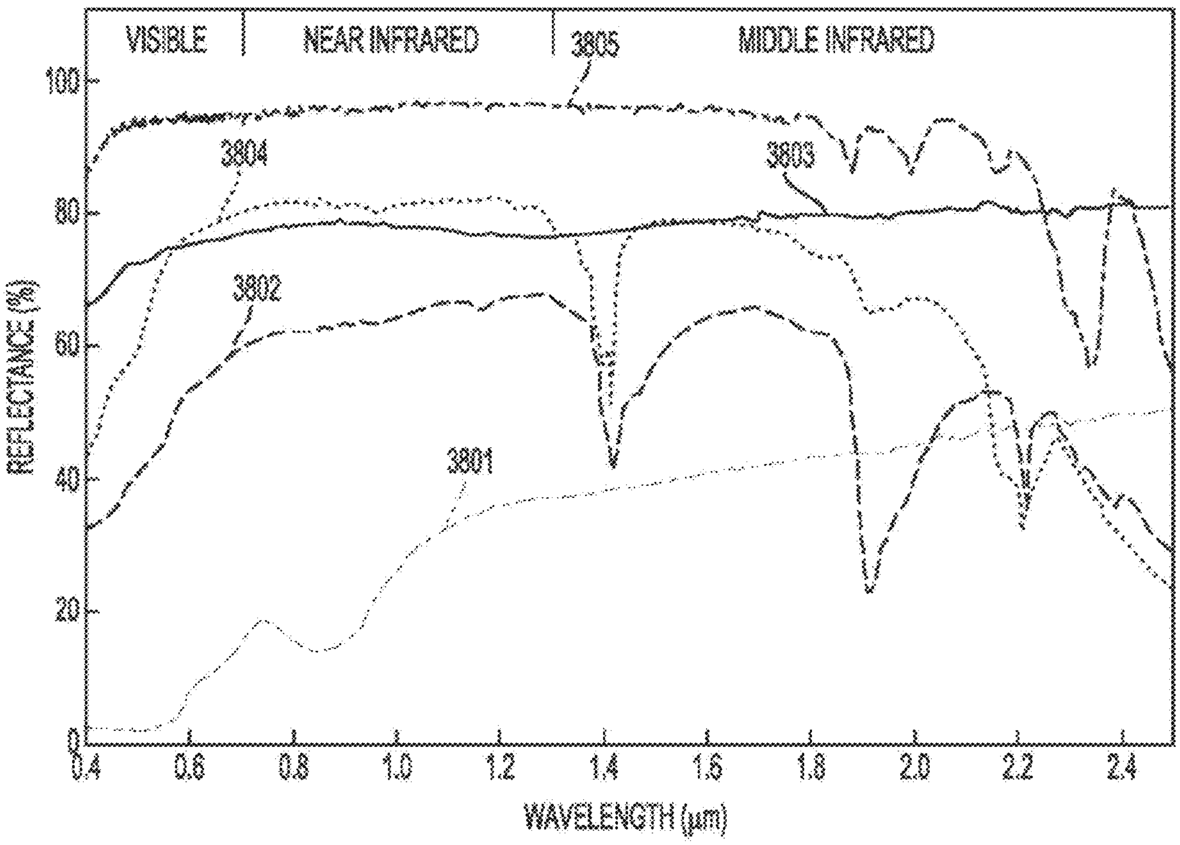
FIG. 38 illustrates the reflectance spectra of some representative minerals that may be major components of rocks and soils.

Remote sensing may also be used for geology and mineralogy mapping or inspection. FIG. 38 shows the reflectance spectra 3800 for some representative minerals that are major components of rocks and soils. In inorganic materials such as minerals, chemical composition and crystalline structure may control the shape of the spectral curve and the locations of absorption bands. Wavelength-specific absorption may arise from particular chemical elements or ions and the geometry of chemical bonds between elements, which is related to the crystal structure. In hematite 3801, the strong absorption in the visible may be caused by ferric iron. In calcite 3805, the carbonate ion may be responsible for the series of absorption bands between 1.8 and 2.4 microns. Kaolinite 3804 and montmorillonite 3802 are clay minerals common in soils. The strong absorption near 1.4 microns in both spectra, along with a weak 1.9 micron band in kaolinite arise from the hydroxide ions, while the stronger 1.9 micron band in montmorillonite may be caused by bound water molecules in the hydrous clay. In contrast to these spectra, orthoclase feldspar 3803, a dominant mineral in granite, shows very little absorption features in the visible or infrared.

Figure 39:
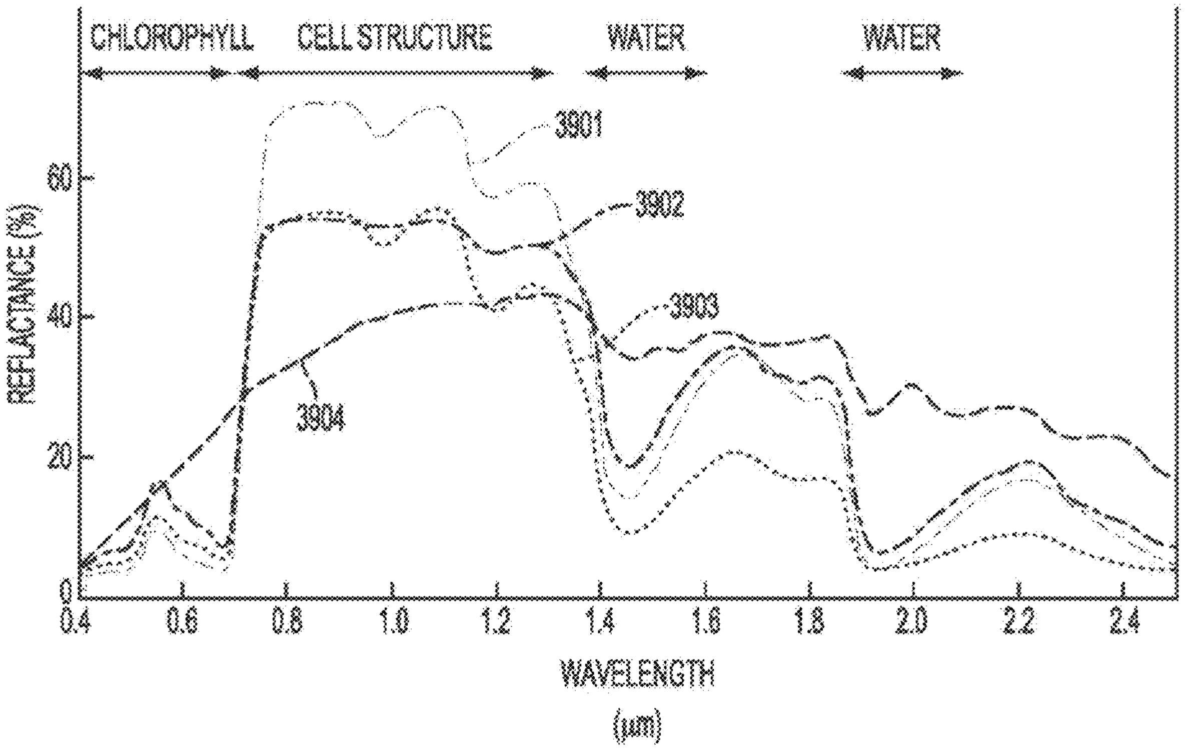
FIG. 39 shows the reflectance spectra of different types of green vegetation compared with dry, yellowed grass.

Remote sensing or hyper-spectral imaging may also be used for agriculture as well as vegetation monitoring. For example, hyper-spectral data may be used to detect the chemical composition of plants, which can be used to detect the nutrient and water status of crops. FIG. 39 illustrates the reflectance spectra 3900 of different types of green vegetation compared with dry, yellowed grass. In the visible spectra, the shape may be determined by absorption effects from chlorophyll and other leaf pigments. The reflectance rises rapidly across the boundary between red and infrared wavelengths, which may be due to interactions with the internal cellular structure of leaves. Leaf structure may vary significantly between plant species, as well as from plant stress. Beyond 1.3 microns the reflectance decreases with increasing wavelength, except for two water absorption bands near 1.4 microns and 1.9 microns. Illustrated in FIG. 39 are the reflectance for green grass 3901, walnut tree canopy 3902, fir tree 3903 and senescent 3904, which is dry, yellowed grass.

Figure 40:
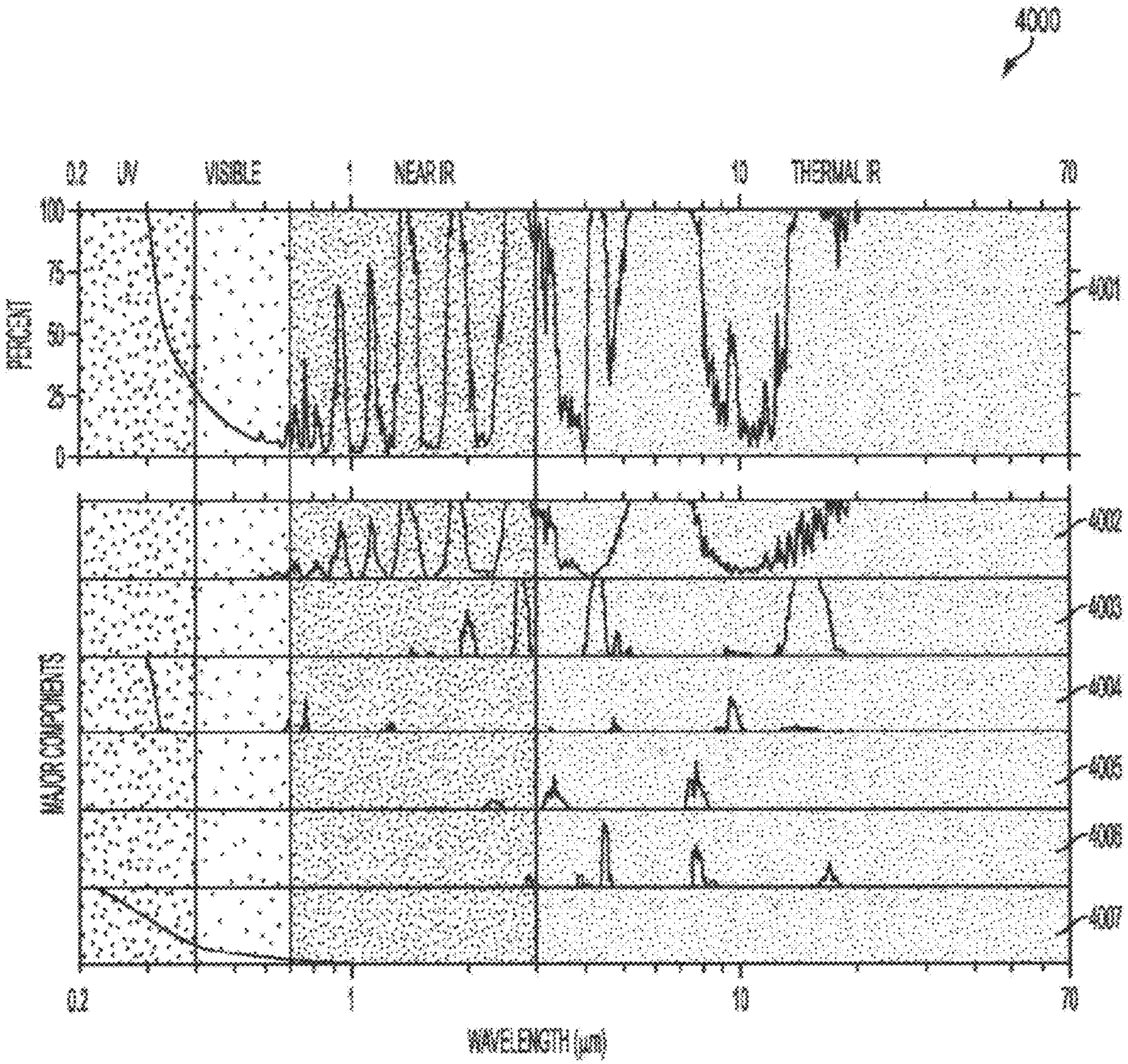
FIG. 40 illustrates the atmospheric absorption and scattering of greenhouse gases at different wavelengths.

Active remote sensing may also be used to measure or monitor gases in the earth's atmosphere, including greenhouse gases, environmental pollutants and aerosols. For instance, greenhouse gases are those that can absorb and emit infrared radiation: In order, the most abundant greenhouse gasses in the Earth's atmosphere are: water vapor (H2O), carbon dioxide (CO2), methane (CH4), nitrous oxide (N2O) and ozone (O3). FIG. 40 shows the atmospheric absorption and scattering of greenhouse gases 4000 at different wavelengths. Included in this figure are the total absorption and scattering 4001, along with the breakdown by major components: water vapor 4002, carbon dioxide 4003, oxygen and ozone 4004, methane 4005, and nitrous oxide 4006. Also shown is the Rayleigh scattering 4007 through the atmosphere, which dominates at shorter wavelengths, particularly wavelengths shorter than about 1 micron. In one embodiment, environmental concerns of climate change have led to the need to monitor the level of carbon dioxide in the atmosphere, and this may be achieved, for example, by performing spectroscopy in the vicinity of 1.6 microns and 2 microns.

Figure 41:
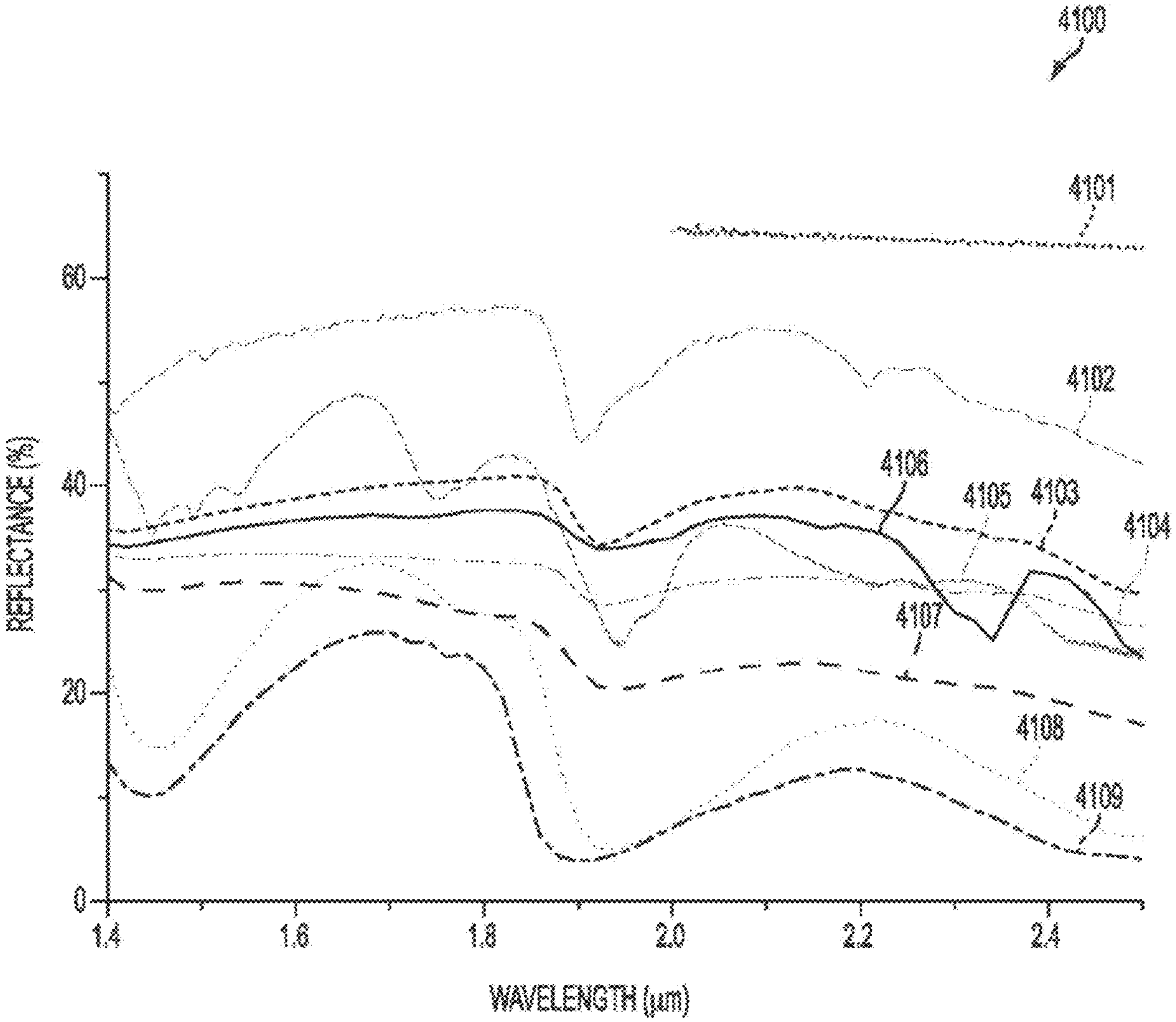
FIG. 41 overlays the reflectance for different building materials from the ASTER spectra library.

In yet another embodiment, different building materials may be identified and distinguished from surrounding vegetation and forestry. FIG. 41 overlays different reflectance data 4100 for samples cataloged in the ASTER spectra library (http://speclib.jpl.nasa.gov). This library has been made available by NASA as part of the Advanced Spaceborne Thermal Emission and Reflection Radiometer, ASTER, imaging instrumentation program. Included in this and other libraries are reflection spectra of natural and man-made materials, including minerals, rocks, soils, water and snow. In FIG. 41 several spectra are included over the SWIR atmospheric transmission bands, and the water absorption between approximately 1.8 and 2 microns has been blocked out (features in there are either due to water or would be masked by the atmospheric moisture). Included in the graph are the spectra for silver metallic paint 4101, light brown loamy sand 4102, construction concrete-1 4103, construction concrete-cement 4104, gypsum 4105, asphaltic concrete 4106, construction concrete-bridges 4107, grass 4108 and conifer trees 4109. As an example, active remote sensing can be used to distinguish different concrete structures, including roadways, buildings, and reinforced structures such as bridges. Also, building materials such as gypsum, painted structures, plywood, and concrete of various sorts, may be distinguished from plant life, soil and trees. Thus, beyond three dimensional imaging, this can add a fourth dimension—namely, identification of objects based on their chemical signature.

Figure 42:
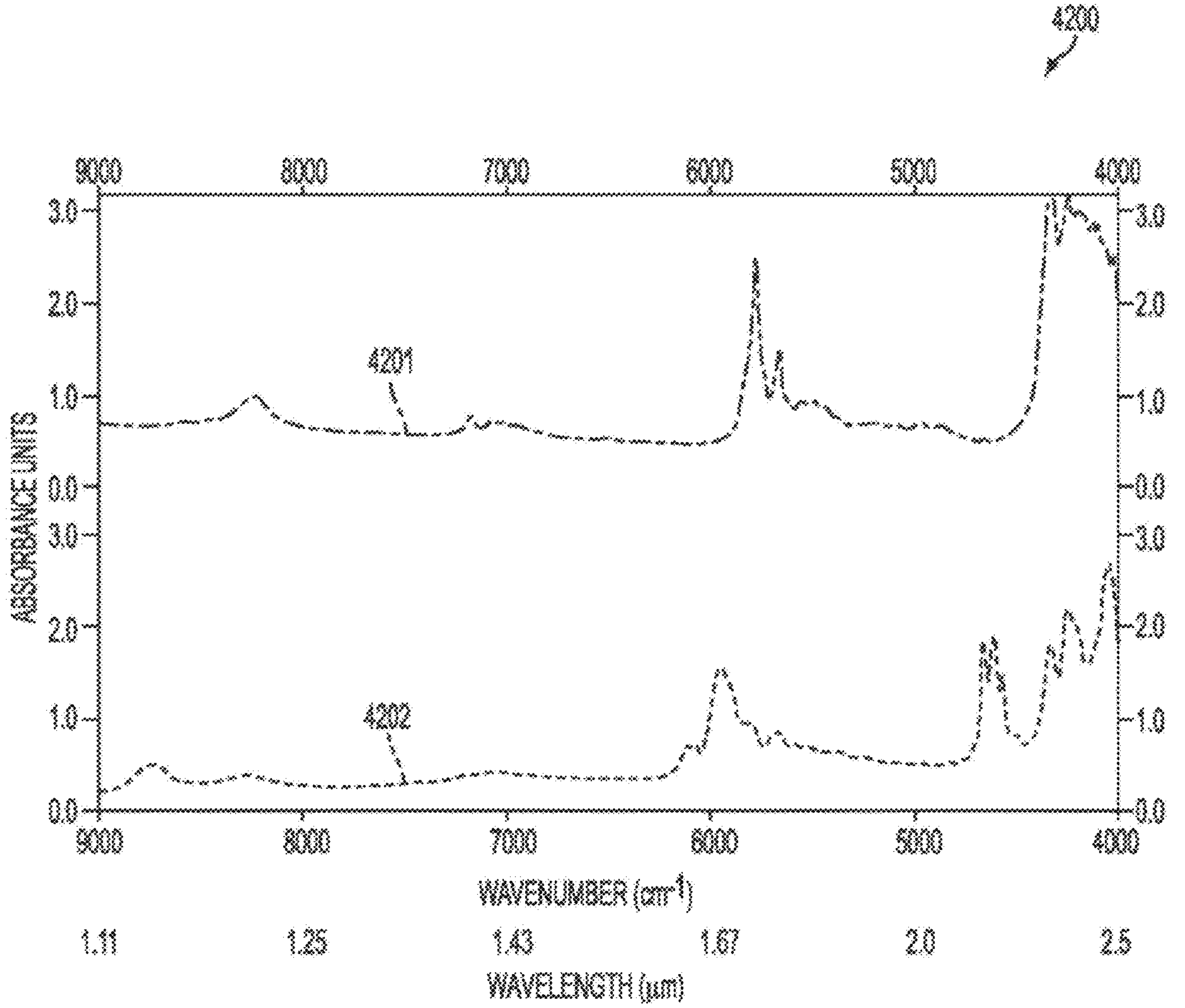
FIG. 42 shows the absorbance for two common plastics, polyethylene and polystyrene.

In a further embodiment, remote sensing or hyper-spectral imaging might be used for process control in a factory or manufacturing setting, particularly when the measurements are to be made at some stand-off or remote distance. As an example, plastics show distinct signatures in the SWIR, and process control may be used for monitoring the manufacture of plastics. Alternately, SWIR light could be used to see through plastics, since the signature for plastics can be subtracted off and there are large wavelength windows where the plastics are transparent. FIG. 42 illustrates the absorbance 4200 for two common plastics: polyethylene 4201 and polystyrene 4202. Because of the hydro-carbon bonds, there are absorption features near 1.7 microns and 2.2-2.5 microns (c.f., discussion on alkanes). In general, the absorption bands in the near infrared are due to overtones and combination bands for various functional group vibrations, including signals from C—H, O—H, C═O, N—H, —COOH, and aromatic C—H groups. It may be difficult to assign an absorption band to a specific functional group due to overlapping of several combinations and overtones. However, with advancements in computational power and chemometrics or multivariate analysis methods, complex systems may be better analyzed. In one embodiment, using software analysis tools the absorption spectrum may be converted to its second derivative equivalent. The spectral differences may permit a fast, accurate, non-destructive and reliable identification of materials. Although particular derivatives are discussed, other mathematical manipulations may be used in the analysis, and these other techniques are also intended to be covered by this disclosure.

Figure 43:
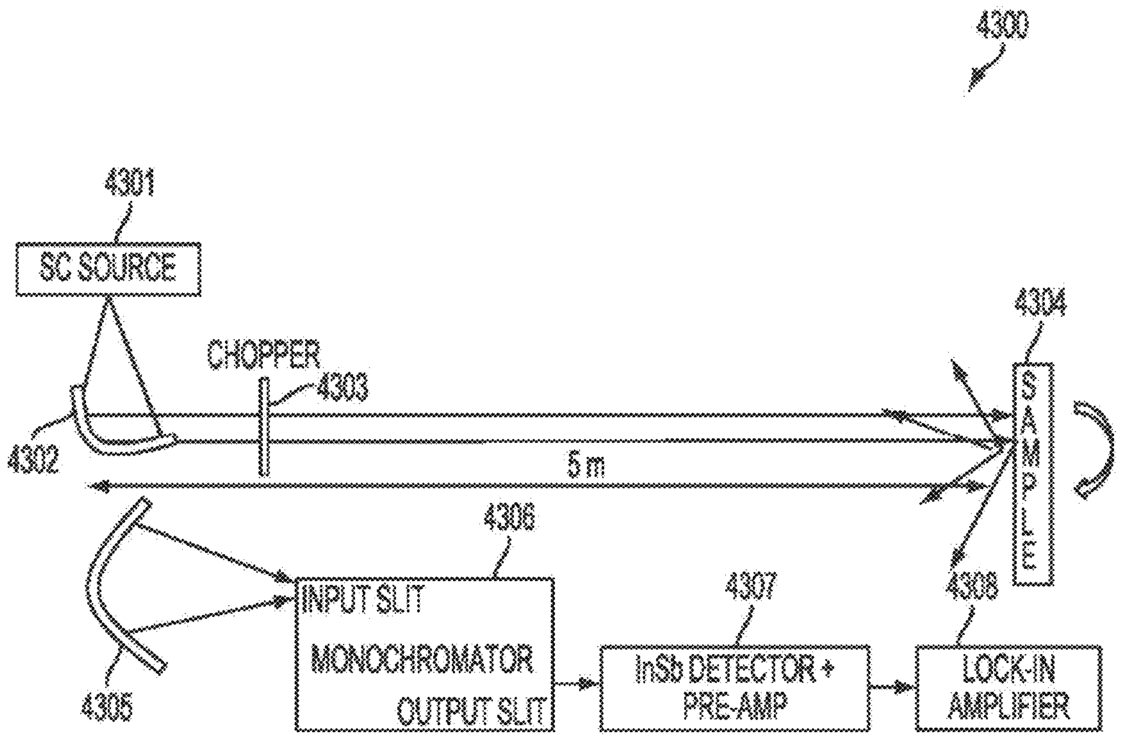
FIG. 43 shows the experimental set-up for a reflection-spectroscopy based stand-off detection system.

In another specific embodiment, experiments have been performed for stand-off detection of solid targets with diffuse reflection spectroscopy using a fiber-based super-continuum source (further described herein). In particular, the diffuse reflection spectrum of solid samples such as explosives (TNT, RDX, PETN), fertilizers (ammonium nitrate, urea), and paints (automotive and military grade) have been measured at stand-off distances of 5 m. Although the measurements were done at 5 m, calculations show that the distance could be anywhere from a few meters to over 150 m. These are specific samples that have been tested, but more generally other materials (particularly comprising hydro-carbons) could also be tested and identified using similar methods. The experimental set-up 4300 for the reflection-spectroscopy-based stand-off detection system is shown in FIG. 43, while details of the SC source 4301 are described later in this disclosure (c.f. FIGS. 20,21, and 23). First, the diverging SC output is collimated to a 1 cm diameter beam using a 25 mm focal length, 90 degrees off-axis, gold coated, parabolic mirror 4302. To reduce the effects of chromatic aberration, refractive optics are avoided in the setup. All focusing and collimation is done using metallic mirrors that have almost constant reflectivity and focal length over the entire SC output spectrum. The sample 4304 is kept at a distance of 5 m from the collimating mirror 4302, which corresponds to a total round trip path length of 10 m before reaching the collection optics 4305. A 12 cm diameter silver coated concave mirror 4305 with a 75 cm focal length is kept 20 cm to the side of the collimation mirror 4302. The mirror 4305 is used to collect a fraction of the diffusely reflected light from the sample, and focus it into the input slit of a monochromator 4306. Thus, the beam is incident normally on the sample 4304, but detected at a reflection angle of tan−1(0.2/5) or about 2.3 degrees. Appropriate long wavelength pass filters mounted in a motorized rotating filter wheel are placed in the beam path before the input slit 4306 to avoid contribution from higher wavelength orders from the grating (300 grooves/mm, 2 μm blaze). The output slit width is set to 2 mm corresponding to a spectral resolution of 10.8 nm, and the light is detected by a 2 mm×2 mm liquid nitrogen cooled (77K) indium antimonide (InSb) detector 4307. The detected output is amplified using a trans-impedance pre-amplifier 4307 with a gain of about 105V/A and connected to a lock-in amplifier 4308 setup for high sensitivity detection. The chopper frequency is 400 Hz, and the lock-in time constant is set to 100 ms corresponding to a noise bandwidth of about 1 Hz. These are exemplary elements and parameter values, but other or different optical elements may be used consistent with this disclosure.

Three sets of solid samples are chosen to demonstrate the stand-off diffuse reflection spectra measurement in the laboratory. The first set comprises 'Non-hazardous Explosives for Security Training and Testing' (NESTT) manufactured by the XM Division of VanAken International. These samples contain small amounts of explosives deposited on an inert fused silica powder substrate. The experiments are conduced with the following samples—trinitrotoluene (TNT), research department explosive (RDX), Pentaerythritol tetranitrate (PETN), and potassium nitrate. The TNT, RDX and potassium nitrate NESTT samples have 8% (by weight) explosives, while the PETN sample has 4%.

The second sample set consists of ammonium nitrate, urea, gypsum, and pinewood. Ammonium nitrate and urea are common fertilizers, but are also often used as explosives. These samples are ground to a fine powder in a mortar and pestle, and filled to a depth of about 5 mm in a shallow glass container. We also measure the reflection spectrum of a 10 cm diameter×0.5 cm thick Gypsum (CaSO4.2H2O) disk and a 5 cm×5 cm×0.5 m piece of pine wood, since these samples are relevant for the remote sensing community (minerals and vegetation).

The final set of samples is selected to distinguish between commercial automotive and military vehicle paints based on their reflection signatures. Red, black, and green acrylic based spray paints are obtained from an auto supply store and sprayed 3 coats on different areas of a sanded Aluminum block to make the automotive paint samples. The sample of the military paint consisted of an Aluminum block coated with a chemical agent resistant coating (CARC) green paint.

Figure 44:
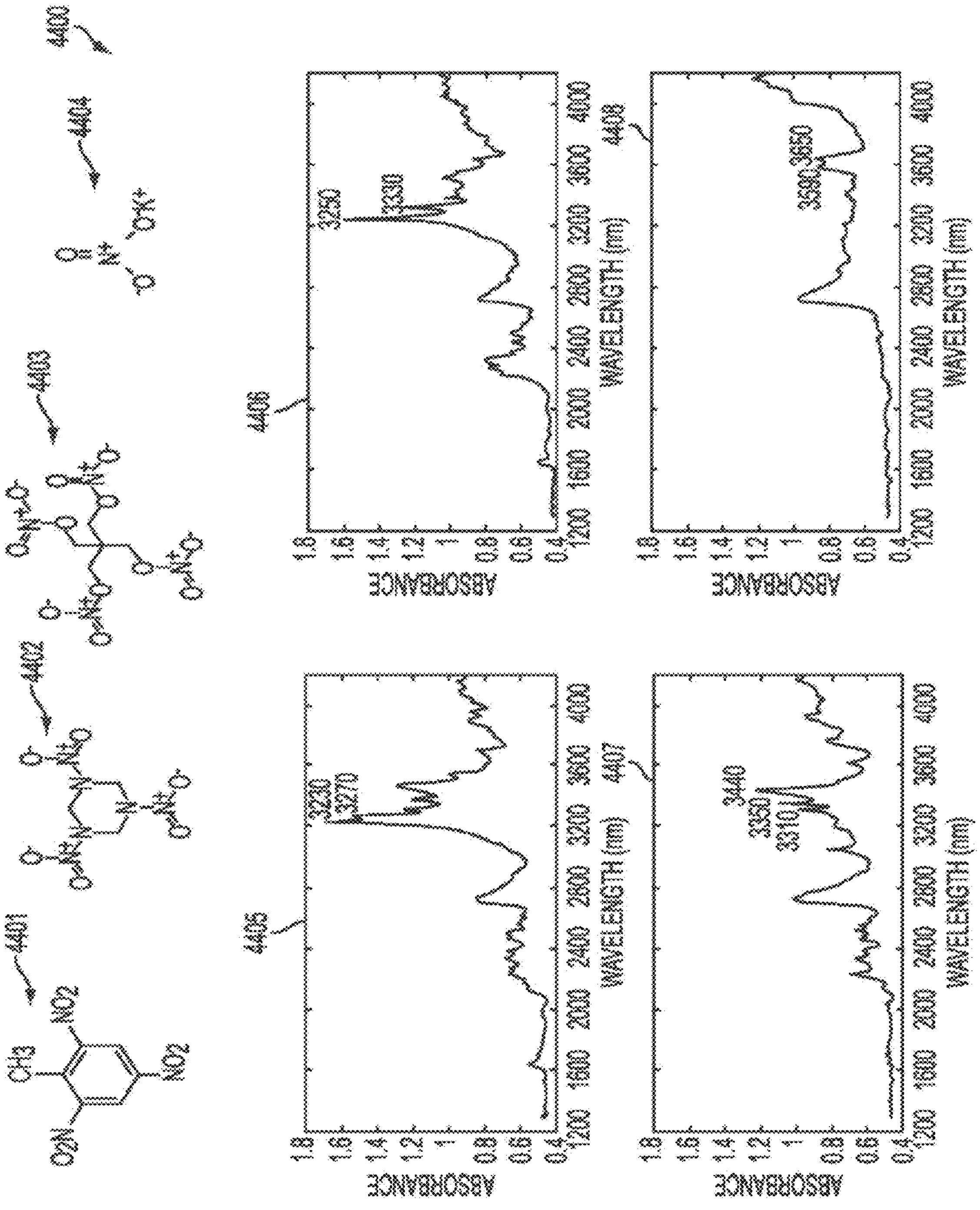
FIG. 44 illustrates the chemical structure and molecular formula for various explosives, along with the absorbance spectra obtained using a super-continuum source.

The chemical structure and molecular formula of the 4 NESTT samples are shown in FIG. 44 (4401, 4402, 4403, 4404), while the absorbance spectra obtained using the SC source are shown below in the same figure (4405, 4406, 4407, 4408). For each sample, the positions of the strongest/unique peaks have been labeled for clarity. TNT 4401, 4405 belongs to a class of compounds known as nitro-aromatics, in which the carbon directly attached to the nitro (NO2) group is part of an aromatic ring. The strongest peaks in the spectrum observed at 3230 nm and 3270 nm are due to the fundamental C—H stretching vibrations in the aromatic ring. There are also features between 2200-2600 nm, which may arise from the combination between the C—H stretch and C—H bend vibrations. RDX 4402, 4406 belongs to the nitramines class containing the N—NO2 bond and also has multiple features in the 3200-3500 nm band due to the C—H stretch vibrations. This spectrum also contains the C—H combination bands from 2200-2600 nm. PETN 4403, 4407 is classified as a nitrate ester containing the C—O—NO2 bond, and its reflection spectrum is characterized by a triplet of peaks at 3310 nm, 3350 nm and 3440 nm due to the C—H stretch vibration from the aliphatic groups. The C—H combination band is also present from 2200-2600 nm. Potassium nitrate 4404, 4408 being an inorganic compound does not contain any absorption features due to the C—H bond present in the other three samples. Instead, the unique spectral feature for this sample is a pair of peaks at 3590 nm and 3650 nm, which arise due to the first overtone of the asymmetric N—O stretching vibration of the nitrate ion (NO3-).

Figure 45A:
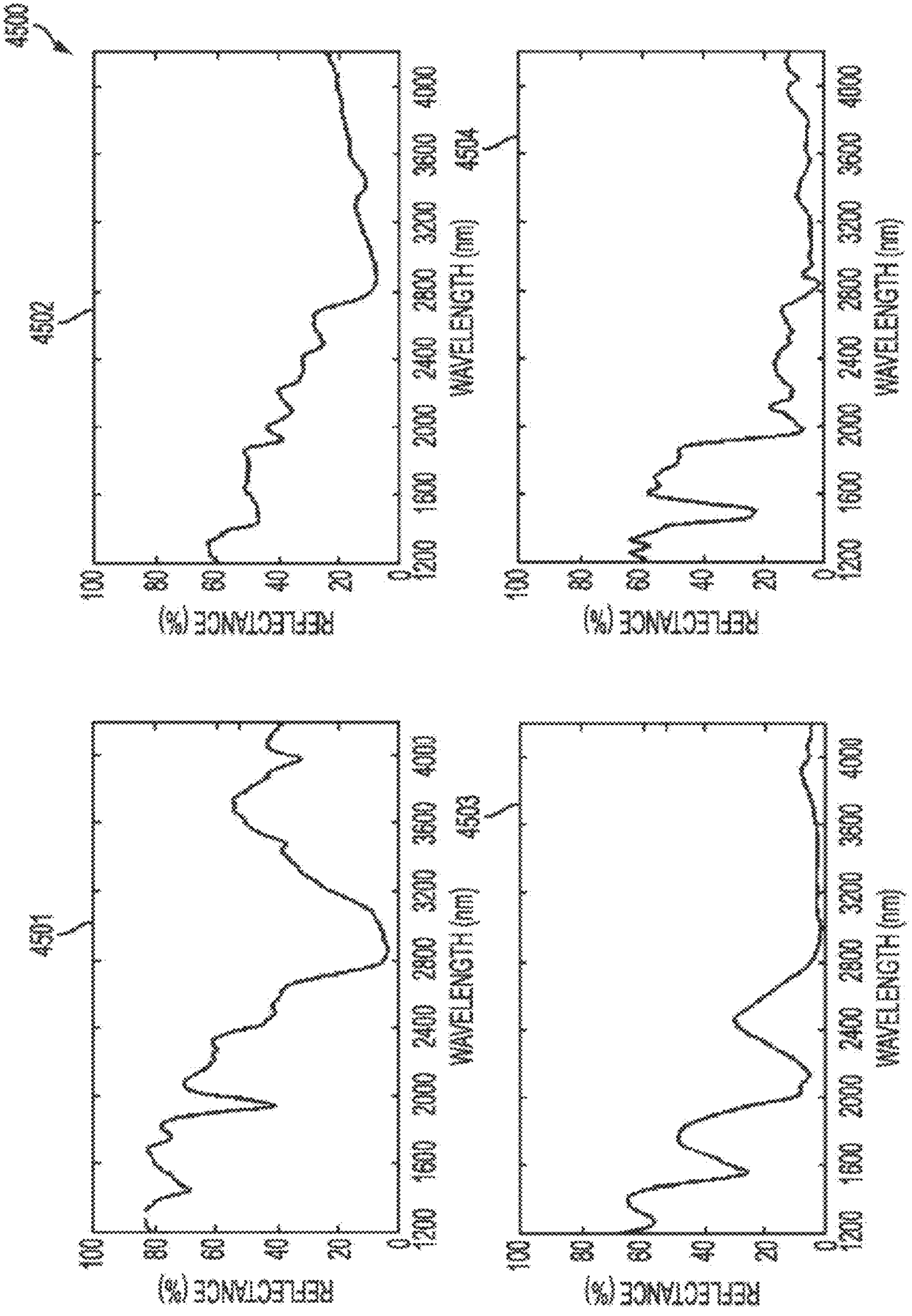
FIG. 45A shows the reflection spectra for gypsum, pine wood, ammonium nitrate and urea.

FIG. 45A illustrates the reflection spectra 4500 for gypsum 4501, pinewood 4502, ammonium nitrate 4503 and urea 4504. The predominant spectral features in the gypsum 4501 (CaSO4.2H2O) reflectance occur due to the fundamental as well as combination bands of the water molecule near 1450 nm, 1750 nm, 1940 nm and 2860 nm. In addition, small dips in the spectrum at 2220, 2260 and 2480 nm which arise due to the first overtone of the S—O bending vibration. Moreover, the valley at 3970 nm occurs due to the first overtone of the —O—S—O stretching vibration of the sulfate (SO42-) ion. The pine wood spectrum 4502 comprises of bands due to its main constituents—cellulose, lignin and water. The valleys at 1450 nm, 1920 nm and 2860 nm are attributed to water. The dip at 2100 nm is due to the first overtone of the C—O asymmetric stretch, the one at 2270 nm due to the combination band of O—H and C—H, and the one at 2490 nm due to combination band of C—H and C—O. Finally, the broad feature around 3450 nm is due to the C—H stretching vibration. The ammonium nitrate (NH4NO3) spectrum 4503 has three prominent features in the near-IR region. The dip at 1270 nm is due to the combination of N—H stretching and N—H bending vibrations, while the dip at 1570 nm is due to the first overtone of N—H stretch. The doublet at 2050 nm and 2140 nm is possibly due to the second overtone of the N—H bending vibrations, while the fundamental N—H stretch appears as a broad feature around 3000 nm. Urea (NH2)2CO 4504 has two amide (—NH2) groups joined by a carbonyl (C═O) functional group. The absorption line at 1490 nm occurs due to the third overtone of the C═O stretching vibration while the line at 1990 nm is due to the second overtone of the same.

Figure 45B:
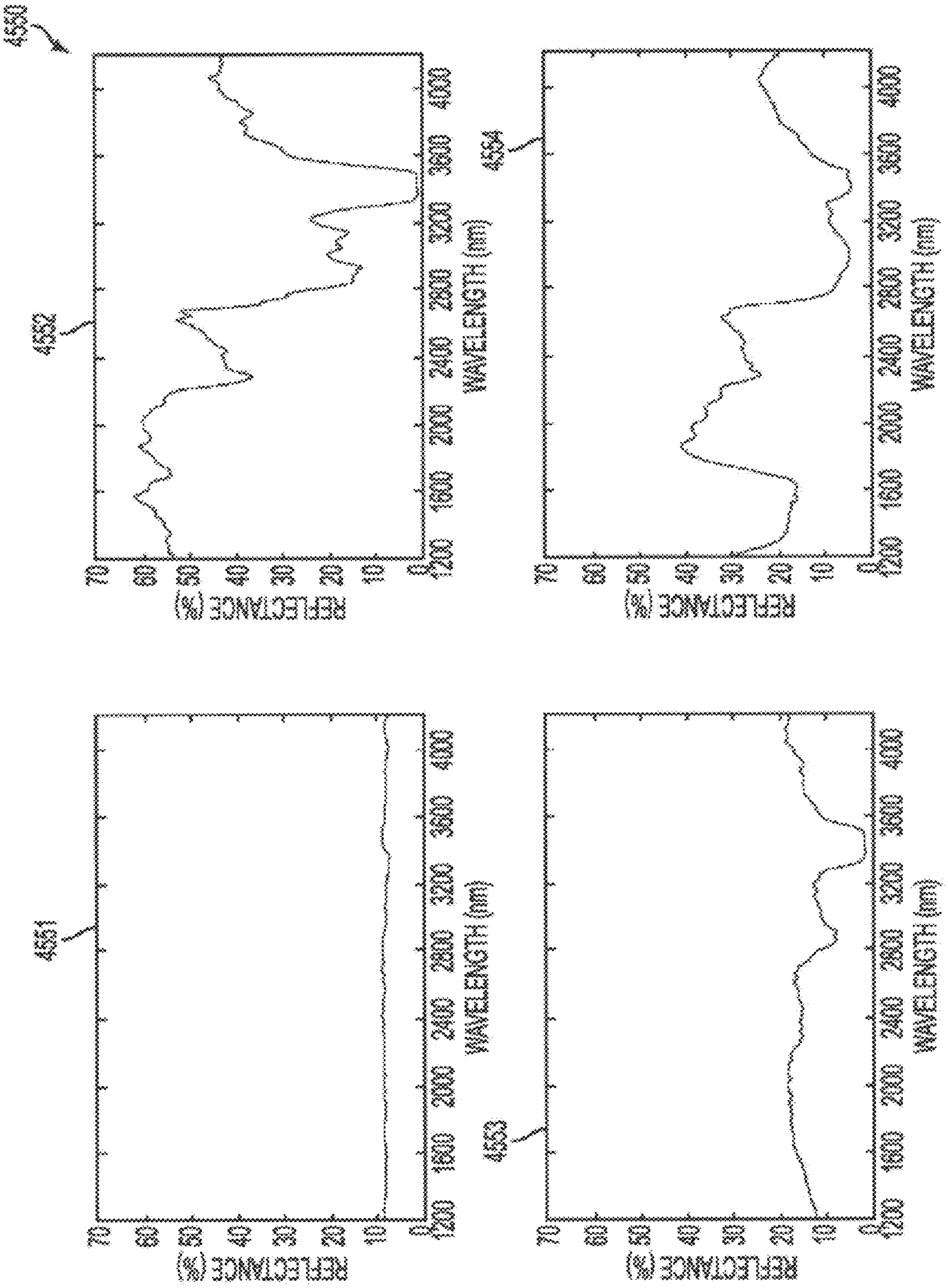
FIG. 45B illustrates the reflection spectra for three commercial automotive paints and military grade CARC paint (chemical agent resistant coating) (reflectance in this case are in arbitrary units).

FIG. 45B shows the reflection spectra 4550 for three commercial automotive paints 4551, 4552, 4553 and military grade CARC (chemical agent resistant coating) paint 4554. The paints consist of a complex mixture of many different chemicals, and, hence, it is very difficult to identify individual absorption lines. Since all four paints contain a variety of organic compounds, features are observed between 3200-3500 nm from the C—H stretch and from 2200-2600 nm due to the C—H stretch and C—H bond combination band. However, the primary difference between the automotive 45451, 4552, 4553 and CARC paint 4554 is the presence of a strong dip between 1200-1850 nm in the latter, which might be attributed to the absorption from Cobalt chromite—a green pigment found in CARC-green.

Figure 46:
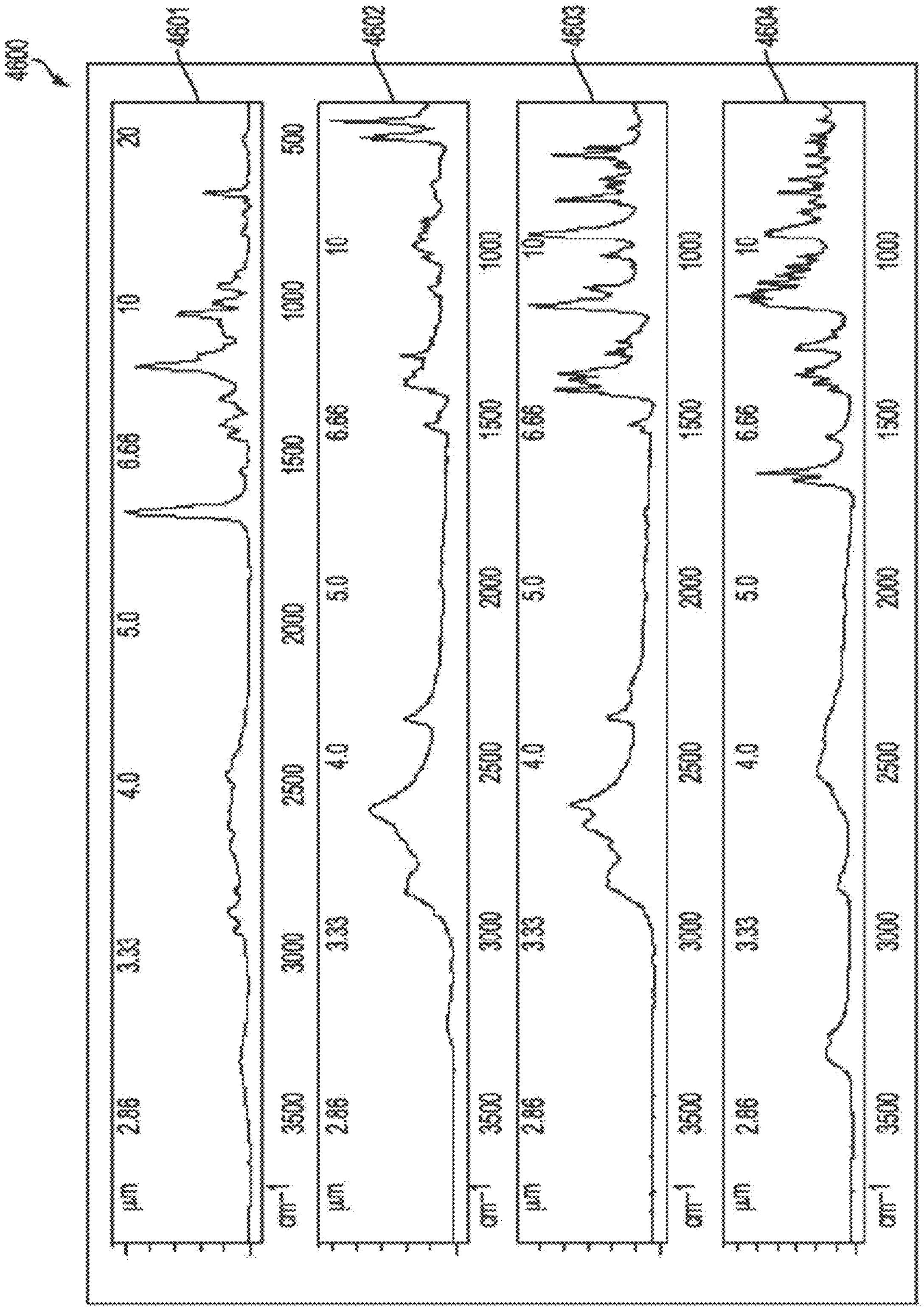
FIG. 46 shows the mid-wave infrared and long-wave infrared absorption spectra for various illicit drugs. It is expected that overtone and combination bands should be evident in the SWIR and near-infrared wavelength bands.

Thus, FIGS. 44 and 45 show that various materials, including explosives, fertilizers, vegetation, and paints have features in the near-infrared and SWIR that can be used to identify the various samples. Although stronger features are found in the mid-infrared, the near-infrared may be easier to measure due to higher quality detection systems, more mature fiber optics and light sources, and transmission through atmospheric transmission windows. Because of these distinct spectral signatures, these materials could also be detected using active remote sensing or hyper-spectral imaging, as described in this disclosure. These are just particular samples that have been tested at stand-off distances, but other materials and samples may also be identified using the SWIR remote sensing or hyper-spectral imaging methods, and these samples are also intended to be covered within this disclosure. As just another example, illicit drugs may be detectable using remote sensing or hyper-spectral imaging. FIG. 46 shows the mid-wave infrared and long-wave infrared absorption spectra 1500 for various illicit drugs. The absorbance for cocaine 4601, methamphetamine 4602, MDMA (ecstasy) 4603, and heroin 4604 are plotted versus wavelength from approximately 2.5-20 microns. Although the fundamental resonances for these drugs may lie in the longer wavelength regions, there are corresponding overtones and combination bands in the SWIR and near-infrared wavelength range. Therefore, the active remote sensing or hyper-spectral imaging techniques described herein may also be applicable to detecting illicit drugs from aircraft, vehicles, or hand held devices.

Detection Systems

As discussed earlier, the active remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, the variations due to sunlight and time-of-day may be factored out. The effects of the weather, such as clouds and rain, might also be reduced. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In an alternate embodiment, change detection schemes may be used, where the detection system captures the signal with the light source on and with the light source off. Again, for this system the light source may be modulated. Then, the signal with and without the light source is differenced. This may enable the sun light changes to be subtracted out. In addition, change detection may help to identify objects that change in the field of view. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 47A:
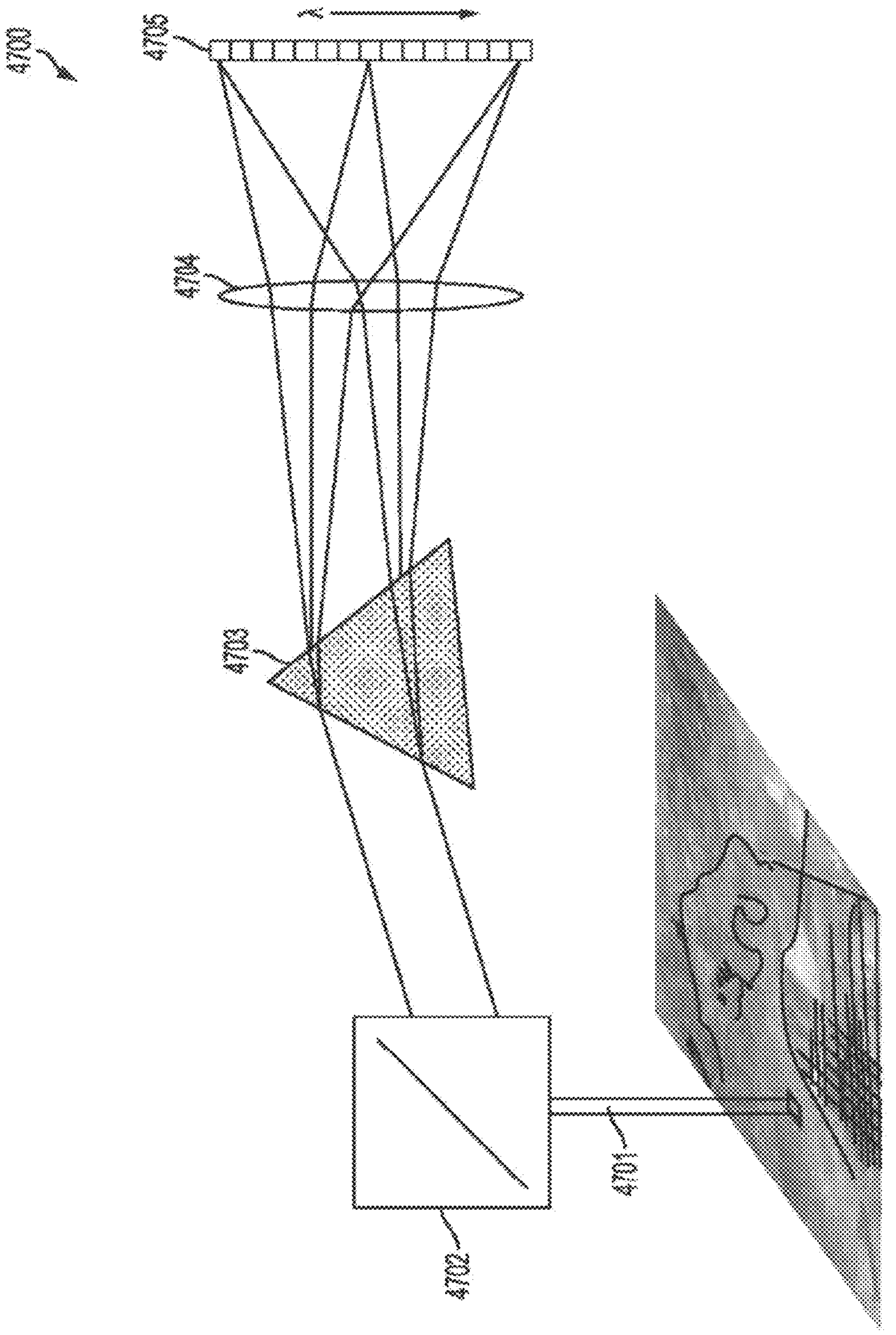
FIG. 47A is a schematic diagram of the basic elements of an imaging spectrometer.

In another embodiment, an imaging spectrometer may be used to detect the light received from the sample. For example, FIG. 47A shows a schematic diagram 4700 of the basic elements of an imaging spectrometer. The input light 4701 from the sample may first be directed by a scanning mirror and/or other optics 4702. An optical dispersing element 4703, such as a grating or prism, in the spectrometer may split the light into many narrow, adjacent wavelength bands, which may then be passed through imaging optics 4704 onto one or more detectors or detector arrays 4705. Some sensors may use multiple detector arrays to measure hundreds of narrow wavelength bands.

Figure 47B:
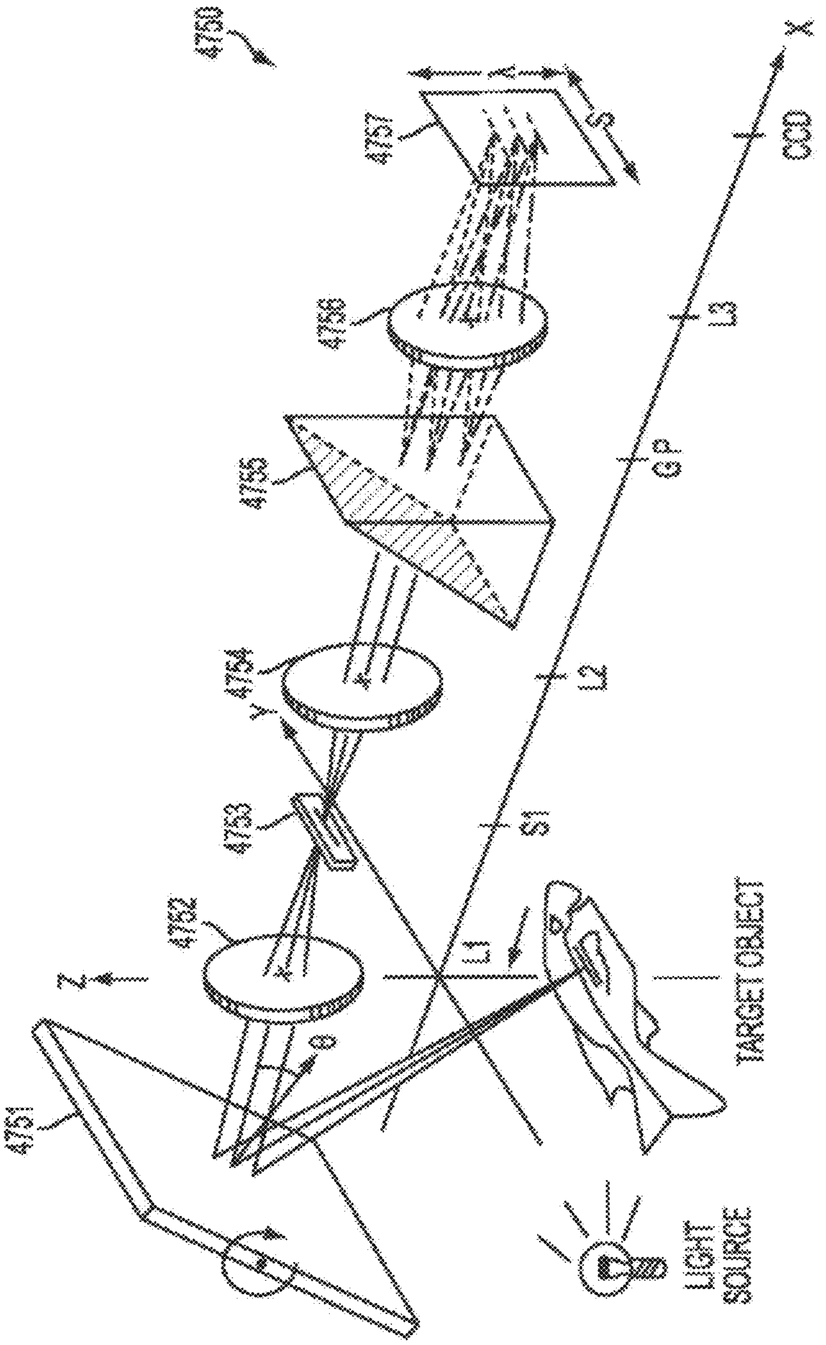
FIG. 47B illustrates one example of a typical imaging spectrometer used in hyper-spectral imaging systems.

An example of a typical imaging spectrometer 4750 used in hyper-spectral imaging systems is illustrated in FIG. 47B. In this particular embodiment, the input light may be directed first by a tunable mirror 4751. A front lens 4752 may be placed before the entrance slit 4753 and the collector lens 4754. In this embodiment, the dispersing element is a holographic grating with a prism 4755, which separates the different wavelength bands. Then, a camera lens 4756 may be used to image the wavelengths onto a detector or camera 4757.

FIGS. 47A and 47B provide particular examples, but some of the elements may not be used, or other elements may be added, and these embodiments are also intended to be covered by this disclosure. For instance, a scanning spectrometer may be used before the detector, where a grating or dispersive element is scanned to vary the wavelength being measured by the detector. In yet another embodiment, filters may be used before one or more detectors to select the wavelengths or wavelength bands to be measured. This may be particularly useful if only a few bands or wavelengths are to be measured. The filters may be dielectric filters, Fabry-Perot filters, absorption or reflection filters, fiber gratings, or any other wavelength selective filter. In an alternate embodiment, a wavelength division multiplexer, WDM, may be used followed by one or more detectors or detector arrays. One example of a planar wavelength division multiplexer may be a waveguide grating router or an arrayed waveguide grating. The WDM may be fiber coupled, and detectors may be placed directly at the output or the detectors may be coupled through fibers to the WDM. Some of these components may also be combined with the configurations in FIGS. 47A and 47B.

Figure 48:
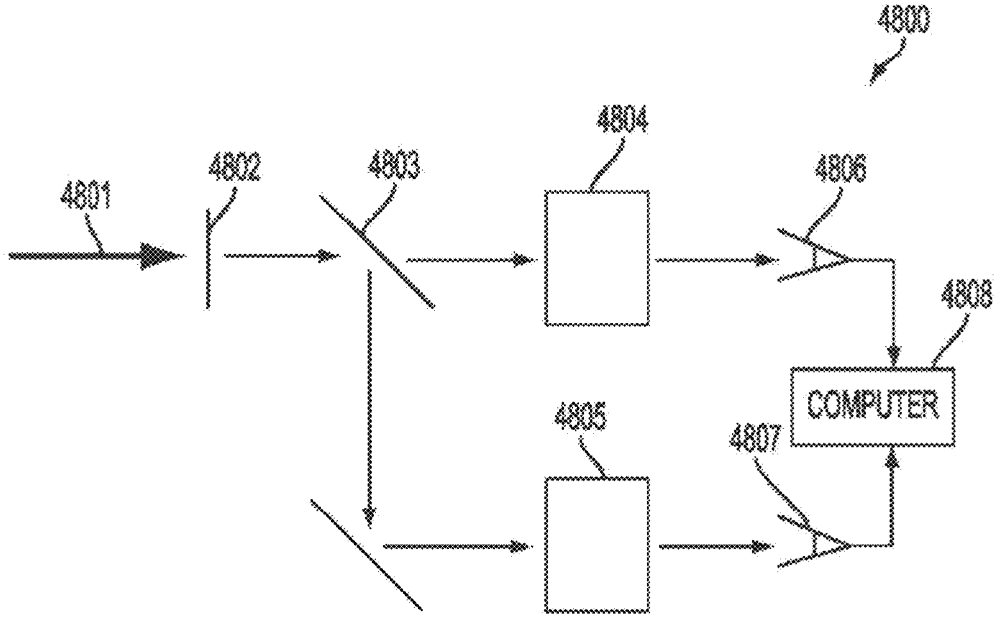
FIG. 48 shows one example of a gas-filter correlation radiometer, which is a detection system that uses a sample of the gas of interest as a spectral filter for the gas.

While the above detection systems could be categorized as single path detection systems, it may be advantageous in some cases to use multi-path detection systems. In one embodiment, when the aim is to measure particular gases or material (rather than identify out of a library of materials), it may advantageous to use gas-filter correlation radiometry (GFCR), such as 4800 in FIG. 48. A GFCR is a detection system that uses a sample of the gas of interest as a spectral filter for the gas. As shown in FIG. 48, the incoming radiation 4801 may first be passed through a narrow band pass filter 4802. The beam may then be split by a beam splitter 4803 along two paths; one path comprising a gas cell filled with the gas of interest 4804 (known as the correlation cell) and the other path comprising no gas 4805. The light from each path may then be measured using two detectors 4806, 4807, and the signals may then be analyzed 4808. The difference in the transmission along the two paths may correspond primarily to the absorption of the gas along the correlation cell path. This GFCR configuration may be advantageous, for example, in the detection of natural gas. Since the goal is to measure methane and ethane, the correlation cells may contain these gases, either in combination or separately. Although a particular configuration for the GFCR has been described, variations of this configuration as well as addition of other components may also be used and are intended to be covered by this disclosure. For example, collection optics and lenses may be used with this configuration, and various modulation techniques may also be used to increase the signal to noise ratio.

Figure 49:
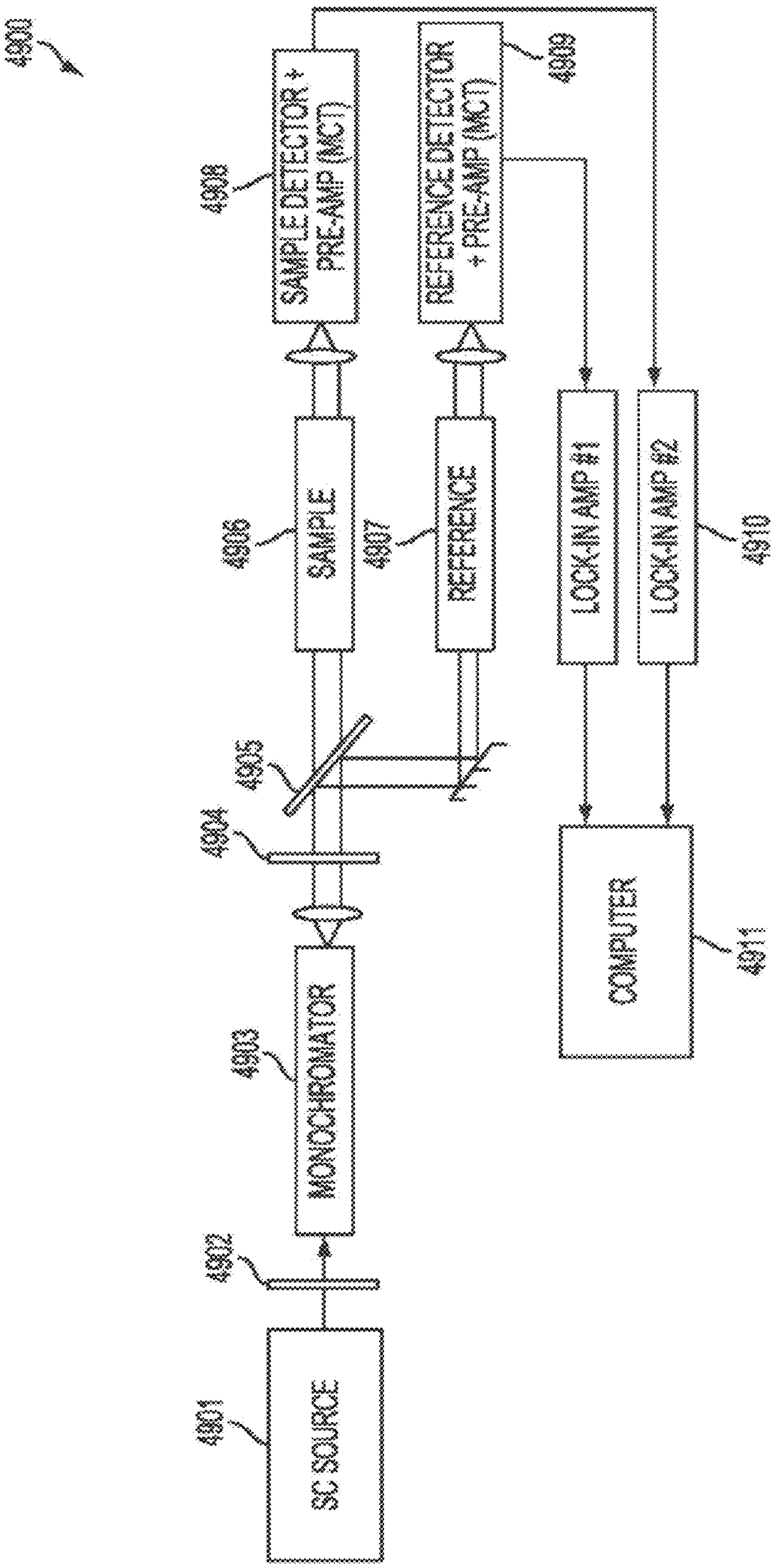
FIG. 49 exemplifies a dual-beam experimental set-up that may be used to subtract out (or at least minimize the adverse effects of) light source fluctuations.

In yet another example of multi-beam detection systems, a dual-beam set-up 4900 such as in FIG. 49 may be used to subtract out (or at least minimize the adverse effects of) light source fluctuations. In one embodiment, the output from an SC source 4901 may be collimated using a calcium fluoride (CaF2) lens 4902 and then focused into the entrance slit of the monochromator 4903. At the exit slit, light at the selected wavelength is collimated again and may be passed through a polarizer 4904 before being incident on a calcium fluoride beam splitter 4905. After passing through the beam splitter 4905, the light is split into a sample 4906 and reference 4907 arm to enable ratiometric detection that may cancel out effects of intensity fluctuations in the SC source 4901. The light in the sample arm 4906 passes through the sample of interest and is then focused onto a HgCdTe detector 4908 connected to a pre-amp. A chopper 4902 and lock-in amplifier 4910 setup enable low noise detection of the sample arm signal. The light in the reference arm 4907 passes through an empty container (cuvette, gas cell etc.) of the same kind as used in the sample arm. A substantially identical detector 4909, pre-amp and lock-in amplifier 4910 is used for detection of the reference arm signal. The signal may then be analyzed using a computer system 4911. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as illustrated in the representative embodiment of FIG. 49 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Described herein are just some examples of the beneficial use of near-infrared or SWIR lasers for active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the active remote sensing or hyper-spectral imagery would also have a location tag on the data. Moreover, the active remote sensing or hyper-spectral imaging information could also be combined with two-dimensional or three-dimensional images to provide a physical picture as well as a chemical composition identification of the materials. These are just some modifications of the active remote sensing or hyper-spectral imaging system described in this disclosure, but other techniques may also be added or combinations of these techniques may be added, and these are also intended to be covered by this disclosure.

Section 4: Short-Wave Infrared Super-Continuum Lasers for Detecting Counterfeit or Illicit Drugs and Pharmaceutical Process Control One advantage of optical systems is that they can perform non-contact, stand-off or remote sensing distance spectroscopy of various materials. As an example, optical systems can be used for identification of counterfeit drugs, detection of illicit drugs, or process control in the pharmaceutical industry, especially when the sensing is to be done at remote or stand-off distances in a non-contact, rapid manner. In general, the near-infrared region of the electromagnetic spectrum covers between approximately 0.7 microns (700 nm) to about 2.5 microns (2500 nm). However, it may also be advantageous to use just the short-wave infrared (SWIR) between approximately 1.4 microns (1400 nm) and about 2.5 microns (2500 nm). One reason for preferring the SWIR over the entire NIR may be to operate in the so-called "eye safe" window, which corresponds to wavelengths longer than about 1400 nm. Therefore, for the remainder of the disclosure the SWIR will be used for illustrative purposes. However, it should be clear that the discussion that follows could also apply to using the near infrared—NIR—wavelength range, or other wavelength bands.

In particular, wavelengths in the eye safe window may not transmit down to the retina of the eye, and therefore, these wavelengths may be less likely to create permanent eye damage from inadvertent exposure. The near-infrared wavelengths have the potential to be dangerous, because the eye cannot see the wavelengths (as it can in the visible), yet they can penetrate and cause damage to the eye. Even if a practitioner is not looking directly at the laser beam, the practitioner's eyes may receive stray light from a reflection or scattering some surface. Hence, it can always be a good practice to use eye protection when working around lasers. Since wavelengths longer than about 1400 nm are substantially not transmitted to the retina or substantially absorbed in the retina, this wavelength range is known as the eye safe window. For wavelengths longer than 1400 nm, in general only the cornea of the eye may receive or absorb the light radiation.

The SWIR wavelength range may be particularly valuable for identifying materials based on their chemical composition because the wavelength range comprises overtones and combination bands for numerous chemical bonds. For example, in the SWIR numerous hydro-carbon chemical compounds have overtone and combinational bands, along with oxygen-hydrogen and carbon-oxygen compounds. Thus, gases, liquids and solids that comprise these chemical compounds may exhibit spectral features in the SWIR wavelength range. In a particular embodiment, the spectra of organic compounds may be dominated by the C—H stretch. The C—H stretch fundamental occurs near 3.4 microns, the first overtone is near 1.7 microns, and a combination band occurs near 2.3 microns.

One embodiment of remote sensing that is used to identify and classify various materials is so-called "hyper-spectral imaging." Hyper-spectral sensors may collect information as a set of images, where each image represents a range of wavelengths over a spectral band. Hyper-spectral imaging may deal with imaging narrow spectral bands over an approximately continuous spectral range. As an example, in hyper-spectral imaging a lamp may be used as the light source. However, the incoherent light from a lamp may spatially diffract rapidly, thereby making it difficult to perform spectroscopy at stand-off distances or remote distances. Therefore, it would be advantageous to have a broadband light source covering the SWIR that may be used in place of a lamp to identify or classify materials in remote sensing or stand-off detection applications.

As used throughout this document, the term "couple" and or "coupled" refers to any direct or indirect communication between two or more elements, whether or not those elements are physically connected to one another. As used throughout this disclosure, the term "spectroscopy" means that a tissue or sample is inspected by comparing different features, such as wavelength (or frequency), spatial location, transmission, absorption, reflectivity, scattering, fluorescence, refractive index, or opacity. In one embodiment, "spectroscopy" may mean that the wavelength of the light source is varied, and the transmission, absorption, fluorescence, or reflectivity of the tissue or sample is measured as a function of wavelength. In another embodiment, "spectroscopy" may mean that the wavelength dependence of the transmission, absorption, fluorescence or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the mid-infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam is coupled to a gain medium to excite the gain medium, which in turn may amplify another input optical signal or beam. In one particular example, the gain medium may be a doped fiber, such as a fiber doped with ytterbium, erbium and/or thulium. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and or "supercontinuum" and or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, parametric amplification, the Raman effect, modulational instability, and self-phase modulation.

As used throughout this disclosure, the terms "optical light" and or "optical beam" and or "light beam" refer to photons or light transmitted to a particular location in space. The "optical light" and or "optical beam" and or "light beam" may be modulated or unmodulated, which also means that they may or may not contain information. In one embodiment, the "optical light" and or "optical beam" and or "light beam" may originate from a fiber, a fiber laser, a laser, a light emitting diode, a lamp, a pump laser, or a light source.

As used throughout this disclosure, the term "remote sensing" may include the measuring of properties of an object from a distance, without physically sampling the object, for example by detection of the interactions of the object with an electromagnetic field. In one embodiment, the electromagnetic field may be in the optical wavelength range, including the infrared or SWIR. One particular form of remote sensing may be stand-off detection, which may range exemplary from non-contact up to hundreds of meters away.

Identification of Counterfeit Drugs

Pharmaceutical counterfeiting is a growing and significant issue for the healthcare community as well as the pharmaceutical industry worldwide. As a result of counterfeiting, users may be threatened by substandard drug quality or harmful ingredients, and legitimate companies may lose significant revenues. The definition for "counterfeit drug" by the World Health Organization was as follows: "A counterfeit medicine is one which is deliberately and fraudulently mislabeled with respect to identity and/or source. Counterfeiting can apply to both branded and generic products and counterfeit products may include products with the correct ingredients or with the wrong ingredients, without active ingredients, with insufficient active ingredient or with fake packaging." Later this definition was slightly modified, "Counterfeiting in relation to medicinal products means the deliberate and fraudulent mislabeling with respect to the identity, composition and/or source of a finished medicinal product, or ingredient for the preparation of a medicinal product."

A rapid screening technique such as near-infrared or SWIR spectroscopy could aid in the search for and identification of counterfeit drugs. In particular, using a non-lamp based light source could lead to contact-free control and analysis of drugs. In a particular embodiment, remote sensing, stand-off detection, or hyper-spectral imaging may be used for process control or counterfeit drug identification in a factory or manufacturing setting, or in a retail, wholesale, or warehouse setting. In one embodiment, the light source for remote sensing may direct the light beam toward the region of interest (e.g., conveyor belt, stocking shelves, boxes or cartons, etc), and the diffuse reflected light may then be measured using a detection system. Various kinds of SWIR light sources will be discussed later in this disclosure. The detection system may comprise, in one embodiment, a spectrometer followed by one or more detectors. In another embodiment, the detection system may be a dispersive element (examples include prisms, gratings, or other wavelength separators) followed by one or more detectors or detector arrays. In yet another embodiment, the detection system may comprise a Fourier transform infrared spectrometer. These are merely specific examples of the detection system, but combinations of these or other detection systems may also be used and are contemplated within the scope of this disclosure.

For monitoring drugs, the SWIR light source and the detection system could be used in transmission, reflection, fluorescence, or diffuse reflection. Also, different system configurations may also be used and are included in the scope of this disclosure. For example, the light source and detection system may be placed in a fixed location, and for reflection the light source and detectors may be close to one another, while for transmission the light source and detectors may be at different locations. The region of interest may be surveyed, and the light beam may also be scanned to cover an area larger than the light source beam. In yet another embodiment, the system could be placed on a vehicle such as an automobile or a truck, or the light source could be placed on one vehicle, while the detection system is on another vehicle. If the light source and detection system are compact and lightweight, they might even be carried by a person in the field, either in their hands or in a backpack.

Figure 50:
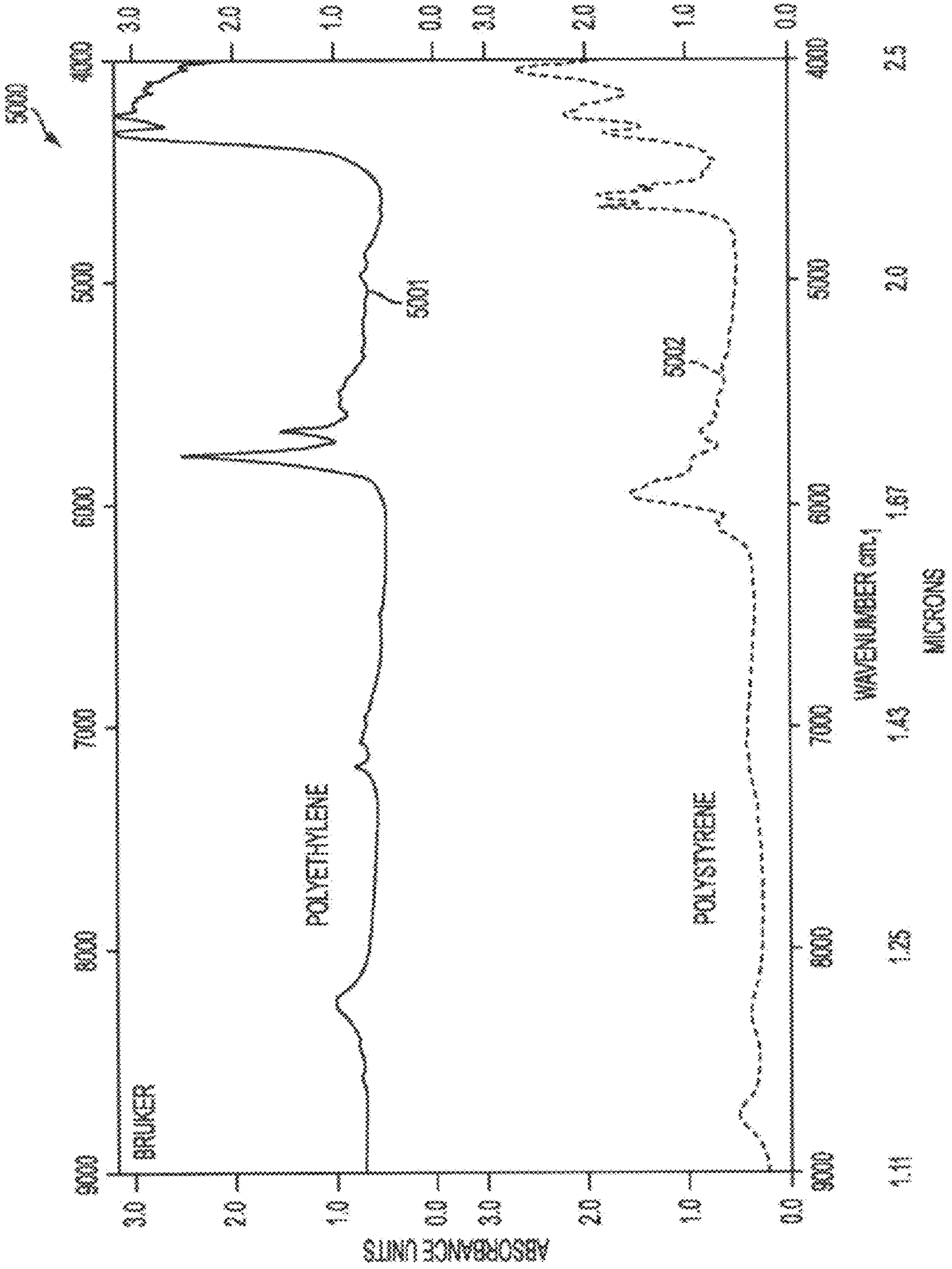
FIG. 50 shows the absorbance for two common plastics, polyethylene and polystyrene.

Another advantage of using the near-infrared or SWIR is that most drug packaging materials are at least partially transparent in this wavelength range, so that drug compositions may be detected and identified through the packaging non-destructively. As an example, SWIR light could be used to see through plastics, since the signature for plastics can be subtracted off and there are large wavelength windows where the plastics are transparent. FIG. 50 illustrates the absorbance 5000 for two common plastics: polyethylene 5001 and polystyrene 5002. Because of the hydro-carbon bonds, there are absorption features near 1.7 microns and 2.2-2.5 microns. In general, the absorption bands in the near infrared are due to overtones and combination bands for various functional group vibrations, including signals from C—H, O—H, C═O, N—H, —COOH, and aromatic C—H groups. It may be difficult to assign an absorption band to a specific functional group due to overlapping of several combinations and overtones. However, with advancements in computational power and chemometrics or multivariate analysis methods, complex systems may be better analyzed. In one embodiment, using software analysis tools the absorption spectrum may be converted to its second derivative equivalent. The spectral differences may permit a fast, accurate, non-destructive and reliable identification of materials. Although particular derivatives are discussed, other mathematical manipulations may be used in the analysis, and these other techniques are also intended to be covered by this disclosure.

Spectroscopy in the near-infrared or SWIR may be sensitive to both the chemical and physical nature of the sample composition and may be performed rapidly with minimal sample preparation. For example, near-infrared or SWIR spectroscopy may be used to study the homogeneity of powder samples, particle size determinations, product composition, the determination of the concentrations and distribution of components in solid tablets and content uniformity, among other applications. In yet other embodiments, applications include tablet identification, determination of moisture, residual solvents, active ingredient potency, the study of blending operations, and the detection of capsule tampering.

Figure 51:
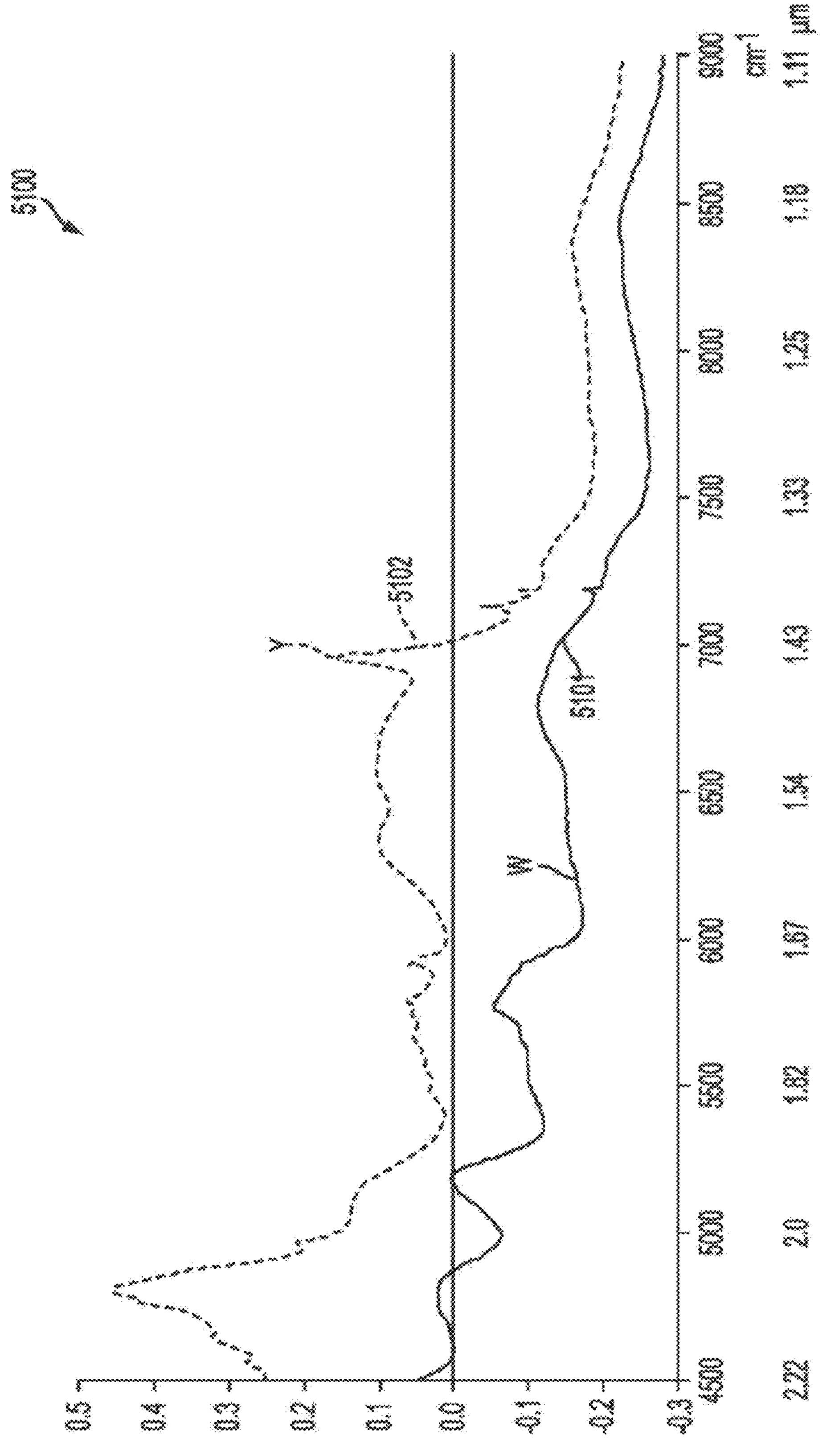
FIG. 51 illustrates one example of the difference in near-infrared spectrum between an authentic tablet and a counterfeit tablet.

FIG. 51 illustrates one example of the difference in near-infrared spectrum 5100 between an authentic tablet and a counterfeit tablet. Two grades of film coated tablets comprising drugs were investigated: curve 5101 is the genuine drug, while 5102 is a counterfeit drug. These two grades of capsules have noticeably different contents, and the differences are apparent in the near-infrared or SWIR spectra. In some cases the differences may not be as distinct. For these cases, more signal processing may be necessary to distinguish between samples.

Figure 52:
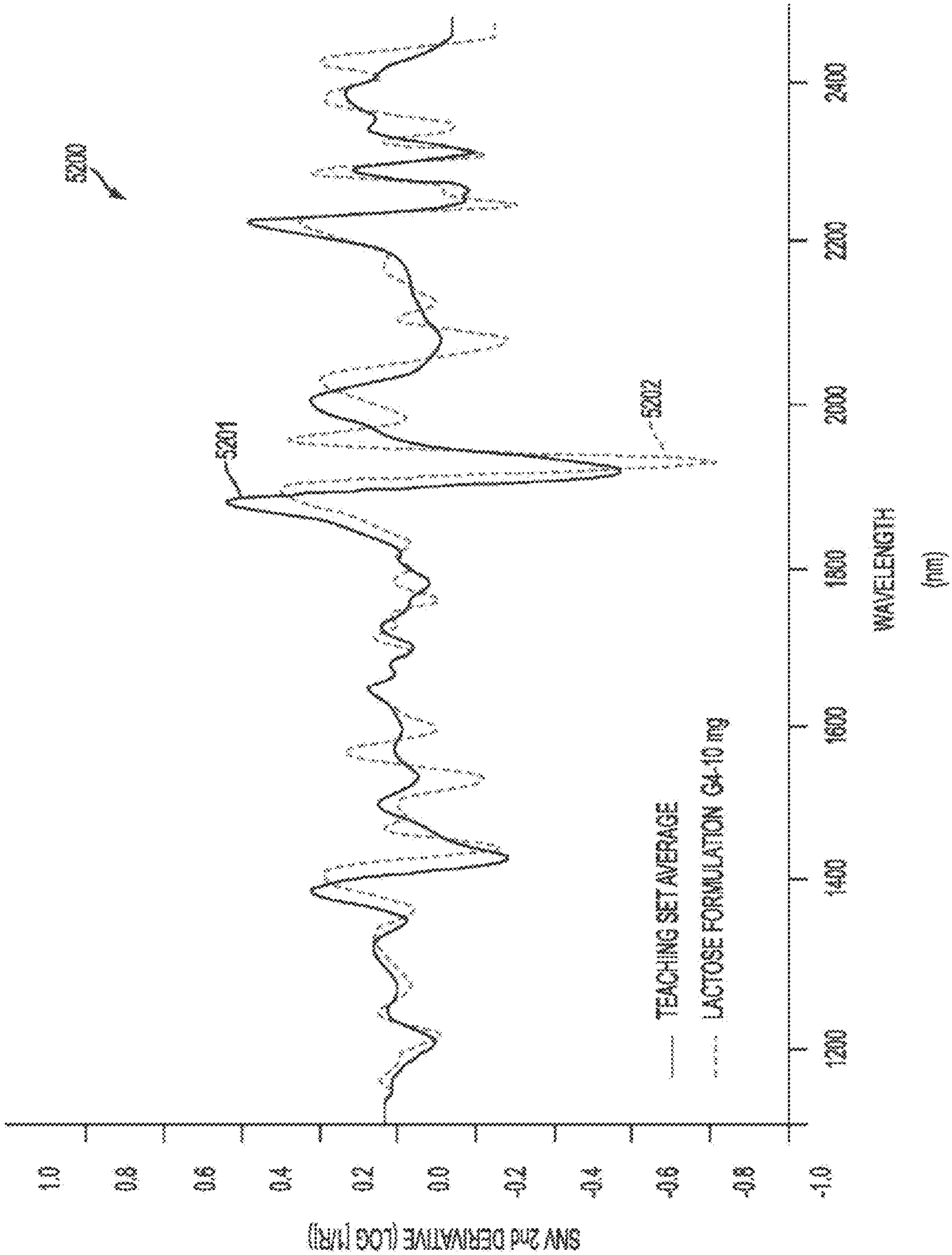
FIG. 52 shows the second derivative of the spectral comparison of Prozac and a similarly formulated generic.

In another embodiment, it may be advantageous to take a first, second or higher order derivative to elucidate the difference between real and counterfeit drugs. For example, FIG. 52 shows the second derivative 5200 of the spectral comparison of Prozac 5201 and a similarly formulated generic 5202, which had a fluoxetine hydrochloride (10 mg). Although the reflectance curves from the two samples are close and, therefore, difficult to distinguish, the second derivative of the data helps to bring out the differences more clearly. Although a second derivative is used in this example, any number of signal processing algorithms and methods may be used, and these are also intended to be covered by this disclosure. For example, partial least square algorithms, multivariate data analysis, principal component analysis, or chemometric software may be implemented without departing from the scope of this disclosure.

In yet another embodiment, near-infrared or SWIR spectroscopy may be used to measure and calibrate various pharmaceutical formulations based on the active pharmaceutical ingredients and excipients. An excipient may be a pharmacologically inactive substance used as a carrier for the active ingredients of a medication. In some cases, the active substance may not be easily administered and/or absorbed by the human body; in such cases the active ingredient may be dissolved into or mixed with an excipient. Also, excipients are also sometimes used to bulk up formulations that contain very potent active ingredients, to allow for convenient and accurate dosage. In addition to their use in the single-dosage quantity, excipients can be used in the manufacturing process to aid in the handling of the active substance concerned.

Figure 53:
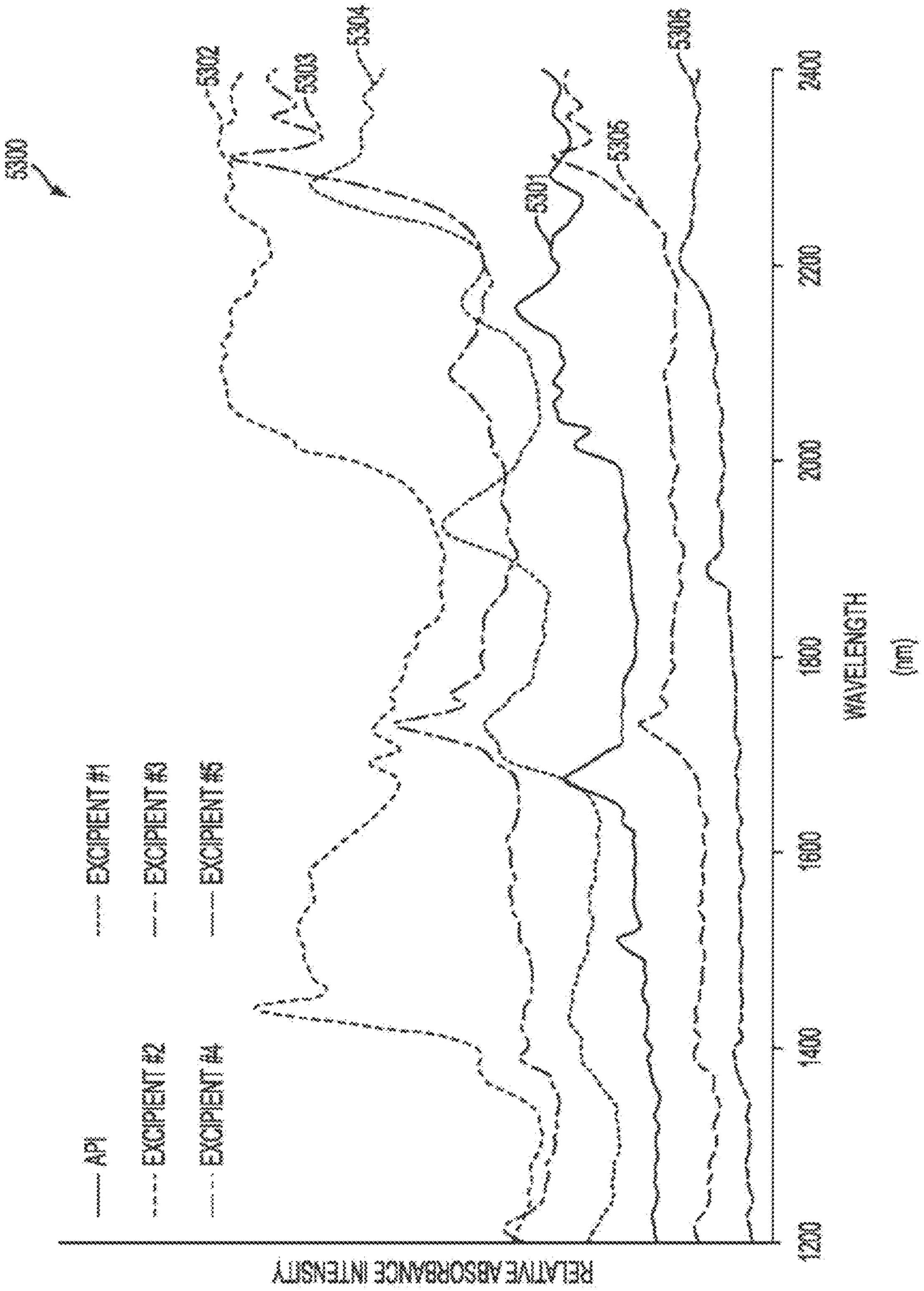
FIG. 53 illustrates an example of the near infrared spectra for different pure components of a studied drug.

FIG. 53 shows an example of the near-infrared spectra 5300 for different pure components of a studied drug. The spectrum for the active pharmaceutical ingredient (API) 5301 is plotted, along with the spectra for five different excipients 5302, 5303, 5304, 5305 and 5306. Each spectrum has been baseline shifted to avoid overlapping. The near-infrared spectra have been obtained by averaging the spectra of each pixel of an area of a hyper-spectral image. As FIG. 53 shows, each of the chemical compositions have a distinct spectrum, and the composition of a drug may be decomposed into its constitutive ingredients. These are just some examples of how near-infrared or SWIR spectroscopy may be applied to counterfeit drug detection, but other methods and analysis techniques may also be used without departing from the scope of this disclosure. As one other example, once the active pharmaceutical ingredient and the excipients spectral distribution of a drug formulation are understood, feedback may be provided of this information to the drug development stages.

Rapid Screening for Illicit Drugs

Figure 54:
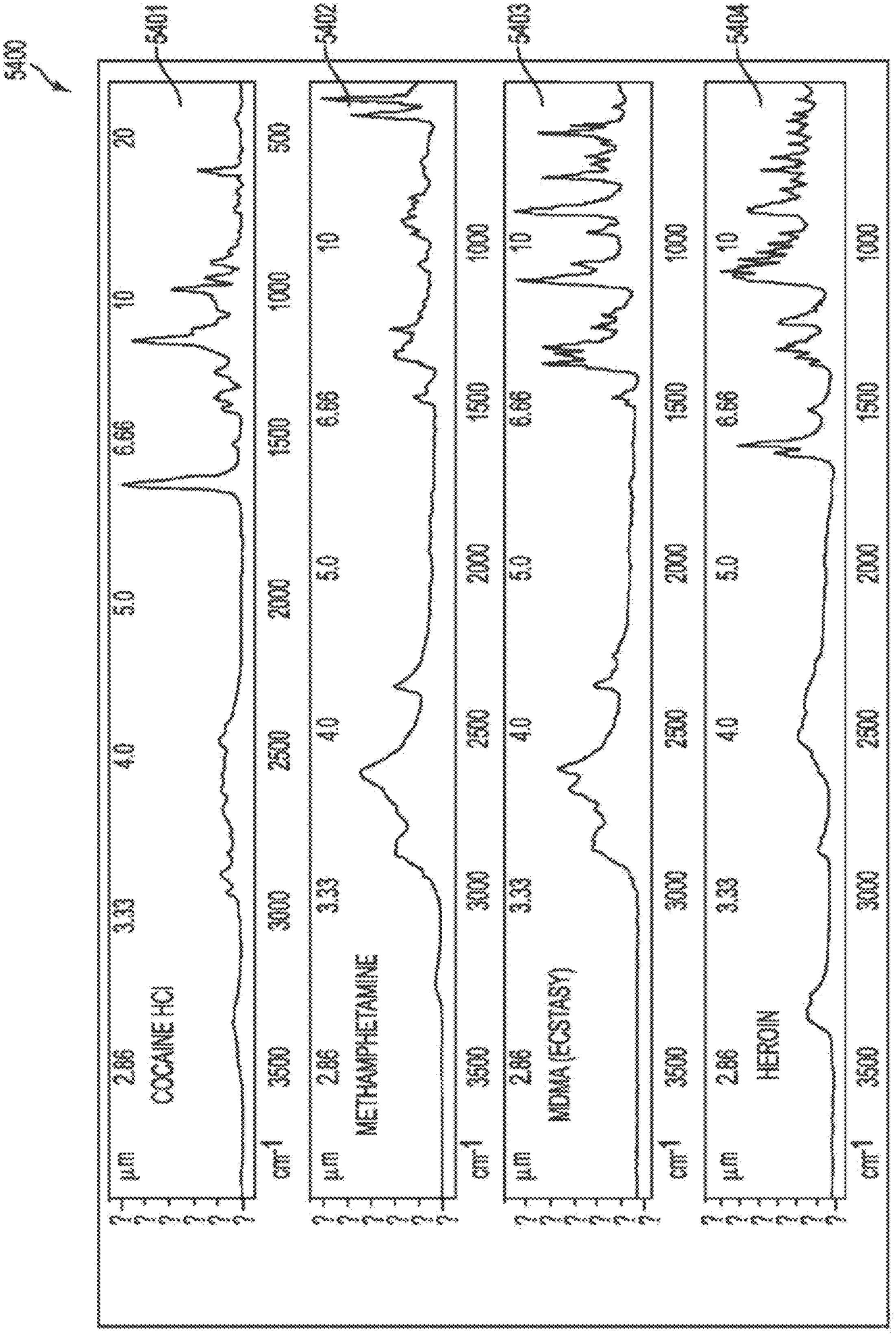
FIG. 54 shows the mid-wave infrared and long-wave infrared absorption spectra for various illicit drugs.

Thus, FIGS. 51-53 show that near-infrared or SWIR spectroscopy may be used to identify counterfeit drugs. More generally, various materials including illicit drugs, explosives, fertilizers, vegetation, and paints have features in the near-infrared and SWIR that can be used to identify the various samples, and these applications are also intended to be within the scope of this disclosure. Although stronger features may be found in the mid-infrared, the near-infrared may be easier to measure due to higher quality detection systems, more mature fiber optics and light sources, and transmission through atmospheric transmission windows. Because of these distinct spectral signatures, these materials could also be detected using active remote sensing, hyper-spectral imaging, or near-infrared or SWIR spectroscopy. As just another example, illicit drugs may be detectable using remote sensing, hyper-spectral imaging, or near-infrared spectroscopy. FIG. 54 shows the mid-wave infrared and long-wave infrared absorption spectra 5400 for various illicit drugs. The absorbance for cocaine 5401, methamphetamine 5402, MDMA (ecstasy) 5403, and heroin 5404 are plotted versus wavelength from approximately 2.5-20 microns. Although the fundamental resonances for these drugs may lie in the longer wavelength regions, there are corresponding overtones and combination bands in the SWIR and near-infrared wavelength range. Therefore, the active remote sensing, hyper-spectral imaging, or near-infrared or SWIR spectroscopy techniques described herein may also be applicable to detecting illicit drugs from aircraft, vehicles, or hand held devices.

Figure 55:
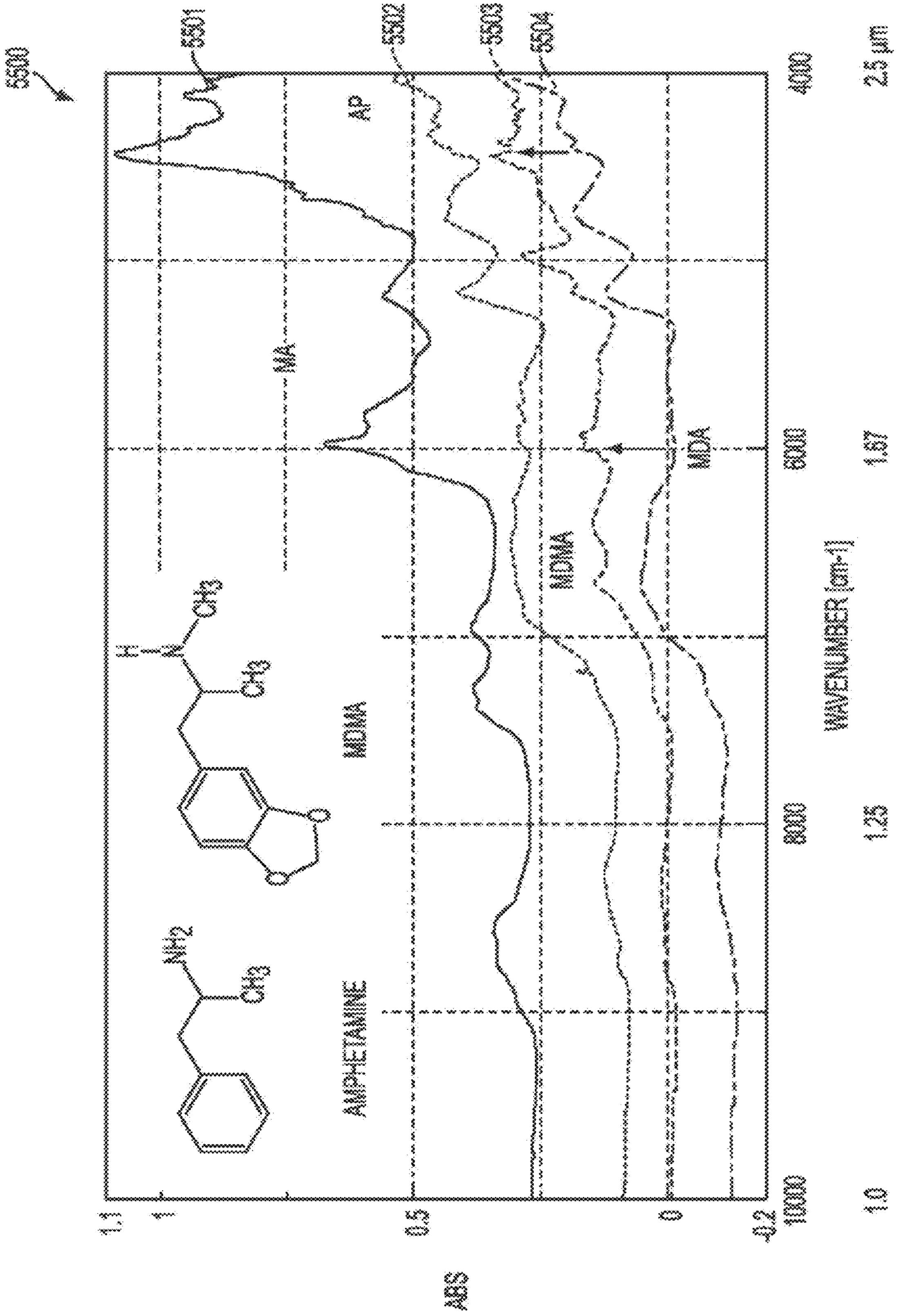
FIG. 55 shows the absorbance versus wavelength in the near-infrared region for four classes of illegal drugs.

The diffuse reflectance technique may be useful with near-infrared or SWIR spectroscopy for rapid identification of illegal drugs due to simple handling and simple use of a search data library created using near-infrared diffuse reflectance. For instance, FIG. 55 illustrates the absorbance 5500 versus wavelength in the near-infrared region for four classes of illegal drugs. In particular, the spectra are shown for methamphetamine (MA) 5501, amphetamine (AP) 5502, MDMA (street name: ecstasy) 5503, and MDA (street name: the love drug) 5504. Each of the illegal drugs have unique spectral features in the near-infrared and SWIR. Also, comparing the mid-infrared spectrum for MDMA (5403 in FIG. 54) with the near-infrared spectrum for MDMA (5503 in FIG. 55), it seems clear that the near-infrared region shows overtones and combination bands that should be discernible. Referring to FIG. 55, sample identification may be accomplished by using the region (indicated by the arrows) where the spectral absorptions may provide specific peaks depending on the drug component.

Figure 56:
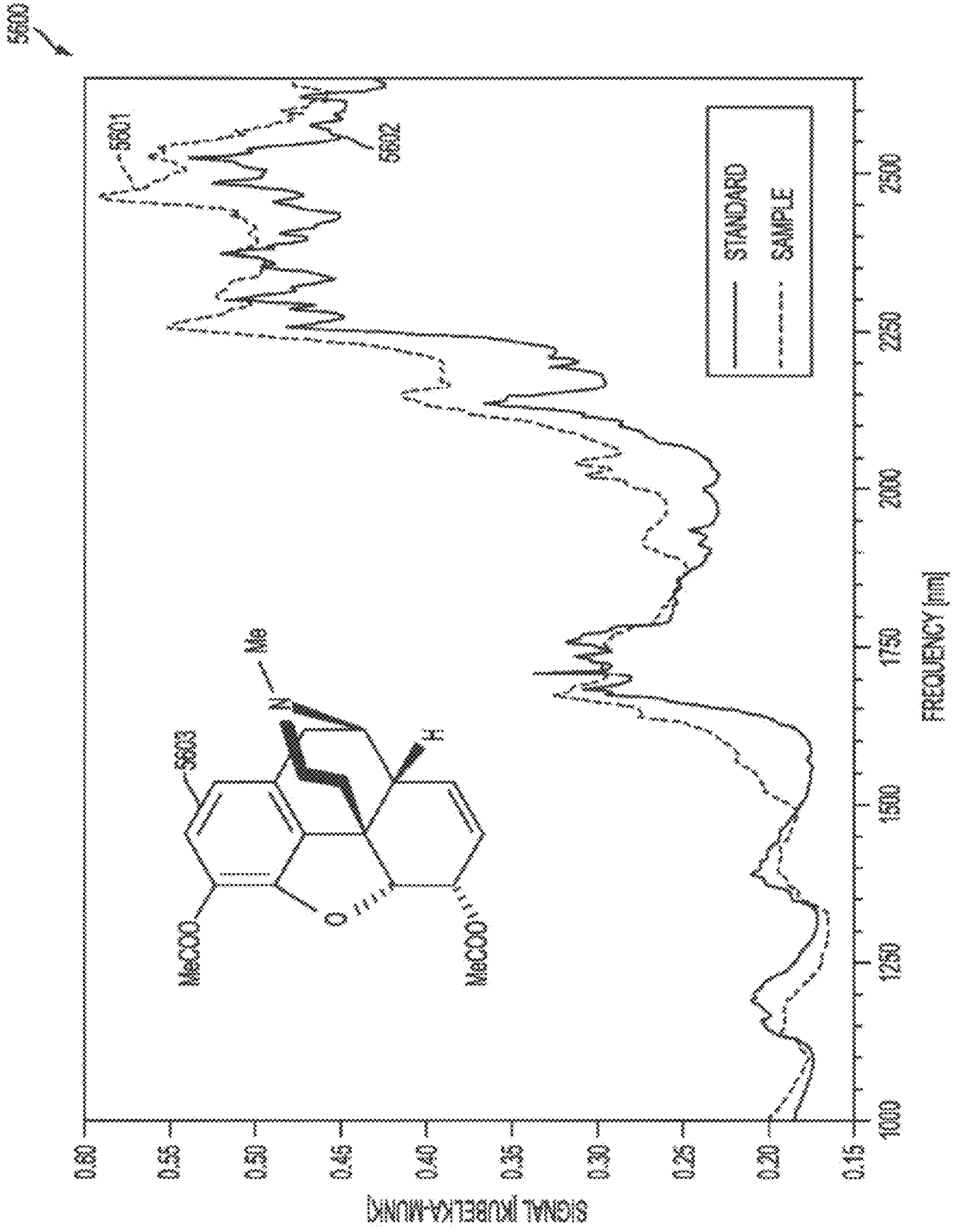
FIG. 56 illustrates the diffuse reflectance near-infrared spectrum of heroin samples.

In another embodiment, FIG. 56 shows the diffuse reflectance near-infrared spectrum 5600 of heroin samples. Heroin, the 3,6-diacetyl derivative of morphine (hence diacetyl-morphine) is an opiate drug synthesized from morphine, which is usually a naturally occurring substance extracted from the seedpod of certain varieties of poppy plants. In particular, 5601 is the near-infrared spectrum for an illicit street drug sample, while 5602 is the spectra for a pure heroin standard. The difference between the spectra may arise at least in part from cutting agents. The inset 5603 shows the molecular structure for heroin. As in the other examples, the absorption in the near-infrared range is caused by overtone and combination vibrations of O—H, C—H, N—H and C═O groups, which exhibit their fundamental molecular stretching and bending absorption in the mid-infrared range (c.f., the mid-infrared spectrum for heroin is shown 5404 in FIG. 54). These overtone and combination bands do not behave in a simple way, making the near-infrared spectra complex and harder to directly interpret. Also, although the near-infrared signatures may be weaker in magnitude, they are probably easier to detect in the near-infrared, and the sample preparation may also be much simpler in the near-infrared. Moreover, for remote sensing, the near-infrared may be preferable because of atmospheric transmission windows between approximately 1.4-1.8 microns and 2-2.5 microns.

Figure 57:
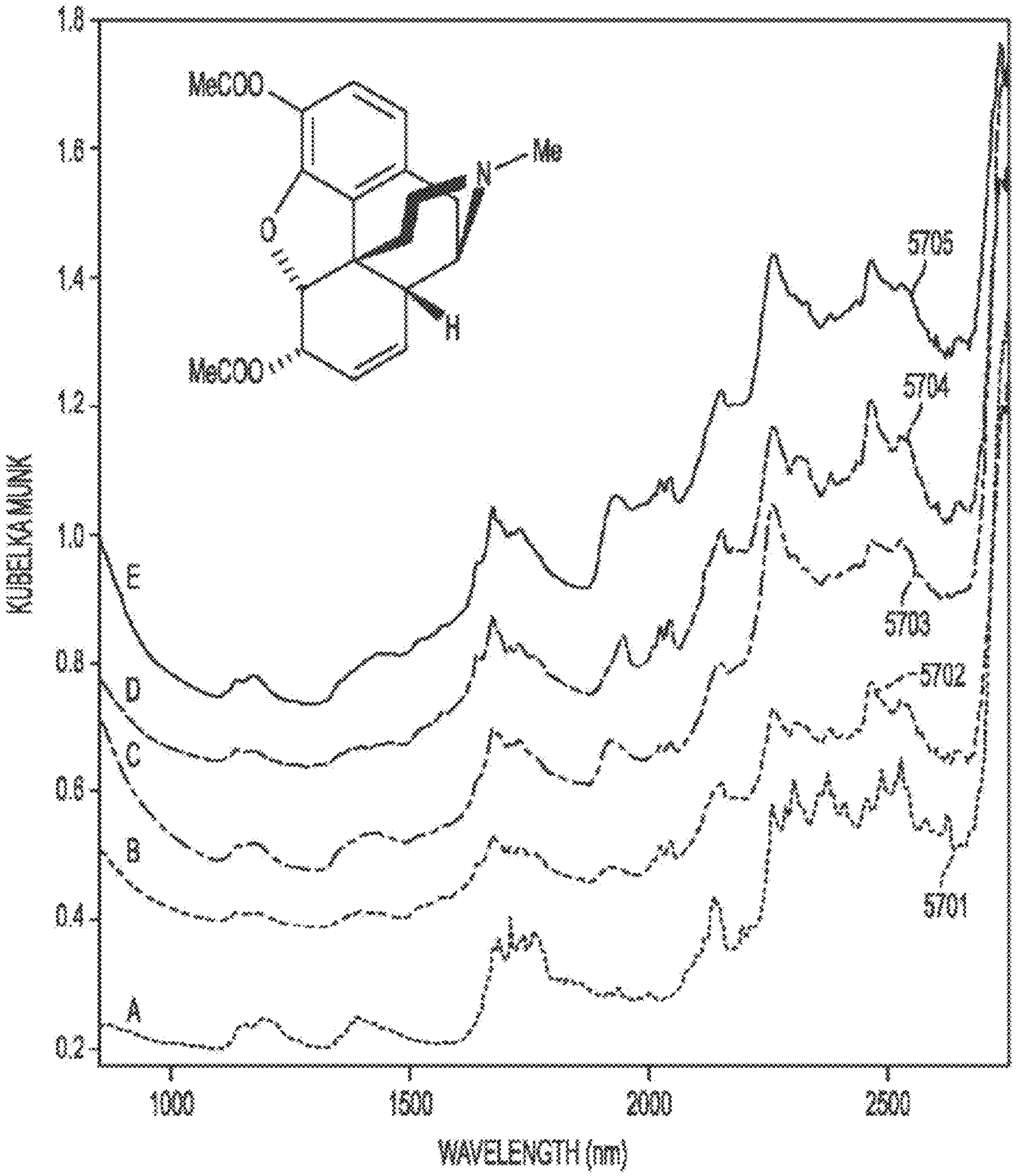
FIG. 57 illustrates the diffuse reflectance near-infrared spectra of different seized illicit drugs containing heroin of different concentrations, along with the spectrum for pure heroin.

Pure heroin may be a white powder with a bitter taste that is rarely sold on the streets, while illicit heroin may be a powder varying in color from white to dark brown due to impurities left from the manufacturing process or the presence of additives. The purity of street heroin may also vary widely, as the drug can be mixed with other white powders. The impurity of the drug may often make it difficult to gauge the strength of the dosage, which runs the risk of overdose. One nice feature of near-infrared or SWIR spectroscopy is that the technique may be used in a non-destructive, non-contact manner to determine rapidly the concentration of compounds present in complex samples at percentage levels with very little sample preparation. In a particular embodiment, FIG. 57 illustrates the diffuse reflectance near-infrared spectra 5700 of different seized illicit drugs containing heroin (between 10.7 and 21.8%) compared with the spectrum of pure heroin 5701. Curve 5702 is for 21.8% by weight, curve 5703 is 13.2% by weight, curve 5704 is 17% by weight, and curve 5705 is 10.7% by weight of heroin. The spectra have been shifted along the vertical axis to better illustrate the differences.

Although quite complex in the near-infrared, it may be possible to identify from the pure heroin near-infrared spectrum (5701 in FIG. 57 or 5602 in FIG. 56) the main wavelengths related to the most common functional groups in heroin. For example, FIG. 58 lists possible band assignments 5800 for the various spectral features in pure heroin. As can be seen from FIG. 58, the absorption in the near-infrared may be mainly due to overtone and combination bands associated with O—H, C—H, N—H and C═O groups.

Figure 59:
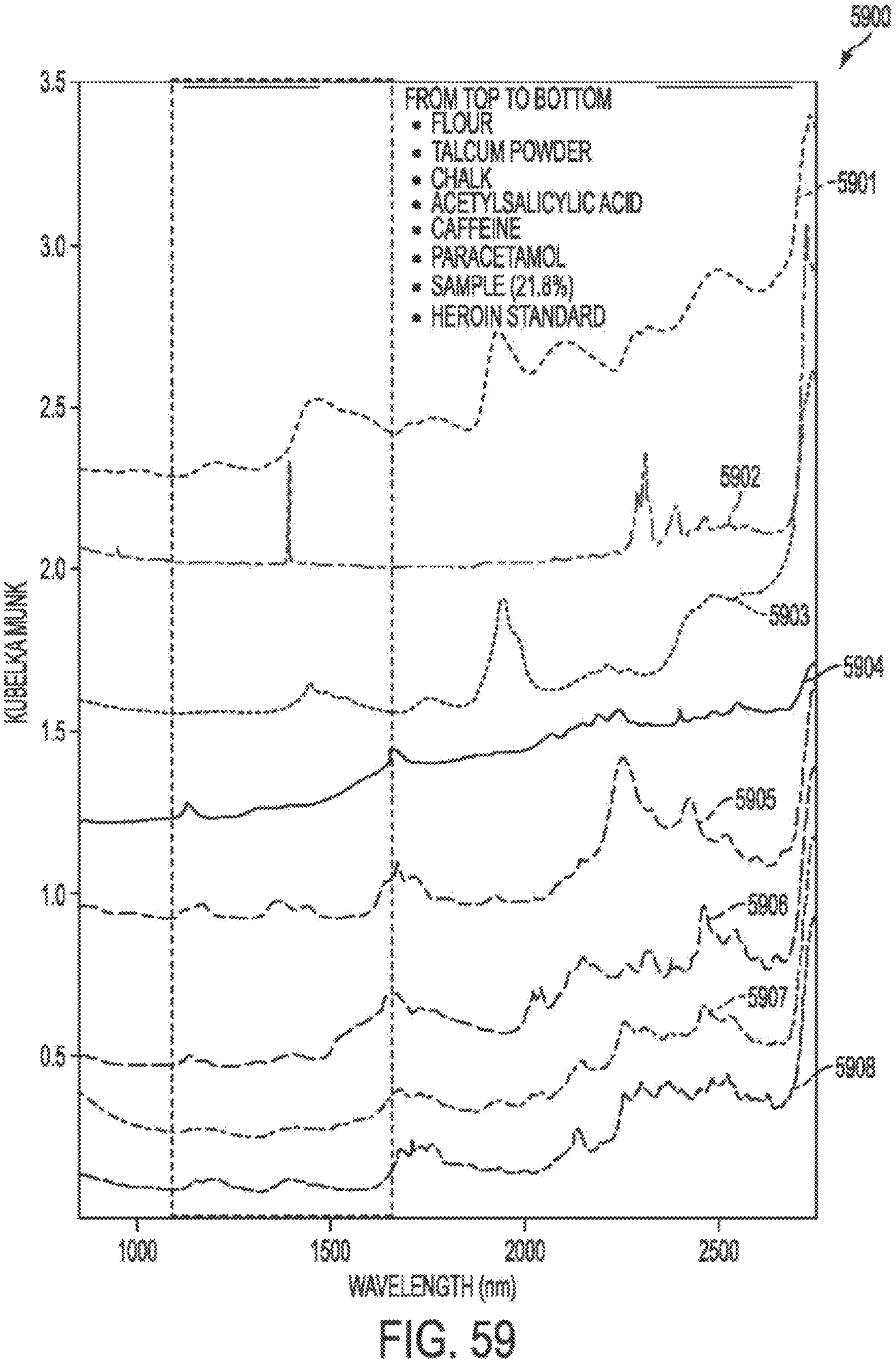
FIG. 59 shows the diffuse reflectance near-infrared spectra of different compounds that may be frequently employed as cutting agents.

As can be appreciated from FIG. 57, there may be significant differences between the spectrum of pure heroin and sample spectra. These differences may be due to the presence of different compounds used as cutting agents, which can affect the shape and intensity of the near-infrared signals. FIG. 59 illustrates the diffuse reflectance near-infrared spectra 5900 of different compounds that may be frequently employed as cutting agents. In the bottom of FIG. 59 are shown the spectra 5908 for pure heroin and the spectra 5907 for a seized illicit street drug sample comprising 21.8% of heroin. The spectra for various cutting agents include: 5901 for flour, 5902 for talcum powder, 5903 for chalk, 5904 for acetylsalicylic acid, 5905 for caffeine, and 5906 for paracetamol. Thus, near-infrared or SWIR spectroscopy may be used to work back to the composition of an unknown drug. Although particular examples of counterfeit and illicit drugs have been described, the near-infrared or SWIR spectroscopy (including diffuse reflectance, reflectance, fluorescence or transmission) may also be applied to the identification of other drugs and substances without departing from the scope of this disclosure. This spectroscopy may be used non-destructively and non-contact over stand-off distances or in remote sensing distances, whether from an airborne, vehicle, hand-held, or stationary platform.

Process Analytical Technology (PAT)

One definition of process analytical technology, PAT, is "a system for designing, analyzing and controlling manufacturing through timely evaluations (i.e., during processing) of significant quality and performance attributes of raw and in-process materials and processes, with the goal of ensuring final product quality." Near-infrared or SWIR spectroscopy may have applications in the PAT of the pharmaceutical industry by providing, for example, quantitative analysis of multiple components in a sample and in pack quantification of drugs in formulation, as well as quality of a drug and quality control of complex excipients used in formulation. The PAT process may benefit from near-infrared or SWIR spectroscopy for some steps, such as: raw material identification, active pharmaceutical ingredient applications, drying, granulation, blend uniformity and content uniformity. Some of the strengths of near-infrared or SWIR spectroscopy include: radiation has good penetration properties, and, thus, minimal sample preparation may be required; measurement results may be obtained rapidly, and simultaneous measurements may be obtained for several parameters; non-destructive methods with little or no chemical waste; and organic chemicals that comprise most pharmaceutical products have unique spectra in the near-infrared and SWIR ranges, for example.

Figure 60:
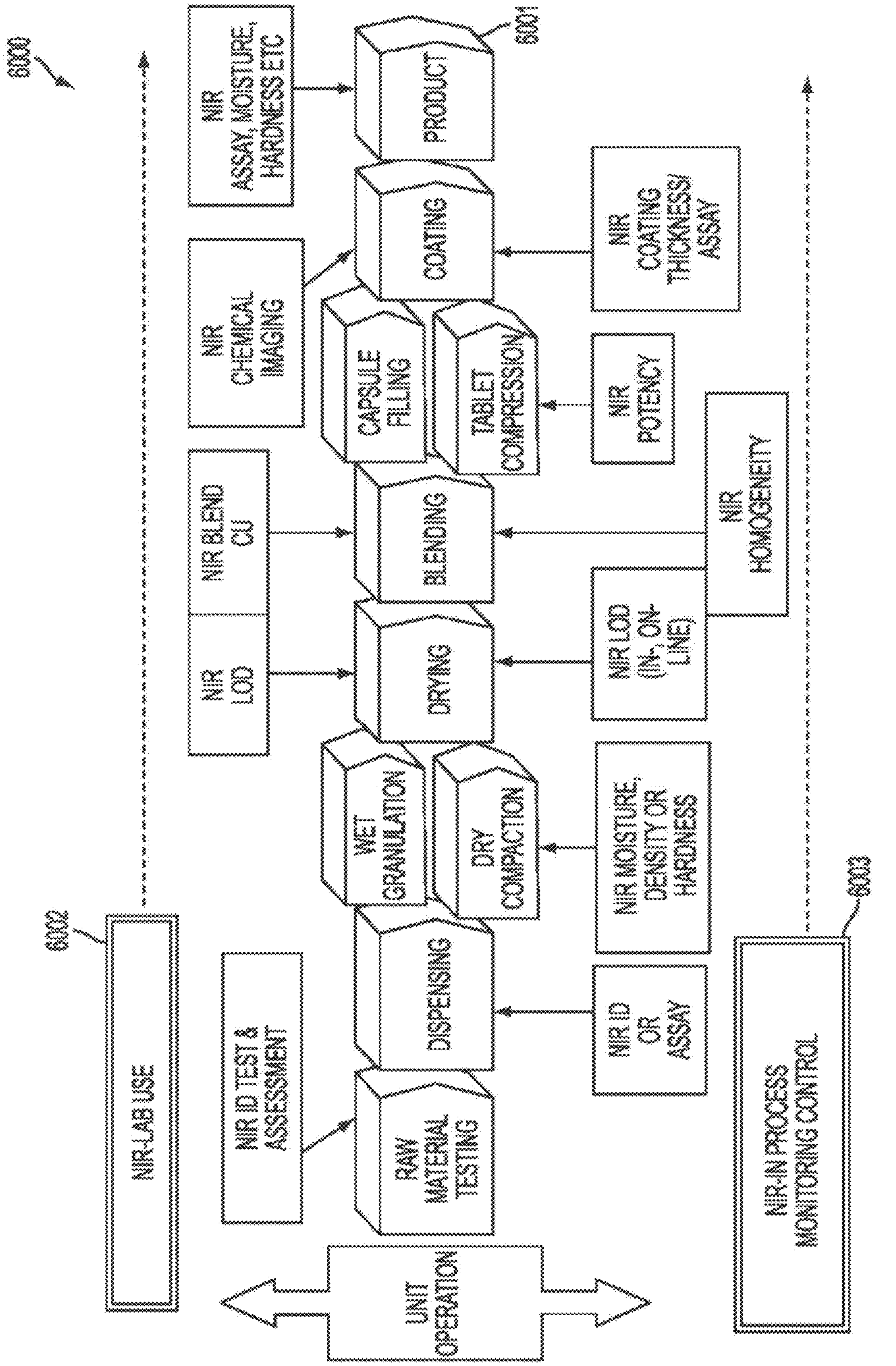
FIG. 60 provides one example of a flow-chart in the process analytical technology for the pharmaceutical industry.

FIG. 60 shows one example of a flow-chart 6000 in the PAT for the pharmaceutical industry. While the center shows the steps of the manufacturing process 6001, the top and bottom sides show where near-infrared spectroscopy could be applicable for lab use 6002 (top) or in process monitoring control 6003 (bottom). Indeed, near-infrared or SWIR spectroscopy has the potential to benefit almost every step in the manufacturing process. Just to provide a few examples of using near-infrared or SWIR spectroscopy in the PAT process, the raw material testing and blending process will be examined briefly.

Figure 61:
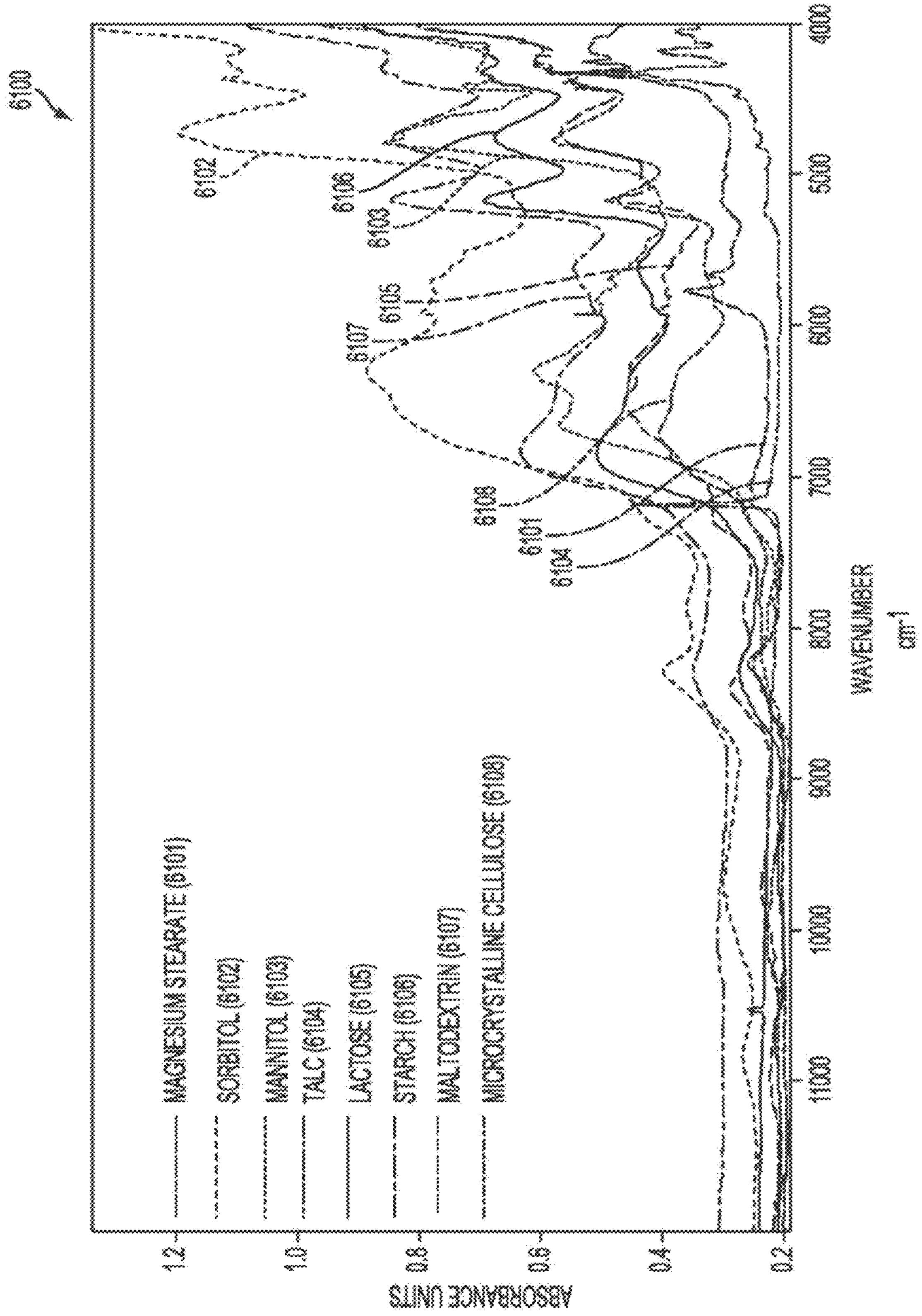
FIG. 61 illustrates the typical near-infrared spectra of a variety of excipients.

At the commencement of manufacture of a drug product, it may be required to identify the correct material and grade of the pharmaceutical excipients to be used in the formulation. FIG. 61 illustrates the typical near-infrared spectra 6100 for a variety of excipients. Included in the graph 6100 are spectra for: magnesium stearate 6101, sorbitol 6102, mannitol 6103, talc 6104, lactose 6105, starch 6106, maltodextrin 6107, and microcrystalline cellulose 6108. A suitable spectral database may be used to rapidly identify and qualify excipients. One nice aspect of the spectroscopy is that the near-infrared and SWIR are sensitive to both the physical and chemical characteristics of the samples.

Figure 62:
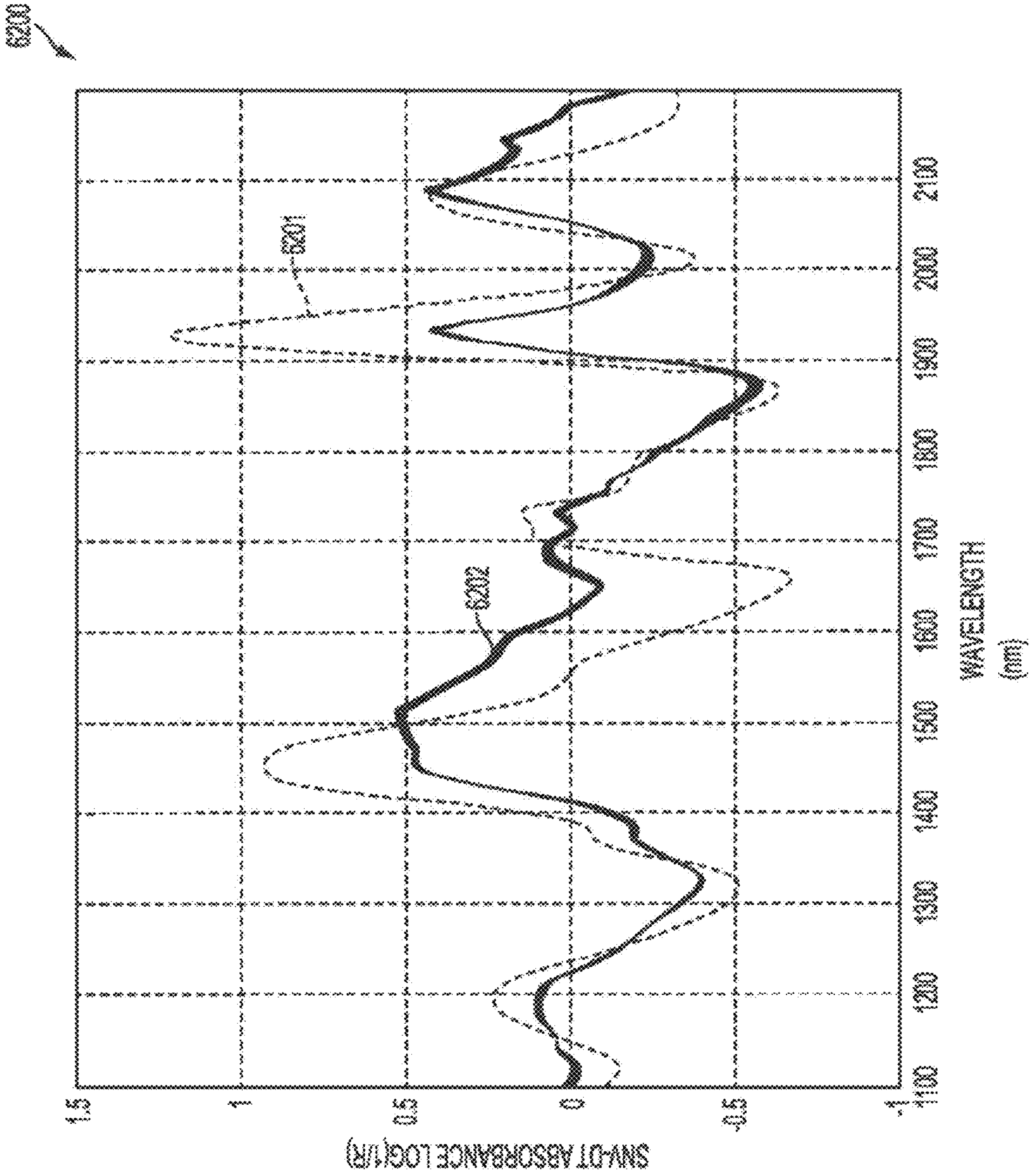
FIG. 62 exemplifies the absorbance from the blending process of a pharmaceutical compound.

One of the next steps in the manufacture of a dosage form is the blending together of the active component with the excipients to produce a homogeneous blend. In one embodiment, the near-infrared or SWIR spectroscopy apparatus may comprise a fiber-optic probe, which may, for example, interface with the blending vessel. For such a fiber-optic probe, near infrared or SWIR spectra may be collected in real-time from a blending process. FIG. 62 exemplifies the absorbance 6200 from the blending process. Although the initial spectra 6201 shows differences from the eventual spectra, as the process continues the blend converges to the final spectra 6202 and continues to overlap that spectra. Similar converging or overlapping spectra may also be used to check the product uniformity at the end of the process. The near-infrared spectra may be acquired in real-time; and, using appropriate data pre-processing and chemometric analysis, blend homogeneity plots may be derived, such as 6200.

One goal of the manufacturing process and PAT may be the concept of a "smart" manufacturing process, which may be a system or manufacturing operation responding to analytical data generated in real-time. Such a system may also have an in-built "artificial intelligence" as decisions may be made whether to continue a manufacturing operation. For example, with respect to the raw materials, integration of the quality measurement into smart manufacturing processes could be used to improve manufacturing operations by ensuring that the correct materials of the appropriate quality are used in the manufacture. Similarly, a smart blender would be under software control and would respond to the real-time spectral data collected.

Figure 63:
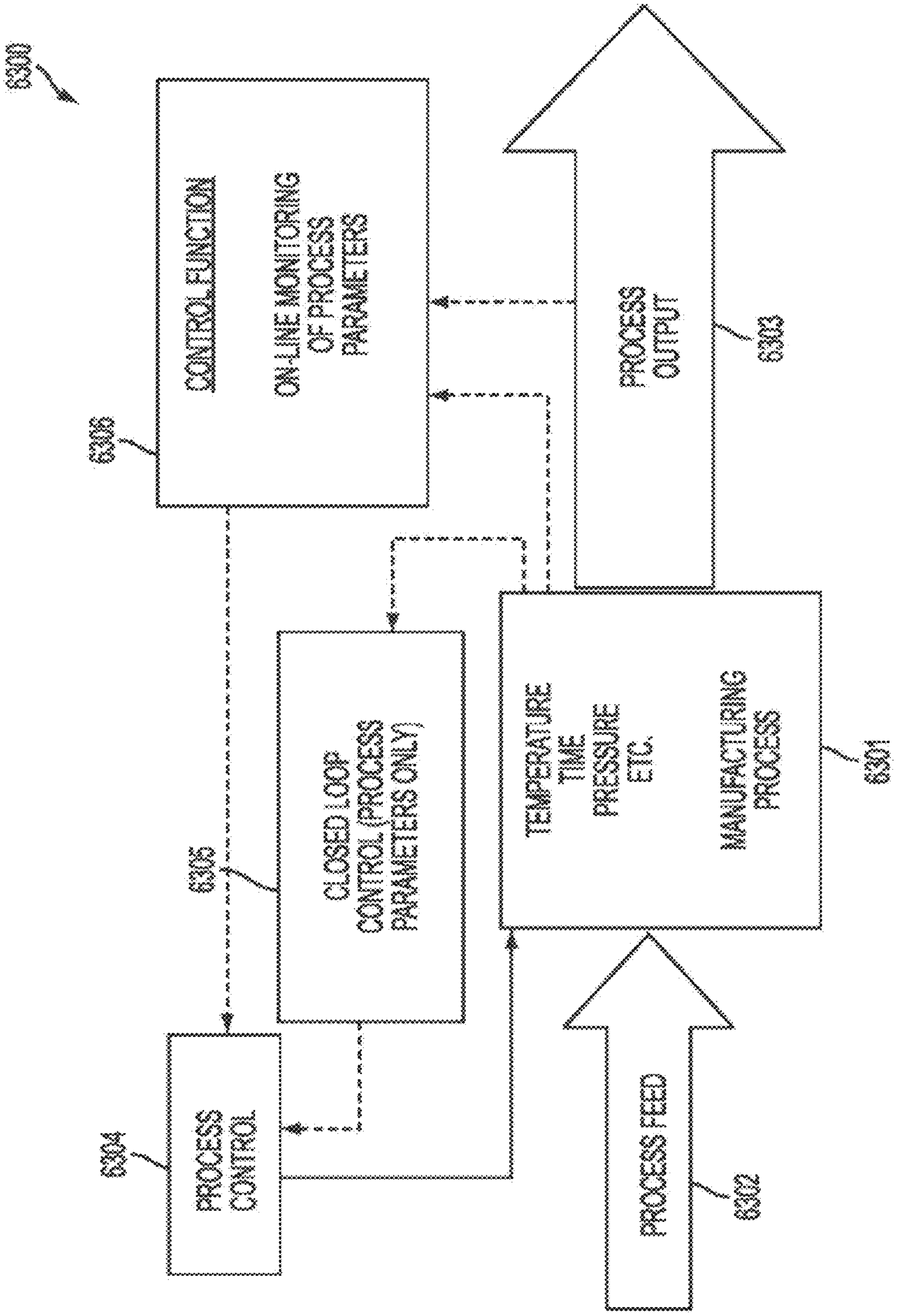
FIG. 63 shows what might be an eventual flow-chart of a smart manufacturing process.

FIG. 63 illustrates what might be an eventual flow-chart 6300 of a smart manufacturing process. The manufacturing process 6301 may have as input the process feed 6302 and result in a process output 6303. A process controller 6304 may at least partially control the manufacturing process 6301, and the controller 6304 may receive inputs from the closed loop control (process parameters) 6305 as well as the on-line monitoring of process parameters 6306. The feedback loops in the process could refine the manufacturing process 6301 and improve the quality of the process output 6303. These are particular embodiments of the use of near-infrared or SWIR spectroscopy in the PAT of the pharmaceutical industry, but other variations, combinations, and methods may also be used and are intended to be covered by this disclosure.

The discussion thus far has centered on use of near-infrared or SWIR spectroscopy in applications such as identification of counterfeit drugs, detection of illicit drugs, and pharmaceutical process control. Although drugs and pharmaceuticals are one example, many other fields and applications may also benefit from the use of near infrared or SWIR spectroscopy, and these may also be implemented without departing from the scope of this disclosure. As just another example, near-infrared or SWIR spectroscopy may also be used as an analytic tool for food quality and safety control. Applications in food safety and quality assessment include contaminant detection, defect identification, constituent analysis, and quality evaluation. The techniques described in this disclosure are particularly valuable when non-destructive testing is desired at stand-off or remote distances.

Figure 64A:
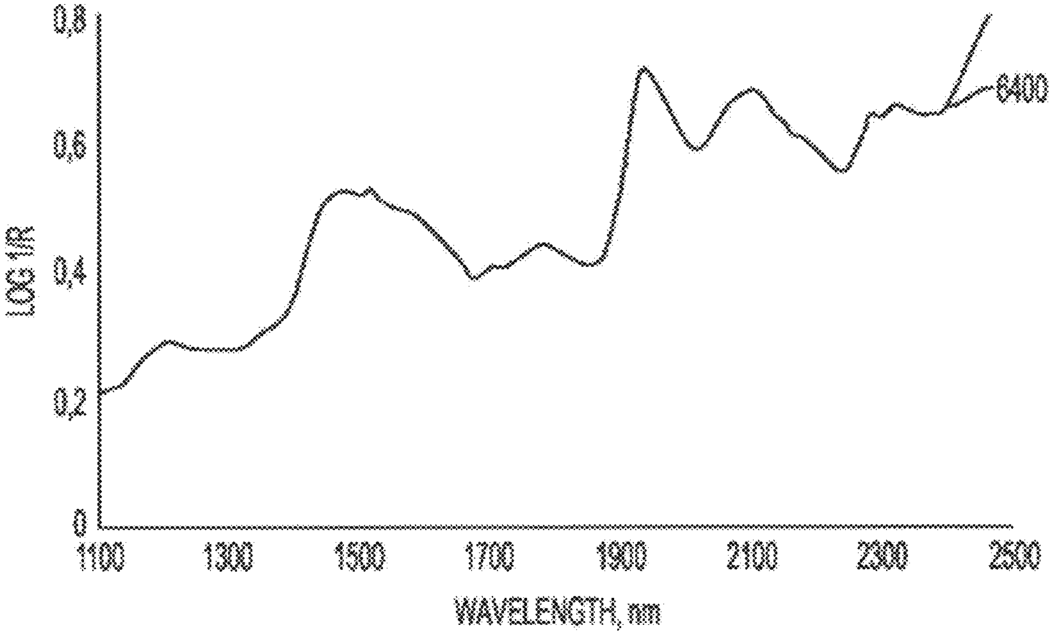
FIG. 64A illustrates the near-infrared reflectance spectrum of wheat flour.

In one example, near-infrared or SWIR spectroscopy may be used in cereal breeding. The breeding purposes may require knowledge on both composition and functional properties of grain, while the functionality of wheat grain is an issue for wheat breeders. Most of the wheat functionality parameters depend on the protein-proteinase complex of wheat grain, as well as the condition of the carbohydrate complex. FIG. 64A illustrates the near-infrared reflectance spectrum 6400 of wheat flour. Since these samples are complex in composition, several organic bonds involving hydrogen vibrate to produce overlapped spectral bands. Thus, the resulting spectrum 6400 appears like a wavy line without clearly defined features. Analytical methods based on this type of spectroscopy may have the potential to improve the quality of final cereal products by testing the products through the entire production process in the processing industry.

Figure 64B:
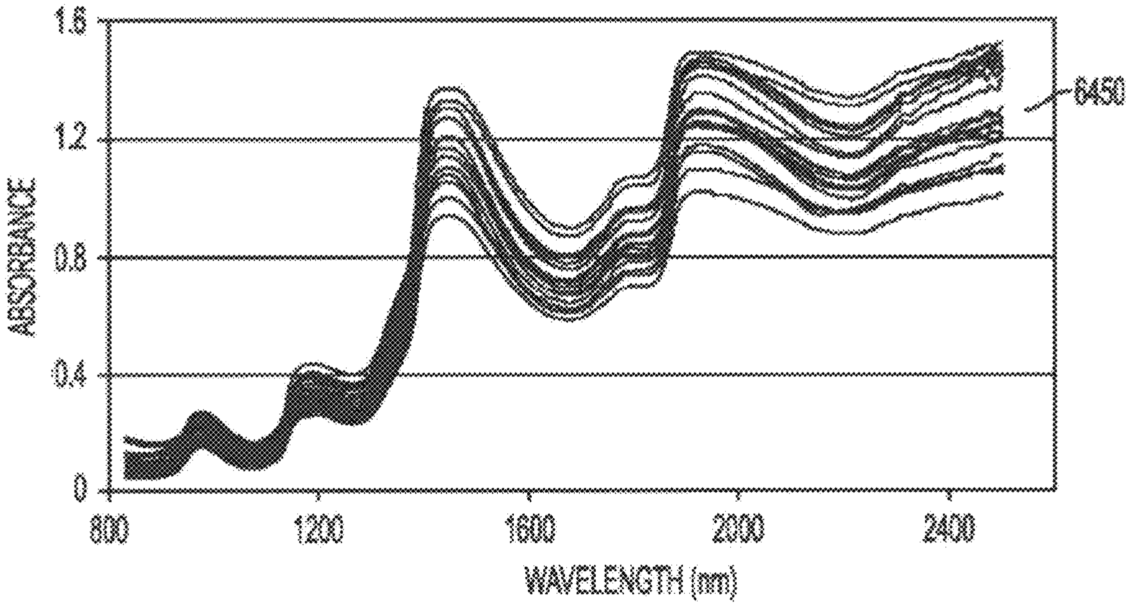
FIG. 64B shows the near-infrared absorbance spectra obtained in diffusion reflectance mode for a series of whole 'Hass' avocado fruit.

In yet another embodiment, near-infrared or SWIR spectroscopy may be used for the assessment of fruit and vegetable quality. Most commercial quality classification systems for fruit and vegetables are based on external features of the product, such as shape, color, size, weight and blemishes. However, the external appearance of most fruit is generally not an accurate guide to the internal eating quality of the fruit. As an example, for avocado fruit the external color is not a maturity characteristic, and its smell is too weak and appears later in its maturity stage. Analysis of the near-infrared or SWIR absorption spectra may provide qualitative and quantitative determination of many constituents and properties of horticulture produce, including oil, water, protein, pH, acidity, firmness, and soluble solids content or total soluble solids of fresh fruits. FIG. 64B shows the near-infrared absorbance spectra 6450 obtained in diffusion reflectance mode for a series of whole 'Hass' avocado fruit. Four oil absorption bands are near 2200-2400 nm (CH2 stretch bend and combinations), with weaker absorption around 750 nm, 1200 nm, and 900-930 nm ranges. On the other hand, near 1300-1750 nm range may be useful for determining the protein and oil content. The 900-920 nm absorbance band may be useful for sugar determination. Although described in the context of grains, fruits, and vegetables, the near-infrared or SWIR spectroscopy may also be valuable for other food quality control and assessment, such as measuring the properties of meats. These and other applications also fall within the scope of this disclosure.

Detection Systems

The near-infrared or SWIR spectroscopy system, remote sensing system or hyper-spectral imaging system may be on an airborne platform, mounted on a vehicle, a stationary transmission or reflection set-up, or even held by a human for a compact system. For such a system, there are fundamentally two hardware parts: the transmitter or light source and the detection system. Between the two, perhaps in a transmission or reflection setting, may be the sample being tested or measured. Moreover, the output from the detection system may go to a computational system, comprising computers or other processing equipment. The output from the computational system may be displayed graphically as well as with numerical tables and perhaps an identification of the material composition. These are just some of the parts of the systems, but other elements may be added or be eliminated, and these modified configurations are also intended to be covered by this disclosure.

By use of an active illuminator, a number of advantages may be achieved. First, stand-off or remote distances may be achieved if a non-lamp system is used—i.e., if the beam does not rapidly diffract. Also, higher signal-to-noise ratios may be achieved. For example, one way to improve the signal-to-noise ratio would be to use modulation and lock-in techniques. In one embodiment, the light source may be modulated, and then the detection system would be synchronized with the light source. In a particular embodiment, the techniques from lock-in detection may be used, where narrow band filtering around the modulation frequency may be used to reject noise outside the modulation frequency. In another embodiment, change detection schemes may be used, where the detection system captures the signal with the light source on and with the light source off. Again, for this system the light source may be modulated. Then, the signal with and without the light source is differenced. Change detection may help to identify objects that change in the field of view. In the following some exemplary detection systems are described.

In one embodiment, a SWIR camera or infrared camera system may be used to capture the images. The camera may include one or more lenses on the input, which may be adjustable. The focal plane assemblies may be made from mercury cadmium telluride material (HgCdTe), and the detectors may also include thermo-electric coolers. Alternately, the image sensors may be made from indium gallium arsenide (InGaAs), and CMOS transistors may be connected to each pixel of the InGaAs photodiode array. The camera may interface wirelessly or with a cable (e.g., USB, Ethernet cable, or fiber optics cable) to a computer or tablet or smart phone, where the images may be captured and processed. These are a few examples of infrared cameras, but other SWIR or infrared cameras may be used and are intended to be covered by this disclosure.

Figure 65A:
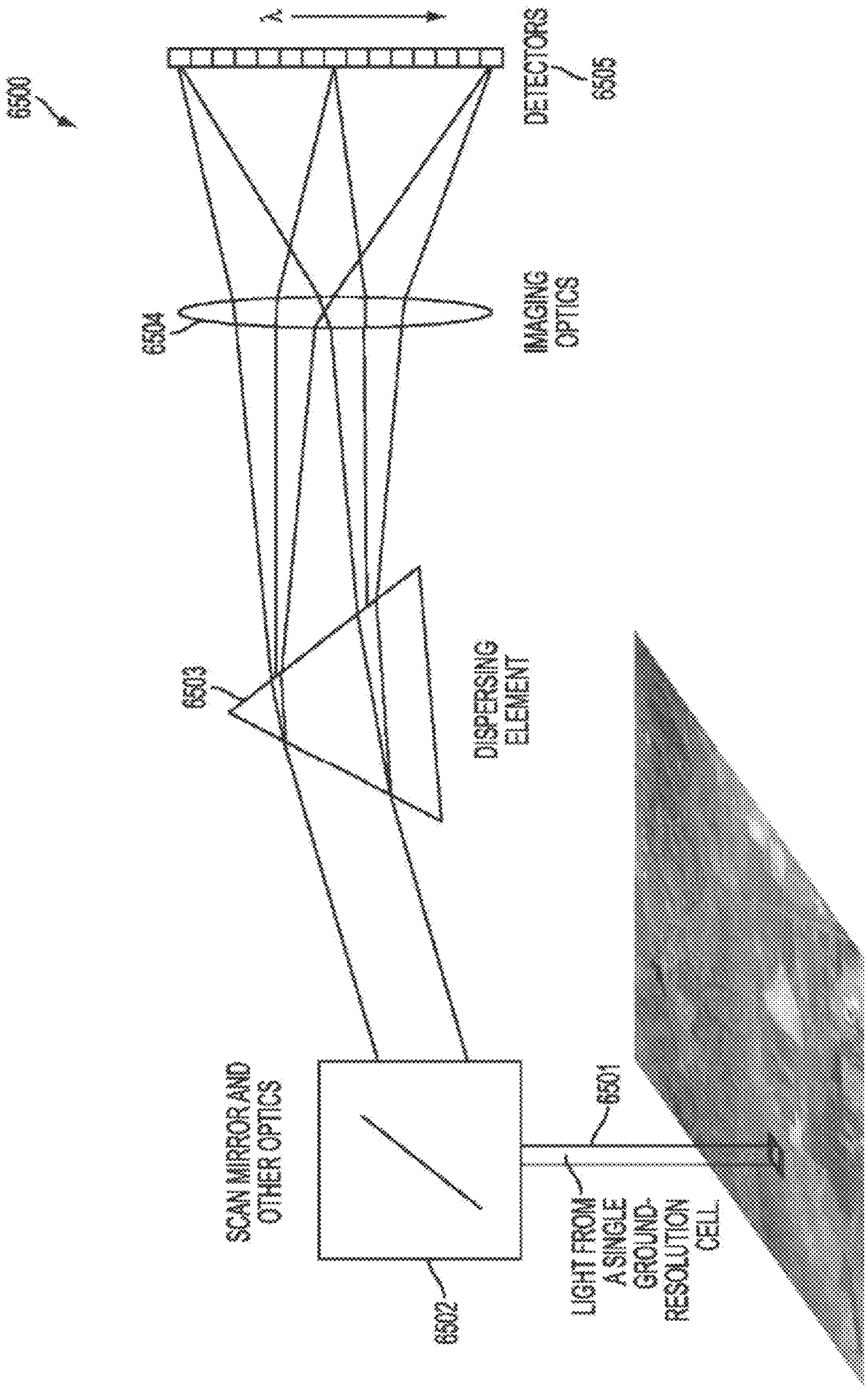
FIG. 65A is a schematic diagram of the basic elements of an imaging spectrometer.

In another embodiment, an imaging spectrometer may be used to detect the light received from the sample. For example, FIG. 65A shows a schematic diagram 6500 of the basic elements of an imaging spectrometer. The input light 6501 from the sample may first be directed by a scanning mirror and/or other optics 6502. An optical dispersing element 6503, such as a grating or prism, in the spectrometer may split the light into many narrow, adjacent wavelength bands, which may then be passed through imaging optics 6504 onto one or more detectors or detector arrays 6505. Some sensors may use multiple detector arrays to measure hundreds of narrow wavelength bands.

Figure 65B:
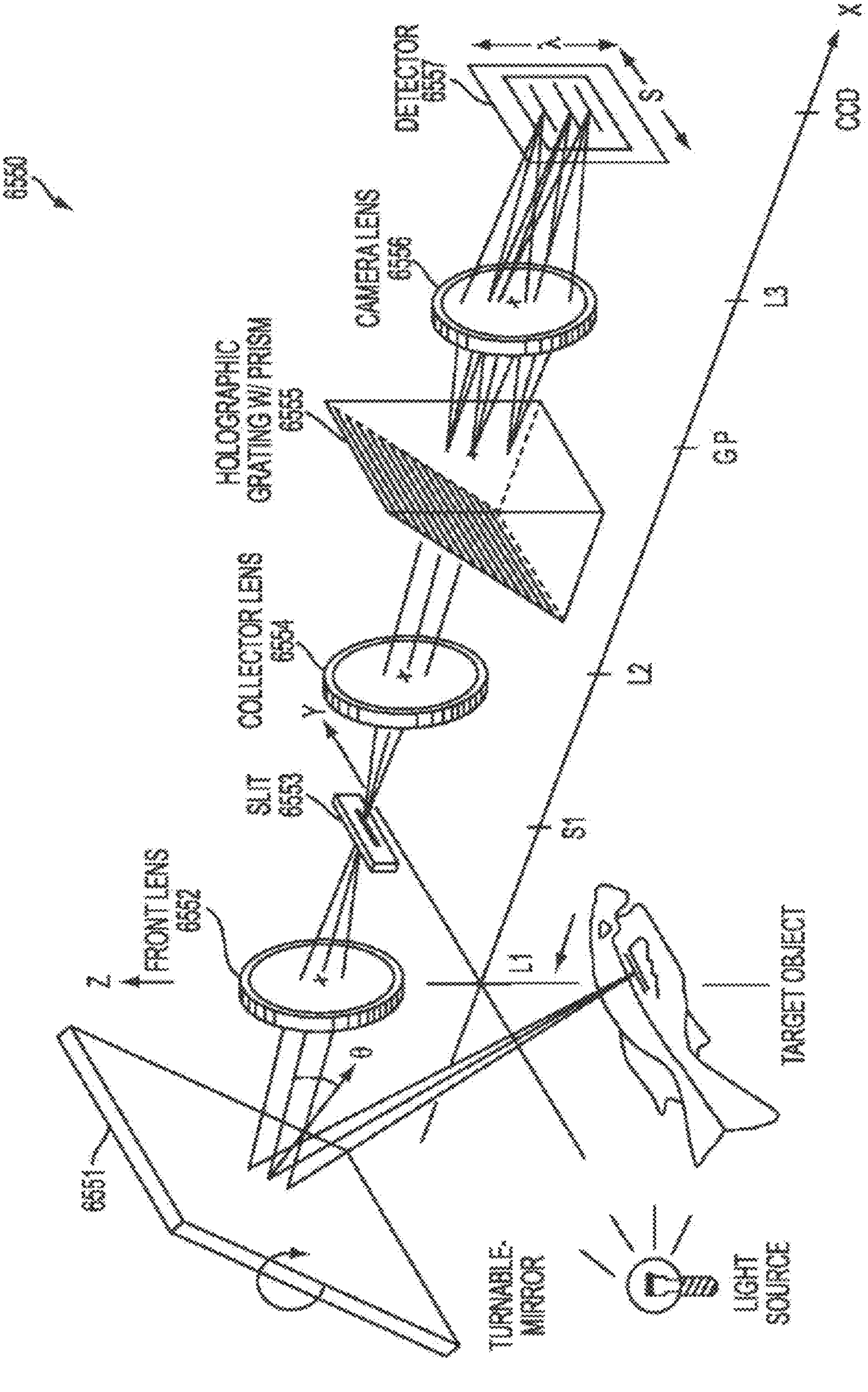
FIG. 65B illustrates one example of a typical imaging spectrometer used in hyper-spectral imaging systems.

An example of a typical imaging spectrometer 6550 used in hyper-spectral imaging systems is illustrated in FIG. 65B. In this particular embodiment, the input light may be directed first by a tunable mirror 6551. A front lens 6552 may be placed before the entrance slit 6553 and the collector lens 6554. In this embodiment, the dispersing element is a holographic grating with a prism 6555, which separates the different wavelength bands. Then, a camera lens 6556 may be used to image the wavelengths onto a detector or camera 6557.

FIG. 65 provide particular examples, but some of the elements may not be used, or other elements may be added, and these are also intended to be covered by this disclosure. For instance, a scanning spectrometer may be used before the detector, where a grating or dispersive element is scanned to vary the wavelength being measured by the detector. In yet another embodiment, filters may be used before one or more detectors to select the wavelengths or wavelength bands to be measured. This may be particularly useful if only a few bands or wavelengths are to be measured. The filters may be dielectric filters, Fabry-Perot filters, absorption or reflection filters, fiber gratings, or any other wavelength selective filter. In one embodiment, a wavelength division multiplexer, WDM, may be used followed by one or more detectors or detector arrays. One example of a planar wavelength division multiplexer may be a waveguide grating router or an arrayed waveguide grating. The WDM may be fiber coupled, and detectors may be placed directly at the output or the detectors may be coupled through fibers to the WDM. Some of these components may also be combined with the configurations in FIG. 65.

While the above detection systems could be categorized as single path detection systems, it may be advantageous in some cases to use multi-path detection systems. In one embodiment, a detection system from a Fourier transform infrared spectrometer, FTIR, may be used. The received light may be incident on a particular configuration of mirrors, called a Michelson interferometer, that allows some wavelengths to pass through but blocks others due to wave interference. The beam may be modified for each new data point by moving one of the mirrors, which changes the set of wavelengths that pass through. This collected data is called an interferogram. The interferogram is then processed, typically on a computing system, using an algorithm called the Fourier transform. One advantageous feature of FTIR is that it may simultaneously collect spectral data in a wide spectral range.

Figure 66:
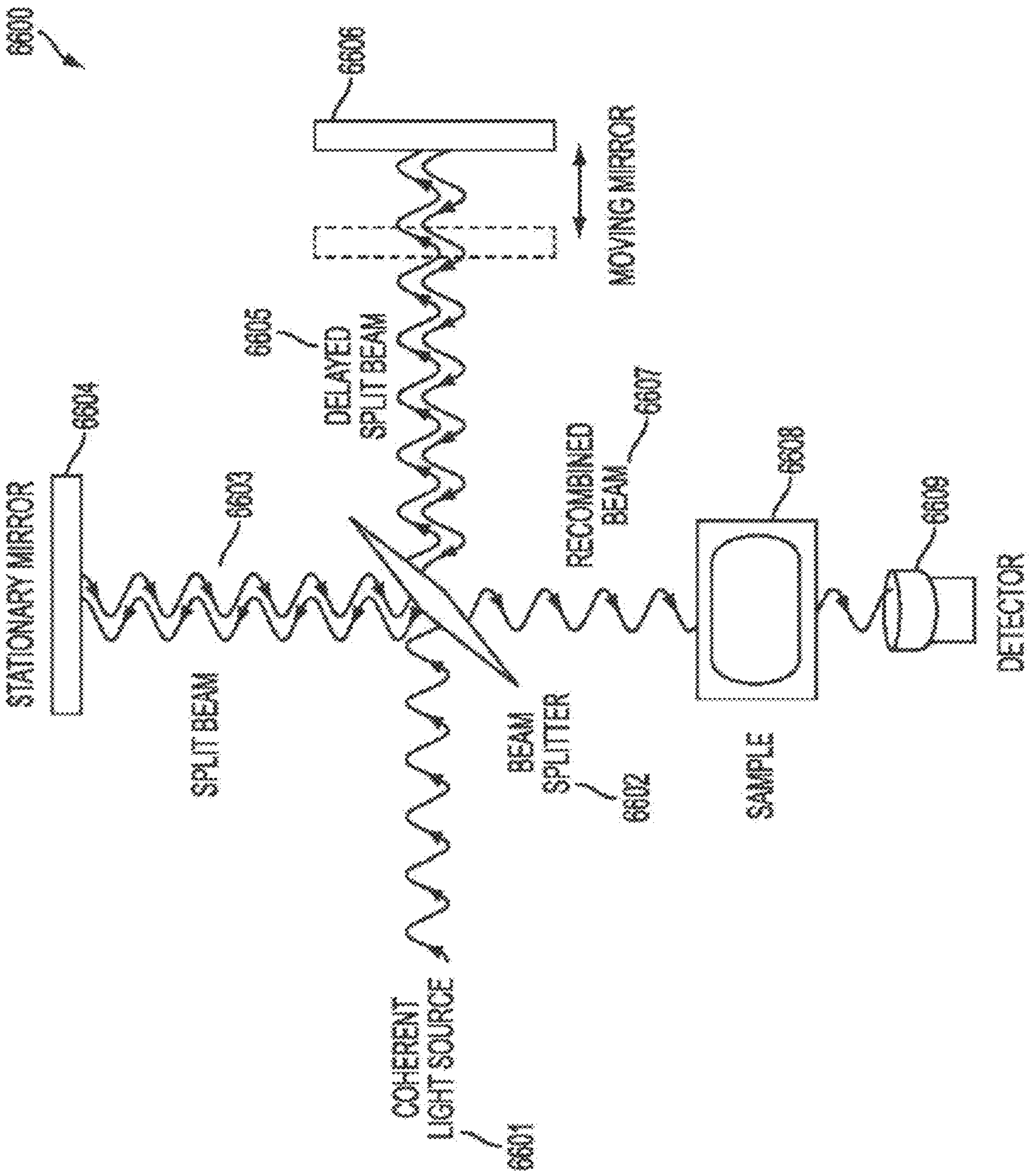
FIG. 66 shows one example of the Fourier transform infrared spectrometer.

FIG. 66 illustrates one example of the FTIR spectrometer 6600. Light from the near-infrared or SWIR light source 6601 may be collimated and directed to a beam splitter 6602. In one embodiment, the beam splitter 6602 may be a 50:50 beam splitter. One portion of the beam 6603 may be reflected toward a stationary mirror 6604, while the other portion of the beam 6605 may be transmitted towards a moving mirror 6606. Light may be reflected from the two mirrors 6604, 6606 back to the beam splitter 6602, and then a portion of the recombined beam 6607 may be directed toward the sample 6608. The recombined beam 6607 may be focused onto the sample 6608, in one embodiment. On leaving the sample 6608, the light may be refocused or at least collected at a detector 6609. A background interferogram may be obtained by using the set-up 6600 without a sample in the chamber 6608. When a sample is inserted into 6608, the background interferogram may be modulated by the presence of absorption bands in the sample. The FTIR spectrometer may have several advantages compared to a scanning (dispersive) spectrometer. Since all the wavelengths may be collected simultaneously, the FTIR may result in a higher signal-to-noise ratio for a given scan time or a shorter scan time for a given resolution. Moreover, unlike a spectrometer where a slit may limit the amount of the beam detected, the FTIR may accommodate the entire diameter of the beam coming from the light source 6601. The configuration 6600 is one example of an FTIR, but other configurations may also be used, and these are also intended to be covered by this disclosure.

Figure 67:
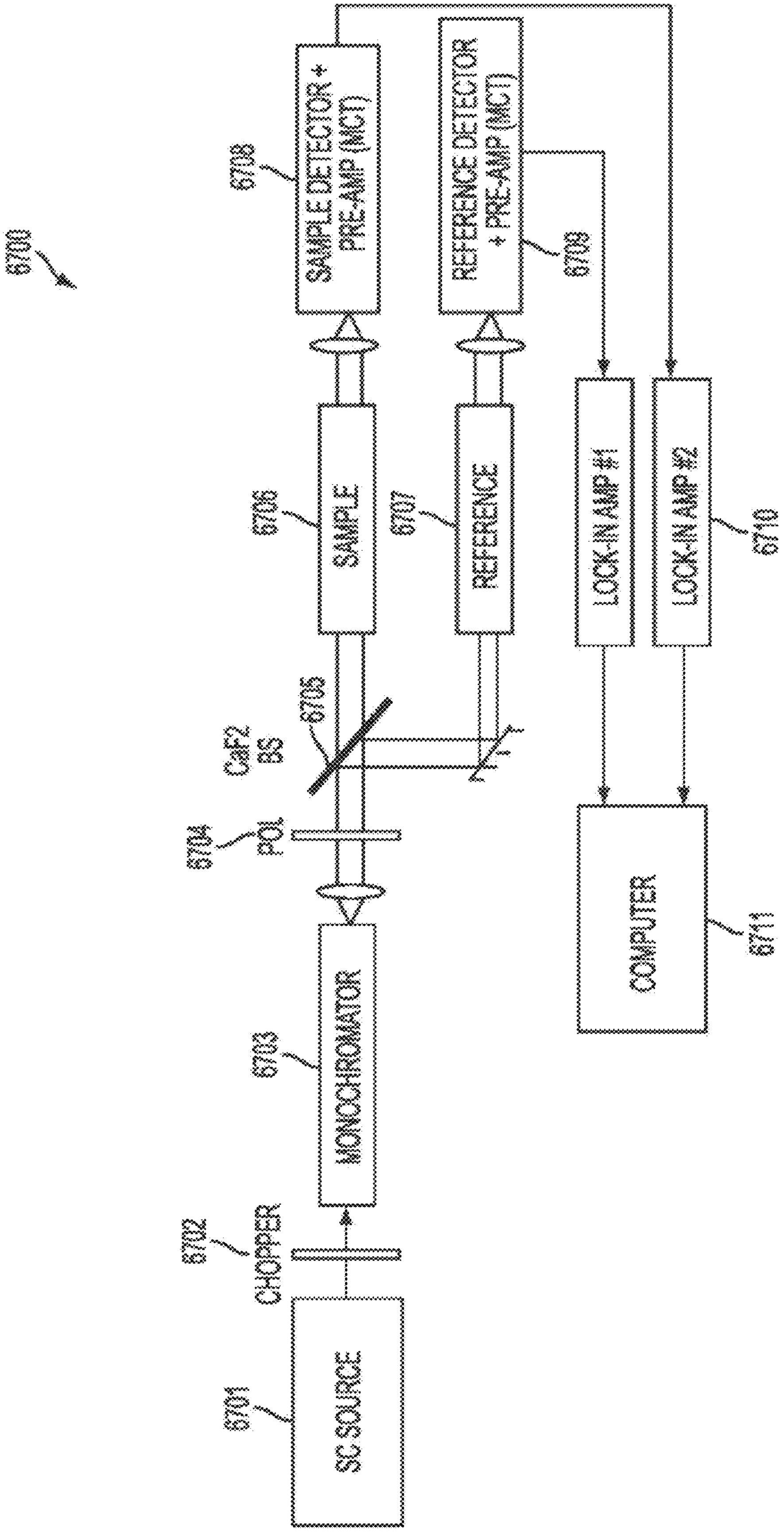
FIG. 67 exemplifies a dual-beam experimental set-up that may be used to subtract out (or at least minimize the adverse effects of) light source fluctuations.

In yet another example of multi-beam detection systems, a dual-beam set-up 6700 such as in FIG. 67 may be used to subtract out (or at least minimize the adverse effects of) light source fluctuations. In one embodiment, the output from an SC source 6701 may be collimated using a $CaF_2$ lens 6702 and then focused into the entrance slit of the monochromator 6703. At the exit slit, light at the selected wavelength is collimated again and may be passed through a polarizer 6704 before being incident on a calcium fluoride beam splitter 6705. After passing through the beam splitter 6705, the light is split into a sample 6706 and reference 6707 arm to enable ratiometric detection that may cancel out effects of intensity fluctuations in the SC source 6701. The light in the sample arm 6706 passes through the sample of interest and is then focused onto a HgCdTe detector 6708 connected to a pre-amp. A chopper 6702 and lock-in amplifier 6710 setup enable low noise detection of the sample arm signal. The light in the reference arm 6707 passes through an empty container (cuvette, gas cell etc.) of the same kind as used in the sample arm. A substantially identical detector 6709, pre-amp and lock-in amplifier 6710 is used for detection of the reference arm signal. The signal may then be analyzed using a computer system 6711. This is one particular example of a method to remove fluctuations from the light source, but other components may be added and other configurations may be used, and these are also intended to be covered by this disclosure.

Although particular examples of detection systems have been described, combinations of these systems or other systems may also be used, and these are also within the scope of this disclosure. As one example, environmental fluctuations (such as turbulence or winds) may lead to fluctuations in the beam for active remote sensing or hyper-spectral imaging. A configuration such as FIG. 67 may be able to remove the effect of environmental fluctuations. Yet another technique may be to "wobble" the light beam after the light source using a vibrating mirror. The motion may lead to the beam moving enough to wash out spatial fluctuations within the beam waist at the sample or detection system. If the vibrating mirror is scanned faster than the integration time of the detectors, then the spatial fluctuations in the beam may be integrated out. Alternately, some sort of synchronous detection system may be used, where the detection is synchronized to the vibrating frequency.

Described herein are just some examples of the beneficial use of near-infrared or SWIR lasers for spectroscopy, active remote sensing or hyper-spectral imaging. However, many other spectroscopy and identification procedures can use the near-infrared or SWIR light consistent with this disclosure and are intended to be covered by the disclosure. As one example, the fiber-based super-continuum lasers may have a pulsed output with pulse durations of approximately 0.5-2 nsec and pulse repetition rates of several Megahertz. Therefore, the near-infrared or SWIR spectroscopy, active remote sensing or hyper-spectral imaging applications may also be combined with LIDAR-type applications. Namely, the distance or time axis can be added to the information based on time-of-flight measurements. For this type of information to be used, the detection system would also have to be time-gated to be able to measure the time difference between the pulses sent and the pulses received. By calculating the round-trip time for the signal, the distance of the object may be judged. In another embodiment, GPS (global positioning system) information may be added, so the near-infrared or SWIR spectroscopy, active remote sensing or hyper-spectral imagery would also have a location tag on the data. Moreover, the near-infrared or SWIR spectroscopy, active remote sensing or hyper-spectral imaging information could also be combined with two-dimensional or three-dimensional images to provide a physical picture as well as a chemical composition identification of the materials. These are just some modifications of the near-infrared or SWIR spectroscopy, active remote sensing or hyper-spectral imaging system described in this disclosure, but other techniques may also be added or combinations of these techniques may be added, and these are also intended to be covered by this disclosure.

Figure 68:
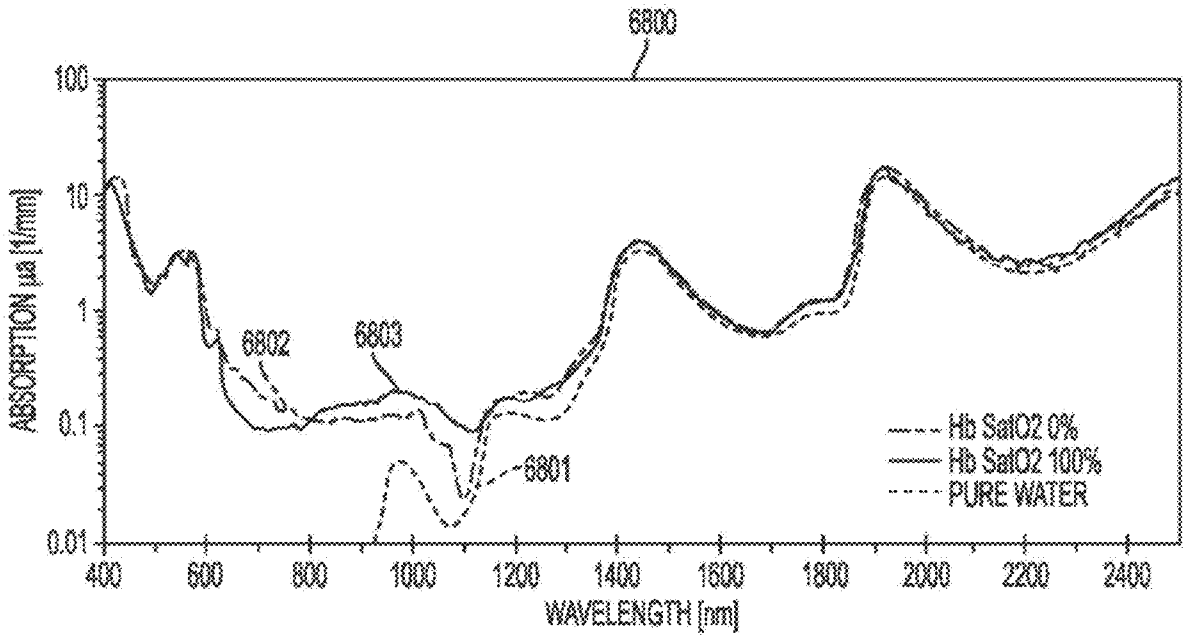
FIG. 68 illustrates the optical absorption of pure water, hemoglobin without oxygen, and hemoglobin saturated with oxygen.

Section 5: Near-Infrared Super-Continuum Lasers for Early Detection of Breast and Other Cancers To perform non-invasive optical mammography, one desired attribute is that the light may penetrate as far as possible into the breast tissue. In diffuse reflection spectroscopy, a broadband light spectrum may be emitted into the tissue, and the spectrum of the reflected or transmitted light may depend on the absorption and scattering interactions within the target tissue. Since breast tissue has significant water and hemoglobin content, it is valuable to examine the wavelength range over which deep penetration of light is possible. FIG. 68 illustrates the optical absorption 6800 of pure water (dotted line) 6801, hemoglobin without oxygen (thinner solid line) 6802, and hemoglobin saturated with oxygen (thicker solid line) 6803. It can be noted that above about 1100 nm, the absorption of hemoglobin is almost the same as water absorption. The penetration depth may be proportional to the inverse of the optical absorption. Therefore, the highest penetration depth will be at the absorption valley, approximately in the wavelength range between about 900 nm and about 1300 nm. Although not as low in absorption compared to the first window, another absorption valley lies between about 1600 nm and 1800 nm. Thus, non-invasive imaging preferably should use wavelengths that fall in one of these two absorption valleys.

Figure 69:
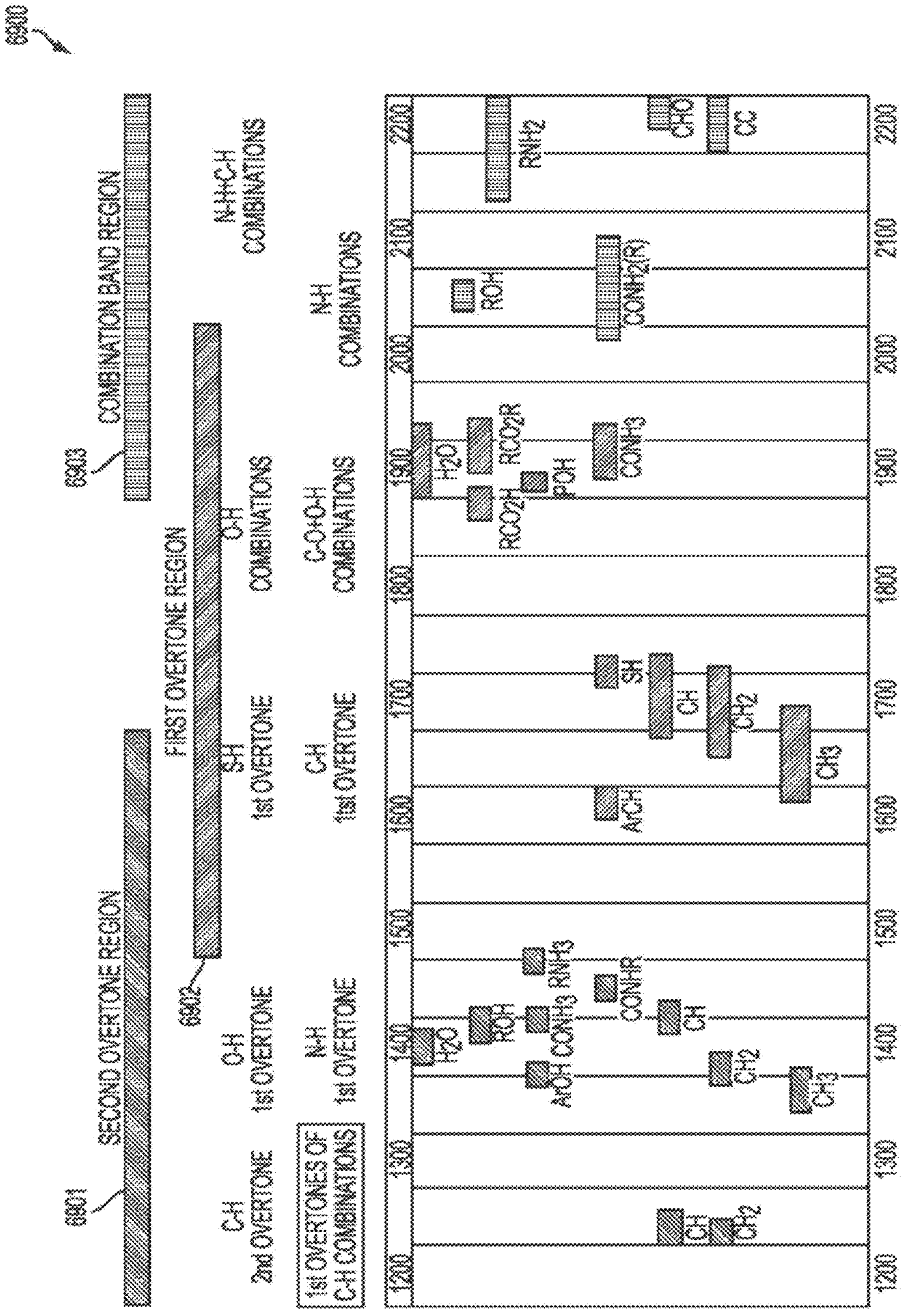
FIG. 69 shows examples of various absorption bands of chemical species in the wavelength range between about 1200-2200 nm.

FIG. 69 shows examples of various absorption bands of chemical species 6900 in the wavelength range between about 1200 nm and 2200 nm. Although the fundamental absorptions usually lie in the mid-infrared (e.g., wavelengths longer than about 3 microns), there are many absorption lines in the NIR corresponding to the second overtone region 6901 between about 1000 nm and 1700 nm, the first overtone region 6902 between about 1500 nm and 2050 nm, and the combination band region 6903 between about 1900 nm and 2300 nm. As an example, hydrocarbon bonds common in many biological substances have their fundamental absorption in the mid-IR near 3300-3600 nm, but they also have many combination band lines between 2000-2500 nm, and other lines at shorter wavelengths corresponding to the first and second overtones. Fortunately, there are spectral features of FIG. 69 that overlap with the absorption valleys in FIG. 68. These are likely to be the wavelengths of interest for spectroscopic analysis of cancerous regions.

Figure 70:
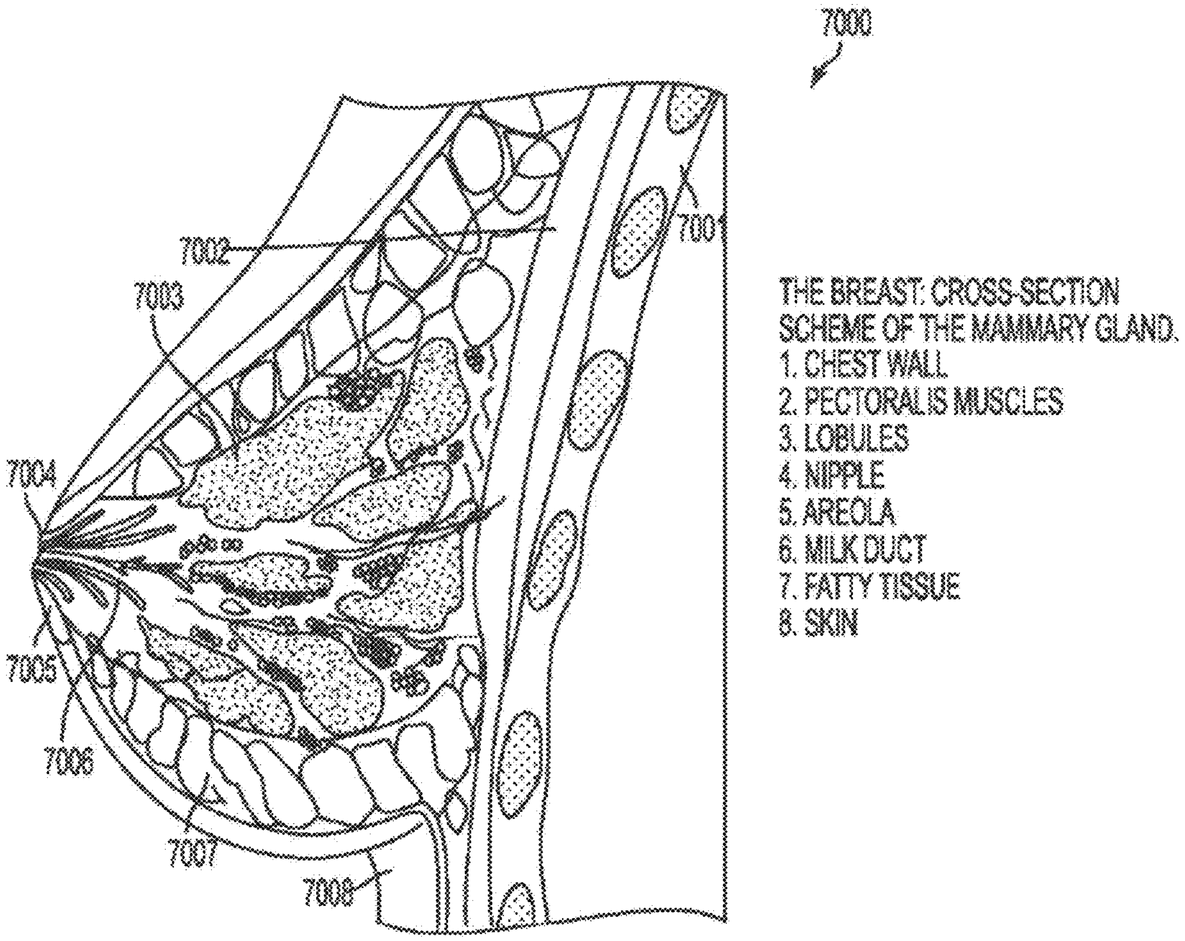
FIG. 70 depicts the structure of a female breast.

In women, the breasts (FIG. 70) 7000 overlay the pectoralis major muscles 7002 and cover much of the chest area and the chest walls 7001. The breast is an apocrine gland that produces milk to feed an infant child; the nipple 7004 of the breast is surrounded by an areola 7005, which has many sebaceous glands. The basic units of the breast are the terminal duct lobules 7003, which produce the fatty breast milk. They give the breast its function as a mammary gland. The lobules 7003 feed through the milk ducts 7006, and in turn these ducts drain to the nipple 7004. The superficial tissue layer (superficial fascia) may be separated from the skin 7008 by about 0.5-2.5 cm of adipose of fatty tissue 7007.

Breast cancer is a type of cancer originating from breast tissue, most commonly from the inner lining of milk ducts 7006, the lobules 7003 that supply the ducts with milk, and/or the connective tissue between the lobules. Cancers originating from ducts 7006 are known as ductal carcinomas, while those originating from lobules 7003 or their connective tissue are known as lobular carcinomas. While the overwhelming majority of human cases occur in women, male breast cancer may also occur.

Figure 71:
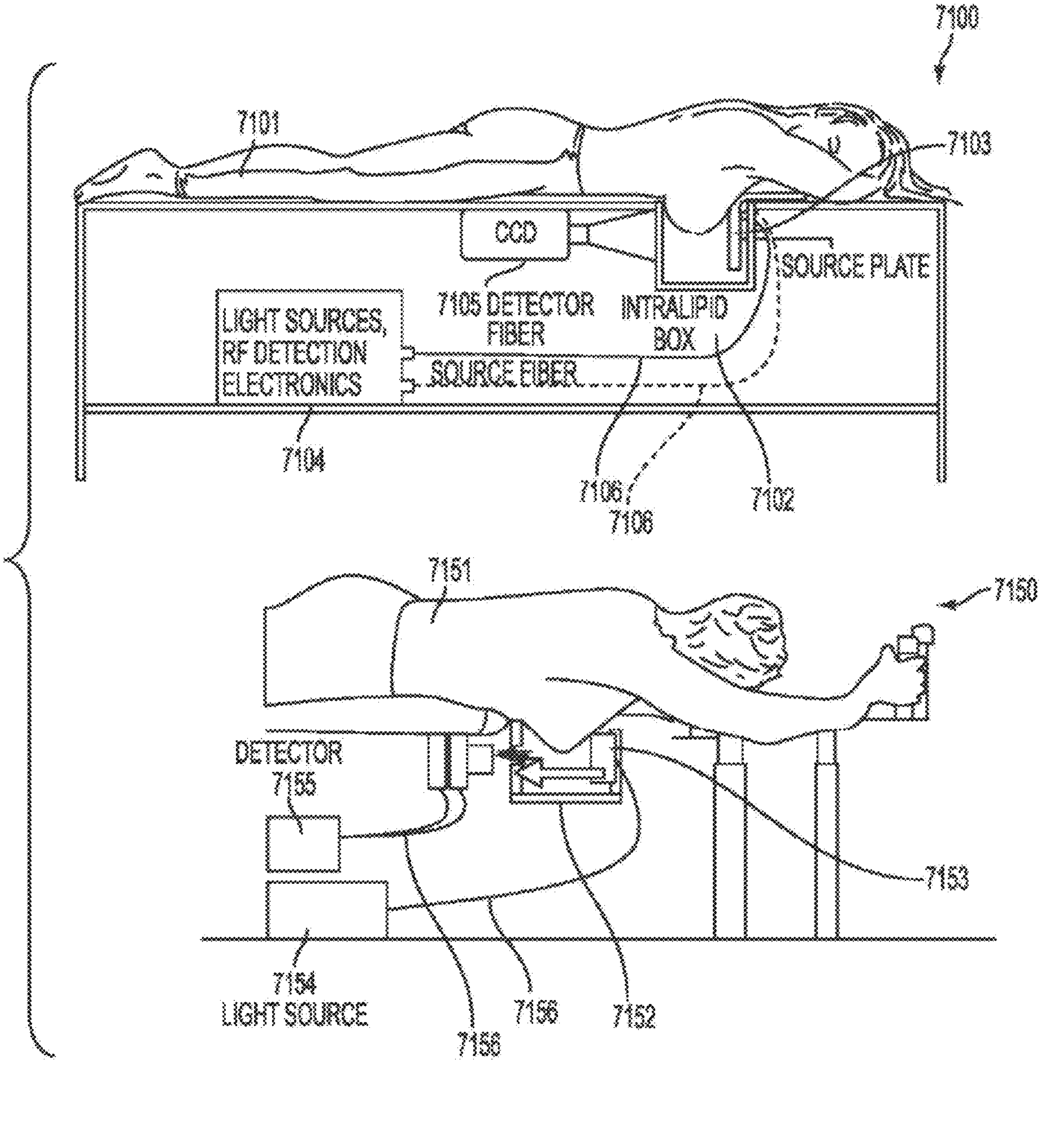
FIG. 71 illustrates particular embodiments of imaging systems for optically scanning a breast.

Several particular embodiments of imaging systems 7100, 7150 for optically scanning abreast are illustrated in FIG. 71. In these particular embodiments, the patient 7101, 7151 may lie in a prone position with her breasts inside a box 7102, 7152 with probably a transparent window on the detector side. A compression plate 7103, 7153 may hold the breast in place against the viewing window by mildly compressing the breast to a thickness between about 5.5 and 7.5 cm. The box 7102, 7152 may then be filled with a matching fluid with optical properties similar to human breast. In one instance, the matching fluid may comprise water, india ink for absorption, and a fat emulsion for scattering. The embodiments in FIG. 71 may also have one or more detectors 7104, 7155, one or more light sources 7104, 7154, various electronics, and even an imaging system based on charge coupled devices 7105. As illustrated in FIG. 71, the light sources 7104, 7154 and detectors 7104, 7155 may be coupled to the box 7102, 7152 through one or more fibers 7106, 7156. Also, the imaging may be in reflection mode (top of FIG. 71), transmission mode (bottom of FIG. 71), or some combination.

Beyond the geometry and apparatus of FIG. 71, the optical imaging system may use one or more of three different illumination methods: continuous wave, time-domain photon migration, and frequency-domain photon migration. In one embodiment, continuous-wave systems emit light at approximately constant intensity or modulated at low frequencies, such as 0.1-100 kHz. In another embodiment, the time-domain photon migration technique uses relatively short, such as 50-400 psec, light pulses to assess the temporal distribution of photons. Since scattering may increase the times of flight spent by photons migrating in tissues, the photons that arrive earliest at the detector probably encountered the fewest scattering events. In yet another embodiment, the frequency-domain photon migration devices modulate the amplitude of the light that may be continuously transmitted at relatively high frequencies, such as 10 MHz to 1 GHz. For example, by measuring the phase shift and amplitude decay of photons as compared to a reference signal, information may be acquired on the optical properties of tissue, and scattering and absorption may be distinguished. Beyond these three methods, other techniques or combinations of these methods may be used, and these other methods are also intended to fall within the scope of this disclosure.

Although particular embodiments of imaging architectures are illustrated in FIG. 71, other system architectures may also be used and are also intended to be covered by this disclosure. For example, in one embodiment several couples of optical fibers for light delivery and collection may be arranged along one or more rings placed at different distances from the nipple 7004. In an alternate embodiment a "cap" with fiber leads for light sources and detectors may be used that fits over the breast. In yet another embodiment, imaging optics and light sources and detectors may surround the nipple 7004 and areola 7005 regions of the breast. As yet another alternative, a minimally invasive procedure may involve inserting needles with fiber enclosure (to light sources and detectors or receivers) into the breast, so as to probe regions such as the lobules 7003 and connective tissue. Both non-invasive and minimally invasive optical imaging methods are intended to be covered by this disclosure.

Optical Wavelength Ranges for Cancer Detection

Figure 72:
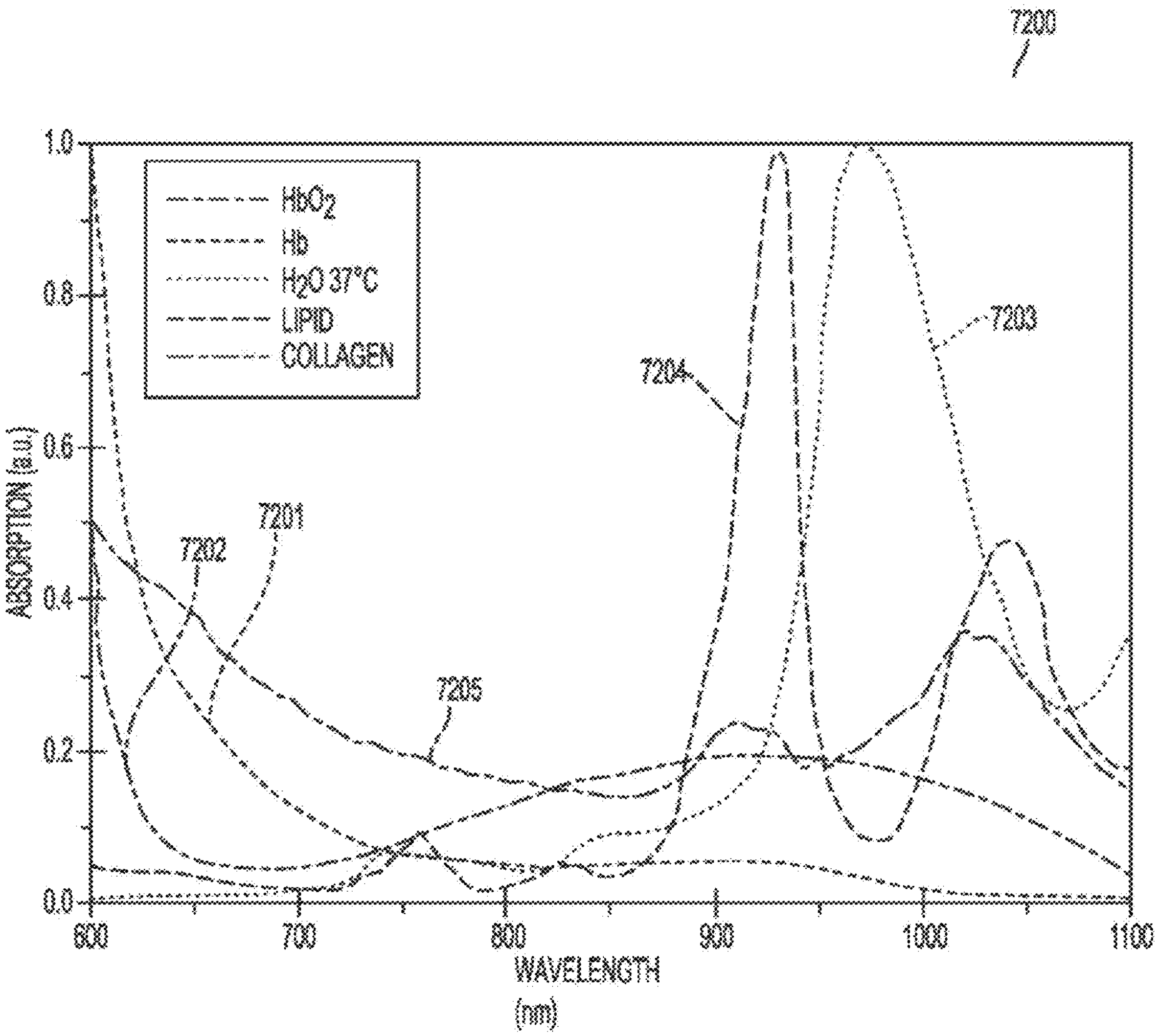
FIG. 72 shows the normalized absorption spectra of main tissue absorbers in the NIR for breast cancer, between about 600-1100 nm.

Many of the diffuse optical tomography studies previously conducted have relied on using NIR in the wavelength range of about 600-1000 nm, where light absorption at these wavelengths may be minimal, allowing for sufficient tissue penetration (up to 15 cm). In these wavelength ranges, it has been claimed that concentrations of oxy- and deoxy-hemoglobin, water, and lipids can be determined. For example, FIG. 72 shows the normalized absorption spectra 7200 of main tissue absorbers in the NIR between about 600 nm and 1100 nm: deoxy-hemoglobin, Hb, 7201, oxy-hemoglobin, HbO2, 7202, water 7203, lipids 7204 and collagen 7205. It is speculated that in a malignant tumor, hemoglobin concentration may be directly related to angiogenesis, one of the main factors required for tumor growth and metastases. Moreover, the proportions of oxy- and deoxy-hemoglobin in a tumor may change due to its metabolism. Thus, by measuring concentrations of the breast components, discrimination of benign and malignant tumors may be possible with diffuse optical imaging. Experiment evidence suggests that cancerous tissue is associated with higher hemoglobin and water concentrations, and a lower lipid concentration with respect to normal breast tissue.

Based on FIG. 68 and the dynamics of carcinoma, it may be advantageous to perform spectroscopy in longer wavelengths, such as windows between 1000-1400 nm or 1600-1800 nm. For example, looking at the absorption curves 6800 in FIG. 68, the absorption between approximately 1000-1300 nm may be comparable to the 600-1000 nm window described in FIG. 72. However, the loss through the soft tissue medium (penetration depth may be inversely related to the loss) will be due to absorption and scattering. In fact, the scattering properties of tissue may also contain valuable information for lesion diagnosis. Since the scattering is inversely proportional to some power of wavelength (for example, in some tissue scattering is inversely proportional to the wavelength cubed), the scattering contribution to the loss may decrease at longer wavelengths. Moreover, these longer wavelength windows may contain diagnostic information on content of collagen and adipose, both of which may be significant indicators for breast cancer.

Figure 73:
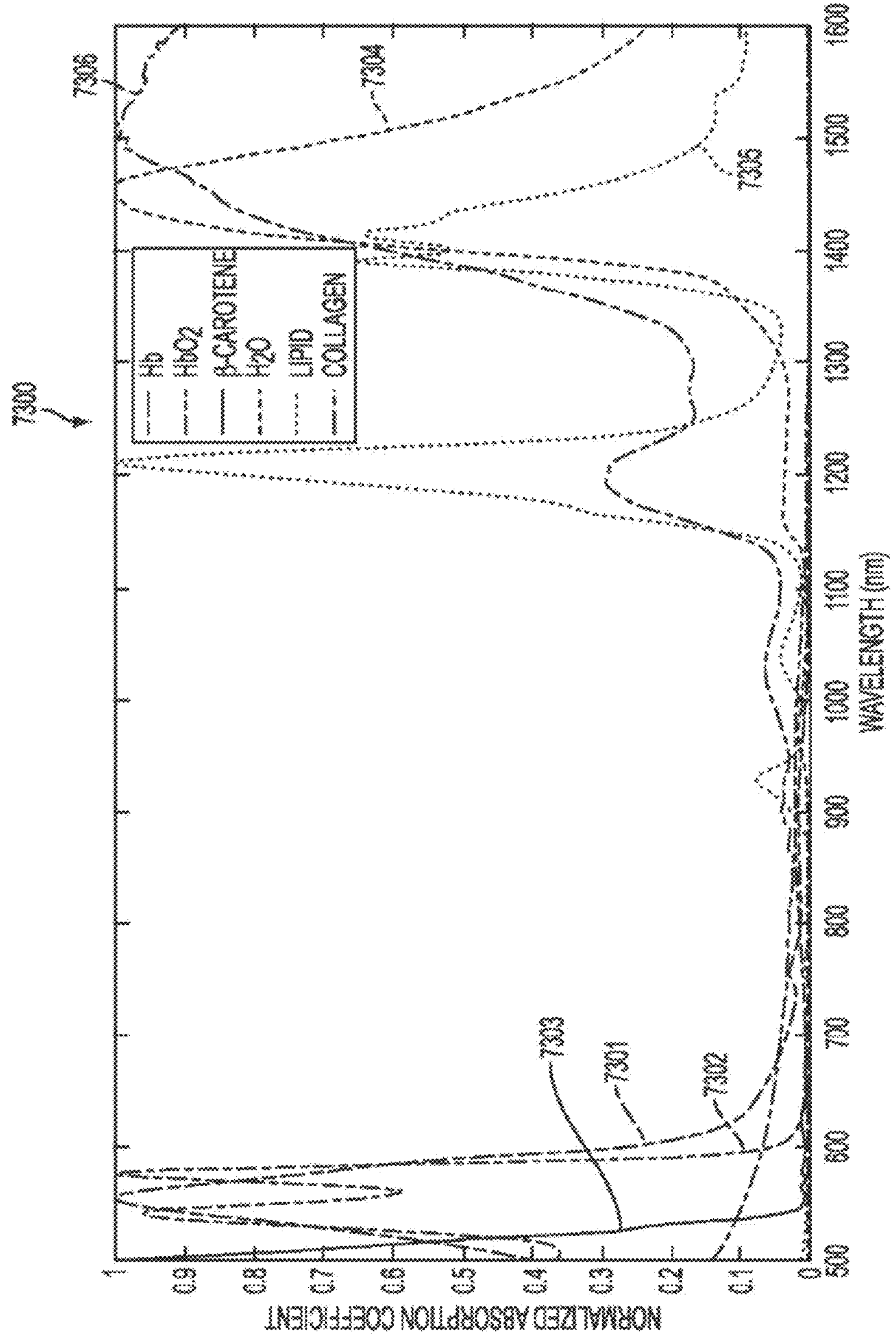
FIG. 73 illustrates the normalized absorption coefficient in the wavelength range between about 500-1600 nm for many of the components of breast tissue.

Breast cancer spectroscopy may benefit from the use of wavelengths longer than about 1000 nm for a number of reasons. As one example, the main absorbers in soft tissues of the visible spectrum of light may be oxy- and deoxygenated hemoglobin and beta-carotene. On the other hand, primary absorbers in the near-infrared spectrum of light may be water, adipose tissue and collagen. Particularly adipose and collagen content may be valuable for early detection of cancers. In one embodiment, increased levels of collagen in breast malignancies are thought to be due to increased vascularity of the tumors. Collagen type I may be an important component of artery walls. FIG. 73 illustrates the normalized absorption coefficient 7300 in the wavelength range between about 500 nm and 1600 nm for Hb 7301, HbO2 7302, beta-carotene 7303, water 7304, lipid 7305 and collagen 7306.

Collagen and Adipose Signatures in Near-Ir

Examining the collagen content may be a valuable indicator for breast cancer detection. Collagen is one of the important extracellular matrix proteins, and fibrillar collagens help to determine stromal architecture. In turn, changes in the stromal architecture and composition are one of the aspects of both benign and malignant pathologies, and, therefore, may play an initial role in breast carcinogenesis. For example, collagen seems to be related to cancer development, because high mammographic density may be recognized as a risk factor for breast cancer. Moreover, collagen type in high-risk dense breasts may appear to be different from collagen in low-density breasts.

Experimental data also shows that malignant mammary gland tissues of animals and humans show a decrease in lipids when compared to normal tissues. The reduced amounts of lipids in the cancerous sites may be caused by a high metabolic demand of lipids in the malignant tumors. For example, due to the rapid proliferation of cancerous cells, there may be reduced lipid content in cancerous tissues. Thus, in addition to collagen, another valuable marker for breast cancer may be the lipid spectral features. It may also be possible to combine the markers from oxy- and deoxygenated hemoglobin and water with lipid and collagen lines to improve the diagnostics and/or therapeutics of optical imaging and/or treatment for breast and other types of cancer. Although specific examples of tissue constituents are discussed, other tissue constituents and related markers may also be associated with breast cancer and other cancers, and these other constituents are also intended to be covered by this disclosure.

Figure 74A:
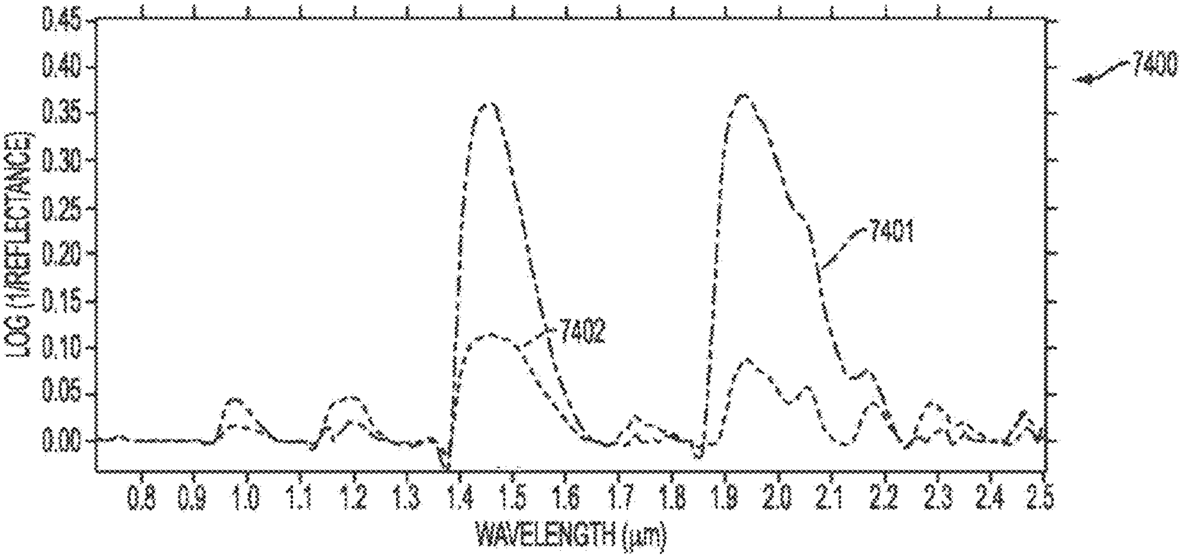
FIG. 74A shows the typical spectra of the cancerous site of a treated rat and the corresponding site of a normal rat and illustrates the logarithm of the inverse of reflection spectra.
Figure 74B:
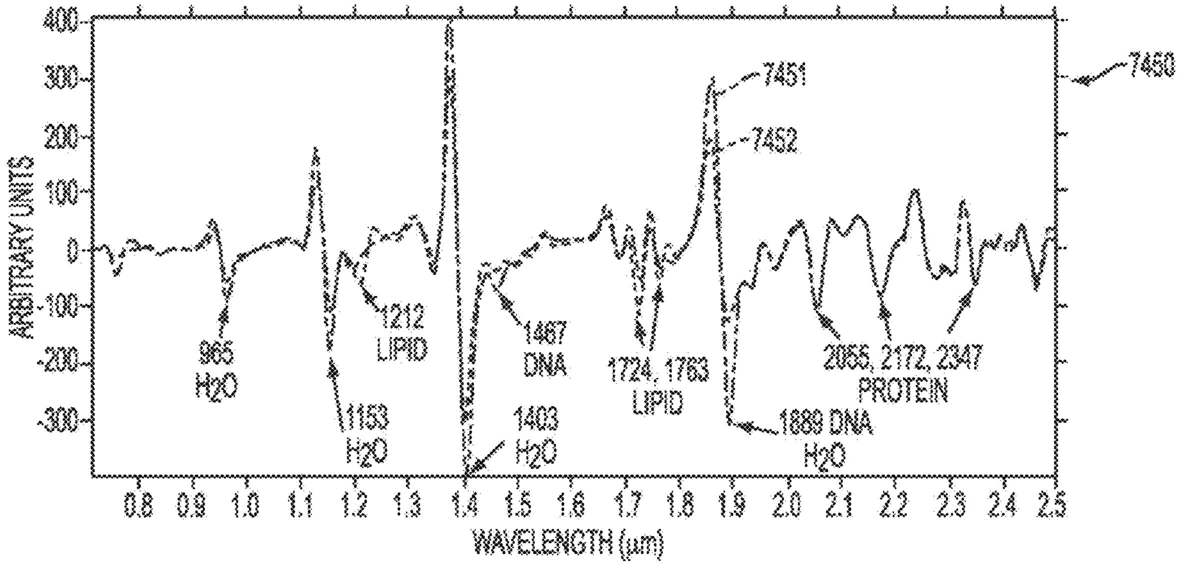
FIG. 74B shows the typical spectra of the cancerous site of a treated rat and the corresponding site of a normal rat and illustrates second derivative spectra.

As an example of the types of spectral signatures that may exist, in vivo investigations of progressive changes in rat mammary gland tumors were conducted using near-infrared spectroscopy with a Fourier-transform infrared spectrometer. In one embodiment, FIG. 74 shows the typical spectra of the cancerous site of the treated rat and the corresponding site of the normal rat. FIG. 74A shows the logarithm of the inverse of reflection spectra 7400, while FIG. 74B shows their second derivative spectra 7450. The curves 7401, 7451 correspond to the spectra of the cancerous sites, while 7402, 7452 correspond to the spectra of the normal sites. Since the second derivative techniques may be useful in the analyses of NIR spectra to minimize baseline offsets and to resolve overlapping absorption without compromising signal-to-noise, FIG. 74B may be used for interpretation of the spectral changes.

In FIG. 74B identification may be made of several of the spectral features. In particular, there are DNA bands near 1471 nm and 1911 nm, while there are water bands near 967 nm, 1154 nm, 1402 nm, and 1888 nm. Moreover, there are lipid bands near 1209 nm, 1721 nm and 1764 nm, and there are protein bands near 2055 nm, 2172 nm and 2347 nm. The NIR spectra of FIG. 74 show that the DNA and water contents in the cancerous tissue may be higher than those in normal tissues. On the other hand, the lipid content in the cancerous tissue may be less than the lipid content in normal tissues. With protein contents, however, little difference may be found between the normal and cancerous tissue.

Figure 75:
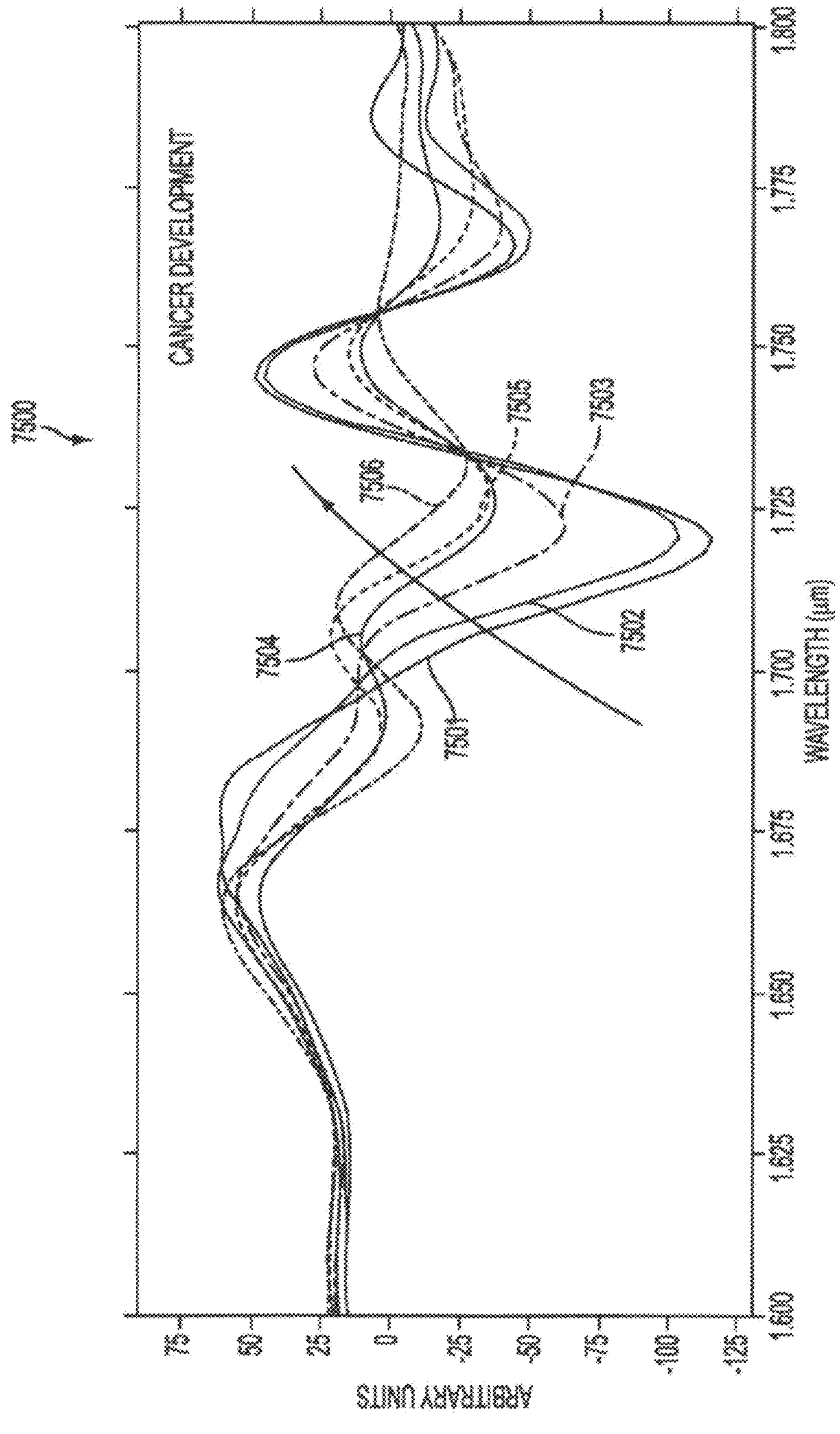
FIG. 75 shows the second derivative of spectral changes over several weeks between about 1600-1800 nm in rats with breast cancer.

These experiments on rats with breast cancer were also used to observe the temporal progression of the cancer. In this embodiment, as the cancer grew, the lipid band intensity decreased, and this band also shifted to higher wavelengths, and collagen peaks appeared in the tissues. In FIG. 75, the second derivative spectral changes 7500 were investigated in the 1600 nm to 1800 nm wavelength range over several weeks. An early cancer was detected in the 5th week, and then it grew rapidly from the 6th 7501 to the 7th 7502 week. The cancer's temporal progression through the 8th 7503, 9th 7504, 10th 7505 and 11th 7506 week are shown in the various curves in FIG. 75. With the cancer growth, the intensity of the lipid band in the vicinity of 1721 nm decreased, and this band shifted to higher wavelengths by 7 nm at the 11th week 7506 compared to the wavelength band at the 5th week. The higher wavelength shift may indicate that an order parameter of the lipids increases with progressive cancer growth.

Figure 78:
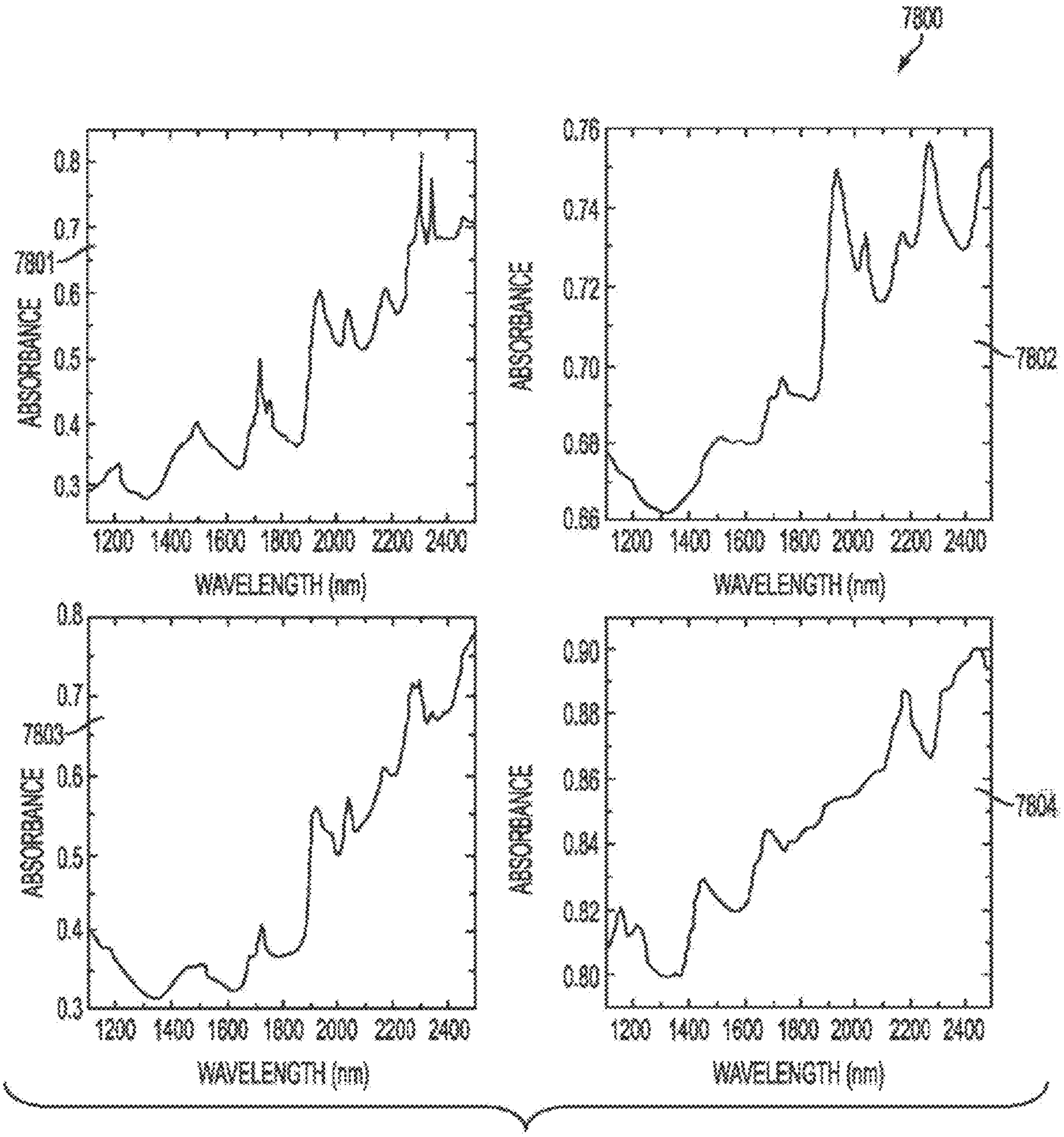
FIG. 78 illustrates the absorbance for four types of collagen: collagen I, collagen II, collagen III, and collagen IV.

Moreover, in the data of FIG. 75 is seen that a new peak appeared as the cancer grew around 1690 nm, which may be assigned to be a collagen absorption by comparison with the absorptions of standard collagen (c.f., FIG. 78). The higher wavelength shift may be attributable to the formation of elastic fibers in the lipid layer with collagen induced in the cancer tissues, thus leading to an increased order parameter of the lipids. Thus, it can be seen that significant information about breast cancer tissue compared with normal tissue may be obtained by spectroscopy at the longer wavelengths in the near-infrared.

Figure 76:
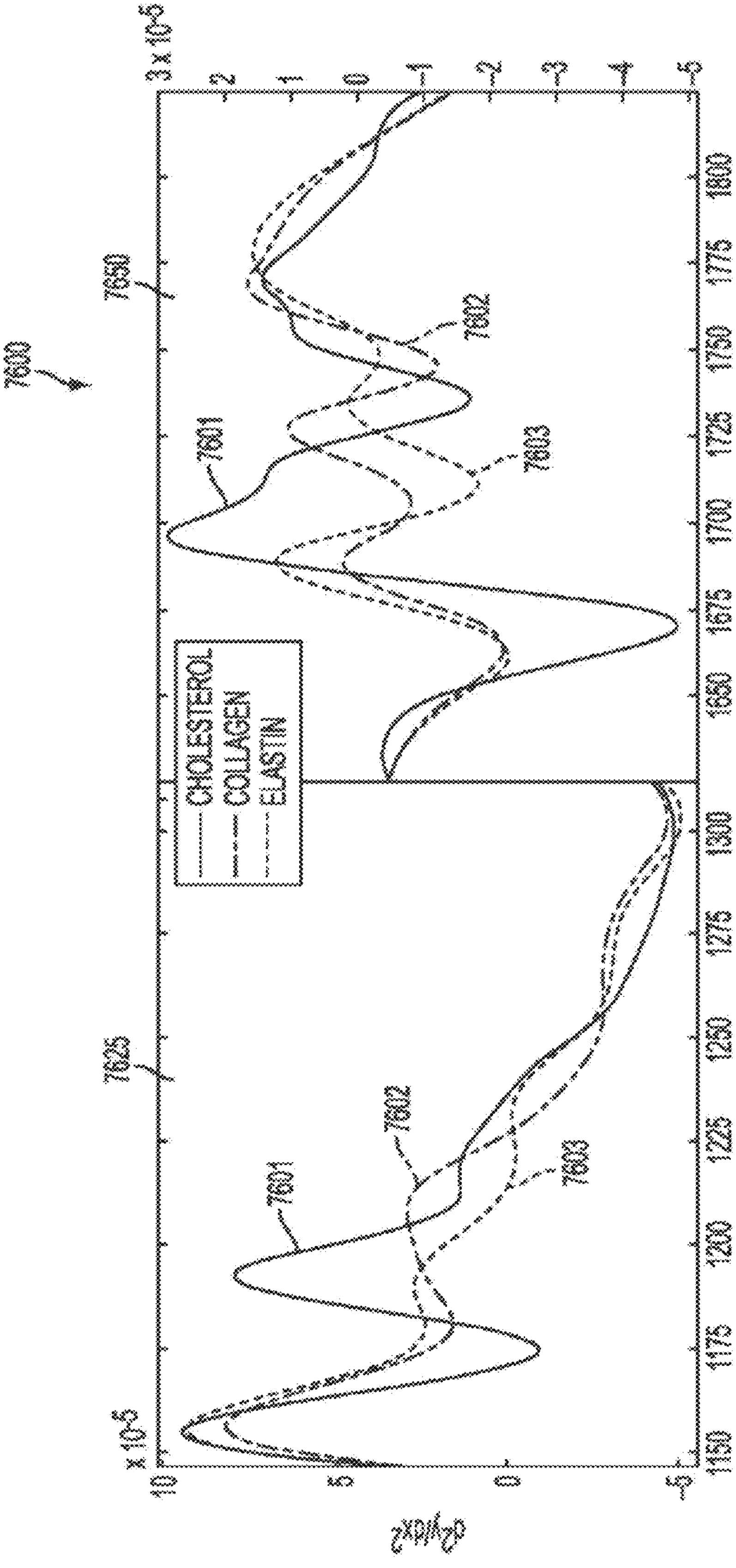
FIG. 76 illustrates the second derivative spectra for cholesterol, collagen and elastin.

The second derivative spectra may also be insightful for observing and monitoring changes in tissue as well as characterizing tissue in the near-infrared wavelength range. As an example, FIG. 76 illustrates the second derivative spectra 7600 for cholesterol (similar to one embodiment of lipids) 7601, collagen 7602, and elastin 7603. The left curve 7625 shows the second derivative data over the wavelength range of about 1150 nm to 1300 nm, while the right curve 7650 shows the second derivative data over the wavelength range of about 1600 nm to 1850 nm. These wavelengths show numerous features for cholesterol/lipid 7601, collagen 7602, and elastin 7603, which again emphasizes the added value of using wavelengths longer than about 1000 nm for cancer diagnostics.

Figure 77:
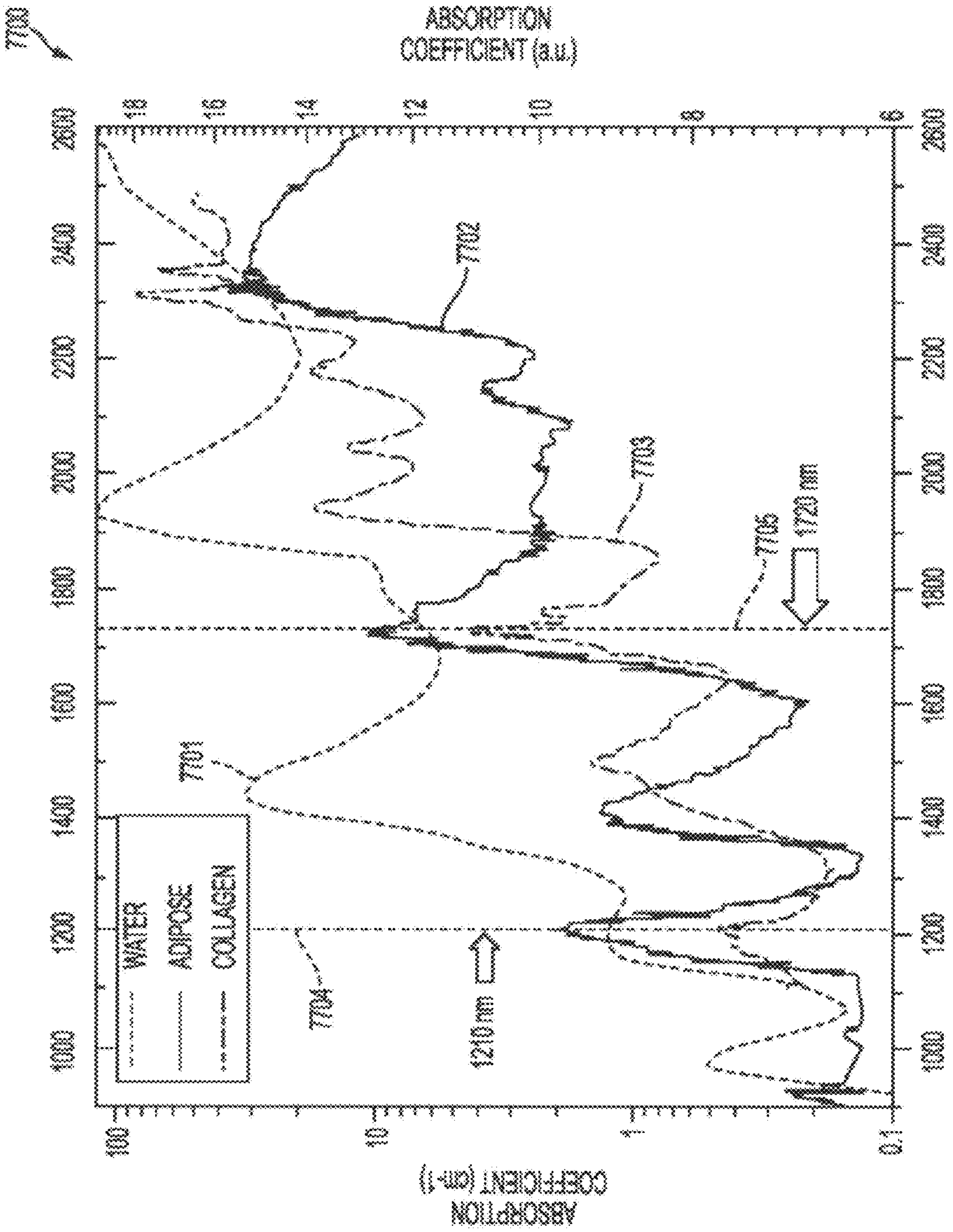
FIG. 77 shows the absorption coefficient as a function of wavelength between about 1000 nm and 2600 nm for water, adipose and collagen.

To further illustrate the value of using longer wavelengths in the NIR or SWIR for observing changes in breast cancer and other cancer markers, the spectra of in water, lipids/adipose and collagen of different varieties may be studied. As one embodiment, the absorption coefficients 7700 are shown in FIG. 77 as a function of wavelength between about 1000 nm and 2600 nm. FIG. 77 overlaps the absorption coefficient for water 7701, adipose 7702 (forms of adipose include fatty tissue and acids, lipids, and cholesterol), and collagen type I 7703. One may note that particular absorption peaks for adipose 7702 and collagen type I 7703 align at wavelengths near 1210 nm 7704 and 1720 nm 7705, which also correspond to local minima in water absorption.

Moreover, the NIR spectra for collagen also depend on the type of collagen. As an example, FIG. 78 illustrates the absorbance 7800 for four types of collagen: collagen I 7801, collagen II 7802, collagen III 7803, and collagen IV 7804. Collagen I, for instance, may be a major constituent of stroma. Also, collagen I and collagen III may be the principal collagens of the aorta. Since the spectra of the four collagens are distinctive, multicomponent analysis of collagens may possibly be used to distinguish the type of collagen involved.

The experimental results discussed thus far indicate that breast cancer detection may benefit from spectroscopy in the NIR and SWIR, particularly wavelengths between approximately 1000-1400 nm and 1600-1800 nm. These are wavelength windows that may have deep penetration into soft tissue, while still falling within lower absorption valleys of water. Moreover, the longer wavelengths lead to less scattering in tissue and water, again permitting deeper penetration of the light. In the NIR and SWIR wavelength range, the spectra of standard samples of cholesterol, protein, collagen, elastin and DNA were measured to obtain information on their characteristic bands in the spectra of mammary gland tissues. Absorption peaks in the standard samples occur at the following exemplary wavelengths:

Collagen: 1182 nm, 1360 nm, 1426 nm, 1496 nm, 1569 nm, 1690 nm, 1732 nm;

Lipids: 1157 nm, 1209 nm, 1404 nm, 1721 nm, 1764 nm;

Cholesterol: 918 nm, 1195 nm, 1376 nm, 1585 nm, 1711 nm, 1757 nm;

Protein: 910 nm, 1143 nm, 1186 nm, 1279 nm, 1420 nm, 1503 nm, 1579 nm, 1690 nm, 1739 nm, 1799 nm; and DNA: 1414 nm, 1471 nm, 1626 nm, 1728 nm.

Comparing these absorption features with the data in FIGS. 73-78 shows that there are absorption features or signatures in the second derivatives that can be used to monitor changes in, for example, collagen and lipids. By using broadband light and performing spectroscopy in at least some part of the wavelength windows between about 1000-1400 nm and/or 1600-1800 nm, the collagen and lipid changes, or other constituent changes, may be monitored. In one embodiment, for breast cancer the decrease in lipid content, increase in collagen content, and possible shift in collagen peaks may be observed by performing broadband light spectroscopy and comparing normal regions to cancerous regions as well as the absorption strength as a function of wavelength. The spectroscopy may be in transmission, reflection, diffuse reflection, diffuse optical tomography, or some combination. Also, this spectroscopy may be augmented by fluorescence data, if particular tags or markers are added. Beyond looking at the absorbance, the data processing may involve also observing the first, second, or higher order derivatives.

Broadband spectroscopy is one example of the optical data that can be collected to study breast cancer and other types of cancer. However, other types of spectral analysis may also be performed to compare the collagen and lipid features between different wavelengths and different tissue regions (e.g., comparing normal regions to cancerous regions), and these methods also fall within the scope of this disclosure. For example, in one embodiment just a few discrete wavelengths may be monitored to see changes in lipid and collagen contents. In a particular embodiment, wavelengths near 1200 nm may be monitored in the second derivative data of FIG. 76 to measure the cholesterol/lipid peak below 1200 nm in 7601 versus the collagen peak above 1200 nm in 7602. In yet another embodiment, the absorption features in FIG. 73 may be relied upon to monitor the lipid content 7305 by measuring near 1200 nm and the collagen content 7306 by measuring near 1300 nm. Although these embodiments use only two wavelengths, any number of wavelengths may be used and are intended to be covered by this disclosure.

Thus, a breast cancer monitoring system, or a system to monitor different types of cancers, may comprise broadband light sources and detectors to permit spectroscopy in transmission, reflection, diffuse optical tomography, or some combination. In one particular embodiment, high signal-to-noise ratio may be achieved using a fiber-based supercontinuum light source (described further herein). Other light sources may also be used, including a plurality of laser diodes, super-luminescent laser diodes, or fiber lasers.

Wavelength ranges that may be advantageous for cancer detection include the NIR and SWIR windows (or some part of these windows) between about 1000-1400 nm and 1600-1800 nm. These longer wavelengths fall within local minima of water absorption, and the scattering loss decreases with increasing wavelength. Thus, these wavelength windows may permit relatively high penetration depths. Moreover, these wavelength ranges contain information on the overtone and combination bands for various chemical bonds of interest, such as hydrocarbons.

These longer wavelength ranges may also permit monitoring levels and changes in levels of important cancer tissue constituents, such as lipids and collagen. Breast cancer tissue may be characterized by decreases in lipid content and increases in collagen content, possibly with a shift in the collagen peak wavelengths. The changes in collagen and lipids may also be augmented by monitoring the levels of oxy- and deoxy-hemoglobin and water, which are more traditionally monitored between 600-1000 nm. Other optical techniques may also be used, such as fluorescent microscopy.

To permit higher signal-to-noise levels and higher penetration depths, higher intensity or brightness of light sources may be used. With the higher intensities and brightness, there may be a higher risk of pain or skin damage. At least some of these risks may be mitigated by using surface cooling and focused infrared light, as further described herein.

Laser Experiments: Penetration Depth, Focusing, Skin Cooling

Some preliminary experiments show the feasibility of using focused infrared light for non-invasive procedures, or other procedures where relatively shallow vessels below the skin are to be thermally coagulated or occluded with minimum damage to the skin upper layers. In one embodiment, the penetration depth and optically induced thermal damage has been studied in chicken breast samples. Chicken breast may be a reasonable optical model for smooth muscle tissue, comprising water, collagen and proteins. Commercially available chicken breast samples were kept in a warm bath (~32 degree Celsius) for about an hour, and then about half an hour at room temperature in preparation for the measurements.

Figure 79:
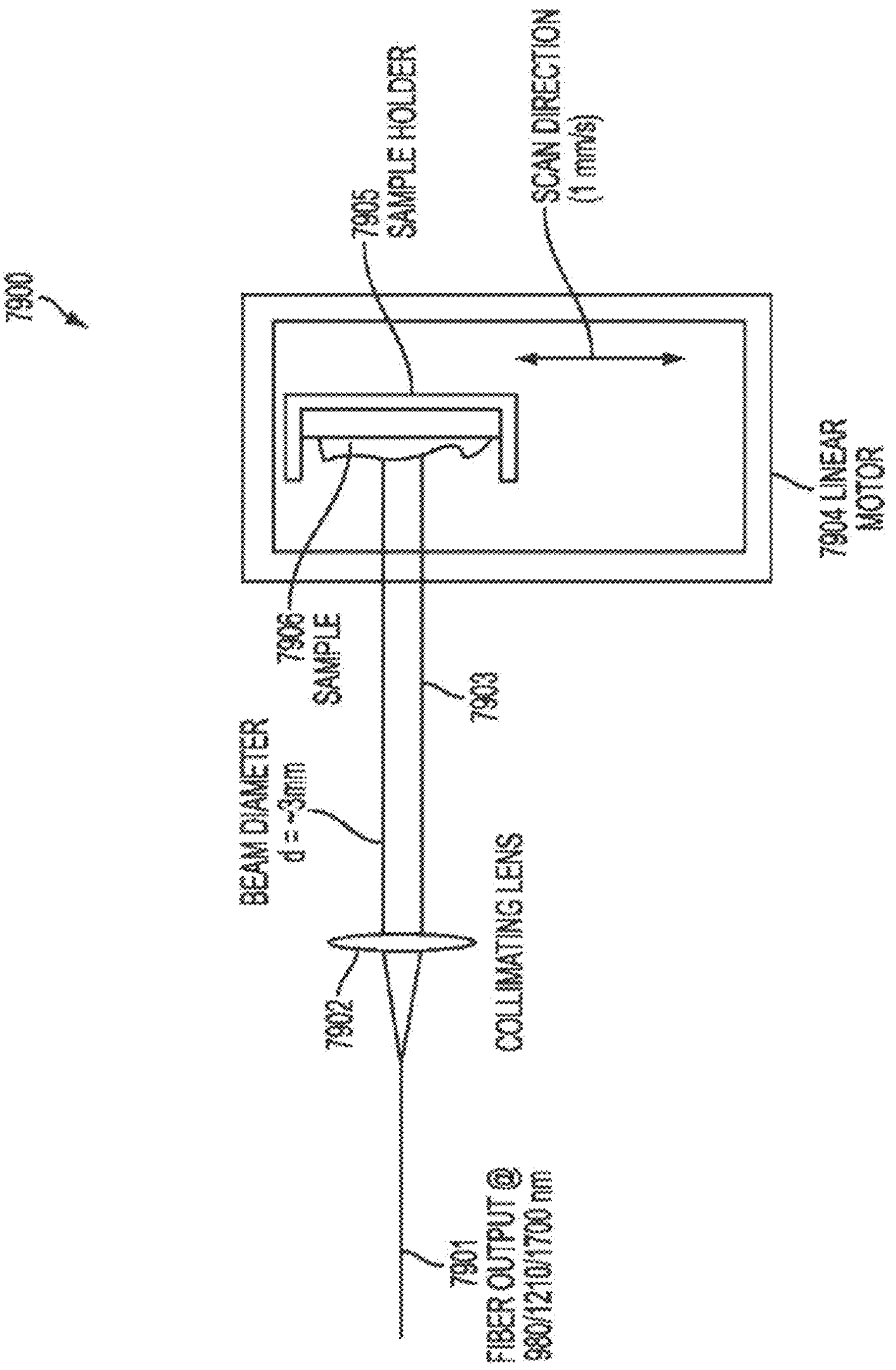
FIG. 79 shows an experimental set-up for testing chicken breast samples using collimated light. In this experiment, the collimated light has a beam diameter of about 3 mm.

An exemplary set-up 7900 for testing chicken breast samples using collimated light is illustrated in FIG. 79. The laser light 7901 near 980 nm, 1210 nm, or 1700 nm may be provided from one or more laser diodes or fiber lasers, as described further below. In this instance, laser diodes were used, which comprise a plurality of laser diode emitters that are combined using one or more multiplexers (particularly spatial multiplexers), and then the combined beam is coupled into a multi-mode fiber (typically 100 microns to 400 microns in diameter). The output from the laser diode fiber was then collimated using one or more lenses 7902. The resulting beam 7903 was approximately round with a beam diameter of about 3 mm. The beam diameter was verified by blade measurements (i.e., translating a blade across the beam). Also, the time-averaged power was measured in the nearly collimated section after the lens using a large power meter. The chicken breast samples 7906 were mounted in a sample holder 7905, and the sampler holder 7905 was mounted in turn on a translation stage 7904 with a linear motor that could move perpendicular to the incoming laser beam. Although particular details of the experiment are described, other elements may be added or eliminated, and these alternate embodiments are also intended to be covered by this disclosure.

Figure 80:
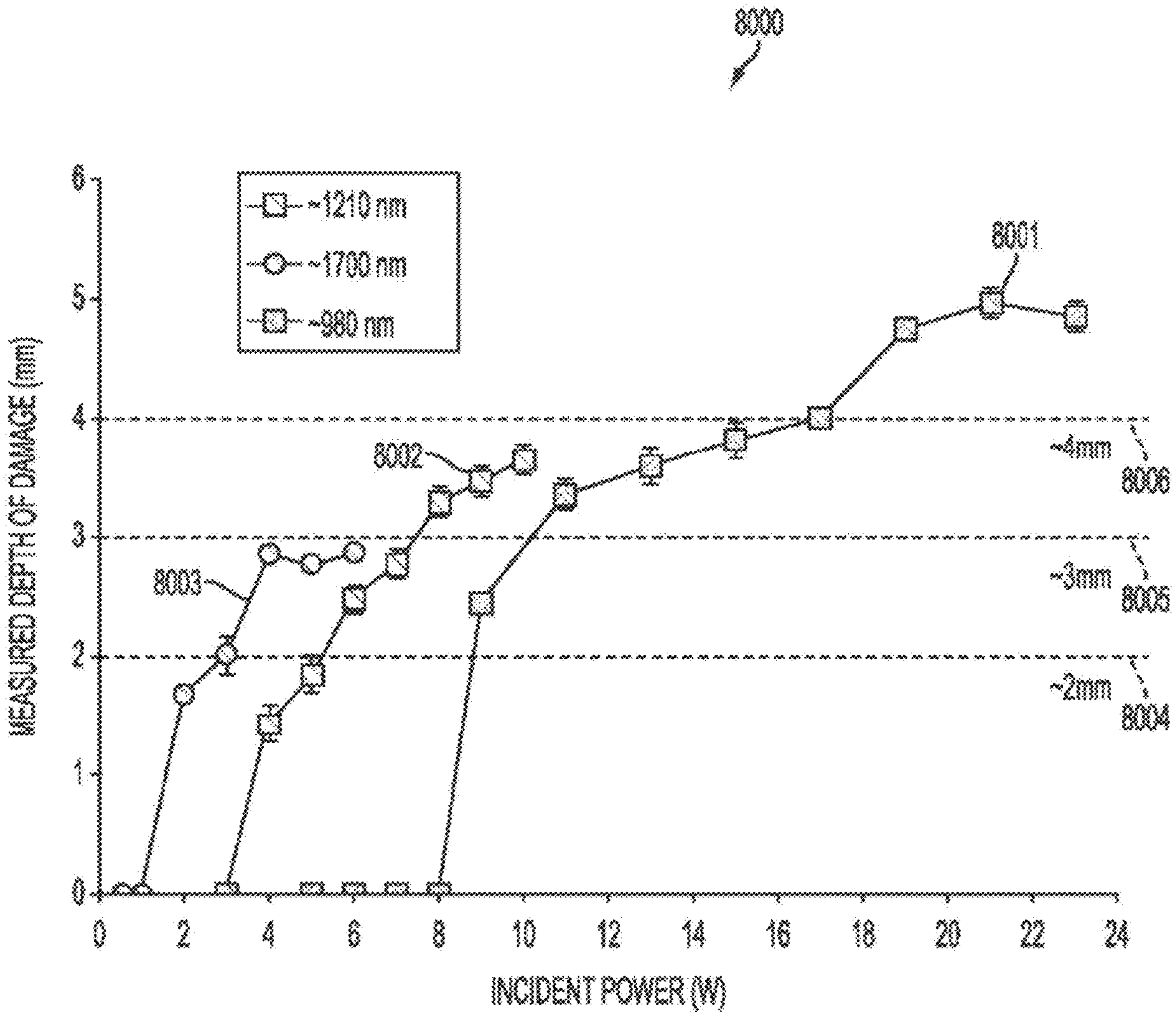
FIG. 80 plots the measured depth of damage (in millimeters) versus the time-averaged incident power (in Watts). Data is presented for laser wavelengths near 980 nm, 1210 nm and 1700 nm, and lines are drawn corresponding to penetration depths of approximately 2 mm, 3 mm, and 4 mm.

For these particular experiments, the measured depth of damage (in millimeters) versus the incident laser power (in Watts) is shown 8000 in FIG. 80. In this embodiment, laser diodes were used at wavelengths near 980 nm, 1210 nm and 1700 nm. The curve 8001 corresponds to about 980 nm, the curve 8002 corresponds to about 1210 nm, and the curve 8003 corresponds to about 1700 nm. It may be noted that there is a threshold power, above which the damage depth increases relatively rapidly. For example, the threshold power for wavelengths around 980 nm may be about 8 W, the threshold power for wavelengths around 1210 nm may be 3 W, and the threshold power for wavelengths around 1700 nm may be about 1 W. The threshold powers may be different at the different wavelengths because of the difference in water absorption (e.g., 7701 in FIG. 77). Part of the difference in threshold powers may also arise from the absorption of proteins such as collagen (e.g., 7703 in FIG. 77). After a certain power level, the damage depth appears to saturate: i.e., the slope flattens out as a function of increasing pump power.

In one embodiment, if the penetration depth is defined as the depth where damage begins to approximately saturate, then for wavelengths of about 980 nm 8001 the penetration depth 8006 may be defined as approximately 4 mm, for wavelengths of about 1210 nm 8002 the penetration depth 8005 may be defined as approximately 3 mm, and for wavelengths of about 1700 nm 8003 the penetration depth 8004 may be defined as approximately 2 mm. These are only approximate values, and other values and criteria may be used to define the penetration depth. It may also be noted that the level of damage at the highest power points differs at the different wavelengths. For example, at the highest power point of 8003 near 1700 nm, much more damage is observed, showing evidence of even boiling and cavitation. This may be due to the higher absorption level near 1700 nm (e.g., 7701 in FIG. 77). On the other hand, at the highest power point 8001 near 980 nm, the damage is not as catastrophic, but the spot size appears larger. The larger spot size may be due to the increased scattering at the shorter wavelengths (e.g., 7701 in FIG. 77). Based on data 8000 such as in FIG. 80, it may be possible to select the particular wavelength for the laser beam to be used in the non-invasive procedure.

Even near wavelengths such as described in FIG. 80, the particular wavelength selected may be more specifically defined based on the target tissue of interest. In one particular embodiment, the vessel lumen may be modeled as water, and for this example assume that wavelengths in the vicinity of 980 nm are being selected to create thermal coagulation or occlusion. FIG. 81 shows the optical absorption or density as a function of wavelength 8100 between approximately 700 nm and 1300 nm. Curves are shown for the water absorption 8101, hemoglobin Hb absorption 8102, and oxygenated hemoglobin HbO2 8103. In this example, two particular wavelengths are compared: 980 nm 8104 and 1075 nm 8105. For instance, 980 nm may be generated using one or more laser diodes, while 1075 nm may be generated using an ytterbium-doped fiber laser. If maximizing the penetration depth is the significant problem, then 1075 nm 8105 may be preferred, since it falls near a local minimum in water 8101, hemoglobin 8102, and oxygenated hemoglobin 8103 absorption. On the other hand, if the penetration depth at 980 nm 8104 is adequate and the problem is to generate heat through water absorption, then 980 nm 8104 may be a preferred wavelength for the light source because of the higher water absorption. This wavelength range is only meant to be exemplary, but other wavelength ranges and particular criteria for selecting the wavelength may be used and are intended to be covered by this disclosure.

In another embodiment, focused infrared light has been used to preserve the top layer of a tissue while damaging nerves at a deeper level. For instance, FIG. 82 illustrates the set-up 8200 used for the focused infrared experiments. In this embodiment, a lens 8201 is used to focus the light. Although a single lens is shown, either multiple lenses, GRIN (gradient index) lenses, curved mirrors, or a combination of lenses and mirrors may be used. In this particular example, the tissue 8204 is placed between two microscope slides 8202 and 8203 for in vitro experiments. The tissue 8204 is renal artery wall either from porcine or bovine animals (about 1.2 mm thick sample)—i.e., this is the artery leading to the kidneys, and it is the artery where typically renal denervation may be performed to treat hypertension. For this example, the minimum beam waist 8205 falls behind the tissue, and the intensity contrast from the front of the tissue (closest to the lens) to the back of the tissue (furthest from the lens) is about 4:1. These are particular ranges used for this experiment, but other values and locations of minimum beam waist may also be used and intended to be covered by this disclosure.

For a particular embodiment, histology of the renal artery is shown in FIG. 83A for no laser exposure 8300 and shown in FIG. 83B with focused infrared laser exposure 8350. In this experiment, the beam diameter incident on the lens was about 4 mm, and the distance from the edge of the flat side of lens to the minimum beam waist was about 3.75 mm. The beam diameter on the front side of the renal artery (i.e., the endothelium side) was about 1.6 mm, and the beam diameter on the back side of the renal artery was about 0.8 mm. In FIG. 83A with no laser exposure, the layers of the artery wall may be identified: top layer of endothelium 8301 that is about 0.05 mm thick, the media comprising smooth muscle cells or tissue 8302 that is about 0.75 mm thick, and the adventitia 8303 comprising some of the renal nerves 8304 that is about 1.1 mm thick. These are particular values for this experiment, and other layers and thicknesses may also be used and are intended to be covered by this disclosure.

The histology with focused infrared light exposure 8350 is illustrated in FIG. 83B. The laser light used is near 1708 nm from a cascaded Raman oscillator (described in greater detail herein), and the power incident on the tissue is about 0.8 W and the beam is scanned across the tissue at a rate of approximately 0.4 mm/sec. The various layers are still observable: the endothelium 8351, the media 8352, and the adventitia 8353. With this type of histology, the non-damaged regions remain darker (similar to FIG. 83A), while the laser induced damaged regions turn lighter in color. In this example, the endothelium 8351 and top layer of the media 8352 remain undamaged—i.e., the top approximately 0.5 mm is the undamaged region 8356. The laser damaged region 8357 extends for about 1 mm, and it includes the bottom layer of the media 8352 and much of the adventitia 8353. The renal nerves 8354 that fall within the damage region 8357 are also damaged (i.e., lighter colored). On the other hand, the renal nerves beyond this depth, such as 8355, may remain undamaged.

Thus, by using focused infrared light near 1708 nm in this example, the top approximately 0.5 mm of the renal artery is spared from laser damage. It should be noted that when the same experiment is conducted with a collimated laser beam, the entire approximately 1.5 mm is damaged (i.e., including regions 8356 and 8357). Therefore, the cone of light with the lower intensity at the top and the higher intensity toward the bottom may, in fact, help preserve the top layer from damage. There should be a Beer's Law attenuation of the light intensity as the light propagates into the tissue. For example, the light intensity should reduce exponentially at a rate determined by the absorption coefficient. In these experiments it appears that the focused light is able to overcome the Beer's law attenuation and still provide contrast in intensity between the front and back surfaces.

In another embodiment, experiments have also been conducted on dermatology samples with surface cooling, and surface cooling is shown to preserve the top layer of the skin during laser exposure. In this particular example, the experimental set-up 8400 is illustrated in FIG. 84. The skin sample 8404, or more generally sample under test, is placed in a sample holder 8403. The sample holder 8403 has a cooling side 8401 and a heating side 8402. The heating side 8402 comprises a heater 8405, which may be adjusted to operate around 37 degrees Celsius—i.e., close to body temperature. The cooling side 8401 is coupled to an ice-water bath 8407 (around 2 degrees Celsius) and a warm-water bath 8406 (around 37 degrees Celsius) through a switching valve 8408. The entire sample holder 8403 is mounted on a linear motor 8409, so the sample can be moved perpendicular 8410 to the incoming light beam.

In this embodiment, the light is incident on the sample 8404 through a sapphire window 8411. The sapphire material 8411 is selected because it is transparent to the infrared wavelengths, while also being a good thermal conductor. Thus, the top layer of the sample 8404 may be cooled by being approximately in contact with the sapphire window 8411. The laser light 8412 used is near 1708 nm from a cascaded Raman oscillator (described in greater detail herein), and one or more collimating lenses 8413 are used to create a beam with a diameter 8414 of approximately 2 mm. This is one particular embodiment of the sample surface cooling arrangement, but other apparatuses and methods may be used and are intended to be covered by this disclosure.

Experimental results obtained using the set-up of FIG. 84 are included in FIG. 18. In this example, FIG. 85 shows the MTT histochemistry of human skin 8500 treated with ~1708 nm laser (5 seconds pre-cool; 2 mm diameter spot exposure for 3 seconds) at 725 mW (A 8501, B 8502) corresponding to about 70 J/cm2 average fluence, and 830 mW (C 8503, D 8504) corresponding to about 80 J/cm2 average fluence. The images in FIG. 85 show that the application of a cold window was effective in protecting the epidermis 8505 (darker top layer) and the top approximately 0.4 or 0.5 mm of the dermis 8506. As before, the darker regions of the histology correspond to undamaged regions, while the lighter regions correspond to damaged regions. In contrast, when no surface cooling is applied, then thermal damage to the dermis occurs in the epidermis and dermis where the laser exposure occurs, and the thermal damage extends to about 1.3 or 1.4 mm or more from the skin surface. Thus, surface cooling applied to the skin may help to reduce or eliminate damage to the top layer of the skin under laser exposure.

In summary, experiments verify that infrared light, such as near 980 nm, 1210 nm, or 1700 nm, may achieve penetration depths between approximately 2 mm to 4 mm or more. The top layer of skin or tissue may be spared damage under laser exposure by focusing the light beyond the top layer, applying surface cooling, or some combination of the two. These are particular experimental results, but other wavelengths, methods and apparatuses may be used for achieving the penetration and minimizing damage to the top layer and are intended to be covered by this disclosure. In an alternate embodiment, it may be beneficial to use wavelengths near 1310 nm if the absorption from skin constituents (FIG. 77), such as collagen 7703, adipose 7702 and elastin 7704, are to be minimized. The water absorption 7701 near 1310 nm may still permit a penetration depth of approximately 1 cm, or perhaps less. In yet another embodiment, wavelengths near 1210 nm may be beneficial, if penetration depths on the order of 3 mm are adequate and less scattering loss (e.g. 7701 in FIG. 77) is desired. Any of FIG. 68, 73, 75, 77, or 78 may be used to select these or other wavelengths to achieve the desired penetration depth and to also perhaps target particular tissue of interest, and these alternate embodiments are also intended to be covered by this disclosure.

Laser Systems for Therapeutics or Diagnostics

Infrared light sources can be used for diagnostics and therapeutics in a number of medical applications. For example, broadband light sources can advantageously be used for diagnostics, while narrower band light sources can advantageously be used for therapeutics. In one embodiment, selective absorption or damage can be achieved by choosing the laser wavelength to lie approximately at an absorption peak of particular tissue types. Also, by using infrared wavelengths that minimize water absorption peaks and longer wavelengths that have lower tissue scattering, larger penetration depths into the biological tissue can be obtained. In this disclosure, infrared wavelengths include wavelengths in the range of approximately 0.9 microns to 10 microns, with wavelengths between about 0.98 microns and 2.5 microns more suitable for certain applications.

As used throughout this document, the term "couple" and or "coupled" refers to any direct or indirect communication between two or more elements, whether or not those elements are physically connected to one another. In this disclosure, the term "damage" refers to affecting a tissue or sample so as to render the tissue or sample inoperable. For instance, if a particular tissue normally emits certain signaling chemicals, then by "damaging" the tissue is meant that the tissue reduces or no longer emits that certain signaling chemical. The term "damage" and or "damaged" may include ablation, melting, charring, killing, or simply incapacitating the chemical emissions from the particular tissue or sample. In one embodiment, histology or histochemical analysis may be used to determine whether a tissue or sample has been damaged.

As used throughout this disclosure, the term "spectroscopy" means that a tissue or sample is inspected by comparing different features, such as wavelength (or frequency), spatial location, transmission, absorption, reflectivity, scattering, refractive index, or opacity. In one embodiment, "spectroscopy" may mean that the wavelength of the light source is varied, and the transmission, absorption or reflectivity of the tissue or sample is measured as a function of wavelength. In another embodiment, "spectroscopy" may mean that the wavelength dependence of the transmission, absorption or reflectivity is compared between different spatial locations on a tissue or sample. As an illustration, the "spectroscopy" may be performed by varying the wavelength of the light source, or by using a broadband light source and analyzing the signal using a spectrometer, wavemeter, or optical spectrum analyzer.

As used throughout this document, the term "fiber laser" refers to a laser or oscillator that has as an output light or an optical beam, wherein at least a part of the laser comprises an optical fiber. For instance, the fiber in the "fiber laser" may comprise one of or a combination of a single mode fiber, a multi-mode fiber, a mid-infrared fiber, a photonic crystal fiber, a doped fiber, a gain fiber, or, more generally, an approximately cylindrically shaped waveguide or light-pipe. In one embodiment, the gain fiber may be doped with rare earth material, such as ytterbium, erbium, and/or thulium. In another embodiment, the infrared fiber may comprise one or a combination of fluoride fiber, ZBLAN fiber, chalcogenide fiber, tellurite fiber, or germanium doped fiber. In yet another embodiment, the single mode fiber may include standard single-mode fiber, dispersion shifted fiber, non-zero dispersion shifted fiber, high-nonlinearity fiber, and small core size fibers.

As used throughout this disclosure, the term "pump laser" refers to a laser or oscillator that has as an output light or an optical beam, wherein the output light or optical beam may be coupled to a gain medium to excite the gain medium, which in turn may amplify another input optical signal or beam. In one particular example, the gain medium may be a doped fiber, such as a fiber doped with ytterbium, erbium, and/or thulium. In another embodiment, the gain medium may be a fused silica fiber or a fiber with a Raman effect from the glass. In one embodiment, the "pump laser" may be a fiber laser, a solid state laser, a laser involving a nonlinear crystal, an optical parametric oscillator, a semiconductor laser, or a plurality of semiconductor lasers that may be multiplexed together. In another embodiment, the "pump laser" may be coupled to the gain medium by using a fiber coupler, a dichroic mirror, a multiplexer, a wavelength division multiplexer, a grating, or a fused fiber coupler.

As used throughout this document, the term "super-continuum" and/or "supercontinuum" and/or "SC" refers to a broadband light beam or output that comprises a plurality of wavelengths. In a particular example, the plurality of wavelengths may be adjacent to one-another, so that the spectrum of the light beam or output appears as a continuous band when measured with a spectrometer. In one embodiment, the broadband light beam may have a bandwidth of at least 10 nm. In another embodiment, the "super-continuum" may be generated through nonlinear optical interactions in a medium, such as an optical fiber or nonlinear crystal. For example, the "super-continuum" may be generated through one or a combination of nonlinear activities such as four-wave mixing, the Raman effect, modulational instability, and self-phase modulation.

As used throughout this disclosure, the terms "optical light" and/or "optical beam" and or "light beam" refer to photons or light transmitted to a particular location in space. The "optical light" and or "optical beam" and/or "light beam" may be modulated or unmodulated, which also means that they may or may not contain information. In one embodiment, the "optical light" and/or "optical beam" and/or "light beam" may originate from a fiber, a fiber laser, a laser, a light emitting diode, a lamp, a pump laser, or a light source.

As used throughout this document, the terms "near" or "about" or the symbol "~" refer to one or more wavelengths of light with wavelengths around the stated wavelength to accomplish the function described. For example, "near 1720 nm" may include wavelengths of between about 1680 nm and 1760 nm. In one embodiment, the term "near 1720 nm" refers to one or more wavelengths of light with a wavelength value anywhere between approximately 1700 nm and 1740 nm. Similarly, as used throughout this document, the term "near 1210 nm" refers to one or wavelengths of light with a wavelength value anywhere between approximately 1170 nm and 1250 nm. In one embodiment, the term "near 1210 nm" refers to one or more wavelengths of light with a wavelength value anywhere between approximately 1190 nm and 1230 nm.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

Section 6: Camera Based System with Processing (CSP) to Evaluate Facial Features Such as Blood Flow, Eyes and Vital Signs Human beings convey an enormous amount of information through their face. In fact, human beings are biologically constructed to evaluate different facial features to decipher much information about a person, ranging from emotions, moods, and mental state to pain and stress. Since humans can observe the facial features using eyes and the brain processing, camera-based systems combined with processing may also be able to extract a significant amount of information from viewing at least the face of a person. In some instances, additional information may be gained by also imaging the upper part of a person (e.g., possibly including neck, torso, chest, abdomen). The processing may include using a computing system that may also include artificial intelligence and machine learning algorithms and operate on hardware such as central processing units and graphical processing units. The camera based system may operate in the visible or near-infrared wavelengths, and the system may include CMOS-based cameras, CCD-based cameras, RGB cameras, near-infrared cameras, time-of-flight cameras, or a combination of these. In another embodiment, the camera system may co-register a high-resolution (e.g., multiple-megapixel) CMOS-camera with a lower resolution time-of-flight (ToF) sensor or camera to create a three-dimensional representation of the face or other scenes or objects. When co-registering the camera and ToF sensor/camera, the two cameras may cover the same region or different regions with partial overlap. Also, the camera and ToF may have similar or different fields-of-view. In one embodiment, the ToF may have lower pixel count than the camera. When co-registering, the depth information from the ToF may be registered with appropriate pixels from the camera image, and for the camera pixels in-between different ToF spots the depth value may be interpolated. Thus, the ToF sensor/camera may provide a framework or skeleton, and the camera image may be overlaid onto the framework or skeleton. The time-of-flight camera enables 3D imaging or mapping, providing, for example, the depth information. It turns out that the depth information from the time-of-flight camera can be used to compensate for at least some of the motion artifacts during the measurement.

In one embodiment, the Camera-based system combined with Processing (CSP) may observe multiple pieces of information on a person's face. For example, the CSP may evaluate the facial blood flow, eye movement, and vital signs/physiological parameters to decipher the state of a person (FIG. 86A). The CSP may first use face-tracking to identify different landmarks on the face and potentially build a bounding box around the face. One algorithm that may be used that is open-source available is MediaPipe, but other proprietary or non-proprietary algorithms may also be used. Once the face tracking has locked onto the face, the eye region can be parametrized to observe eye features. The facial blood flow in different regions of interest (ROIs) on the face may be observed and compared, such as the forehead, cheeks, nose, chin, etc. The physiological parameters/vital signs, such as heart rate, respiratory rate and heart rate variability, may be measured using methodologies earlier described in this application. These are three aspects of the facial features, but some or all of these may be used, or some or all of these may be combine with other features such as muscle movements, facial expressions, tilt of the head, etc. In some examples the facial features may also be combined with other information for lower parts of the body, such as the chest, hands, or what is often referred to as body language. In one embodiment, for example, motion of the chest may be used to measure physiological parameters such as respiratory rate. A ToF sensor/camera may easily be able to measure the chest motion during breathing, since the peak-to-peak motion may be in the range of 4 mm, 8 mm, 12 mm or more.

In one embodiment, the CSP system may combine cameras and ToF sensors to gather information about a user (cameras and sensors may be used interchangeably in this disclosure). For example, some cameras may be directed to the eye regions of the user to observe eye movement features, as well as eye closure and blink rates. Some cameras may be directed to the face of the user to observe the facial expressions, muscle movements, and facial blood flow on different regions of interest. Further cameras may be directed to hands or chest regions to judge gestures or hand and chest movements and to provide hand tracking. Yet other cameras may be directed toward the legs and feet of the user, so that movements of the body may be observed, perhaps using that information to help to compensate for motion artifacts. The ToF cameras or sensors may also be used to provide spatial or three-dimensional (3D) information about the user's environment, permitting the user to observe objects in the surrounding area, or position of the user relative to the environment. These are just some examples, but other benefits may be gained by combining the camera systems with the ToF sensor, and these as well as other combinations are intended to be covered by this disclosure. For example, the cameras and ToF sensors may also be combined with voice recognition systems and/or artificial intelligence/machine learning (AI/ML) processing to enhance the system performance or user experience.

Although much information is conveyed through the facial features, one problem is that many of the signatures are indirect measures. Since they are indirect measures of the state of the person, the information may be subject to errors, such as false positives or false negatives. For example, increased facial blood flow may indicate that the person just did a long running exercise, or it may indicate that the person is embarrassed about an event or something that was commented. To reduce the errors, the concept herein is to combine different features from the face as observed by the CSP to increase the reliability and accuracy of the diagnosis. Therefore, in one embodiment, the combination of facial blood flow analysis of different ROIs on the face, eye analysis (e.g., eye blink rate, percent of eye closure PERCLOS, pupil dilation, eye gaze direction, and/or eye movement parameters, such as saccade or fixation), and vital signs (such as heart rate, heart rate variability and/or respiratory rate) could lead to a more reliable indication of the state of the person. This is just one example, but only some of the CSP indicators could be use, or some or all of these could be combined with other features, such as facial expressions, muscle movements, head tilt or angle of head, speaking rate, other physiological parameters such as temperature, blood pressure, glucose level, HbA1c, or oximetry, etc. In addition, the data from the CSP system may be augmented with meta data, such as the person's age, height, weight, gender, body mass index, body fat percentage, body muscle percentage, demographic or ethnicity data, etc.

As described earlier in this application (e.g., in Sections 1-5), vital signs or physiological parameters (both terms are used synonymously used in this disclosure) of a user can be observed by changes in the blood flow through light absorption changes. As one example, photo-plethysmography (PPG) may be used, which relies on absorption of the light by blood in the tissue or skin. It might be noted that sometimes this may also be called remote photo-plethysmography (rPPG) or indirect photo-plethysmography (iPPG), typically corresponding to when a camera-based system is used that is non-contact and non-intrusive. Among the vital signs or physiological parameters that can be measured are heart rate and respiratory rate. As the heart beats, the blood flow oscillates up and down in the arteries and veins. As the blood volume oscillates, the absorption of the light also oscillates (c.f. FIG. 86B). Thus, by looking at the AC or oscillatory features, the heart rate may be measured. Also, generally as a person breaths in, the heart rate increases, and as a person breaths out, the heart rate decreases. So, the respiratory rate can also be measured by looking at the modulation of the heart rate. The respiratory rate may be derived from the heart rate by analyzing the envelope modulation, the frequency modulation, the baseline modulation, or other pattern changes in the heart beats. Alternately, the respiratory rate may also be measured by observing the chest motions of an individual. From the heart rate measurement, other physiological parameters may also be extracted, such as heart rate variability. For instance, the heart rate variability may correspond to the changes in peak-to-peak separation for heart rate measurements. In one embodiment, the standard deviation of the peak-to-peak separation of the heart rate distribution may correspond to the heart rate variability. These are just exemplary measurements, but many other techniques can be used to evaluate the physiological parameters by observing blood flow changes. Moreover, other physiological parameters may also be measured, including potentially blood pressure, blood oxygen level (oximetry), glucose or HbA1C levels, etc.

In a similar manner, the facial blood flow may be measured by changes in light absorption due to blood volume changes (particularly the absorption by hemoglobin), which may vary spatially across the facial region. In one particular embodiment, the facial blood flow may be measured at different ROIs on the face and compared, such as the forehead, nose, cheeks, chin, eye regions, and ear regions. In a particular embodiment, wavelengths of light near 850 nanometers or 940 nanometers may be incident on the user's face. At these near-infrared wavelengths, light is absorbed by blood. For example, FIG. 86C illustrates the wavelength dependence of the AC/DC ratio of reflection PPG signal. Although the peak ratio occurs near green wavelengths around 530 nanometers, there is still a change in the PPG signal at the near-infrared wavelengths. However, since the signal strength close to 850 nm or 940 nm is only about one-ninth of the signal strength in the green, operation in the near-infrared requires a higher signal-to-noise ratio than in the visible. The wavelengths near 850 nm or 940 nm are merely exemplary, and other wavelengths or combination of wavelengths for measuring PPG can be used consistent with this disclosure.

There are several advantages of using near-infrared wavelengths rather than visible wavelengths. First, the near-infrared light can be non-intrusive, since most people's eyes are not sensitive in the near-infrared. Second, the near-infrared wavelengths beyond 700 nm should be less sensitive to skin color, since melanin in the skin, which is responsible for the skin tone, absorbs much less at wavelengths longer than 700 nm. Third, because scattering in tissue reduces at longer wavelengths, the penetration depth into tissue may be deeper at some near-infrared wavelengths compared to visible wavelengths (c.f., FIG. 86D). However, it should be noted that at wavelengths longer than approximately 1000 nm, the penetration depth reduces again due to water absorption in the tissue. Finally, high efficiency light sources are available in the near-infrared wavelengths, such as light emitting diodes (LEDs) and vertical cavity surface emitting lasers (VCSELs).

One reason for the change in blood flow at different facial regions is due to activation of different muscles on the face. As an example, FIG. 87A illustrates some of the muscles on the face that lie below the skin, and FIG. 87B shows some of the arteries (red) and veins (blue) near the surface of the face. Different activation of muscles may be represented by different Action Units (AU). FIG. 87A exemplary shows 24 different AUs on the face. In order to change these muscles, blood flow to that region of the face may change (e.g., more blood flow to active the muscles for the arteries or veins in FIG. 87B). As an illustration, FIG. 88 shows the different activation units that may be activated for different emotions, such as happiness, surprise, or sadly fearful. Happiness may require changes in AU 6, 12, 25, surprise may require changes in AU 1, 2, 5, 26, and sadly fearful may require changes in AU 1, 4, 5, 20, 25. Thus, the changes in blood flow across the face may be correlated with different activation units, or it may also be an independent metric to judge the state of the person. In fact, facial color (e.g., changes in blood flow) may be an efficient mechanism to visually transmit emotion, over and beyond facial muscle movements.

In one embodiment, a face can send emotion information to observers by changing the blood flow or blood composition on the network of blood vessels close to the surface of the skin or tissue. For example, different blood flow patterns (e.g., differences in blood flow across different ROIs on the face) have been shown to be associated with emotions such as anger, disgust, happiness, happily disgusted, sad, and fearfully surprised. People are able to observe and understand these different color variations across the face, and the emotion-dependent variations in facial blood flow may be correctly interpreted even in the absence of facial muscle movement. Thus, it appears that the emotion information transmitted by color or blood flow changes may be at least partially independent from that by facial movements.

The blood flow on the face is at least partially controlled by a person's autonomic nervous system (ANS), as illustrated in FIG. 89. Within the ANS there are two branches, the sympathetic response ("fight or flight") and the parasympathetic response ("rest and digest"). When the sympathetic nerves dominate, a person's reactions may include pressure, tension, insomnia, anxiety, or going to toilet at night. When the parasympathetic nerves dominate, a person's reactions may include relaxation, sleep, massage, and warmth and fuzziness. Since different parts of the face are more dominantly controlled by different parts of the ANS, comparing the facial blood flow in different ROIs may provide insights into the state of the person. In one embodiment, the sympathetic and parasympathetic ANS are responsive to stress and pain. Thus, the state of a person's stress or pain may also be detected by monitoring the facial blood flow. For example, experiments have shown that the differential blood flow on the face, exemplary nose area minus forehead area, show changes as the pain level is changed in cold pressor tests.

According to research, blood flow in most parts of the face such as eyelids, cheeks, and chin is predominantly controlled by the sympathetic vasodilator neurons (FIG. 89). On the other hand, blood flowing in the nose and ears is mainly controlled by the sympathetic vasoconstrictor neurons. Moreover, the blood flow in the forehead region is innervated by both sympathetic and parasympathetic vasodilators. Thus, different internal physiological states have different spatial and temporal activations patterns on the different parts of the face. By illuminating the face with light and observing the absorption of hemoglobin or blood from the system, facial hemoglobin or blood concentration changes in various specific ROIs may be extracted. It may be noted that the sympathetic and parasympathetic ANS systems have influence of the blood flow throughout the face, but in different regions one may dominate over the other. For example, vasoconstrictive reactivity to sympathetic activation is stronger in the nose skin areas than in other measured facial areas. Vasoconstriction means that the blood vessels are made narrower, which would reduce the blood flow and, thereby, decrease the light absorption. On the other hand, vasodilation means that the blood vessels are made wider, which would increase the blood flow and, thereby, increase the light absorption.

One advantage of measuring and deciphering the facial blood flow and vital signs is that they may provide early indicators in the state of the person. As one example, consider drowsiness. To measure drowsiness of drivers, a common method is to observe the percent of eye closure, or PERCLOS. However, PERCLOS indicates that a person is drowsy, but does not predict drowsiness. On the other hand, respiratory rate or heart rate or heart rate variability may be potentially earlier indicators of drowsiness. As a person becomes drowsy, their resting heart and respiratory rate may decline, and the heart rate variability may also decrease. The drowsiness may also be observable by differential blood flow on the face. In one embodiment, consider the blood volume difference of nose minus forehead. As a person becomes sleepy, the parasympathetic ANS becomes stronger, and the difference (nose−forehead) increases. In contrast, when the person wakes up or becomes more alert, the difference (nose−forehead) decreases, since the sympathetic vasoconstriction leads to decreased blood flow on the nose region. This is just one example, but using the CSP with facial blood flow, eye movements, and physiological measurements may also help with measuring or predicting multiple driver state monitoring functions, including drowsiness, inebriation, impairment, cognitive load, sudden sickness, etc. Some or all of these features with the CSP may be used, or some or all of these features may be combined with other changes such as facial expressions, muscle changes or head movements. Also, the ROIs used may include forehead, cheeks, nose, chin, eyelids, or some subset of these ROIs. The CSP system may be used in the aforementioned driver state monitoring functions as well as others, and these are intended to fall within the scope of this disclosure.

As previously mentioned, facial blood flow changes may also be used for physiological measurements, such as heart rate, respiratory rate, heart rate variability, blood pressure, glucose level, HbA1c, etc. To further appreciate the amount of information contained within the facial blood flow, further insight might be gained by looking in more detail at blood pressure, glucose level, and HbA1c measurements. The comparison of different ROIs on the face provide significant information, since different regions may be controlled by either sympathetic or parasympathetic vasomotor neurons. For example, sympathetic activity may constrict subcutaneous blood vessels in the nose and lips and actively dilate vessels elsewhere like the forehead, cheeks and chin. Parasympathetic activity contributes to vasodilation in the lips and forehead. Thus, comparing different ROIs on the face captures rich information about the state of the vasculature and the autonomic nervous system that would be lost if signals from multiple regions of the face were simply averaged together.

In one embodiment, systolic and diastolic blood pressure can also be estimated using PPG signal features. Some of the features of the PPG signal include pulse shape, pulse energy (rates of change in pulse shape), pulse transit time, pulse rate variability, and pulse rate. Pulse shape features include distances between various landmarks in the waveform, areas of certain sections within the waveform, or the ratio of one of these measurements with respect to another. Pulse energy features may capture the rate at which certain pulse shape features emerge in the waveform as a function of time. Pulse transit time may be inversely related to the speed at which the pulse propagates across a fixed distance in the vasculature. For example, the pulse transit time may be approximated based on pulse waveform phase differences between two regions of the face. Since the propagation speed of pressure pulses may be largely influenced by arterial stiffness, and arterial stiffness is associated with blood pressure, there may be a strong correlation of blood pressure with pulse transit time. Pulse rate variability provides information about the state of the autonomic nervous system (sympathetic-parasympathetic balance, for example), so a greater sympathetic tone may be associated with blood pressure increases. Moreover, pulse rate increases typically are correlated with blood pressure increases, since both are key mechanisms for increasing cardiac output to meet the demands of the body. Thus, pulse rate has information about blood pressure as it indicates increases in cardiac output. These facial blood flow features may also be combined with physical characteristics such as gender, age, weight, height, race and skin tone. By collecting significant amount of data over participants and using supervised learning, artificial intelligence, machine learning and deep learning techniques, the information from multiple features and multiple ROIs may be combined to predict blood pressure. In other words, PPG signals captured in the face may provide information about brachial artery pressure. Also, signal processing techniques may be used to improve the signal-to-noise ratio of the measurement. For example, digital filters (e.g., high-pass, low-pass, band-pass) may be used for removing high-frequency noise inherent to the signal acquisition process, as well as low and ultra-low frequency oscillations of physiological origin that naturally occur in humans.

In another embodiment, facial blood flow changes may be associated with blood glucose level or HbA1c. In general, glucose levels may be measured by extraction of a patient's blood (e.g., so-called finger prick methods or continuous glucose monitoring with a small needle inserted in the arm or abdomen or stomach of the patient). The glycated hemoglobin A1c (HbA1c) test is often referred to as the gold standard assessment for diabetes management. The test measures the amount of glucose attached to the HbA1c protein, thus providing an average blood glucose level over the three-month life span of the protein. To measure HbA1c generally blood samples are drawn and sent to a laboratory for assessment. Since HbA1c levels and glucose levels are associated with changes in the cardiovascular system, it might be expected that changes or the levels of glucose and HbA1c might be reflected in changes in the facial blood flow.

HbA1c and glucose levels can affect the blood vessels in a number of possible ways. In turn, these changes may lead to changes in the facial blood flow. First, there may be slight changes in light absorption by the blood depending on the HbA1c and glucose. For example, in FIGS. 1, 2, 3 and 4 illustrate the spectrum of glucose and HbA1c. Thus, as the glucose or HbA1c levels change, there could be slight changes in the absorption spectrum of the blood due to the changes. Since HbA1c may be 7% or even higher in the blood, this may lead to a measurable change in the absorption spectrum of the blood.

Another way in which HbA1c may affect the blood flow is through changes in blood viscosity. The viscosity of blood may be a direct measure of the resistance of blood to flow through blood vessels, and an increase in blood viscosity could results in retarded blood flow, which in turn could cause reduced delivery of substrates such as oxygen, insulin, and glucose to metabolically active tissues. Measurement data has shown that the mean values of blood viscosity are higher in groups with higher HbA1c levels. It is apparently also generally accepted that the blood viscosity is higher in type-2 diabetes patients than in non-diabetic control participants. Other studies have shown that participants with diabetes had higher whole blood viscosity levels both at low shear rate (3/second) and high shear rate (200/second) than those without diabetes. Since the higher HbA1c levels appear to be correlated with higher blood viscosity, the facial blood flow changes may also be expected to change. Thus, it might be possible that a system such as CSP could potentially measure the level of HbA1c, or potentially even glucose level.

Yet another way in which excess blood sugar or glucose can affect the blood flow is through the decrease in the elasticity of blood vessels, thereby causing the blood vessels to narrow and impede blood flow. This can lead to a reduced supply of blood and oxygen, increasing the risk of high blood pressure and damage of large and small blood vessels. Damage to large blood vessels is known as macro-vascular disease, while micro-vascular disease refers to damage to small blood vessels. Hence, the facial blood flow measured by a system such as CSP may change as the excess blood sugar or glucose changes.

A further way in which diabetes can affect the blood flow is through the reduction in compliance of blood vessels. Changes in the structure and function of large and small arterial vessels are known to occur for hypertension and diabetes. The change in compliance in the circulatory system from diabetes and hypertension may influence the blood pressure, cardiac output, and the impedance to left ventricular ejection. Compliance may be described as the ability of a hollow organ (e.g., a vessel) to distend and increase volume with increasing transmural pressure of the tendency of a hollow organ to recoil toward its original dimensions upon removal of a distending or compressing force. In compliance, an increase in volume occurs in a vessel when the pressure in that vessel is increased. The tendency of the arteries and veins to stretch in response to pressure has a large effect on perfusion and blood pressure. In other words, blood vessels with higher compliance deform easier than lower compliance blood compliance blood vessels under the same pressure and volume conditions. Venous compliance may be much larger than arterial compliance (for example, in one embodiment venous compliance is approximately 30 time larger than arterial compliance). Veins typically have a much larger compliance than arteries because they generally have thinner walls. Reduced arterial compliance has been observed in patients with diabetes, and it is also characteristic of patients with hypertension. To summarize, because of the possible spectral changes, blood viscosity changes, and blood vessel changes (elasticity and compliance), changes in glucose level or HbA1c may be reflected in changes in the facial blood flow. By measuring a person's characteristics over a period of time and using artificial intelligence or machine learning algorithms, as well as taking training sets and validation sets over numerous individuals, it may be possible to detect glucose level or HbA1c.

Eye Analysis from Camera Images

Using the CSP system, the eyes of a user may also be observed to derive valuable and complementary information. For example, some of the information that may be derived from analysis of the eyes include gaze direction, eye closure, 3D and 2D pupil coordinates and pupil dilation, screen-space gaze point, age and gender estimation and face recognition. Depending on the resolution of the camera (e.g., the number of pixels on the eye region), different levels of information may be extracted. In one embodiment, lower resolution cameras may observe features such as eye blink rate and percent of eye closure PERCLOS. In another embodiment, higher resolution cameras may observe additional features, such as eye gaze direction and pupil size. The lower resolution cameras may include, for instance, VGA cameras (640×480 pixels), while higher resolution cameras may include, for instance, one megapixel, 1.5 megapixel, five megapixel, or higher. These are merely exemplary numbers, but other pixel counts may also be used and are intended to be covered by this disclosure. Also, the number of pixels on the eye region may also depend on other features, such as the distance between the camera and the person, and the field-of-view of the camera or the lens system in front of the camera.

In one embodiment, eye detection and blink counting may use a method called PERCLOS, which is an eye detection method that involves detecting when the eye is at least a certain percentage closed, exemplary being about 80 percent closed from its normal open state. Thus, PERCLOS provides a metric that determines the percentage of eye closure, and it is a technique that is often used for drowsy driving detection in driver monitoring systems in vehicles. In a particular embodiment, eye blink and PERCLOS detection may be performed using facial landmark detectors that can capture many of the characteristic points on a human face, including eye corners and eyelids. Many of the landmark detection methods formulate a regression problem, where a mapping from an image into landmark positions or into other landmark parametrization is learned. By training many of these state-of-the-art landmark detectors on so-called in-the-wild datasets, the detectors may be robust to varying illumination, various facial expressions, and moderate non-frontal head rotations.

As one example of a method for eye blink and closure detection, FIG. 90 illustrates on the top a flow chart of the steps involved. First, the face may be detected, which may use any number of face tracking or bounding box algorithms. Then, based on techniques such as landmark detection, the eye region may be extracted. With the eye regions parametrized, the eye blink may be detected, and then eye-blinking classification may be conducted to determine if the eye is open or closed. One method to make the determination of eye open or closed is to use a single scalar quantity called eye aspect ratio (EAR). In a particular embodiment, the EAR may be determined using the eye pictures, as shown in the bottom of FIG. 90. The picture of the eye may be parametrized by six locations: p1, p2, p3, p4, p5 and p6. On the left side is shown that the eye aspect ratio will be larger and relatively constant over time when the eye is open. On the right side is shown that they eye aspect ratio will be almost equal to zero when a blink occurs. The formula in FIG. 90 is one formula for EAR, and a threshold value may be set (e.g., EAR greater than or equal to 0.8) to classify the eye as open.

FIG. 90 illustrates just one way to judge eye blink and PERCLOS, but many other methods and algorithms may be used and are intended to be covered by this disclosure. For example, an alternate method uses a computer vision technique involving a deep learning method called YOLOv2, which is an artificial intelligence model to detect the percentage of eye closure. Yet another method for driver drowsiness detection is based on facial features and PERCLOS using computer vision. The eye may be detected based on support vector machine. Then, a Kalman filter and mean shift may be used to track the person's pupil. Yet another eye detection technique combines a Viola-Jones method, template matching and a support vector machine.

All of these variations in eye detection and blink and PERCLOS characterization may be used along with parts or combinations of the techniques and would fall within the scope of this disclosure.

Beyond eye blink and PERCLOS, there are many other features of the eyes that can reveal information about a person. In one embodiment, the pupil's diameter (e.g., degree of pupil dilation) may be indicative of cognitive load. In particular, cognitive load refers to the amount of working memory resources that are being used by an individual. For example, there are three types of cognitive load: intrinsic cognitive load is the effort associated with a specific topic; extraneous cognitive load refers to the way information or tasks are presented to a learner; and germane cognitive load refers to the work put into creating a permanent store of knowledge. Task-involved pupillary response is believed to be a reliable and sensitive measurement of cognitive load that is directly related to working memory. Even though the experience of cognitive load is not the same in every person, in general heavy cognitive load may have negative effects on task completion. With the increase in secondary tasks inside a cockpit, cognitive load estimation has grown in importance for both automobile drivers and pilots.

Pupil dilation has been shown to correlate with task difficulty, with pupil diameter increasing with problem difficulty. There seems agreement in the research literature that pupil diameter provides an index of the momentary load on a subject as they perform a mental task, and many reports confirm that pupil size may be considered as a valid index of cognitive load. Thus, the task difficulty perceived by an individual may be determined from pupil-size features such as the mean pupil diameter change, the average percentage change in pupil size, peak dilation, and time to peak. Despite all of this evidence, one major challenge in using pupil dilation systems implemented using one or more camera systems is the pupil's sensitivity to a number of factors unrelated to cognitive load, including ambient lighting and off-axis distortion. Thus, alternative methods of deriving cognitive load from the eye other than pupil dilation are also being investigated.

In another embodiment to understand cognitive load, a vision-based method may be used to extract eye movement parameters through a person's facial images. As an example, two eye movement parameters, saccade and fixation, can be calculated using the eye pupil positions. The signal is fixation when eye gaze pauses in a certain position, and the signal is saccade when it moves to another position. In particular, saccade is a quick, simultaneous movement of both eyes between two or more phases of fixation in the same direction. Unlike pupil diameter, saccade magnitude should be free from the influence of ambient light, thereby possibly providing a more reliable, non-invasive, measure of cognitive load. With a camera-based system, the eye movement system also has the potential of real-time implementation.

The ability to observe cognitive load is another attribute that can potentially be monitored using the CSP system. The camera data could be trained and then classified using artificial intelligence, machine learning, and deep learning. As an example, some of the machine learning algorithms that have been applied for cognitive load classification include support vector machine, logistic regression, linear discriminant analysis, k-nearest neighbor, and decision tree. Moreover, some of the deep learning architectures used for feature extraction and classification from eye movement signals include convolutional neural networks, long-short-term memory, and auto-encoder. In addition, combined deep learning and machine learning approaches (e.g., convolutional neural networks and support vector machines, or auto-encoder and support vector machines) may also be used for feature extraction and classification. These are just some examples of algorithms and techniques that can be used with the eye analysis, but other methods, algorithms, techniques, and combinations of these, may also be used and are intended to be covered by this disclosure.

In general, many of the functions of the CSP system may be enhanced by using artificial intelligence and/or machine learning (AI/ML). In one embodiment, the regular routines, habits, physiological parameters, etc., of an individual or driver may be learned over time, and then AI/ML may be able to detect and set alerts for unusual ranges of parameters, perhaps using AI/ML techniques such as anomaly detection. In other words, AI/ML may be used to establish baseline readings for individuals. Also, since CSP system and sensors may collect an enormous amount of data, AI/ML may be used to study the data and detect and send out alerts for data that is out of the ordinary, perhaps out of range by certain percentage. Thus, the data processing can be assisted, streamlined, and made more efficient using AI/ML, and only when things are sufficiently out of the ordinary require attention or human intervention. These are just some of the benefits and advantages of using AI/ML with the CSP system, but other AI/ML techniques, and other combinations of AI/ML with the CSP system may be used and are intended to be covered by this disclosure. As one other example, CSP systems may be combined with newer categories of AI such as what is known as generative AI or artificial general intelligence. Generative AI describes algorithms that can be used to create new content, including audio, code, images, text, simulations and videos. Examples of generative AI include programs such as ChatGPT (GPT stands for generative pre-trained transformer), a chatbot that can generate an answer to almost any question it is asked, and DALL-E, a tool for AI-generated art. For example, after analyzing abnormal data collected by the CSP system, such generative AI systems might be used to compose an audible sentence or visual picture to convey to the user or driver the alert or warning. Rather than just an alarm noise or vibration that may not convey much information to the user or driver (other than the fact that there is something out of the ordinary), the generative AI message, text, audible language, or visuals may provide much more details of what is out of the ordinary and what kind of remedies the user or driver may seek to overcome the situation. In yet another embodiment, the generative AI tools may be used to help optimize the performance or experience for the user or driver.

As another example of the CSP system use in understanding a person's condition, the eye analysis and three-dimensional imaging capable using the CSP may provide insight the person's emotions. For example, eye movements may indicate how a person allocates their attention, while their pupil dilation may indicate the strength of their motivation. The emotional state may be expressed through the body posture: a straighter and upright posture may indicate a positive emotion, while a hanging posture may indicate a negative emotional state. Thus, the CSP system may permit addressing questions regarding the underlying mechanisms of behavior (e.g., using eye movements and pupil dilation), as well as emotional expressions that accompany the behavior (e.g., using depth sensor imaging to measure posture).

Eye tracking may be based on corneal reflection technology and may provide numerous indicators of attention, including fixations, saccades, anticipatory looking, scan patterns and pupil diameter. It has been shown that eye movements and pupil dilation are able to measure changes in the autonomous nervous system activity. For example, similar to other physiological measures such as heart rate, heart rate variability and skin conductance, changes in pupil dilation reflect activation of the autonomous nervous system, and changes in pupil diameter are a function of both sympathetic and parasympathetic nervous system activity. Thus, eye movements may reflect the distribution of attention, changes in pupil dilation may provide a measure of the degree of psychological involvement.

In addition, adults and children often express social emotions through the body—with an elevated body posture signaling positive social emotions, and lowered body posture indicating negative social emotions. Elevated and lowered body posture are established indicators of positive and negative emotional experiences in adults and children. For example, research has shown that children's posture is lowered when they fail to achieve a positive outcome for themselves, and more elevated when they receive a fun reward to play a game. Children display an erect posture after succeeding on difficult tasks, and, conversely, their posture decreases when they fail at easy tasks. Studies have also shown that adults' posture is more slumped when they imagine negative emotions compared with positive ones. For instance, in recent studies adults showed increased upper-body posture after recalling emotional episodes of joy and pride, but showed decreased body posture if episodes of shame and disappointment were recalled. Adults display a more erect posture following athletic success, as a cue of social dominance, social status, and expertise.

In one embodiment, the body posture may be measured by the CSP system, since it incorporates a depth sensor imaging camera, such as the time-of-flight camera. For instance, the CSP system may estimate the person's skeletal joints (e.g., the chest's center, hips, etc.) as three-dimensional coordinates on x-y-z axes. Thus, the depth sensor imaging technology may capture individual difference and changes in a person's posture.

In an alternate embodiment involving the application in driver monitoring systems, camera-based eye-tracking systems may be used unobtrusively and remotely in real-time to detect drivers' eye movements. This may be a valuable addition for CSP because for safe driving, it may be necessary to keep track of the state of the driver to allow detection of when short-term driving performance deviates from the normal driving state. Multiple parameters may help in evaluating the state of the driver, such as cognitive distraction, cognitive load, mental fatigue and emotions. The literature appears to show that most road accidents happen due to the driver's cognitive load; i.e., high cognitive load may lead to inattentiveness to the road. Research shows that measurements of pupil dilation and eye movements are often used factors that statistically correlate with the concept of mental workload.

Although described above is one method of determining cognitive load, other methods may also be used, and are intended to be covered by this disclosure. For example, cognitive load may also be determined from differential facial blood flow on the face. In particular, a person's prefrontal cortex may reflect the level of cognitive load, and prefrontal cortex has also been shown to correlate with facial skin blood flow. The prefrontal cortex (PFC) is the cerebral cortex covering the front part of the frontal lobe. This brain region has been shown to be involved in planning complex cognitive behavior, personality expression, decision making and moderating social behavior. Also, there is extensive clinical evidence that the PFC plays a role in cognitive control and executive function. The PFC is engaged in emotional recognition and processing as well as multiple functions such as attention, planning of motor act, and cognitive function; thus, the PFC may play a key role in creating emotional feeling, and the PFC affects the autonomic nervous system.

Experiments have shown that facial skin blood flow may serve as a sensitive tool to assess a person's emotional status and that both prefrontal oxygenation and facial skin blood flow decrease during positive-charged emotional stimulation. For example, a pleasantly-charged or comedy stimulation causes a decrease in oxygenated hemoglobin in the PFC. This decrease in prefrontal oxygenation was found to be correlated with a decrease in blood flow in the forehead and cheek of the participants. In other words, the experiments demonstrated a positive correlation between the decreases in prefrontal oxygenation and facial skin blood flow in the check and forehead during positively-charged emotional stimulation (incidentally, the facial blood flow failed to show a significant response to negatively-charged emotional stimulation). In these particular experiments the facial skin blood flow as measured with laser speckle and/or Doppler flowmetry, and functional near-infrared spectroscopy was used to measure the oxygenation in the PFC. However, as described earlier in this specification, the facial blood flow can also be measured using the CSP.

As further evidence that cognitive load assessment can be observed in facial blood flow, other studies have also shown cognitive load assessment from facial temperature. The main energy source of the brain is glucose. Around one-third of the energy produced from glucose and oxygen reaction is released as heat. For the brain, blood circulation is the main heat exchange mechanism. So, more glucose and oxygen is needed when the brain is dealing with a higher workload, which means that the brain produces more heat when it is in higher cognitive engagement. The higher temperature also means that there is more blood flow; i.e., the increase in temperature will be directly correlated with increase in blood flow. Since certain blood vessels connect the facial tissues with the brain, cognitive workload can be estimated by detecting the temperature differences between facial areas supplied by different blood vessels (and these temperature changes are correlated with facial blood flow). In this particular experiment, the cognitive load is estimated by measuring temperature changes between the forehead and the nose using a smart eyewear. In their experiments, the facial tissues near the nose and forehead center have the largest temperature differences for different cognitive loads. They find that there is a correlation between the facial temperature changes (forehead minus nose) and cognitive load. In other words, the temperature difference between the forehead and nose becomes bigger when participants are performing a harder task, compared to simpler tasks or resting time. Since the blood flow is correlated with the temperature changes, in one embodiment we may be able to measure the cognitive load by using the CSP system and comparing the facial blood flow on the forehead versus the nose ROIs. Although this is one example of the differential blood flow, other ROIs on the face may also be used, or a combination of ROIs may be used, and these are intended to be covered by this disclosure.

CSP Using Semiconductor Chip-Based Hardware

One attractive implementation of the CSP is to use semiconductor chip-based hardware combined with appropriate processing. Because semiconductor chip-based hardware follows in many cases Moore's Law scaling, the cost and size of the hardware decreases with increased volume and with advances in semiconductor processing, while the performance and number of on-chip devices may also increase. In one example, the large and fast-moving smart phone and tablet market is driving advances in compact light sources, time-of-flight sensors, and high-resolution RGB and near-infrared cameras, and the applications described in this disclosure may coattail off some of these advances. As an illustration of semiconductor chip-based hardware, vertical cavity surface emitting lasers (VCSELs), CMOS or CCD cameras, and single photon avalanche photodiodes (SPADs) may be used for the CSP hardware, possibly also including micro-electro-mechanical system (MEMs) scanner. This is just one example, but many other embodiments are possible for the CSP hardware and are intended to be covered by this disclosure.

Different light sources for active illumination have been described earlier in Sections 1-5 of this disclosure. Among the various laser options, one type described earlier was laser diodes comprising one or more Bragg Reflectors. In one embodiment, laser diodes with Bragg reflectors can be VCSELs, which are increasingly becoming commodity items as their volume and applications increase rapidly. Also, VCSEL provide some attractive properties, such as sub-milliamp threshold current, multi-gigahertz modulation capability and/or relative intensity noise close to the quantum limit. As a consequence, VCSELS are increasingly becoming a preferred light source for optical sensor technologies and imaging systems.

Semiconductor laser diodes are available in many flavors. For example, Fabry-Perot edge emitting laser diodes have features such as: wide bandwidth typically greater than a nanometer, power range from several milli-watts but scalable to 10 s of watts, output beam shape that is elliptical, and high wall-plug efficiency. In another example, distributed feedback (DFB) edge emitting laser diodes have features such as: narrower bandwidth typically less than a nanometer, power range from several milli-watts but scalable to 10 s of watts, output beam shape that is elliptical, and the possibility of wavelength locking with temperature control. In comparison, VCSELs are laser diodes that emit light from the top surface (hence the name "vertical cavity") and have features such as: narrower bandwidth typically less than a nanometer, power range from several milli-watts but scalable to 10 s of watts, output beam shape that is circular, which can have a real advantage for imaging or coupling into other structures such as fibers or diffractive optical elements, and also the possibility of wavelength locking with temperature control. Because of the planar structure of the VCSEL and beam emerging from the top surface, one major advantage is that VCSELs can be relatively easily grown into arrays, and the output power can be scaled by making larger and larger arrays and combining the spatial beams from the various VCSELs.

An example of VCSEL laser diodes and arrays is illustrated in FIG. 91. The top left shows a cut-away cross-section of an exemplary VCSEL device. As noted earlier, the VCSEL emits light perpendicular from the top surface, and the beam can be round or circular (vertical beam in the figure). Because the active region (e.g., region where lasing action occurs due to carrier population inversion) is relatively narrow, high reflectivity mirrors are generally required surrounding the active region to achieve lasing. The two high-reflective mirrors comprise the p-doped Bragg reflector and the n-doped Bragg reflector, which are in-turn are surrounded by an n-contact and a p-contact for electrical current excitation (e.g., electrical pumping). With an appropriate number of layers in the Bragg reflectors, very high reflectivity mirrors, such as 99.9% reflectors, may be achieved. The bottom of FIG. 91 shows from left to right a single VCSEL, a VCSEL array, a VCSEL chip, an emitter with two controllable lines, and a two-dimensional scalable line array. Finally, the top right illustration in FIG. 91 shows that the beams from an array can combine to form a higher power output beam.

VCSEL active illuminators comprise several attributes that make them particularly attractive for time-of-flight or LiDAR (light detection and ranging) applications. For example, VCSELs have lower coherence that results in speckle-free images, and higher peak power illuminates the scene with more photons resulting in less noise and better immunity to ambient light. Moreover, VCSELs have faster rise and fall times compared with light-emitting diodes, and the VCSELs can be modulated at higher frequencies for better accuracy and precision for shorter distances. VCSELs are one type of active illuminator that can be used for ToF or LiDAR, but other lasers described herein may also be used and would fall within the scope of this disclosure. Also, if the ToF is to be operated at relatively short distances, exemplary less than a meter or less than 20 centimeters, then the active illuminator might alternately be LEDs or other incoherent light sources.

Visible or NIR Cameras and Time-of-Flight Sensors or Cameras

Various camera or sensor systems may be used with the active illuminators to implement the CSP in an all-semiconductor chip form. Some the earlier cameras were based on charge-coupled device (CCD) technology. However, many systems have moved to CMOS active-pixel image sensors (CMOS sensors) due to largely reduced power consumption compared to CCD. Some systems, particularly mobile phone cameras, are moving toward CMOS back-illuminated sensors, which use even less energy, although typically at higher price than CMOS and CCD. As one advantage, CMOS sensors typically perform better against smearing and blooming compared to CCD, thus reducing image artifacts and errors that would occur in time-of-flight calculations (smearing and blooming occurs when charge overflows the pixel well capacity and spills into adjacent pixels). Moreover, unlike more traditional front-side CMOS sensor design, backside illuminated sensors place the wiring layer below the photodiode, thereby improving light sensitivity by reducing any wiring or circuit obstructions that might otherwise block some of the incoming light.

Whereas the above cameras generally generate a two-dimensional image, a three dimensional image may be generated by using or adding a time-of-flight (ToF) sensor (also known as LiDAR sensors, the terminology typically used with larger distance imaging). There are two general categories of ToF techniques: indirect ToF (iToF) and direct ToF (dToF). iToF measures a phase shift, may have modulation frequencies between about 20 to 100 MHz or higher, comprise demodulation pixels with two to four taps, perform the depth calculation in-pixel, and generally have medium to high pixel count sensors (e.g., ranging from 30K pixels to 1.2 megapixels or higher). On the other hand, dToF uses a "stop watch" approach (i.e., sends out a short pulse and measures the time for the pulse to return to the detector), may use pulse widths between approximately 0.2 to 5 nanoseconds (more preferably 0.5-2 nanoseconds), comprise detection system based on avalanche photodiodes (APDs) or single photon avalanche photodiodes (SPADs), perform the depth calculation based on histogram analysis, and generally smaller pixel count compared to the iToF counterparts (because dToF requires higher speed electronics, each pixel may have more circuitry). For dToF the pulse repetition rate may be exemplary in the range of several kilohertz up to 100 MHz. ToF is one method of generating 3D images, but other methods may be used and would fall within the scope of this disclosure. For example, structured light or stereographic imaging using multiple cameras are other methods of generating 3D images.

In one embodiment, iToF works by illuminating a scene using modulated light and measuring the phase delay of the returning light after it has been reflected by the objects in the scene. The phase delay is then measured and converted to distance using mathematical techniques, such as a quadrature sampling technique. As a particular example, the iToF uses lock-in detection with active light modulation based on the principle familiar from lock-in amplifiers. For example, the signal input may serve as the input to an amplifier, which is then passed through a band pass filter. There may also be a reference input, which can be phase shifted by different amounts (e.g., 0, 90, 180, and/or 270 degrees). The signal input after the band pass filter as well as the phase shifted reference input may serve as inputs to a mixer, whose output is passed through a low-pass filter and then sent to an output amplifier. If the input signal is $|A| \exp\{j\phi\}$, then the output may be proportional to $|A| \cos\{\phi\}$. All of the pixels in the iToF sensor may be controlled by a demodulation input signal that is synchronized with the modulation of the illumination block. In one embodiment, a model of a pixel may be approximated by the block diagram of FIG. 92. The top of the figure shows the active illumination unit, which may use one or more VCSEL or LED sources, and the bottom of the figure shows the mixer and filtering to generated the signal with different phase shifts. This is just one embodiment, but other implementations of the iToF sensor may be used and are intended to be covered by this disclosure. Also, in one embodiment the output from an iToF provides a two-dimensional image (e.g., a monochrome image) as well as the depth information for each pixel.

In another embodiment, depth sensing in dToF is may be achieved by transmitting a periodic light source, which is typically a pulsed laser (such as pulsed one or more VCSELs), to a target and detecting the arrival of the reflected photons by high performance photodetectors such as avalanche photodiodes (APDs), single-photon avalanche diodes (SPADs), or silicon photomultipliers (SiPMs). A block diagram of an exemplary dToF sensor or system is illustrated in FIG. 93. A supporting electronic circuitry then measures the arrival time of these photons (the "stop watch" function mentioned earlier). In dToF sensors, time-to-digital converters (TDCs) are typically used for the stop watch function, and the TDCs may be implemented at a per-pixel level or in shared architectures. As shown in FIG. 93 in the box labeled electronics, the driver for the pulsed light source may be synchronized to the TDCs, and the output from the TDCs may enter into memory and a histogram readout. This may be called a dToF image sensor based on time-correlated single-photon counting (TCSPC), which often have high-speed and accurate ranging capabilities both for time-or-flight measurements or what are often called LiDAR measurements. In some embodiments, ambient light suppression may be achieved at the sensor level by coincidence detection on the chip, a technique that utilizes the spatio-temporal closeness of photons within a laser pulse to filter out background noise photons.

A dToF measurement may be performed using TCSPC, where detected events are accumulated over multiple laser pulses that are incident on the target. The recovered signal then may be a train of pulses represented as a histogram corresponding to the time-of-arrival of individual photons incident on the SPAD with a distinguishable peak centered around the target location (c.f., left side of FIG. 93). This is one implementation of a dToF, but other architectures may also be used and are intended to be covered by this disclosure. For example, the SPAD may be an array of detectors or comprising a number of pixels on a semiconductor chip. In another embodiment, the output from the pulsed laser may be divided into a sample and a reference arm, and one SPAD array may detect the reference arm, while another SPAD array may detect the sample arm after reflecting from the target object. In one embodiment, the beam splitter for separating into the sample and reference arms may be a cover glass or some sort of protective cover. Alternately, a large SPAD array may be used, where on section of the SPAD array is used to detect the reference arm, while another section of the SPAD array is used to detect the sample arm. The ToF to the target may then be derived by comparing the sample and reference SPAD outputs. The two-arm detection technique may be advantageous for subtracting out laser fluctuations or environmental fluctuations from effects such as ambient lighting. These and other embodiments are intended to be covered by this disclosure. One advantage that dToF sensors may have over iToF is that dToF may be able to detect objects at a larger distance, which is why dToF may be more useful for LiDAR applications at distances over 25 meters. For example, how much time-averaged power may be incident on the target may be limited by eye safety considerations. Since dToF uses short pulses instead of a continuous square or sine wave used in iToF, higher peak powers may be used to enable larger distance measurements.

One example of the detectors used in dToF are SPADs, which are also known as detectors operating in a Geiger-counter mode. The SPADs digital output may be used to count arrival of single photons and/or time arrival of single photons, and it may be fully integrated in CMOS. Like many semiconductor photodetectors, SPADs operation is based on a reverse biased p-n junction that generates current when photons are absorbed. As illustrated in FIG. 94, SPADs correspond to when the p-n junction may be biased well above its reverse-bias breakdown voltage, but to accommodate this the SPADs are made with a structure that may minimize damage or undue noise. Because of the high gain, a single charge carrier injected into the depletion layer (e.g., through absorption of a photon) can trigger a self-sustaining avalanche, potentially saturating that detector pixel—hence called the Geiger counter mode. Once saturated, a quenching circuit may be used with the SPAD, so that after the quenching of the avalanche current, the SPAD bias slowly recovers to the operating bias, returning the detector to a state to be ignited again. The quenching circuit may be passive (e.g., a resistor in series with the SPAD) or active (e.g., involving resistors as well as a fast discriminator). This is just one example of a detector that can be used in the dToF system, but other detectors may be used consistent with this disclosure. For example, APDs, PIN diodes, Schottky diodes or simply p-n junction diodes are other possible detectors.

Although iToF and dToF sensors have been described, other types of detectors, sensors or cameras as well as combinations may be used consistent with this disclosure. In one embodiment, advanced ToF system may use multi-frequency techniques to extend the distance without reducing the modulation frequency (e.g., in one technique multiple repetition rates may be used). In another embodiment, a compression sensing SPAD camera may be used to achieve a higher image resolution or enhance the temporal resolution (e.g., image resolution 800×400 pixels may be achieved while using a SPAD array with a resolution of 64×32, and/or enhance the temporal resolution to a few tens of picoseconds). In yet another embodiment, a hybrid ToF may be used, which may be like a iToF system with short pulses (e.g., instead of a typical iToF using CW modulated light or 50% duty cycle modulated light trains, short pulses may be used with a much lower duty cycle, exemplary less than 5%). In a further embodiment, an iToF or dToF sensor may co-registered with an RGB and/or NIR camera that typically has higher resolution. By using such a combination, the ToF camera can provide the 3D depth information for a frame or skeleton, and the higher resolution 2D RGB and/or NIR image may be overlaid on top of the ToF frame or skeleton. In one example, the depth may be interpolated between the coarse spatial grid of the lower resolution ToF to provide a depth for each of the pixels in the higher resolution RGB or NIR camera. All of these ToF techniques as well as RGB and/or NIR cameras, or combination of these, may be used and would fall within the scope of this disclosure.

As mentioned earlier, the distance or range for the ToF or LiDAR sensors as well as the time-averaged laser power that may be used could be limited by eye-safety limits. Nonetheless, there are techniques that can be used to extend to distance or range. In one embodiment, a diffractive optical element or beam splitting unit may be used in front of the active illuminator to create a dot pattern from the laser output, thereby concentrating the power in certain spots while maintaining the spatially averaged power level within acceptable limits. In another embodiment, the ToF light source may transmit a dot pattern, which is temporally sequenced through different patterns. For example, the output of a VCSEL array may be sequenced so that one quarter of the VCSELS are excited at a time, and then temporally switched four times so that all of the lasers in the array are excited at one time or another. In yet another embodiment, as discussed with the hybrid ToF sensors, shorter temporal pulses may be used, which would increase the peak power without exceeding the time-averaged power. In a further embodiment, the wavelength of light used with the active illuminator may be selected such that higher eye-safe limits apply. For example, by using wavelengths longer than 1.4 microns, preferably wavelengths in the telecommunications band around 1.55 microns, higher eye safety power levels can be tolerated. These are just some examples of techniques to extend the distance or range, but others as well as combinations of these may be used and would fall within the scope of this disclosure. In yet another embodiment, light near 1700 nm may be used or detected (actively or passively) monitor for animals or people, relying on their body heat (e.g., night vision type system). More generally, these night vision or animal/people detection systems may use light in the SWIR wavelength range, and the detection system may be made from semiconductor materials such as indium-gallium-arsenide or other III-V materials, or even quantum dot materials that are sensitive to SWIR wavelengths. These are other night vision embodiments or combinations are intended to be covered by this disclosure.

An additional method of extending the distance of ToF or LiDAR may be to use a scanning architecture rather than flash illumination (e.g., flash is when the entire scene is illuminated at once). For example, a one-dimensional line-scan may be used, or yet slower a two-dimensional raster scan may be used. The 1D line-scan may be a reasonable compromise between speed of scanning and distance required for the ToF or LiDAR. As one example, FIG. 95 illustrates a configuration for 1D line-scan where a scanning mirror is placed after the light source and scans a line across the target that in turn reaches the detector array. In this example the light source may be a VCSEL array, and the detector may be a SPAD array. In a particular embodiment, a semiconductor chip-based solution may be maintained by using a MEMS scanning mirror. In the case of the MEMS mirror, the scanning mirror may be a linear or 2D array of MEMS moving mirrors rather than a single mirror that is illustrated in FIG. 95. The MEMS could be digital mirrors with two positions (e.g., DLP from Texas Instruments), or analog mirrors with many more positions (e.g., voltage controlled mirrors that can span a continuous range of angles). FIG. 95 is just one embodiment of a scanning ToF or LiDAR architecture, but other devices may be used, or additional elements may be added and are intended to be covered by this disclosure. For example, the VCSEL array may be replaced by one or more edge-emitting laser diodes, the SPAD array may be replaced by one or more APDs or SiPMs or RBG/NIR cameras, and the scanning mirror may be a galvanometer or a polygon scanner. These or combinations with additional elements may be used and would fall within the scope of this disclosure.

Applications of CSP Systems

The CSP system described or variations of this may be advantageously used in numerous applications, a few of which will be described below. A preferred embodiment of the CSP may be VCSEL active illumination and ToF sensor receiver, possibly the ToF sensor being co-registered with a higher resolution RGB and/or NIR CMOS or CCD camera. Another possibility would be to have one or more cameras used with and synchronized to active illuminators, such as light sources comprising VCSELs or LEDs. Any of the other embodiments described in the disclosure, or combinations with other devices may also be used and are intended to be covered by this disclosure. One advantage of the semiconductor chip-based solution is that it can be made very compact, enabling the implementation of CSP even in smart phones or tablets. Also, another advantage of using a CSP system is that it may not only measure features about a person, but the information may actually predict future actions. For example, if a person is drowsy, the earliest indication may be that vital signs such as heart rate, respiratory rate and heart rate variability are decreasing. These changes may occur before the person yawns or starts having increased closure of the eyes, which are more outwardly signs of the drowsiness that may be noticed by others. In addition, there can also be significant value in combining the CSP system data with artificial intelligence or machine learning algorithms. Based on the AI or ML processing trained over time and/or over a possibly large number of participants, it may be able determine if a person has abnormal symptoms, or if they are out of their normal parameter range under similar circumstances. MI/AI may also permit personalizing the readings to an individual, such as determining baseline readings for the person.

In many physiological measurements, one of the big challenges is from motion artifacts (e.g., the person or subject moves during a measurement). Since the CSP system may be looking for blood flow changes by change in light intensity (e.g., due to PPG, the light absorption changes in with volume of blood), the changes of intensity from motion can be confused with blood flow changes, or the motion adds noise to the measurement. Experiments have shown that the depth information from the time-of-flight sensor or camera may help compensate for motion artifacts, since the depth information can be used to differentiate the gray scale intensity variations caused by underlying heart beat or PPG versus the user's motion. Motion artifacts are known to be a challenging issue for contactless PPG system, but even more so for systems that operate in the near-infrared wavelengths because the absorption by hemoglobin is much weaker in the near-infrared compared to visible wavelengths. For example, it is estimated that the PPG signal strength between 850 nanometers and 1000 nanometers is only about one-eight the peak amplitude in the green around 530 nanometers (c.f., FIG. 86). Since the ToF camera directly measures the body motion of the participant, this information may be useful in distinguishing intensity changes caused by body motion versus PPG signal changes, which then allows the ToF to compensate for motion artifacts. It might also be noted that movements in the x-y horizontal plane may be compensated using the face or body tracking software, much like the bounding box in a smart phone camera moves with the subject while trying to take a picture or a video. In one embodiment, the AI/ML software may follow the face by using landmarks on the face and following the locations of the landmarks. So, the z-axis motion, i.e., the depth motion, can be then compensated using the ToF depth information. Other benefits may also be gained by using a ToF camera. For example, by measuring the motion of the chest wall using the ToF camera or sensor, the respiratory rate or breathing rate of a participant can be directly measured, rather than having to extract the respiratory rate from heart rate or other indirect body motion when an RGB camera is used. In a particular embodiment, the ToF camera or sensor can be used to compensate for intensity variations caused by motion artifacts in heart rate or heart rate variability measurements. For example, when using an indirect ToF camera to measure heart rate, the underlying logic in the motion artifacts compensation may be three fold. First, because active illumination from a point source is used, the change in grayscale intensity may be non-linearly correlated to the relative position between the head and the camera. Secondly, the depth information recorded by the ToF camera should contain only a negligible heart rate component, since the micro-motion created by the heart beat should be too small to be measured by the ToF camera. Lastly, after the motion artifacts are removed, the compensated intensity information should have a minimum correlation with the depth information. These are exemplary methods of compensating for motion artifacts in physiological measurements, but other motion compensation techniques may also be used and are intended to be covered by this disclosure. For example, particularly for wearable devices, another method of compensating for motion may be to use data from an accelerometer or gyroscope. In one embodiment, the accelerometer may indicate that there is motion and the magnitude of the motion, and the information may be fed to the PPG sensor or other optical sensor to perform motion compensation. For non-contact, remote sensing or monitoring devices such as in the CSP, the ToF depth information may augment or substitute for the accelerometer or gyroscope data.

In one embodiment, the CSP used in smart phones or tablets may be used to judge a user's sentiment or reaction. As an illustration, consider if the CSP is used with or in the user-facing screen of a smart phone or tablet. When the user is looking at material on the screen, the CSP may judge the reaction or sentiment of the user, such as what might excite the user, make the user happy, or other sentiments (e.g., like, love, laugh, wow, sad, angry, etc.). Currently, the user sentiments or reactions are often judged based on what the user clicks on, but the CSP may be able to augment or make judgements in a passive manner without the user having to user their hands or fingers. This may be advantageous in settings such as when the user is driving or when the hands are already tied up holding objects or while working on something. Also, based on the sentiment or reaction of the user derived from the CSP, the content delivered to the smart phone or tablet may be tailored, whether it be announcements or notifications, music playing, videos displayed, reading material displayed, or advertisements or product recommendations delivered. In one embodiment, the data from the CSP system may be sent up the cloud for processing using artificial intelligence and/or machine learning, and then based on the processed data appropriate content may be sent at least to the user's smart phone or tablet, or potentially designated people. These are just some examples, but other applications of the CSP in smart phones or tablets are also intended to be covered by this disclosure. For example, the CSP system may use the physiological parameters or other measurements to monitor the health of the user, and alerts or warnings may be sent if unusual readings or trends are observed. Also, even though the example is provided of smart phones or tablets, the user sentiment or reaction may also be used in other devices, such as computers, PDAs, wearable devices such as smart watches, smart glasses, or augmented or virtual reality goggles, headsets or hand-held devices. The CSP system data may also be augmented by facial muscle, eye, or other physical body movements observed by cameras coupled to the CSP.

In another embodiment, the CSP system may be used with devices made for the so-called metaverse. For example, the metaverse could be an iteration of the internet as a universal and immersive virtual world that may be facilitated by the use of virtual reality (VR) and augmented reality (AR) headsets. As a particular embodiment, an avatar of a person may be used in virtual meetings, hangouts, or gaming. The early avatars look like cartoon characters in Wii games. In an attempt to make avatars more realistic, cameras may be added to AR and VR devices to look at the facial muscle movements, and to have the avatar replicate these movements. Beyond this, the next generation iteration to make the avatars even more realistic may be to observe the facial features such as facial blood flow, eye movements, and physiological parameters on the user using a CSP system and then reflect some of the emotions, color changes, and eye movements in the avatars. Alternately, the information regarding a particular user may be sent to other participants so they may know the sentiments or reactions of the particular user to the event or material being presented. In a particular embodiment, a multi-user virtual game may be played, where the CSP information sent to other users allows them to make judgements based on the data sent. In yet another embodiment, people working on their computing devices may be observed using a CSP system to observe if they are becoming drowsy, distracted, disturbed, angry, or excited about some material on the screen. For example, the CSP system may be observing stock or financial traders to check that they are fully cognizant of operations being performed. These are just some examples, but many other applications of CSP systems in AR, VR or metaverse devices are possible and are intended to be covered by this disclosure.

In yet another embodiment, the CSP system may have advantages in the healthcare and medical monitoring space, for example in telemedicine or remote patient monitoring. With events such as the COVID-19 pandemic and wider availability of internet and the ubiquitous use of smart phone and tablets, there is a rise in the use of telemedicine and/or remote patient monitoring. In one example, a patient may sit in front of a tablet or smart phone and interact with a healthcare provider. With the use of the CSP system, the healthcare provider may gain insight about the patient through the transmission of data associated with the patient's physiological parameters, facial blood flow and eye movements. This may be achieved in a contactless, non-intrusive, non-invasive manner that would be convenient to the user and relatively easy to use. The data may also be sent to the cloud for additional processing using AI/ML to look for ailments such as cardiovascular irregularities, one example of which could be atrial fibrillation. Moreover, if the data is stored, then the current measurements can be compared with the patient's history to see if there is a trend or unexpected changes. Alerts, alarms, or notifications may be sent to users, healthcare providers, or designated recipients if unusual readings or trends are observed.

The above is just one example of using CSP system in healthcare or medical monitoring, but many other applications are possible in this space and are intended to be covered by this disclosure. For example, in one embodiment on-line psycho-therapy sessions could benefit from using a CSP system. The care giver could then get a better sense of the state of the patient, physical as well as psychological, with more insight into sentiments and reactions. In another embodiment, the CSP system could be beneficial when used with elderly patients or infants or young patients, more generally patients who may not be able to express how they feel or react to treatments. By using the CSP system, the healthcare worker or care giver could obtain a better sense of when the non-communicative patient has abnormal symptoms, or how the patient is reacting to treatment or medications.

In yet another embodiment, the CSP system could be used in a hospital room or out-patient facility to monitor patients on a more-or-less continuous manner or for periodic measurements of the state of the patient. As an example, hospital admitted patients generally complain about difficulty in sleeping because the healthcare workers come in roughly every four hours to measure vitals such as heart rate, oximetry, respiratory rate and blood pressure. Moreover, for medical diagnosis there is only data every four hours, as opposed to an intensive care unit where there is continuous monitoring. By mounting or placing the CSP system above or near the patient's bed where the patient can be viewed (particularly the patient's face), the state of the patient can be measured in a non-intrusive, non-invasive, and contactless manner, resulting in less disturbance to the patient. Moreover, the data from the CSP system could be sent wirelessly or via cables (wires, fibers, or coaxial cables) to the central monitoring station, the nurse station, or other caregiver or monitoring systems. Additional benefits may also arise by using the CSP system in a hospital room (or, for that matter, in any elderly care facility, room in a home, or any other location), particularly when the CSP has 3D imaging capabilities by using a ToF sensor/camera. Since the body motion, posture, and position can be observed by the ToF, the CSP may detect if a patient has fallen or had a sudden motion interruption. Since there are significant concerns about elderly patients or any patient falling, this may be a major benefit for the room monitoring system. Also, if only a low resolution ToF is used that provides a "skeleton" of the patient, such a system may also be implemented with less privacy invasion concerns. In another embodiment, another advantage of a CSP system that may have a ToF sensor/camera is that it may be able to monitor a number of individuals more or less simultaneously, as well as observing the physical interaction between or among those individuals. This may be advantageous when, for example, the physical interaction among people is being observed for psychological analysis. In yet another embodiment, the monitoring of the motion of multiple individuals may be valuable in sports events or venues, and then it may even be possible to predict a potential sports injury. These are just some examples, but other multiple person body motion monitoring scenarios may be observed using a ToF sensor/camera or CSP system (note that the terms camera and sensor are being used interchangeably with respect to the ToF device).

In a further embodiment, the CSP system may be beneficial for anaphylaxis patients (e.g., patients who may experience an anaphylactic shock). Anaphylaxis is a severe, and some cases even life-threatening allergic reaction. The most common anaphylaxis triggers in children are food allergies, such as an allergy to peanuts or tree nuts, fish, shellfish, wheat, soy, sesame and milk. Beyond allergy to peanuts, nuts, fish, sesame and shellfish, anaphylaxis triggers in adults include: (a) certain medications, including antibiotics, aspirin, and other pain relievers available without a prescription, and the intravenous contrast dye used in some imaging tests; (b) stings from bees, yellow jackets, wasps, hornets and fire ants; and (c) latex. The reactions may be immediate (approximately 90 percent of the response reactions fall within this uni-phasic category), or there may be a second reaction (approximately 10 percent of the second reactions fall in this biphasic anaphylaxis). As one example, a patient coming to a doctor's office or hospital may have incorrectly filled out the allergy list (or may be unaware), and then when given a medicine the patient suddenly has an anaphylaxis event.

The CSP system may be able to detect the anaphylaxis event because some of the physiological symptoms may fall within what the CSP system observes. Anaphylaxis causes the immune system to release a flood of chemicals (e.g., histamines) that cause the person to go into shock—blood pressure drops suddenly and the airways narrow, blocking breathing. Thus, some of the physiological markers include low blood pressure (hypotension), elevated heart rate and respiratory rate, wheezing and trouble breathing (due to the constriction of the airways and a swollen tongue or throat), as well as potentially nausea, vomiting, diarrhea, dizziness or fainting. Thus, if the CSP system is installed or used in the doctor's office or hospital, when a patient has an anaphylaxis event the CSP system may be able to detect the changes in the vital signs due to the allergic reaction and alert the healthcare provider of a potential emergency situation. In response, the healthcare provider may be able to provide an injection of epinephrine (e.g., epi-pen) and follow up with other medications or monitoring in the emergency room. Although discussed in the context of the healthcare facility, similar benefits may also happen in home or outside situations if the CSP system is used, for example, on a smart phone, tablet, computer or wearable device, or even an AR/VR or mixed reality device such as goggles or eye wear.

In yet another embodiment, the CSP system may be attractive for use with vehicle driver or occupant monitoring systems. By measuring the facial features, the state of the driver could be determined in a passive, non-intrusive, contactless manner. For example, the parameters measured by the CSP system could indicate changes such as drowsiness, impairment, inebriated state, sudden sickness, heart attacks or atrial fibrillation events, strokes, etc. The signal from the CSP system could be fed to a controller in a semi-autonomous or autonomous vehicle to slow the vehicle, put on four-way flashers, pull to the side of the road, and/or call emergency numbers or contacts for help. Alternately, sound or vibration alerts may be used with the driver or occupants, or the vehicle could be prevented from starting. These are just some of the controls in the vehicle that could altered based on the information from the CSP system, but other actions could also be taken and are intended to be covered by this disclosure. The CSP camera may be mounted on the steering column, on the dashboard or instrument panel, on the roof interior, on the door interior, or near or on the rear view mirror. In a particular embodiment, the CSP system for driver and occupant monitoring may be mounted on or near the rear view mirror. In this example, if the CSP system is a hybrid system using ToF sensors and a wide field of view camera, then the wide field-of-view camera may be able to see both the driver and passengers, while multiple ToF sensors may be used, for example one looking at the driver and another looking at the front passenger seat occupant. Then, the ToF sensor data may be co-registered or overlapped with the wide field-of-view camera data to get a 3D view of the driver and the passenger seat occupant, potentially even other back seat occupants of the vehicle. This is just one example, but other locations and examples, or combinations of these examples, are intended to be covered by this disclosure.

The CSP system used with a driver or occupant monitoring system could perform multiple tasks that could be beneficial for the vehicle. Since there is limited space in the cockpit, vehicle makers are usually desirous of multiple applications for the hardware and software that is deployed in the vehicle. Since the CSP system may have a time-of-flight sensor, potentially co-registered with a higher resolution camera, the CSP system may provide a three dimensional image of the driver or occupants. The ToF sensor may be particularly valuable for compensating for motion artifacts, in addition to providing the depth information for 3D imaging. With the two- and three-dimensional imaging, the CSP can contribute to five or more vehicle tasks, including: (a) driver head pose and eye gaze direction, as well as potentially pupil dilation; (b) face-ID or facial authentication; (c) vital signs, such as heart rate and respiratory or breathing rate; (d) facial blood flow for drowsiness, impaired or drunk driving detection; and (e) smart restraint control systems, such as smart air bag or seat belt adjustment. Driver monitoring system already use infrared cameras to look at the head pose and eye gaze of the driver, so that the advance driver assistance systems—ADAS—can determine that the driver is looking at the road and is able to resume control of the vehicle at any moment. For higher resolution cameras, the infrared cameras may also be able to look at the pupil dilation, which may be used for attention or cognitive load determinations. The infrared cameras may also be able to authenticate the driver based on face-ID. For a face-ID system, the third dimension may play an important role, so that the system is not fooled by a picture (e.g., use the 3D imaging to verify it is a person). Also, additional anti-spoofing techniques may also be used, such as verifying that there is a heart rate or respiratory rate. Authenticating the driver not only provides a convenient way to identify the driver and adjust settings in the vehicle (e.g., set settings, mirror adjustments, entertainment settings, etc.), but it may also be valuable as more and more artificial intelligence and machine learning is used in the vehicle. For example, as machine learning is being used to collect the data of the driver, it may be valuable to know which driver is involved (e.g., to make software or features customized to the driver). Rather than the driver having to identify themselves each time, the face-ID system could know which driver is involved and tag the data corresponding to that user.

In addition to the above task, this disclosure has previously described that the CSP system may measure physiological parameters or vital signs for the driver, which can help determine the state of the driver. As described previously, the CSP system can be used to measure parameters such as heart rate, respiratory rate, and heart rate variability. It may also be augmented with relative or absolute blood pressure. Moreover, because the facial blood flow is controlled by the autonomic nervous system and since different ROIs on the face may reflect different vasodilation or vasoconstriction in response to cognitive load, intoxication, drowsiness or impairment, comparing the blood flow on different ROI's of the driver's face could provide additional insight into the state of the driver and their ability to drive properly.

The 2D/3D imaging capabilities of the CSP system can also be used for smart restraint control systems for the driver as well as occupants in the vehicle. In many of the current vehicles, safety restraint control systems such as the air bags and seat belts are adjusted for the average size and weight adult male. Therefore, when accidents or sudden stops occur (for example, in response to an automatic braking system), people who are not the average adult male may be injured. As an example, women and children report being injured more than males by vehicle restraint systems. However, using the 3D imaging and motion detection that can be seen by a time-of-flight sensor or a CSP system, when something like the automatic braking occurs, the motion of the driver and passengers can be seen, and the deployment of the airbags, seatbelts, and other restraint control systems can be appropriately adjusted—making it a smart restraint control system. Thus, in short, by using a 2D/3D imaging system such as the CSP system, five or more functions may be implemented in advanced driver assistance systems, or advanced driver or occupant monitoring systems. In one embodiment, such CSP systems may use infrared cameras co-registered with one or more dToF sensors, an iToF camera, or parts or combinations of such systems.

In a particular embodiment, the CSP system may be used for advanced driver monitoring or driver assistant systems to view multiple aspects of the driver (and, potentially, the occupants). The facial blood flow may be monitored, and different ROI's on the face may be compared. The CSP system can also be used to monitor vital signs, such as heart rate, respiratory rate, and heart rate variability. The regions around the eye may also be observed, thereby monitoring the blink rate, PERCLOS or percentage of eye closure, and potentially the pupil dilation. The body position and motion may also be observed, which may be particularly important for smart restraint control systems. The CSP system may involve time-of-flight sensors, potentially co-registered with higher resolution cameras, and also having processors that may implement various artificial intelligence and machine learning algorithms. Beyond the various functionalities that such a system may offer, the combined information may also be beneficial for improving the reliability of the assessment. Also, the ToF sensors may help to compensate for motion artifacts, since the depth information contains much of the motion information.

In one embodiment that illustrates how the various information can be used to better assess the scenario, consider what might be expected for different environmental temperatures, exercise conditions, as compared with intoxication. As mentioned earlier, one of the potential challenges of the CSP system is that it provides an indirect measurement of different conditions. For example, the facial blood flow may change for different conditions, and one of the tasks of the CSP system is to sort through and identify the most likely condition. The combination of the various data may help to improve the assessment. In a particular example, assume that the system is trying to distinguish conditions of high environmental temperature, low environmental temperature, short exercise by the user (e.g., running to the car in the rain), long exercise by the user (e.g., coming to the car after running a 10K race), and the driver being intoxicated. The parameters measured by the CSP system may include PERCLOS, eye blinks per minute, facial blood flow on different ROIs (e.g., forehead, nose, cheek, etc.), breathing or respiratory rate, blood pressure (systolic and diastolic), heart rate, heart rate variability, and facial temperature. Based on a survey of the literature, one might expect the following changes under the different conditions (as compared with a baseline measurement of the person at rest). Although any one of the metrics may not be able to identify the appropriate condition, adding together the different information may improve the reliability and accuracy of the condition assessment. As an example, for cold temperatures (environmental temperature lower than the baseline condition), the PERCLOS, and heart rate may increase, while the eye blinks, facial blood flow, and facial temperature may decrease. On the other hand, for hotter temperatures (environmental temperature higher than the baseline condition), the blood pressure and heart rate variability may decrease, but an expectation that the other parameters may increase, such as PERCLOS, eye blinks, facial blood flow, breathing rate, heart rate and facial temperature. For a long exercise, the facial blood flow, breathing rate, systolic blood pressure, and heart rate may be expected to increase, but the heart rate variability and facial temperature may be expected to decrease. A similar set of parameters may also be expected for the short exercise scenario. Finally, for intoxication, the literature suggests that the eye blink rate, breathing rate, and heart rate variability may decrease, but the PERCLOS, facial blood flow, heart rate and facial temperature may increase. In this particular embodiment, although an indirect measurement, the case of intoxication may be distinguished from the other environmental or exercise scenarios by combining information PERCLOS, facial blood flow (e.g. the forehead ROI), breathing rate, and heart rate. All of these parameters may be potentially measured using the CSP system. This is just one example, but some parts of this data, other data, or combinations of this data may be used to improve the prediction reliability and are intended to be covered by this disclosure. Also, the CSP data may be combined with inputs from other systems, such as steering wheel movements, lane tracking on the roadway, automatic braking system data, etc., as well as meta data of the driver or passenger.

Although various embodiments using the CSP system in a driver or occupant monitoring system have been described herein, combinations of some or all of these embodiments as well as potentially other embodiments may be implemented and are intended to be covered by this disclosure. As an example of an alternate embodiment, the camera and time-of-flight combination in the CSP system may be used for eye-tracking and hand-tracking, which could in turn be used for the driver or occupant to control different functions. In one embodiment, a vehicle may have a head-up display, or a region of the dashboard with an on-screen item, such as a button, application icon, or list entry. The driver or occupant may select the item by looking at it on the head up display or dashboard. To minimize errors, there may be an addition eye movement required to confirm, such as two blinks in rapid succession, or some other eye movement. The eye tracking system could use the eye selection and verification to activate the screen item, thus reducing the need for the driver to take their hands off of the steering wheel. In another embodiment, the 2D/3D nature of the CSP system could be used to observe the hand and finger gestures of the driver or occupant. As a particular example, the driver could pinch their thumb and index finger together to activate a task. In other words, hand movements that might be used commonly on touch screens, smart phones or tablets could be implement using gestures of the driver or occupant recognized by the CSP system. As much as the eye tracking and hand tracking may be valuable in a vehicle to select or perform tasks, similar functions using the CSP system may also be performed in other settings or devices. In an alternate embodiment, using the camera and time-of-flight sensors for the CSP system, the eye-tracking and hand-tracking for controlling functions could also be implemented in a wearable device or an augmented/virtual/mixed reality device, such as a headset, goggle, or smart eye glasses. In this case, rather than the screen item being on the head up display or dashboard, the screen item may be on the display of the wearable or head-mounted reality device. Such systems may also be used with smart phones, tablets or computing systems, and these are also intended to be covered by this disclosure.

In yet another embodiment, the CSP system may be used with robotics, machine vision, or industrial vision applications. Robots or industrial automated equipment or vehicles may need machine vision to accomplish their tasks or move around. Active illumination and ToF sensors, as in the CSP system, may be valuable for providing inputs to the machine vision algorithms or processing or serving as virtual eyes. Moreover, robots or industrial equipment that interacts with a user may benefit from the functions that can be performed by the CSP system. For example, if a robot maid such as “Rosie in the Jetsons” cartoon series were to be implemented, the robot could use the CSP system to view the users face and potentially decipher the intent or sentiments or reaction of the user. Combined with artificial intelligence and machine learning, the robot could learn over time the preferences of the user. Also, using facial recognition, the learning could be specialized to each person (e.g., personal preferences of the regular dwellers at a location).

In yet another embodiment, a CSP system could be used at the entrance to a factory of office location. Again, if combined with facial recognition or palm recognition or other types of biometrics, the entrance system (e.g., a kiosk) could recognize or authenticate whether a person should have access, or perhaps even clock in the person. Also, the CSP system could check the physiological parameters to make sure the person is healthy (including possibly a thermal camera or sensor to measure the person’s temperature). This could be valuable during pandemics, such as recently experienced with COVID-19, or even during normal influenza season. Moreover, for a factory setting, air traffic controller tower or other monitoring/controlling facilities, it may be valuable to know that an employee is not coming to work intoxicated or impaired, especially when using heavy machinery, potentially harmful equipment, or putting others in peril. The CSP system using the facial features may be able to flag or set a warning when an individual is sufficiently out of their normal range of parameters, perhaps then requiring additional testing or questioning before returning to work. Again, the combination of the CSP system with artificial intelligence and machine learning can lead to each person’s baseline being established, and then after authenticating a person the measured facial features can be compared with the more typical or normal baseline. These are just some examples in robotics, industrial machinery, and computer vision, but many other applications of the CSP system exist and are intended to be covered by this disclosure.

The attributes of the CSP system, particularly looking at facial features such as facial blood flow, eye movement and physiological parameters, may have many other applications beyond those described above. As another example, the CSP system may be used with indoor or outdoor exercise equipment to monitor the performance of an athlete, and the exercise equipment may include bicycles, ellipticals, treadmills, rowers, as well as mirror-based devices or wall-mounted weights or pulleys. In some instances, the data from the CSP system may be fed back to the exercise equipment controller to change parameters, such as speed, incline, resistance, etc. In another embodiment, the CSP system may be used in tasks requiring high dexterity or performance from an individual, such as astronauts, airplane pilots or fighter jet pilots, etc. While positioned in the cockpit, for instance, the CSP system may monitor the state of the individual to insure that they are able to maintain high performance standards. In yet another embodiment, the CSP system may be used in a set-up such as a kiosk at an entrances to verify the health of individuals entering, such as at entrances to airports, high-end establishments or stores, or secure facilities. In a further embodiment, the CSP system may be used to measure or monitor the cognitive load of individuals, particularly when their near complete attention may be required to perform a task. In yet another embodiment, the CSP system may be used at least in part for lie detection, or more generally to observe how an individual is reacting to particular stimuli. These are just further examples, but these and other applications as well as combinations of these applications of the CSP system are also intended to be covered by this disclosure.

Improving Signal-to-Noise Ratio (SNR) in the CSP System

FIG. 96 illustrates one preferred embodiment of the CSP system. The light source may be a one or more VCSELs or VCSEL arrays, whose light may be incident on and penetrate tissue comprising skin. The VCSELs may operate in the NIR wavelength range, and pulsed or modulated or a combination of these. Lenses, diffractive optical elements, or other beam shaping modules may be placed in front of the light source to collimate/focus/spread the beam, direct the beam, change the beam shape into more square/rectangular/circular shape, or possibly separate the beam into a plurality of spots. The light may measure blood in the skin through for example PPG, and the measurement can include variation over time or variation among different spatial locations, or a combination of spatial and temporal comparisons. Some of the reflected light may be captured by one or more photo-detectors or a photo-detector array and/or a RGB or NIR camera. There may be spectral filters and/or lenses placed in front of the photo-detectors and/or camera. There may also be other beam shaping modules, such as diffractive optical elements. The photo-detector may include iToF or dToF sensors, where the depth information may help to compensate for motion artifacts. The photo-detector and camera signals may be co-registered, and the outputs from the photo-detector and camera may be sent to a processor. This is just one embodiment, but not all the elements may be required, or other elements may be added, or some combination of this configuration with others described may be used and are intended to be covered by this disclosure.

As with many of the optical systems described in this disclosure, for the CSP system one of the goals is to improve the SNR using a number of techniques. Although many SNR improving methods have been described throughout this disclosure, below is a summary of at least some of the SNR improving techniques that would be potentially beneficial for the CSP system. Some of these techniques, combinations of these techniques, or in combination with additional techniques may be used with the CSP implementation and would fall within the scope of this disclosure.

- Operate the active illuminator, such as VCSELs, at NIR wavelengths near 850 nm or 940 nm, such as where sunlight is weaker and the human eye may be less responsive
- Use spectral filters in front of the photo-detectors and/or camera that may be centered on one or more active illuminator wavelengths, thus reducing noise from ambient light or stray light or other light sources
- Use polarizers in front of the photo-detectors and/or camera, which may help to selectively observe the light penetrating the tissue. For example, the active illuminator may be polarized, but the light penetrating the tissue may become more depolarized because of scattering and collagen in the tissue. Orienting the polarizer orthogonal to the active illuminator polarization would then preferentially observe the light penetrating the tissue rather than the light reflecting off the tissue surface.
- Use apertures or spatial filters to selectively collect the desired light while reducing the capture of the undesired or stray light
- Co-register the photo-detectors with a camera system, perhaps using adjustable lenses, and the camera system may use illumination centered at one wavelength, while the photo-detectors may use illumination at a different wavelength, thereby reducing interference
- Synchronize photo-detectors to the light source, such as the VCSELs
- Synchronize the camera to light source, such as the VCSELs. Alternately, many camera systems use light-emitting diodes for active illumination
- Use change detection, meaning measure with light on and light off and then difference the two, thereby reducing effects from ambient lighting or other common mode noise sources or other background noise or environmental noise sources
- Increase intensity or power of the active illuminator to improve SNR
- Increase pulse repetition rate of the active illuminator to improve SNR
- Differential measurements may be used to reduce noise from, for example, the active illuminator. This may include having a multiple arm set-up, such as a reference arm and a signal arm.
- Multiple wavelengths of light may be used, where some wavelengths of light may serve as references or multiple wavelengths may improve the accuracy of a measurement.
- Multiple pulse repetition rates may be used, so that in some instances the distance ambiguity may be reduced enabling longer distances or range
- Processor may use Fourier transform analysis, or other methods to highlight the periodicity of the signal desired from other noise sources
- Use beam shaping modules such as diffractive optical elements to concentrate the optical power into spots, thereby providing higher intensity at the spots without exceeding eye safety power levels averaged over the beam Processor may use artificial intelligence or machine learning algorithms, or other techniques such as regression, classification, multivariate analysis, principal component analysis, independent component analysis, factor-based algorithms, partial least squares, mathematical derivatives, etc.

CSP Enhanced Using Artificial Intelligence, Machine Learning, or Deep Learning

Since the use of artificial intelligence and machine learning has been discussed a number of times for enhancing the capabilities of CSP and other optical systems, it would be worth reviewing some of the common techniques used that may be beneficial in processing the data. Although Artificial Intelligence (AI) may be described as the broader category, machine learning (ML) and neural networks have become recently very powerful techniques. Among neural networks, the sub-category called deep learning has become even more important, particularly as the computing power has increased. Within ML, the two main categories are supervised learning and unsupervised learning, although there are also other branches such as reinforcement learning and recommender systems. Supervised learning may be described as teach the computer how to do something, then let the computer use its new found knowledge to do the task. Unsupervised learning may be described as let the computer learn how to do something, and use this to determine structure and patterns in the data. Supervised learning usually works from a training set that may be labeled, while unsupervised learning may be when data is provided without any label (i.e., without any right answer). For example, one way to perform unsupervised learning is to cluster data into groups, what is often called clustering algorithms. Within ML, a regression problem may be described as a problem to predict a continuous valued output (e.g., an output that can take on many values). On the other hand, a classification problem may be described as a problem to predict a discrete valued output (e.g., an output can have a few discrete values).

Within the continuous output case, one embodiment is to have linear regression, which may be with one or more variables (multiple variables is called multi-variate problem). In another embodiment, there may be multiple features and a polynomial regression. One way to determine the parameters for regression is to define a cost or loss function (e.g., least square error or mean square error), and then use algorithms such as gradient descent to minimize the cost function. Beyond gradient descent, there are alternate methods of minimizing the cost function, such as Broyden-Fletcher-Goldbarb-Shanno, BFGS, and limited memory BFGS, L-BFGS. An alternate method of determining the parameters is to use a normal equation method, which unlike gradient descent is not an iterative process, but it may become computationally intensive if the number of features or training data set is too large. In supervised learning, the labeled data may be divided into a training set, a cross-validation set (also called a development or dev set), and a test set. In one embodiment, the training set may use 60 percent of the labeled data, the cross-validation set or dev set may use 20 percent of the data, and then the test set may use the remaining 20 percent of the data. The training set may be used to determine the parameters or weights for the ML network, the cross-validation set may be used to select the model to be used, and then the test set may be used to predict how accurate the selected model with the parameter or weights will function for new incoming data. As an example, this split in the data may be used to see if the ML problem has "high bias" (under-fitting the problem) or "high variance" (over-fitting the problem).

With the discrete output case, the classification problem in ML may be called logistic regression (note that even though it is called "logistic regression," it is for discrete outputs). In this case, the hypothesis may be modified using a function, such as a sigmoid function, ReLU (rectified linear activation) function, etc. The classification problem may be a binary problem with two choices, or it may be multi-class classification, in which case a one-versus-all method may be used. To simplify the calculations, techniques such as regularization may also be used to avoid problems such as overfitting.

Neural networks may be powerful ML algorithms because they can handle non-linear hypotheses. Nonlinear classification problems may not easily be solved using techniques such as linear regression, multivariate linear regression or simple logistic regression. But, neural networks, and what are now popularly called deep learning, may be very useful in this instance. One example of a nonlinear problem is computer vision, which may be the category of problems encountered using the CSP systems. In a neural network, there are neurons or nodes, that may use an activation function, such as the sigmoid function or ReLU function. The neural network may have multiple layers, with the first layer called the input layer, the last layer called the output layer, and the in-between layers called the hidden layers. Each layer may have a number of neurons or nodes, and these can be all interconnected with weights to each connection. After combining all the inputs to the node or neuron, the activation function is applied at each node. Thus, the basic idea of a neural network is to solve a complex non-linear classification problem by using many sequences of simple logistic regression. Neural networks may be used for a single output node, or multiple output nodes in a multi-class classification problem. Neural networks often use a combination of forward and backward propagation to calculate the parameters or weights in the network. In the forward propagation step, the output of the neural network may be computed, and in the back propagation step, the gradients and derivatives may be computed for the gradient descent application. Depending on the problem to be solved, the neural network architecture may be selected in terms of the number of layers and the number or nodes or neurons for each of the layers. Also, neural networks can be made more efficient by vectorising the computations, since graphical processor units are often optimized for vector processing and matrix manipulation.

AI/ML have a number of different features and aspects that may be valuable, depending on the problem at hand. For example, error analysis techniques may help to debug and optimize a ML algorithm. In the case of what is known as a skewed class (e.g., when a particular occurrence is relatively rare in the entire data set), one error analysis method is known as precision/recall. Precision may be defined as the number of true positives divided by the sum of true positives and false positives. Recall may be defined as the number of true positives divided by the sum of true positives and false negatives. These two metrics may be put together in an F-score or F1-score, which may be defined as two times the product of the precision and recall divided by the sum of the precision and recall. Other figures-of-merit may also be used.

There are also different classes of ML algorithms. One algorithm is called support vector machines, which falls in the category of large margin classifiers. Also, for unsupervised learning (e.g., data with no labels or identification of the correct answers), clustering algorithms may be used, such as the K-means algorithm. The K-means algorithm is among the most popular and widely used algorithm for automatically grouping data into somewhat coherent subsets. There are also ML techniques for reducing the dimensionality of the data, which might be valuable for data compression, easier visualization, or to speed up the ML processing. For example, popular dimensionality reduction algorithms include principal component analysis or independent component analysis. Another category of ML problems is known as anomaly detection, which may be commonly used in detecting fraud or, more generally, when there are a very small number of anomalous cases. It may also be valuable in healthcare type ML situations, since there may be only a few cases of anomalous behavior. Also, for evaluating the anomaly detection algorithm the metrics may include precision/recall or the F1-score previously mentioned. Yet another type of ML algorithm is a recommender system, which may be a popular application for things like movie recommendations or recommending a product based on what has already been purchased or observed. These are just some examples of AI/ML algorithms, but there are others as well as and are intended to be covered by this disclosure.

Among neural network techniques, of growing popularity has been the field called deep learning. Deep learning may be an artificial intelligence function that imitates the workings of the human brain in processing data and creating patterns for use in decision making. Deep learning has transformed internet businesses like search and advertising, and it is enabling brand new products and businesses. Applications of deep learning include speech recognition, object recognition on images, autonomous vehicle driving, image processing including facial recognition, and advertisements. There are also different categories of deep learning, such as convolutional neural networks, which are often applied to image processing, natural language processing, which is used with language or sequence of words, and recurrent neural networks. Deep learning refers to typically large neural networks, such as pattern recognition and the passage of the input through various layers of simulated neural connections. Deep learning is being used extensively for problems of classification and regression, and it has risen in importance because much more data has become available, and it turns out that if a very large neural network is trained with more and more data, then its performance may continue to improve. Also, beyond the increase in computing power with both central processing units and graphical processing units, recently there have been tremendous algorithmic innovations that are making neural networks run much faster. For example, switching from a sigmoid activation function to a ReLU function has been one of the huge breakthroughs in neural networks with large impact on their performance.

In the deep learning network, just like in the neural networks, there can be an input layer, an output layer, and intermediate hidden layers—in deep learning networks, there are usually many hidden layers, such as three or more, in many cases many more. Within each layer, there can be any number of nodes, and at each node the hypothesis is calculated, and then the activation function is applied. The activation function may be the sigmoid function, the arc tangent function, the ReLU function, or what is often called a leaky ReLU function. It may be valuable that the activation function is non-linear, which permits the deep network to perform non-linear processing. Gradient descent may be again used to calculate the parameters or weights of the network, and forward and backward propagation may be used to aid in the calculations—e.g., forward propagation is used to compute the parameters and predicted output, while back-propagation is used to update the parameters using gradient descent.

The intuition behind deep neural networks might be thought as trying to find relations with the data, going from simple to more complex relations. The first hidden layer may be trying to perform a simple function, and as the computation moves deeper into the network, these simple functions combine together to form more complex functions. For example, for facial recognition the starting point may be an image, and then the functions in various layers first identify edges, then face parts, then faces, and then the desired face. In another example, for audio recognition the starting point may be an audio recording, and then the functions in various layers first identify low level sound features, then phonemes, then words, and then sentences. For each layer in the deep network, the inputs to a layer will be the activations from the previous layer, and the output of this layer will be its own activations. When performing forward propagation, values along the way can be cached, and those cached values can be used during the backward propagation for gradient descent. Again, the efficiency of the computation in processors such as graphical processor units can be improved by vectorising all the functions. One reason that deep neural networks seem to perform surprisingly well is that they are usually fed a large amount of data, and the deep network is learning from that data using the hidden layers. The efficiency of the deep learning algorithms can be made more efficient by tuning the hyper-parameters, regularization, and optimization. Examples of the hyper-parameters include the learning rate, number of iterations, number of hidden layers, units (nodes or neurons) in each hidden layer, and choice of activation function.

In summary, artificial intelligence may be considered the broad category of algorithms, and machine learning being a subset of AI, with many different ML methods. Within ML, one category is neural networks, and within neural networks is an important category of deep learning. In one embodiment, artificial intelligence may be defined as a program that can sense, reason, act and adapt; machine learning are algorithms whose performance improve as they are exposed to more data over time; and, deep learning is a sub-set of machine learning in which multi-layered neural networks learn from vast amounts of data. In another embodiment, AI may be described as a technique that enables machines to mimic human behavior; ML may be considered a sub-set of AI technique that uses statistical methods to enable machines to improve with experience; and, deep learning may be considered a sub-set of ML that makes the computation of multi-layered neural networks feasible. In yet another embodiment, AI may be thought of as algorithms that mimic the intelligence of humans, able to resolve problems in ways that may be considered smart, from the simplest to the most complex of algorithms; ML may be thought of as algorithms that parse data, learn from it, and then apply what it has learned to make informed decisions (ML may use human extracted features from data and improve with experience); and, deep learning may be thought of as neural network algorithms that learn the important feature in data by themselves, and are able to adapt themselves through repetitive training to uncover hidden patterns and insights. Finally, in another embodiment, AI may be considered as engineering of machines that mimic cognitive functions, ML as the ability to perform tasks without explicit instructions and relying on patterns, and deep learning as machine learning based on artificial neural networks. This is a rapidly advancing field, with major breakthroughs recently in generative AI, such as ChatGPT, DALL-E, etc., and these and other advances are also intended to be covered by this disclosure.

Beyond Diagnostics, Potential Therapeutics Using NIR Light Sources on Face

Although much of the disclosure has discussed diagnostics, the light sources described herein may also be used for therapeutic treatments in some embodiments, or the diagnostics may be combined with therapeutics. In one embodiment, near-infrared light based therapeutics might include what is known as photo-bio-modulation (PBM), which may also be called transcranial infrared-laser stimulation, photo-neuro-modulation, or low-level laser therapy. In PBM, light from relatively low-power lasers, VCSELs, or LEDs are applied to the body as a form of medical treatment. Unlike other light-based treatments that may heat or cut the tissue, PBM employs relatively low power and does not cause a significant increase in tissue temperature. As one example of the use of PBM, near-infrared light may be applied to the head of a participant, such as on the right side of the forehead so that the light can penetrate into the pre-frontal cortex. Multiple human studies have shown that PBM applied to the forehead with a 1064 nanometer wavelength light source photo-oxidizes the mitochondrial enzyme cytochrome-c-oxidase (CCO) and promotes hemoglobin oxygenation in the pre-frontal cortex, and the experiments have verified that the actions are not due to thermal effects. The benefits observed include more efficient oxygen consumption for bio-energetics, resulting in enhanced pre-frontal cortex cognitive functions such as attention and working memory, executive function, and rule-based category learning. There is also evidence that transcranial PBM promotes behavioral changes, such as improved mood, attention, learning and memory, in addition to anti-depressant effects. For example, PBM has been shown to be beneficial for patients with dementia, traumatic brain injury, stroke and depression.

The literature supports the hypothesis that during PBM, photons enter the tissue and interact with CCO complex within mitochondria. In other words, CCO is the light sensitive chemical that absorbs the NIR light and is affected by the exposure. This interaction triggers a biological cascade of events that leads to an increase in cellular metabolism, which may lead to beneficial effects such as decrease in pain as well as acceleration of the healing process. PBM may be defined as light therapy that uses non-ionizing light sources, including lasers (e.g., VCSELs), LEDs, and/or broadband light in the visible (e.g., approximately 400-700 nanometers) and near-infrared (e.g., approximately 700-1100 nanometers) electromagnetic spectrum. PBM is supposedly a non-thermal process that involves endogenous chromophores eliciting photo-physical (i.e., linear and non-linear) and photo-chemical events at various scales. This process may result in beneficial therapeutic outcomes including but not limited to the alleviation of pain, immuno-modulation, and promotion of wound healing and tissue regeneration.

Evidence suggests that the primary target for the PBM process is the CCO complex, which is found in the inner membrane of the cell mitochondria. CCO is an important component of the electron transport chain that drives cellular metabolism. As light is absorbed by CCO, it stimulates the electron transport chain to increase the production of adenosine triphosphate, ATP, within the mitochondria. For example, changes in CCO reflect the brain cell's metabolic activity, and CCO is the photo-sensitive enzyme that reacts with oxygen in the last step of the mitochondrial transport chain. It is estimated that CCO is responsible for approximately 95 percent of oxygen metabolism in the body and is important for efficient generation of ATP, which is the energy needed for cells to live and function. When tissue is damaged, the production of ATP in the cell is impaired, which in turn slows down the metabolism of the cell as a protective mechanism. As a consequence, PBM may help to restore the oxidative process that helps restore normal cellular function. In addition to ATP, light stimulation is also believed to produce free nitric oxide and to modulate reactive oxygen species. Nitric oxide may be a vasodilator and an important cellular signaling molecule participating in many physiological processes. Moreover, reactive oxygen species have been shown to affect many important physiological signal pathways including the inflammatory response. The resulting metabolic effects following PBM increase cerebral metabolic energy production, oxygen consumption, and blood flow, both in animals and humans.

For PBM to occur, light has to reach the mitochondria of the target tissue. A number of factors affect how much light reaches the target tissue, including light wavelength, minimizing unwanted absorption, light power and reducing reflections. In particular, CCO has a broad absorption between approximately 750 and 900 nm (peak absorption around 810 nm), with tails of the absorption at shorter and longer wavelengths. In principle, NIR wavelengths in the 750 to 900 nm range could be used for PBM, although wavelengths shorter and longer that are absorbed in the tails of the CCO spectrum may also be used. However, to achieve optimal PBM of the human brain there may be a trade-off between the absorption of light by CCO and the depth of light penetration. For example, Monte Carlo simulations for photon delivery into the pre-frontal cortex with three representative wavelengths (660 nm, 810 nm and 1064 nm) have shown that 1064 nm is the optimal, benefiting from its reduced tissue scattering. Other photo-acceptors such as water also absorb photons in both the lower and higher wavelengths in this range. The longer 1064 nm wavelength allows for deeper tissue penetration and less scattering. To illustrate the wavelength selection, FIG. 86D shows the optical penetration depth versus wavelength (in this instance for human skin). As can be seen, around 1064 nm is the peak in the penetration depth (approximately 3.6 mm in this example). In comparison, the penetration depth near the maximum CCO absorption near 810 nm is approximately 64 percent of that at 1064 nm, and the penetration depth near 610 nm is approximately 53 percent of that at 1064 nm. Since PBM light excitation applied, for example, near the right side of the forehead should penetrate the scalp/skin followed by the skull bone and finally be absorbed in at least a part of the pre-frontal cortex section of the brain, it may be valuable for the penetration depth of the light to exceed about 2.5 mm, more preferably about 3 mm in FIG. 86D. These are exemplary wavelengths, but other wavelengths and penetration depths may be used and are intended to be covered by this disclosure.

In a particular embodiment, light was exposed to the right side of the forehead with a collimated beam that was roughly circular and covered an area of about 13.6 $cm^2$ (the light is supposed to penetrate down to the right pre-frontal cortex, the so-called Broadmann Area 10). The measured output was 3.4 W; therefore, the treated region was exposed to a power density of approximately 250 $mW/cm^2$ for 8 minutes for a total of 1632 Joules or an energy density of approximately 120 $J/cm^2$. This is one embodiment, but higher and lower power levels, and different wavelengths may be used and are intended to be covered by this disclosure. Also, for a particular treatment, there may be a preferred or optimal wavelength and a preferred or optimal power level at that wavelength.

In one embodiment, PBM may reduce the cognitive efforts needed to complete tasks with high memory loads. For example, in an experiment involving a number of human participants, young adults who received a single session of PBM demonstrated substantially significant improvement in the learning task category, and substantially significant improvement in sustained attention and short-term memory. Similar improvements have been reported among older adults wherein they showed an improved performance on flexible thinking and inhibitory control after receiving a single stimulation. To show that PBM enhances the neural efficiency by reducing the mental efforts necessary for the task with the same level of difficulty, functional near infrared spectroscopy was used to examine the oxygenated hemoglobin in the pre-frontal cortex (e.g., the harder the brain works, the more oxy-hemoglobin is needed in that region of the brain, and thus the level of oxy-hemoglobin may estimate how much effort the individual's brain is working to accomplish the task). These results suggest that PBM may affect the hemodynamic response of the brain, which is associated with improving memory.

In yet another embodiment, PBM with 1064 nm light applied to the right pre-frontal cortex (e.g. applying light to the right forehead) improved or enhanced the visual working memory capacity and increased the contralateral delay activity, which is a negative slow wave sensitive to the number of objects maintained in visual working memory. Working memory may be described as the ability to actively store useful information "in mind" over seconds, and it plays an important role in many cognitive functions. The experiments show that 1064 nanometer PBM applied to the right pre-frontal cortex enhances visual working memory capacity in humans, although the effect was not found when exposing light to the left pre-frontal cortex or using light at 852 nm. The experiments employed a diode-pumped solid-state laser with continuous power output of 2271 mW, or around one-fifth of the skin's maximum permissible exposure. The handheld light source was positioned over the right pre-frontal cortex of 90 young adults for 12 minutes, followed by tests of visual working memory capacity. For example, the participants were asked to memorize the orientation of lines as well as blocks of colors. This is an exemplary wavelength and power level, but PBM may use other wavelengths and power levels which are also intended to be covered by this disclosure. Wavelengths near 810 nm, 850 nm, 905 nm, 940 nm, 975 nm, or 1064 nm may be used since VCSELs can be conveniently found at those wavelengths, and power levels near 2 W to 5 W or higher may be obtained by using an array of VCSELs.

Thus, light in the near-infrared wavelength range, such as exemplary 700 to 1100 nm, may be applied to areas on the face, such as exemplary the right side of the forehead, to potentially enhance the performance of a person. In one embodiment, as described above, near-infrared light applied to the right forehead to excite the pre-frontal cortex may enhance cognitive functions such as attention and working memory, executive function, and rule-based learning. Such near-infrared light exposure may also enhance visual working memory and reduce cognitive efforts needed to complete tasks with high memory loads. These benefits may be helpful in a range of activities, including while learning or studying, while working in the office or in front of a computer or computing device (e.g., tablet, or even smart phone), or while in meeting settings. They may also be beneficial in tasks requiring high-performance cognitive function, such as airplane pilots or fighter jet pilots, air traffic controllers, or highly-complex control centers. They may also be useful in settings such as driver monitoring systems in a vehicle cockpit or driver's seat.

As an example of how PBM may be beneficial for drivers in a vehicle or aircraft cockpit, it may be valuable to examine the parts of the brain used while driving, and existing evidence of the activities of the pre-frontal cortex related to driving activities. Driving requires a person to integrate information from multiple visual and auditory sources. Visual information includes activity on the road, mirrors and instrument display, while auditory information includes sounds made by the vehicle, other vehicles and pedestrians. The driver also has activities including stabilizing the vehicle, steering, braking and acceleration. All of these involve various parts of the brain. More specifically, the frontal lobe is activated whenever potential danger lurks and may be involved in analyzing the best response to the situation. The frontal lobe also helps in areas such as planning routes and controlling memorized body movement, and at least the dorsal lateral pre-frontal cortex may play a part in judgments and decision-making.

In one embodiment, studies on mental workload in simulated driving using functional near-infrared spectroscopy have shown a center of activation in the right anterior dorsolateral pre-frontal cortex, an area of the brain that is highly involved in spatial working memory processing. This may be a consequence of the fact that a main component of driver's mental workload in complex surroundings might stem from the fact that large amounts of spatial information about the course of the road as well as other road users has to be constantly be upheld, processed and updated. It would seem reasonable that spatial working memory plays a significant role in maneuvering complex driving scenarios because drivers have to be aware of and integrate a multitude of fixed and moving parts to derive operating action plans. In this case, mental workload may be defined as the portion of the processing capacity and resources of an individual that a given task demands, and the finding is that pre-frontal cortex activity rises with rising workload. It has been reported that mental workload related problems are responsible for the majority of road traffic accidents with both high and low levels causing insufficient perception and attention, which in turn may lead to driver error.

As another example of the brain functions used in driving, experiments have shown that vehicle deceleration requires more brain activation, focused in the pre-frontal cortex, than does acceleration. This may be important because many rear-end collisions are caused by deceleration that occurs too late. The studies demonstrated that pre-frontal cortical activation increased with faster deceleration during actual road driving, meaning that strong brain activation is required in situation when a driver has to brake rapidly. In other words, if the driver's pre-frontal cortex does not work well during vehicle deceleration, the risk of an accident may increase.

In yet another embodiment, research has examined the pre-frontal cortex activation of young drivers and the changes in activation associated with manipulations of mental workload and inhibitory control, both of which are also related to road traffic accidents. The experiments showed that more activity during driving occurs in the right hemisphere of the pre-frontal cortex than the left. Inhibitory control may be considered as the ability to weigh up consequences and suppress impulse and inappropriate behaviors, all of which are believed to be heavily dependent on the pre-frontal cortex. It should be noted that development in the brain occurs in the back to front pattern, with the pre-frontal cortex being the last area of the brain to fully develop. This is a process that is believed not to complete until around 25 year of age in typically developing adults. The studies conclude that pre-frontal cortex activity is associated with the mental workload required for overtaking a vehicle. The suggestion from the studies is that the reduced activation of the pre-frontal cortex in younger drivers may be related to lack of pre-frontal maturation, which might contribute to the increased crash risk observed in this population.

The therapeutics associated with PBM may be combined with the earlier described diagnostics, such as in medical diagnostics (e.g., for telemedicine or remote patient monitoring, or in a hospital room setting), in office or studying settings (e.g., in a tablet or smart phone, or when individual is sitting in front of a computing system), or in aircraft or vehicle cockpit for driver monitoring systems. These are just some of the scenarios contemplated for using PBM, but other situations and conditions may also be used and are intended to be covered by this disclosure. Since PBM may be associated with exciting CCO, the wavelength of light use may range over the near-infrared from 700 to 1100 nm, or potentially tails of the spectrum at shorter or longer wavelengths. Exemplary wavelengths for PBM may include wavelengths near 810 nm, 850 nm, 905 nm, 940 nm, or 1064 nm. The light sources may be selected from semiconductor diodes such as light emitting diodes, VCSELs, edge emitting laser diodes, or other semiconductor diodes. Although semiconductor sources may be advantageous because of their compact size, high-efficiency and low weight, other light sources may also be used, such as solid state lasers, lamps or glow bars, or gas-based light sources. The time-averaged power levels used may be in the range of 1 W, 2 W, up to 5 W or potentially even higher.

In one embodiment, the PBM light sources may be applied to the forehead of a participant. Based on the studies described earlier, a preferred embodiment may be to apply the PBM light sources to the right forehead, so as to penetrate into the pre-frontal cortex region. Different types of light mounts may be used to expose the therapeutic light on the participant or vehicle driver. For example, a nearly collimated beam may be used from a distance of several inches or more to shine the PBM light onto the participant. In a vehicle or cockpit, this might be a light source mounted on the rearview mirror or somewhere along the windshield or toward the top part of the dashboard. In another embodiment, the light source for PBM may be in contact with or very close to the forehead of the participant. For example, the PBM light source may be placed on or near the forehead region using a headband or a cap or hat. In yet another embodiment, the PBM light source may be attached to the top section of an eye glass frame, or potentially on a headset (e.g., goggles) to shine light onto the forehead. Alternately, the light source may in an adapter coupled to the eye glasses or headset to preferentially shine light onto a part of the forehead, such as the right side of the forehead so as to penetrate the pre-frontal cortex. In another embodiment, the PBM light source could be a flashlight or hand held device, where the participant either holds the unit or mounts it in a holder and directs the light to the appropriate region of the face, such as the forehead, or perhaps preferably the right side of the forehead.

These are just some embodiments for using a PBM light source with a participant, but other configurations may also be used and are intended to be covered by this disclosure. For example, in a driver monitoring system, the PBM light source might be added to take advantage of the head pose and eye gaze tracking that is already being used. Based on the identification of the head pose position, the light beam from the PBM light source might be adjusted to impinge on the forehead, or preferably the right forehead region. The light source might be moved physically using actuators, or alternately moving mirrors, galvanometer mirror systems, or micro-electro-mechanical MEMS mirrors may be used to direct and position the light beam. In some embodiments, it may be desired for the user to wear protective eyewear to avoid any damage to the eyes from the near-infrared light. Due to their light weight, high-efficiency, and environmental stability, preferred light sources for PBM systems may be VCSELs or LEDs, and preferred wavelengths may be near 810 nm, 850 nm, 905 nm, 940 nm or 1064 nm, which are wavelengths where large markets already exist for light sources. In yet another embodiment, the PBM light source may be modulated, or made to operate at prescribed frequency or repetition rates. For example, the PBM light source may operate at 10 Hertz, which may be useful for relaxation, stress, and alertness. In another example, the PBM light source may operate at 40 Hertz, which may be useful for meditation state, traumatic brain injury, concussion, Alzheimer's disease, or dementia. These are exemplary, but other frequencies or repetition rates may be used. Although these are exemplary embodiments, other configurations, light source types, light wavelengths, combinations of these and combinations with diagnostics may be used and are intended to be covered by this disclosure.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure. While various embodiments may have been described as providing advantages or being preferred over other embodiments with respect to one or more desired characteristics, as one skilled in the art is aware, one or more characteristics may be compromised to achieve desired system attributes, which depend on the specific application and implementation. These attributes include, but are not limited to: cost, strength, durability, life cycle cost, marketability, appearance, packaging, size, serviceability, weight, manufacturability, ease of assembly, etc. The embodiments described herein that are described as less desirable than other embodiments or prior art implementations with respect to one or more characteristics are not outside the scope of the disclosure and may be desirable for particular applications.

As an example of different variations of the CSP system, the camera in the CSP system may be combined with other sensors that may complement the CSP camera either with another modality or a different distance range. This may be referred to as "data fusion;" i.e., where the inputs from various sensors or detection systems are combined to produce an output or reach a decision. In one embodiment, the CSP system may further comprise a RAdio Detection And Ranging (Radar) sensor, which may complement the data provided by the camera system, or may increase reliability when the camera system may not be able to provide a reading. For example, camera systems generally require line-of-sight, or the ability to see the object. On the other hand, a Radar system may penetrate through different materials, at least those that are non-conductive. Radar systems may detect motions by reflected signal timing or phase information, and some of the advantages include: unobtrusive, no line-of-sight required, may not give rise to privacy issues. Radar may detect even small motions associated with vital signs (e.g. respiratory rate, heart rate, tidal volume, heart rate variability, and radar cross section), and Radar may be relatively insensitive to ambient lighting conditions as well as environmental changes such as fog, dust and temperature. Radar systems may operate based on Doppler effect or frequency modulated continuous wave, and some systems may operate between 2.4 GHz to 24 GHz frequency range, while others may operate near 60 GHz. As an example, 60 GHz Radar may operate for distances up to 10 m, while 24 GHz Radar may operate up to distances of 100 m.

As one particular example of using the CSP system and/or a Radar system may be to perform respiratory measurements. Simple respiratory measurements may be particularly valuable in the diagnosis of pulmonary ailments, such as asthma or chronic obstructive pulmonary disease (COPD). The CSP system may use a simple time-of-flight sensor to measure the motion of the chest, which may then provide the respiratory rate. Also, since there may be a linear relationship between the volume of the air inhaled or exhaled during the breathing cycle and the chest wall displacement, the CSP system with the time-of-flight sensor may also measure tidal volume. Typically, the tidal volume and breathing capacity may be measured using a spirometer. But, the CSP system using a time-of-flight sensor may be simple to use, non-contact, and not suffer from contamination between users. Instead of the time-of-flight sensor, the CSP system may also use a structure light approach (e.g., an IR camera plus a dot projector) to measure the vital signs such as respiratory rate. In a similar fashion, a Radar system may be able to detect the displacement of the chest wall and derive the respiratory rate (as well as heart rate). Either the CSP with a time-of-flight sensor or the Radar may measure respiratory rate and tidal volume non-intrusively and without contact, and combining the two modalities may improve the robustness or reliability of the measurement. If both are able to measure the respiratory rate, then the confidence level in the measurement may be increase by checking that the two are providing similar readings. These are just some examples of how Radar sensors may be combined with a CSP system using cameras and/or time-of-flight sensors, but other embodiments, combinations, or addition of other sensor modalities and applications may also be used and are also intended to fall within the scope of this disclosure. For example, another application of the CSP system and/or Radar system may be remote patient monitoring, possibly in a hospital room or even in a home setting. The CSP system may be able to measure vital signs and motion or fall detection as long as the participant is in line-of-sight, but Radar may also be able to detect even with intervening objects, such as curtains, dividers, doors, or other non-conductive barriers. Therefore, the robustness and reliability of the remote patient monitoring system may be improved by using the dual modality. More generally, fusing the data from various sensors, including cameras, Radar, and other sensing modalities may improve the power or reliability of the predictions or determinations.

In yet another embodiment, the CSP system may be combined with other sensors, such as breath based or touch based sensors. As one example, consider a driver monitoring system that may be used for intoxication or impairment detection. A breathalyzer may be used to measure blood alcohol concentration, either with the person breathing into a tube or by capturing part of the breath from the surrounding air in a breathalyzer. Alternately, a touch based sensor may be used, where near-infrared spectroscopy may be used on the finger to measure substances such as ethanol in the blood vessels. As described earlier, the CSP system may also be able to detect the state of the driver and intoxication, impairment or drowsiness by using facial blood flow, vital signs, eye movements, or combinations of these. By combining the breath and/or touch based sensors with the CSP vision-based approach, a more reliable and robust safety system could potentially be implemented. Moreover, further improvements may also be made by combining some or all of this system with a Radar system, which may also measure the vital signs. This is one example of multi-modal detection systems, but others modalities, sensors, and combinations may also be used and are intended to also fall within the scope of this disclosure. The data fusion from various sensors and camera systems may enhance the reliability and power of the outputs.

In a further embodiment, different types of cameras may be combined in the CSP system to cover different distances or perform different functions. For example, an IR camera may be combined with a time-of-flight sensor and a structured light sensor to provide 3D capabilities in an apparatus, a wearable device, or an augmented/virtual or mixed reality device. The IR camera may also be coupled to active illuminators operating in the IR (e.g. 850 nm or 940 nm), such as one or more LEDs or VCSELs. The IR camera may provide a two-dimensional image of the surroundings. The time-of-flight sensor may provide 3D imaging capabilities at distances up to 4 or 5 meters, perhaps even up to 10 meters or more. A lower resolution time-of-flight sensor may be co-registered with the higher-resolution IR camera to provide a higher resolution 3D image. Moreover, the IR camera and/or time-of-flight sensor may be further coupled to a structured light camera, comprising a dot projector (e.g., in one embodiment implemented with one or more VCSELS followed by a diffractive optical element and/or one or more lenses that may serve as a beam shaping module). The structured light camera may provide 3D imaging exemplary at distances up to around one or two meters. As an example, the shorter range 3D camera may be used to observe gestures or finger or hand movements by one or more participants. In this combination, 3D imaging may be achieved at the longer distances by using the time-of-flight sensor with or without the IR camera, while the 3D imaging may be achieved at the shorter distances by using the structured light camera with or without the IR camera. This is just one embodiment where different types of cameras may be combined to achieve a CSP system with different capabilities and operation over different distances, but other modalities and camera combinations may also be used and are also intended to fall within the scope of this disclosure. Data fusion between different cameras, different sensors, different sensing modalities, etc., may be beneficial for output determinations made by the system, or for producing more reliable or robust decisions, observations or predictions. The data fusion may also benefit from processing that may combine the various inputs, and algorithms that may seek to find patterns in the data provided by the sensors. As described below, various AI/ML techniques that rely at least in part on patterns in the data may help to strengthen the outputs achieved from the data fusion systems.

Section 7: AI/ML Processing to Flag Anomalous Occurrences Measured by CSP System or to Improve Performance In one embodiment, the CSP system has been described to identify or classify healthcare issues or anomalous state of a person being measured. Also, various exemplary applications of the CSP system have been described, such as use with a telemedicine or remote patient monitoring or patient monitoring in a hospital or clinic room setting. In yet another embodiment, the CSP system may be used in an advanced driver monitoring system that is examining the state of the driver or occupants and seeking to identify intoxication, drowsiness, impairment, drug use, sudden sickness, etc. In all of these and other applications, it would be valuable to be able to create an individualized baseline for a person. The good news is that every person is different. But, this also the bad news, so each person requires their own baseline for prescribed situations.

One way to produce the individualized baseline would be to measure over time the person and characterize certain features and create a distribution for the person. For example, the regular or normal distribution for facial blood flow, vital signs and eye movement for a person under particular conditions may be measured and registered. Then, if the readings fall two or more standard deviations (or whatever threshold that is set, based on criteria for the particular application) outside of the mean of the distribution, then a flag or alert may be initiated. This way of creating the flag or alert may be much more manual tuning, based on knowledge of the parameters that are expected to be altered by the anomalous situation.

With the growing sophistication and processing capabilities for AI/ML, a more automated approach for creating the individualized baseline over time may be to use AI/ML. As described below, different specializations within AI/ML may be beneficially used, such as anomaly detection, generative adversarial networks (GANs), or auto-encoders. These are exemplary methods, but other AI/ML methodologies may also be used, or combination of these methods may be used, and these are also intended to be covered by this disclosure. The CSP system may not be able to set flags or alerts when first using the system. However, after using the CSP for a period of time (e.g., several days, weeks or months), it may recognize the behavior or physiology patterns and create an individual's baseline, or at least a distribution of the more likely characteristics. The AI/ML may require less manual tuning, and it may be able to pick up distinguishing features because the AI/ML is able to identify patterns in the video and images provided. Moreover, the AI/ML system may improve in performance over time, since it is learning from more and more data as time progresses. Once the "normal" or regular distribution is established for the individual's baseline, AI/ML may be able to identify the anomalous occurrences as measured by the CSP system. In the following some exemplary AI/ML methods are described that may be used advantageously to process and help flag or alert the anomalous occurrences. These AI/ML techniques are only exemplary, and combinations of these or other techniques may also be used, and they are also contemplated to be covered within the scope of this disclosure.

Figure 24:
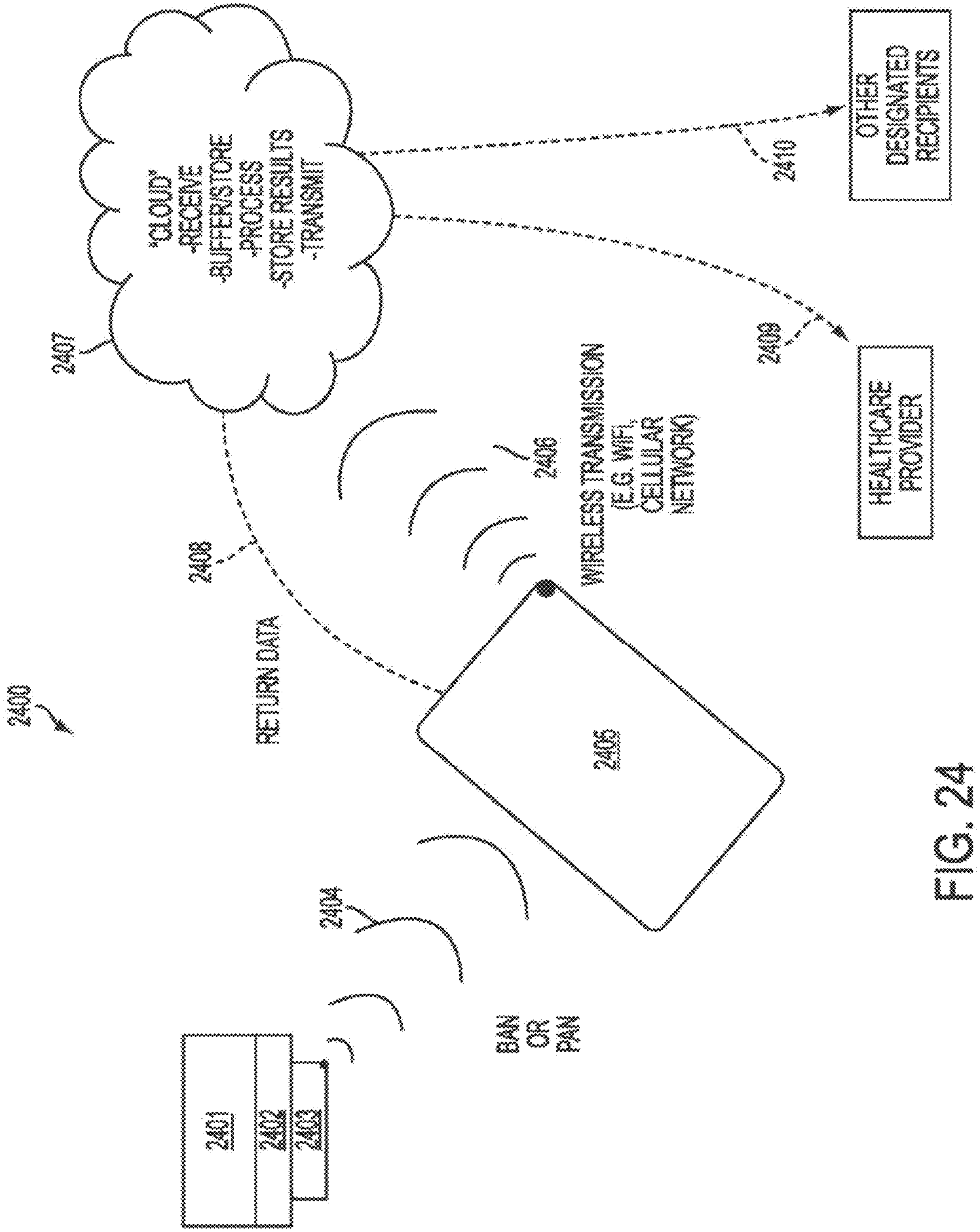
FIG. 24 schematically shows that the medical measurement device can be part of a personal or body area network that communicates with another device (e.g., smart phone or tablet) that communicates with the cloud. The cloud may in turn communicate information with the user, healthcare providers, or other designated recipients.
Figure 31:
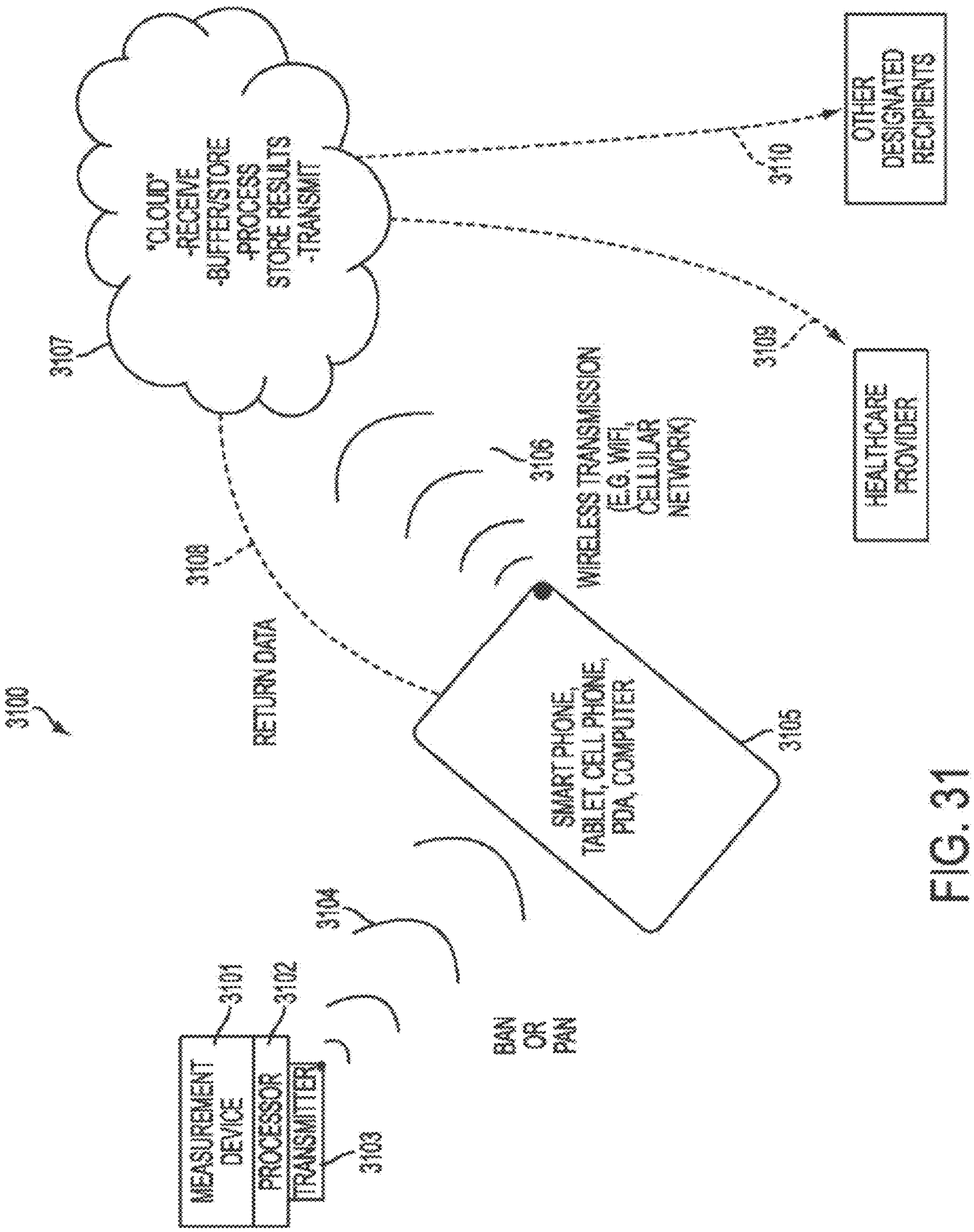
FIG. 31 schematically shows that the medical measurement device can be part of a personal or body area network that communicates with another device (e.g., smart phone or tablet) that communicates with the cloud. The cloud may in turn communicate information with the user, dental or healthcare providers, or other designated recipients.

In one embodiment, the starting point can be the hardware of a CSP system for detecting the anomalous occurrences. The CSP system may comprise cameras that are 2D, or more preferably 3D, for imaging and video capture. In one embodiment, the depth or third dimension may be helpful in compensating for motion artifacts. The camera output may be sent to a processor, and the incoming data as well as the processed data may be stored in a non-transitory computer readable medium (CRM). The processor may employ the AI/ML methods to generate an output, or the output may be generated using the manually tuned processing. Alternately, a combination of the manual tuning and AI/ML methods may be used to generate the output. The output may then be displayed, sent wired or wirelessly to a remote location or cloud, or the signal may be sent to some sort of a control system. Additionally, a flag or alert may be sent to smart phones or tablets or other designated recipients or healthcare professionals (c.f., FIG. 24 or 31).

For the CSP system, in one embodiment the camera may be a 2D camera, such as an RGB camera, and IR camera, or a combination such as an RGB-IR camera. For example, in an RGB-IR camera each pixel may have four sensors, each for red, green, blue and infrared. In another embodiment, the camera may be a 3D camera, many examples of which have been described earlier in this disclosure. Alternately, a combination of 2D and 3D cameras or parts of the cameras may be used, and these and other embodiments are also intended to be covered by this disclosure.

One embodiment of a 3D camera may be a stereographic camera, which typically has two or more cameras that are spatially separated. Other embodiments of 3D cameras that may be used in the CSP system include time-of-flight cameras or structured light. For example, one embodiment may be an indirect time-of-flight (iToF) camera, where each pixel measures an amplitude and a distance. In another embodiment, the 3D camera may comprise a direct time-of-flight (dToF) sensor, or a dToF sensor co-registered with an 2D camera such as an RGB, IR or RGB-IR camera. In yet another embodiment, the 3D camera may comprise structured light, which may comprise a dot-projector co-registered with a 2D camera such as an RGB, IR or RGB-IR camera. As an example, the dot-projector may comprise one or more VCSEL illuminators followed by a diffractive optical element and/or a lens system for implementing a beam shaping module or a beam splitter. In a particular embodiment, the 2D IR image may be co-registered with the dot pattern received by the camera, and the distance between the dots may be processed to determine the depth information for the 3D image. The dot pattern may be regular spacing or irregular spacing, or alternately the structured light may comprise lines or some other pattern. Whereas the iToF camera may determine the depth for every pixel, a more cost-effective solution may be to co-register an IR camera with a dToF sensor with lower resolution (perhaps interpolating between each pixel) or a dot-projector co-registered with an IR camera. These are just some examples of cameras that may be used in the CSP system, but other cameras or combinations of cameras may also be used, and these are also intended to be covered by this disclosure.

In the CSP system, it may also be advantageous to combine the camera systems with active illuminators, particularly operating in the near-infrared such as near 850 nm or 940 nm. In one embodiment, the 2D camera may comprise an IR camera that is synchronized with an active illuminator comprising LED's or VCSELs. In the time-of-flight or structured light the active illuminator may compromise one or more VCSELs or one or more VCSEL arrays, or possibly LEDs for shorter range applications. One advantage of using an actively illuminated system is that the system may then be more resilient to ambient light interference and motion artifacts. For instance, active illumination may permit using various signal-to-noise improving techniques commonly used in spectroscopy, such as synchronizing the light source and detectors, change detection (subtracting light on from light off), using lock-in techniques, and/or increasing the source light intensity or repetition rate if the SNR is not adequate. The data from the CSP system may then go to a processor and non-transitory computer readable media, where the processor may employ AI/ML to process the images or video for flagging or alerting for anomalous occurrences. For this application, one aspect of the AI/ML processing takes into consideration that there may be many examples of normal data, and relatively few instances of anomalous data. Therefore, the training set may comprise mostly normal data, and anomalous detection may require identifying when a data is significantly deviated from the normal range.

One exemplary AI/ML method that may be used in for the CSP processing is ANOMALY DETECTION. In AI/ML, classification in supervised or unsupervised learning may be typically used when there are a large number of positive and negative examples. In other words, the training set may be more evenly divided into classes. On the other hand, anomaly detection may be advantageously used when there are a very small number of positive (or anomalous) examples and a large number of negative (or normal) examples. Also, there may be different types of anomalies, which may make it hard for any algorithm to learn from positive examples what the anomalies look like. For example, future anomalies may look nothing like any of the previous anomalous examples. Some of the familiar uses of anomaly detection include fraud detection, manufacturing (e.g., finding new previously unseen defects), monitoring machines in a data center, and security applications.

In anomaly detection, a model p(x) may be defined that represents the probability that the example is not anomalous. Then, a threshold epsilon (ε) may be set at a diving line between which example are anomalous and which are not. If the anomaly detector flags too many anomalous examples, then the threshold may be decreased. The available data (e.g., labeled data) may be divided into a training set, a cross-validation (or development or dev) set and a test set, and the cross-validation set may be used to set the optimum value for the threshold. As an example, the features for the data may be assumed to follow a Gaussian distribution, with a mean and standard deviation or variance.

In one embodiment, the algorithm for anomaly detection may be as follows. A training set of examples (x) may be provided, and a number of features may be selected that might be indicative of anomalous examples. Using the training data set, each of those features may then be fit to determine the mean and standard deviation (square of the standard deviation is also called the variance). In other words, from the training data, the values of the features may be extracted, and then the distribution may be fit to a Gaussian distribution to calculate the parameters of mean and standard deviation. As a simplifying assumption, in one embodiment the independent assumption may be made, which means that the values of the features inside the training set are independent of one another. Under this assumption, the model p(x) (e.g., the probability that a sample fits within the Gaussian distribution) would be given by the product of the probability distribution functions for all of the features, which are given by the Gaussian distribution with the mean and standard deviation for each of the features calculated from the training set. Finally, if p(x) is less than epsilon (ε), then a data point is considered to be anomalous.

To summarize, one embodiment of the anomaly detection algorithm may be: (a) choose features that may be indicative of anomalous examples; (b) from the training data, fit parameters mean and standard deviation for each of the features; (c) calculate p(x) as the product of the Gaussian probability distributions for all of the features; and (d) for a data point x, determine if p(x) is less than epsilon, in which case it may be said to be anomalous. Note that the value for the threshold epsilon may be optimized by using the cross-validation or development set of data. To evaluate the anomaly detection algorithm, possible metrics include number of true positives, false positives, false negatives, true negatives, or the figures-of-merit described earlier, such as Precision, Recall and F1 score. This is one example of an algorithm, but other anomaly detection algorithms may also be used and are intended fall within the scope of this disclosure. For example, transforms may be performed to adjust features that can appear to be more bell-shaped curve distribution. In general, the goal is to make p(x) to be large for normal examples and small for anomalous examples.

In another embodiment, another AI/ML method that may be used in the CSP processing is AUTOENCODERS. Autoencoders comprise a fundamental architecture that may be used for various types of unsupervised learning applications (e.g., data is provided without labels, or the data is provided without the "correct" answers or outputs). The simplest Autoencoders with linear layers may correspond to dimensionality reduction techniques, such as what is known as singular value decomposition. In other words, Autoencoders may include data compression techniques, which may have loss associated with them. Examples of dimensional reduction techniques include principal component analysis and independent component analysis. Moreover, deep autoencoders with nonlinearity may map to complex models that might not exist in traditional machine learning.

The autoencoder may be one technique to reduce the data dimensionality (e.g., compression) in what might be called a constricted layer. In an exemplary embodiment, there could be an input layer, a constricted layer in the middle, and then an output layer (in general, there may be more than one layer in the middle, but for exemplary purposes a single layer will be discussed here). The basic idea of an autoencoder may be to have an output layer with the same dimensionality as the input layer. The idea may be to try to reconstruct the input data at the output, even though there is a bottle neck in the middle layer. Since an autoencoder tries to replicate the data from the input to the output, it is sometimes also referred to as a replicator neural network. Although reconstructing the data might seem like a trivial matter by simply copying the data forward from one layer to another, this may not be that simple because the number of units in the middle are constricted. In other words, the number of units in each middle layer may be typically fewer than that in the input and output, so that one may not simply copy the data from one layer to another. The weights or parameters to generate the middle layers may be selected to minimize a loss function. The loss function of this neural network may use the sum-of-square differences between the input and the output feature values to force the output to be as similar as possible to the input.

The reduced representation of the data in the constricted layer may sometimes be referred to as the code, and the number of units in this layer may be the dimensionality of the reduction (e.g., the degree of compression). The initial part of the neural architecture before the bottleneck may be referred to as the encoder (because it may create a reduced code), and the final part of the architecture may be referred to as the decoder (because it reconstructs from the code). This is one example of an autoencoder and loss function, but other architectures and loss functions may be used and are also intended to be within the scope of this disclosure.

For the problem with CSP system where the anomalous occurrence is to be flagged or set off an alert, this may be considered an outlier detection. Autoencoders and dimensionality reduction may be closely related to outlier detection, because outlier points may be difficult to encode and decode without losing substantial information (e.g., the outlier cases will be very lossy). In other words, the compressed or constricted representation of the data may be a de-noised representation of the data, and the compressed representation captures primarily the regularities in the data. The compressed or constricted representation generally may not capture the unusual variations in specific points, resulting in a large deviation between the input and output data for the anomalous cases.

The error metric for detection of the anomalous occurrences may be the absolute value of the difference in the parameters between the input and output from the autoencoder. For the normal data, the error metric may be relatively small, perhaps lower than some threshold value. However, since the anomalous occurrences will have irregularities that lead to poor reproduction by the decoder layer, the expectation is that the error metric may be considerably higher for these cases. Hence, the autoencoder approach may be one method to find outlier images, videos or data points. Moreover, the autoencoder may also be able to identify the outlier features, which may be valuable for understanding or classifying the type of outlier or anomaly. This is one example of use of an autoencoder AI/ML architecture for outlier detection, but other architectures, dimensionality reduction methods, linear or nonlinear activation functions, matrix factorization, singular value decomposition methods, or shallow neural systems may also be used, or combinations of these, and these are also intended to fall within the scope of this disclosure.

In yet another embodiment, a different AI/ML method that may be used in the CSP processing is GENERATIVE ADVERSARIAL NETWORKS (GANs). Whereas many ML algorithms fall in the class of discriminative models (e.g., a classifier), GANs fall in the category of generative models. For example, given a noise input and a desired class, the GAN will output the features of that class (the noise input may be added so the same output is not generated every time). GANs generally comprise two neural networks in tandem. The first may be a "generator," or a generative model that may produce synthetic or fake examples of objects, based on a real repository of examples. The goal of the generator may be to produce "fakes" that are sufficiently realistic that it is very difficult to distinguish whether a particular object is real or fake. The second neural network may be a "discriminator," which is a discriminative network that may judge whether the generated examples are sufficiently realistic. The discriminator may be a binary classifier designed to recognize whether images are real or fake. The training of the generator and discriminator may occur iteratively and nearly simultaneously using feedback from one another. Thus, the two neural networks are adversaries, and training may continuously improve the adversaries to become better and better, until an equilibrium is reached between the two (hence the name generative adversarial networks). So, the generative models may learn to produce examples, the discriminative models may distinguish between the classes, in particular between real and fake.

In a GAN there may be a competition between the generator and the discriminator, which have different goals. The generator learns to make fakes that look real, and in this sense may be thought of as painting forger. The discriminator learns to distinguish real from fake, and in this sense may be thought of as a painting inspector. The generator may start by generating a relatively bad fake (without any examples or real objects), and the discriminator may be given the fakes and examples of the real objects, thereby being able to judge the probability of what is generated is fake (or one minus real). The discriminator may feedback how likely the input from the generator was fake, and the generator ma use this feedback to improve the fakes to get closer to real. The competition may end when the generator produces very good fakes that the discriminator cannot distinguish from real.

The discriminator may be a neural network that acts as a classifier, outputting either real or fake. The training of the discriminator may comprise: (a) input a set of features to the discriminator; (b) the discriminator produces an output of the probability that it thinks the features are fake (hypothesis); (c) the training set has labels of real and fake; (d) a cost function compares the output of the discriminator with the labels (e.g., ground truth), and the cost function is minimized, using a method such as gradient descent; and (e) the parameters or weights in the neural network are updated to minimize the cost function. The probabilities of real or fake from the discriminator are fed back to the generator, so the generator has the direction it needs to move in to improve the fakes toward the real responses.

The generator may be a separate neural network, with noise or random features as inputs. Again, random noise may be added at the input so each run produces a different output. The training of the generator may comprise: (a) random noise input to the generator, causing the generator to produce an output of the features it thinks will be real (hypothesis); (b) these features are fed into the discriminator, which produces an output of the probability that it thinks the features are fake; (c) the cost function compares the output of the discriminator, and the cost function is minimized; and (d) the parameters or weights in the generator neural network are updated based on the minimization of the cost function. Thus, the discriminator may help the generator produce fakes that are closer to real each time. When the fakes and real become acceptably close, then the parameters or weights in the generator neural network may be saved and frozen. Since the discriminator may be a binary classifier (real and fake), the loss function used may be a binary cross entropy function.

The different neural networks may now be assembled to put it all together. In one embodiment, the GAN model comprises: (a) a noise input to the generator, which produces fakes with features; (b) the output of the generator, as well as real inputs are fed into the discriminator, and (c) the discriminator outputs whether it believes the input from the generator is fake or real. The job of the generator may be to make the fakes look like the reals, and the job of the discriminator may be to distinguish the fakes from the reals. The training of the GAN discriminator, where only the discriminator parameters are updated, may comprise: (a) feeding the output from the generator as well as real inputs to the discriminator, (b) generating from the discriminator its output hypothesis, (c) minimizing a cost function, such as the binary cross entropy, with the labels for the real and fake, and (d) updating or adjusting the parameters in the discriminator based on the minimization of the loss function. The training of the GAN generator, where only the generator parameters are updated, comprises: (a) with a noise input, the generator produces, fake examples, (b) the output of the generator is fed into the discriminator to generate the hypothesis of fake or real, (c) the cost function, such as binary cross entropy, is minimized against the real labels, and (d) updating or adjusting the parameters of the generator based on the minimization of the loss function. It should be noted that the generator and discriminator should be at comparable levels, so that the learning may continue. In summary, the GANs train in an adversarial, alternating fashion, and the two neural networks should be at a similar "skill" level so that the parameters can be honed in.

With this understanding of the GANs, the application to CSP system to identify anomalous occurrences may be clearer. Using the normal training data (e.g., data accumulated over the normal situations in which the CSP is used), the parameters for the GAN can be optimized and locked down. In this situation, the "real" could be the normal CSP videos or images, and the "fakes" could be the abnormal CSP occurrences. Since the discriminator has been optimized to distinguish the real from the fake, the output videos or images from the CSP system can be fed into the discriminator. Then, when an abnormal or anomalous occurrence is fed into the discriminator, the discriminator may detect the fake or anomalous occurrence and send out a flag or alert. This is one example of how a GAN could be used with the CSP system to identify anomalous occurrences, but other applications and methods using the GAN can also be employed, and these would still fall within the scope of this disclosure.

In summary, several AI/ML methods or algorithms that may be used with the CSP system to flag anomalous occurrences has been presented. The AI/ML techniques may include anomaly detection, autoencoders, or generative adversarial networks. Although these are some embodiments of using AI/ML for flagging CSP system anomalous occurrences, other AI/ML techniques may also be used for processing the output of the CSP camera system, or combinations of these techniques, and these are also intended to fall within the scope of this disclosure. For example, techniques used in AI/ML for imbalanced data sets may be beneficial for use with the CSP system, as further described in the following.

A classification data set with skewed class proportions may be called imbalanced. Classes that make up the large proportion of the data set are called the majority class, while those that make up a smaller proportion are the minority classes. One method of handing the imbalanced data may be to down-sample and up-weight the majority class. Down-sampling may mean to train on a disproportionately low subset of the majority class examples, and up-weighting may mean adding an example weight to the down-sampled class that may be equal or close to the factor by which it was down-sampled. This is just one way of dealing with imbalanced data in AI/ML, but there are many other techniques that may also be used including: (1) resampling techniques: a common approach may be to resample the data set (e.g., oversample the minority class, under-sample the majority class, or a mixture of both); (2) synthetic minority oversampling technique: this technique may generate synthesized instances of the minority class to cope with the imbalance issue; (3) use of appropriate evaluation metrics: rather than using accuracy, better measurement tools when dealing with imbalanced data sets may be to use Precision, Recall, F1 score, etc.; (4) cost-sensitive training: this may involve providing higher penalties to mis-classifications from the minority class during the learning process; (5) data augmentation: new instances may be created, for example, by adding a small perturbation to existing examples in the minority class; (6) more appropriate ML algorithms, such as Decision Trees and Random Forests may perform better on imbalanced data sets; and (7) several ensemble learning techniques may be used that are more specifically designed for imbalanced data problems, such as Bagging, Boosting, and Adaptive Synthetic Sampling. To illustrate some of these AI/ML techniques, it may be worth examining in more detail Decision Trees, Bagging and Random Forests.

In one embodiment, a decision tree may be a flowchart-like structure in which each internal node may represent a feature (or attribute), each branch may represent a decision rule, and each leaf node may represent an outcome. The decisions trees may be used for classification and regression tasks in machine learning. In this technique, the population or sample may be split into two or more homogeneous sets (or sub-populations) based on a particularly significant splitter/differentiator in input variables. The decision tree may then follow a set of if-then-else conditions for making decisions. The topmost node in a decision tree may be known as the root node, and it learns to partition on the basis of an attribute value. It may partition recursively in such a manner called as recursive partitioning. One advantage of a decision tree may be its intuitive and easy-to-understand representation, which can also be visually interpreted. On the downside, decision trees may be sensitive to minor changes in data and may lead to overfitting if not properly handled.

In another embodiment, Bagging, or Bootstrap Aggregating, may be a powerful ensemble AI/ML algorithm. It may involve creating multiple sub-sets of the original dataset by resampling, fitting a decision tree model to each subset, and then combining the predictions. Bagging may be a technique used to reduce the variance of a decision tree. A breakdown of the steps in bagging include the following: (1) subset creation: bagging may use a technique called bootstrapping to create subsets. In bootstrapping, "n" observations may be randomly chosen with replacement from the dataset to form a new subset that also has "n" observations. Thus, the same observation may appear more than once in a subset; (2) model building: a separate model may be built for each subset, and these models may run independently of each other. Due to the different data in each subset, a diverse set of models may result; and (3) combining the predictions: once the models provide their predictions, the predictions may be combined using a method appropriate to the particular problem. For regression problems, it may be common to combine by taking the mean of the various predictions. On the other hand, for classification problems, voting may be used, and the most voted prediction may be selected as the final prediction. Some of the benefits of bagging include reducing overfitting by creating an aggregated model with low variance, and handling higher dimensionality data well. One example of a bagging algorithm is the Random Forest algorithm.

In yet another embodiment, a random forest may be used, which may be an ensemble method improving on bagging. It may create a multitude or decision trees (a "forest") at training time and may output the mode of the classes (for classification) or mean prediction (for regression) of the individual trees. One difference between bagging and random forests is that random forests may chose random subsets of features at each split in the decision tree, which adds randomness to the model and helps the model to generalize better. Some of the steps in random forest may include: (1) random subsets of the data set are created; (2) from these subsets, the random forest algorithm may select random features for training each individual decision tree; (3) each tree may generate a prediction. In a classification problem, each tree may "vote" for a class, and the class receiving the most votes may be chosen as the final prediction. In a regression problem, the average of all the tree outputs may be considered as the final prediction; and (4) random forest may also use the concept of bootstrapping (random sampling with replacement) and aggregates (combining results from different decision trees) that may help in improving the predictive accuracy and controlling over-fitting. Advantages of random forest algorithms include flexibility and high accuracy, and they also maintain good accuracy even when a large proportion of the data is missing. The algorithm also may have a built-in method for measuring variable importance, and the random forest may also be relatively easy to use because the default hyper-parameters it comes with often produce good predictive results. On the other hand, random forests may have some downsides such as complexity, more resource-intensive, they do not usually predict beyond the range in the training data, and they may over-fit datasets that are noisy.

In a further embodiment, an AI/ML method known as XGBoost (Extreme Gradient Boosting) may be used that is based on the gradient boosting framework. The core of the XGBoost may be a decision tree-based algorithm, which is designed to improve speed and performance. For example, XGBoost may apply a better regularization technique to reduce overfitting, and it may be capable of handling missing values in the data. Some of the features of XGBoost include: (1) speed and performance: XGBoost may be highly optimized, parallelizable, and may provide fast, reliable performance both in training and prediction phases; (2) handling of missing values: XGBoost has an in-built routine to handle missing values; (3) regularization: XGBoost may implement regularization to prevent the model from overfitting, which may result in better and more generalized performance; (4) tree pruning: XGBoost may grow the tree to a fixed maximum depths and then prune backwards (i.e., removing splits beyond certain limits) to improve the model performance; (5) built-in cross-validation: XGBoost may allow a user to perform cross-validation at each iteration of the boosting process, which may provide a method to handle overfitting; and (6) flexibility: XGBoost may support user-defined functions as well as several built-in loss functions for classification, regression, ranking, etc.

Also, beyond AI/ML techniques, manual tuning may also be used in place of or to augment the AI/ML processing. For example, understanding that the facial blood flow, vital signs and eye movements may be particularly helpful in identifying the anomalous occurrences may improve the performance of the processing. In one embodiment, the AI/ML processing may benefit from reinforcement learning from human feedback, which is an ML method wherein an AI system may learn or improve performance from feedback provided by humans, rather than traditional reinforcement learning that may use pre-defined reward functions. First, consider the more traditional reinforcement learning methodology, wherein an "agent" may learn how to behave in an environment by performing actions and seeing the results. The idea is that the agent learns from the consequences of its actions through continuous feedback, making decisions based on trial and error. The main components of a reinforcement learning system may be: (1) agent: this may be the entity that is learning by interacting with an environment; (2) environment: this may be where the agent acts, or it is the context or situation where the agent interacts; (3) actions: these may be the steps taken by the agent in the environment; (4) reward: a feedback signal that guides the agent. For example, if an action benefits the agent, the agent receives a positive reward (or reinforcement). On the other hand, if it harms the agent, the agent receives a negative reward (also known as a punishment); (5) policy: this may be the strategy that the agent uses to determine the next action based on its current state. This may be the core of the reinforcement learning agent, defining the learning element of the agent; and (6) state, which may be a snapshot of the current situation of the agent in the environment.

In contrast to the more traditional reinforcement learning, the reinforcement learning from human feedback may involve the following steps: (1) initial training: first, an initial policy may be trained using supervised learning, where a human operator may provide examples of correct behavior; (2) ranking-based feedback: next, the AI system may generate trajectories (i.e., sequences of states and actions). A human may then rank these trajectories based on their quality, thus providing a simple yet powerful form of feedback; (3) reward modeling: the AI system may then utilize these ranking to create a reward model; (4) training and proximal policy optimization: once the reward model is prepared, the AI system may use the proximal policy optimization algorithm (or another reinforcement learning algorithm) to improve its policy; and (5) iterative refinement: above steps 2-4 may be repeated in an iterative manner, allowing the policy to gradually improve over time. Therefore, through reinforcement learning from human feedback an AI/ML system may incorporate feedback to learn the complexities and subtleties of a task that a simple pre-defined reward function may not have been able to capture. This is just one example, but other types or combinations of human feedback or manual tuning may be used with the AI/ML systems working with CSP systems, and these also fall within the scope of this disclosure.

Furthermore, AI/ML techniques may also be added to the CSP system not only to process the videos or images, but also perhaps to provide output information, potential diagnoses, or possible next actions to implement. For example, generative AI using transformers may be able to supplement the CSP system and further improve the performance and utility of the CSP system. In one particular embodiment, the interaction of the CSP system with the user may be through a generative AI (GAI) system, which may be based on what are called large language models (LLM). One example is a ChatBot, where a question may be asked to the ChatBot, and the Chatbot can then provide a response, whether with text output, possibly a voice activated output, or perhaps even a visual output. LLMs may be trained over trillion or more words, generally require large amount of compute power and memory, may have billions of parameters, and may even display emergent properties beyond language. For example, emergent properties may be behaviors and characteristics that may arise from the interactions of simpler components, but may not be explicitly programmed or designed by the creators of the GAI. In one embodiment, the LLM model may have as an input a "prompt," which may comprise a context window with words entered by the user. For example, the prompt may be the user typing in a question or words. The prompt is fed to the LLM model, and the LLM output is a "completion"; more specifically, the output may be repeating the prompt followed by the answer or completion. The larger the LLM model, the more processing power and memory it may require, but the more capabilities the LLM could have.

At a high level, LLMs may be thought of as calculating the next word in a sentence. Earlier LLMs used what are called recurrent neural networks (RNNs). But, the major breakthrough (circa 2017) has been with the LLMs using what is known as a transformer architecture. For example, RNNs may predict the next word based on the previous word, but the problem is that the AI has not seen enough of the input to make a good prediction of the next word. To increase the accuracy, models may need to see more than just the previous key words, and it may need an understanding of the whole sentence. As might be expected, the more words used, the larger the model space (processing) and memory that may be required.

The transformers go beyond RNN by using many more words, and by using what is called an attention mechanism. As an example, humans may not actively use all of the information available to them from the environment at any given time. Rather, the humans may focus on specific portions of the data that may be relevant to the task at hand. This biological notion may be referred to as that of attention. Similarly, neural networks that use attention models may have an attention focus on smaller portions of the data that may be more relevant to the task at hand. In fact, one of the key papers that launched what has been almost a revolution in AI using transformers was entitled, "Attention is all you need."

The power of GAI may be derived from learning relevance and context from all the words in a sentence, not just the adjacent words (such as in a RNN). The transformer may learn the relevance of each word to each other word, no matter the location. In an attention map, every word in a sentence may be tied to every other word. However, for "self-attention," higher weights or heavier lines are drawn between some words that may have a larger connection. With this heavier influence from some words, the model's ability to encode language may be significantly improved. Moreover, the positional information (e.g., relative position of words) may also be used to enhance the model performance.

In one embodiment, a simplified transformer architecture may comprise on the left side an encoder and on the right side a decoder. The inputs (e.g., prompts) may be fed into embedding units, one at the input to the encoder and another at the input to the decoder. The output of the encoder may also be sent to the decoder. The output from the decoder may be sent to a softmax output (e.g., an output with several output nodes or values), and the resulting output from the softmax is the model output, a copy of which may also be delivered to the input of the embedding layer to the decoder. Since the transformer works with numbers not text, before passing words into the model, the model may have to tokenize words. Thus, a tokenizer may convert the words into numbers. There may be choices in the tokenizer (e.g., token ID's may be entire words or parts of words), but whatever tokenizer is selected should also be used when generating text at the output. So, at this point the words may be represented as numbers.

The tokenized inputs may then be sent into the embedding layers before the encoder and decoder. The embedding comprises representation of each token as a vector in space, and it turns out that these vectors may learn to encode meaning and context to the individual tokens. Thus, at this point each word may be mapped to a token, and each token in turn may be mapped to a vector. After the embedding, there may also be positional encoding, so that the relevance of the position of the word in the sentence may not be lost. Next, the vectors from the embedding layers may be sent to a self-attention layer in both the encoder and decoder. The self-attention layer may analyze relationships between the tokens, capture contextual dependencies between words, and possible relationships between words in sequence. Generally, it may be a multi-headed self-attention, with multiple self-attentions occurring in parallel (not uncommon to have 12 to 20 parallel processes). Each of these self-attention processes may learn different aspects of the language, and the weights or parameters for the self-attention units may be learned from the training data. The outputs from the multi-headed self-attention units in the encoder and decoder may then be processed through a fully connected, feed-forward network, whose output may be a vector of logic with the probability score for each and every token. The output from the encoder may be sent to the decoder, and then the output of the decoder may be sent to a softmax layer that may generate a normalized probability score for each word (e.g., what is the most likely next word, or what is the probability of each of the words to be the next word).

In summary, in one embodiment the transformer architecture comprises an encoder and a decoder. The encoder inputs "prompts" with contextual understand and may produce one vector per input token. The decoder may accept input tokens and may generate new tokens. This is one architecture, but there are variations of this architecture, either parts or combinations, and these are also intended to fall within the scope of this disclosure. For example, there may be encoder only models, which may be particularly valuable when the input and output sequences are of the same length. There may be encoder-decoder models, which may be more appropriate when input and output sequence could be of different lengths. There may also be decoder only models, which may be common in many generative pre-trained transformer (GPT) models. It should be noted that there are many existing GAI models. Therefore, a starting point in many cases may be to start using an existing GAI that is close to the task that may be desired, and then to modify, tweak, or adjust from that starting point.

Much of this disclosure has described the hardware and software associated with the CSP system. How might GAI using LLM's enhance the performance of the CSP? The CSP may capture camera images or video, which may then be processed to flag an anomalous occurrence. Once an anomaly is detected, the user or monitoring personnel may desire to have more information about the anomaly. For example, what might be the cause of the anomaly, what kind of steps might be appropriate for mitigating the anomaly, and what are typical situations in which such anomalous occurrences arise? For a better understand the cause, remedies, and circumstances corresponding to the anomaly detected, GAI based on LLMs and transformers may be valuable for providing a more holistic response and plan of action to the users. This is one embodiment of how a GAI based on LLMs and transformers may be used to enhance the CSP system, but other uses of the GAI's within the CSP may apply, or combination of GAI's with other AI/ML techniques or models may also be used, and these are also intended to fall within the scope of this disclosure.

As an example, in another embodiment GAI's may be used in the broader context of an application involving telemedicine, remote patient monitoring, in-room hospital patient monitoring, or advanced driver monitoring systems. The GAI's may call on the CSP system to operate and provide data as appropriate, perhaps combining that data with data from other sensing systems. This combining of data from the CSP or parts of the CSP system with other sensors may be called "data fusion." For example, data fusion may comprise combining at least some of the data from the 2D or 3D camera systems in the CSP with data from other sensors, such as Radar, touch sensors, temperature or humidity sensors or other environmental sensors, accelerometers, gyroscopes, or other motion tracking sensors. Alternately, data from physiological sensors (either wearables or contactless) may be fused with data from some of these other sensors, particularly motion tracking sensors. In the context of a vehicle, the CSP system data may be fused with data from the vehicle, such as lane tracking, steering wheel motion, speed control, or other vehicle motion cameras/sensors or driver tracking sensors. The GAI's may also take input from the CSP and send signals to one or more control systems in the vehicle or healthcare setting to change an instrument or device. The GAI may also provide advice on tuning or adjusting the settings in the CSP system to improve the performance or provide more desired data that can be acted upon. This example illustrates how GAI's may be beneficial for applications within a vehicle, but the GAI's may also be used in conjunction with other hardware including pendants, glasses, wearable devices, or combinations of these devices. The AI/ML or GAI may operate on a processor coupled to or incorporate within the CSP system, or the AI/ML or GAI may operate in the cloud, smart phone or tablet, or computing system that may be remote from the CSP. Moreover, the AI/ML or GAI may be coupled with non-transitory, computer readable media for storing, processing, or transmitting the data. Various combinations or permutations of these configurations may be used, and these and others are also intended to fall within the scope of this disclosure.

Beyond GAI's assisting in the communication and interface with users, GAI's may also be beneficially used to improve the processing of data from 2D or 3D camera systems, such as the CSP. These GAI's may be based on transformers (including attention mechanisms and positional encoding) comprising encoders and/or decoders and prompts that may be text, visual, video or verbal formats. GAI's may enhance camera systems for processing images or videos in several ways, including some of the following: (1) Improved image quality: GAI algorithms, such as GANs, may be used for enhancing and up-scaling low-resolution images to higher-resolution images; (2) Object detection and recognition: by generating multiple versions of labeled objects, the AI may augment the training data for object detection and recognition, thereby increasing accuracy; (3) Scene reconstruction: convolutional neural networks and similar generative models may reconstruct 3D scenes from 2D images captured by camera systems; (4) Anomaly detection: generative models may be used to learn what normal objects or scenes should look like. Something that deviates sufficiently from the norms may be classified as an anomaly, as has been described earlier in this disclosure; (5) Image synthesis: GAI may create new images that resemble those in the training set; (6) Facial recognition: GAI may assist in the generation and recognition of human faces; (7) Image inpainting: AI may be used to fill in missing or corrupted parts of an image accurately; (8) Transformation of visual styles: GAI may enable camera systems to transform the visual styles of captured images (e.g., changing the image from day to night) even under different lighting conditions; (9) Semantic segmentation: GAI may separate out and categorize the various structures and objects in images, enabling differentiation between different regions or classes in the space; (10) Data augmentation: GAI may create a large amount of artificial but realistic data, which may be beneficial for training deep learning models without further data acquisition; and (11) super-resolution and noise reduction: GAIs such as GANs may help in the process of reducing the noise in the captured images and increasing the resolution of these images, potentially making them clearer and more detailed. These are just some of the ways in which GAI's may improve the performance of 2D/3D camera systems, but combinations of these or yet other techniques may also be used and are intended to fall within the scope of this disclosure.

Although generative AI based on LLM's has been described, other GAI algorithms and methodologies may also be used and may be used with the systems disclosed herein. For example, for some applications using more domain specific, application related or proprietary information, prompt tuning of existing LLM's may be used. Prompt tuning may be a technique used for improving the performance of LLM's, which are often pre-trained on large amounts of text data. However, they may not directly produce the desired output when given a prompt. The reason may be that they are trained to predict the next word in a piece of text, not necessarily to solve tasks defined by the specifics of a prompt. To better align the LLM with a required task, one technique may be to fine-tune the model using a more specific set of training examples. However, this technique may be computationally demanding and may lead to overfitting, if the set of examples is too specific or too small. Prompt tuning may provide a middle ground. Instead of fine-tuning the parameters of the entire model, task-specific prompts may be designed and tuned that guide the model towards the desired behavior. In other words, prompt tuning may be creating a set of instructions for the model to follow, so the model's response may be tailored while minimizing computational costs.

In other embodiments, other extensions of GAI and LLM's may also be developed, and these are also intended to fall within the scope of this disclosure. For example, vision transformers may be valuable for CSP systems, since there is a lot of image data gathered from the 2D or 3D cameras. Whereas LLM's are based on text transformers (e.g., language models based on the transformer neural network architecture), the next generation of GAI's may be based on vision transformers, which adapt transformers to computer vision tasks such as recognizing objects in images. For the vision transformers, the prompt may be an image rather than a string of text. Alternately, the prompt may be a video, which may comprise a temporal sequence of images. Visual transformer models appropriate concepts drawn from the transformer models used in natural language processing. It may do so by applying similar mechanisms, such as self-attention and positional encoding, to interpret visual inputs instead of text. More specifically, transformer models may work by assigning different degrees of attention to different elements in a sequence, allowing them to prioritize relevant features and ignore non-relevant ones. In the visual domain, vision transformers may treat an image as a sequence of patches and may identify the inherent and complex relations between them. One advantage of vision transformers may be that they can also leverage pre-training on large scale image datasets to enhance their performance, similar to language models. There are other algorithms that may also rely on the transformer concept, and combinations of text, vision, voice and other transformers may be used in GAI's to augment the functionality of the CSP systems.

With these different AI transformer models, the prompts may be text, images, videos, verbal, or some combination of these prompts. In one embodiment, voice prompts may be used with GAI, which may rely on GAI models optimized for voice-based interactions or combined with voice synthesis technology to provide spoken responses, similar to those used by virtual assistants like Amazon's Alexa or Apple's Siri. Additionally, these GAI models may incorporate aspects of natural language understanding and may generate voice prompts that sound more natural and human-like. As an example, LLMs or GPT models may be integrated with voice-recognition and text-to-speech systems to enable acceptance of voice inputs and provide voice outputs.

In yet another embodiment, visual prompts may be used with GAI systems, which may involve a combination of computer vision and natural language processing systems. An exemplary process for combining these technologies may be: (1) image analysis: this step may involve using AI to analyze a give image. This may usually involve deep learning and computer vision models, like convolutional neural networks (described further below), which may identify objects, colors, patterns, locations, etc., within an image; (2) image description generation: once the image analysis step is completed, the data should be organized in a format appropriate for the AI algorithm, which may be a list of identified items or as a scene description; (3) natural language generation: after the elements in the image have been identified and structured, a GAI model may then take these elements as input and may generate an appropriate output in natural language form. For example, the AI might generate a description of the image, answer questions about it, or create a story based on it, among other possibilities; and (4) use case application: the aforementioned steps may be adjusted and refined according to the specific use case. As one example, there may be text models such as ChatGPT and sibling image models such as DALL-E, and integration between such models may enable the use of visual prompts with GAI more seamlessly.

Thus, GAI's may be substantially beneficial for use with CSP systems or 2D/3D camera-based imaging systems. The performance of the GAI's themselves may also be enhanced in these and other applications using a number of techniques, including some of the following: (1) Reinforcement learning from human feedback, which involves using human feedback to guide the AI's learning process (as described earlier in this disclosure); (2) Active learning: AI systems may ask for feedback or supervision when they are uncertain about a task, which can lead to greater learning efficiency; (3) Curriculum learning: in this approach data may be arranged in a more meaningful order, presenting simpler concepts before introducing complex ones; (4) Reward modeling: this may involve training the AI model to learn a reward function from human feedback, which may be used to generated specialized rewards given a particular input-output pair; (5) Domain knowledge incorporation: incorporating domain-specific knowledge or expertise may help craft solutions that enable the AI model to generate more realistic or useful outputs; and (6) Transfer learning: techniques such as transformer models may also be used to allow the model to apply knowledge learned from one context to another. These are just some examples of techniques that may be used to improve GAI models, but combinations of these as well as other techniques may also be used and are intended to fall within the scope of this disclosure.

Beyond 2D/3D imaging systems, GAI's may also enhance the performance of remote or imaging photo-plethysmography systems using a number of techniques. For example, GAI may offer several benefits to processing and analysis in camera-based PPG including: (1) Noise reduction: GAI, such as auto-encoders, may be used to learn the underlying distribution in PPG signals and may use this knowledge to effectively separate signals from noise, thus enhancing signal quality; (2) Synthetic data generation: techniques such as GANs may create synthetic data that closely mirrors real-world data. This may be used to augment the existing dataset, making the PPG algorithms more robust and accurate; (3) Multi-modal data fusion: generative models may be useful to integrate data from multiple sensors or modalities, which may improve the accuracy and robustness of the PPG estimates; (4) Anomaly detection: by training GAI to understand the 'normal' heartbeat intervals and patterns, any significant deviation from this pattern may be marked as an anomaly; (5) Improved learning: GAI may transform a few-shot learning problem into a many-shot one by generating more examples from each class, which may help the AI system to learn better and make more precise evaluations; and (6) Signal forecasting: generative models, such as time-series forecasting models, could possibly be trained to predict future physiological parameter based on past trends. These are just some of the methods by which GAIs may improve PPG data, but combinations and others are also intended to fall within the scope of this disclosure.

Since the CSP system may involve processing of images and video, the AI/ML techniques commonly employed may also comprise CONVOLUTIONAL NEURAL NETWORKS (CNNs). The CNNs may be applied in addition to or in combination with the other AI/ML techniques that have been described in this disclosure. Computer vision problems may include image classification, object detection and neural style transfer, among many other types of problems. Because images and videos may involve many pixels of data, one of the challenges of computer vision problems may be that the images may contain a significant amount of data, and yet fast and accurate algorithms may be desired to handle the massive volume of data. CNNs are one solution where the AI/ML algorithms use what are called convolution layers rather than the fully connected layers (e.g., where every node in one layer of a neural network may be connected to every node in the next layer).

In a CNN, one challenge may be to detect the edges, such as the horizontal and vertical edges. To meet this challenge, CNNs may create the notion of a filter (aka, a kernel), which is a matrix of particular dimensions (e.g., 3×3 or larger) that may be applied to the image data to look at a block of data at a time. The kernel or filter is "convolved" with the image data, where it may be multiplied by the block of data, and then shifted over and applied repeatedly. There may be a stride, which refers to how many pixels or data points that the filter is shifted by. There are various flavors of filters that may be used, including the Sobel filter and the Sharr filter, that may enhance the vertical or horizontal edges. Alternately, the parameters of the filters may be learned from the data through the machine learning process (e.g., use supervised learning and minimize a cost function to learn the parameters). While sliding the filter across the image with a particular stride, it may also be valuable to add padding around the edge of the image, since applying the convolution operation tends to shrink the matrix size and edge pixels may be used less than other pixels in an image. When applying to a 3D image (for example, RGB image or image with depth), the image may be thought of as having a height, width, and number of channels (sometimes also called depth). For CNNs the filter or kernel may also have a height, a width, but also have the same number of channels as the image (also called stacked filter for each channel). Moreover, multiple filters may be used in parallel to detect multiple features or edges. In one example, if there are multiple filters, then they can be applied to the same image and then the multiple outputs may be stacked as if there were different channels. These are one embodiment of filters or kernels, but other types or combinations of these may be used and are also intended to fall within the scope of this disclosure.

In a particular embodiment, one layer of the CNN may perform as follows. The input image may be a 3D image, an RGB image, or some combination. The CNN may first perform the convolution of the input image across all the channels using multiple filters, thereby creating multiple convolution outputs (e.g., stacked outputs). A bias term may then be added to the output of the convolution of each filter, yielding an output similar to that from the earlier described neural networks. Next, an activation function may be applied to all channels of the output, such as a ReLU function. Alternative activation functions include the sigmoid function, hyperbolic tangent function, leaky ReLU function, etc. Then, the outputs from the activation function may be stacked to create a “cube” that may be the network layer’s output. This may be one layer of the CNN, but a CNN may comprise a number of such layers. For instance, the ConvNet may comprise an input layer, three different convolution layers, then a fully connected output layer that uses the logistic or sigmoid or softmax function. Additionally, there may what are called pooling layers, which may be used to reduce the size of the representations (e.g., width and height) as well as perhaps to speed up calculations or enhance some of the feature detection to be more robust. Exemplary pooling layers include max pooling (take maximum in a region) or average pooling (take average in a region). Finally, the fully connected layer(s) are layers that may take the output of the convolution or convolution plus pool layers and take each individual pixel as an input (e.g., collapse the volume of the output into a vector with an equivalent size). The fully connected layer may be like a typical neural network layer with activation functions that may take the collapsed output of the previous layer. This is one example, but different versions of layers, different number of layers, different activation functions, different filters sizes, different padding and stride values, etc., or combinations of these may be used and are also intended to fall within the scope of the disclosure.

For the CSP system with video or image outputs, it may be advantageous to use CNNs for a number of reasons. One advantage may be parameter sharing; for example, a feature detector (such as a vertical edge detector) that is useful in one part of the image may also be useful in another part of the image. Another advantage may be sparsity of connections; e.g., in each layer the output value may depend only on a small number of inputs, which makes it more translation invariant. As with many computer vision problems, the CSP system processing may start from previously solved problems and then customize or adjust the network. For instance, some of the existing CNNs include LeNet-5, AlexNet, VGG, and ResNet. It may be valuable to start with open source code, when possible. Also, the CSP system may not have enough data to fully train the model, so the data may be augmented with existing data, or the data may be manipulated to produce more data. Since a system like CSP may not have enough data to fully train the model, it may be beneficial to have more hand engineering, as is often done in computer vision. This is just one embodiment of how a CNN may be beneficial to the CSP system, but other CNNs and combinations with other AI/ML methods may be used and are also intended to fall within the scope of this disclosure.

In one embodiment, CNN’s may be used to implement object detection, localization, and classification on images. Image classification may refer to classifying an image to a specific class, even if the location of the object in the image may not be known. In classification with localization, the image may be analyzed to learn the class of the image and where the class is located within the image. For example, a red box or bounding box may be drawn around where the object may be in the image. For object detection, the problem may be that given an image, the system wants to detect all the objects in the image that belong to the various classes as well as provide their location. In general, an image may comprise more than one object with different classes. For example, an image may comprise a dog, a bicycle and a car. To implement this type of problem, the output vector from the CNN may now have not only the particular class that the object fits within (e.g., dog, bicycle, car), but also an output that indicates there is an object in the image, and for the object the bounding box coordinates (e.g., object center coordinates x, y, as well as the object height and object width). This type of vector may serve as an output from the neural network, and there may also be a softmax fully connected layer at the output that separates out the various classes. The training data may provide the “ground truth” answers, and the typical neural network learning process may be used to quantify the model parameters (e.g., define loss function, minimize using gradient descent to obtain the parameter values, and then iterate). This is just one example of object classification, localization, and detection, but other methods may also be use and are intended to fall within the scope of this disclosure. For example, it may also be valuable to use sliding window approaches to help with object detection, ConvNet approaches with smaller images fed into the algorithm, and single pass CNNs that calculate a number of sliding windows at a time.

In a particular embodiment relevant to CSP systems, a CNN may be used for landmark detection on the face and other locations within a subject’s body (e.g., in another embodiment, the landmarks may correspond to the skeleton of the person, such as elbows, legs, knees, arms, etc.). This may be used, for example, for the eye movement detection, as well as the determination of regions of interest along with face tracking in the CSP system. Landmark detection refers to placing coordinates or dots on various parts of the face or body; for example, the chin, mouth, nose, eyes, eyebrow, skeleton of the body, shoulders, chest, etc. Since a CNN may be used to output the coordinate of the points of interest, there may actually be a large number of landmarks. These landmark labels should also be consistent between the training data set and the development and test examples. Since this may still be considered a supervised learning process, the training data should have all the landmarks identified, from which the CNN may learn how to identify the landmarks. With the large number of landmarks and potentially large training set, the computational and memory required may be significant.

In yet another embodiment, CNNs may be beneficially used with the CSP system for face recognition or face verification. For example, in a driver monitoring system, when the driver sits in the seat, the CSP system may use face recognition to identify the driver and then the data processing will be used for that particular participant. Face verification may determine if the input image is that of the claimed person. On the other hand, face recognition may determine if the output identification is the image of any of the known persons, or possibly not recognized; i.e., attempting to answer the question of who is this person? One of the face recognition challenges may be to solve the one shot learning problem; e.g., a recognition system may be able to recognize a person learning from one image. This may be achieved by using a similarity function, which may observe the degree of difference between images. For instance, the difference between images may be calculated, and if this difference is below some threshold, then the system may be able to determine that it is the same person.

In an alternate embodiment, a face recognition system may use what is called a Siamese network. In such a network, each photo may be passed through a CNN, and the output may be used as an "encoding" of the picture. Then, the distance between two encodings may be calculated; if it is the same person, the distance should be small, while if it is a different person, then the distance should be large. In a different embodiment, the face recognition system may use what is called triplet loss. For triplet loss, the learning objective may be that given an image A (Anchor), it may be desired to find a function d such that d is small for another image of the same person P (Positive) and at the same time higher by a margin when compared with an image of a different person N (Negative). For the triplet loss, a loss function can be defined, and the parameters for the CNN may be determined by using training data. In yet another embodiment, the face recognition problem may be treated as a combination of face verification and binary classification, using for example a logistic regression approach. Moreover, the face recognition that may be used with the CSP system may rely on some of the implementations using deep learning including Openface, FaceNet, DeepFace, MediaPipe, etc. In short, in a deep learning method for CNNs, each layer of the CNN is learning more and more complicated features of images. For instance, the first CNN layers may be looking for edges, and the deeper units may be learning increasingly more complex/higher-level features and shapes.

Thus, the CSP system involves processing, and that processing may be aided by using some of the AI/ML methods and algorithms described herein. Face identification and recognition may be used to help the CSP system know whose data set to use in the decisions and learning. CNNs may be used in the CSP system to help with processing of the typically large data set associated with images and videos. The CSP system may also use various AI/ML algorithms to identify anomalous occurrences, such as anomaly detection, autoencoders, or GANs. Other algorithms for skewed sets may also be used, such as decision trees, bagging, random forests, and XGBoost. Moreover, generative AI methods may help in communicating results with the user as well as potentially providing some context or providing some helpful suggestions or remedial steps. GAIs may also be used to improve the performance of 2D/3D camera systems. Also, there are a variety of techniques for improving the performance of GAIs, such as reinforcement learning based on human feedback. The CSP system may not have to develop the AI/ML processes from scratch, but may start with existing algorithms, and then customizing or adjusting the algorithms to the particular needs of the CSP system. These are just some of the ways in which AI/ML may be used with CSP systems and other systems described in this disclosure, but there are other AI/ML techniques that may be used, or combinations of these and other AI/ML methods may be used, and these are also intended to fall within the scope of this disclosure.

The CSP system described comprising 2D or 3D cameras have many applications that can benefit from fusing data not only from different sensors, but also from different information gathered on a person. Several examples may illustrate the point, such as looking at intoxicated vehicle drivers, impaired vehicle drivers under the influence of drugs such as marijuana, or pose estimation of a person. In a first example, AI/ML based systems that combine with cameras or sensors within a vehicle may help to identify a drunk driver by detecting some representative signatures that may potentially include facial recognition and analysis (for symptoms such as red or bloodshot eyes, lack of motor control), pattern recognition (for erratic driving), and natural language processing techniques (for slurred speech). In one embodiment, a camera in a vehicle may potentially detect a drunk driver using a combination of methods including AI/ML and computer vision. Here are some examples of data that may be used either individually or combination: (1) facial recognition and analysis: the camera may be used to detect the face of the driver and analyze facial features. The system might leverage AI/ML algorithms trained to identify signs of alcohol impairment such as droopy eyelids, flushed cheeks or a dazed look; (2) detection of erratic movements: erratic, sudden or unusually slow movements may also indicate a driver under the influence of alcohol. The system might monitor the driver's movements and use analytics to detect anomalies compared with normal behavior; (3) eye movement tracking: certain eye movement patterns, such as slow or delayed reaction to stimuli, difficulty in maintaining eye focus, or a high frequency of blinking, may indicate intoxication. Techniques such as gaze tracking may be employed to observe these indicators; (4) speech analysis: if the system has audio capabilities, then it may be combined with speech recognition technology to analyze the driver's speech. Alcohol may cause slurred speech or affect the coherency and pace or speaking; (5) continuous monitoring: the system may might continuously monitor the driver and use AI/ML to learn normal patterns for the particular driver, thus allowing the system to better detect when the driver's behavior deviates from the norm due to potential intoxication.

In another embodiment, further information on a drunk driver may also be gathered and combined when using a 3D camera, such as involving time-of-flight cameras, stereographic cameras, or structured light cameras. For example, the 3D camera may be able to observe the balance and coordination of the driver. Intoxication may also affect a person's balance and coordination, and actions such as a person swaying while standing still may be detectable in 3D space. In yet another example, the 3D camera may be used for gait analysis (e.g., human motion). Intoxicated individuals may exhibit changes in the way they walk, such as staggering or inability to walk in a straight line. For instance, a gait analysis system might comprise the following steps: (1) motion capture: the 3D camera could use depth perception to capture the driver's entrance or exit from the vehicle. It might try to focus on tracking specific points on the body to create a model of the driver's movements; (2) feature extraction: by monitoring some key features of the subject's gain, such as stride length, speed, balance, symmetry, and regularity, the system might extract valuable data regarding the driver's walking pattern; (3) AI/ML algorithms: the extracted features may then be fed into an AI/ML algorithm that has been trained on a database of gait patterns. The algorithm might not only predict normal and abnormal patterns but also categorize patterns associated specific conditions such as alcohol impairment, fatigue, or neurological disorders; and (4) alert and actions: if the system detects abnormal gait patterns, it might initiate an alert, or take certain actions, such as sending a notification to authorities or emergency contacts, sending an alert to the driver, limit the vehicle's speed, or, in highly automated vehicles, bring the car safely to a halt. Although discussed in the context of a vehicle driver, it should be noted that gait analysis is more commonly used in medical and sports applications or for identifying individuals based on their walking patterns in security settings.

In another application or embodiment, the CSP system may advantageously be used to detect impaired vehicle drivers under the influence of drugs, such as marijuana. Camera-based systems may help to detect impaired drivers using a number of techniques including: (1) advanced computer vision: AI/ML combined with advanced computer vision might be trained to recognize specific signs of drug use; (2) physical detection: camera combined with AI/ML might detect common symptoms of drug use, including red eyes, delayed reaction times, and altered motor functions; (3) driver behavior: the system might monitor for erratic driving patterns often associated with impairment, such as swerving or sudden starts and stops; and (4) combined approach: the system might use input from a multitude of sensors (including but not limited to cameras) to evaluate the likely state of the driver.

In one embodiment, the CSP system might be used to detect impairment of the driver by combining facial blood flow, vital signs and eye movements. As an example, consider the effects of marijuana on these physiological parameters. Marijuana may have several effects on the body due to its active ingredient, tetra-hydro-cannabinol (THC), which is a vasodilator. Thus, marijuana may lead to changes in the facial blood flow including: (1) increased blood flow: THC may cause blood vessels to expand, increasing facial blood flow and possibly leading to flushed faces or the facial skin looking redder than usual; (2) bloodshot eyes: THC may cause blood vessels in the eyes to expand and increase blood flow, causing redness; (3) lowered blood pressure: while THC may initially increase heart rate and blood pressure, over time it may actually lower blood pressure, leading to potential feelings of dizziness.

Beyond facial blood flow, marijuana may also affect the vital signs of the user, since THC may act on the cannabinoid receptors of the body's endocannabinoid system. Some of the effects on the vital signs may include: (1) heart rate: marijuana use may increase heart rate for up to three hours after smoking, and this effect may be longer with new users and with edibles or other oral consumption methods; (2) blood pressure: although marijuana may case a brief period of increased blood pressure, it may then lead to reduced blood pressure, particularly when lying down; (3) respiratory rate: smoking marijuana may lead to airway inflammation, increased airway resistance and lung hyperinflation, and thus may contribute to elevated respiratory rate; (4) temperature: THC may appear to interact with temperature regulation in the hypothalamus, potentially leading to hypothermia or hyperthermia; and (5) other effects: marijuana may also affect other physiological functions such as motor control, memory, appetite, and cognition, due to wide range of brain systems influenced by THC.

In addition to changes in the vital signs, marijuana may have a variety of effects on the eyes, which might potentially impact blink rate and eye closure. Some of the effects may include: (1) eye pressure: marijuana may reduce intraocular eye pressure, which is the fluid pressure in the eyes; (2) redness: THC is a vasodilator and may cause redness of the eyes; and (3) dryness: like alcohol, marijuana may lead to feeling of dryness in the eyes, which may cause more blinking as the body tries to address the dryness.

Thus, detecting impaired drivers could benefit from using or combining computer vision, AI/ML and image processing systems. In image processing, 2D or 3D cameras equipped with image processing systems may detect physical symptoms associated with marijuana use, such as red, glassy or droopy eyes, altered coordination, or delayed reaction times. Using AI/ML algorithms, the system may be trained to recognize patterns by providing a set of images or real-time video feeds. Computer vision may analyze real-time images to detect activities related to marijuana use. Moreover, infrared cameras may help to detect changes in body or face temperature, which might indicate substance use.

In yet another embodiment, 2D or 3D cameras may also be used for pose estimation or gesture analysis of a person, which is information that may be fused with data from other sensors. Pose estimation may refer to the process of determining the position and orientation of a 3D object, such as a person. Gesture analysis may comprise measuring and interpreting of hand or finger motions, or motion of other parts of the body (e.g., head motions, or even facial muscle movements). In terms of psychological interpretation, pose estimation and/or gesture analysis may be utilized for understanding human behavior, emotions and interactions. For instance, understanding the pose and movements of a person may help in psychological therapy, sports analysis or human-computer interactions. In the context of psychology, pose estimation might play a role in understanding non-verbal communication as it provides details about body language, which is a powerful mode of communication beyond verbal exchanges. Body language, including poses and gestures, may depend on cultural contexts and are in many instances interpreted sub-consciously by people. Digitally learning and interpreting these postures using pose estimation may enable a more effective understanding of human behavior, since body language often communicates more information than verbal communication. Also, non-congruent body language and verbal communication may indicate that a person may not be completely forthright. The pose and gesture estimation may also be beneficial when trying to analyze and understand the behavior of people who have communication impairments, include young children as well as elderly people who may not be able to express how they are feeling. Pose estimation and/or gesture analysis may be used in conjunction with AI/ML algorithms to predict and interpret human emotions or detect abnormal behaviors, contributing to the diagnosis and treatment of psychological disorders. In short, 3D cameras used for pose estimation and gesture analysis may be beneficial for enabling deeper understanding of human behavior, emotions and non-verbal communication.

The CSP system, particularly when using AI/ML, may require adequate computing or processing power. In one embodiment, the CSP system may operate on computing systems such as desktop or laptop computers, which may be using central processor units (CPUs) and/or graphical processor units (GPUs). In another embodiment, the CSP system may be operating on a customized processor, such as a processor chip in a vehicle or measurement instrument or on an application specific integrated circuit (ASIC). As an alternative, the CSP system may have the interface on a local system (such as a smart phone, tablet, vehicle system, or laptop), and the data may be sent to the cloud for detailed computations (c.f., FIG. 24 or 31). These are just some possible processing platforms, but others may be used, or combinations of these may be used, and are also intended to fall within the scope of this disclosure. In any of these processing scenarios, data from the CSP and the results may be sent to and stored in non-transitory computer readable media.

Various embodiments of camera and sensor based systems have been described in this disclosure, but modifications and any number of combinations of these may also be used and are intended to be covered by this disclosure. For example, a 2D or 3D camera system (e.g., including time-of-flight sensors or structured light) may be used to observe the facial muscle movements or potentially facial blood flow, and such a camera system may also have active illumination by one or more semiconductor diodes, such as LEDs or VCSELs. In addition, the same or another camera system may be used to observe eye movements, and this system may also have active illumination by either one or more LED or VCSEL semiconductor diodes. Moreover, the same or yet another camera system may be used to observe motion of hands or feet or pose or gestures. In one embodiment, these cameras could be mounted in a head-mounted device, such as an augmented/virtual/mixed reality unit. The data from these camera systems may also be fused with data from wearable devices, which may provide physiological parameters such as heart rate, heart rate variability, breathing rate, ECG or EKG, temperature, oximetry, etc. In one embodiment, the wearable device may include active illuminators (e.g., LEDs or VCSELs) and optical sensors that may be based on PPG, as well as electrodes or temperature sensors or other contact-based sensors. The wearable devices may be worn on a user's arm, wrist, ears, or other body parts.

In this particular example, by combining the camera data with wearable device data, a more holistic view of a person may be obtained. Also, artificial intelligence/machine learning may be used to process the fused data to obtain more information about the state of the person. In one embodiment, the mental health or psychological state of a person may be gained from the fused data from the camera and wearable data. The diagnosis and treatment for disorders such as depression, stress, anxiety, post-traumatic stress disorder, etc., may be based on signals received from the camera or wearable devices. For example, by using machine learning with inputs from the physiological parameters and camera data about facial expressions and/or eye movements and/or facial blood flow, the system may able to surmise that the person is depressed. As one possible outcome, the output from the AI/ML algorithms might be stored and processed in non-transitory computer readable media, and the data may then be used to change environmental parameters or sounds or visual inputs. In one embodiment, music may be played that could change the mood, or videos or scenes may be displayed to also alter the mood. Moreover, the lighting or temperature or other environmental conditions in the room may be changed to help lighten or alter the mood. This is just one example of data fusion from many of the camera and sensor systems described in this disclosure, but some parts or other combinations may also be used and are intended to fall within the scope of this disclosure.

What is claimed is:

1. A remote sensing system comprising:

a housing configured to be physically applied to a user, the housing having an inward side facing the user and an outward side;

a time-of-flight sensor attached to the outward side, the time-of-flight sensor comprising:

an array of laser diodes configured to generate laser light having one or more optical wavelengths between 600 nanometers and 1000 nanometers, wherein a first laser diode of the array of laser diodes comprises one or more Bragg reflectors, and pulses at a modulation frequency between 10 Megahertz and 1 Gigahertz and has a phase associated with the pulses of the first laser diode;

at least a portion of the laser light generated by the array of laser diodes is configured to be directed to an object;

at least one photo-detector, provided with a lens and a spectral filter at an input to the at least one photo-detector, a processor processing digitized signals received from the at least one photo-detector, the processor being configured to (i) measure a phase shift of at least a reflected portion of the laser light from the array of laser diodes reflected from the object relative to the at least a portion of the laser light generated by the array of laser diodes, (ii) measure a time-of-flight measurement of the at least the reflected portion of the laser light and (iii) generate a first image of the object based at least in part on an amplitude of the at least a reflected portion of the laser light;

wherein the photo-detector is configured to synchronize to the pulses of the first laser diode, and wherein the processor is configured to generate the time-of-flight measurement; and a first camera attached to the outward side, the first camera coupled to a second lens and the processor, wherein the first camera is configured to capture a second image of at least a part of the object; and the processor being coupled to a second camera attached to the inward side, the second camera being configured to be illuminated by one or more light emitting diodes generating incoherent light configured to operate in a near-infrared wavelength range, wherein the second camera is configured to at least in part monitor at least one eye of the user.

2. The remote sensing system of claim 1, further comprising:

a non-transitory computer readable medium coupled to the processor, wherein at least a portion of the time-of-flight measurement, at least a portion of the first image, and at least a portion of the second image are configured to serve as at least a part of an input to an artificial intelligence assistant configured to communicate with or operate on the processor, the artificial intelligence assistant comprising a multi-modal generative artificial intelligence model comprising a transformer including self-attention and positional encoding layers and configured to perform computer vision processing and natural language processing; and wherein the multi-modal generative artificial intelligence model is configured to accept as prompt inputs comprising images, videos, text, and voice control or interactions and is configured to include memory that records prompt inputs.

3. The remote sensing system of claim 2, wherein the processor is configured to be at least a part of a smart glasses or an augmented, virtual, or mixed reality goggles, and wherein the glasses or goggles have a speaker, a microphone, and one or more displays, wherein the one or more displays are configured to be connected on the inward side and directed toward the at least one eye of the user.

4. The remote sensing system of claim 3, wherein the processor is configured to perform gesture analysis of user's bodily movements using the time-of-flight sensor or the first camera and is configured to track eye movements using the second camera.

5. The remote sensing system of claim 4, wherein the processor is configured to perform speech recognition and provide speech outputs configured to be sent to the speaker and video outputs configured to be sent to the one or more displays.

6. The remote sensing system of claim 5, wherein the multi-modal generative artificial model is configured to operate as an artificial intelligence agent that is configured to have awareness of an environment or context in which the agent interacts, and wherein the artificial intelligence assistant comprising the multi-modal generative artificial intelligence model is configured to at least in part operate on a remote computing apparatus comprising a cloud server, a smart phone, a tablet, or a computer, and the remote computing apparatus is configured to perform data fusion of an output from the processor with data from a plurality of other sensors.

7. The remote sensing system of claim 6, further comprising:

a light sensing system coupled to the processor, the light sensing system comprising:

one or more wavelength filters configured to separate incoming ambient light into one or more optical wavelength bands;

one or more detectors configured to capture at least some of the one or more optical wavelength bands; and an analog-to-digital converter coupled to the one or more detectors that is configured to generate a color output; and wherein the processor is configured to receive at least a portion of the color output and adjust a visual output from the one or more displays or a setting for the first camera.

8. A wearable system comprising:

smart glasses configured to be worn by a user, the smart glasses comprising an outward side configured to be opposite an inward side facing the user;

one or more cameras that are CMOS back-illuminated sensors attached to the outward side of the smart glasses and configured to capture a camera image or a camera video including an object, and wherein the one or more cameras are also configured to perform hand tracking for gesture analysis;

the smart glasses comprising touch sensors configured to accept user inputs and motion tracking sensors configured to track user movements;

the smart glasses further comprising a processor, one or more displays attached to the inward side, speakers, and one or more microphones configured to receive sound inputs including voice control or interactions;

the smart glasses including the processor configured to be coupled to a smart phone or a tablet for further processing capabilities;

the processor being configured to be coupled to a non-transitory computer readable medium;

wherein smart glasses data comprises the camera image, the camera video, the sound inputs, the gesture analysis or the user inputs, and the smart glasses data is configured to serve as at least a part of an input to an artificial intelligence assistant configured to communicate with or operate on the processor, the artificial intelligence assistant comprising a multi-modal generative artificial intelligence model comprising a transformer including self-attention and positional encoding layers and configured to perform computer vision processing and natural language processing; and wherein the multi-modal generative artificial intelligence model is configured to recognize at least some of the object captured in the camera image or the camera video.

9. The wearable system of claim 8, wherein the processor is configured to perform speech recognition and provide speech outputs configured to be sent to the speakers and video or image outputs configured to be sent to the one or more displays.

10. The wearable system of claim 9, wherein the multi-modal generative artificial intelligence model is configured to accept as prompt inputs images, videos, text, verbal inputs or sounds and configured to include memory that records prompt inputs, and wherein the multi-modal generative artificial intelligence model is configured to perform data fusion of the smart glasses data with an accelerometer input and a gyroscope sensor input.

11. The wearable system of claim 10, wherein the one or more cameras comprises a plurality of cameras attached to the outward side of the smart glasses, and wherein the plurality of cameras are configured for stereographic imaging.

12. The wearable system of claim 10, wherein the artificial intelligence assistant comprising the multi-modal generative artificial intelligence model is configured to at least in part operate on a remote computing apparatus comprising a cloud server or a computer, and wherein the multi-modal generative artificial model is configured to operate as an artificial intelligence agent that is configured to have awareness of an environment or context in which the agent interacts.

13. The wearable system of claim 10, wherein the processor is further configured to be coupled to a light sensing system, the light sensing system comprising:

one or more wavelength filters configured to separate incoming ambient light into one or more optical wavelength bands;

one or more detectors configured to capture at least some of the one or more optical wavelength bands; and an analog-to-digital converter coupled to the one or more detectors that is configured to generate a color output;

wherein the processor is configured to receive at least a portion of the color output and adjust a visual output from the one or more displays or a setting for the one or more cameras.

14. A measurement system comprising:

an array of laser diodes configured to generate a light having an initial light intensity and one or more optical wavelengths, wherein at least a portion of the one or more optical wavelengths is a near-infrared wavelength between 700 nanometers and 2500 nanometers, wherein at least a portion of the array of laser diodes comprises one or more Bragg reflectors, and wherein the array of laser diodes is further coupled to driver electronics and one or more safety shut-offs;

a beam splitter configured to receive at least a portion of the light from the array of laser diodes and to direct at least some of the light from the array of laser diodes to an object, wherein the beam splitter is further configured to separate the at least a portion of the light into a plurality of spatially separated lights;

a first camera, wherein the first camera further comprises one or more lenses and one or more spectral filters in front of the first camera, wherein the first camera is further coupled to a processor, wherein the processor is configured to be coupled to a non-transitory computer readable medium;

wherein the first camera is configured to receive at least a portion of the plurality of spatially separated lights reflected from the object and configured to capture a first image, and wherein the first camera is further configured to be synchronized to the at least a portion of the array of laser diodes comprising Bragg reflectors;

wherein the processor is configured to perform an analysis of a pattern of the received spatially separated lights reflected from the object in the first image and configured to analyze the first image; and the processor further being coupled to a second camera, the second camera being configured to be illuminated by one or more light emitting diodes generating incoherent light and being configured to operate in a near-infrared wavelength range, wherein the second camera is configured to at least in part monitor at least one eye of a user.

15. The measurement system of claim 14, wherein at least a portion of the first image is configured to serve as at least a part of an input to an artificial intelligence assistant configured to communicate with or operate on the processor, the artificial intelligence assistant comprising a multi-modal generative artificial intelligence model comprising a transformer including self-attention and positional encoding layers and configured to perform computer vision processing and natural language processing; and wherein the multi-modal generative artificial intelligence model is configured to accept as prompt inputs images, videos, text, and voice control or interactions and configured to include memory that records previous prompt inputs.

16. The measurement system of claim 15, wherein the measurement system including the processor is configured to perform gesture analysis of user's bodily movements using the first camera and configured to perform eye tracking using the second camera.

17. The measurement system of claim 16, wherein the processor is configured to be at least a part of smart glasses or augmented, virtual, or mixed reality goggles, and wherein the glasses or the goggles have a speaker, a microphone, and one or more displays configured to be directed toward the at least one eye of the user.

18. The measurement system of claim 17, wherein the measurement system including the processor is configured to perform speech recognition and provide speech outputs configured to be sent to the speaker and video outputs configured to be sent to the one or more displays.

19. The measurement system of claim 18, wherein the artificial intelligence assistant comprising the multi-modal generative artificial intelligence model is configured to at least in part operate on a remote computing apparatus comprising a cloud server, a smart phone, a tablet, or a computer;

wherein the remote computing apparatus is configured to perform data fusion of an output from the processor with data from a plurality of other sensors; and wherein the multi-modal generative artificial model is configured to operate as an artificial intelligence agent that is configured to have awareness of an environment or context in which the agent interacts.

20. The measurement system of claim 19, wherein the processor is further configured to be coupled to a light sensing system comprising:

one or more wavelength filters configured to separate incoming ambient light into one or more optical wavelength bands;

one or more detectors configured to capture at least some of the one or more optical wavelength bands; and an analog-to-digital converter coupled to the one or more detectors that is configured to generate a color output;

wherein the processor is configured to receive at least a portion of the color output and adjust a visual output from the one or more displays or a setting for the first camera.

* * * * *